(12) United States Patent
Ye et al.

(10) Patent No.: US 12,378,243 B2
(45) Date of Patent: Aug. 5, 2025

(54) QUINOLINE COMPOUNDS AS INHIBITORS OF KRAS

(71) Applicant: Incyte Corporation, Wilmington, DE (US)

(72) Inventors: Qinda Ye, Claymont, DE (US); Matthew McCammant, West Chester, PA (US); Rocco Policarpo, Wilmington, DE (US); Artem Shvartsbart, Wilmington, DE (US); Wenyu Zhu, Wilmington, DE (US); Jeremy Roach, Philadelphia, PA (US); Gia Hoang, Wilmington, DE (US); Bin Hu, Garnet Valley, PA (US); Gencheng Li, Claymont, DE (US); Robert Susick, Wilmington, DE (US); Padmaja Polam, Kennett Square, PA (US); Fenglei Zhang, Berwyn, PA (US); Chao Qi, Wilmington, DE (US); Xiaozhao Wang, Mt. Laurel, NJ (US); Wenqing Yao, Wilmington, DE (US); Alexander Sokolsky, Wilmington, DE (US); Haolin Yin, Wilmington, DE (US); Le Zhao, Wilmington, DE (US); Peter Carlsen, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 18/437,502

(22) Filed: Feb. 9, 2024

(65) Prior Publication Data
US 2024/0368152 A1 Nov. 7, 2024

Related U.S. Application Data

(62) Division of application No. 18/046,303, filed on Oct. 13, 2022, now Pat. No. 11,939,328.

(60) Provisional application No. 63/368,563, filed on Jul. 15, 2022, provisional application No. 63/363,270, filed on Apr. 20, 2022, provisional application No. 63/279,464, filed on Nov. 15, 2021, provisional application No. 63/255,610, filed on Oct. 14, 2021.

(51) Int. Cl.
*A61K 31/4745* (2006.01)
*A61P 35/00* (2006.01)
*C07D 471/04* (2006.01)

(52) U.S. Cl.
CPC ........ *C07D 471/04* (2013.01); *A61K 31/4745* (2013.01); *A61P 35/00* (2018.01)

(58) Field of Classification Search
CPC ................................................ A61K 31/4745
See application file for complete search history.

(56) References Cited

U.S. PATENT DOCUMENTS

| | | |
|---|---|---|
| 5,051,508 A | 9/1991 | Brown et al. |
| 5,281,608 A | 1/1994 | Skotnicki et al. |
| 5,360,799 A | 11/1994 | Bachy et al. |
| 5,420,135 A | 5/1995 | Brown et al. |
| 5,626,633 A | 5/1997 | Roschger |
| 7,592,453 B2 | 9/2009 | Kajino et al. |
| 7,897,609 B2 | 3/2011 | Niwas et al. |
| 8,034,802 B2 | 10/2011 | Averett |
| 8,143,270 B2 | 3/2012 | Kshirsagar et al. |
| 8,158,794 B2 | 4/2012 | Kshirsagar et al. |
| 8,207,187 B2 | 6/2012 | Beek et al. |
| 8,241,917 B2 | 8/2012 | Fan et al. |
| 8,354,405 B2 | 1/2013 | Garcia et al. |
| 8,455,491 B2 | 6/2013 | Puech et al. |
| 8,513,250 B2 | 8/2013 | Escaich et al. |
| 8,546,395 B2 | 10/2013 | Pacaud et al. |
| 8,557,984 B2 | 10/2013 | Bouillot et al. |
| 8,563,565 B2 | 10/2013 | Norimine et al. |
| 8,637,670 B2 | 1/2014 | Kumar et al. |
| 8,658,666 B2 | 2/2014 | Rice et al. |
| 8,697,744 B2 | 4/2014 | Bolea et al. |
| 8,822,448 B2 | 9/2014 | Kaizawa et al. |
| 8,846,710 B2 | 9/2014 | Kshirsagar et al. |
| 8,895,581 B2 | 11/2014 | McConnell et al. |
| 9,045,419 B2 | 6/2015 | Lee et al. |
| 9,062,046 B2 | 6/2015 | Kumar et al. |
| 9,169,246 B2 | 10/2015 | Benazet et al. |
| 9,403,769 B2 | 8/2016 | Chand et al. |
| 9,550,776 B2 | 1/2017 | Norimine et al. |
| 9,573,947 B2 | 2/2017 | Ozaki |
| 9,694,006 B2 | 7/2017 | Beck et al. |
| 9,771,327 B2 | 9/2017 | Zawistoski et al. |
| 9,873,694 B2 | 1/2018 | Lipford et al. |
| 9,960,359 B2 | 5/2018 | Hwang et al. |

(Continued)

FOREIGN PATENT DOCUMENTS

| | | |
|---|---|---|
| CN | 102399218 A | 4/2012 |
| CN | 103012397 B | 3/2017 |

(Continued)

OTHER PUBLICATIONS

U.S. Appl. No. 18/491,224, filed Oct. 20, 2023, Xiaozhao Wang.

(Continued)

*Primary Examiner* — Laura L Stockton
(74) *Attorney, Agent, or Firm* — Lathrop GPM LLP; Brian C. Trinque; Nicole Sassu

(57) ABSTRACT

Disclosed are compounds of Formula I, methods of using the compounds for inhibiting KRAS activity and pharmaceutical compositions comprising such compounds. The compounds are useful in treating, preventing or ameliorating diseases or disorders associated with KRAS activity such as cancer.

34 Claims, No Drawings

(56) References Cited

U.S. PATENT DOCUMENTS

| | | |
|---|---|---|
| 10,039,753 B2 | 8/2018 | Coffman et al. |
| 10,081,637 B2 | 9/2018 | Yu et al. |
| 10,208,055 B2 | 2/2019 | Yu et al. |
| 10,249,826 B2 | 4/2019 | Ogiwara et al. |
| 10,251,870 B2 | 4/2019 | Prossnitz et al. |
| 10,326,084 B2 | 6/2019 | Ise et al. |
| 10,351,557 B2 | 7/2019 | Fortte et al. |
| 10,544,138 B2 | 1/2020 | Gray et al. |
| 11,053,240 B2 | 7/2021 | Li et al. |
| 11,530,218 B2 | 12/2022 | Zhao et al. |
| 2003/0149069 A1 | 8/2003 | Li et al. |
| 2004/0147747 A1 | 7/2004 | Diwu et al. |
| 2005/0136537 A1 | 6/2005 | Sinclair et al. |
| 2006/0025337 A1 | 2/2006 | Sinclair et al. |
| 2006/0084135 A1 | 4/2006 | Howitz et al. |
| 2006/0276393 A1 | 12/2006 | Milburn et al. |
| 2006/0276416 A1 | 12/2006 | Sinclair et al. |
| 2007/0149466 A1 | 6/2007 | Milburn et al. |
| 2007/0191379 A1 | 8/2007 | Abelman et al. |
| 2008/0174474 A1 | 7/2008 | Harris et al. |
| 2010/0120818 A1 | 5/2010 | Enderle |
| 2010/0167925 A1 | 7/2010 | Koradin et al. |
| 2011/0003776 A1 | 1/2011 | Snyder et al. |
| 2011/0230476 A1 | 9/2011 | Niu et al. |
| 2011/0312934 A1 | 12/2011 | Garcia et al. |
| 2012/0015953 A1 | 1/2012 | Beauregard et al. |
| 2012/0065187 A1 | 3/2012 | Borchardt et al. |
| 2013/0190314 A1 | 7/2013 | Chiang et al. |
| 2014/0084217 A1 | 3/2014 | Ohya et al. |
| 2014/0243286 A1 | 8/2014 | Arnold et al. |
| 2016/0264570 A1 | 9/2016 | McKew et al. |
| 2017/0197945 A1 | 7/2017 | Li et al. |
| 2017/0217960 A1 | 8/2017 | Ferguson |
| 2017/0294489 A1 | 10/2017 | Lim et al. |
| 2019/0088887 A1 | 3/2019 | Feldman et al. |
| 2019/0131544 A1 | 5/2019 | Park et al. |
| 2019/0177338 A1 | 6/2019 | Kettle et al. |
| 2021/0269434 A1 | 9/2021 | Wang et al. |
| 2021/0308123 A1 | 10/2021 | Zhang et al. |
| 2021/0317118 A1 | 10/2021 | Zhang et al. |
| 2021/0355121 A1 | 11/2021 | Zhu et al. |
| 2021/0355141 A1 | 11/2021 | Hoang et al. |
| 2022/0064188 A1 | 3/2022 | Carlsen et al. |
| 2022/0106309 A1 | 4/2022 | Huang et al. |
| 2022/0306633 A1 | 9/2022 | Qi et al. |
| 2022/0389033 A1 | 12/2022 | Sokolsky et al. |
| 2023/0056631 A1 | 2/2023 | Gan et al. |
| 2023/0114765 A1 | 4/2023 | Li et al. |
| 2023/0143938 A1 | 5/2023 | Zhu et al. |
| 2023/0144051 A1 | 5/2023 | Ye et al. |
| 2023/0151005 A1 | 5/2023 | Carlsen et al. |
| 2023/0174555 A1 | 6/2023 | Li et al. |

FOREIGN PATENT DOCUMENTS

| | | |
|---|---|---|
| CN | 108003153 A | 5/2018 |
| EP | 1 142 889 A1 | 10/2001 |
| IN | 2012MUM02281 A | 6/2014 |
| WO | WO 1994/014777 A1 | 7/1994 |
| WO | WO 1996/009304 A1 | 3/1996 |
| WO | WO 1999/067238 A2 | 12/1999 |
| WO | WO 2000/043397 A1 | 7/2000 |
| WO | WO 2001/042247 A1 | 6/2001 |
| WO | WO 2002/020489 A2 | 3/2002 |
| WO | WO 2004/067513 A1 | 8/2004 |
| WO | WO 2008/035356 A2 | 3/2008 |
| WO | WO 2008/056151 A1 | 5/2008 |
| WO | WO 2008/079139 A1 | 7/2008 |
| WO | WO 2009/010824 A1 | 1/2009 |
| WO | WO 2009/123967 A1 | 10/2009 |
| WO | WO 2010/049366 A1 | 5/2010 |
| WO | WO 2010/070238 A1 | 6/2010 |
| WO | WO 2010/130934 A1 | 11/2010 |
| WO | WO 2010/135571 A1 | 11/2010 |
| WO | WO 2012/011642 A1 | 1/2012 |
| WO | WO 2012/040924 A1 | 4/2012 |
| WO | WO 2012/041227 A1 | 4/2012 |
| WO | WO 2012/116623 A1 | 9/2012 |
| WO | WO 2012/154731 A1 | 11/2012 |
| WO | WO 2013/045400 A1 | 4/2013 |
| WO | WO 2013/059559 A2 | 4/2013 |
| WO | WO 2013/147431 A1 | 10/2013 |
| WO | WO 2014/050417 A1 | 4/2014 |
| WO | WO 2014/097866 A1 | 6/2014 |
| WO | WO 2014/142467 A1 | 9/2014 |
| WO | WO 2016/161361 A1 | 10/2016 |
| WO | WO 2016/168540 A1 | 10/2016 |
| WO | WO 2016/199943 A1 | 12/2016 |
| WO | WO 2017/058805 A1 | 4/2017 |
| WO | WO 2017/070293 A1 | 4/2017 |
| WO | WO 2017/092413 A1 | 6/2017 |
| WO | WO 2018/119183 A2 | 6/2018 |
| WO | WO 2018/217651 A1 | 11/2018 |
| WO | WO 2018/221545 A1 | 12/2018 |
| WO | WO 2018/221546 A1 | 12/2018 |
| WO | WO 2018/221550 A1 | 12/2018 |
| WO | WO 2018/221551 A1 | 12/2018 |
| WO | WO 2019/049024 A1 | 3/2019 |
| WO | WO 2019/150305 A1 | 8/2019 |
| WO | WO 2019/177971 A1 | 9/2019 |
| WO | WO 2019/194481 A1 | 10/2019 |
| WO | WO 2019/201283 A1 | 10/2019 |
| WO | WO 2019/209896 A1 | 10/2019 |
| WO | WO 2019/213516 A1 | 11/2019 |
| WO | WO 2020/051207 A2 | 3/2020 |
| WO | WO 2021/063346 A1 | 4/2021 |
| WO | WO 2022/037631 A1 | 2/2022 |

OTHER PUBLICATIONS

U.S. Appl. No. 17/153,065 / 2021-230162 A1 / U.S. Pat. No. 11,530,218, filed Jan. 20, 2021 / Jul. 29, 2021 Dec. 20, 2022, Le Zhao.
U.S. Appl. No. 18/052,347 / 2023-0192696 A1, filed Nov. 3, 2022 / Jun. 22, 2023, Le Zhao.
U.S. Appl. No. 18/464,575, filed Sep. 11, 2023, Wenyu Zhu.
U.S. Appl. No. 17/318,720 / 2021-0355141 A1 / U.S. Pat. No. 11,739,102, filed May 12, 2021 / Nov. 18, 2021 / Aug. 29, 2023, Gia Hoang.
U.S. Appl. No. 17/458,964 / 2022-0064188 A1, filed Aug. 27, 2021 / Mar. 3, 2022, Peter Carlsen.
U.S. Appl. No. 17/449,696 / 2022/0106309 A1 / U.S. Pat. No. 11,767,320, filed Oct. 1, 2021 / Apr. 7, 2022 / Sep. 26, 2023, Taisheng Huang.
U.S. Appl. No. 17/700,923 / 2022/0306633 A1, filed Mar. 22, 2022 / Sep. 29, 2022, Chao Qi.
U.S. Appl. No. 17/661,182 / 2022-0389033 A1, filed Apr. 28, 2022 / Dec. 8, 2022, Alexander Sokolsky.
U.S. Appl. No. 18/480,307, filed Oct. 3, 2023, Alexander Sokolsky.
U.S. Appl. No. 17/810,915 / 2023-0056631 A1, filed Jul. 6, 2022 / Feb. 23, 2023, Pei Gan.
U.S. Appl. No. 17/812,310 / 2023-0114765 A1, filed Jul. 13, 2022 / Apr. 13, 2023, Zhenwu Li.
U.S. Appl. No. 17/823,254 / 2023-0174555 A1, filed Aug. 30, 2022 Jun. 8, 2023, Gencheng Li.
U.S. Appl. No. 17/933,660 / 2023-0151005 A1, filed Sep. 20, 2022 / May 18, 2023, Peter Carlsen.
U.S. Appl. No. 17/937,106 / 2023-0143938 A1, filed Sep. 30, 2022 / May 11, 2023, Wenyu Zhu.
U.S. Appl. No. 18/046,303 / 2023-0144051 A1, filed Oct. 13, 2022 / May 11, 2023, Qinda Ye.
U.S. Appl. No. 18/437,502, filed Feb. 9, 2024, Qinda Ye.
U.S. Appl. No. 18/349,606, filed Jul. 10, 2023, Gencheng Li.
Bauer, R.A., "Covalent inhibitors in drug discovery: from accidental discoveries to avoided liabilities and designed therapies", *Drug Discovery Today* 20(9):1061-1073 (2015).
Chen et al., "Small-Molecule Inhibitors Directly Targeting KRAS as Anticancer Therapeutics", *Journal of Medicinal Chemistry* 63(3):14404-14424 (2020).

(56) References Cited

OTHER PUBLICATIONS

Cox et al., "Drugging the undruggable Ras: mission impossible?", *Nature Reviews Drug Discovery* 13(11):828-851 (2014).
Fernandez-Medarde et al., "Ras in Cancer and Developmental Diseases", *Genes & Cancer* 2(3):344-358 (2011).
International Search Report and Written Opinion for International Application No. PCT/US2022/077350, mailed Nov. 24, 2022, 13 pages.
International Search Report and Written Opinion for International Application No. PCT/US2022/078048, mailed Feb. 9, 2023, 13 pages.
Korzeniecki et al., "Targeting KRAS mutant cancers by preventing signaling transduction in the MAPK pathway", *European Journal of Medicinal Chemistry* 211 (2021) 113006.
Ostrem et al., "K-Ras (G12C) inhibitors allosterically control GTP affinity and effector interactions", *Nature* 503(7477):548-551 (2013).
Written Opinion of the International Searching Authority for PCT/US2021/027513, dated Oct. 21, 2021, 6 pages.
Zhu et al., "Structure-based discovery of selective BRPF1 bromodomain inhibitors", *European Journal of Medicinal Chemistry* 155:337-352 (2018).

QUINOLINE COMPOUNDS AS INHIBITORS OF KRAS

RELATED APPLICATIONS

This application is a divisional of U.S. patent application Ser. No. 18/046,303, filed on Oct. 13, 2022, which claims priority to U.S. Provisional Application No. 63/255,610, filed Oct. 14, 2021, U.S. Provisional Application No. 63/279,464, filed Nov. 15, 2021, U.S. Provisional Application No. 63/363,270, filed Apr. 20, 2022, and U.S. Provisional Application No. 63/368,563, filed Jul. 15, 2022, the entire contents of which are hereby incorporated by reference in their entirety.

FIELD OF THE INVENTION

The disclosure provides compounds as well as their compositions and methods of use. The compounds modulate KRAS activity and are useful in the treatment of various diseases including cancer.

BACKGROUND OF THE INVENTION

Ras proteins are part of the family of small GTPases that are activated by growth factors and various extracellular stimuli. The Ras family regulates intracellular signaling pathways responsible for growth, migration, survival and differentiation of cells. Activation of RAS proteins at the cell membrane results in the binding of key effectors and initiation of a cascade of intracellular signaling pathways within the cell, including the RAF and PI3K kinase pathways. Somatic mutations in RAS may result in uncontrolled cell growth and malignant transformation while the activation of RAS proteins is tightly regulated in normal cells (Simanshu, D. et al. Cell 170.1 (2017):17-33).

The Ras family is comprised of three members: KRAS, NRAS and HRAS. RAS mutant cancers account for about 25% of human cancers. KRAS is the most frequently mutated isoform accounting for 85% of all RAS mutations whereas NRAS and HRAS are found mutated in 12% and 3% of all Ras mutant cancers respectively (Simanshu, D. et al. Cell 170.1 (2017):17-33). KRAS mutations are prevalent amongst the top three most deadly cancer types: pancreatic (97%), colorectal (44%), and lung (30%) (Cox, A. D. et al. Nat Rev Drug Discov (2014) 13:828-51). The majority of RAS mutations occur at amino acid residue 12, 13, and 61. The frequency of specific mutations varies between RAS gene isoforms and while G12 and Q61 mutations are predominant in KRAS and NRAS respectively, G12, G13 and Q61 mutations are most frequent in HRAS. Furthermore, the spectrum of mutations in a RAS isoform differs between cancer types. For example, KRAS G12D mutations predominate in pancreatic cancers (51%), followed by colorectal adenocarcinomas (45%) and lung cancers (17%) while KRAS G12V mutations are associated with pancreatic cancers (30%), followed by colorectal adenocarcinomas (27%) and lung adenocarcinomas (23%) (Cox, A. D. et al. Nat Rev Drug Discov (2014) 13:828-51). In contrast, KRAS G12C mutations predominate in non-small cell lung cancer (NSCLC) comprising 11-16% of lung adenocarcinomas, and 2-5% of pancreatic and colorectal adenocarcinomas (Cox, A. D. et al. Nat. Rev. Drug Discov. (2014) 13:828-51). Genomic studies across hundreds of cancer cell lines have demonstrated that cancer cells harboring KRAS mutations are highly dependent on KRAS function for cell growth and survival (McDonald, R. et al. Cell 170 (2017): 577-592). The role of mutant KRAS as an oncogenic driver is further supported by extensive in vivo experimental evidence showing mutant KRAS is required for early tumour onset and maintenance in animal models (Cox, A. D. et al. Nat Rev Drug Discov (2014) 13:828-51).

Taken together, these findings suggest that KRAS mutations play a critical role in human cancers; development of inhibitors targeting mutant KRAS may therefore be useful in the clinical treatment of diseases that are characterized by a KRAS mutation.

SUMMARY

The present disclosure provides, inter alia, a compound of Formula I:

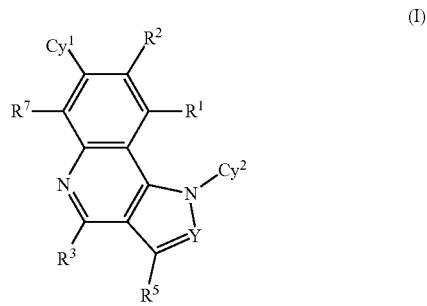

or a pharmaceutically acceptable salt thereof, wherein constituent variables are defined herein.

The present disclosure further provides a pharmaceutical composition comprising a compound of the disclosure, or a pharmaceutically acceptable salt thereof, and at least one pharmaceutically acceptable carrier or excipient.

The present disclosure further provides methods of inhibiting KRAS activity, which comprises administering to an individual a compound of the disclosure, or a pharmaceutically acceptable salt thereof. The present disclosure also provides uses of the compounds described herein in the manufacture of a medicament for use in therapy. The present disclosure also provides the compounds described herein for use in therapy.

The present disclosure further provides methods of treating a disease or disorder in a patient comprising administering to the patient a therapeutically effective amount of a compound of the disclosure, or a pharmaceutically acceptable salt thereof.

DETAILED DESCRIPTION

Compounds

In an aspect, provided herein is a compound having Formula (I):

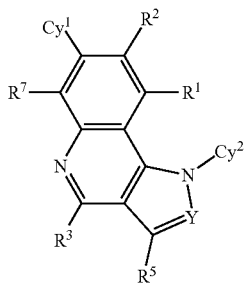

or a pharmaceutically acceptable salt thereof, wherein:
Y is N or $CR^6$;
$R^1$ is selected from H, $C_{1-3}$ alkyl, $C_{1-3}$ haloalkyl, cyclopropyl, halo, D, CN, and $OR^{a1}$; wherein said $C_{1-3}$ alkyl and cyclopropyl are each optionally substituted with 1 or 2 substituents independently selected from $R^9$;
$R^2$ is selected from H, $C_{1-3}$ alkyl, $C_{1-3}$ haloalkyl, 4-6 membered heterocycloalkyl, phenyl, 5-6 membered heteroaryl, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, and $OR^{a2}$; wherein said $C_{1-3}$ alkyl, 4-6 membered heterocycloalkyl, phenyl, 5-6 membered heteroaryl, 4-6 membered heterocycloalkyl-$C_{1-3}$ alkylene, phenyl-$C_{1-3}$ alkylene, 5-6 membered heteroaryl-$C_{1-3}$ alkylene are each optionally substituted with 1 or 2 substituents independently selected from $R^9$;
$Cy^1$ is selected from $C_{3-10}$ cycloalkyl, 4-10 membered heterocycloalkyl, $C_{6-10}$ aryl and 6-10 membered heteroaryl; wherein the 4-10 membered heterocycloalkyl and 6-10 membered heteroaryl each has at least one ring-forming carbon atom and 1, 2, 3, or 4 ring-forming heteroatoms independently selected from N, O, and S; wherein a ring-forming carbon atom of 6-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 6-10 membered heteroaryl are each optionally substituted with 1, 2, 3, or 4 substituents independently selected from $R^{10}$;
$R^3$ is selected from H, $C_{1-3}$ alkyl, $C_{1-3}$ haloalkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, $OR^{f3}$, $C(O)NR^{c3}R^{d3}$, $NR^{c3}R^{f3}$, and $NR^{c3}C(O)R^{b3}$; wherein said $C_{1-3}$ alkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, or 3 substituents independently selected from $R^{30}$;
$R^5$ is selected from H, $C_{1-3}$ alkyl, $C_{1-3}$ haloalkyl, cyclopropyl, halo, D, CN, and $OR^{a5}$;
wherein said $C_{1-3}$ alkyl and cyclopropyl are each optionally substituted with 1 or 2 substituents independently selected from $R^9$;
$R^6$ is selected from H, $C_{1-3}$ alkyl, $C_{1-3}$ haloalkyl, $C_{3-6}$ cycloalkyl, 4-9 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, $OR^{a6}$, and $C(O)NR^{c6}R^{d6}$; wherein said $C_{1-3}$ alkyl, $C_{3-6}$cycloalkyl, 4-9 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, and 5-6 membered heteroaryl-$C_{1-3}$ alkylene are each optionally substituted with 1 or 2 substituents independently selected from $R^{60}$;
$R^7$ is selected from H, $C_{1-3}$ alkyl, $C_{1-3}$ haloalkyl, cyclopropyl, halo, D, CN, and $OR^{a7}$;
wherein said $C_{1-3}$ alkyl and cyclopropyl are each optionally substituted with 1 or 2 substituents independently selected from $R^9$;
$Cy^2$ is selected from

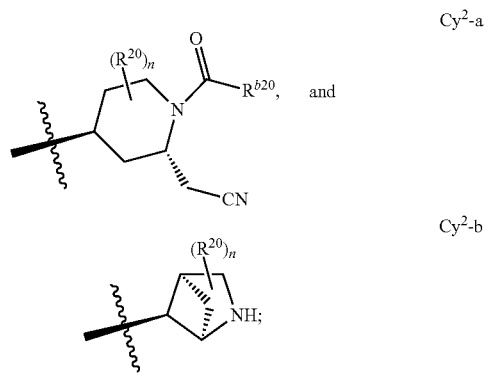

wherein n is 0, 1, or 2;
each $R^{10}$ is independently selected from $C_{1-3}$ alkyl, $C_{1-3}$ haloalkyl, halo, D, CN, $OR^{a10}$, $C(O)R^{b10}$, $C(O)NR^{c10}R^{d10}$, $C(O)OR^{a10}$, $NR^{c10}R^{d10}$, and $S(O)_2R^{b10}$;
each $R^{20}$ is independently selected from $C_{1-3}$ alkyl, $C_{1-3}$ haloalkyl, halo, D, CN, and $OR^{a20}$;
each $R^{30}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a30}$, $C(O)R^{b30}$, $C(O)NR^{c30}R^{d30}(O)OR^{a30}$, $NR^{c30}R^{d30}$, and $S(O)_2R^{b30}$; wherein said $C_{1-3}$ alkyl, $C_{3-6}$ cycloalkyl, 4-6 membered heterocycloalkyl, phenyl, and 5-6 membered heteroaryl are each optionally substituted with 1 or 2 substituents independently selected from $R^{31}$;
each $R^{31}$ is independently selected from $C_{1-3}$ alkyl, $C_{1-3}$ haloalkyl, halo, D, CN, $OR^{a31}$, $C(O)R^{b31}$, $C(O)NR^{c31}R^{d31}$, $C(O)OR^{a31}$, $NR^{c31}R^{d31}$, and $S(O)_2R^{b31}$;
each $R^{33}$ is independently selected from $C_{1-3}$ alkyl, $C_{1-3}$ haloalkyl, $C_{3-6}$ cycloalkyl, 4-membered heterocycloalkyl, 6-membered heterocycloalkyl, phenyl, 5-6 membered heteroaryl, halo, D, CN, $OR^{a30}$, $C(O)NR^{c30}R^{d30}$, and $NR^{c30}R^{d30}$; wherein said $C_{1-3}$ alkyl, $C_{3-6}$ cycloalkyl, 4-membered heterocycloalkyl, 6-membered heterocycloalkyl, phenyl, and 5-6 membered heteroaryl are each optionally substituted with 1 or 2 substituents independently selected from $R^{31}$;
each $R^{60}$ is independently selected from $C_{1-3}$ alkyl, $C_{1-3}$ haloalkyl, 4-6 membered heterocycloalkyl, 5-6 membered heteroaryl, halo, D, CN, $OR^{a60}$, $C(O)R^{b60}$, $C(O)NR^{c60}R^{d60}$ $NR^{c60}C(O)R^{b60}$, $C(O)OR^{a60}$, $NR^{c60}C(O)OR^{a60}$, $NR^{c60}R^{d60}$, $NR^{c60}S(O)_2R^{b60}$, and $S(O)_2R^{b60}$;
wherein said $C_{1-3}$ alkyl, 4-6 membered heterocycloalkyl, and 5-6 membered heteroaryl are each optionally substituted with 1 or 2 substituents independently selected from $R^{61}$;

each $R^{61}$ is independently selected from $C_{1-3}$ alkyl, $C_{1-3}$ haloalkyl, halo, D, CN, $OR^{a61}$, and $NR^{c61}R^{d61}$;

$R^{a1}$ is selected from H, $C_{1-3}$ alkyl, and $C_{1-3}$ haloalkyl;

each $R^{a2}$ is independently selected from H, $C_{1-3}$ alkyl, and $C_{1-3}$ haloalkyl;

each $R^{b3}$, $R^{c3}$ and $R^{d3}$ is independently selected from H, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said, $C_{1-3}$ alkyl, $C_{3-6}$ cycloalkyl, 4-6 membered heterocycloalkyl, phenyl and 5-6 membered heteroaryl are each optionally substituted with 1, 2, or 3 substituents independently selected from $R^{30}$;

or $R^{c3}$ and $R^{d3}$ attached to the same N atom, together with the N atom to which they are attached, form a 4-, 5-, or 6-membered heterocycloalkyl group optionally substituted with 1, 2, or 3 substituents independently selected from $R^{30}$;

$R^{\beta3}$ is selected from $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said, $C_{1-3}$ alkyl, $C_{3-6}$ cycloalkyl, 4-6 membered heterocycloalkyl, phenyl and 5-6 membered heteroaryl are each optionally substituted with 1, 2, or 3 substituents independently selected from $R^{30}$;

or $R^{c3}$ and $R^{\beta3}$ attached to the same N atom, together with the N atom to which they are attached, form a 4-, 5-, or 6-membered heterocycloalkyl group optionally substituted with 1, 2, or 3 substituents independently selected from $R^{30}$ $R^{\beta3}$ is selected from $C_{1-3}$ haloalkyl, $C_{3-6}$ cycloalkyl, 4-6 membered heterocycloalkyl, phenyl and 5-6 membered heteroaryl; wherein said $C_{1-3}$ haloalkyl, $C_{3-6}$ cycloalkyl, 4-6 membered heterocycloalkyl, phenyl, and 5-6 membered heteroaryl are each optionally substituted with 1, 2, or 3 substituents independently selected from $R^{30}$; or $R^{\beta3}$ is selected from

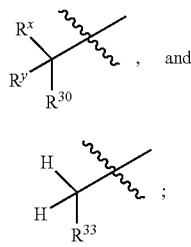

wherein $R^x$ is H or $C_{1-2}$ alkyl and $R^y$ is $C_{1-2}$ alkyl;

or $R^x$ and $R^y$, together with the C atom to which they are attached, form a 3-, or 4-membered cycloalkyl group;

$R^{a5}$ is selected from H, $C_{1-3}$ alkyl, and $C_{1-3}$ haloalkyl;

each $R^{a6}$, $R^{c6}$ and $R^{d6}$ is independently selected from H, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl and 5-6 membered heteroaryl are each optionally substituted with 1 or 2 substituents independently selected from $R^{60}$;

$R^{a7}$ is selected from H, $C_{1-3}$ alkyl, and $C_{1-3}$ haloalkyl;

each $R^{a10}$, $R^{b10}$, $R^{c10}$ and $R^{d10}$ is independently selected from H, $C_{1-3}$ alkyl, and $C_{1-3}$ haloalkyl;

each $R^{a20}$ is independently selected from H, $C_{1-3}$ alkyl, and $C_{1-3}$ haloalkyl;

$R^{b20}$ is selected from $NH_2$, $C_{1-3}$ alkyl, and $C_{1-3}$ haloalkyl;

each $R^{a30}$, $R^{b30}$, $R^{c30}$ and $R^{d30}$ is independently selected from H, $C_{1-3}$ alkyl, and $C_{1-3}$ haloalkyl;

each $R^{a31}$, $R^{b31}$, $R^{c31}$ and $R^{d31}$ is independently selected from H, $C_{1-3}$ alkyl, and $C_{1-3}$ haloalkyl;

each $R^{a60}$, $R^{b60}$, $R^{c60}$ and $R^{d60}$ is independently selected from H, $C_{1-3}$ alkyl, $C_{1-3}$ haloalkyl, $C_{3-6}$ cycloalkyl, 4-6 membered heterocycloalkyl, and 5-6 membered heteroaryl;

wherein said $C_{1-3}$ alkyl, $C_{3-6}$ cycloalkyl, 4-6 membered heterocycloalkyl, and 5-6 membered heteroaryl are each optionally substituted with 1 or 2 substituents independently selected from $R^{61}$;

or any $R^{c60}$ and $R^{d60}$ attached to the same N atom, together with the N atom to which they are attached, form a 4-, 5-, or 6-membered heterocycloalkyl group optionally substituted with 1 or 2 substituents independently selected from $R^{61}$; and each $R^{a61}$, $R^{c61}$, and $R^{d61}$, is independently selected from H, $C_{1-3}$ alkyl, and $C_{1-3}$ haloalkyl; and each $R^g$ is independently selected from D, OH, CN, halo, $C_{1-3}$ alkyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino;

provided that the compound of Formula I is other than, 3-(1-((1R,4R,5S)-2-azabicyclo[2.1.1]hexan-5-yl)-8-(2-cyanoethyl)-4-ethoxy-6-fluoro-7-(3-hydroxynaphthalen-1-yl)-1H-pyrrolo[3,2-c]quinolin-2-yl)-N,N-dimethylpropanamide.

In an embodiment of Formula I, or a pharmaceutically acceptable salt thereof,

Y is N or $CR^6$;

$R^1$ is selected from H, $C_{1-3}$ alkyl, $C_{1-3}$ haloalkyl, cyclopropyl, halo, D, CN, and $OR^{a1}$;

wherein said $C_{1-3}$ alkyl and cyclopropyl are each optionally substituted with 1 or 2 substituents independently selected from $R^9$;

$R^2$ is selected from H, $C_{1-3}$ alkyl, $C_{1-3}$ haloalkyl, 4-6 membered heterocycloalkyl, phenyl, 5-6 membered heteroaryl, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, and $OR^{a2}$; wherein said $C_{1-3}$ alkyl, 4-6 membered heterocycloalkyl, phenyl, 5-6 membered heteroaryl, 4-6 membered heterocycloalkyl-$C_{1-3}$ alkylene, phenyl-$C_{1-3}$ alkylene, 5-6 membered heteroaryl-$C_{1-3}$ alkylene are each optionally substituted with 1 or 2 substituents independently selected from $R^9$;

$Cy^1$ is selected from $C_{3-10}$ cycloalkyl, 4-10 membered heterocycloalkyl, $C_{6-10}$ aryl and 6-10 membered heteroaryl; wherein the 4-10 membered heterocycloalkyl and 6-10 membered heteroaryl each has at least one ring-forming carbon atom and 1, 2, 3, or 4 ring-forming heteroatoms independently selected from N, O, and S; wherein a ring-forming carbon atom of 6-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 6-10 membered heteroaryl are each optionally substituted with 1, 2, 3, or 4 substituents independently selected from $R^{10}$;

$R^3$ is selected from H, $C_{1-3}$ alkyl, $C_{1-3}$ haloalkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, $OR^{f3}$, $C(O)NR^{c3}R^{d3}$, $NR^{c3}R^{f3}$, and $NR^{c3}C(O)R^{b3}$; wherein said C$_{1-3}$ alkyl, C$_{3-6}$ cycloalkyl, 4-6 membered heterocycloalkyl, phenyl, 5-6 membered heteroaryl, C$_{3-6}$ cycloalkyl-C$_{1-3}$ alkylene, 4-6 membered heterocycloalkyl-C$_{1-3}$ alkylene, phenyl-C$_{1-3}$ alkylene, and 5-6 membered heteroaryl-C$_{1-3}$ alkylene are each optionally substituted with 1, 2, or 3 substituents independently selected from R$^{30}$;

R$^5$ is selected from H, C$_{1-3}$ alkyl, C$_{1-3}$ haloalkyl, cyclopropyl, halo, D, CN, and OR$^{a6}$;

wherein said C$_{1-3}$ alkyl and cyclopropyl are each optionally substituted with 1 or 2 substituents independently selected from R$^g$;

R$^6$ is selected from H, C$_{1-3}$ alkyl, C$_{1-3}$ haloalkyl, C$_{3-6}$ cycloalkyl, 4-8 membered heterocycloalkyl, phenyl, 5-6 membered heteroaryl, C$_{3-6}$ cycloalkyl-C$_{1-3}$ alkylene, 4-6 membered heterocycloalkyl-C$_{1-3}$ alkylene, phenyl-C$_{1-3}$ alkylene, 5-6 membered heteroaryl-C$_{1-3}$ alkylene, halo, D, CN, OR$^{a6}$, and C(O)NR$^{c6}$R$^{d6}$; wherein said C$_{1-3}$ alkyl, C$_{3-6}$cycloalkyl, 4-8 membered heterocycloalkyl, phenyl, 5-6 membered heteroaryl, C$_{3-6}$ cycloalkyl-C$_{1-3}$ alkylene, 4-6 membered heterocycloalkyl-C$_{1-3}$ alkylene, phenyl-C$_{1-3}$ alkylene, and 5-6 membered heteroaryl-C$_{1-3}$ alkylene are each optionally substituted with 1 or 2 substituents independently selected from R$^{60}$;

R$^7$ is selected from H, C$_{1-3}$ alkyl, C$_{1-3}$ haloalkyl, cyclopropyl, halo, D, CN, and OR$^{a7}$;

wherein said C$_{1-3}$ alkyl and cyclopropyl are each optionally substituted with 1 or 2 substituents independently selected from R$^9$;

Cy$^2$ is selected from

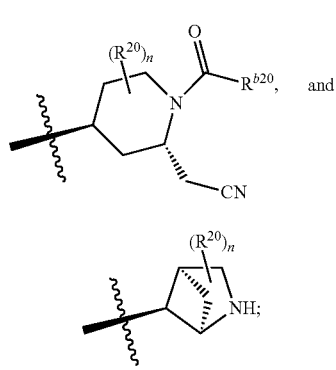

wherein n is 0, 1, or 2;

each R$^{10}$ is independently selected from C$_{1-3}$ alkyl, C$_{1-3}$ haloalkyl, halo, D, CN, OR$^{a10}$, C(O)R$^{b10}$, C(O)NR$^{c10}$R$^{d10}$, C(O)OR$^{a10}$, NR$^{c10}$R$^{d10}$, and S(O)$_2$R$^{b10}$;

each R$^{20}$ is independently selected from C$_{1-3}$ alkyl, C$_{1-3}$ haloalkyl, halo, D, CN, and OR$^{a20}$;

each R$^{30}$ is independently selected from C$_{1-3}$ alkyl, C$_{1-3}$ haloalkyl, C$_{3-6}$ cycloalkyl, 4-6 membered heterocycloalkyl, phenyl, 5-6 membered heteroaryl, halo, D, CN, OR$^{a30}$, C(O)R$^{b30}$, C(O)NR$^{c30}$R$^{d30}$, C(O)OR$^{a30}$, NR$^{c30}$R$^{d30}$, and S(O)$_2$R$^{b30}$; wherein said C$_{1-3}$ alkyl, C$_{3-6}$ cycloalkyl, 4-6 membered heterocycloalkyl, phenyl, and 5-6 membered heteroaryl are each optionally substituted with 1 or 2 substituents independently selected from R$^{31}$;

each R$^{31}$ is independently selected from C$_{1-3}$ alkyl, C$_{1-3}$ haloalkyl, halo, D, CN, OR$^{a31}$, C(O)R$^{b31}$, C(O)NR$^{c31}$R$^{d31}$, C(O)OR$^{a31}$, NR$^{c31}$R$^{d31}$, and S(O)$_2$R$^{b31}$;

each R$^{33}$ is independently selected from C$_{1-3}$ alkyl, C$_{1-3}$ haloalkyl, C$_{3-6}$ cycloalkyl, 4-membered heterocycloalkyl, 6-membered heterocycloalkyl, phenyl, 5-6 membered heteroaryl, halo, D, CN, OR$^{a30}$, C(O)NR$^{c30}$R$^{d30}$, and NR$^{c30}$R$^{d30}$; wherein said C$_{1-3}$ alkyl, C$_{3-6}$ cycloalkyl, 4-membered heterocycloalkyl, 6-membered heterocycloalkyl, phenyl, and 5-6 membered heteroaryl, are each optionally substituted with 1 or 2 substituents independently selected from R$^{31}$ each R$^{60}$ is independently selected from C$_{1-3}$ alkyl, C$_{1-3}$ haloalkyl, 4-6 membered heterocycloalkyl, 5-6 membered heteroaryl, halo, D, CN, OR$^{a60}$, C(O)R$^{b60}$, C(O) NR$^{c60}$R$^{d60}$ NR$^{c60}$C(O)R$^{b60}$, C(O)OR$^{a60}$, NR$^{c60}$C(O) OR$^{a60}$, NR$^{c60}$R$^{d60}$, NR$^{c60}$S(O)$_2$R$^{b60}$, and S(O)$_2$R$^{b60}$;

wherein said C$_{1-3}$ alkyl, 4-6 membered heterocycloalkyl, and 5-6 membered heteroaryl are each optionally substituted with 1 or 2 substituents independently selected from R$^{61}$;

each R$^{61}$ is independently selected from C$_{1-3}$ alkyl, C$_{1-3}$ haloalkyl, halo, D, CN, OR$^{a61}$, and NR$^{c61}$R$^{d61}$ R$^{a1}$ is selected from H, C$_{1-3}$ alkyl, and C$_{1-3}$ haloalkyl;

each R$^{a2}$ is independently selected from H, C$_{1-3}$ alkyl, and C$_{1-3}$ haloalkyl;

each R$^{b3}$, R$^{c3}$ and R$^{d3}$ is independently selected from H, C$_{1-3}$ alkyl, C$_{1-3}$ haloalkyl, C$_{3-6}$ cycloalkyl, 4-6 membered heterocycloalkyl, phenyl and 5-6 membered heteroaryl; wherein said, C$_{1-3}$ alkyl, C$_{3-6}$ cycloalkyl, 4-6 membered heterocycloalkyl, phenyl and 5-6 membered heteroaryl are each optionally substituted with 1, 2, or 3 substituents independently selected from R$^{30}$;

or R$^{c3}$ and R$^{d3}$ attached to the same N atom, together with the N atom to which they are attached, form a 4-, 5-, or 6-membered heterocycloalkyl group optionally substituted with 1, 2, or 3 substituents independently selected from R$^{30}$ R$^{j3}$ is selected from C$_{1-3}$ alkyl, C$_{1-3}$ haloalkyl, C$_{3-6}$ cycloalkyl, 4-6 membered heterocycloalkyl, phenyl and 5-6 membered heteroaryl; wherein said, C$_{1-3}$ alkyl, C$_{3-6}$ cycloalkyl, 4-6 membered heterocycloalkyl, phenyl and 5-6 membered heteroaryl are each optionally substituted with 1, 2, or 3 substituents independently selected from R$^{30}$;

or R$^{c3}$ and R$^{j3}$ attached to the same N atom, together with the N atom to which they are attached, form a 4-, 5-, or 6-membered heterocycloalkyl group optionally substituted with 1, 2, or 3 substituents independently selected from R$^{30}$;

R$^{j3}$ is selected from C$_{1-3}$ haloalkyl, C$_{3-6}$ cycloalkyl, 4-6 membered heterocycloalkyl, phenyl and 5-6 membered heteroaryl; wherein said C$_{1-3}$ haloalkyl, C$_{3-6}$ cycloalkyl, 4-6 membered heterocycloalkyl, phenyl and 5-6 membered heteroaryl are each optionally substituted with 1, 2, or 3 substituents independently selected from R$^{30}$; or R$^{j3}$ is selected from

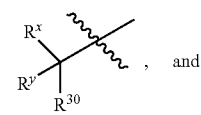

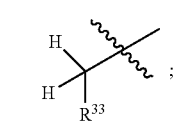

wherein $R^x$ is H or $C_{1-2}$ alkyl and $R^y$ is $C_{1-2}$ alkyl;
or $R^x$ and $R^y$, together with the C atom to which they are attached, form a 3-, or 4-membered cycloalkyl group;
$R^{a5}$ is selected from H, $C_{1-3}$ alkyl, and $C_{1-3}$ haloalkyl;
each $R^{a6}$, $R^{c6}$ and $R^{d6}$ is independently selected from H, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl and 5-6 membered heteroaryl are each optionally substituted with 1 or 2 substituents independently selected from $R^{60}$;
$R^{a7}$ is selected from H, $C_{1-3}$ alkyl, and $C_{1-3}$ haloalkyl;
each $R^{a10}$, $R^{b10}$, $R^{c10}$ and $R^{d10}$ is independently selected from H, $C_{1-3}$ alkyl, and $C_{1-3}$ haloalkyl;
each $R^{a20}$ is independently selected from H, $C_{1-3}$ alkyl, and $C_{1-3}$ haloalkyl;
$R^{b20}$ is selected from $NH_2$, $C_{1-3}$ alkyl, and $C_{1-3}$ haloalkyl;
each $R^{a30}$, $R^{b30}$, $R^{c30}$ and $R^{d30}$ is independently selected from H, $C_{1-3}$ alkyl, and $C_{1-3}$ haloalkyl;
each $R^{a31}$, $R^{b31}$, $R^{c31}$ and $R^{d31}$ is independently selected from H, $C_{1-3}$ alkyl, and $C_{1-3}$ haloalkyl;
each $R^{a60}$, $R^{b60}$, $R^{c60}$ and $R^{d60}$ is independently selected from H, $C_{1-3}$ alkyl, $C_{1-3}$ haloalkyl, $C_{3-6}$ cycloalkyl, 4-6 membered heterocycloalkyl, and 5-6 membered heteroaryl;
wherein said $C_{1-3}$ alkyl, $C_{3-6}$ cycloalkyl, 4-6 membered heterocycloalkyl, and 5-6 membered heteroaryl are each optionally substituted with 1 or 2 substituents independently selected from $R^{61}$;
or any $R^{c60}$ and $R^{d60}$ attached to the same N atom, together with the N atom to which they are attached, form a 4-, 5-, or 6-membered heterocycloalkyl group optionally substituted with 1 or 2 substituents independently selected from $R^{61}$; and
each $R^{a61}$, $R^{c61}$, and $R^{d61}$, is independently selected from H, $C_{1-3}$ alkyl, and $C_{1-3}$ haloalkyl; and
each $R^g$ is independently selected from D, OH, CN, halo, $C_{1-3}$ alkyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino;
provided that the compound of Formula I is other than, 3-(1-((1R,4R,5S)-2-azabicyclo[2.1.1]hexan-5-yl)-8-(2-cyanoethyl)-4-ethoxy-6-fluoro-7-(3-hydroxynaphthalen-1-yl)-1H-pyrrolo[3,2-c]quinolin-2-yl)-N,N-dimethylpropanamide.

In an embodiment of Formula I, or a pharmaceutically acceptable salt thereof,
Y is $CR^6$;
$R^1$ is selected from H, $C_{1-3}$ alkyl, and $C_{1-3}$ haloalkyl;
$R^2$ is selected from H, $C_{1-3}$ alkyl, $C_{1-3}$ haloalkyl, halo, D, CN, and $OR^{a2}$; wherein said $C_{1-3}$ alkyl, is optionally substituted with 1 or 2 substituents independently selected from $R^9$;
$Cy^1$ is selected from $C_{3-10}$ cycloalkyl, 4-10 membered heterocycloalkyl, $C_{6-10}$ aryl and 6-10 membered heteroaryl; wherein the 4-10 membered heterocycloalkyl and 6-10 membered heteroaryl each has at least one ring-forming carbon atom and 1, 2, 3, or 4 ring-forming heteroatoms independently selected from N, O, and S; wherein a ring-forming carbon atom of 6-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 6-10 membered heteroaryl are each optionally substituted with 1, 2, 3, or 4 substituents independently selected from $R^{10}$;
$R^3$ is selected from H, $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $C(O)NR^{c3}R^{d3}$ and $NR^{c3}C(O)R^{b3}$; wherein said $C_{1-3}$ alkyl, $C_{3-6}$ cycloalkyl, 4-6 membered heterocycloalkyl, phenyl, and 5-6 membered heteroaryl are each optionally substituted with 1, 2, or 3 substituents independently selected from $R^{30}$;
$R^5$ is selected from H, $C_{1-3}$ alkyl, $C_{1-3}$ haloalkyl, and halo;
$R^6$ is selected from H, $C_{1-3}$ haloalkyl, $C_{3-6}$ cycloalkyl, 4-8 membered heterocycloalkyl, phenyl, 5-6 membered heteroaryl, halo, D, CN, $OR^{a6}$, and $C(O)NR^{c6}R^{d6}$; wherein said $C_{3-6}$ cycloalkyl, 4-8 membered heterocycloalkyl, phenyl, and 5-6 membered heteroaryl are each optionally substituted with 1 or 2 substituents independently selected from $R^{60}$; or
$R^6$ is selected from $C_{1-3}$ alkyl; wherein said $C_{1-3}$ alkyl, is substituted with 1 or 2 substituents independently selected from $R^{60}$;
$R^7$ is selected from H, $C_{1-3}$ alkyl, $C_{1-3}$ haloalkyl, halo, and CN;
$Cy^2$ is selected from

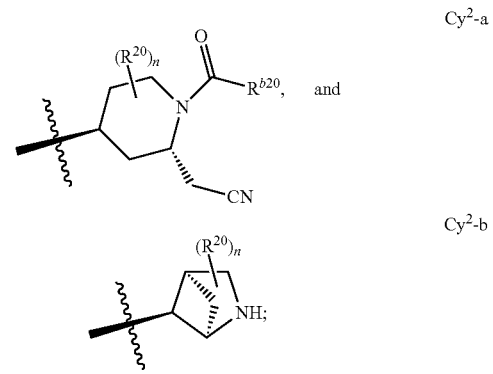

wherein n is 0, 1, or 2;
each $R^{10}$ is independently selected from $C_{1-3}$ alkyl, $C_{1-3}$ haloalkyl, halo, D, CN, $OR^{a10}$, $C(O)R^{b10}$, $C(O)NR^{c10}R^{d10}$, $C(O)OR^{a10}$, $NR^{c10}R^{d10}$, and $S(O)_2R^{b10}$;
each $R^{20}$ is independently selected from $C_{1-3}$ alkyl, $C_{1-3}$ haloalkyl, halo, D, CN, and $OR^{a20}$;
each $R^{30}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a30}$, $C(O)R^{b30}$, $C(O)NR^{c30}R^{d30}$, $C(O)OR^{a30}$, $NR^{c30}R^{d30}$, and $S(O)_2R^{b30}$; wherein said $C_{1-3}$ alkyl, $C_{3-6}$ cycloalkyl, 4-6 membered heterocycloalkyl, phenyl, and 5-6 membered heteroaryl are each optionally substituted with 1 or 2 substituents independently selected from $R^{31}$;
each $R^{31}$ is independently selected from $C_{1-3}$ alkyl, $C_{1-3}$ haloalkyl, halo, D, CN, $OR^{a31}$, $C(O)R^{b31}$, $C(O)NR^{c31}R^{d31}$, $C(O)OR^{a31}$, $NR^{c31}R^{d31}$, and $S(O)_2R^{b31}$;
each $R^{60}$ is independently selected from $C_{1-3}$ alkyl, $C_{1-3}$ haloalkyl, 4-6 membered heterocycloalkyl, 5-6 membered heteroaryl, halo, D, CN, $OR^{a60}$, $C(O)R^{b60}$, $C(O)NR^{c60}R^{d60}$ $NR^{c60}C(O)R^{b60}$, $C(O)OR^{a60}$, $NR^{c60}C(O)OR^{a60}$, $NR^{c60}R^{d60}$, $NR^{c60}S(O)_2R^{b60}$, and $S(O)_2R^{b60}$;
wherein said $C_{1-3}$ alkyl, 4-6 membered heterocycloalkyl, and 5-6 membered heteroaryl are each optionally substituted with 1 or 2 substituents independently selected from $R^{61}$;
each $R^{61}$ is independently selected from $C_{1-3}$ alkyl, $C_{1-3}$ haloalkyl, halo, D, CN, $OR^{a61}$, and $NR^{c61}R^{d61}$;

each $R^{a2}$ is independently selected from H, $C_{1-3}$ alkyl, and $C_{1-3}$ haloalkyl;

each $R^{b3}$, $R^{c3}$ and $R^{d3}$ is independently selected from H, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said, $C_{1-3}$ alkyl, $C_{3-6}$ cycloalkyl, 4-6 membered heterocycloalkyl, phenyl and 5-6 membered heteroaryl are each optionally substituted with 1, 2, or 3 substituents independently selected from $R^{30}$;

or $R^{c3}$ and $R^{d3}$ attached to the same N atom, together with the N atom to which they are attached, form a 4-, 5-, or 6-membered heterocycloalkyl group optionally substituted with 1, 2, or 3 substituents independently selected from $R^{30}$ each $R^{a6}$, $R^{c6}$ and $R^{d6}$ is independently selected from H, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl and 5-6 membered heteroaryl are each optionally substituted with 1 or 2 substituents independently selected from $R^{60}$;

each $R^{a10}$, $R^{b10}$, $R^{c10}$ and $R^{d10}$ is independently selected from H, $C_{1-3}$ alkyl, and $C_{1-3}$ haloalkyl;

each $R^{a20}$ is independently selected from H, $C_{1-3}$ alkyl, and $C_{1-3}$ haloalkyl;

$R^{b20}$ is selected from $NH_2$, $C_{1-3}$ alkyl, and $C_{1-3}$ haloalkyl;

each $R^{a30}$, $R^{b30}$, $R^{c30}$ and $R^{d30}$ is independently selected from H, $C_{1-3}$ alkyl, and $C_{1-3}$ haloalkyl;

each $R^{a31}$, $R^{b31}$, $R^{c31}$ and $R^{d31}$ is independently selected from H, $C_{1-3}$ alkyl, and $C_{1-3}$ haloalkyl;

each $R^{a60}$, $R^{b60}$, $R^{c60}$ and $R^{d60}$ is independently selected from H, $C_{1-3}$ alkyl, $C_{1-3}$ haloalkyl, $C_{3-6}$ cycloalkyl, 4-6 membered heterocycloalkyl, and 5-6 membered heteroaryl;

wherein said $C_{1-3}$ alkyl, $C_{3-6}$ cycloalkyl, 4-6 membered heterocycloalkyl, and 5-6 membered heteroaryl are each optionally substituted with 1 or 2 substituents independently selected from $R^{61}$;

or any $R^{c60}$ and $R^{d60}$ attached to the same N atom, together with the N atom to which they are attached, form a 4-, 5-, or 6-membered heterocycloalkyl group optionally substituted with 1 or 2 substituents independently selected from $R^{61}$; and each $R^{a61}$, $R^{c61}$, and $R^{d61}$, is independently selected from H, $C_{1-3}$ alkyl, and $C_{1-3}$ haloalkyl; and each $R^g$ is independently selected from D, CN, halo, $C_{1-3}$ alkyl, and $C_{1-3}$ haloalkyl.

In another embodiment of Formula I, or a pharmaceutically acceptable salt thereof, Y is $CR^6$;

$R^1$ is H;

$R^2$ is selected from $C_{1-3}$ alkyl, $C_{1-3}$ haloalkyl, halo, CN, and $-CH_2CH_2CN$;

$Cy^1$ is selected from $C_{3-10}$ cycloalkyl, $C_{6-10}$ aryl and 6-10 membered heteroaryl;

wherein the 6-10 membered heteroaryl has at least one ring-forming carbon atom and 1, ring-forming heteroatoms independently selected from N and S; and wherein the $C_{3-10}$ cycloalkyl, $C_{6-10}$ aryl and 6-10 membered heteroaryl are each optionally substituted with 1 or 2 substituents independently selected from $R^{10}$;

$R^3$ is selected from H, $C_{1-3}$ alkyl, $C_{1-3}$ haloalkyl, 4-6 membered heterocycloalkyl, phenyl, and 5-6 membered heteroaryl; wherein said $C_{1-3}$ alkyl, 4-6 membered heterocycloalkyl, phenyl, and 5-6 membered heteroaryl are each optionally substituted with 1, 2, or 3 substituents independently selected from $R^{30}$;

$R^5$ is selected from H and halo;

$R^6$ is selected from H, $C_{1-3}$ haloalkyl, 4-8 membered heterocycloalkyl, and 5-6 membered heteroaryl; wherein said 4-8 membered heterocycloalkyl, and 5-6 membered heteroaryl are each optionally substituted with 1 or 2 substituents independently selected from $R^{60}$; or $R^6$ is selected from $C_{1-3}$ alkyl; wherein said $C_{1-3}$ alkyl, is substituted with 1 or 2 substituents independently selected from $R^{60}$;

$R^7$ is halo;

$Cy^2$ is $Cy^2$-b each $R^{10}$ is independently selected from $C_{1-3}$ alkyl, $C_{1-3}$ haloalkyl, halo, D, CN, and $OR^{a10}$;

each $R^{30}$ is independently selected from $C_{1-3}$ alkyl, $C_{1-3}$ haloalkyl, 4-6 membered heterocycloalkyl, halo, D, CN, $OR^{a30}$, $C(O)NR^{c30}R^{d30}$, and $NR^{c30}R^{d30}$; wherein said $C_{1-3}$ alkyl, and 4-6 membered heterocycloalkyl are each optionally substituted with 1 or 2 substituents independently selected from $R^{31}$;

each $R^{31}$ is independently selected from $C_{1-3}$ alkyl, $C_{1-3}$ haloalkyl, halo, CN, $OR^{a31}$ and $NR^{c31}R^{d31}$;

each $R^{60}$ is independently selected from $C_{1-3}$ alkyl, $C_{1-3}$ haloalkyl, 4-6 membered heterocycloalkyl, 5-6 membered heteroaryl, halo, D, CN, $OR^{a60}$, $C(O)R^{b60}$, $C(O)NR^{c60}R^{d60}$ $NR^{c60}C(O)R^{b60}$, $C(O)OR^{a60}$, $NR^{c60}C(O)OR^{a60}$, $NR^{c60}R^{d60}$, $NR^{c60}S(O)_2R^{b60}$, and $S(O)_2R^{b60}$;

wherein said $C_{1-3}$ alkyl, 4-6 membered heterocycloalkyl, and 5-6 membered heteroaryl are each optionally substituted with 1 or 2 substituents independently selected from $R^{61}$;

each $R^{61}$ is independently selected from $C_{1-3}$ alkyl, $C_{1-3}$ haloalkyl, halo, and CN;

each $R^{a10}$ is independently selected from H, and $C_{1-3}$ alkyl;

each $R^{a30}$, $R^{c30}$ and $R^{d30}$ is independently selected from H, and $C_{1-3}$ alkyl;

each $R^{a31}$, $R^{c31}$ and $R^{d31}$ is independently selected from H, and $C_{1-3}$ alkyl;

each $R^{a60}$, $R^{b60}$, $R^{c60}$ and $R^{d60}$ is independently selected from H, $C_{1-3}$ alkyl, $C_{1-3}$ haloalkyl, $C_{3-6}$ cycloalkyl, 4-6 membered heterocycloalkyl, and 5-6 membered heteroaryl;

wherein said $C_{1-3}$ alkyl, $C_{3-6}$ cycloalkyl, 4-6 membered heterocycloalkyl, and 5-6 membered heteroaryl are each optionally substituted with 1 or 2 substituents independently selected from $R^{61}$;

or any $R^{c60}$ and $R^{d60}$ attached to the same N atom, together with the N atom to which they are attached, form a 4-, 5-, or 6-membered heterocycloalkyl group optionally substituted with 1 or 2 substituents independently selected from $R^{61}$.

In yet another embodiment of Formula I, or a pharmaceutically acceptable salt thereof, Y is $CR^6$;

$R^1$ is H;

$R^2$ is $-CH_2CH_2CN$;

Cy¹ is phenyl; wherein the phenyl is optionally substituted with 1 or 2 substituents independently selected from $R^{10}$;

$R^3$ is selected from H, $C_{1-3}$ alkyl, phenyl, and 5-6 membered heteroaryl; wherein said $C_{1-3}$ alkyl, phenyl, and 5-6 membered heteroaryl are each optionally substituted with 1, 2 or 3 substituents independently selected from $R^{30}$ $R^5$ is selected from H and halo;

$R^6$ is selected from $C_{1-3}$ alkyl and 5-9 membered heterocycloalkyl; wherein said $C_{1-3}$ alkyl and 5-9 membered heterocycloalkyl is optionally substituted with 1 or 2 substituents independently selected from $R^{60}$;

$R^7$ is halo;

Cy² is

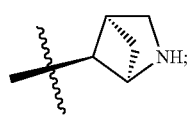

each $R^{10}$ is independently selected from $C_{1-3}$ alkyl and halo;

each $R^{30}$ is independently selected from $C_{1-3}$ alkyl, halo, OH, and $C(O)NR^{c30}R^{d30}$;

wherein said $C_{1-3}$ alkyl is optionally substituted with 1 substituent independently selected from $R^{31}$ each $R^{31}$ is independently selected from OH, $O(C_{1-3}$ alkyl), and $N(C_{1-3}$ alkyl)$_2$;

each $R^{60}$ is independently selected from $C_{1-3}$ alkyl, 4-6 membered heterocycloalkyl, 5-6 membered heteroaryl, halo, $C(O)R^{b60}$, $C(O)NR^{c60}R^{d60}$, $NR^{c60}C(O)R^{b60}$, $C(O)OR^{a60}$, $NR^{c60}C(O)OR^{a60}$, and $NR^{c60}S(O)_2R^{b60}$;

wherein said $C_{1-3}$ alkyl, 4-6 membered heterocycloalkyl, and 5-6 membered heteroaryl are each optionally substituted with 1 or 2 substituents independently selected from $R^{61}$;

each $R^{61}$ is independently selected from $C_{1-3}$ alkyl and halo;

each $R^{c30}$ and $R^{d30}$ is independently selected from H and $C_{1-3}$ alkyl; and each $R^{a60}$, $R^{b60}$, $R^{c60}$ and $R^{d60}$ is independently selected from H, $C_{1-3}$ alkyl, $C_{1-3}$ haloalkyl, $C_{3-6}$ cycloalkyl, 4-6 membered heterocycloalkyl, and 5-6 membered heteroaryl;

wherein said $C_{1-3}$ alkyl, $C_{3-6}$ cycloalkyl, 4-6 membered heterocycloalkyl, and 5-6 membered heteroaryl are each optionally substituted with 1 or 2 substituents independently selected from $R^{61}$;

or any $R^{c60}$ and $R^{d60}$ attached to the same N atom, together with the N atom to which they are attached, form a 4-, 5-, or 6-membered heterocycloalkyl group optionally substituted with 1 or 2 substituents independently selected from $R^{61}$.

In still another embodiment of Formula I, or a pharmaceutically acceptable salt thereof, Y is $CR^6$;

$R^1$ is H;

$R^2$ is —CH$_2$CH$_2$CN;

Cy¹ is phenyl; wherein the phenyl is optionally substituted with 1 or 2 substituents independently selected from $R^{10}$;

$R^3$ is selected from H, $C_{1-3}$ alkyl, phenyl, and 5-6 membered heteroaryl; wherein said $C_{1-3}$ alkyl, phenyl, and 5-6 membered heteroaryl are each optionally substituted with 1, 2 or 3 substituents independently selected from $R^{30}$ $R^5$ is selected from H and halo;

$R^6$ is selected from $C_{1-3}$ alkyl and 6-9 membered fused heterocycloalkyl; wherein said $C_{1-3}$ alkyl and 6-9 membered fused heterocycloalkyl is optionally substituted with 1 or 2 substituents independently selected from $R^{60}$;

$R^7$ is halo;

Cy² is

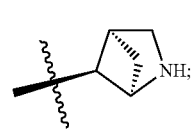

each $R^{10}$ is independently selected from $C_{1-3}$ alkyl and halo;

each $R^{30}$ is independently selected from $C_{1-3}$ alkyl, halo, OH, and $C(O)NR^{c30}R^{d30}$;

wherein said $C_{1-3}$ alkyl is optionally substituted with 1 substituent independently selected from $R^{31}$;

each $R^{31}$ is independently selected from OH, $O(C_{1-3}$ alkyl), and $N(C_{1-3}$ alkyl)$_2$;

each $R^{60}$ is independently selected from $C_{1-3}$ alkyl, 4-6 membered heterocycloalkyl, 5-6 membered heteroaryl, halo, $C(O)R^{b60}$, $C(O)NR^{c60}R^{d60}$, $NR^{c60}C(O)R^{b60}$, $C(O)OR^{a60}$, $NR^{c60}C(O)OR^{a60}$, and $NR^{c60}S(O)_2R^{b60}$;

wherein said $C_{1-3}$ alkyl, 4-6 membered heterocycloalkyl, and 5-6 membered heteroaryl are each optionally substituted with 1 or 2 substituents independently selected from $R^{61}$;

each $R^{61}$ is independently selected from $C_{1-3}$ alkyl and halo;

each $R^{c30}$ and $R^{d30}$ is independently selected from H and $C_{1-3}$ alkyl; and each $R^{a60}$, $R^{b60}$, $R^{c60}$ and $R^{d60}$ is independently selected from H, $C_{1-3}$ alkyl, $C_{1-3}$ haloalkyl, $C_{3-6}$ cycloalkyl, 4-6 membered heterocycloalkyl, and 5-6 membered heteroaryl;

wherein said $C_{1-3}$ alkyl, $C_{3-6}$ cycloalkyl, 4-6 membered heterocycloalkyl, and 5-6 membered heteroaryl are each optionally substituted with 1 or 2 substituents independently selected from $R^{61}$;

or any $R^{c60}$ and $R^{d60}$ attached to the same N atom, together with the N atom to which they are attached, form a 4-, 5-, or 6-membered heterocycloalkyl group optionally substituted with 1 or 2 substituents independently selected from $R^{61}$.

In yet another embodiment of Formula I, or a pharmaceutically acceptable salt thereof, Y is $CR^6$;

$R^1$ is H;

$R^2$ is —CH$_2$CH$_2$CN;

Cy¹ is phenyl; wherein the phenyl is optionally substituted with 1 or 2 substituents independently selected from $R^{10}$;

$R^3$ is selected from H, $C_{1-3}$ alkyl, phenyl, and 5-6 membered heteroaryl; wherein said $C_{1-3}$ alkyl, phenyl, and 5-6 membered heteroaryl are each optionally substituted with 1, 2 or 3 substituents independently selected from $R^{30}$ $R^5$ is selected from H and halo;

R⁶ is selected from 4-8 membered heterocycloalkyl; wherein said 4-8 membered heterocycloalkyl, is optionally substituted with 1 or 2 substituents independently selected from R⁶⁰; or R⁶ is selected from $C_{1-3}$ alkyl; wherein said $C_{1-3}$ alkyl is substituted with 1 or 2 substituents independently selected from R⁶⁰;

R⁷ is halo;

Cy² is

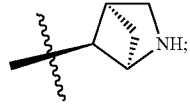

each R¹⁰ is independently selected from $C_{1-3}$ alkyl, and halo;

each R³⁰ is independently selected from $C_{1-3}$ alkyl, halo, D, and $C(O)NR^{c30}R^{d30}$;

wherein said $C_{1-3}$ alkyl is optionally substituted with 1 substituents independently selected from R³¹ each R³¹ is $OR^{a31}$ each R⁶⁰ is independently selected from $C_{1-3}$ alkyl, 4-6 membered heterocycloalkyl, 5-6 membered heteroaryl, halo, $C(O)R^{b60}$, $C(O)NR^{c60}R^{d60}$, $NR^{c60}C(O)R^{b60}$, $C(O)OR^{a6}$, $NR^{c60}C(O)OR^{a6}$, and $NR^{c60}S(O)_2R^{b60}$; wherein said $C_{1-3}$ alkyl, 4-6 membered heterocycloalkyl, and 5-6 membered heteroaryl are each optionally substituted with 1 or 2 substituents independently selected from R⁶¹;

each R⁶¹ is independently selected from $C_{1-3}$ alkyl and halo;

each $R^{c30}$ and $R^{d30}$ is independently selected from H and $C_{1-3}$ alkyl;

each $R^{a31}$ is independently selected from H and $C_{1-3}$ alkyl; and each $R^{a60}$, $R^{b60}$, $R^{c60}$ and $R^{d60}$ is independently selected from H, $C_{1-3}$ alkyl, $C_{1-3}$ haloalkyl, $C_{3-6}$ cycloalkyl, 4-6 membered heterocycloalkyl, and 5-6 membered heteroaryl;

wherein said $C_{1-3}$ alkyl, $C_{3-6}$ cycloalkyl, 4-6 membered heterocycloalkyl, and 5-6 membered heteroaryl are each optionally substituted with 1 or 2 substituents independently selected from R⁶¹;

or any $R^{c60}$ and $R^{d60}$ attached to the same N atom, together with the N atom to which they are attached, form a 4-, 5-, or 6-membered heterocycloalkyl group optionally substituted with 1 or 2 substituents independently selected from R⁶¹.

In still another embodiment of Formula I, or a pharmaceutically acceptable salt thereof, Y is CR⁶;

R¹ is H;

R² is —CH₂CH₂CN;

Cy¹ is phenyl; wherein the phenyl is optionally substituted with 1 or 2 substituents independently selected from R¹⁰;

R³ is selected from H, methyl, phenyl, 1,2,4-triazolyl, pyrazyl, and pyridyl; wherein said methyl, phenyl, 1,2,4-triazolyl, pyrazyl, and pyridyl are each optionally substituted with 1, 2 or 3 substituents independently selected from R³⁰;

R⁵ is selected from H and chloro;

R⁶ is selected from pyrrolidinyl, 2-azabicyclo[3.1.0]hexanyl, and 5-oxo-1,2,3,5-tetrahydroindolizin-3-yl; wherein said pyrrolidinyl, 2-azabicyclo[3.1.0]hexanyl, and 5-oxo-1,2,3,5-tetrahydroindolizin-3-yl are optionally substituted with 1 or 2 substituents independently selected from R⁶⁰; or R⁶ is selected from $C_{1-2}$ alkyl; wherein said $C_{1-2}$ alkyl is substituted with 1 or 2 substituents independently selected from R⁶⁰;

R⁷ is fluoro;

Cy² is

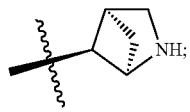

each R¹⁰ is independently selected from methyl, fluoro, and chloro;

each R³⁰ is independently selected from methyl, fluoro, D, and $C(O)NR^{c30}R^{d30}$;

wherein said methyl is optionally substituted with 1 substituents independently selected from R³¹;

each R³¹ is $OR^{a31}$ each R⁶⁰ is independently selected from methyl, fluoro, 3-oxomorpholinyl, 2-oxopyrazin-1(2H)-yl), $C(O)R^{b60}$, $C(O)NR^{c60}R^{d60}$, $NR^{c60}C(O)R^{b60}$, $C(O)OR^{a60}$, $NR^{c60}C(O)OR^{a60}$, and $NR^{c60}S(O)_2R^{b60}$; wherein said 3-oxomorpholinyl and 2-oxopyrazin-1(2H)-yl) are each optionally substituted with 1 or 2 substituents independently selected from R⁶¹;

each R⁶¹ is independently selected from methyl and fluoro;

each $R^{c30}$ and $R^{d30}$ is independently selected from H and methyl;

each $R^{a31}$ is independently selected from H and methyl; and each $R^{a60}$, $R^{b60}$, $R^{c60}$ and $R^{d60}$ is independently selected from H, $C_{1-2}$ alkyl, $C_1$ haloalkyl, cyclopropyl, tetrahydrofuranyl, and thiazolyl; wherein said $C_{1-2}$ alkyl, cyclopropyl, tetrahydrofuranyl, and thiazolyl are each optionally substituted with 1 or 2 substituents independently selected from R⁶¹;

or any $R^{c60}$ and $R^{d60}$ attached to the same N atom, together with the N atom to which they are attached, form an azetidinyl group optionally substituted with 1 or 2 substituents independently selected from R⁶¹.

In another embodiment of Formula I, or a pharmaceutically acceptable salt thereof, Y is N or CR⁶;

R¹ is H;

R² is —CH₂CH₂CN;

Cy¹ is $C_{6-10}$ aryl or 6-10 membered heteroaryl; wherein $C_{6-10}$ aryl and 6-10 membered heteroaryl are optionally substituted with 1 or 2 substituents independently selected from R¹⁰;

R³ is selected from H, $C_{1-3}$ alkyl, phenyl, 5-6 membered heteroaryl, and $OR^{f3}$; wherein said $C_{1-3}$ alkyl, phenyl, and 5-6 membered heteroaryl are each optionally substituted with 1, 2 or 3 substituents independently selected from R³⁰;

R⁵ is selected from H and halo;

R⁶ is selected from H, pyridinyl, pyrrolidinyl, 2-azabicyclo[3.1.0]hexanyl, and 5-oxo-1,2,3,5-tetrahydroindolizin-3-yl; wherein said pyrrolidinyl, 2-azabicyclo [3.1.0]hexanyl, and 5-oxo-1,2,3,5-tetrahydroindolizin-3-yl are optionally substituted with 1 or 2 substituents independently selected from $R^{60}$; or $R^6$ is selected from $C_{1-2}$ alkyl; wherein said $C_{1-2}$ alkyl is substituted with 1 or 2 substituents independently selected from $R^{60}$;

$R^7$ is halo;

$Cy^2$ is

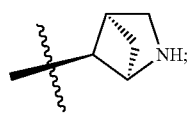

Cy²-b each $R^{10}$ is independently selected from methyl and halo;

each $R^{30}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, CN, $OR^{a30}$, $C(O)R^{b30}$, $C(O)NR^{c30}R^{d30}$, $C(O)OR^{a30}$, $NR^{c30}R^{d30}$, and $S(O)_2R^{b30}$; wherein said $C_{1-3}$ alkyl, $C_{3-6}$ cycloalkyl, 4-6 membered heterocycloalkyl, phenyl, and 5-6 membered heteroaryl are each optionally substituted with 1 or 2 substituents independently selected from $R^{31}$ each $R^{31}$ is $OR^{a31}$ each $R^{60}$ is independently selected from methyl, halo, 3-oxomorpholinyl, 2-oxopyrazin-1(2H)-yl), $C(O)R^{b60}$, $C(O)NR^{c60}R^{d60}$, $NR^{c60}C(O)R^{b60}$, $C(O)OR^{a60}$, $NR^{c60}C(O)OR^{a60}$, and $NR^{c60}S(O)_2R^{b60}$; wherein said 3-oxomorpholinyl, and 2-oxopyrazin-1(2H)-yl are each optionally substituted with 1 or 2 substituents independently selected from $R^{61}$;

each $R^{61}$ is independently selected from methyl and halo;

$R^{f3}$ is $R^{f3}$-a;

each $R^{c30}$ and $R^{d30}$ is independently selected from H and methyl;

each $R^{a31}$ is independently selected from H and methyl; and each $R^{a60}$, $R^{b60}$, $R^{c60}$ and $R^{d60}$ is independently selected from H, $C_{1-2}$ alkyl, $C_1$ haloalkyl, cyclopropyl, tetrahydrofuranyl, and thiazolyl; wherein said $C_{1-2}$ alkyl, cyclopropyl, tetrahydrofuranyl, and thiazolyl are each optionally substituted with 1 or 2 substituents independently selected from $R^{61}$;

or any $R^{c60}$ and $R^{d60}$ attached to the same N atom, together with the N atom to which they are attached, form an azetidinyl group optionally substituted with 1 or 2 substituents independently selected from $R^{61}$.

In another aspect, provided herein is a compound of Formula I:

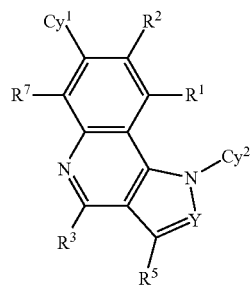

I or a pharmaceutically acceptable salt thereof, wherein:

Y is N or $CR^6$;

$R^1$ is selected from H, $C_{1-3}$ alkyl, $C_{1-3}$ haloalkyl, cyclopropyl, halo, D, CN, and $OR^{a1}$;

wherein said $C_{1-3}$ alkyl and cyclopropyl are each optionally substituted with 1 or 2 substituents independently selected from $R^g$;

$R^2$ is selected from H, $C_{1-3}$ alkyl, $C_{1-3}$ haloalkyl, 4-6 membered heterocycloalkyl, phenyl, 5-6 membered heteroaryl, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, and $OR^{a2}$; wherein said $C_{1-3}$ alkyl, 4-6 membered heterocycloalkyl, phenyl, 5-6 membered heteroaryl, 4-6 membered heterocycloalkyl-$C_{1-3}$ alkylene, phenyl-$C_{1-3}$ alkylene, 5-6 membered heteroaryl-$C_{1-3}$ alkylene are each optionally substituted with 1 or 2 substituents independently selected from $R^9$;

$Cy^1$ is selected from $C_{3-10}$ cycloalkyl, 4-10 membered heterocycloalkyl, $C_{6-10}$ aryl and 6-10 membered heteroaryl; wherein the 4-10 membered heterocycloalkyl and 6-10 membered heteroaryl each has at least one ring-forming carbon atom and 1, 2, 3, or 4 ring-forming heteroatoms independently selected from N, O, and S; wherein a ring-forming carbon atom of 6-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 6-10 membered heteroaryl are each optionally substituted with 1, 2, 3, or 4 substituents independently selected from $R^{10}$;

$R^3$ is selected from H, $C_{1-3}$ alkyl, $C_{1-3}$ haloalkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, $OR^3$, $C(O)NR^{c3}R^{d3}$, $NR^{c3}R^{f3}$, and $NR^{c3}C(O)R^{b3}$; wherein said $C_{1-3}$ alkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, or 3 substituents independently selected from $R^{30}$ $R^5$ is selected from H, $C_{1-3}$ alkyl, $C_{1-3}$ haloalkyl, cyclopropyl, halo, D, CN, and $OR^{a5}$; wherein said $C_{1-3}$ alkyl and cyclopropyl are each optionally substituted with 1 or 2 substituents independently selected from $R^9$;

$R^6$ is selected from H, $C_{1-3}$ alkyl, $C_{1-3}$ haloalkyl, $C_{3-6}$ cycloalkyl, 4-8 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, $OR^{a6}$, and $C(O)NR^{c6}R^{d6}$; wherein said $C_{1-3}$ alkyl, $C_{3-6}$cycloalkyl, 4-8 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, and 5-6 membered heteroaryl-$C_{1-3}$ alkylene are each optionally substituted with 1 or 2 substituents independently selected from $R^{60}$;

$R^7$ is selected from H, $C_{1-3}$ alkyl, $C_{1-3}$ haloalkyl, cyclopropyl, halo, D, CN, and $OR^{a7}$;

wherein said $C_{1-3}$ alkyl and cyclopropyl are each optionally substituted with 1 or 2 substituents independently selected from $R^g$;

Cy² is selected from

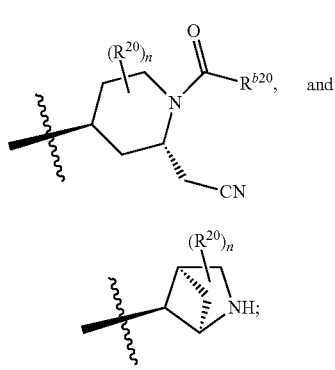

wherein n is 0, 1, or 2;
each $R^{10}$ is independently selected from $C_{1-3}$ alkyl, $C_{1-3}$ haloalkyl, halo, D, CN, $OR^{a10}$, $C(O)R^{b10}$, $C(O)NR^{c10}R^{d10}$, $(O)OR^{a10}$, $NR^{c10}R^{d10}$, and $S(O)_2R^{b10}$;
each $R^{20}$ is independently selected from $C_{1-3}$ alkyl, $C_{1-3}$ haloalkyl, halo, D, CN, and $OR^{a20}$;
each $R^{30}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a30}$, $C(O)R^{b30}$, $C(O)NR^{c30}R^{d30}$, $C(O)OR^{a30}$, $NR^{c30}R^{d30}$, and $S(O)_2R^{b30}$; wherein said $C_{1-3}$ alkyl, $C_{3-6}$ cycloalkyl, 4-6 membered heterocycloalkyl, phenyl, and 5-6 membered heteroaryl are each optionally substituted with 1 or 2 substituents independently selected from $R^{31}$
each $R^{31}$ is independently selected from $C_{1-3}$ alkyl, $C_{1-3}$ haloalkyl, halo, D, CN, $OR^{a31}C(O)R^{b31}$, $C(O)NR^{c31}R^{d31}$, $C(O)OR^{a31}$, $NR^{c31}R^{d31}$, and $S(O)_2R^{b31}$;
each $R^{33}$ is independently selected from $C_{1-3}$ alkyl, $C_{1-3}$ haloalkyl, $C_{3-6}$ cycloalkyl, 4-membered heterocycloalkyl, 6-membered heterocycloalkyl, phenyl, 5-6 membered heteroaryl, halo, D, CN, $OR^{a30}$, $C(O)NR^{c30}R^{d30}$, and $NR^{c30}R^{d30}$; wherein said $C_{1-3}$ alkyl, $C_{3-6}$ cycloalkyl, 4-membered heterocycloalkyl, 6-membered heterocycloalkyl, phenyl, and 5-6 membered heteroaryl are each optionally substituted with 1 or 2 substituents independently selected from $R^{31}$
each $R^{60}$ is independently selected from $C_{1-3}$ alkyl, $C_{1-3}$ haloalkyl, 4-6 membered heterocycloalkyl, 5-6 membered heteroaryl, halo, D, CN, $OR^{a60}$, $C(O)R^{b60}$, $C(O)NR^{c60}R^{d60}$, $C(O)OR^{a60}$, $NR^{c60}R^{d60}$, and $S(O)_2R^{b60}$; wherein said $C_{1-3}$ alkyl, 4-6 membered heterocycloalkyl, and 5-6 membered heteroaryl are each optionally substituted with 1 or 2 substituents independently selected from $R^{61}$;
each $R^{61}$ is independently selected from $C_{1-3}$ alkyl, $C_{1-3}$ haloalkyl, halo, D, CN, $OR^{a61}$, and $NR^{c61}R^{d61}$;
$R^{a1}$ is selected from H, $C_{1-3}$ alkyl, and $C_{1-3}$ haloalkyl;
each $R^{a2}$ is independently selected from H, $C_{1-3}$ alkyl, and $C_{1-3}$ haloalkyl;
each $R^{b3}$, $R^{c3}$ and $R^{d3}$ is independently selected from H, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said, $C_{1-3}$ alkyl, $C_{3-6}$ cycloalkyl, 4-6 membered heterocycloalkyl, phenyl, and 5-6 membered heteroaryl are each optionally substituted with 1, 2, or 3 substituents independently selected from $R^{30}$;
or $R^{c3}$ and $R^{d3}$ attached to the same N atom, together with the N atom to which they are attached, form a 4-, 5-, or 6-membered heterocycloalkyl group optionally substituted with 1, 2, or 3 substituents independently selected from $R^{30}$
$R^{f3}$ is selected from $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl, and 5-6 membered heteroaryl are each optionally substituted with 1, 2, or 3 substituents independently selected from $R^{30}$;
or $R^{c3}$ and $R^{f3}$ attached to the same N atom, together with the N atom to which they are attached, form a 4-, 5-, or 6-membered heterocycloalkyl group optionally substituted with 1, 2, or 3 substituents independently selected from $R^{30}$
$R^{f3}$ is selected from $C_{1-3}$ haloalkyl, $C_{3-6}$ cycloalkyl, 4-6 membered heterocycloalkyl, phenyl and 5-6 membered heteroaryl; wherein said, $C_{1-3}$ alkyl, $C_{3-6}$ cycloalkyl, 4-6 membered heterocycloalkyl, phenyl, and 5-6 membered heteroaryl are each optionally substituted with 1, 2, or 3 substituents independently selected from $R^{30}$; or $R^{f3}$ is selected from

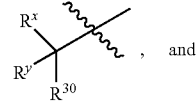

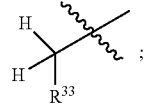

wherein $R^x$ is H or $C_{1-2}$ alkyl and $R^y$ is $C_{1-2}$ alkyl;
or $R^x$ and $R^y$, together with the C atom to which they are attached, form a 3-, or 4-membered cycloalkyl group;
$R^{a5}$ is selected from H, $C_{1-3}$ alkyl, and $C_{1-3}$ haloalkyl;
each $R^{a6}$, $R^{c6}$ and $R^{d6}$ is independently selected from H, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl, and 5-6 membered heteroaryl are each optionally substituted with 1 or 2 substituents independently selected from $R^{60}$;
$R^{a7}$ is selected from H, $C_{1-3}$ alkyl, and $C_{1-3}$ haloalkyl;
each $R^{a10}$, $R^{b10}$, $R^{c10}$ and $R^{d10}$ is independently selected from H, $C_{1-3}$ alkyl, and $C_{1-3}$ haloalkyl;
each $R^{a20}$ is independently selected from H, $C_{1-3}$ alkyl, and $C_{1-3}$ haloalkyl;
$R^{b20}$ is selected from $NH_2$, $C_{1-3}$ alkyl, and $C_{1-3}$ haloalkyl;
each $R^{a30}$, $R^{b30}$, $R^{c30}$ and $R^{d30}$ is independently selected from H, $C_{1-3}$ alkyl, and $C_{1-3}$ haloalkyl;
each $R^{a31}$, $R^{b31}$, $R^{c31}$ and $R^{d31}$ is independently selected from H, $C_{1-3}$ alkyl, and $C_{1-3}$ haloalkyl;
each $R^{a60}$, $R^{b60}$, $R^{c60}$ and $R^{d60}$ is independently selected from H, $C_{1-3}$ alkyl, $C_{1-3}$ haloalkyl, $C_{3-6}$ cycloalkyl, 4-6 membered heterocycloalkyl, and 5-6 membered heteroaryl;
wherein said $C_{1-3}$ alkyl, $C_{3-6}$ cycloalkyl, 4-6 membered heterocycloalkyl, and 5-6 membered heteroaryl are each optionally substituted with 1 or 2 substituents independently selected from $R^{61}$;

or any $R^{c60}$ and $R^{d60}$ attached to the same N atom, together with the N atom to which they are attached, form a 4-, 5-, or 6-membered heterocycloalkyl group optionally substituted with 1 or 2 substituents independently selected from $R^{61}$; and each $R^{a61}$, $R^{c61}$, and $R^{d61}$, is independently selected from H, $C_{1-3}$ alkyl, and $C_{1-3}$ haloalkyl; and each $R^9$ is independently selected from D, OH, CN, halo, $C_{1-3}$ alkyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino;

provided that the compound of Formula I is other than, 3-(1-((1R,4R,5S)-2-azabicyclo[2.1.1]hexan-5-yl)-8-(2-cyanoethyl)-4-ethoxy-6-fluoro-7-(3-hydroxynaphthalen-1-yl)-1H-pyrrolo[3,2-c]quinolin-2-yl)-N,N-dimethylpropanamide.

In an embodiment of Formula I, or a pharmaceutically acceptable salt thereof,

Y is $CR^6$;

$R^1$ is selected from H, $C_{1-3}$ alkyl, $C_{1-3}$ haloalkyl, cyclopropyl, halo, D, CN, and $OR^{a1}$;

wherein said $C_{1-3}$ alkyl and cyclopropyl are each optionally substituted with 1 or 2 substituents independently selected from $R^9$;

$R^2$ is selected from H, $C_{1-3}$ alkyl, $C_{1-3}$ haloalkyl, 4-6 membered heterocycloalkyl, phenyl, 5-6 membered heteroaryl, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, and $OR^{a2}$; wherein said $C_{1-3}$ alkyl, 4-6 membered heterocycloalkyl, phenyl, 5-6 membered heteroaryl, 4-6 membered heterocycloalkyl-$C_{1-3}$ alkylene, phenyl-$C_{1-3}$ alkylene, 5-6 membered heteroaryl-$C_{1-3}$ alkylene are each optionally substituted with 1 or 2 substituents independently selected from $R^g$;

$Cy^1$ is selected from $C_{3-10}$ cycloalkyl, 4-10 membered heterocycloalkyl, $C_{6-10}$ aryl, and 6-10 membered heteroaryl; wherein the 4-10 membered heterocycloalkyl and 6-10 membered heteroaryl each has at least one ring-forming carbon atom and 1, 2, 3, or 4 ring-forming heteroatoms independently selected from N, O, and S; wherein a ring-forming carbon atom of 6-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl, and 6-10 membered heteroaryl are each optionally substituted with 1, 2, 3, or 4 substituents independently selected from $R^{10}$;

$R^3$ is selected from H, $C_{1-3}$ alkyl, $C_{1-3}$ haloalkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, C(O)$NR^{c3}R^{d3}$, and $NR^{c3}C(O)R^{b3}$; wherein said $C_{1-3}$ alkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, or 3 substituents independently selected from $R^{30}$;

$R^5$ is selected from H, $C_{1-3}$ alkyl, $C_{1-3}$ haloalkyl, cyclopropyl, halo, D, CN, and $OR^{a6}$;

wherein said $C_{1-3}$ alkyl and cyclopropyl are each optionally substituted with 1 or 2 substituents independently selected from $R^9$;

$R^6$ is selected from H, $C_{1-3}$ haloalkyl, $C_{3-6}$ cycloalkyl, 4-8 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, $OR^{a6}$, and C(O)$NR^{c6}R^{d6}$; wherein said $C_{3-6}$ cycloalkyl, 4-8 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, and 5-6 membered heteroaryl-$C_{1-3}$ alkylene are each optionally substituted with 1 or 2 substituents independently selected from $R^{60}$; or $R^6$ is selected from $C_{1-3}$ alkyl; wherein said $C_{1-3}$ alkyl is substituted with 1 or 2 substituents independently selected from $R^{60}$;

$R^7$ is selected from H, $C_{1-3}$ alkyl, $C_{1-3}$ haloalkyl, cyclopropyl, halo, D, CN, and $OR^{a7}$;

wherein said $C_{1-3}$ alkyl and cyclopropyl are each optionally substituted with 1 or 2 substituents independently selected from $R^9$;

$Cy^2$ is selected from

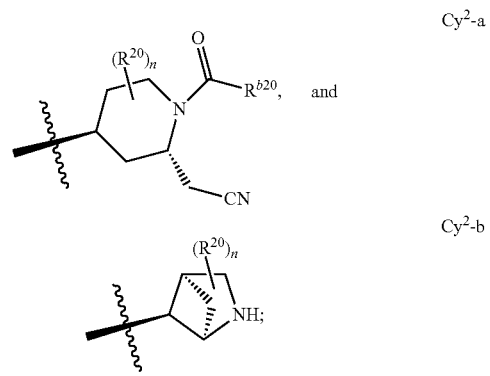

wherein n is 0, 1, or 2;

each $R^{10}$ is independently selected from $C_{1-3}$ alkyl, $C_{1-3}$ haloalkyl, halo, D, CN, $OR^{a10}$, C(O)$R^{b10}$, C(O)$NR^{c10}R^{d10}$, C(O)$OR^{a10}$, $NR^{c10}R^{d10}$, and S(O)$_2R^{b10}$;

each $R^{20}$ is independently selected from $C_{1-3}$ alkyl, $C_{1-3}$ haloalkyl, halo, D, CN, and $OR^{a20}$;

each $R^{30}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a30}$, C(O)$R^{b30}$, C(O)$NR^{c30}R^{d30}$, C(O)$OR^{a30}$, $NR^{c30}R^{d30}$, and S(O)$_2R^{b30}$; wherein said $C_{1-3}$ alkyl, $C_{3-6}$ cycloalkyl, 4-6 membered heterocycloalkyl, phenyl, and 5-6 membered heteroaryl are each optionally substituted with 1 or 2 substituents independently selected from $R^{31}$ each $R^{31}$ is independently selected from $C_{1-3}$ alkyl, $C_{1-3}$ haloalkyl, halo, D, CN, $OR^{a31}$C(O)$R^{b31}$, C(O)$NR^{c31}R^{d31}$, C(O)$OR^{a31}$, $NR^{c31}R^{d31}$, and S(O)$_2R^{b31}$;

each $R^{60}$ is independently selected from $C_{1-3}$ alkyl, $C_{1-3}$ haloalkyl, 4-6 membered heterocycloalkyl, 5-6 membered heteroaryl, halo, D, CN, $OR^{a60}$, C(O)$R^{b60}$, C(O)$NR^{c60}R^{d60}$, C(O)$OR^{a60}$, $NR^{c60}R^{d60}$, and S(O)$_2R^{b60}$; wherein said $C_{1-3}$ alkyl, 4-6 membered heterocycloalkyl, and 5-6 membered heteroaryl are each optionally substituted with 1 or 2 substituents independently selected from $R^{61}$;

each $R^{61}$ is independently selected from $C_{1-3}$ alkyl, $C_{1-3}$ haloalkyl, halo, D, CN, $OR^{a61}$, and $NR^{c61}R^{d61}$;

$R^{a1}$ is selected from H, $C_{1-3}$ alkyl, and $C_{1-3}$ haloalkyl;

each $R^{a2}$ is independently selected from H, $C_{1-3}$ alkyl, and $C_{1-3}$ haloalkyl;

each $R^{b3}$, $R^{c3}$ and $R^{d3}$ is independently selected from H, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said, $C_{1-3}$ alkyl, $C_{3-6}$ cycloalkyl, 4-6 membered heterocycloalkyl, phenyl, and 5-6 membered heteroaryl are each optionally substituted with 1, 2, or 3 substituents independently selected from $R^{30}$;

or $R^{c3}$ and $R^{d3}$ attached to the same N atom, together with the N atom to which they are attached, form a 4-, 5-, or 6-membered heterocycloalkyl group optionally substituted with 1, 2, or 3 substituents independently selected from $R^{30}$ $R^{a5}$ is selected from H, $C_{1-3}$ alkyl, and $C_{1-3}$ haloalkyl;

each $R^{a6}$, $R^{c6}$ and $R^{d6}$ is independently selected from H, $C_{1-3}$ alkyl, $C_{1-3}$ haloalkyl, $C_{3-6}$ cycloalkyl, 4-6 membered heterocycloalkyl, phenyl, and 5-6 membered heteroaryl; wherein said $C_{1-3}$ alkyl, $C_{3-6}$ cycloalkyl, 4-6 membered heterocycloalkyl, phenyl, and 5-6 membered heteroaryl are each optionally substituted with 1 or 2 substituents independently selected from $R^{60}$;

$R^{a7}$ is selected from H, $C_{1-3}$ alkyl, and $C_{1-3}$ haloalkyl;

each $R^{a10}$, $R^{b10}$, $R^{c10}$ and $R^{d10}$ is independently selected from H, $C_{1-3}$ alkyl, and $C_{1-3}$ haloalkyl;

each $R^{a20}$ is independently selected from H, $C_{1-3}$ alkyl, and $C_{1-3}$ haloalkyl; $R^{b20}$ is selected from $NH_2$, $C_{1-3}$ alkyl, and $C_{1-3}$ haloalkyl;

each $R^{a30}$, $R^{b30}$, $R^{c30}$ and $R^{d30}$ is independently selected from H, $C_{1-3}$ alkyl, and $C_{1-3}$ haloalkyl;

each $R^{a31}$, $R^{b31}$, $R^{c31}$ and $R^{d31}$ is independently selected from H, $C_{1-3}$ alkyl, and $C_{1-3}$ haloalkyl;

each $R^{a60}$, $R^{b60}$, $R^{c60}$ and $R^{d60}$ is independently selected from H, $C_{1-3}$ alkyl, $C_{1-3}$ haloalkyl, $C_{3-6}$ cycloalkyl, 4-6 membered heterocycloalkyl, and 5-6 membered heteroaryl;

wherein said $C_{1-3}$ alkyl, $C_{3-6}$ cycloalkyl, 4-6 membered heterocycloalkyl, and 5-6 membered heteroaryl are each optionally substituted with 1 or 2 substituents independently selected from $R^{61}$;

or any $R^{c60}$ and $R^{d60}$ attached to the same N atom, together with the N atom to which they are attached, form a 4-, 5-, or 6-membered heterocycloalkyl group optionally substituted with 1 or 2 substituents independently selected from $R^{61}$; and each $R^{a61}$, $R^{c61}$, and $R^{d61}$, is independently selected from H, $C_{1-3}$ alkyl, and $C_{1-3}$ haloalkyl; and each $R^9$ is independently selected from D, OH, CN, halo, $C_{1-3}$ alkyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino.

In another embodiment of Formula I, or a pharmaceutically acceptable salt thereof, Y is $CR^6$;

$R^1$ is H;

$R^2$ is selected from $C_{1-3}$ alkyl, $C_{1-3}$ haloalkyl, halo, CN, and —$CH_2CH_2CN$;

$Cy^1$ is selected from $C_{3-10}$ cycloalkyl, $C_{6-10}$ aryl, and 6-10 membered heteroaryl;

wherein the 6-10 membered heteroaryl has at least one ring-forming carbon atom and 1, ring-forming heteroatoms independently selected from N and S; and wherein the $C_{3-10}$ cycloalkyl, $C_{6-10}$ aryl, and 6-10 membered heteroaryl are each optionally substituted with 1 or 2 substituents independently selected from $R^{10}$;

$R^3$ is selected from H, $C_{1-3}$ alkyl, $C_{1-3}$ haloalkyl, 4-6 membered heterocycloalkyl, and 5-6 membered heteroaryl; wherein said $C_{1-3}$ alkyl, 4-6 membered heterocycloalkyl, and 5-6 membered heteroaryl are each optionally substituted with 1 or 2 substituents independently selected from $R^{30}$;

$R^5$ is H;

$R^6$ is selected from H, $C_{1-3}$ haloalkyl, 4-8 membered heterocycloalkyl, and 5-6 membered heteroaryl; wherein said 4-8 membered heterocycloalkyl, and 5-6 membered heteroaryl are each optionally substituted with 1 or 2 substituents independently selected from $R^{60}$; or $R^6$ is selected from $C_{1-3}$ alkyl; wherein said $C_{1-3}$ alkyl, is substituted with 1 or 2 substituents independently selected from $R^{60}$;

$R^7$ is halo;

$Cy^2$ is

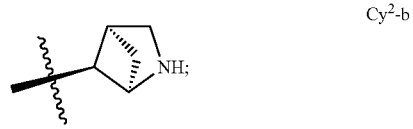

Cy²-b each $R^{10}$ is independently selected from $C_{1-3}$ alkyl, $C_{1-3}$ haloalkyl, halo, CN, and $OR^{a10}$;

each $R^{30}$ is independently selected from $C_{1-3}$ alkyl, $C_{1-3}$ haloalkyl, 4-6 membered heterocycloalkyl, halo, D, CN, $OR^{a30}$, $C(O)NR^{c30}R^{d30}$, and $NR^{c30}R^{d30}$; wherein said $C_{1-3}$ alkyl, and 4-6 membered heterocycloalkyl are each optionally substituted with 1 or 2 substituents independently selected from $R^{31}$;

each $R^{31}$ is independently selected from $C_{1-3}$ alkyl, $C_{1-3}$ haloalkyl, halo, CN, $OR^{a31}$ and $NR^{c31}R^{d31}$ each $R^{60}$ is independently selected from $C_{1-3}$ alkyl, $C_{1-3}$ haloalkyl, 4-6 membered heterocycloalkyl, 5-6 membered heteroaryl, halo, CN, $OR^{a60}$, $C(O)R^{b60}$, $C(O)NR^{c60}R^{d60}$, $C(O)OR^{a60}$, and $NR^{c60}R^{d60}$; wherein said $C_{1-3}$ alkyl, 4-6 membered heterocycloalkyl, and 5-6 membered heteroaryl are each optionally substituted with 1 or 2 substituents independently selected from $R^{61}$;

each $R^{61}$ is independently selected from $C_{1-3}$ alkyl, $C_{1-3}$ haloalkyl, halo, and CN;

each $R^{a10}$ is independently selected from H, and $C_{1-3}$ alkyl;

each $R^{a30}$, $R^{c30}$ and $R^{d30}$ is independently selected from H, and $C_{1-3}$ alkyl;

each $R^{a31}$, $R^{c31}$ and $R^{d31}$ is independently selected from H, and $C_{1-3}$ alkyl; and each $R^{a60}$, $R^{b60}$, $R^{c60}$ and $R^{d60}$ is independently selected from H, $C_{1-3}$ alkyl, $C_{1-3}$ haloalkyl, and $C_{3-6}$ cycloalkyl; wherein said $C_{1-3}$ alkyl, and $C_{3-6}$ cycloalkyl are each optionally substituted with 1 or 2 substituents independently selected from $R^{61}$;

or any $R^{c60}$ and $R^{d60}$ attached to the same N atom, together with the N atom to which they are attached, form a 4-, 5-, or 6-membered heterocycloalkyl group optionally substituted with 1 or 2 substituents independently selected from $R^{61}$.

In yet another embodiment of Formula I, or a pharmaceutically acceptable salt thereof, Y is $CR^6$;

$R^1$ is H;

$R^2$ is —$CH_2CH_2CN$;

Cy$^1$ is phenyl; wherein phenyl is optionally substituted with 1 or 2 substituents independently selected from R$^{10}$;
R$^3$ is selected from 5-6 membered heteroaryl; wherein said 5-6 membered heteroaryl are optionally substituted with 1 or 2 substituents independently selected from R$^{30}$;
R$^5$ is H;
R$^6$ is selected from 4-6 membered heterocycloalkyl, and 5-6 membered heteroaryl;
wherein said 4-6 membered heterocycloalkyl, and 5-6 membered heteroaryl are each optionally substituted with 1 or 2 substituents independently selected from R$^{60}$; or
R$^6$ is selected from C$_{1-3}$ alkyl; wherein said C$_{1-3}$ alkyl, is substituted with 1 or 2 substituents independently selected from R$^{60}$;
R$^7$ is halo;
Cy$^2$ is

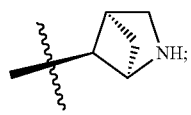

Cy$^2$-b each R$^{10}$ is independently selected from C$_{1-3}$ alkyl, and halo;
each R$^{30}$ is independently selected from C$_{1-3}$ alkyl, halo and C(O)NR$^{c30}$R$^{d30}$; wherein said C$_{1-3}$ alkyl, is optionally substituted with 1 substituent selected from R$^{31}$
each R$^{31}$ is OR$^{a31}$
each R$^{60}$ is independently selected from 4-6 membered heterocycloalkyl, 5-6 membered heteroaryl, C(O)R$^{b60}$, C(O)NR$^{c60}$R$^{d60}$, and C(O)OR$^{a60}$; wherein said 4-6 membered heterocycloalkyl, and 5-6 membered heteroaryl are each optionally substituted with 1 or 2 substituents independently selected from R$^{61}$;
each R$^{61}$ is independently selected from C$_{1-3}$ alkyl, and halo;
each R$^{c30}$ and R$^{d30}$ is independently selected from H, and C$_{1-3}$ alkyl;
each R$^{a31}$ is independently selected from H, and C$_{1-3}$ alkyl; and
each R$^{a60}$, R$^{b60}$, R$^{c60}$ and R$^{d60}$ is independently selected from H, C$_{1-3}$ alkyl, and C$_{3-6}$ cycloalkyl; wherein said C$_{1-3}$ alkyl and C$_{3-6}$ cycloalkyl are each optionally substituted with 1 or 2 substituents independently selected from R$^{61}$;
or any R$^{c60}$ and R$^{d60}$ attached to the same N atom, together with the N atom to which they are attached, form a 4-membered heterocycloalkyl group optionally substituted with 1 or 2 substituents independently selected from R$^{61}$.
In another embodiment of Formula I, or a pharmaceutically acceptable salt thereof,
Y is CR$^6$;
R$^1$ is H;
R$^2$ is —CH$_2$CH$_2$CN;
Cy$^1$ is phenyl; wherein the phenyl is optionally substituted with 1 or 2 substituents independently selected from R$^{10}$;
R$^3$ is selected from C$_{1-3}$ alkyl and 5-6 membered heteroaryl; wherein said 5-6 membered heteroaryl is optionally substituted with 1 or 2 substituents independently selected from R$^{30}$;
R$^5$ is H;
R$^6$ is selected from 4-6 membered heterocycloalkyl and 5-6 membered heteroaryl;
wherein said 4-6 membered heterocycloalkyl and 5-6 membered heteroaryl are each optionally substituted with 1 or 2 substituents independently selected from R$^{60}$; or
R$^6$ is C$_{1-3}$ alkyl; wherein said C$_{1-3}$ alkyl is substituted with 1 or 2 substituents independently selected from R$^{60}$;
R$^7$ is halo;
Cy$^2$ is

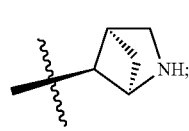

Cy$^2$-b each R$^{10}$ is independently selected from C$_{1-3}$ alkyl and halo;
each R$^{30}$ is independently selected from C$_{1-3}$ alkyl, halo and, C(O)NR$^{c30}$R$^{d30}$; wherein said C$_{1-3}$ alkyl is optionally substituted with 1 substituent selected from R$^{31}$
each R$^{31}$ is OR$^{a31}$
each R$^{60}$ is independently selected from 4-6 membered heterocycloalkyl, 5-6 membered heteroaryl, C(O)R$^{b60}$, C(O)NR$^{c60}$R$^{d60}$, and C(O)OR$^{a60}$; wherein said 4-6 membered heterocycloalkyl and 5-6 membered heteroaryl are each optionally substituted with 1 or 2 substituents independently selected from R$^{61}$;
each R$^{61}$ is independently selected from C$_{1-3}$ alkyl and halo;
each R$^{c30}$ and R$^{d30}$ is independently selected from H and C$_{1-3}$ alkyl;
each R$^{a31}$ is independently selected from H and C$_{1-3}$ alkyl; and
each R$^{a60}$, R$^{b60}$, R$^{c60}$ and R$^{d60}$ is independently selected from H, C$_{1-3}$ alkyl, and C$_{3-6}$ cycloalkyl; wherein said C$_{1-3}$ alkyl and C$_{3-6}$ cycloalkyl are each optionally substituted with 1 or 2 substituents independently selected from R$^{61}$;
or any R$^{c60}$ and R$^{d60}$ attached to the same N atom, together with the N atom to which they are attached, form a 4-membered heterocycloalkyl group optionally substituted with 1 or 2 substituents independently selected from R$^{61}$.
In yet another embodiment of Formula I, or a pharmaceutically acceptable salt thereof,
Y is CR$^6$;
R$^1$ is H;
R$^2$ is —CH$_2$CH$_2$CN;
Cy$^1$ is phenyl or naphthyl; wherein the phenyl and napthyl are each optionally substituted with 1 or 2 substituents independently selected from R$^{10}$;
R$^3$ is selected from H and 5-6 membered heteroaryl; wherein said 5-6 membered heteroaryl is optionally substituted with 1 or 2 substituents independently selected from R$^{30}$;
R$^5$ is H;
R$^6$ is selected from 4-6 membered heterocycloalkyl and 5-6 membered heteroaryl;
wherein said 4-6 membered heterocycloalkyl and 5-6 membered heteroaryl are each optionally substituted with 1 or 2 substituents independently selected from R$^{60}$; or $R^6$ is selected from $C_{1-3}$ alkyl; wherein said $C_{1-3}$ alkyl is substituted with 1 or 2 substituents independently selected from $R^{60}$;
$R^7$ is halo;
$Cy^2$ is

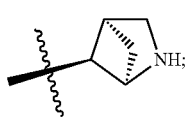

each $R^{10}$ is independently selected from $C_{1-3}$ alkyl and halo;
each $R^{30}$ is independently selected from $C_{1-3}$ alkyl and $C(O)NR^{c30}R^{d30}$; wherein said $C_{1-3}$ alkyl is optionally substituted with 1 substituent selected from $R^{31}$
each $R^{31}$ is $OR^{a31}$
each $R^{60}$ is independently selected from 4-6 membered heterocycloalkyl, 5-6 membered heteroaryl, $C(O)R^{b60}$, $C(O)NR^{c60}R^{d60}$, and $C(O)OR^{a60}$; wherein said 4-6 membered heterocycloalkyl and 5-6 membered heteroaryl are each optionally substituted with 1 or 2 substituents independently selected from $R^{61}$;
each $R^{61}$ is independently selected from $C_{1-3}$ alkyl, and halo;
each $R^{c30}$ and $R^{d30}$ is independently selected from H and $C_{1-3}$ alkyl;
each $R^{a31}$ is independently selected from H and $C_{1-3}$ alkyl; and
each $R^{a60}$, $R^{b60}$, $R^{c60}$ and $R^{d60}$ is independently selected from H, $C_{1-3}$ alkyl, and $C_{3-6}$ cycloalkyl; wherein said $C_{1-3}$ alkyl and $C_{3-6}$ cycloalkyl are each optionally substituted with 1 or 2 substituents independently selected from $R^{61}$;
or any $R^{c60}$ and $R^{d60}$ attached to the same N atom, together with the N atom to which they are attached, form a 4-membered heterocycloalkyl group optionally substituted with 1 or 2 substituents independently selected from $R^{61}$.

In an aspect, provided herein is a compound having Formula I:

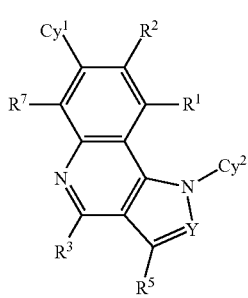

or a pharmaceutically acceptable salt thereof, wherein:
Y is N or $CR^6$;
$R^1$ is selected from H, $C_{1-3}$ alkyl, $C_{1-3}$ haloalkyl, cyclopropyl, halo, D, CN, and $OR^{a1}$;
wherein said $C_{1-3}$ alkyl and cyclopropyl are each optionally substituted with 1 or 2 substituents independently selected from $R^g$;

$R^2$ is selected from H, $C_{1-3}$ alkyl, $C_{1-3}$ haloalkyl, 4-6 membered heterocycloalkyl, phenyl, 5-6 membered heteroaryl, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, and $OR^{a2}$; wherein said $C_{1-3}$ alkyl, 4-6 membered heterocycloalkyl, phenyl, 5-6 membered heteroaryl, 4-6 membered heterocycloalkyl-$C_{1-3}$ alkylene, phenyl-$C_{1-3}$ alkylene, 5-6 membered heteroaryl-$C_{1-3}$ alkylene are each optionally substituted with 1 or 2 substituents independently selected from $R^9$;

$Cy^1$ is selected from $C_{3-10}$ cycloalkyl, 4-10 membered heterocycloalkyl, $C_{6-10}$ aryl, and 6-10 membered heteroaryl; wherein the 4-10 membered heterocycloalkyl and 6-10 membered heteroaryl each has at least one ring-forming carbon atom and 1, 2, 3, or 4 ring-forming heteroatoms independently selected from N, O, and S; wherein a ring-forming carbon atom of 6-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl, and 6-10 membered heteroaryl are each optionally substituted with 1, 2, 3, or 4 substituents independently selected from $R^{10}$;

$R^3$ is selected from H, $C_{1-3}$ alkyl, $C_{1-3}$ haloalkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, $OR^3$, $C(O)NR^{c3}R^{d3}$, $NR^{c3}R^{j3}$, and $NR^{c3}C(O)R^{b3}$; wherein said $C_{1-3}$ alkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, or 3 substituents independently selected from $R^{30}$;

$R^5$ is selected from H, $C_{1-3}$ alkyl, $C_{1-3}$ haloalkyl, cyclopropyl, halo, D, CN, and $OR^{a5}$;
wherein said $C_{1-3}$ alkyl and cyclopropyl are each optionally substituted with 1 or 2 substituents independently selected from $R^g$;

$R^6$ is selected from H, $C_{1-3}$ alkyl, $C_{1-3}$ haloalkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, $OR^{a6}$, and $C(O)NR^{c6}R^{d6}$; wherein said $C_{1-3}$ alkyl, $C_{3-6}$cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, and 5-6 membered heteroaryl-$C_{1-3}$ alkylene are each optionally substituted with 1 or 2 substituents independently selected from $R^{60}$;

$R^7$ is selected from H, $C_{1-3}$ alkyl, $C_{1-3}$ haloalkyl, cyclopropyl, halo, D, CN, and $OR^{a7}$;
wherein said $C_{1-3}$ alkyl and cyclopropyl are each optionally substituted with 1 or 2 substituents independently selected from $R^g$;

Cy² is selected from

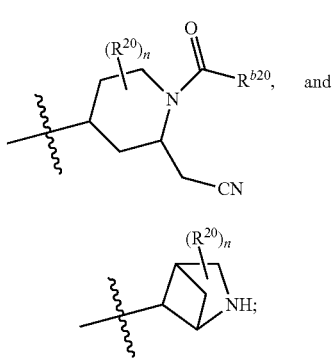

wherein n is 0, 1, or 2;
each $R^{10}$ is independently selected from $C_{1-3}$ alkyl, $C_{1-3}$ haloalkyl, halo, D, CN, $OR^{a10}$, $C(O)R^{b10}$, $C(O)NR^{c10}R^{d10}$ $(O)OR^{a10}$, $NR^{c10}R^{d10}$, and $S(O)_2R^{b10}$;
each $R^{20}$ is independently selected from $C_{1-3}$ alkyl, $C_{1-3}$ haloalkyl, halo, D, CN, and $OR^{a20}$;
each $R^{30}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a30}$, $C(O)R^{b30}$, $C(O)NR^{c30}R^{d30}$, $C(O)OR^{a30}$, $NR^{c30}R^{d30}$, and $S(O)_2R^{b30}$; wherein said $C_{1-3}$ alkyl, $C_{3-6}$ cycloalkyl, 4-6 membered heterocycloalkyl, phenyl, and 5-6 membered heteroaryl are each optionally substituted with 1 or 2 substituents independently selected from $R^{31}$;
each $R^{31}$ is independently selected from $C_{1-3}$ alkyl, $C_{1-3}$ haloalkyl, halo, D, CN, $OR^{a31}$, $C(O)R^{b31}$, $C(O)NR^{c31}R^{d31}$, $C(O)OR^{a31}$, $NR^{c31}R^{d31}$, and $S(O)_2R^{b31}$;
each $R^{33}$ is independently selected from $C_{1-3}$ alkyl, $C_{1-3}$ haloalkyl, $C_{3-6}$ cycloalkyl, 4-membered heterocycloalkyl, 6-membered heterocycloalkyl, phenyl, 5-6 membered heteroaryl, halo, D, CN, $OR^{a30}$, $C(O)NR^{c30}R^{d30}$, and $NR^{c30}R^{d30}$; wherein said 1-3 alkyl, $C_{3-6}$ cycloalkyl, 4-membered heterocycloalkyl, 6-membered heterocycloalkyl, phenyl, and 5-6 membered heteroaryl are each optionally substituted with 1 or 2 substituents independently selected from $R^{31}$
each $R^{60}$ is independently selected from $C_{1-3}$ alkyl, $C_{1-3}$ haloalkyl, 4-6 membered heterocycloalkyl, 5-6 membered heteroaryl, halo, D, CN, $OR^{a60}$, $C(O)R^{b60}$, $C(O)NR^{c60}R^{d60}$, $C(O)OR^{a60}$, $NR^{c60}R^{d60}$, and $S(O)_2R^{b60}$; wherein said $C_{1-3}$ alkyl, 4-6 membered heterocycloalkyl, and 5-6 membered heteroaryl are each optionally substituted with 1 or 2 substituents independently selected from $R^{61}$;
each $R^{61}$ is independently selected from $C_{1-3}$ alkyl, $C_{1-3}$ haloalkyl, halo, D, CN, $OR^{a61}$, and $NR^{c61}R^{d61}$;
$R^{a1}$ is selected from H, $C_{1-3}$ alkyl, and $C_{1-3}$ haloalkyl;
each $R^{a2}$ is independently selected from H, $C_{1-3}$ alkyl, and $C_{1-3}$ haloalkyl;
each $R^{b3}$, $R^{c3}$ and $R^{d3}$ is independently selected from H, $C_{1-3}$ alkyl, $C_{1-3}$ haloalkyl, $C_{3-6}$ cycloalkyl, 4-6 membered heterocycloalkyl, phenyl, and 5-6 membered heteroaryl; wherein said $C_{1-3}$ alkyl, $C_{3-6}$ cycloalkyl, 4-6 membered heterocycloalkyl, phenyl, and 5-6 membered heteroaryl are each optionally substituted with 1, 2, or 3 substituents independently selected from $R^{30}$;
or $R^{c3}$ and $R^{d3}$ attached to the same N atom, together with the N atom to which they are attached, form a 4-, 5-, or 6-membered heterocycloalkyl group optionally substituted with 1, 2, or 3 substituents independently selected from $R^{30}$
$R^{f3}$ is selected from $C_{1-3}$ alkyl, $C_{1-3}$ haloalkyl, $C_{3-6}$ cycloalkyl, 4-6 membered heterocycloalkyl, phenyl, and 5-6 membered heteroaryl; wherein said $C_{1-3}$ alkyl, $C_{3-6}$ cycloalkyl, 4-6 membered heterocycloalkyl, phenyl, and 5-6 membered heteroaryl are each optionally substituted with 1, 2, or 3 substituents independently selected from $R^{30}$;
or $R^{c3}$ and $R^{f3}$ attached to the same N atom, together with the N atom to which they are attached, form a 4-, 5-, or 6-membered heterocycloalkyl group optionally substituted with 1, 2, or 3 substituents independently selected from $R^{30}$
$R^{f3}$ is selected from $C_{1-3}$ haloalkyl, $C_{3-6}$ cycloalkyl, 4-6 membered heterocycloalkyl, phenyl, and 5-6 membered heteroaryl; wherein said $C_{1-3}$ haloalkyl, $C_{3-6}$ cycloalkyl, 4-6 membered heterocycloalkyl, phenyl, and 5-6 membered heteroaryl are each optionally substituted with 1, 2, or 3 substituents independently selected from $R^{30}$; or
$R^{f3}$ is selected from

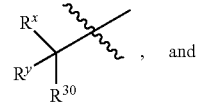

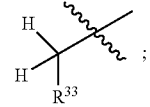

wherein $R^x$ is H or $C_{1-2}$ alkyl and $R^y$ is $C_{1-2}$ alkyl;
or $R^x$ and $R^y$, together with the C atom to which they are attached, form a 3-, or 4-membered cycloalkyl group;
$R^{a5}$ is selected from H, $C_{1-3}$ alkyl, and $C_{1-3}$ haloalkyl;
each $R^{a6}$, $R^{c6}$ and $R^{d6}$ is independently selected from H, $C_{1-3}$ alkyl, $C_{1-3}$ haloalkyl, $C_{3-6}$ cycloalkyl, 4-6 membered heterocycloalkyl, phenyl, and 5-6 membered heteroaryl; wherein said $C_{1-3}$ alkyl, $C_{3-6}$ cycloalkyl, 4-6 membered heterocycloalkyl, phenyl, and 5-6 membered heteroaryl are each optionally substituted with 1 or 2 substituents independently selected from $R^{60}$;
$R^{a7}$ is selected from H, $C_{1-3}$ alkyl, and $C_{1-3}$ haloalkyl;
each $R^{a10}$, $R^{b10}$, $R^{c10}$ and $R^{d10}$ is independently selected from H, $C_{1-3}$ alkyl, and $C_{1-3}$ haloalkyl;
each $R^{a20}$ is independently selected from H, $C_{1-3}$ alkyl, and $C_{1-3}$ haloalkyl;
$R^{b20}$ is selected from $NH_2$, $C_{1-3}$ alkyl, and $C_{1-3}$ haloalkyl;
each $R^{a30}$, $R^{b30}$, $R^{c30}$ and $R^{d30}$ is independently selected from H, $C_{1-3}$ alkyl, and $C_{1-3}$ haloalkyl;
each $R^{a31}$, $R^{b31}$, $R^{c31}$ and $R^{d31}$ is independently selected from H, $C_{1-3}$ alkyl, and $C_{1-3}$ haloalkyl;
each $R^{a60}$, $R^{b60}$, $R^{c60}$ and $R^{d60}$ is independently selected from H, $C_{1-3}$ alkyl, $C_{1-3}$ haloalkyl, 4-6 membered heterocycloalkyl, and 5-6 membered heteroaryl; wherein said $C_{1-3}$ alkyl, 4-6 membered heterocycloalkyl, and 5-6 membered heteroaryl are each optionally substituted with 1 or 2 substituents independently selected from $R^{61}$;
or any $R^{c60}$ and $R^{d60}$ attached to the same N atom, together with the N atom to which they are attached, form a 4-, 5-, or 6-membered heterocycloalkyl group optionally substituted with 1 or 2 substituents independently selected from $R^{61}$; and each $R^{a61}$, $R^{c61}$, and $R^{d61}$, is independently selected from H, $C_{1-3}$ alkyl, and $C_{1-3}$ haloalkyl; and each $R^g$ is independently selected from D, OH, CN, halo, $C_{1-3}$ alkyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino;

provided that the compound of Formula I is other than, 3-(1-((1R,4R,5S)-2-azabicyclo[2.1.1]hexan-5-yl)-8-(2-cyanoethyl)-4-ethoxy-6-fluoro-7-(3-hydroxynaphthalen-1-yl)-1H-pyrrolo[3,2-c]quinolin-2-yl)-N,N-dimethylpropanamide.

In an embodiment of Formula I, or a pharmaceutically acceptable salt thereof,

Y is N or $CR^6$;

$R^1$ is selected from H, $C_{1-3}$ alkyl, $C_{1-3}$ haloalkyl, cyclopropyl, halo, D, CN, and $OR^{a1}$;

wherein said $C_{1-3}$ alkyl and cyclopropyl are each optionally substituted with 1 or 2 substituents independently selected from $R^g$;

$R^2$ is selected from H, $C_{1-3}$ alkyl, $C_{1-3}$ haloalkyl, 4-6 membered heterocycloalkyl, phenyl, 5-6 membered heteroaryl, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, and $OR^{a2}$; wherein said $C_{1-3}$ alkyl, 4-6 membered heterocycloalkyl, phenyl, 5-6 membered heteroaryl, 4-6 membered heterocycloalkyl-$C_{1-3}$ alkylene, phenyl-$C_{1-3}$ alkylene, 5-6 membered heteroaryl-$C_{1-3}$ alkylene are each optionally substituted with 1 or 2 substituents independently selected from $R^g$;

$Cy^1$ is selected from $C_{3-10}$ cycloalkyl, 4-10 membered heterocycloalkyl, $C_{6-10}$ aryl, and 6-10 membered heteroaryl; wherein the 4-10 membered heterocycloalkyl and 6-10 membered heteroaryl each has at least one ring-forming carbon atom and 1, 2, 3, or 4 ring-forming heteroatoms independently selected from N, O, and S; wherein a ring-forming carbon atom of 6-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl, and 6-10 membered heteroaryl are each optionally substituted with 1, 2, 3, or 4 substituents independently selected from $R^{10}$;

$R^3$ is selected from H, $C_{1-3}$ alkyl, $C_{1-3}$ haloalkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, $OR^3$, C(O)$NR^{c3}R^{d3}$, $NR^{c3}R^{j3}$, and $NR^{c3}C(O)R^{b3}$; wherein said $C_{1-3}$ alkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, or 3 substituents independently selected from $R^{30}$ $R^5$ is selected from H, $C_{1-3}$ alkyl, $C_{1-3}$ haloalkyl, cyclopropyl, halo, D, CN, and $OR^{a5}$;

wherein said $C_{1-3}$ alkyl and cyclopropyl are each optionally substituted with 1 or 2 substituents independently selected from $R^9$;

$R^6$ is selected from H, $C_{1-3}$ alkyl, $C_{1-3}$ haloalkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, $OR^{a6}$, and C(O)$NR^{c6}R^{d6}$; wherein said $C_{1-3}$ alkyl, $C_{3-6}$cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, and 5-6 membered heteroaryl-$C_{1-3}$ alkylene are each optionally substituted with 1 or 2 substituents independently selected from $R^{60}$;

$R^7$ is selected from H, $C_{1-3}$ alkyl, $C_{1-3}$ haloalkyl, cyclopropyl, halo, D, CN, and $OR^{a7}$;

wherein said $C_{1-3}$ alkyl and cyclopropyl are each optionally substituted with 1 or 2 substituents independently selected from $R^g$;

$Cy^2$ is selected from

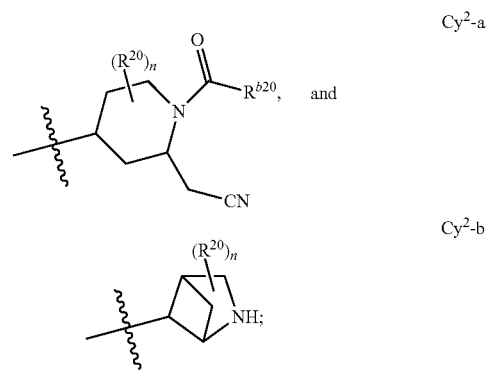

wherein n is 0, 1, or 2;

each $R^{10}$ is independently selected from $C_{1-3}$ alkyl, $C_{1-3}$ haloalkyl, halo, D, CN, $OR^{a10}$, C(O)$R^{b10}$, C(O)$NR^{c10}R^{d10}$, C(O)$OR^{a10}$, $NR^{c10}R^{d10}$, and S(O)$_2R^{b10}$;

each $R^{20}$ is independently selected from $C_{1-3}$ alkyl, $C_{1-3}$ haloalkyl, halo, D, CN, and $OR^{a20}$;

each $R^{30}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a30}$, C(O)$R^{b30}$, C(O)$NR^{c30}R^{d30}$, C(O)$OR^{a30}$, $NR^{c30}R^{d30}$, and S(O)$_2R^{b30}$; wherein said $C_{1-3}$ alkyl, $C_{3-6}$ cycloalkyl, 4-6 membered heterocycloalkyl, phenyl, and 5-6 membered heteroaryl are each optionally substituted with 1 or 2 substituents independently selected from $R^{31}$ each $R^{31}$ is independently selected from $C_{1-3}$ alkyl, $C_{1-3}$ haloalkyl, halo, D, CN, $OR^{a31}$, C(O)$R^{b31}$, C(O)$NR^{c31}R^{d31}$, C(O)$OR^{a31}$, $NR^{c31}R^{d31}$, and S(O)$_2R^{b31}$;

$R^{33}$ is selected from $C_{2-3}$ alkyl, $C_{1-3}$ haloalkyl, $C_{3-6}$ cycloalkyl, 4-membered heterocycloalkyl, 6-membered heterocycloalkyl, phenyl, 5-6 membered heteroaryl, halo, D, CN, $OR^{a30}$, C(O)$NR^{c30}R^{d30}$, and $NR^{c30}R^{d30}$; wherein said $C_{2-3}$ alkyl, $C_{3-6}$ cycloalkyl, 4-membered heterocycloalkyl, 6-membered heterocycloalkyl, phenyl, and 5-6 membered heteroaryl are each optionally substituted with 1 or 2 substituents independently selected from $R^{31}$ each $R^{60}$ is independently selected from $C_{1-3}$ alkyl, $C_{1-3}$ haloalkyl, 4-6 membered heterocycloalkyl, 5-6 membered heteroaryl, halo, D, CN, $OR^{a60}$, C(O)$R^{b60}$, C(O)$NR^{c60}R^{d60}$, C(O)$OR^{a60}$, $NR^{c60}R^{d60}$, and S(O)$_2R^{b60}$; wherein said $C_{1-3}$ alkyl, 4-6 membered heterocycloalkyl, and 5-6 membered heteroaryl are each optionally substituted with 1 or 2 substituents independently selected from $R^{61}$;

each $R^{61}$ is independently selected from $C_{1-3}$ alkyl, $C_{1-3}$ haloalkyl, halo, D, CN, $OR^{a61}$, and $NR^{c61}R^{d61}$ $R^{a1}$ is selected from H, $C_{1-3}$ alkyl, and $C_{1-3}$ haloalkyl;

$R^{a2}$ is selected from H, $C_{1-3}$ alkyl, and $C_{1-3}$ haloalkyl;

each $R^{b3}$, $R^{c3}$ and $R^{d3}$ is independently selected from H, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl and 5-6 membered heteroaryl are each optionally substituted with 1, 2, or 3 substituents independently selected from $R^{30}$;

or $R^{c3}$ and $R^{d3}$ attached to the same N atom, together with the N atom to which they are attached, form a 4-, 5-, or 6-membered heterocycloalkyl group optionally substituted with 1, 2, or 3 substituents independently selected from $R^{30}$ $R^{j3}$ is selected from $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl and 5-6 membered heteroaryl are each optionally substituted with 1, 2, or 3 substituents independently selected from $R^{30}$;

or $R^{c3}$ and $R^{j3}$ attached to the same N atom, together with the N atom to which they are attached, form a 4-, 5-, or 6-membered heterocycloalkyl group optionally substituted with 1, 2, or 3 substituents independently selected from $R^{30}$;

$R^{j3}$ is selected from $C_{1-3}$ haloalkyl, $C_{3-6}$ cycloalkyl, 4-6 membered heterocycloalkyl, phenyl and 5-6 membered heteroaryl; wherein said $C_{3-6}$ cycloalkyl, 4-6 membered heterocycloalkyl, phenyl and 5-6 membered heteroaryl are each optionally substituted with 1, 2, or 3 substituents independently selected from $R^{30}$; or $R^{j3}$ is selected from

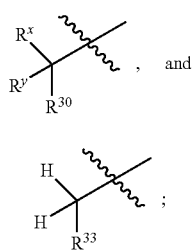

wherein $R^x$ is H or $C_{1-2}$ alkyl and $R^y$ is $C_{1-2}$ alkyl;

or $R^x$ and $R^y$, together with the C atom to which they are attached, form a 3-, or 4-membered cycloalkyl group;

$R^{a5}$ is selected from H, $C_{1-3}$ alkyl, and $C_{1-3}$ haloalkyl;

each $R^{a6}$, $R^{c6}$ and $R^{d6}$ is independently selected from H, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl and 5-6 membered heteroaryl are each optionally substituted with 1 or 2 substituents independently selected from $R^{60}$;

$R^{a7}$ is selected from H, $C_{1-3}$ alkyl, and $C_{1-3}$ haloalkyl;

each $R^{a10}$, $R^{b10}$, $R^{c10}$ and $R^{d10}$ is independently selected from H, $C_{1-3}$ alkyl, and $C_{1-3}$ haloalkyl;

each $R^{a20}$ is independently selected from H, $C_{1-3}$ alkyl, and $C_{1-3}$ haloalkyl;

$R^{b20}$ is selected from $NH_2$, $C_{1-3}$ alkyl, and $C_{1-3}$ haloalkyl;

each $R^{a30}$, $R^{b30}$, $R^{c30}$ and $R^{d30}$ is independently selected from H, $C_{1-3}$ alkyl, and $C_{1-3}$ haloalkyl;

each $R^{a31}$, $R^{b31}$, $R^{c31}$ and $R^{d31}$ is independently selected from H, $C_{1-3}$ alkyl, and $C_{1-3}$ haloalkyl;

each $R^{a60}$, $R^{b60}$, $R^{c60}$ and $R^{d60}$ is independently selected from H, $C_{1-3}$ alkyl, $C_{1-3}$ haloalkyl, 4-6 membered heterocycloalkyl, and 5-6 membered heteroaryl; wherein said $C_{1-3}$ alkyl, 4-6 membered heterocycloalkyl, and 5-6 membered heteroaryl are each optionally substituted with 1 or 2 substituents independently selected from $R^{61}$;

or any $R^{c60}$ and $R^{d60}$ attached to the same N atom, together with the N atom to which they are attached, form a 4-, 5-, or 6-membered heterocycloalkyl group optionally substituted with 1 or 2 substituents independently selected from $R^{61}$;

each $R^{a61}$, $R^{c61}$, and $R^{d61}$, is independently selected from H, $C_{1-3}$ alkyl, and $C_{1-3}$ haloalkyl; and each $R^g$ is independently selected from D, OH, CN, halo, $C_{1-3}$ alkyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino.

In another embodiment of Formula I, or a pharmaceutically acceptable salt thereof, Y is N or $CR^6$;

$R^1$ is selected from H, $C_{1-3}$ alkyl, $C_{1-3}$ haloalkyl, cyclopropyl, halo, D, CN, and $OR^{a1}$;

wherein said $C_{1-3}$ alkyl and cyclopropyl are each optionally substituted with 1 or 2 substituents independently selected from $R^9$;

$R^2$ is selected from H, $C_{1-3}$ alkyl, $C_{1-3}$ haloalkyl, 4-6 membered heterocycloalkyl, phenyl, 5-6 membered heteroaryl, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, and $OR^{a2}$; wherein said $C_{1-3}$ alkyl, 4-6 membered heterocycloalkyl, phenyl, 5-6 membered heteroaryl, 4-6 membered heterocycloalkyl-$C_{1-3}$ alkylene, phenyl-$C_{1-3}$ alkylene, and 5-6 membered heteroaryl-$C_{1-3}$ alkylene are each optionally substituted with 1 or 2 substituents independently selected from $R^g$;

$Cy^1$ is selected from $C_{3-10}$ cycloalkyl, 4-10 membered heterocycloalkyl, $C_{6-10}$ aryl and 6-10 membered heteroaryl; wherein the 4-10 membered heterocycloalkyl and 6-10 membered heteroaryl each has at least one ring-forming carbon atom and 1, 2, 3, or 4 ring-forming heteroatoms independently selected from N, O, and S; wherein a ring-forming carbon atom of 6-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 6-10 membered heteroaryl are each optionally substituted with 1, 2, 3, or 4 substituents independently selected from $R^{10}$;

$R^3$ is selected from H, $C_{1-3}$ alkyl, $C_{1-3}$ haloalkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, $OR^3$, $C(O)NR^{c3}R^{d3}$, $NR^{c3}R^{j3}$, and $NR^{c3}C(O)R^{b3}$; wherein said $C_{1-3}$ alkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, and 5-6 membered heteroaryl-$C_{1-3}$ alkylene are each optionally substituted with 1, 2, or 3 substituents independently selected from $R^{30}$ $R^5$ is selected from H, $C_{1-3}$ alkyl, $C_{1-3}$ haloalkyl, cyclopropyl, halo, D, CN, and $OR^{a5}$;
wherein said $C_{1-3}$ alkyl and cyclopropyl are each optionally substituted with 1 or 2 substituents independently selected from $R^9$;

$R^6$ is selected from H, $C_{1-3}$ alkyl, $C_{1-3}$ haloalkyl, $C_{3-6}$ cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, 5-6 membered heteroaryl-$C_{1-3}$ alkylene, halo, D, CN, $OR^{a6}$, and $C(O)NR^{c6}R^{d6}$; wherein said $C_{1-3}$ alkyl, $C_{3-6}$cycloalkyl, 4-6 membered heterocycloalkyl, phenyl, 5-6 membered heteroaryl, $C_{3-6}$ cycloalkyl-$C_{1-3}$ alkylene, 4-6 membered heterocycloalkyl-$C_{1-3}$ alkylene, phenyl-$C_{1-3}$ alkylene, and 5-6 membered heteroaryl-$C_{1-3}$ alkylene are each optionally substituted with 1 or 2 substituents independently selected from $R^{60}$;

$R^7$ is selected from H, $C_{1-3}$ alkyl, $C_{1-3}$ haloalkyl, cyclopropyl, halo, D, CN, and $OR^{a7}$;
wherein said $C_{1-3}$ alkyl and cyclopropyl are each optionally substituted with 1 or 2 substituents independently selected from $R^9$;

$Cy^2$ is selected from

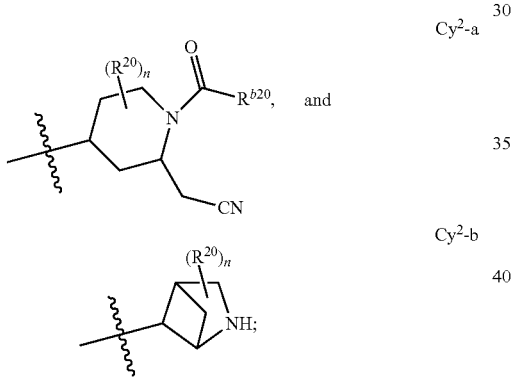

wherein n is 0, 1, or 2;

each $R^{10}$ is independently selected from $C_{1-3}$ alkyl, $C_{1-3}$ haloalkyl, halo, D, CN, $OR^{a10}$, $C(O)R^{b10}$, $C(O)NR^{c10}R^{d10}$, $C(O)OR^{a10}$, $NR^{c10}R^{d10}$, and $S(O)_2R^{b10}$;

each $R^{20}$ is independently selected from $C_{1-3}$ alkyl, $C_{1-3}$ haloalkyl, halo, D, CN, and $OR^{a20}$;

each $R^{30}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a30}$, $C(O)R^{b30}$, $C(O)NR^{c30}R^{d30}$, $C(O)OR^{a30}$, $NR^{c30}R^{d30}$, and $S(O)_2R^{b30}$; wherein said $C_{1-3}$ alkyl, $C_{3-6}$ cycloalkyl, 4-6 membered heterocycloalkyl, phenyl, and 5-6 membered heteroaryl are each optionally substituted with 1 or 2 substituents independently selected from $R^{31}$;

each $R^{31}$ is independently selected from $C_{1-3}$ alkyl, $C_{1-3}$ haloalkyl, halo, D, CN, $OR^{a31}$, $C(O)R^{b31}$, $C(O)NR^{c31}R^{d31}$, $C(O)OR^{a31}$, $NR^{c31}R^{d31}$, and $S(O)_2R^{b31}$;

each $R^{33}$ is independently selected from $C_{1-3}$ alkyl, $C_{1-3}$ haloalkyl, $C_{3-6}$ cycloalkyl, 4-membered heterocycloalkyl, 6-membered heterocycloalkyl, phenyl, 5-6 membered heteroaryl, halo, D, CN, $OR^{a30}$, $C(O)NR^{c30}R^{d30}$, and $NR^{c30}R^{d30}$; wherein said $C_{1-3}$ alkyl, $C_{3-6}$ cycloalkyl, 4-membered heterocycloalkyl, 6-membered heterocycloalkyl, phenyl, and 5-6 membered heteroaryl are each optionally substituted with 1 or 2 substituents independently selected from $R^{31}$;

each $R^{60}$ is independently selected from $C_{1-3}$ alkyl, $C_{1-3}$ haloalkyl, 4-6 membered heterocycloalkyl, 5-6 membered heteroaryl, halo, D, CN, $OR^{a60}$, $C(O)R^{b60}$, $C(O)NR^{c60}R^{d60}$, $C(O)OR^{a60}$, $NR^{c60}R^{d60}$, and $S(O)_2R^{b60}$; wherein said $C_{1-3}$ alkyl, 4-6 membered heterocycloalkyl, and 5-6 membered heteroaryl are each optionally substituted with 1 or 2 substituents independently selected from $R^{61}$;

each $R^{61}$ is independently selected from $C_{1-3}$ alkyl, $C_{1-3}$ haloalkyl, halo, D, CN, $OR^{a61}$, and $NR^{c61}R^{d61}$;

$R^{a1}$ is selected from H, $C_{1-3}$ alkyl, and $C_{1-3}$ haloalkyl;

each $R^{a2}$ is independently selected from H, $C_{1-3}$ alkyl, and $C_{1-3}$ haloalkyl;

each $R^{b3}$, $R^{c3}$ and $R^{d3}$ is independently selected from H, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl and 5-6 membered heteroaryl are each optionally substituted with 1, 2, or 3 substituents independently selected from $R^{30}$;

or $R^{c3}$ and $R^{d3}$ attached to the same N atom, together with the N atom to which they are attached, form a 4-, 5-, or 6-membered heterocycloalkyl group optionally substituted with 1, 2, or 3 substituents independently selected from $R^{30}$ $R^{j3}$ is selected from $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl and 5-6 membered heteroaryl are each optionally substituted with 1, 2, or 3 substituents independently selected from $R^{30}$;

or $R^{c3}$ and $R^{j3}$ attached to the same N atom, together with the N atom to which they are attached, form a 4-, 5-, or 6-membered heterocycloalkyl group optionally substituted with 1, 2, or 3 substituents independently selected from $R^{30}$ $R^{j3}$ is selected from $C_{1-3}$ haloalkyl, $C_{3-6}$ cycloalkyl, 4-6 membered heterocycloalkyl, phenyl and 5-6 membered heteroaryl; wherein said $C_{1-3}$ haloalkyl, $C_{3-6}$ cycloalkyl, 4-6 membered heterocycloalkyl, phenyl and 5-6 membered heteroaryl are each optionally substituted with 1, 2, or 3 substituents independently selected from $R^{30}$; or $R^{j3}$ is selected from

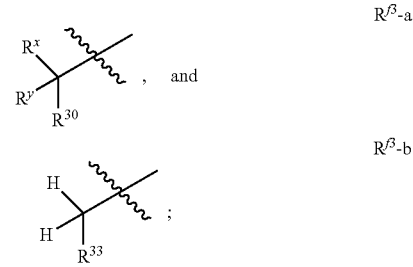

wherein $R^x$ is H or $C_{1-2}$ alkyl and $R^y$ is $C_{1-2}$ alkyl;
or $R^x$ and $R^y$, together with the C atom to which they are attached, form a 3-, or 4-membered cycloalkyl group;

$R^{a5}$ is selected from H, $C_{1-3}$ alkyl, and $C_{1-3}$ haloalkyl;

each $R^{a6}$, $R^{c6}$ and $R^{d6}$ is independently selected from H, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl and 5-6 membered heteroaryl are each optionally substituted with 1 or 2 substituents independently selected from $R^{60}$;

$R^{a7}$ is selected from H, $C_{1-3}$ alkyl, and $C_{1-3}$ haloalkyl;

each $R^{a10}$, $R^{b10}$, $R^{c10}$ and $R^{d10}$ is independently selected from H, $C_{1-3}$ alkyl, and $C_{1-3}$ haloalkyl;

each $R^{a20}$ is independently selected from H, $C_{1-3}$ alkyl, and $C_{1-3}$ haloalkyl;

$R^{b20}$ is selected from $NH_2$, $C_{1-3}$ alkyl, and $C_{1-3}$ haloalkyl;

each $R^{a30}$, $R^{b30}$, $R^{c30}$ and $R^{d30}$ is independently selected from H, $C_{1-3}$ alkyl, and $C_{1-3}$ haloalkyl;

each $R^{a31}$, $R^{b31}$, $R^{c31}$ and $R^{d31}$ is independently selected from H, $C_{1-3}$ alkyl, and $C_{1-3}$ haloalkyl;

each $R^{a60}$ and $R^{b60}$ is independently selected from H, $C_{1-3}$ alkyl, $C_{1-3}$ haloalkyl, 4-6 membered heterocycloalkyl, and 5-6 membered heteroaryl; wherein said $C_{1-3}$ alkyl, 4-6 membered heterocycloalkyl, and 5-6 membered heteroaryl are each optionally substituted with 1 or 2 substituents independently selected from $R^{61}$;

each $R^{c60}$ and $R^{d60}$ is independently selected from H, $C_{2-3}$ alkyl, $C_{1-3}$ haloalkyl, 4-6 membered heterocycloalkyl, and 5-6 membered heteroaryl; wherein said $C_{2-3}$ alkyl, 4-6 membered heterocycloalkyl, and 5-6 membered heteroaryl are each optionally substituted with 1 or 2 substituents independently selected from $R^{61}$;

or any $R^{c60}$ and $R^{d60}$ attached to the same N atom, together with the N atom to which they are attached, form a 4-, 5-, or 6-membered heterocycloalkyl group optionally substituted with 1 or 2 substituents independently selected from $R^{61}$; and each $R^{a61}$, $R^{c61}$, and $R^{d61}$ is independently selected from H, $C_{1-3}$ alkyl, and $C_{1-3}$ haloalkyl; and each $R^g$ is independently selected from D, OH, CN, halo, $C_{1-3}$ alkyl, $C_{1-3}$ haloalkyl, $C_{1-3}$ alkoxy, $C_{1-3}$ haloalkoxy, amino, $C_{1-3}$ alkylamino, and di($C_{1-3}$ alkyl) amino.

In yet another embodiment of Formula I, or a pharmaceutically acceptable salt thereof, Y is N or $CR^6$;

$R^1$ is selected from H, $C_{1-3}$ alkyl, $C_{1-3}$ haloalkyl, and D;

$R^2$ is selected from H, $C_{1-3}$ alkyl, $C_{1-3}$ haloalkyl, halo, D, CN, and $OR^{a2}$; wherein said $C_{1-3}$ alkyl is optionally substituted with 1 or 2 substituents independently selected from $R^9$;

$Cy^1$ is selected from $C_{6-10}$ aryl and 6-10 membered heteroaryl; wherein the 6-10 membered heteroaryl has at least one ring-forming carbon atom and 1, 2, or 3 ring-forming heteroatoms independently selected from N, O, and S; wherein the ring-forming carbon atom of the 6-10 membered heteroaryl is optionally substituted by oxo to form a carbonyl group; and wherein the $C_{6-10}$ aryl and 6-10 membered heteroaryl are each optionally substituted with 1, 2, or 3 substituents independently selected from $R^{10}$;

$R^3$ is selected from H, $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^3$, and $NR^{c3}R^{d3}$; wherein said $C_{1-3}$ alkyl, $C_{3-6}$ cycloalkyl, 4-6 membered heterocycloalkyl, phenyl, and 5-6 membered heteroaryl are each optionally substituted with 1, 2, or 3 substituents independently selected from $R^{30}$;

$R^5$ is selected from H, $C_{1-3}$ alkyl, $C_{1-3}$ haloalkyl, and D;

$R^6$ is selected from H, $C_{1-3}$ alkyl, $C_{1-3}$ haloalkyl, 4-6 membered heterocycloalkyl, 5-6 membered heteroaryl, halo, D, and CN; wherein said $C_{1-3}$ alkyl, 4-6 membered heterocycloalkyl, and 5-6 membered heteroaryl are each optionally substituted with 1 or 2 substituents independently selected from $R^{60}$;

$R^7$ is selected from H, $C_{1-3}$ alkyl, $C_{1-3}$ haloalkyl, halo, D, and CN;

$Cy^2$ is selected from

Cy²-a

Cy²-b wherein n is 0 or 1;

each $R^{10}$ is independently selected from $C_{1-3}$ alkyl, $C_{1-3}$ haloalkyl, halo, D, CN, $OR^{a10}$, and $NR^{c10}R^{d10}$;

each $R^{20}$ is independently selected from $C_{1-3}$ alkyl, $C_{1-3}$ haloalkyl, halo, D, and CN;

each $R^{30}$ is independently selected from $C_{1-3}$ alkyl, $C_{1-3}$ haloalkyl, 4-6 membered heterocycloalkyl, 5-6 membered heteroaryl, halo, D, CN, $OR^{a30}$, and $NR^{c30}R^{d30}$; wherein said $C_{1-3}$ alkyl, 4-6 membered heterocycloalkyl, and 5-6 membered heteroaryl are each optionally substituted with 1 or 2 substituents independently selected from $R^{31}$;

each $R^{31}$ is independently selected from $C_{1-3}$ alkyl, $C_{1-3}$ haloalkyl, halo, D, CN, $OR^{a31}$ and $NR^{c31}R^{d31}$;

$R^{33}$ is selected from $C_{2-3}$ alkyl, $C_{1-3}$ haloalkyl, 4-membered heterocycloalkyl, 6-membered heterocycloalkyl, 5-6 membered heteroaryl, halo, D, CN, $OR^{a30}$, and $NR^{c30}R^{d30}$;

wherein said $C_{2-3}$ alkyl, 4-membered heterocycloalkyl, 6-membered heterocycloalkyl, and 5-6 membered heteroaryl are each optionally substituted with 1 or 2 substituents independently selected from $R^{31}$ each $R^{60}$ is independently selected from $C_{1-3}$ alkyl, $C_{1-3}$ haloalkyl, 4-6 membered heterocycloalkyl, 5-6 membered heteroaryl, halo, D, CN, $OR^{a60}$, $C(O)NR^{c60}R^{d60}$ and $NR^{c60}R^{d60}$; wherein said $C_{1-3}$ alkyl, 4-6 membered heterocycloalkyl, and 5-6 membered heteroaryl are each optionally substituted with 1 or 2 substituents independently selected from $R^{61}$;

each $R^{61}$ is independently selected from $C_{1-3}$ alkyl, $C_{1-3}$ haloalkyl, halo, D, and CN;

$R^{a2}$ is selected from H, $C_{1-3}$ alkyl, and $C_{1-3}$ haloalkyl;

$R^{c3}$ is selected from H, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl and 5-6 membered heteroaryl are each optionally substituted with 1, 2, or 3 substituents independently selected from $R^{30}$;

$R^{j3}$ is selected from $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl and 5-6 membered heteroaryl are each optionally substituted with 1, 2, or 3 substituents independently selected from $R^{30}$;

or $R^{c3}$ and $R^{j3}$ attached to the same N atom, together with the N atom to which they are attached, form a 4-, 5-, or 6-membered heterocycloalkyl group optionally substituted with 1, 2, or 3 substituents independently selected from $R^{30}$ $R^{j3}$ is selected from $C_{1-3}$ haloalkyl, $C_{3-6}$ cycloalkyl, 4-6 membered heterocycloalkyl, phenyl and 5-6 membered heteroaryl; wherein said $C_{3-6}$ cycloalkyl, 4-6 membered heterocycloalkyl, phenyl and 5-6 membered heteroaryl are each optionally substituted with 1, 2, or 3 substituents independently selected from $R^{30}$; or $R^{j3}$ is selected from

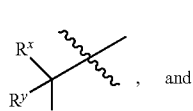
$R^{j3}$-a

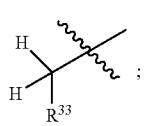
$R^{j3}$-b wherein $R^x$ is H or $C_{1-2}$ alkyl and $R^y$ is $C_{1-2}$ alkyl;

or $R^x$ and $R^y$, together with the C atom to which they are attached, form a 3-, or 4-membered cycloalkyl group;

each $R^{a10}$, $R^{c10}$ and $R^{d10}$ is independently selected from H, $C_{1-3}$ alkyl, and $C_{1-3}$ haloalkyl;

$R^{b20}$ is selected from $NH_2$, $C_{1-3}$ alkyl, and $C_{1-3}$ haloalkyl;

each $R^{a30}$, $R^{c30}$ and $R^{d30}$ is independently selected from H, $C_{1-3}$ alkyl, and $C_{1-3}$ haloalkyl;

each $R^{a31}$, $R^{c31}$ and $R^{d31}$ is independently selected from H, $C_{1-3}$ alkyl, and $C_{1-3}$ haloalkyl;

each $R^{a60}$, $R^{c60}$ and $R^{d60}$ is independently selected from H, $C_{1-3}$ alkyl, $C_{1-3}$ haloalkyl, 4-6 membered heterocycloalkyl, and 5-6 membered heteroaryl; wherein said $C_{1-3}$ alkyl, 4-6 membered heterocycloalkyl, and 5-6 membered heteroaryl are each optionally substituted with 1 or 2 substituents independently selected from $R^{61}$;

or any $R^{c60}$ and $R^{d60}$ attached to the same N atom, together with the N atom to which they are attached, form a 4-, 5-, or 6-membered heterocycloalkyl group optionally substituted with 1 or 2 substituents independently selected from $R^{61}$; and each $R^9$ is independently selected from D, CN, halo, $C_{1-3}$ alkyl, and $C_{1-3}$ haloalkyl.

In still another embodiment of Formula I, or a pharmaceutically acceptable salt thereof, Y is N or $CR^6$;

$R^1$ is H;

$R^2$ is selected from H, $C_{1-3}$ alkyl, $C_{1-3}$ haloalkyl, halo, D, CN, and $-CH_2CH_2CN$;

$Cy^1$ is selected from $C_{6-10}$ aryl and 6-10 membered heteroaryl; wherein the 6-10 membered heteroaryl has at least one ring-forming carbon atom and 1 or 2 ring-forming heteroatoms independently selected from N, O, and S; and wherein the $C_{6-10}$ aryl and 6-10 membered heteroaryl are each optionally substituted with 1, 2, or 3 substituents independently selected from $R^{10}$;

$R^3$ is selected from H, $C_{1-3}$ alkyl, $C_{1-3}$ haloalkyl, 4-6 membered heterocycloalkyl, 5-6 membered heteroaryl, halo, D, CN, and $OR^{j3}$; wherein said $C_{1-3}$ alkyl, 4-6 membered heterocycloalkyl, and 5-6 membered heteroaryl are each optionally substituted with 1 or 2 substituents independently selected from $R^{30}$;

$R^5$ is H;

$R^6$ is selected from H, $C_{1-3}$ alkyl, $C_{1-3}$ haloalkyl, 4-6 membered heterocycloalkyl, 5-6 membered heteroaryl, halo, D, and CN; wherein said $C_{1-3}$ alkyl, 4-6 membered heterocycloalkyl, and 5-6 membered heteroaryl are each optionally substituted with 1 or 2 substituents independently selected from $R^{60}$;

$R^7$ is halo;

$Cy^2$ is selected from

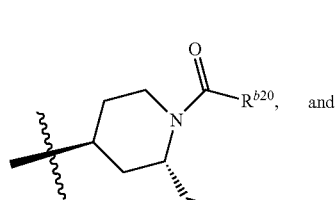
$Cy^2$-a

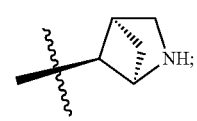
$Cy^2$-b each $R^{10}$ is independently selected from $C_{1-3}$ alkyl, $C_{1-3}$ haloalkyl, halo, D, CN, and $OR^{a10}$;

each $R^{30}$ is independently selected from $C_{1-3}$ alkyl, $C_{1-3}$ haloalkyl, 4-6 membered heterocycloalkyl, halo, D, CN, $OR^{a30}$, and $NR^{c30}R^{d30}$; wherein said $C_{1-3}$ alkyl and 4-6 membered heterocycloalkyl are each optionally substituted with 1 or 2 substituents independently selected from $R^{31}$;

each $R^{31}$ is independently selected from $C_{1-3}$ alkyl, $C_{1-3}$ haloalkyl, halo, D, CN, $OR^{a31}$ and $NR^{c31}R^{d31}$;

$R^{33}$ is selected from $C_{2-3}$ alkyl, $C_{1-3}$ haloalkyl, 4-membered heterocycloalkyl, 6-membered heterocycloalkyl, halo, D, CN, $OR^{a30}$, and $NR^{c30}R^{d30}$; wherein said $C_{2-3}$ alkyl, 4-membered heterocycloalkyl, and 6-membered heterocycloalkyl are each optionally substituted with 1 or 2 substituents independently selected from $R^{31}$ each $R^{60}$ is independently selected from $C_{1-3}$ alkyl, $C_{1-3}$ haloalkyl, 4-6 membered heterocycloalkyl, halo, D, CN, $OR^{a6}$, $C(O)NR^{c60}R^{d60}$ and $NR^{c60}R^{d60}$; wherein said $C_{1-3}$ alkyl and 4-6 membered heterocycloalkyl are each optionally substituted with 1 or 2 substituents independently selected from $R^{61}$;

each $R^{61}$ is independently selected from $C_{1-3}$ alkyl, $C_{1-3}$ haloalkyl, halo, D, and CN;

$R^{j3}$ is selected from $C_{1-3}$ haloalkyl, 4-6 membered heterocycloalkyl, and 5-6 membered heteroaryl; wherein said 4-6 membered heterocycloalkyl and 5-6 membered heteroaryl are each optionally substituted with 1 or 2 substituents independently selected from $R^{30}$; or $R^{f3}$ is selected from

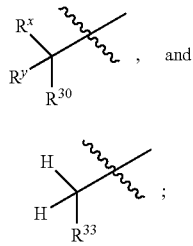
$R^{f3}$-a and

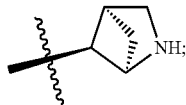
$R^{f3}$-b ;

wherein $R^x$ is H or $C_{1-2}$ alkyl and $R^y$ is $C_{1-2}$ alkyl;
each $R^{a10}$ is independently selected from H, $C_{1-3}$ alkyl, and $C_{1-3}$ haloalkyl;
$R^{b20}$ is selected from $C_{1-3}$ alkyl and $C_{1-3}$ haloalkyl;
each $R^{a30}$, $R^{c30}$ and $R^{d30}$ is independently selected from H, $C_{1-3}$ alkyl, and $C_{1-3}$ haloalkyl;
each $R^{a31}$, $R^{c31}$ and $R^{d31}$ is independently selected from H, $C_{1-3}$ alkyl, and $C_{1-3}$ haloalkyl; and
each $R^{a6}$, $R^{c60}$ and $R^{d60}$ is independently selected from H, $C_{1-3}$ alkyl, $C_{1-3}$ haloalkyl, and 4-6 membered heterocycloalkyl; wherein said $C_{1-3}$ alkyl and 4-6 membered heterocycloalkyl are each optionally substituted with 1 or 2 substituents independently selected from $R^{61}$;
or any $R^{c60}$ and $R^{d60}$ attached to the same N atom, together with the N atom to which they are attached, form a 4-, 5-, or 6-membered heterocycloalkyl group optionally substituted with 1 or 2 substituents independently selected from $R^{61}$.

In an embodiment of Formula I, or a pharmaceutically acceptable salt thereof,
Y is N or $CR^6$;
$R^1$ is H;
$R^2$ is selected from $C_{1-3}$ alkyl, $C_{1-3}$ haloalkyl, halo, CN, and —$CH_2CH_2CN$;
$Cy^1$ is selected from $C_{6-10}$ aryl and 6-10 membered heteroaryl; wherein the 6-10 membered heteroaryl has at least one ring-forming carbon atom and 1 ring-forming heteroatom independently selected from N and S; and wherein the $C_{6-10}$ aryl and 6-10 membered heteroaryl are each optionally substituted with 1, 2, or 3 substituents independently selected from $R^{10}$;
$R^3$ is selected from $C_{1-3}$ alkyl, $C_{1-3}$ haloalkyl, 4-6 membered heterocycloalkyl, 5-6 membered heteroaryl, and $OR^3$; wherein said $C_{1-3}$ alkyl, 4-6 membered heterocycloalkyl, and 5-6 membered heteroaryl are each optionally substituted with 1 or 2 substituents independently selected from $R^{30}$;
$R^5$ is H;
$R^6$ is selected from H, $C_{1-3}$ alkyl, $C_{1-3}$ haloalkyl, and 5-6 membered heteroaryl;
wherein said $C_{1-3}$ alkyl and 5-6 membered heteroaryl are each optionally substituted with 1 or 2 substituents independently selected from $R^{60}$;
$R^7$ is halo;
$Cy^2$ is selected from

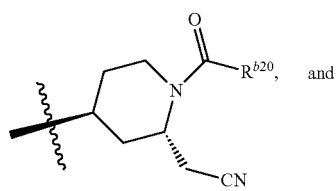
$Cy^2$-a and

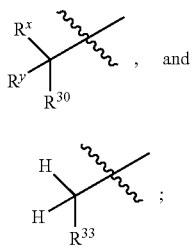
$Cy^2$-b each $R^{10}$ is independently selected from $C_{1-3}$ alkyl, $C_{1-3}$ haloalkyl, halo, CN, and $OR^{a10}$;
each $R^{30}$ is independently selected from $C_{1-3}$ alkyl, $C_{1-3}$ haloalkyl, 4-6 membered heterocycloalkyl, halo, and $NR^{c30}R^{d30}$; wherein said $C_{1-3}$ alkyl and 4-6 membered heterocycloalkyl are each optionally substituted with 1 or 2 substituents independently selected from $R^{31}$
each $R^{31}$ is independently selected from $C_{1-3}$ alkyl, $C_{1-3}$ haloalkyl, halo, and $NR^{c31}R^{d31}$;
$R^{33}$ is selected from $C_{2-3}$ alkyl, $C_{1-3}$ haloalkyl, 4-membered heterocycloalkyl, 6-membered heterocycloalkyl, halo, and CN; wherein said $C_{2-3}$ alkyl, 4-membered heterocycloalkyl, and 6-membered heterocycloalkyl are each optionally substituted with 1 or 2 substituents independently selected from $R^{31}$
each $R^{60}$ is independently selected from $C_{1-3}$ alkyl, $C_{1-3}$ haloalkyl, 4-6 membered heterocycloalkyl, halo, and $C(O)NR^{c60}R^{d60}$; wherein said $C_{1-3}$ alkyl and 4-6 membered heterocycloalkyl are each optionally substituted with 1 or 2 substituents independently selected from $R^{61}$;
each $R^{61}$ is independently selected from $C_{1-3}$ alkyl, $C_{1-3}$ haloalkyl, and halo;
$R^{13}$ is $C_{1-3}$ haloalkyl; or
$R^{f3}$ is selected from $R^{f3}$-a and $R^{f3}$-b ;

wherein $R^x$ is H or $C_{1-2}$ alkyl and $R^y$ is $C_{1-2}$ alkyl;
each $R^{a10}$ is independently selected from H, $C_{1-3}$ alkyl, and $C_{1-3}$ haloalkyl;
$R^{b20}$ is selected from $C_{1-3}$ alkyl, and $C_{1-3}$ haloalkyl;
each $R^{c30}$ and $R^{d30}$ is independently selected from H, $C_{1-3}$ alkyl, and $C_{1-3}$ haloalkyl;
each $R^{c31}$ and $R^{d31}$ is independently selected from H, $C_{1-3}$ alkyl, and $C_{1-3}$ haloalkyl; and
each $R^{c60}$ and $R^{d60}$ is independently selected from H, $C_{1-3}$ alkyl, $C_{1-3}$ haloalkyl, and 4-6 membered heterocycloalkyl; wherein said $C_{1-3}$ alkyl, and 4-6 membered heterocycloalkyl are each optionally substituted with 1 or 2 substituents independently selected from $R^{61}$;
or any $R^{c60}$ and $R^{d60}$ attached to the same N atom, together with the N atom to which they are attached, form a 4- or 5-membered heterocycloalkyl group optionally substituted with 1 or 2 substituents independently selected from $R^{61}$.

In an embodiment,
Y is N or $CR^6$;
$R^1$ is H;
$R^2$ is selected from $C_{1-3}$ alkyl, halo, CN, and —$CH_2CH_2CN$;
$Cy^1$ is phenyl, naphthyl, indolyl, benzothiophenyl, and isoquinolinyl, all of which are each optionally substituted with 1, 2, or 3 substituents independently selected from $R^{10}$;
$R^3$ is selected from $C_{1-3}$ alkyl, 4-6 membered heterocycloalkyl, 5-6 membered heteroaryl, and $OR^{f3}$; wherein said $C_{1-3}$ alkyl, 4-6 membered heterocycloalkyl, and 5-6 membered heteroaryl are each optionally substituted with 1 or 2 substituents independently selected from $R^{30}$;
$R^5$ is H;
$R^6$ is selected from H, $C_{1-3}$ alkyl, and 5-6 membered heteroaryl; wherein said $C_{1-3}$ alkyl and 5-6 membered heteroaryl are each optionally substituted with 1 or 2 substituents independently selected from $R^{60}$;
$R^7$ is halo;
$Cy^2$ is selected from

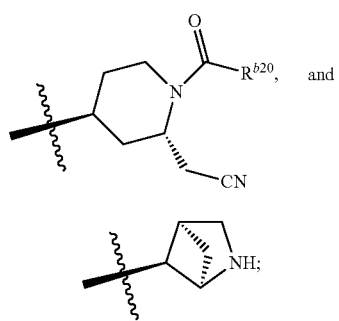

each $R^{10}$ is independently selected from $C_{1-3}$ alkyl, $C_{1-3}$ haloalkyl, halo, CN, and OH;
each $R^{30}$ is independently selected from $C_{1-3}$ alkyl, $C_{1-3}$ haloalkyl, 4-6 membered heterocycloalkyl, halo, and $N(C_{1-3}$ alkyl$)_2$; wherein said $C_{1-3}$ alkyl and 4-6 membered heterocycloalkyl are each optionally substituted with 1 or 2 substituents independently selected from $R^{31}$;
each $R^{31}$ is independently selected from $C_{1-3}$ alkyl, $C_{1-3}$ haloalkyl, halo, and $N(C_{1-3}$ alkyl$)_2$;
$R^{33}$ is selected from $C_{2-3}$ alkyl, $C_{1-3}$ haloalkyl, 4-membered heterocycloalkyl, 6-membered heterocycloalkyl, halo, and CN; wherein said $C_{2-3}$ alkyl, 4-membered heterocycloalkyl, and 6-membered heterocycloalkyl are each optionally substituted with 1 or 2 substituents independently selected from $R^{31}$;
each $R^{60}$ is independently selected 4-6 membered heterocycloalkyl and $C(O)NR^{d60}R^{d60}$; wherein 4-6 membered heterocycloalkyl is each optionally substituted with 1 or 2 substituents independently selected from $R^{61}$;
each $R^{61}$ is independently selected from $C_{1-3}$ alkyl, $C_{1-3}$ haloalkyl, and halo;
$R^{f3}$ is selected from

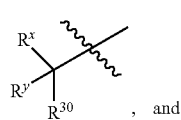, and

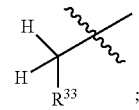

wherein $R^x$ is H or $C_{1-2}$ alkyl and $R^y$ is $C_{1-2}$ alkyl;
$R^{b20}$ is $C_{1-3}$ alkyl; and
each $R^{c60}$ and $R^{d60}$ is independently selected from H and $C_{1-3}$ alkyl;
or any $R^{c60}$ and $R^{d60}$ attached to the same N atom, together with the N atom to which they are attached, form a 4- or 5-membered heterocycloalkyl group optionally substituted with 1 or 2 substituents independently selected from $R^{61}$.

In yet another embodiment, the compound of Formula I is a compound of Formula Ia:

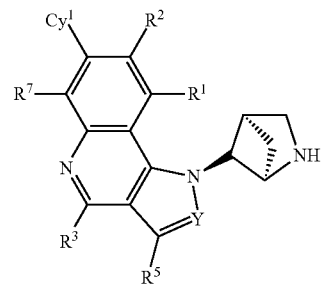

or a pharmaceutically acceptable salt thereof.

In yet another embodiment, the compound of Formula I is a compound of Formula Ib:

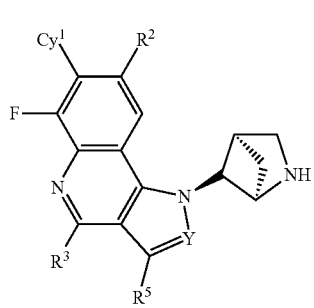

or a pharmaceutically acceptable salt thereof.

In an embodiment, Y is N. In another embodiment, Y is $CR^6$.

In yet another embodiment, $R^1$ is selected from H, $C_{1-3}$ alkyl, $C_{1-3}$ haloalkyl, cyclopropyl, halo, D, CN, and $OR^{a1}$. In still another embodiment, $R^1$ is selected from H, $C_{1-3}$ alkyl, $C_{1-3}$ haloalkyl, and D. In an embodiment, $R^1$ is H. In an embodiment, $R^1$ is selected from H, $C_{1-3}$ alkyl, and $C_{1-3}$ haloalkyl.

In another embodiment, $R^2$ is selected from H, $C_{1-3}$ alkyl, $C_{1-3}$ haloalkyl, halo, D, CN, and $OR^{a2}$; wherein said $C_{1-3}$ alkyl, is optionally substituted with 1 or 2 substituents independently selected from $R^9$. In yet another embodiment, $R^2$ is selected from H, $C_{1-3}$ alkyl, $C_{1-3}$ haloalkyl, halo, D, CN, and —$CH_2CH_2CN$. In still another embodiment, $R^2$ is selected from $C_{1-3}$ alkyl, $C_{1-3}$ haloalkyl, halo, CN, and —$CH_2CH_2CN$. In an embodiment, $R^2$ is —$CH_2CH_2CN$.

In an embodiment, $Cy^1$ is selected from $C_{3-10}$ cycloalkyl, 4-10 membered heterocycloalkyl, $C_{6-10}$ aryl and 6-10 membered heteroaryl; wherein the 4-10 membered heterocycloalkyl and 6-10 membered heteroaryl each has at least one ring-forming carbon atom and 1, 2, 3, or 4 ring-forming heteroatoms independently selected from N, O, and S; wherein a ring-forming carbon atom of 6-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 6-10 membered heteroaryl are each optionally substituted with 1, 2, or 3 substituents independently selected from $R^{10}$.

In an embodiment, $Cy^1$ is selected from $C_{3-10}$cycloalkyl, $C_{6-10}$ aryl and 6-10 membered heteroaryl; wherein the 6-10 membered heteroaryl has at least one ring-forming carbon atom and 1, ring-forming heteroatoms independently selected from N and S; and wherein the $C_{3-10}$ cycloalkyl, $C_{6-10}$ aryl and 6-10 membered heteroaryl are each optionally substituted with 1 or 2 substituents independently selected from $R^{10}$.

In another embodiment, $Cy^1$ is selected from $C_{6-10}$ aryl and 6-10 membered heteroaryl; wherein the 6-10 membered heteroaryl each has at least one ring-forming carbon atom and 1, 2, or 3 ring-forming heteroatoms independently selected from N, O, and S; wherein a ring-forming carbon atom of the 6-10 membered heteroaryl is optionally substituted by oxo to form a carbonyl group; and wherein the $C_{6-10}$ aryl and 6-10 membered heteroaryl are each optionally substituted with 1, 2, or 3 substituents independently selected from $R^{10}$.

In yet another embodiment, $Cy^1$ is selected from $C_{6-10}$ aryl and 6-10 membered heteroaryl; wherein the 6-10 membered heteroaryl has at least one ring-forming carbon atom and 1 ring-forming heteroatom independently selected from N and S; and wherein the $C_{6-10}$ aryl and 6-10 membered heteroaryl are each optionally substituted with 1, 2, or 3 substituents independently selected from $R^{10}$.

In an embodiment, $Cy^1$ is phenyl; wherein the phenyl is optionally substituted with 1 or 2 substituents independently selected from $R^{10}$. In another embodiment, $Cy^1$ is 2,3-dichlorophenyl.

In still another embodiment, $Cy^1$ is phenyl, naphthyl, indole, benzothiophene, and isoquinoline, all of which are each optionally substituted with 1, 2, or 3 substituents independently selected from $R^{10}$.

In an embodiment, $Cy^1$ is phenyl optionally substituted with 1, 2, or 3 substituents independently selected from $R^{10}$. In another embodiment, $Cy^1$ is naphthyl optionally substituted with 1, 2, or 3 substituents independently selected from $R^{10}$. In another embodiment, $Cy^1$ is indolyl optionally substituted with 1, 2, or 3 substituents independently selected from $R^{10}$. In yet another embodiment, $Cy^1$ is benzothiophenyl optionally substituted with 1, 2, or 3 substituents independently selected from $R^{10}$. In an embodiment, $Cy^1$ is isoquinolinyl optionally substituted with 1, 2, or 3 substituents independently selected from $R^{10}$.

In still another embodiment, $R^3$ is selected from H, $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{f3}$, and $NR^{c3}R^{d3}$; wherein said $C_{1-3}$ alkyl, $C_{3-6}$cycloalkyl, 4-6 membered heterocycloalkyl, phenyl, and 5-6 membered heteroaryl are each optionally substituted with 1, 2, or 3 substituents independently selected from $R^{30}$.

In an embodiment, $R^3$ is selected from H, $C_{1-3}$ alkyl, $C_{1-3}$ haloalkyl, 4-6 membered heterocycloalkyl, 5-6 membered heteroaryl, halo, D, CN, and $OR^{f}$; wherein said $C_{1-3}$ alkyl, 4-6 membered heterocycloalkyl, and 5-6 membered heteroaryl are each optionally substituted with 1 or 2 substituents independently selected from $R^{30}$.

In another embodiment, $R^3$ is selected from $C_{1-3}$ alkyl, $C_{1-3}$ haloalkyl, 4-6 membered heterocycloalkyl, 5-6 membered heteroaryl, and $OR^{f3}$; wherein said $C_{1-3}$ alkyl, 4-6 membered heterocycloalkyl, and 5-6 membered heteroaryl are each optionally substituted with 1 or 2 substituents independently selected from $R^{30}$.

In an embodiment, $R^3$ is selected from H, $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $C(O)NR^{c3}R^{d3}$, and $NR^{c3}C(O)R^{b3}$; wherein said $C_{1-3}$ alkyl, $C_{3-6}$ cycloalkyl, 4-6 membered heterocycloalkyl, phenyl, and 5-6 membered heteroaryl are each optionally substituted with 1, 2, or 3 substituents independently selected from $R^{30}$.

In another embodiment, $R^3$ is selected from H, $C_{1-3}$ alkyl, $C_{1-3}$ haloalkyl, 4-6 membered heterocycloalkyl, phenyl, and 5-6 membered heteroaryl; wherein said $C_{1-3}$ alkyl, 4-6 membered heterocycloalkyl, phenyl, and 5-6 membered heteroaryl are each optionally substituted with 1, 2, or 3 substituents independently selected from $R^{30}$.

In an embodiment, $R^3$ is selected from H, $C_{1-3}$ alkyl, $C_{1-3}$ haloalkyl, 4-6 membered heterocycloalkyl, and 5-6 membered heteroaryl; wherein said $C_{1-3}$ alkyl, 4-6 membered heterocycloalkyl, and 5-6 membered heteroaryl are each optionally substituted with 1 or 2 substituents independently selected from $R^{30}$. In another embodiment, $R^3$ is selected from H, $C_{1-3}$ alkyl, phenyl, and 5-6 membered heteroaryl; wherein said $C_{1-3}$ alkyl, phenyl, and 5-6 membered heteroaryl are each optionally substituted with 1, 2 or 3 substituents independently selected from $R^{30}$. In yet another embodiment, $R^3$ is selected from H, methyl, phenyl, 1,2,4-triazolyl, pyrazyl, and pyridyl; wherein said methyl, phenyl, 1,2,4-triazolyl, pyrazyl, and pyridyl are each optionally substituted with 1, 2 or 3 substituents independently selected from $R^{30}$.

In an embodiment, $R^3$ is 5-6 membered heteroaryl; wherein said 5-6 membered heteroaryl is optionally substituted with 1 or 2 substituents independently selected from $R^{30}$. In an embodiment, $R^3$ is 6 membered heteroaryl; wherein said 6 membered heteroaryl is optionally substituted with 1 or 2 substituents independently selected from $R^{30}$.

In another embodiment, $R^3$ is $C_{1-3}$ alkyl. In yet another embodiment, $R^3$ is methyl.

In yet another embodiment, $R^5$ is selected from H, $C_{1-3}$ alkyl, $C_{1-3}$ haloalkyl, cyclopropyl, halo, D, CN, and $OR^{a5}$. In still another embodiment, $R^5$ is selected from H, $C_{1-3}$ alkyl, $C_{1-3}$ haloalkyl, and D. In an embodiment, $R^5$ is selected from H, $C_{1-3}$ alkyl, $C_{1-3}$ haloalkyl, and halo. In another embodiment, $R^5$ is selected from H and halo. In yet another embodiment, $R^5$ is selected from H and chloro. In an embodiment, $R^5$ is H. In another embodiment, $R^5$ is chloro.

In another embodiment, $R^6$ is selected from H, $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a6}$, and $C(O)NR^{c6}R^{d6}$; wherein said $C_{1-3}$ alkyl, $C_{3-6}$cycloalkyl, 4-6 membered heterocycloalkyl, phenyl, and 5-6 membered heteroaryl are each optionally substituted with 1 or 2 substituents independently selected from $R^{60}$.

In yet another embodiment, $R^6$ is selected from H, $C_{1-3}$ alkyl, $C_{1-3}$ haloalkyl, 4-6 membered heterocycloalkyl, 5-6 membered heteroaryl, halo, D, and CN; wherein said $C_{1-3}$ alkyl, 4-6 membered heterocycloalkyl, and 5-6 membered heteroaryl are each optionally substituted with 1 or 2 substituents independently selected from $R^{60}$.

In yet another embodiment, $R^6$ is selected from H, $C_{1-3}$ alkyl, $C_{1-3}$ haloalkyl, 4-6 membered heterocycloalkyl, halo, D, and CN; wherein said $C_{1-3}$ alkyl and 4-6 membered heterocycloalkyl are each optionally substituted with 1 or 2 substituents independently selected from $R^{60}$.

In still another embodiment, $R^6$ is selected from H, $C_{1-3}$ alkyl, $C_{1-3}$ haloalkyl, and 5-6 membered heteroaryl; wherein said $C_{1-3}$ alkyl and 5-6 membered heteroaryl are each optionally substituted with 1 or 2 substituents independently selected from $R^{60}$.

In an embodiment, $R^6$ is selected from H, $C_{1-3}$ haloalkyl, $C_{3-6}$cycloalkyl, 4-8 membered heterocycloalkyl, phenyl, 5-6 membered heteroaryl, halo, D, CN, $OR^{a6}$, and $C(O)NR^{c6}R^{d6}$; wherein said $C_{3-6}$cycloalkyl, 4-8 membered heterocycloalkyl, phenyl, and 5-6 membered heteroaryl are each optionally substituted with 1 or 2 substituents independently selected from $R^{60}$; or $R^6$ is $C_{1-3}$ alkyl; wherein said $C_{1-3}$ alkyl is substituted with 1 or 2 substituents independently selected from $R^{60}$.

In an embodiment, $R^6$ is selected from H, $C_{1-3}$ haloalkyl, 4-8 membered heterocycloalkyl, and 5-6 membered heteroaryl; wherein said 4-8 membered heterocycloalkyl and 5-6 membered heteroaryl are each optionally substituted with 1 or 2 substituents independently selected from $R^{60}$; or $R^6$ is selected from $C_{1-3}$ alkyl; wherein said $C_{1-3}$ alkyl is substituted with 1 or 2 substituents independently selected from $R^{60}$.

In an embodiment, $R^6$ is selected from 4-6 membered heterocycloalkyl and 5-6 membered heteroaryl; wherein said 4-6 membered heterocycloalkyl and 5-6 membered heteroaryl are each optionally substituted with 1 or 2 substituents independently selected from $R^{60}$; or $R^6$ is selected from $C_{1-3}$ alkyl; wherein said $C_{1-3}$ alkyl is substituted with 1 or 2 substituents independently selected from $R^{60}$.

In an embodiment, $R^6$ is selected from pyrrolidinyl, 2-azabicyclo[3.1.0]hexanyl, and 5-oxo-1,2,3,5-tetrahydroindolizin-3-yl; wherein said pyrrolidinyl, 2-azabicyclo[3.1.0]hexanyl, and 5-oxo-1,2,3,5-tetrahydroindolizin-3-yl are optionally substituted with 1 or 2 substituents independently selected from $R^{60}$; or $R^6$ is $C_{1-2}$ alkyl; wherein said $C_{1-2}$ alkyl is substituted with 1 or 2 substituents independently selected from $R^{60}$.

In an embodiment, $R^7$ is selected from H, $C_{1-3}$ alkyl, $C_{1-3}$ haloalkyl, cyclopropyl, halo, D, CN, and $OR^{a7}$. In another embodiment, $R^7$ is selected from H, $C_{1-3}$ alkyl, $C_{1-3}$ haloalkyl, halo, D, and CN. In another embodiment, $R^7$ is selected from H, $C_{1-3}$ alkyl, $C_{1-3}$ haloalkyl, halo, and CN. In yet another embodiment, $R^7$ is halo. In an embodiment, $R^7$ is F.

In still another embodiment, $Cy^2$ is selected from

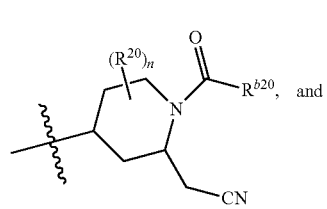

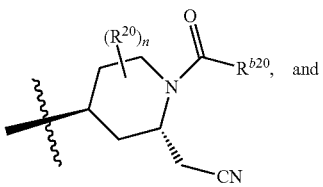

wherein n is 0 or 1.

In an embodiment, $Cy^2$ is selected from

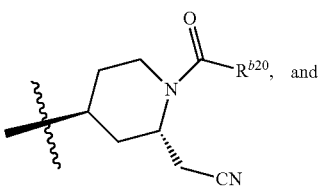

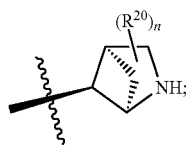

wherein n is 0 or 1.

In another embodiment, $Cy^2$ is selected from

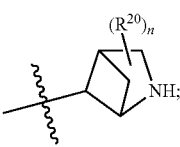

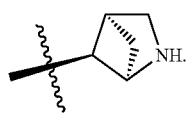

In an embodiment, $Cy^2$ is selected from $Cy^2$-a and $Cy^2$-b; wherein n is 0. In an embodiment, $Cy^2$ is $Cy^2$-b; wherein n is 0. In an embodiment, $Cy^2$ is selected from $Cy^2$-a; wherein n is 0. In another embodiment, $Cy^2$ is $Cy^2$-a. In yet another embodiment, $Cy^2$ is $Cy^2$-b.

In still another embodiment, n is 0 or 1. In an embodiment, n is 0. In an embodiment, n is 1. In yet another embodiment, n is 2.

In still another embodiment, each $R^{10}$ is independently selected from $C_{1-3}$ alkyl, $C_{1-3}$ haloalkyl, halo, D, CN, $OR^{a10}$, and $NR^{c10}R^{d10}$. In an embodiment, each $R^{10}$ is independently selected from $C_{1-3}$ alkyl, $C_{1-3}$ haloalkyl, halo, D, CN, and $OR^{a10}$. In another embodiment, each $R^{10}$ is independently selected from $C_{1-3}$ alkyl, $C_{1-3}$ haloalkyl, halo, CN, and $OR^{a10}$. In an embodiment, each $R^{10}$ is independently selected from $C_{1-3}$ alkyl, and halo. In another embodiment, each $R^{10}$ is independently selected from methyl, fluoro, and chloro. In an embodiment, each $R^{10}$ is chloro.

In yet another embodiment, each $R^{20}$ is independently selected from $C_{1-3}$ alkyl, $C_{1-3}$ haloalkyl, halo, D, and CN.

In still another embodiment, each $R^{30}$ is independently selected from $C_{1-3}$ alkyl, $C_{1-3}$ haloalkyl, 4-6 membered heterocycloalkyl, 5-6 membered heteroaryl, halo, D, CN, $OR^{a30}$, and $NR^{c30}R^{d30}$; wherein said $C_{1-3}$ alkyl, 4-6 membered heterocycloalkyl, and 5-6 membered heteroaryl are each optionally substituted with 1 or 2 substituents independently selected from $R^{31}$.

In an embodiment, each $R^{30}$ is independently selected from $C_{1-3}$ alkyl, $C_{1-3}$ haloalkyl, 4-6 membered heterocycloalkyl, halo, D, CN, $OR^{a30}$, and $NR^{c30}R^{d30}$; wherein said $C_{1-3}$ alkyl and 4-6 membered heterocycloalkyl are each optionally substituted with 1 or 2 substituents independently selected from $R^{31}$.

In an embodiment, each $R^{30}$ is independently selected from $C_{1-3}$ alkyl, $C_{1-3}$ haloalkyl, 4-6 membered heterocycloalkyl, halo, D, CN, $OR^{a30}$, $C(O)NR^{c30}R^{d30}$, and $NR^{c30}R^{d30}$; wherein said $C_{1-3}$ alkyl and 4-6 membered heterocycloalkyl are each optionally substituted with 1 or 2 substituents independently selected from $R^{31}$. In an embodiment, each $R^{30}$ is independently selected from $C_{1-3}$ alkyl, halo, and $C(O)NR^{c30}R^{d30}$; wherein said $C_{1-3}$ alkyl is optionally substituted with 1 substituent selected from $R^{31}$.

In an embodiment, each $R^{30}$ is independently selected from $C_{1-3}$ alkyl, halo, D, and $C(O)NR^{c30}R^{d30}$; wherein said $C_{1-3}$ alkyl is optionally substituted with 1 substituent selected from $R^{31}$. In an embodiment, each $R^{30}$ is independently selected from methyl, fluoro, D, and $C(O)NR^{c30}R^{d30}$; wherein said methyl is optionally substituted with 1 substituent selected from $R^{31}$.

In another embodiment, each $R^{30}$ is independently selected from $C_{1-3}$ alkyl, $C_{1-3}$ haloalkyl, 4-6 membered heterocycloalkyl, halo, and $NR^{c30}R^{d30}$; wherein said $C_{1-3}$ alkyl and 4-6 membered heterocycloalkyl are each optionally substituted with 1 or 2 substituents independently selected from $R^{31}$.

In an embodiment, each $R^{31}$ is independently selected from $C_{1-3}$ alkyl, $C_{1-3}$ haloalkyl, halo, D, CN, $OR^{a31}$, and $NR^{c31}R^{d31}$. In another embodiment, each $R^{31}$ is independently selected from $C_{1-3}$ alkyl, $C_{1-3}$ haloalkyl, halo, and $NR^{c31}R^{d31}$. In an embodiment, each $R^{31}$ is independently selected from $C_{1-3}$ alkyl, $C_{1-3}$ haloalkyl, halo, CN, $OR^{a31}$, and $NR^{c31}R^{d31}$. In an embodiment, each $R^{31}$ is independently selected from $OR^{a31}$.

In another embodiment, $R^{33}$ is selected from $C_{2-3}$ alkyl, $C_{1-3}$ haloalkyl, 4-membered heterocycloalkyl, 6-membered heterocycloalkyl, halo, D, CN, $OR^{a30}$, and $NR^{c30}R^{d30}$; wherein said $C_{2-3}$ alkyl, 4-membered heterocycloalkyl, and 6-membered heterocycloalkyl are each optionally substituted with 1 or 2 substituents independently selected from $R^{31}$.

In yet another embodiment, $R^{33}$ is selected from $C_{2-3}$ alkyl, $C_{1-3}$ haloalkyl, 4-membered heterocycloalkyl, 6-membered heterocycloalkyl, halo, and CN; wherein said $C_{2-3}$ alkyl, 4-membered heterocycloalkyl, and 6-membered heterocycloalkyl are each optionally substituted with 1 or 2 substituents independently selected from $R^{31}$.

In an embodiment, each $R^{60}$ is independently selected from $C_{1-3}$ alkyl, $C_{1-3}$ haloalkyl, 4-6 membered heterocycloalkyl, 5-6 membered heteroaryl, halo, CN, $OR^{a60}$, $C(O)R^{b60}$, $C(O)NR^{c60}R^{d60}$, $C(O)OR^{a60}$, and $NR^{c60}R^{d60}$; wherein said $C_{1-3}$ alkyl, 4-6 membered heterocycloalkyl, and 5-6 membered heteroaryl are each optionally substituted with 1 or 2 substituents independently selected from $R^{61}$. In an embodiment, each $R^{60}$ is independently selected from $C_{1-3}$ alkyl, $C_{1-3}$ haloalkyl, 4-6 membered heterocycloalkyl, 5-6 membered heteroaryl, $C(O)R^{b6}$s, $C(O)NR^{c60}R^{d60}$, and $C(O)OR^{a60}$; wherein said 4-6 membered heterocycloalkyl and 5-6 membered heteroaryl are each optionally substituted with 1 or 2 substituents independently selected from $R^{61}$.

In still another embodiment, each $R^{60}$ is independently selected from $C_{1-3}$ alkyl, $C_{1-3}$ haloalkyl, 4-6 membered heterocycloalkyl, 5-6 membered heteroaryl, halo, D, CN, $OR^{a60}$, $C(O)NR^{c60}R^{d60}$ and $NR^{c60}R^{d60}$; wherein said $C_{1-3}$ alkyl, 4-6 membered heterocycloalkyl, and 5-6 membered heteroaryl are each optionally substituted with 1 or 2 substituents independently selected from $R^{61}$.

In an embodiment, each $R^{60}$ is independently selected from $C_{1-3}$ alkyl, $C_{1-3}$ haloalkyl, 4-6 membered heterocycloalkyl, halo, D, CN, $OR^{a60}$, $C(O)NR^{c60}R^{d60}$ and $NR^{c60}R^{d60}$; wherein said $C_{1-3}$ alkyl and 4-6 membered heterocycloalkyl are each optionally substituted with 1 or 2 substituents independently selected from $R^{61}$.

In another embodiment, each $R^{60}$ is independently selected from $C_{1-3}$ alkyl, $C_{1-3}$ haloalkyl, 4-6 membered heterocycloalkyl, halo, and $C(O)NR^{c60}R^{d60}$; wherein said $C_{1-3}$ alkyl and 4-6 membered heterocycloalkyl are each optionally substituted with 1 or 2 substituents independently selected from $R^{61}$.

In another embodiment, each $R^{60}$ is independently selected from $C_{1-3}$ alkyl, $C_{1-3}$ haloalkyl, 4-6 membered heterocycloalkyl, halo, $C(O)OR^{a60}$, and $C(O)NR^{c60}R^{d60}$; wherein said $C_{1-3}$ alkyl and 4-6 membered heterocycloalkyl are each optionally substituted with 1 or 2 substituents independently selected from $R^{61}$.

In an embodiment, each $R^{60}$ is independently selected from $C_{1-3}$ alkyl, $C_{1-3}$ haloalkyl, 4-6 membered heterocycloalkyl, 5-6 membered heteroaryl, halo, D, CN, $OR^{a60}$, $C(O)R^{b60}$, $C(O)NR^{c60}R^{d60}$, $NR^{c60}C(O)R^{b60}$, $C(O)OR^{a60}$, $NR^{a60}C(O)OR^{a60}$, $NR^{c60}R^{d60}$, $NR^{c60}S(O)_2R^{b60}$, and $S(O)_2R^{b60}$; wherein said $C_{1-3}$ alkyl, 4-6 membered heterocycloalkyl, and 5-6 membered heteroaryl are each optionally substituted with 1 or 2 substituents independently selected from $R^{61}$.

In another embodiment, each $R^{60}$ is independently selected from $C_{1-3}$ alkyl, 4-6 membered heterocycloalkyl, 5-6 membered heteroaryl, halo, $C(O)R^{b60}$, $C(O)NR^{c60}R^{d60}$, $NR^{c60}C(O)R^{b60}$, $C(O)OR^{a60}$, $NR^{c60}C(O)OR^{a60}$, and $NR^{c60}S(O)_2R^{b60}$; wherein said $C_{1-3}$ alkyl, 4-6 membered heterocycloalkyl, and 5-6 membered heteroaryl are each optionally substituted with 1 or 2 substituents independently selected from $R^{61}$. In another embodiment, each $R^{60}$ is independently selected from methyl, fluoro, 3-oxomorpholinyl, 2-oxopyrazin-1(2H)-yl), $C(O)R^{b60}$, $C(O)NR^{c6}R^{d60}$, $NR^{c60}C(O)R^{b60}$, $C(O)OR^{a60}$, $NR^{c60}C(O)OR^{a60}$, and $NR^{c60}S(O)_2R^{b60}$; wherein said 3-oxomorpholinyl and 2-oxopyrazin-1(2H)-yl) are each optionally substituted with 1 or 2 substituents independently selected from $R^{61}$.

In yet another embodiment, each $R^{61}$ is independently selected from $C_{1-3}$ alkyl, $C_{1-3}$ haloalkyl, halo, D, and CN. In still another embodiment, each $R^{61}$ is independently selected from $C_{1-3}$ alkyl, $C_{1-3}$ haloalkyl, and halo. In an embodiment, each $R^{61}$ is independently selected from $C_{1-3}$ alkyl, $C_{1-3}$ haloalkyl, halo, and CN. In an embodiment, each $R^{61}$ is independently selected from $C_{1-3}$ alkyl, and halo. In an embodiment, each $R^{61}$ is independently selected from methyl and fluoro.

In an embodiment, $R^{f3}$ is selected from $C_{1-3}$ haloalkyl, $C_{3-6}$cycloalkyl, 4-6 membered heterocycloalkyl, phenyl, and 5-6 membered heteroaryl; wherein said $C_{3-6}$cycloalkyl, 4-6 membered heterocycloalkyl, phenyl, and 5-6 membered heteroaryl are each optionally substituted with 1, 2, or 3 substituents independently selected from $R^{30}$; or $R^{\beta}$ is selected from

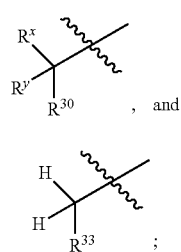

wherein $R^x$ is H or $C_{1-2}$ alkyl; and
$R^Y$ is $C_{1-2}$ alkyl.

In another embodiment, $R^{\beta}$ is selected from $C_{1-3}$ haloalkyl, 4-6 membered heterocycloalkyl, and 5-6 membered heteroaryl; wherein said 4-6 membered heterocycloalkyl and 5-6 membered heteroaryl are each optionally substituted with 1 or 2 substituents independently selected from $R^{30}$; or
$R^{\beta}$ is selected from $R^{\beta}$-a and $R^{\beta}$-b;
wherein $R^x$ is H or $C_{1-2}$ alkyl; and
$R^Y$ is $C_{1-2}$ alkyl.

In yet another embodiment, $R^{\beta}$ is $C_{1-3}$ haloalkyl; or $R^{\beta}$ is selected from $R^{\beta}$-a and $R^3$-b; wherein $R^x$ is H or $C_{1-2}$ alkyl and $R^y$ is $C_{1-2}$ alkyl.

In still another embodiment, $R^{\beta}$ is $R^{\beta}$-a. In an embodiment, $R^{\beta}$ is $R^{\beta}$-b.

In another embodiment, $R^x$ is H. In yet another embodiment, $R^x$ is $C_{1-2}$ alkyl.

In an embodiment, each $R^{a30}$, $R^{b30}$, $R^{c30}$ and $R^{d30}$ is independently selected from H, $C_{1-3}$ alkyl, and $C_{1-3}$ haloalkyl.

In an embodiment, each $R^{a30}$, $R^{c30}$ and $R^{d30}$ is independently selected from H, $C_1$-3 alkyl, and $C_{1-3}$ haloalkyl. In an embodiment, each $R^{a30}$, $R^{c30}$ and $R^{d30}$ is independently selected from H, and $C_{1-3}$ alkyl. In another embodiment, each $R^{c30}$ and $R^{d30}$ is independently selected from H and $C_{1-3}$ alkyl. In yet another embodiment, each $R^{c30}$ and $R^{d30}$ is independently selected from H and methyl.

In another embodiment, each $R^{a31}$, $R^{b31}$, $R^{c31}$ and $R^{d31}$ is independently selected from H, $C_{1-3}$ alkyl, and $C_{1-3}$ haloalkyl. In another embodiment, each $R^{a31}$, $R^{c31}$ and $R^{d31}$ is independently selected from H and $C_{1-3}$ alkyl. In yet another embodiment, each $R^{a31}$ is independently selected from H and methyl.

In an embodiment, each $R^{a60}$, $R^{c60}$ and $R^{d60}$ is independently selected from H, $C_{1-3}$ alkyl, and $C_{1-3}$ haloalkyl; or any $R^{c60}$ and $R^{d60}$ attached to the same N atom, together with the N atom to which they are attached, form a 4-membered heterocycloalkyl group.

In another embodiment, each $R^{c60}$ and $R^{d60}$ is independently selected from H, $C_{1-3}$ alkyl, and $C_{1-3}$ haloalkyl; or any $R^{c60}$ and $R^{d60}$ attached to the same N atom, together with the N atom to which they are attached, form a 4-membered heterocycloalkyl group. In yet another embodiment, each $R^{c60}$ and $R^{d60}$ is independently selected from H, $C_{23}$ alkyl, and $C_{1-3}$ haloalkyl; or any $R^{c60}$ and $R^{d60}$ attached to the same N atom, together with the N atom to which they are attached, form a 4-membered heterocycloalkyl group.

In an embodiment, each $R^{a60}$, $R^{b60}$, $R^{c60}$ and $R^{d60}$ is independently selected from H, $C_{1-3}$ alkyl, $C_{1-3}$ haloalkyl, and $C_{3-6}$cycloalkyl; wherein said $C_{1-3}$ alkyl and $C_{3-6}$cycloalkyl are each optionally substituted with 1 or 2 substituents independently selected from $R^{61}$; or any $R^{c60}$ and $R^{d60}$ attached to the same N atom, together with the N atom to which they are attached, form a 4-, 5-, or 6-membered heterocycloalkyl group optionally substituted with 1 or 2 substituents independently selected from $R^{61}$.

In an embodiment, each $R^{a60}$, $R^{b60}$, $R^{c60}$ and $R^{d60}$ is independently selected from H, $C_{1-3}$ alkyl, and $C_{3-6}$ cycloalkyl; wherein said $C_{1-3}$ alkyl and $C_{3-6}$ cycloalkyl are each optionally substituted with 1 or 2 substituents independently selected from $R^{61}$;
or any $R^{c60}$ and $R^{d60}$ attached to the same N atom, together with the N atom to which they are attached, form a 4-, 5-, or 6-membered heterocycloalkyl group optionally substituted with 1 or 2 substituents independently selected from $R^{61}$.

In an embodiment, each $R^{a60}$, $R^{b60}$, $R^{c60}$ and $R^{d60}$ is independently selected from H, $C_{1-3}$ alkyl, $C_{1-3}$ haloalkyl, $C_{3-6}$ cycloalkyl, 4-6 membered heterocycloalkyl, and 5-6 membered heteroaryl; wherein said $C_{1-3}$ alkyl, $C_{3-6}$ cycloalkyl, 4-6 membered heterocycloalkyl, and 5-6 membered heteroaryl are each optionally substituted with 1 or 2 substituents independently selected from $R^{61}$;
or any $R^{c60}$ and $R^{d60}$ attached to the same N atom, together with the N atom to which they are attached, form a 4-, 5-, or 6-membered heterocycloalkyl group optionally substituted with 1 or 2 substituents independently selected from $R^{61}$.

In another embodiment, each $R^{a60}$, $R^{b60}$, $R^{c60}$ and $R^{d60}$ is independently selected from H, $C_{1-2}$ alkyl, $C_1$ haloalkyl, cyclopropyl, tetrahydrofuranyl, and thiazolyl; wherein said $C_{1-2}$ alkyl, cyclopropyl, tetrahydrofuranyl, and thiazolyl are each optionally substituted with 1 or 2 substituents independently selected from $R^{61}$;
or any $R^{c60}$ and $R^{d60}$ attached to the same N atom, together with the N atom to which they are attached, form an azetidinyl group optionally substituted with 1 or 2 substituents independently selected from $R^{61}$.

In an embodiment, the compound of Formula I, or a pharmaceutically acceptable salt thereof, is deuterated.

In still another embodiment, the compound of Formula I is other than 3-(1-(((1R,4R,5S)-2-azabicyclo[2.1.1]hexan-5-yl)-8-(2-cyanoethyl)-4-ethoxy-6-fluoro-7-(3-hydroxynaphthalen-1-yl)-1H-pyrrolo[3,2-c]quinolin-2-yl)-N,N-dimethylpropanamide.

In some embodiments:
Y is $CR^6$—
$R^1$ is H;
$R^2$ is $C_{1-3}$ alkyl, which is substituted by CN;
$Cy^1$ is phenyl substituted with 1 or 2 substituents independently selected from $R^{10}$ wherein each $R^{10}$ is independently halo;
$R^3$ is selected from —$CH_3$, —$CH(CH_3)$—OH and 6-membered heteroaryl substituted with —$C(CH_3)_2$OH;
$R^5$ is H;
$R^6$ is selected from –6-membered heterocycloalkyl-C(O)$R^{b60}$, —$CH(CH_3)$—$R^{60}$, and —$CH(CH_3)$—NHC(O)$R^{b60}$;
$R^7$ is halo;
$Cy^2$ is

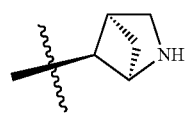

$R^{60}$ is 6-membered heterocyclalkyl;
$R^{b60}$ is $C_{3-4}$ cycloalkyl, which is substituted with $R^{61}$; and
$R^{61}$ is halo.

In a further embodiment, R² is CH₂CH₂CN.
In another embodiment, R¹⁰ is Cl.
In another embodiment, Cy¹ is 2,3-dichlorophenyl.
In a further embodiment, R³ is —CH₃. In another embodiment, R³ is —CH(CH₃)—OH. In a further embodiment, R³ is 6-membered heteroaryl substituted with —C(CH₃)₂OH. In a further embodiment, R³ is pyridine substituted with —C(CH₃)₂OH.
In another embodiment, R⁶ is —CH(CH₃)—R⁶⁰. In a further embodiment, R⁶ is —CH(CH₃)—NHC(O)R^{b60}. In another embodiment, R⁶ is 6-membered heterocycloalkyl-C(O)R^{b60}.
In a further embodiment, R⁶ is —CH(CH₃)—R⁶⁰, wherein R⁶⁰ is

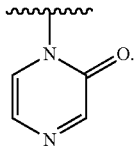 [SMILES: *n1ccncc1=O]

In another embodiment, R⁶ is —CH(CH₃)—NHC(O)R^{b60}, wherein R^{b60} is 1-fluorocycloalkyl. In a further embodiment, R⁶ is

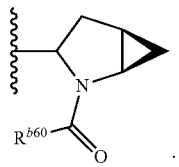

In another embodiment, R⁶ is

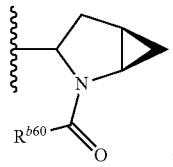

wherein R^{b60} is 1-fluorocycloalkyl.
In a further embodiment, R⁷ is F.
In still another embodiment, the compound of Formula I is selected from:
3-(1-((1R,4R,5S)-2-Azabicyclo[2.1.1]hexan-5-yl)-7-(7-chloro-3-hydroxynaphthalen-1-yl)-6-fluoro-2-methyl-4-(1H-1,2,4-triazol-1-yl)-1H-pyrrolo[3,2-c]quinolin-8-yl)propanenitrile;
3-(1-((1R,4R,5S)-2-Azabicyclo[2.1.1]hexan-5-yl)-7-(5,7-difluoro-1H-indol-3-yl)-6-fluoro-2-methyl-4-((S)-1-((S)-1-methylpyrrolidin-2-yl)ethoxy)-1H-pyrrolo[3,2-c]quinolin-8-yl)propanenitrile;
3-(1-((1R,4R,5S)-2-Azabicyclo[2.1.1]hexan-5-yl)-6-fluoro-7-(6-fluoro-5-methyl-1H-indol-3-yl)-2-methyl-4-((S)-1-((S)-1-methylpyrrolidin-2-yl)ethoxy)-1H-pyrrolo[3,2-c]quinolin-8-yl)propanenitrile;
3-(2-(3-(Azetidin-1-yl)-3-oxopropyl)-1-((1R,4R,5S)-2-azabicyclo[2.1.1]hexan-5-yl)-7-(2,3-dichlorophenyl)-6-fluoro-4-((S)-1-((S)-1-methylpyrrolidin-2-yl)ethoxy)-1H-pyrrolo[3,2-c]quinolin-8-yl)propanenitrile;
3-((1-((1R,4R,5S)-2-Azabicyclo[2.1.1]hexan-5-yl)-6-fluoro-7-(3-hydroxynaphthalen-1-yl)-8-methyl-4-((S)-1-((S)-1-methylpyrrolidin-2-yl)ethoxy)-1H-pyrrolo[3,2-c]quinolin-2-yl)methyl)oxazolidin-2-one;
8-(1-((1R,4R,5S)-2-Azabicyclo[2.1.1]hexan-5-yl)-6-fluoro-2,8-dimethyl-4-((S)-1-((S)-1-methylpyrrolidin-2-yl)ethoxy)-1H-pyrrolo[3,2-c]quinolin-7-yl)-1-naphthonitrile;
1-((2S,4S)-1-Acetyl-2-(cyanomethyl)piperidin-4-yl)-7-(8-cyanonaphthalen-1-yl)-6-fluoro-4-((S)-1-((S)-1-methylpyrrolidin-2-yl)ethoxy)-1H-pyrazolo[4,3-c]quinoline-8-carbonitrile;
8-(1-((1R,4R,5S)-2-Azabicyclo[2.1.1]hexan-5-yl)-6-fluoro-8-methyl-4-((S)-1-((S)-1-methylpyrrolidin-2-yl)ethoxy)-2-((3-oxomorpholino)methyl)-1H-pyrrolo[3,2-c]quinolin-7-yl)-1-naphthonitrile;
3-(7-(Benzo[b]thiophen-3-yl)-1-((1R,4R,5S)-2-azabicyclo[2.1.1]hexan-5-yl)-6-fluoro-4-((S)-1-((S)-1-methylpyrrolidin-2-yl)ethoxy)-2-((2-oxopyrrolidin-1-yl)methyl)-1H-pyrrolo[3,2-c]quinolin-8-yl)propanenitrile;
3-(1-((1R,4R,5S)-2-Azabicyclo[2.1.1]hexan-5-yl)-4-(((S)-1-(dimethylamino)propan-2-yl)oxy)-6-fluoro-7-(7-fluoronaphthalen-1-yl)-2-((2-oxopyrrolidin-1-yl)methyl)-1H-pyrrolo[3,2-c]quinolin-8-yl)propanenitrile;
8-(1-((1R,4R,5S)-2-Azabicyclo[2.1.1]hexan-5-yl)-8-(2-cyanoethyl)-6-fluoro-2-methyl-4-((S)-1-((S)-1-methylpyrrolidin-2-yl)ethoxy)-1H-pyrrolo[3,2-c]quinolin-7-yl)-1-naphthonitrile;
3-(1-((1R,4R,5S)-2-Azabicyclo[2.1.1]hexan-5-yl)-7-(2,3-dichloro-5-hydroxyphenyl)-6-fluoro-2-methyl-4-((S)-1-((S)-1-methylpyrrolidin-2-yl)ethoxy)-1H-pyrrolo[3,2-c]quinolin-8-yl)propanenitrile;
3-(1-((1R,4R,5S)-2-Azabicyclo[2.1.1]hexan-5-yl)-8-(2-cyanoethyl)-6-fluoro-4-((3-fluoro-1-methylazetidin-3-yl)methoxy)-7-(3-hydroxynaphthalen-1-yl)-1H-pyrrolo[3,2-c]quinolin-2-yl)-N,N-dimethylpropanamide;
3-(1-((1R,4R,5S)-2-Azabicyclo[2.1.1]hexan-5-yl)-6-fluoro-7-(3-hydroxynaphthalen-1-yl)-2-methyl-4-(5-methylpyrazin-2-yl)-1H-pyrrolo[3,2-c]quinolin-8-yl)propanenitrile;
3-(1-((1R,4R,5S)-2-Azabicyclo[2.1.1]hexan-5-yl)-6-fluoro-7-(7-fluoronaphthalen-1-yl)-4-methyl-2-((4-methyl-2-oxopiperazin-1-yl)methyl)-1H-pyrrolo[3,2-c]quinolin-8-yl)propanenitrile;
3-(1-((1R,4R,5S)-2-azabicyclo[2.1.1]hexan-5-yl)-7-(2,3-dichloro-5-hydroxyphenyl)-4-ethoxy-6-fluoro-2-((4-isopropyl-2-oxopiperazin-1-yl)methyl)-1H-pyrrolo[3,2-c]quinolin-8-yl)propanenitrile;
3-(1-((1R,4R,5S)-2-Azabicyclo[2.1.1]hexan-5-yl)-4-(3-(dimethylamino)-3-methylazetidin-1-yl)-6-fluoro-7-(7-fluoronaphthalen-1-yl)-2-((3-oxomorpholino)methyl)-1H-pyrrolo[3,2-c]quinolin-8-yl)propanenitrile;
3-(1-((1R,4R,5S)-2-azabicyclo[2.1.1]hexan-5-yl)-4-ethoxy-6-fluoro-7-(3-hydroxynaphthalen-1-yl)-2-(1-(3-oxomorpholino)ethyl)-1H-pyrrolo[3,2-c]quinolin-8-yl)propanenitrile;
3-(1-((endo)-2-Azabicyclo[2.1.1]hexan-5-yl)-6-fluoro-7-(3-hydroxynaphthalen-1-yl)-4-((S)-1-((S)-1-methylpyrrolidin-2-yl)ethoxy)-2-(pyridin-3-yl)-1H-pyrrolo[3,2-c]quinolin-8-yl)propanenitrile;
3-(2-(3-(azetidin-1-yl)-3-oxopropyl)-1-((1R,4R,5S)-2-azabicyclo[2.1.1]hexan-5-yl)-7-(7,8-difluoronaphthalen-1-yl)-6-fluoro-4-((S)-1-((S)-1-methylpyrrolidin-2-yl)ethoxy)-1H-pyrrolo[3,2-c]quinolin-8-yl)propanenitrile;
3-(2-(3-(azetidin-1-yl)-3-oxopropyl)-1-((1R,4R,5S)-2-azabicyclo[2.1.1]hexan-5-yl)-7-(6,7-difluoronaphthalen- 1-yl)-6-fluoro-4-((S)-1-((S)-1-methylpyrrolidin-2-yl)
ethoxy)-1H-pyrrolo[3,2-c]quinolin-8-yl)propanenitrile;
3-(1-((1R,4R,5S)-2-azabicyclo[2.1.1]hexan-5-yl)-6-fluoro-
7-(7-fluoro-3-hydroxynaphthalen-1-yl)-2-methyl-4-((S)-
1-((S)-1-methylpyrrolidin-2-yl)ethoxy)-1H-pyrrolo[3,2-
c]quinolin-8-yl)propanenitrile;
1-(1-((2S,4S)-1-Acetyl-2-(cyanomethyl)piperidin-4-yl)-8-
chloro-6-fluoro-4-((S)-1-((S)-1-methylpyrrolidin-2-yl)
ethoxy)-1H-pyrazolo[4,3-c]quinolin-7-yl)isoquinoline-8-
carbonitrile;
8-(1-((2S,4S)-1-acetyl-2-(cyanomethyl)piperidin-4-yl)-8-
chloro-6-fluoro-4-((S)-1-((S)-1-methylpyrrolidin-2-yl)
ethoxy)-1H-pyrrolo[3,2-c]quinolin-7-yl)-1-naphthoni-
trile;
8-(1-((2S,4S)-1-acetyl-2-(cyanomethyl)piperidin-4-yl)-8-
chloro-6-fluoro-4-((S)-1-((S)-1-methylpyrrolidin-2-yl)
ethoxy)-1H-pyrazolo[4,3-c]quinolin-7-yl)-1-naphthoni-
trile;
3-(1-((1R,4R,5S)-2-Azabicyclo[2.1.1]hexan-5-yl)-6-fluoro-
7-(7-fluoro-3-hydroxynaphthalen-1-yl)-2-methyl-4-(1H-
1,2,4-triazol-1-yl)-1H-pyrrolo[3,2-c]quinolin-8-yl)propa-
nenitrile; and
3-(1-((1R,4R,5S)-2-Azabicyclo[2.1.1]hexan-5-yl)-6-fluoro-
7-(7-fluoronaphthalen-1-yl)-2-methyl-4-((S)-1-((S)-1-
methylpyrrolidin-2-yl)ethoxy)-1H-pyrrolo[3,2-c]quino-
lin-8-yl)propanenitrile;
or a pharmaceutically acceptable salt thereof.
In another embodiment, the compound of Formula I is selected from:
3-(1-((1R,4R,5S)-2-Azabicyclo[2.1.1]hexan-5-yl)-7-(7-
chloro-3-hydroxynaphthalen-1-yl)-6-fluoro-2-methyl-4-
(1H-1,2,4-triazol-1-yl)-1H-pyrrolo[3,2-c]quinolin-8-yl)
propanenitrile;
3-(1-((1R,4R,5S)-2-Azabicyclo[2.1.1]hexan-5-yl)-7-(5,7-
difluoro-1H-indol-3-yl)-6-fluoro-2-methyl-4-((S)-1-((S)-
1-methylpyrrolidin-2-yl)ethoxy)-1H-pyrrolo[3,2-c]qui-
nolin-8-yl)propanenitrile;
3-(1-((1R,4R,5S)-2-Azabicyclo[2.1.1]hexan-5-yl)-6-fluoro-
7-(6-fluoro-5-methyl-1H-indol-3-yl)-2-methyl-4-((S)-1-
((S)-1-methylpyrrolidin-2-yl)ethoxy)-1H-pyrrolo[3,2-c]
quinolin-8-yl)propanenitrile;
3-(2-(3-(Azetidin-1-yl)-3-oxopropyl)-1-((1R,4R,5S)-2-
azabicyclo[2.1.1]hexan-5-yl)-7-(2,3-dichlorophenyl)-6-
fluoro-4-((S)-1-((S)-1-methylpyrrolidin-2-yl)ethoxy)-
1H-pyrrolo[3,2-c]quinolin-8-yl)propanenitrile;
3-((1-((1R,4R,5S)-2-Azabicyclo[2.1.1]hexan-5-yl)-6-
fluoro-7-(3-hydroxynaphthalen-1-yl)-8-methyl-4-((S)-1-
((S)-1-methylpyrrolidin-2-yl)ethoxy)-1H-pyrrolo[3,2-c]
quinolin-2-yl)methyl)oxazolidin-2-one;
8-(1-((1R,4R,5S)-2-Azabicyclo[2.1.1]hexan-5-yl)-6-fluoro-
2,8-dimethyl-4-((S)-1-((S)-1-methylpyrrolidin-2-yl)
ethoxy)-1H-pyrrolo[3,2-c]quinolin-7-yl)-1-naphthoni-
trile;
1-((2S,4S)-1-Acetyl-2-(cyanomethyl)piperidin-4-yl)-7-(8-
cyanonaphthalen-1-yl)-6-fluoro-4-((S)-1-((S)-1-meth-
ylpyrrolidin-2-yl)ethoxy)-1H-pyrazolo[4,3-c]quinoline-
8-carbonitrile;
8-(1-((1R,4R,5S)-2-Azabicyclo[2.1.1]hexan-5-yl)-6-fluoro-
8-methyl-4-((S)-1-((S)-1-methylpyrrolidin-2-yl)ethoxy)-
2-((3-oxomorpholino)methyl)-1H-pyrrolo[3,2-c]quino-
lin-7-yl)-1-naphthonitrile;
3-(7-(Benzo[b]thiophen-3-yl)-1-((1R,4R,5S)-2-azabicyclo
[2.1.1]hexan-5-yl)-6-fluoro-4-((S)-1-((S)-1-methylpyrro-
lidin-2-yl)ethoxy)-2-((2-oxopyrrolidin-1-yl)methyl)-1H-
pyrrolo[3,2-c]quinolin-8-yl)propanenitrile;
3-(1-((1R,4R,5S)-2-Azabicyclo[2.1.1]hexan-5-yl)-4-(((S)-
1-(dimethylamino)propan-2-yl)oxy)-6-fluoro-7-(7-fluo-
ronaphthalen-1-yl)-2-((2-oxopyrrolidin-1-yl)methyl)-1H-
pyrrolo[3,2-c]quinolin-8-yl)propanenitrile;
8-(1-((1R,4R,5S)-2-Azabicyclo[2.1.1]hexan-5-yl)-8-(2-cya-
noethyl)-6-fluoro-2-methyl-4-((S)-1-((S)-1-methylpyrro-
lidin-2-yl)ethoxy)-1H-pyrrolo[3,2-c]quinolin-7-yl)-1-
naphthonitrile;
3-(1-((1R,4R,5S)-2-Azabicyclo[2.1.1]hexan-5-yl)-7-(2,3-
dichloro-5-hydroxyphenyl)-6-fluoro-2-methyl-4-((S)-1-
((S)-1-methylpyrrolidin-2-yl)ethoxy)-1H-pyrrolo[3,2-c]
quinolin-8-yl)propanenitrile;
3-(1-((1R,4R,5S)-2-Azabicyclo[2.1.1]hexan-5-yl)-8-(2-cya-
noethyl)-6-fluoro-4-((3-fluoro-1-methylazetidin-3-yl)
methoxy)-7-(3-hydroxynaphthalen-1-yl)-1H-pyrrolo[3,2-
c]quinolin-2-yl)-N,N-dimethylpropanamide;
3-(1-((1R,4R,5S)-2-Azabicyclo[2.1.1]hexan-5-yl)-6-fluoro-
7-(3-hydroxynaphthalen-1-yl)-2-methyl-4-(5-meth-
ylpyrazin-2-yl)-1H-pyrrolo[3,2-c]quinolin-8-yl)propa-
nenitrile;
3-(1-((1R,4R,5S)-2-Azabicyclo[2.1.1]hexan-5-yl)-6-fluoro-
7-(7-fluoronaphthalen-1-yl)-4-methyl-2-((4-methyl-2-
oxopiperazin-1-yl)methyl)-1H-pyrrolo[3,2-c]quinolin-8-
yl)propanenitrile;
3-(1-((1R,4R,5S)-2-Azabicyclo[2.1.1]hexan-5-yl)-4-(3-(di-
methylamino)-3-methylazetidin-1-yl)-6-fluoro-7-(7-fluo-
ronaphthalen-1-yl)-2-((3-oxomorpholino)methyl)-1H-
pyrrolo[3,2-c]quinolin-8-yl)propanenitrile;
3-(1-((endo)-2-Azabicyclo[2.1.1]hexan-5-yl)-6-fluoro-7-(3-
hydroxynaphthalen-1-yl)-4-((S)-1-((S)-1-methylpyrroli-
din-2-yl)ethoxy)-2-(pyridin-3-yl)-1H-pyrrolo[3,2-c]qui-
nolin-8-yl)propanenitrile;
3-(2-(3-(azetidin-1-yl)-3-oxopropyl)-1-((1R,4R,5S)-2-
azabicyclo[2.1.1]hexan-5-yl)-7-(7,8-difluoronaphthalen-
1-yl)-6-fluoro-4-((S)-1-((S)-1-methylpyrrolidin-2-yl)
ethoxy)-1H-pyrrolo[3,2-c]quinolin-8-yl)propanenitrile;
3-(2-(3-(azetidin-1-yl)-3-oxopropyl)-1-((1R,4R,5S)-2-
azabicyclo[2.1.1]hexan-5-yl)-7-(6,7-difluoronaphthalen-
1-yl)-6-fluoro-4-((S)-1-((S)-1-methylpyrrolidin-2-yl)
ethoxy)-1H-pyrrolo[3,2-c]quinolin-8-yl)propanenitrile;
3-(1-((1R,4R,5S)-2-azabicyclo[2.1.1]hexan-5-yl)-6-fluoro-
7-(7-fluoro-3-hydroxynaphthalen-1-yl)-2-methyl-4-((S)-
1-((S)-1-methylpyrrolidin-2-yl)ethoxy)-1H-pyrrolo[3,2-
c]quinolin-8-yl)propanenitrile;
1-(1-((2S,4S)-1-Acetyl-2-(cyanomethyl)piperidin-4-yl)-8-
chloro-6-fluoro-4-((S)-1-((S)-1-methylpyrrolidin-2-yl)
ethoxy)-1H-pyrazolo[4,3-c]quinolin-7-yl)isoquinoline-8-
carbonitrile;
8-(1-((2S,4S)-1-acetyl-2-(cyanomethyl)piperidin-4-yl)-8-
chloro-6-fluoro-4-((S)-1-((S)-1-methylpyrrolidin-2-yl)
ethoxy)-1H-pyrrolo[3,2-c]quinolin-7-yl)-1-naphthoni-
trile;
8-(1-((2S,4S)-1-acetyl-2-(cyanomethyl)piperidin-4-yl)-8-
chloro-6-fluoro-4-((S)-1-((S)-1-methylpyrrolidin-2-yl)
ethoxy)-1H-pyrazolo[4,3-c]quinolin-7-yl)-1-naphthoni-
trile;
3-(1-((1R,4R,5S)-2-Azabicyclo[2.1.1]hexan-5-yl)-6-fluoro-
7-(7-fluoro-3-hydroxynaphthalen-1-yl)-2-methyl-4-(1H-
1,2,4-triazol-1-yl)-1H-pyrrolo[3,2-c]quinolin-8-yl)propa-
nenitrile; and
3-(1-((1R,4R,5S)-2-Azabicyclo[2.1.1]hexan-5-yl)-6-fluoro-
7-(7-fluoronaphthalen-1-yl)-2-methyl-4-((S)-1-((S)-1-
methylpyrrolidin-2-yl)ethoxy)-1H-pyrrolo[3,2-c]quino-
lin-8-yl)propanenitrile;
or a pharmaceutically acceptable salt thereof.
In another embodiment, the compound of Formula I is selected from:

3-(1-((1R,4R,5S)-2-Azabicyclo[2.1.1]hexan-5-yl)-7-(7-chloro-3-hydroxynaphthalen-1-yl)-6-fluoro-2-methyl-4-(1H-1,2,4-triazol-1-yl)-1H-pyrrolo[3,2-c]quinolin-8-yl)propanenitrile;

3-(1-((1R,4R,5S)-2-Azabicyclo[2.1.1]hexan-5-yl)-7-(5,7-difluoro-1H-indol-3-yl)-6-fluoro-2-methyl-4-((S)-1-((S)-1-methylpyrrolidin-2-yl)ethoxy)-1H-pyrrolo[3,2-c]quinolin-8-yl)propanenitrile;

3-(1-((1R,4R,5S)-2-Azabicyclo[2.1.1]hexan-5-yl)-6-fluoro-7-(6-fluoro-5-methyl-1H-indol-3-yl)-2-methyl-4-((S)-1-((S)-1-methylpyrrolidin-2-yl)ethoxy)-1H-pyrrolo[3,2-c]quinolin-8-yl)propanenitrile;

3-(2-(3-(Azetidin-1-yl)-3-oxopropyl)-1-((1R,4R,5S)-2-azabicyclo[2.1.1]hexan-5-yl)-7-(2,3-dichlorophenyl)-6-fluoro-4-((S)-1-((S)-1-methylpyrrolidin-2-yl)ethoxy)-1H-pyrrolo[3,2-c]quinolin-8-yl)propanenitrile;

3-((1-((1R,4R,5S)-2-Azabicyclo[2.1.1]hexan-5-yl)-6-fluoro-7-(3-hydroxynaphthalen-1-yl)-8-methyl-4-((S)-1-((S)-1-methylpyrrolidin-2-yl)ethoxy)-1H-pyrrolo[3,2-c]quinolin-2-yl)methyl)oxazolidin-2-one;

8-(1-((1R,4R,5S)-2-Azabicyclo[2.1.1]hexan-5-yl)-6-fluoro-2,8-dimethyl-4-((S)-1-((S)-1-methylpyrrolidin-2-yl)ethoxy)-1H-pyrrolo[3,2-c]quinolin-7-yl)-1-naphthonitrile;

1-((2S,4S)-1-Acetyl-2-(cyanomethyl)piperidin-4-yl)-7-(8-cyanonaphthalen-1-yl)-6-fluoro-4-((S)-1-((S)-1-methylpyrrolidin-2-yl)ethoxy)-1H-pyrazolo[4,3-c]quinoline-8-carbonitrile;

8-(1-((1R,4R,5S)-2-Azabicyclo[2.1.1]hexan-5-yl)-6-fluoro-8-methyl-4-((S)-1-((S)-1-methylpyrrolidin-2-yl)ethoxy)-2-((3-oxomorpholino)methyl)-1H-pyrrolo[3,2-c]quinolin-7-yl)-1-naphthonitrile;

3-(7-(Benzo[b]thiophen-3-yl)-1-((1R,4R,5S)-2-azabicyclo[2.1.1]hexan-5-yl)-6-fluoro-4-((S)-1-((S)-1-methylpyrrolidin-2-yl)ethoxy)-2-((2-oxopyrrolidin-1-yl)methyl)-1H-pyrrolo[3,2-c]quinolin-8-yl)propanenitrile;

3-(1-((1R,4R,5S)-2-Azabicyclo[2.1.1]hexan-5-yl)-4-(((S)-1-(dimethylamino)propan-2-yl)oxy)-6-fluoro-7-(7-fluoronaphthalen-1-yl)-2-((2-oxopyrrolidin-1-yl)methyl)-1H-pyrrolo[3,2-c]quinolin-8-yl)propanenitrile;

8-(1-((1R,4R,5S)-2-Azabicyclo[2.1.1]hexan-5-yl)-8-(2-cyanoethyl)-6-fluoro-2-methyl-4-((S)-1-((S)-1-methylpyrrolidin-2-yl)ethoxy)-1H-pyrrolo[3,2-c]quinolin-7-yl)-1-naphthonitrile;

3-(1-((1R,4R,5S)-2-Azabicyclo[2.1.1]hexan-5-yl)-7-(2,3-dichloro-5-hydroxyphenyl)-6-fluoro-2-methyl-4-((S)-1-((S)-1-methylpyrrolidin-2-yl)ethoxy)-1H-pyrrolo[3,2-c]quinolin-8-yl)propanenitrile;

3-(1-((1R,4R,5S)-2-Azabicyclo[2.1.1]hexan-5-yl)-6-fluoro-7-(3-hydroxynaphthalen-1-yl)-2-methyl-4-(5-methylpyrazin-2-yl)-1H-pyrrolo[3,2-c]quinolin-8-yl)propanenitrile;

3-(1-((1R,4R,5S)-2-Azabicyclo[2.1.1]hexan-5-yl)-6-fluoro-7-(7-fluoronaphthalen-1-yl)-4-methyl-2-((4-methyl-2-oxopiperazin-1-yl)methyl)-1H-pyrrolo[3,2-c]quinolin-8-yl)propanenitrile;

3-(1-(2-Azabicyclo[2.1.1]hexan-5-yl)-7-(2,3-dichloro-5-hydroxyphenyl)-4-ethoxy-6-fluoro-2-((4-isopropyl-2-oxopiperazin-1-yl)methyl)-1H-pyrrolo[3,2-c]quinolin-8-yl)propanenitrile;

3-(1-((1R,4R,5S)-2-Azabicyclo[2.1.1]hexan-5-yl)-4-(3-(dimethylamino)-3-methylazetidin-1-yl)-6-fluoro-7-(7-fluoronaphthalen-1-yl)-2-((3-oxomorpholino)methyl)-1H-pyrrolo[3,2-c]quinolin-8-yl)propanenitrile;

3-(1-(2-Azabicyclo[2.1.1]hexan-5-yl)-4-ethoxy-6-fluoro-7-(3-hydroxynaphthalen-1-yl)-2-(1-(3-oxomorpholino)ethyl)-1H-pyrrolo[3,2-c]quinolin-8-yl)propanenitrile;

3-(1-((endo)-2-Azabicyclo[2.1.1]hexan-5-yl)-6-fluoro-7-(3-hydroxynaphthalen-1-yl)-4-((S)-1-((S)-1-methylpyrrolidin-2-yl)ethoxy)-2-(pyridin-3-yl)-1H-pyrrolo[3,2-c]quinolin-8-yl)propanenitrile;

3-(2-(3-(azetidin-1-yl)-3-oxopropyl)-1-((1R,4R,5S)-2-azabicyclo[2.1.1]hexan-5-yl)-7-(7,8-difluoronaphthalen-1-yl)-6-fluoro-4-((S)-1-((S)-1-methylpyrrolidin-2-yl)ethoxy)-1H-pyrrolo[3,2-c]quinolin-8-yl)propanenitrile;

3-(2-(3-(azetidin-1-yl)-3-oxopropyl)-1-((1R,4R,5S)-2-azabicyclo[2.1.1]hexan-5-yl)-7-(6,7-difluoronaphthalen-1-yl)-6-fluoro-4-((S)-1-((S)-1-methylpyrrolidin-2-yl)ethoxy)-1H-pyrrolo[3,2-c]quinolin-8-yl)propanenitrile;

3-(1-((1R,4R,5S)-2-azabicyclo[2.1.1]hexan-5-yl)-6-fluoro-7-(7-fluoro-3-hydroxynaphthalen-1-yl)-2-methyl-4-((S)-1-((S)-1-methylpyrrolidin-2-yl)ethoxy)-1H-pyrrolo[3,2-c]quinolin-8-yl)propanenitrile;

1-(1-((2S,4S)-1-Acetyl-2-(cyanomethyl)piperidin-4-yl)-8-chloro-6-fluoro-4-((S)-1-((S)-1-methylpyrrolidin-2-yl)ethoxy)-1H-pyrazolo[4,3-c]quinolin-7-yl)isoquinoline-8-carbonitrile;

8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-1H-pyrrolo[3,2-c]quinolin-7-yl)-1-naphthonitrile;

8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-1H-pyrazolo[4,3-c]quinolin-7-yl)-1-naphthonitrile;

3-(1-((1R,4R,5S)-2-Azabicyclo[2.1.1]hexan-5-yl)-6-fluoro-7-(7-fluoro-3-hydroxynaphthalen-1-yl)-2-methyl-4-(1H-1,2,4-triazol-1-yl)-1H-pyrrolo[3,2-c]quinolin-8-yl)propanenitrile; and 3-(1-((1R,4R,5S)-2-Azabicyclo[2.1.1]hexan-5-yl)-6-fluoro-7-(7-fluoronaphthalen-1-yl)-2-methyl-4-((S)-1-((S)-1-methylpyrrolidin-2-yl)ethoxy)-1H-pyrrolo[3,2-c]quinolin-8-yl)propanenitrile;

or a pharmaceutically acceptable salt thereof.

In yet another embodiment, the compound of Formula I is selected from:

(2R)-2-(1-((1R,4R,5S)-2-azabicyclo[2.1.1]hexan-5-yl)-8-(2-cyanoethyl)-7-(2,3-dichlorophenyl)-6-fluoro-4-(1H-1,2,4-triazol-1-yl)-1H-pyrrolo[3,2-c]quinolin-2-yl)-N,N-dimethylpyrrolidine-1-carboxamide; and methyl (2R)-2-(1-((1R,4R,5S)-2-azabicyclo[2.1.1]hexan-5-yl)-7-(2-chloro-3-methylphenyl)-8-(2-cyanoethyl)-6-fluoro-4-(1H-1,2,4-triazol-1-yl)-1H-pyrrolo[3,2-c]quinolin-2-yl)pyrrolidine-1-carboxylate;

or a pharmaceutically acceptable salt thereof.

In another embodiment, the compound of Formula I is selected from:

Methyl (1S,3R,5S)-3-(1-((1R,4R,5S)-2-azabicyclo[2.1.1]hexan-5-yl)-8-(2-cyanoethyl)-7-(2,3-dichlorophenyl)-4-(6-(dimethylcarbamoyl)pyridin-3-yl)-6-fluoro-1H-pyrrolo[3,2-c]quinolin-2-yl)-2-azabicyclo[3.1.0]hexane-2-carboxylate;

3-(1-((1R,4R,5S)-2-Azabicyclo[2.1.1]hexan-5-yl)-7-(2,3-dichlorophenyl)-6-fluoro-4-methyl-2-(5-oxo-1,2,3,5-tetrahydroindolizin-3-yl)-1H-pyrrolo[3,2-c]quinolin-8-yl)propanenitrile;

Methyl (2R)-2-(1-((1R,4R,5S)-2-azabicyclo[2.1.1]hexan-5-yl)-8-(2-cyanoethyl)-7-(2,3-dichlorophenyl)-4-(6-(dimethylcarbamoyl)pyridin-3-yl)-6-fluoro-1H-pyrrolo[3,2-c]quinolin-2-yl)pyrrolidine-1-carboxylate;

Methyl (2R)-2-(1-((1R,4R,5S)-2-azabicyclo[2.1.1]hexan-5-yl)-8-(2-cyanoethyl)-7-(2,3-dichlorophenyl)-6-fluoro-4-(6-(methylcarbamoyl)pyridin-3-yl)-1H-pyrrolo[3,2-c]quinolin-2-yl)pyrrolidine-1-carboxylate;

3-(1-((1R,4R,5S)-2-Azabicyclo[2.1.1]hexan-5-yl)-7-(2-chloro-3-fluorophenyl)-2-((R)-1-(cyclopropanecarbonyl)pyrrolidin-2-yl)-6-fluoro-4-methyl-1H-pyrrolo[3,2-c]quinolin-8-yl)propanenitrile;

8-(2-((R)-1-Acetylpyrrolidin-2-yl)-1-((1R,4R,5S)-2-azabicyclo[2.1.1]hexan-5-yl)-6-fluoro-8-methyl-4-(2-methylpyridin-4-yl)-1H-pyrrolo[3,2-c]quinolin-7-yl)-1,2,3,4-tetrahydronaphthalene-1-carbonitrile;

5-(1-((1R,4R,5S)-2-Azabicyclo[2.1.1]hexan-5-yl)-7-(3-chloro-2-methylphenyl)-8-(2-cyanoethyl)-6-fluoro-2-((R)-1-(2-oxopyrazin-1(2H)-yl)ethyl)-1H-pyrrolo[3,2-c]quinolin-4-yl)-N-methylpicolinamide;

3-(1-((1R,4R,5S)-2-Azabicyclo[2.1.1]hexan-5-yl)-6-fluoro-7-(7-fluoronaphthalen-1-yl)-4-(6-(2-hydroxypropan-2-yl)pyridin-3-yl)-2-((R)-1-(2-oxopyrazin-1(2H)-yl)ethyl)-1H-pyrrolo[3,2-c]quinolin-8-yl)propanenitrile;

3-(1-((1R,4R,5S)-2-Azabicyclo[2.1.1]hexan-5-yl)-7-(3-chloro-2-methylphenyl)-6-fluoro-4-(5-methylpyrazin-2-yl)-2-((R)-1-(2-oxopyrazin-1(2H)-yl)ethyl)-1H-pyrrolo[3,2-c]quinolin-8-yl)propanenitrile;

Methyl (2R)-2-(1-((1R,4R,5S)-2-azabicyclo[2.1.1]hexan-5-yl)-8-(2-cyanoethyl)-7-(2,3-dichlorophenyl)-6-fluoro-4-(5-fluoro-6-(methylcarbamoyl)pyridin-3-yl)-1H-pyrrolo[3,2-c]quinolin-2-yl)pyrrolidine-1-carboxylate;

Methyl (2R)-2-(1-((1R,4R,5S)-2-azabicyclo[2.1.1]hexan-5-yl)-8-(2-cyanoethyl)-7-(2,3-dichlorophenyl)-6-fluoro-4-(6-(2-hydroxypropan-2-yl)pyridin-3-yl)-1H-pyrrolo[3,2-c]quinolin-2-yl)pyrrolidine-1-carboxylate;

Ethyl (2R)-2-(1-((1R,4R,5S)-2-azabicyclo[2.1.1]hexan-5-yl)-8-(2-cyanoethyl)-7-(2,3-dichlorophenyl)-6-fluoro-4-(6-(2-hydroxypropan-2-yl)pyridin-3-yl)-1H-pyrrolo[3,2-c]quinolin-2-yl)pyrrolidine-1-carboxylate;

3-(1-((1R,4R,5S)-2-Azabicyclo[2.1.1]hexan-5-yl)-7-(2,3-dichlorophenyl)-2-((R)-1-(3,3-difluoroazetidine-1-carbonyl)pyrrolidin-2-yl)-6-fluoro-4-(methyl-d3)-1H-pyrrolo[3,2-c]quinolin-8-yl)propanenitrile;

3-(1-((1R,4R,5S)-2-Azabicyclo[2.1.1]hexan-5-yl)-7-(2,3-dichlorophenyl)-2-((R)-1-(3,3-difluoroazetidine-1-carbonyl)pyrrolidin-2-yl)-6-fluoro-1H-pyrrolo[3,2-c]quinolin-8-yl)propanenitrile;

3-(1-((1R,4R,5S)-2-Azabicyclo[2.1.1]hexan-5-yl)-7-(3-chloro-2-methylphenyl)-6-fluoro-4-(5-methylpyrazin-2-yl)-2-((R)-1-(3-oxomorpholino)ethyl)-1H-pyrrolo[3,2-c]quinolin-8-yl)propanenitrile;

5-(1-((1R,4R,5S)-2-Azabicyclo[2.1.1]hexan-5-yl)-8-(2-cyanoethyl)-6-fluoro-7-(7-fluoronaphthalen-1-yl)-2-((R)-1-(3-oxomorpholino)ethyl)-1H-pyrrolo[3,2-c]quinolin-4-yl)-N-methylpicolinamide;

3-(1-((1R,4R,5S)-2-Azabicyclo[2.1.1]hexan-5-yl)-6-fluoro-7-(7-fluoronaphthalen-1-yl)-4-(6-(2-hydroxypropan-2-yl)pyridin-3-yl)-2-((R)-1-(3-oxomorpholino)ethyl)-1H-pyrrolo[3,2-c]quinolin-8-yl)propanenitrile;

3-(1-((1R,4R,5S)-2-Azabicyclo[2.1.1]hexan-5-yl)-6-fluoro-7-(7-fluoronaphthalen-1-yl)-4-(5-methylpyrazin-2-yl)-2-((R)-1-(3-oxomorpholino)ethyl)-1H-pyrrolo[3,2-c]quinolin-8-yl)propanenitrile;

Methyl (1R,3R,5R)-3-(1-((1R,4R,5S)-2-azabicyclo[2.1.1]hexan-5-yl)-8-(2-cyanoethyl)-7-(2,3-dichlorophenyl)-4-(6-(dimethylcarbamoyl)pyridin-3-yl)-6-fluoro-1H-pyrrolo[3,2-c]quinolin-2-yl)-2-azabicyclo[3.1.0]hexane-2-carboxylate;

3-(1-((1R,4R,5S)-2-Azabicyclo[2.1.1]hexan-5-yl)-2-((1R,3R,5R)-2-(cyclopropanecarbonyl)-2-azabicyclo[3.1.0]hexan-3-yl)-7-(2,3-dichlorophenyl)-6-fluoro-4-methyl-1H-pyrrolo[3,2-c]quinolin-8-yl)propanenitrile; and 3-(1-((1R,4R,5S)-2-Azabicyclo[2.1.1]hexan-5-yl)-7-(2,3-dichlorophenyl)-6-fluoro-4-(6-(2-hydroxypropan-2-yl)pyridin-3-yl)-2-((R)-1-(2-oxopyrazin-1(2H)-yl)ethyl)-1H-pyrrolo[3,2-c]quinolin-8-yl)propanenitrile;

or a pharmaceutically acceptable salt thereof.

In yet another embodiment, the compound of Formula I is selected from:

5-(1-((1R,4R,5S)-2-Azabicyclo[2.1.1]hexan-5-yl)-7-(3-chloro-2-methylphenyl)-8-(2-cyanoethyl)-6-fluoro-2-((R)-1-(2-oxopyrazin-1(2H)-yl)ethyl)-1H-pyrrolo[3,2-c]quinolin-4-yl)-N-methylpicolinamide;

3-(1-((1R,4R,5S)-2-Azabicyclo[2.1.1]hexan-5-yl)-7-(3-chloro-2-methylphenyl)-6-fluoro-4-(5-methylpyrazin-2-yl)-2-((R)-1-(3-oxomorpholino)ethyl)-1H-pyrrolo[3,2-c]quinolin-8-yl)propanenitrile;

3-(1-((1R,4R,5S)-2-Azabicyclo[2.1.1]hexan-5-yl)-2-((1R,3R,5R)-2-(cyclopropanecarbonyl)-2-azabicyclo[3.1.0]hexan-3-yl)-7-(2,3-dichlorophenyl)-6-fluoro-4-methyl-1H-pyrrolo[3,2-c]quinolin-8-yl)propanenitrile; and 3-(1-((1R,4R,5S)-2-Azabicyclo[2.1.1]hexan-5-yl)-7-(2,3-dichlorophenyl)-6-fluoro-4-(6-(2-hydroxypropan-2-yl)pyridin-3-yl)-2-((R)-1-(2-oxopyrazin-1(2H)-yl)ethyl)-1H-pyrrolo[3,2-c]quinolin-8-yl)propanenitrile;

or a pharmaceutically acceptable salt thereof.

In still another embodiment, the compound of Formula I is selected from:

Methyl (2R,4S)-2-(1-((1R,4R,5S)-2-azabicyclo[2.1.1]hexan-5-yl)-8-(2-cyanoethyl)-7-(2,3-dichlorophenyl)-6-fluoro-4-(6-(2-hydroxypropan-2-yl)pyridin-3-yl)-1H-pyrrolo[3,2-c]quinolin-2-yl)-4-fluoropyrrolidine-1-carboxylate;

Methyl (2R,5R)-2-(1-((1R,4R,5S)-2-azabicyclo[2.1.1]hexan-5-yl)-8-(2-cyanoethyl)-7-(2,3-dichlorophenyl)-6-fluoro-4-(6-(2-hydroxypropan-2-yl)pyridin-3-yl)-1H-pyrrolo[3,2-c]quinolin-2-yl)-5-methylpyrrolidine-1-carboxylate;

Methyl (2R)-2-(1-((1R,4R,5S)-2-azabicyclo[2.1.1]hexan-5-yl)-3-chloro-8-(2-cyanoethyl)-7-(2,3-dichlorophenyl)-6-fluoro-4-(6-(2-hydroxypropan-2-yl)pyridin-3-yl)-1H-pyrrolo[3,2-c]quinolin-2-yl)pyrrolidine-1-carboxylate;

4-(1-((1R,4R,5S)-2-Azabicyclo[2.1.1]hexan-5-yl)-8-(2-cyanoethyl)-7-(2,3-dichlorophenyl)-6-fluoro-2-((R)-1-(2-oxopyrazin-1(2H)-yl)ethyl)-1H-pyrrolo[3,2-c]quinolin-4-yl)-2-fluoro-N-methylbenzamide;

Methyl ((1R)-1-(1-((1R,4R,5S)-2-azabicyclo[2.1.1]hexan-5-yl)-8-(2-cyanoethyl)-7-(2,3-dichlorophenyl)-6-fluoro-4-methyl-1H-pyrrolo[3,2-c]quinolin-2-yl)ethyl)carbamate;

N-((1R)-1-(1-((1R,4R,5S)-2-Azabicyclo[2.1.1]hexan-5-yl)-8-(2-cyanoethyl)-7-(2,3-dichlorophenyl)-6-fluoro-4-methyl-1H-pyrrolo[3,2-c]quinolin-2-yl)ethyl)-2,2-difluoroacetamide;

N-((1R)-1-(1-((1R,4R,5S)-2-Azabicyclo[2.1.1]hexan-5-yl)-8-(2-cyanoethyl)-7-(2,3-dichlorophenyl)-6-fluoro-4-methyl-1H-pyrrolo[3,2-c]quinolin-2-yl)ethyl)-2,2-difluoroacetamide;

(2S)—N-((1R)-1-(1-((1R,4R,5S)-2-Azabicyclo[2.1.1]hexan-5-yl)-8-(2-cyanoethyl)-7-(2,3-dichlorophenyl)-6-fluoro-4-methyl-1H-pyrrolo[3,2-c]quinolin-2-yl)ethyl)tetrahydrofuran-2-carboxamide;

N-((1R)-1-(1-((1R,4R,5S)-2-Azabicyclo[2.1.1]hexan-5-yl)-8-(2-cyanoethyl)-7-(2,3-dichlorophenyl)-6-fluoro-4-methyl-1H-pyrrolo[3,2-c]quinolin-2-yl)ethyl)cyclopropanesulfonamide;

N-((1R)-1-(1-((1R,4R,5S)-2-Azabicyclo[2.1.1]hexan-5-yl)-8-(2-cyanoethyl)-7-(2,3-dichlorophenyl)-6-fluoro-4-methyl-1H-pyrrolo[3,2-c]quinolin-2-yl)ethyl)thiazole-4-carboxamide; and N-((1R)-1-(1-(((1R,4R,5S)-2-Azabicyclo[2.1.1]hexan-5-yl)-8-(2-cyanoethyl)-7-(2,3-dichlorophenyl)-6-fluoro-4-methyl-1H-pyrrolo[3,2-c]quinolin-2-yl)ethyl)-N-methylcyclopropanecarboxamide;

or a pharmaceutically acceptable salt thereof.

In another embodiment, the compound of Formula I is selected from

N-((1R)-1-(1-(((1R,4R,5S)-2-Azabicyclo[2.1.1]hexan-5-yl)-8-(2-cyanoethyl)-7-(2,3-dichlorophenyl)-6-fluoro-4-(1-hydroxyethyl)-1H-pyrrolo[3,2-c]quinolin-2-yl)ethyl)-1-methylcyclopropane-1-carboxamide;

3-(1-(((1R,4R,5S)-2-Azabicyclo[2.1.1]hexan-5-yl)-7-(2,3-dichlorophenyl)-6-fluoro-4-(1-hydroxyethyl)-2-((1R,3R,5R)-2-(1-methylcyclopropane-1-carbonyl)-2-azabicyclo[3.1.0]hexan-3-yl)-1H-pyrrolo[3,2-c]quinolin-8-yl)propanenitrile;

3-(1-(((1R,4R,5S)-2-Azabicyclo[2.1.1]hexan-5-yl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-(1-hydroxyethyl)-1H-pyrrolo[3,2-c]quinolin-8-yl)propanenitrile;

3-(1-(((1R,4R,5S)-2-Azabicyclo[2.1.1]hexan-5-yl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-methyl-1H-pyrrolo[3,2-c]quinolin-8-yl)propanenitrile;

N-((1R)-1-(1-(((1R,4R,5S)-2-Azabicyclo[2.1.1]hexan-5-yl)-8-(2-cyanoethyl)-7-(2,3-dichlorophenyl)-6-fluoro-4-(1-hydroxyethyl)-1H-pyrrolo[3,2-c]quinolin-2-yl)ethyl)-1-fluorocyclopropane-1-carboxamide;

N-((1R)-1-(1-(((1R,4R,5S)-2-azabicyclo[2.1.1]hexan-5-yl)-8-(2-cyanoethyl)-7-(2,3-dichlorophenyl)-6-fluoro-4-(1-hydroxyethyl)-1H-pyrrolo[3,2-c]quinolin-2-yl)ethyl)-1-fluorocyclobutane-1-carboxamide;

3-(1-(((1R,4R,5S)-2-azabicyclo[2.1.1]hexan-5-yl)-7-(3-chloro-2-methylphenyl)-2-(1-(2,6-dimethyl-3-oxo-2,3-dihydropyridazin-4-yl)ethyl)-6-fluoro-4-methyl-1H-pyrrolo[3,2-c]quinolin-8-yl)propanenitrile;

N-((1R)-1-(1-(((1R,4R,5S)-2-azabicyclo[2.1.1]hexan-5-yl)-8-(2-cyanoethyl)-7-(2,3-dichlorophenyl)-6-fluoro-4-methyl-1H-pyrrolo[3,2-c]quinolin-2-yl)ethyl)pyrimidine-4-carboxamide;

N-((1R)-1-(1-(((1R,4R,5S)-2-azabicyclo[2.1.1]hexan-5-yl)-8-(2-cyanoethyl)-7-(2,3-dichlorophenyl)-6-fluoro-4-methyl-1H-pyrrolo[3,2-c]quinolin-2-yl)ethyl)pyridazine-3-carboxamide;

N-((1R)-1-(1-(((1R,4R,5S)-2-azabicyclo[2.1.1]hexan-5-yl)-8-(2-cyanoethyl)-7-(2,3-dichlorophenyl)-6-fluoro-4-methyl-1H-pyrrolo[3,2-c]quinolin-2-yl)ethyl)-3,3-difluoroazetidine-1-carboxamide;

3-(1-(((1R,4R,5S)-2-azabicyclo[2.1.1]hexan-5-yl)-7-(2,3-dichlorophenyl)-6-fluoro-4-methyl-2-((R)-1-((1-methyl-1H-pyrazol-4-yl)amino)ethyl)-1H-pyrrolo[3,2-c]quinolin-8-yl)propanenitrile;

5-(1-(((1R,4R,5S)-2-Azabicyclo[2.1.1]hexan-5-yl)-8-(2-cyanoethyl)-7-(2,3-dichlorophenyl)-6-fluoro-2-((R)-1-(1-fluorocyclopropane-1-carbonyl)pyrrolidin-2-yl)-1H-pyrrolo[3,2-c]quinolin-4-yl)-N,N-dimethylpicolinamide; and methyl (2R)-2-(1-(((1R,4R,5S)-2-Azabicyclo[2.1.1]hexan-5-yl)-8-(2-cyanoethyl)-7-(2,3-dichlorophenyl)-4-(4-((dimethylamino)methyl)-2,3-difluorophenyl)-6-fluoro-1H-pyrrolo[3,2-c]quinolin-2-yl)pyrrolidine-1-carboxylate;

or a pharmaceutically acceptable salt thereof.

In another embodiment, the compound of Formula I is a pharmaceutically acceptable salt.

In another aspect, provided herein is a pharmaceutical composition comprising a compound of Formula I, or a pharmaceutically acceptable salt thereof, and a pharmaceutically acceptable carrier.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula I can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydronaphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted," unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "$C_{n-m}$ alkyl," refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkylene," employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, ethan-1,1-diyl, propan-1,3-diyl, propan-1,2-diyl, propan-1,1-diyl, butan-1,4-diyl, butan-1,3-diyl, butan-1,2-diyl, 2-methyl-propan-1,3-diyl and the like.

The term "alkoxy," employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms. The term "$C_{n-m}$ dialkoxy" refers to a linking group of formula —O—($C_{n-m}$ alkyl)-O—, the alkyl group of which has n to m carbons. Example dialkyoxy groups include —OCH$_2$CH$_2$O— and OCH$_2$CH$_2$CH$_2$O—. In some embodiments, the two O atoms of a $C_{n-m}$ dialkoxy group may be attached to the same B atom to form a 5- or 6-membered heterocycloalkyl group.

The term "amino," employed alone or in combination with other terms, refers to a group of formula —NH$_2$, wherein the hydrogen atoms may be substituted with a substituent described herein. For example, "alkylamino" can refer to —NH(alkyl) and —N(alkyl)$_2$.

The terms "halo" or "halogen," used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1}halogen atoms, which may either be the same or different. In some embodiments, the halogen atoms are fluoro atoms. In some embodiments, the haloalkyl group has 1 to 6 or 1 to 4 carbon atoms. Example haloalkyl groups include CF$_3$, C$_2$F$_5$, CHF$_2$, CH$_2$F, CCl$_3$, CHCl$_2$, C$_2$Cl$_5$ and the like. In some embodiments, the haloalkyl group is a fluoroalkyl group.

The term "haloalkoxy," employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" or "oxy" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "oxidized" in reference to a ring-forming N atom refers to a ring-forming N-oxide.

The term "oxidized" in reference to a ring-forming S atom refers to a ring-forming sulfonyl or ring-forming sulfinyl.

The term "aromatic" refers to a carbocycle or heterocycle having one or more polyunsaturated rings having aromatic character (i.e., having (4n+2) delocalized □ (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like. In some embodiments, aryl groups have from 6 to about 10 carbon atoms. In some embodiments, aryl groups have 6 carbon atoms. In some embodiments, aryl groups have 10 carbon atoms. In some embodiments, the aryl group is phenyl. In some embodiments, the aryl group is naphthyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl (pyridyl), pyrimidinyl, pyrazinyl, pyridazinyl, pyrrolyl, pyrazolyl, azolyl, oxazolyl, isoxazolyl, thiazolyl, imidazolyl, furanyl, thiophenyl, quinolinyl, isoquinolinyl, naphthyridinyl (including 1,2-, 1,3-, 1,4-, 1,5-, 1,6-, 1,7-, 1,8-, 2,3- and 2,6-naphthyridine), indolyl, isoindolyl, benzothiophenyl, benzofuranyl, benzisoxazolyl, imidazo[1,2-b]thiazolyl, purinyl, and the like. In some embodiments, the heteroaryl group is pyridone (e.g., 2-pyridone).

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl, isoindolyl, and pyridazinyl.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl. In some embodiments, the cycloalkyl group is tetrahydronaphthalenyl (e.g., 1,2,3,4-tetrahydronaphthalenyl).

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur, oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) or spirocyclic ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or S(O)$_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include 2,5-diazobicyclo[2.2.1]heptanyl; pyrrolidinyl; hexahydropyrrolo[3,4-b]pyrrol-1(2H)-yl; 1,6-dihydropyridinyl; morpholinyl; azetidinyl; piperazinyl; and 4,7-diazaspiro[2.5]octan-7-yl.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term "compound" as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *March's Advanced Organic Chemistry: Reactions, Mechanisms, and Structure*, 6$^{th}$ Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high-performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

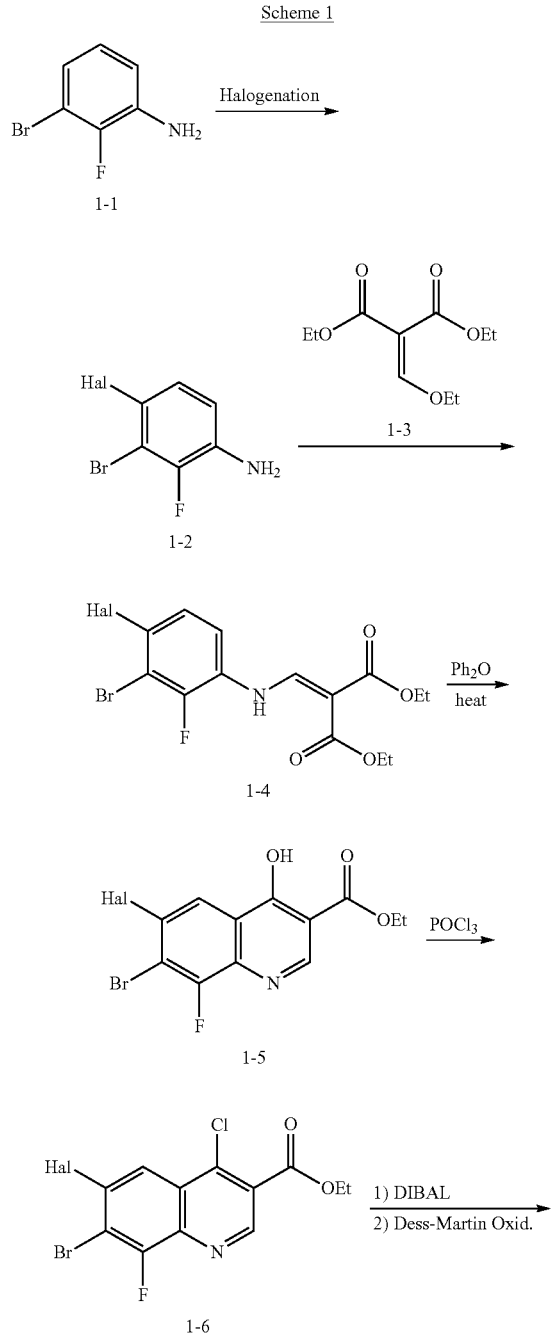

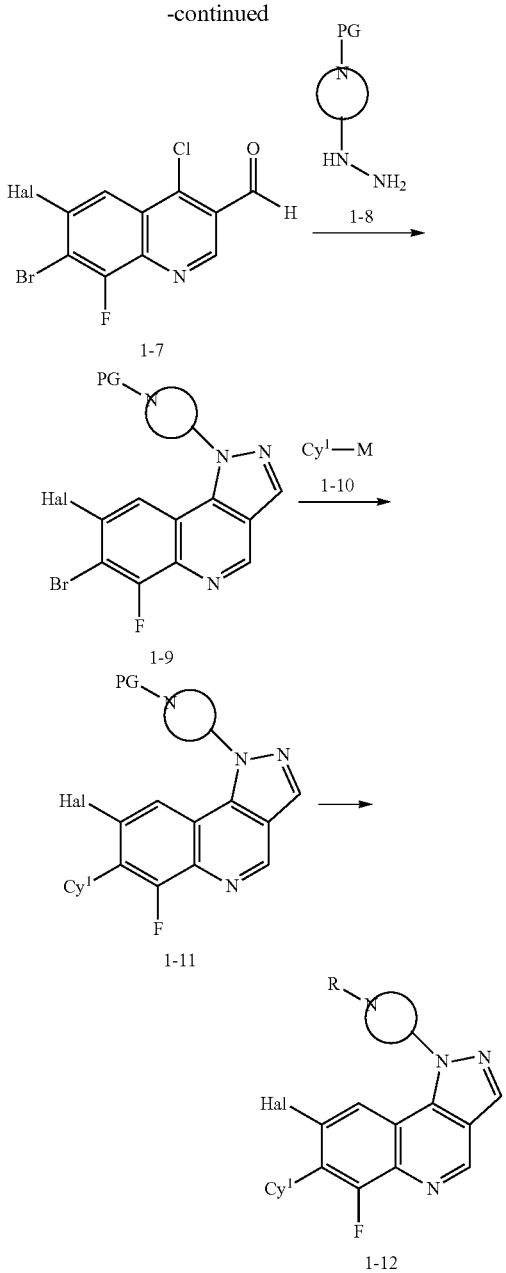

Compounds of formula 1-12 can be prepared via the synthetic route outlined in Scheme 1. Halogenation of commercially available starting material 1-1 with an appropriate reagent, such as N-Chlorosuccinimide (NCS), affords intermediate 1-2 (Hal is a halide, such as F, Cl, Br, or 1). Intermediate 1-4 can then be prepared by condensation of intermediate 1-2 with diethyl 2-(ethoxymethylene)malonate (1-3), followed by cyclized by heating in an appropriate high-boiling solvent (e.g., Ph$_2$O) to yield quinolone 1-5. Treatment of intermediate 1-5 with POCl$_3$ yields intermediate 1-6. Reduction of ethyl ester with reducing reagent (such as DIBAL) followed by oxidation of alcohol with appropriate reagent, such as Dess-Martin Periodinane affords intermediate 1-7. Cyclization reaction of with hydrazine 1-8 (PG is an appropriate protecting group, such as Boc) gives tricyclic adduct 1-9. Compound 1-11 can then be prepared by coupling of 1-9 with an adduct of formula 1-10, in which M is a boronic acid, boronic ester or an appropriately substituted metal [e.g., M is B(OR)$_2$, Sn(Alkyl)$_3$, or Zn-Hal], under standard Suzuki Cross-Coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palldium catalyst). Removal of the protecting group in 1-11 and subsequent functionalization of the resulting adduct (such as coupling with acid chloride, e.g. acryloyl chloride) affords the desired product 1-12.

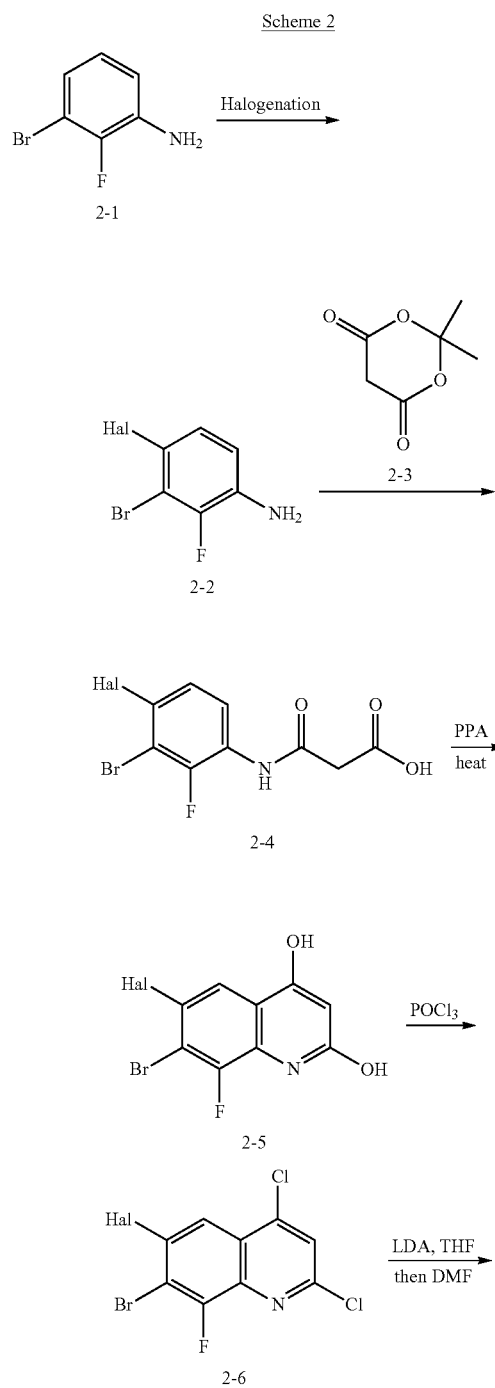

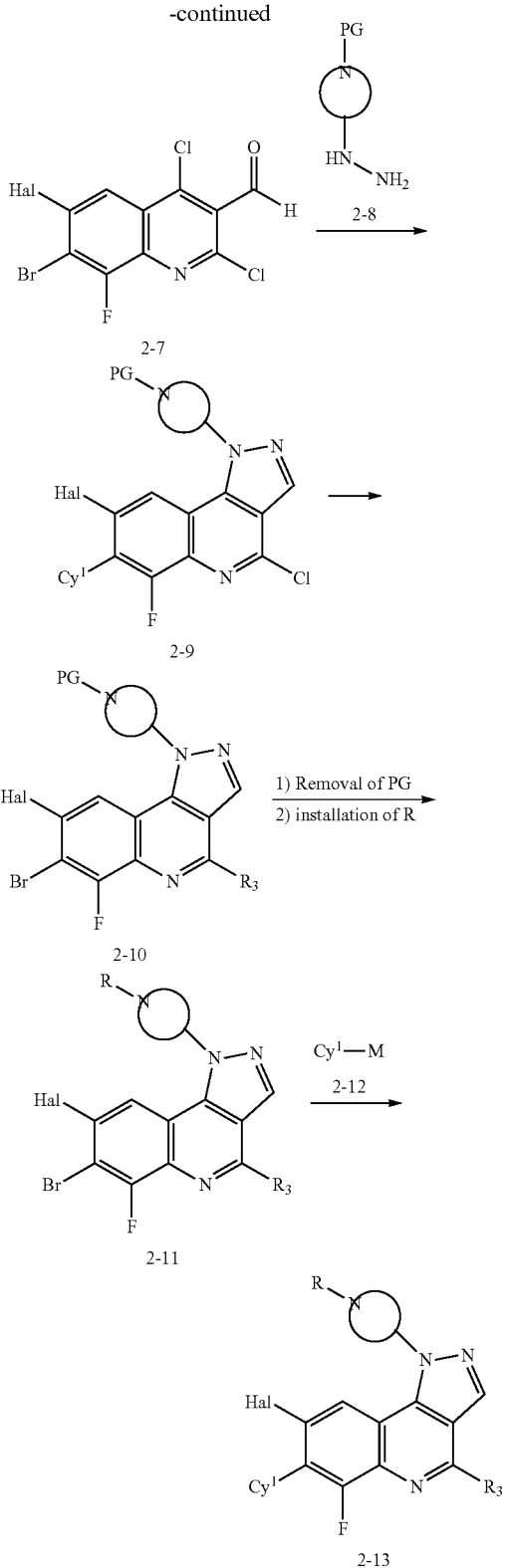

Compounds of formula 2-13 can be prepared via the synthetic route outlined in Scheme 2. Halogenation of commercially available starting material 2-1 with an appropriate reagent, such as N-Chlorosuccinimide (NCS), affords intermediate 2-2 (Hal is a halide, such as F, Cl, Br, or I). Compound 2-4 can be prepared by treating 2-2 with reagents such as 2,2-dimethyl-1,3-dioxane-4,6-dione (2-3). Intermediate 2-4 can undergo a cyclization reaction (in Polyphosphoric acid in thermal condition) to deliver the compound 2-5, which can be treated with an appropriate reagent (e.g. POCl₃) to afford compound 2-6. Intermediate 2-6 can be treated with appropriate reagent (such as LDA in THF, then DMF) to generate compound 2-7. Condensation of intermediate 2-7 with hydrazine 2-8 (PG is an appropriate protecting group, such as Boc) can be carried out to generate compound 2-9. The $R^3$ group in 2-10 can then be installed via a suitable transformation, such as a $S_NAr$ reaction or a coupling reaction. Intermediate 2-10 can first undergo a deprotection of protecting group PG, followed by functionalization of the resulting amine (such as coupling with acid chloride, e.g. acryloyl chloride) then afford compound 2-11. The desired product 2-13 can be prepared by a cross coupling reaction between 2-11 and an adduct of formula 2-12, in which M is a boronic acid, boronic ester or an appropriately substituted metal [e.g., M is $B(OR)_2$, $Sn(Alkyl)_3$, or Zn-Hal], under standard Suzuki Cross-Coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palldium catalyst). The order of the above described chemical reactions can be rearranged as appropriate to suite the preparation of different analogues.

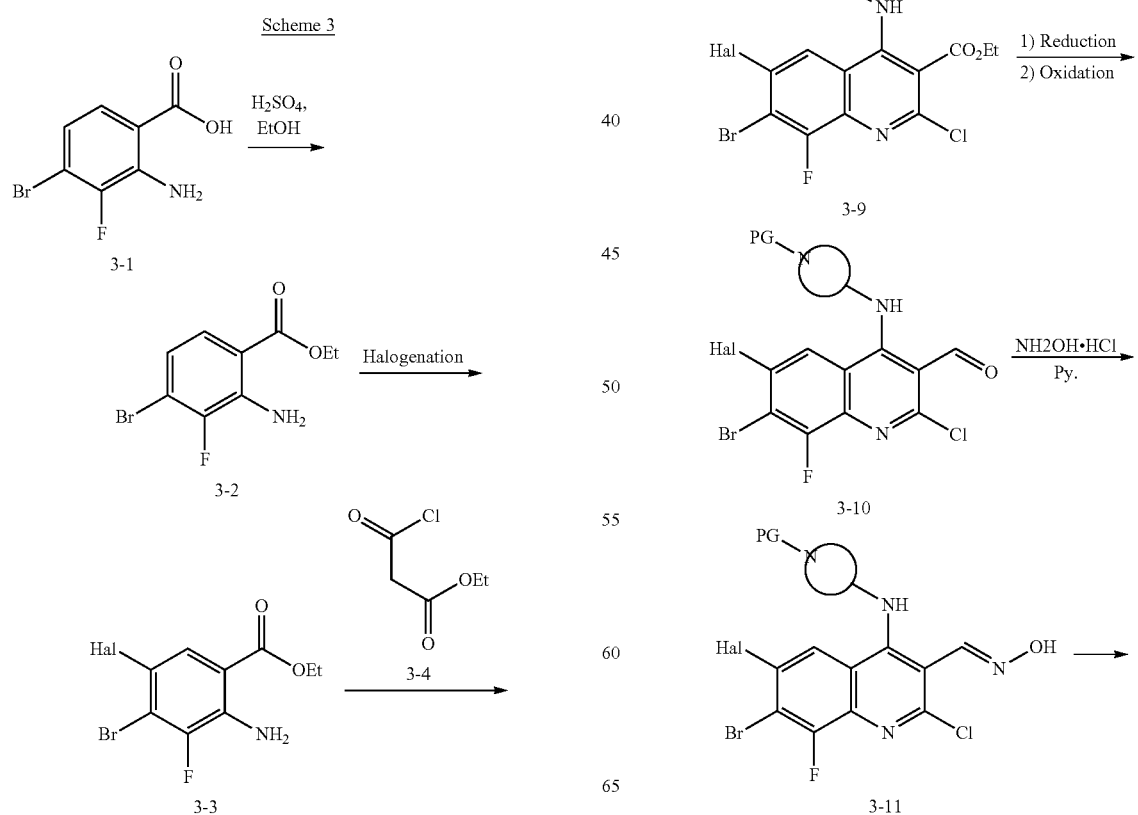

Scheme 3

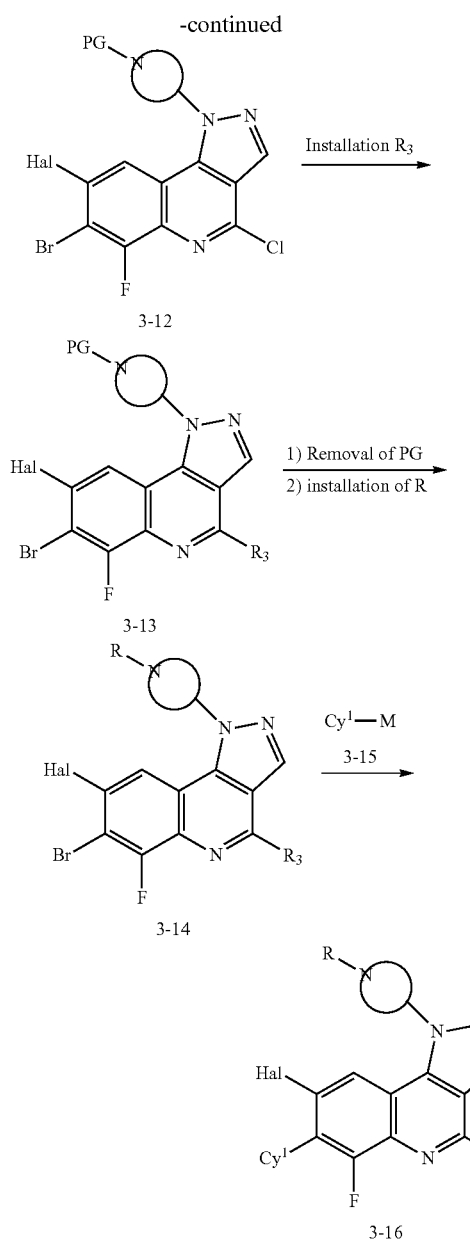

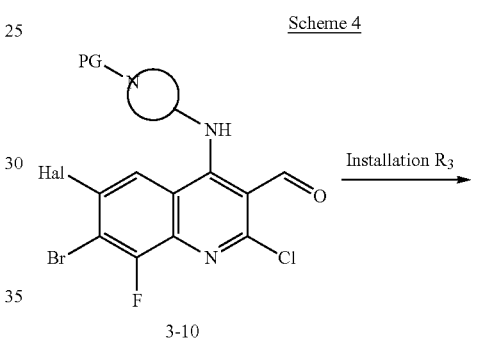

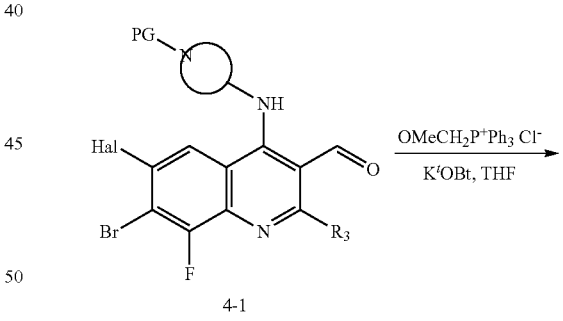

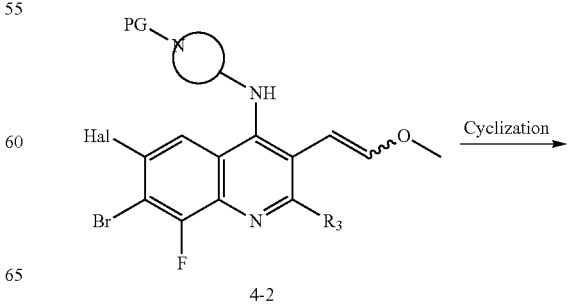

pyridine get compound 3-11. Intermediate 3-11 can undergo a cyclization reaction (such as methanesulfonyl chloride, aminopyridine in DCM) to deliver the compound 3-12. The $R^3$ group in 3-13 can then be installed via a suitable transformation, such as a $S_NAr$ reaction or a coupling reaction. Intermediate 3-13 can first undergo a deprotection of protecting group PG, followed by functionalization of the resulting amine (such as coupling with acid chloride, e.g. acryloyl chloride) then afford compound 3-14. The desired product 3-16 can be prepared by a cross coupling reaction between 3-14 and an adduct of formula 3-15, in which M is a boronic acid, boronic ester or an appropriately substituted metal [e.g., M is $B(OR)_2$, $Sn(Alkyl)_3$, or Zn-Hal], under standard Suzuki Cross-Coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palldium catalyst). The order of the above described chemical reactions can be rearranged as appropriate to suite the preparation of different analogues.

Compounds of formula 3-16 can be prepared via the synthetic route outlined in Scheme 3. Esterification of commercially available starting material 3-1 with $H_2SO_4$ in ethanol. Halogenation of compound 3-2 with an appropriate reagent, such as N-chlorosuccinimide (NCS), affords intermediate 3-3 (Hal is a halide, such as F, Cl, Br, or I). Compound 3-5 can be prepared by treating 3-3 with reagents such as ethyl malonyl chloride (3-4). Intermediate 3-5 can undergo a cyclization reaction (such as sodium ethoxide in ethanol) to deliver the compound 3-6, which can be treated with an appropriate reagent (e.g. $POCl_3$) to afford compound 3-7. Condensation of intermediate 3-7 with amine 3-8 (PG is an appropriate protecting group, such as Boc) can be carried out to generate compound 3-9. Reduction of ester with reducing reagent (such as DIBAL), followed by oxidation of intermediate with oxidation reagent (such as Dess-Martin periodinane) to yield aldehyde 3-10. Treatment of intermediate 3-10 with hydroxylamine hydrochloride and

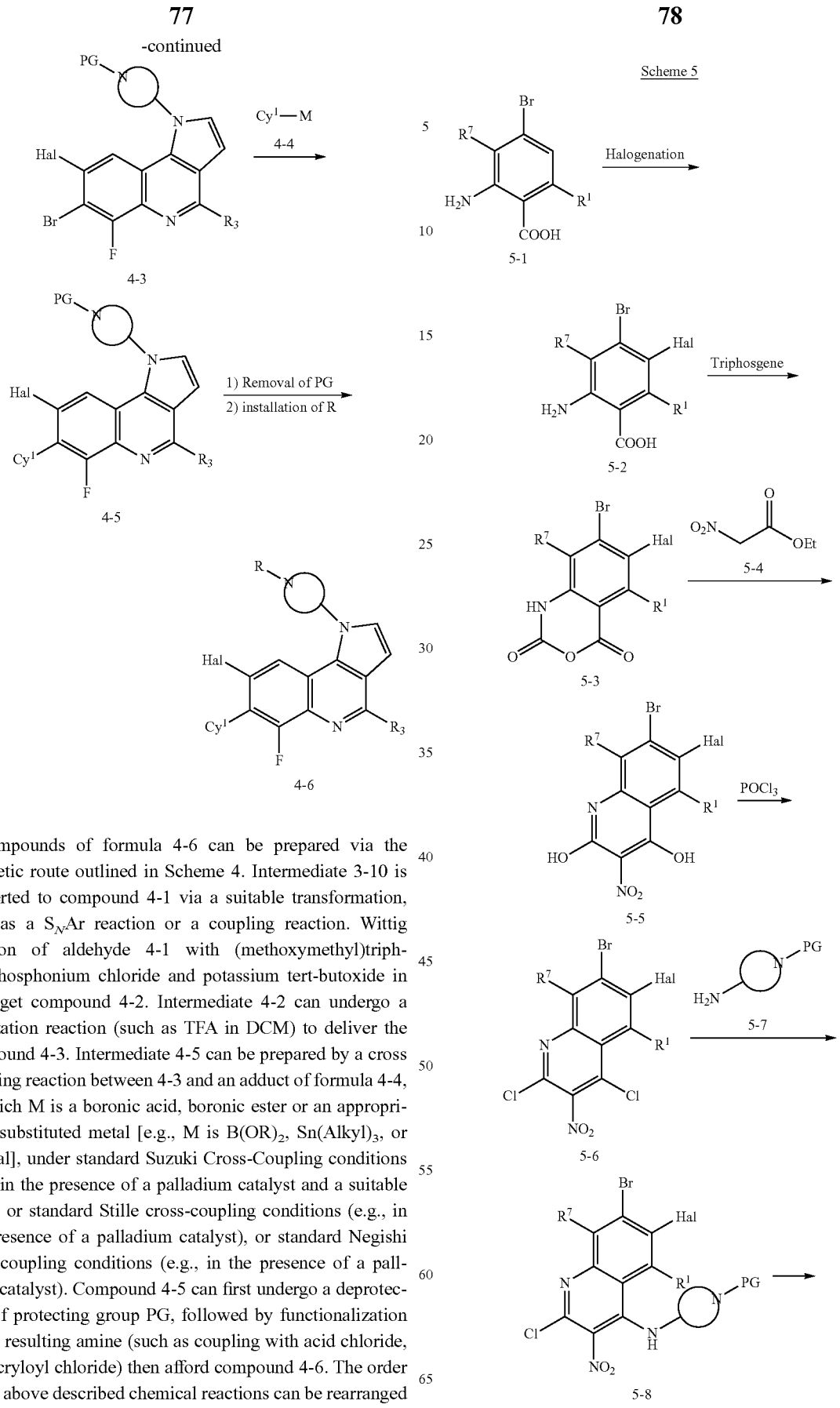

Compounds of formula 4-6 can be prepared via the synthetic route outlined in Scheme 4. Intermediate 3-10 is converted to compound 4-1 via a suitable transformation, such as a $S_NAr$ reaction or a coupling reaction. Wittig reaction of aldehyde 4-1 with (methoxymethyl)triphenylphosphonium chloride and potassium tert-butoxide in THF get compound 4-2. Intermediate 4-2 can undergo a cyclization reaction (such as TFA in DCM) to deliver the compound 4-3. Intermediate 4-5 can be prepared by a cross coupling reaction between 4-3 and an adduct of formula 4-4, in which M is a boronic acid, boronic ester or an appropriately substituted metal [e.g., M is $B(OR)_2$, $Sn(Alkyl)_3$, or Zn-Hal], under standard Suzuki Cross-Coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst). Compound 4-5 can first undergo a deprotection of protecting group PG, followed by functionalization of the resulting amine (such as coupling with acid chloride, e.g. acryloyl chloride) then afford compound 4-6. The order of the above described chemical reactions can be rearranged as appropriate to suite the preparation of different analogues.

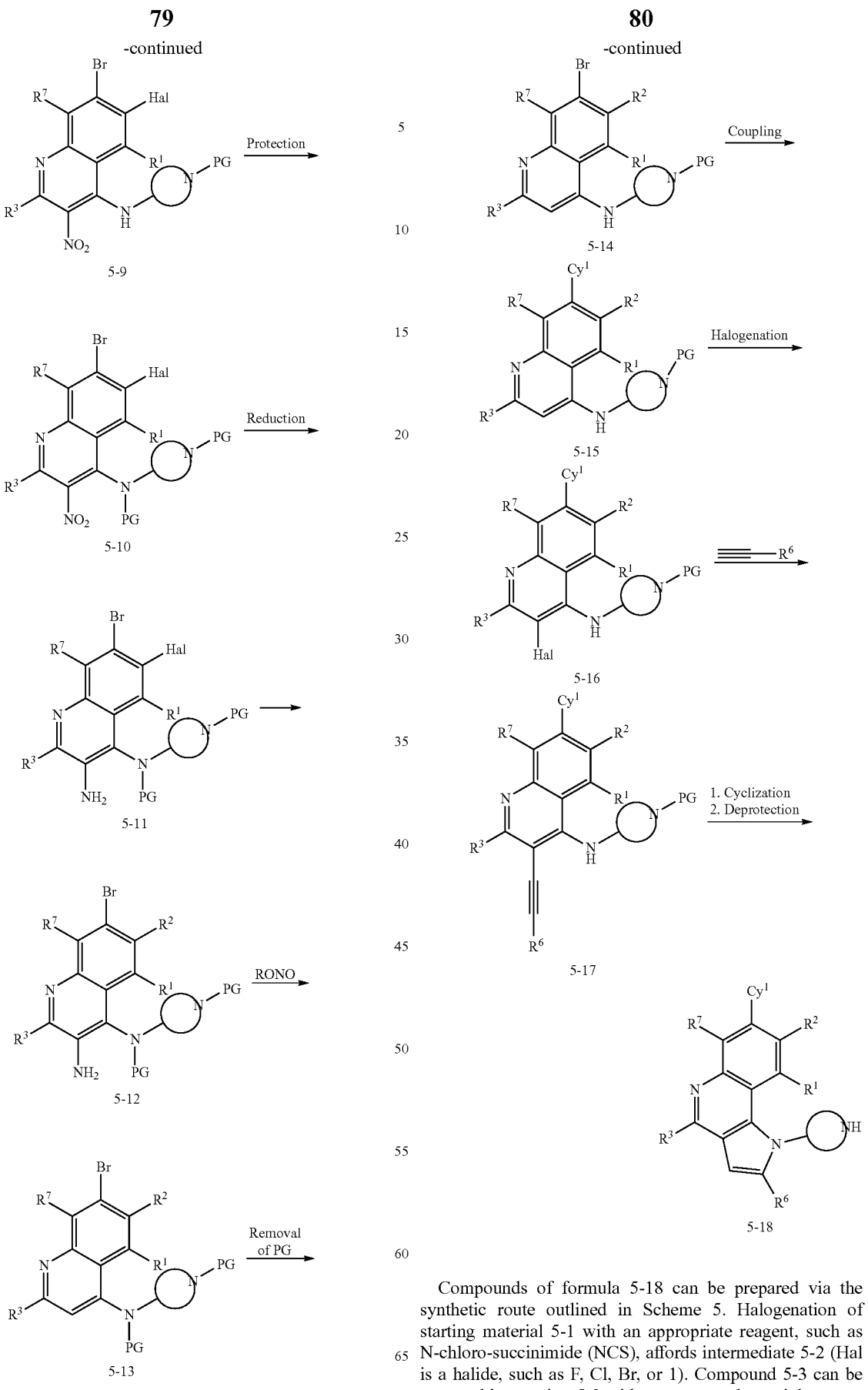
Compounds of formula 5-18 can be prepared via the synthetic route outlined in Scheme 5. Halogenation of starting material 5-1 with an appropriate reagent, such as N-chloro-succinimide (NCS), affords intermediate 5-2 (Hal is a halide, such as F, Cl, Br, or I). Compound 5-3 can be prepared by treating 5-2 with reagents such as triphosgene.

Intermediate 5-3 can then react with ester 5-4 to deliver the nitro compound 5-5, which can be treated with an appropriate reagent (e.g. POCl₃) to afford compound 5-6. A S$_N$Ar reaction of intermediate 5-6 with amine 5-7 (PG is an appropriate protecting group, such as Boc) can be carried out to generate compound 5-8. The $R^3$ group in 5-9 can then be installed via a suitable transformation, such as a S$_N$Ar reaction or a coupling reaction. Protection of the amino group affords intermediate 5-10, which can be reduced in the presence reducing agents (e.g. Fe in acetic acid) to provide 5-11. The halogen of 5-11 (Hal) can optionally be converted to $R^2$ via transition metal mediated coupling or other suitable method to obtain 5-12. Diazotization and reduction of the amino group in 5-12 affords intermediate 5-13, which after protecting group (PG) removal provides 5-14. Coupling of the bromo in 5-14 gives 5-15, which can be halogenated to provide intermediate 5-16. Sonagashira coupling affords 5-17, which after cyclization and deprotection provides compounds of the formula 5-18.

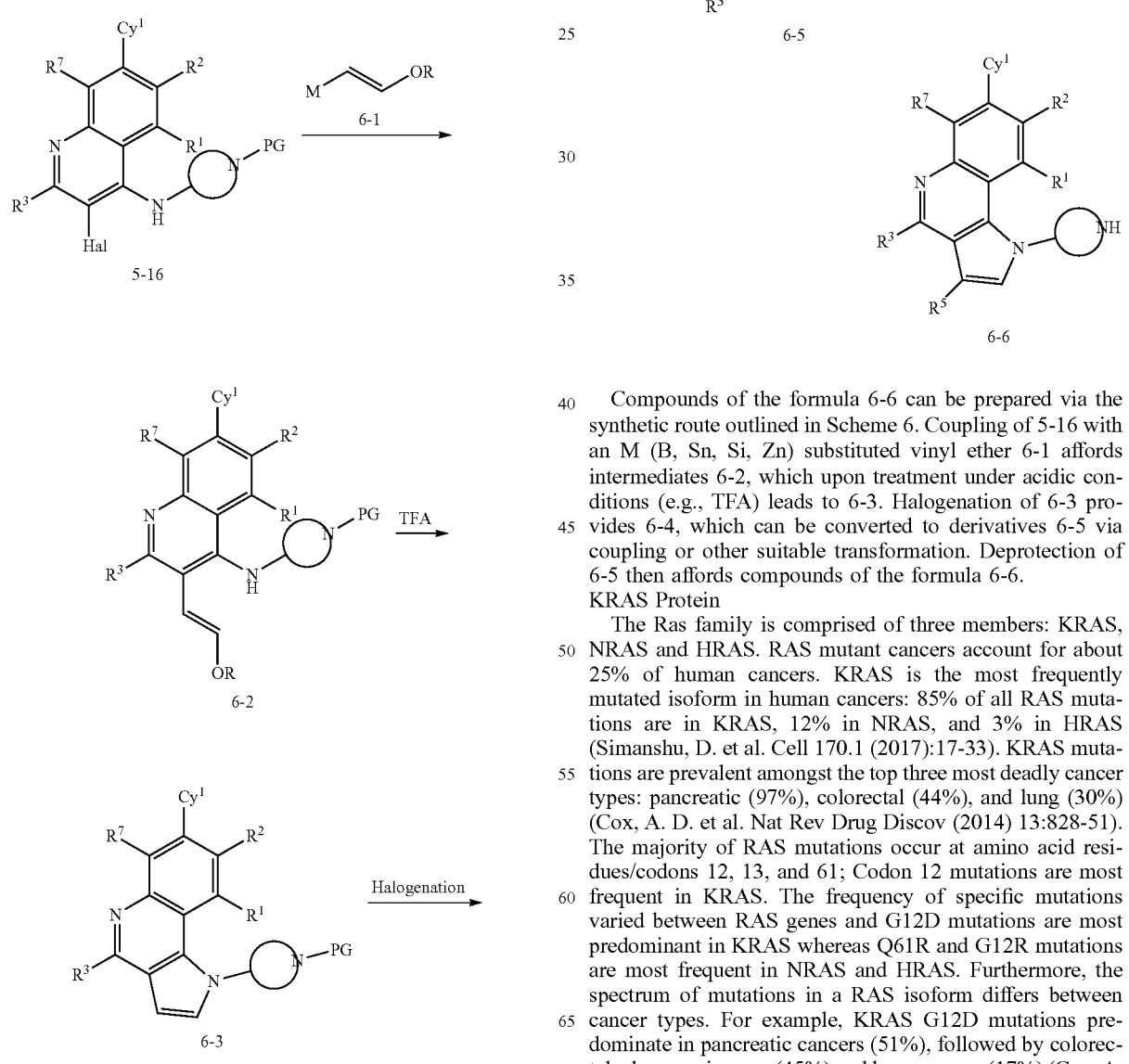

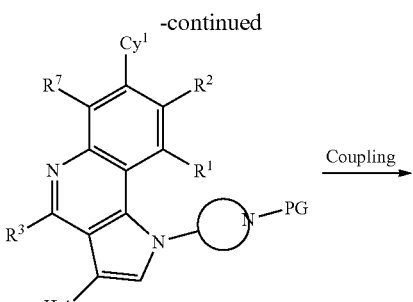

Compounds of the formula 6-6 can be prepared via the synthetic route outlined in Scheme 6. Coupling of 5-16 with an M (B, Sn, Si, Zn) substituted vinyl ether 6-1 affords intermediates 6-2, which upon treatment under acidic conditions (e.g., TFA) leads to 6-3. Halogenation of 6-3 provides 6-4, which can be converted to derivatives 6-5 via coupling or other suitable transformation. Deprotection of 6-5 then affords compounds of the formula 6-6.

KRAS Protein

The Ras family is comprised of three members: KRAS, NRAS and HRAS. RAS mutant cancers account for about 25% of human cancers. KRAS is the most frequently mutated isoform in human cancers: 85% of all RAS mutations are in KRAS, 12% in NRAS, and 3% in HRAS (Simanshu, D. et al. Cell 170.1 (2017):17-33). KRAS mutations are prevalent amongst the top three most deadly cancer types: pancreatic (97%), colorectal (44%), and lung (30%) (Cox, A. D. et al. Nat Rev Drug Discov (2014) 13:828-51). The majority of RAS mutations occur at amino acid residues/codons 12, 13, and 61; Codon 12 mutations are most frequent in KRAS. The frequency of specific mutations varied between RAS genes and G12D mutations are most predominant in KRAS whereas Q61R and G12R mutations are most frequent in NRAS and HRAS. Furthermore, the spectrum of mutations in a RAS isoform differs between cancer types. For example, KRAS G12D mutations predominate in pancreatic cancers (51%), followed by colorectal adenocarcinomas (45%) and lung cancers (17%) (Cox, A.

D. et al. Nat Rev Drug Discov (2014) 13:828-51). In contrast, KRAS G12C mutations predominate in non-small cell lung cancer (NSCLC) comprising 11-16% of lung adenocarcinomas (nearly half of mutant KRAS is G12C), as well as 2-5% of pancreatic and colorectal adenocarcinomas, respectively (Cox, A. D. et al. Nat. Rev. Drug Discov. (2014) 13:828-51). Using shRNA knockdown thousands of genes across hundreds of cancer cell lines, genomic studies have demonstrated that cancer cells exhibiting KRAS mutations are highly dependent on KRAS function for cell growth (McDonald, R. et al. Cell 170 (2017): 577-592). Taken together, these findings suggested that KRAS mutations play a critical role in human cancers, therefore development of the inhibitors targeting mutant KRAS may be useful in the clinical treatment of diseases that have characterized by a KRAS mutation.

Methods of Use

The cancer types in which KRAS harboring G12C, G12V and G12D mutations are implicated include, but are not limited to: carcinomas (e.g., pancreatic, colorectal, lung, bladder, gastric, esophageal, breast, head and neck, cervical skin, thyroid); hematopoietic malignancies (e.g., myeloproliferative neoplasms (MPN), myelodysplastic syndrome (MDS), chronic and juvenile myelomonocytic leukemia (CMML and JMML), acute myeloid leukemia (AML), acute lymphocytic leukemia (ALL) and multiple myeloma (MM)); and other neoplasms (e.g., glioblastoma and sarcomas). In addition, KRAS mutations were found in acquired resistance to anti-EGFR therapy (Knickelbein, K. et al. Genes & Cancer, (2015): 4-12). KRAS mutations were found in immunological and inflammatory disorders (Fernandez-Medarde, A. et al. Genes & Cancer, (2011): 344-358) such as Ras-associated lymphoproliferative disorder (RALD) or juvenile myelomonocytic leukemia (JMML) caused by somatic mutations of KRAS or NRAS.

Compounds of the present disclosure can inhibit the activity of the KRAS protein. For example, compounds of the present disclosure can be used to inhibit activity of KRAS in a cell or in an individual or patient in need of inhibition of the enzyme by administering an inhibiting amount of one or more compounds of the present disclosure to the cell, individual, or patient.

As KRAS inhibitors, the compounds of the present disclosure are useful in the treatment of various diseases associated with abnormal expression or activity of KRAS. Compounds which inhibit KRAS will be useful in providing a means of preventing the growth or inducing apoptosis in tumors, or by inhibiting angiogenesis. It is therefore anticipated that compounds of the present disclosure will prove useful in treating or preventing proliferative disorders such as cancers. In particular, tumors with activating mutants of receptor tyrosine kinases or upregulation of receptor tyrosine kinases may be particularly sensitive to the inhibitors.

In an aspect, provided herein is a method of inhibiting KRAS activity, said method comprising contacting a compound of the instant disclosure with KRAS. In an embodiment, the contacting comprises administering the compound to a patient.

In an aspect, provided herein is a method of inhibiting a KRAS protein harboring a G12C mutation, said method comprising contacting a compound of the instant disclosure with KRAS.

In an aspect, provided herein is a method of inhibiting a KRAS protein harboring a G12D mutation, said method comprising contacting a compound of the instant disclosure with KRAS.

In an aspect, provided herein is a method of inhibiting a KRAS protein harboring a G12V mutation, said method comprising contacting a compound of the instant disclosure with KRAS.

In another aspect, provided herein a is method of treating a disease or disorder associated with inhibition of KRAS interaction, said method comprising administering to a patient in need thereof a therapeutically effective amount of a compound of any of the formulae disclosed herein, or pharmaceutically acceptable salt thereof.

In an embodiment, the disease or disorder is an immunological or inflammatory disorder. In another embodiment, the immunological or inflammatory disorder is Ras-associated lymphoproliferative disorder and juvenile myelomonocytic leukemia caused by somatic mutations of KRAS.

In yet another aspect, provided herein is a method of treating a disease or disorder associated with inhibiting a KRAS protein harboring a G12D mutation, said method comprising administering to a patient in need thereof a therapeutically effective amount of a compound of any of the formulae disclosed herein, or pharmaceutically acceptable salt thereof.

In another aspect, provided herein is a method of treating a disease or disorder associated with inhibiting a KRAS protein harboring a G12V mutation, said method comprising administering to a patient in need thereof a therapeutically effective amount of a compound of any of the formulae disclosed herein, or pharmaceutically acceptable salt thereof.

In another aspect, provided herein is also a method of treating cancer in a patient in need thereof comprising administering to the patient a therapeutically effective amount of the compounds disclosed herein In still another aspect, provided herein is also a method of treating cancer in a patient in need thereof comprising administering to the patient a therapeutically effective amount of the compounds disclosed herein wherein the cancer is characterized by an interaction with a KRAS protein harboring a G12D mutation.

In another aspect, provided herein is also a method of treating cancer in a patient in need thereof comprising administering to the patient a therapeutically effective amount of the compounds disclosed herein wherein the cancer is characterized by an interaction with a KRAS protein harboring a G12V mutation.

In yet another aspect, provided herein is a method for treating a cancer in a patient, said method comprising administering to the patient a therapeutically effective amount of any one of the compounds disclosed herein, or pharmaceutically acceptable salt thereof.

In an embodiment, the cancer is selected from carcinomas, hematological cancers, sarcomas, and glioblastoma. In another embodiment, the hematological cancer is selected from myeloproliferative neoplasms, myelodysplastic syndrome, chronic and juvenile myelomonocytic leukemia, acute myeloid leukemia, acute lymphocytic leukemia, and multiple myeloma. In yet another embodiment, the carcinoma is selected from pancreatic, colorectal, lung, bladder, gastric, esophageal, breast, head and neck, cervical, skin, and thyroid.

In an aspect, provided herein is a method for treating a disease or disorder associated with inhibition of KRAS interaction or a mutant thereof, in a patient in need thereof, comprising the step of administering to the patient a compound disclosed herein, or a pharmaceutically acceptable salt thereof, or a composition comprising a compound disclosed herein or a pharmaceutically acceptable salt thereof, in combination with another therapy or therapeutic agent as described herein.

In an embodiment, the cancer is selected from hematological cancers, sarcomas, lung cancers, gastrointestinal cancers, genitourinary tract cancers, liver cancers, bone cancers, nervous system cancers, gynecological cancers, and skin cancers.

In another embodiment, the lung cancer is selected from non-small cell lung cancer (NSCLC), small cell lung cancer, bronchogenic carcinoma, squamous cell bronchogenic carcinoma, undifferentiated small cell bronchogenic carcinoma, undifferentiated large cell bronchogenic carcinoma, adenocarcinoma, bronchogenic carcinoma, alveolar carcinoma, bronchiolar carcinoma, bronchial adenoma, chondromatous hamartoma, mesothelioma, pavicellular and non-pavicellular carcinoma, bronchial adenoma, and pleuropulmonary blastoma.

In yet another embodiment, the lung cancer is non-small cell lung cancer (NSCLC). In still another embodiment, the lung cancer is adenocarcinoma.

In an embodiment, the gastrointestinal cancer is selected from esophagus squamous cell carcinoma, esophagus adenocarcinoma, esophagus leiomyosarcoma, esophagus lymphoma, stomach carcinoma, stomach lymphoma, stomach leiomyosarcoma, exocrine pancreatic carcinoma, pancreatic ductal adenocarcinoma, pancreatic insulinoma, pancreatic glucagonoma, pancreatic gastrinoma, pancreatic carcinoid tumors, pancreatic vipoma, small bowel adenocarcinoma, small bowel lymphoma, small bowel carcinoid tumors, Kaposi's sarcoma, small bowel leiomyoma, small bowel hemangioma, small bowel lipoma, small bowel neurofibroma, small bowel fibroma, large bowel adenocarcinoma, large bowel tubular adenoma, large bowel villous adenoma, large bowel hamartoma, large bowel leiomyoma, colorectal cancer, gall bladder cancer, and anal cancer.

In an embodiment, the gastrointestinal cancer is colorectal cancer.

In another embodiment, the cancer is a carcinoma. In yet another embodiment, the carcinoma is selected from pancreatic carcinoma, colorectal carcinoma, lung carcinoma, bladder carcinoma, gastric carcinoma, esophageal carcinoma, breast carcinoma, head and neck carcinoma, cervical skin carcinoma, and thyroid carcinoma.

In still another embodiment, the cancer is a hematopoietic malignancy. In an embodiment, the hematopoietic malignancy is selected from multiple myeloma, acute myelogenous leukemia, and myeloproliferative neoplasms.

In another embodiment, the cancer is a neoplasm. In yet another embodiment, the neoplasm is glioblastoma or sarcomas.

In certain embodiments, the disclosure provides a method for treating a KRAS-mediated disorder in a patient in need thereof, comprising the step of administering to said patient a compound according to the invention, or a pharmaceutically acceptable composition thereof.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET), 8p11 myeloproliferative syndrome, myelodysplasia syndrome (MDS), T-cell acute lymphoblastic lymphoma (T-ALL), multiple myeloma, cutaneous T-cell lymphoma, adult T-cell leukemia, Waldenstrom's Macroglubulinemia, hairy cell lymphoma, marginal zone lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, lymphosarcoma, leiomyosarcoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, mesothelioma, pavicellular and non-pavicellular carcinoma, bronchial adenoma and pleuropulmonary blastoma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (exocrine pancreatic carcinoma, ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), colorectal cancer, gall bladder cancer and anal cancer.

Exemplary genitourinary tract cancers include cancers of the kidney (adenocarcinoma, Wilm's tumor [nephroblastoma], renal cell carcinoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma) and urothelial carcinoma.

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors, neuro-ectodermal tumors), and spinal cord (neurofibroma, meningioma, glioma, sarcoma), neuroblastoma, Lhermitte-Duclos disease and pineal tumors.

Exemplary gynecological cancers include cancers of the breast (ductal carcinoma, lobular carcinoma, breast sarcoma, triple-negative breast cancer, HER2-positive breast cancer, inflammatory breast cancer, papillary carcinoma), uterus (endometrial carcinoma), cervix (cervical carcinoma, pretumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers, tumors of the eye, tumors of the lips and mouth and squamous head and neck cancer.

The compounds of the present disclosure can also be useful in the inhibition of tumor metastases.

In addition to oncogenic neoplasms, the compounds of the invention are useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes. In some embodiments, the present disclosure provides a method for treating a patient suffering from a skeletal and chondrocyte disorder.

In some embodiments, compounds described herein can be used to treat Alzheimer's disease, HIV, or tuberculosis.

As used herein, the term "8p11 myeloproliferative syndrome" is meant to refer to myeloid/lymphoid neoplasms associated with eosinophilia and abnormalities of FGFR1.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" KRAS with a compound described herein includes the administration of a compound described herein to an individual or patient, such as a human, having KRAS, as well as, for example, introducing a compound described herein into a sample containing a cellular or purified preparation containing KRAS.

As used herein, the term "individual," "subject," or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy*, 21 st ed.; Lippincott Williams & Wilkins: Philadelphia, Pa., 2005; *Handbook of Pharmaceutical Excipients*, 6th ed.; Rowe et al., Eds.; The Pharmaceutical Press and the American Pharmaceutical Association: 2009; *Handbook of Pharmaceutical Additives*, 3rd ed.; Ash and Ash Eds.; Gower Publishing Company: 2007; *Pharmaceutical Preformulation and Formulation*, 2nd ed.; Gibson Ed.; CRC Press LLC: Boca Raton, Fla., 2009.

As used herein, the term "treating" or "treatment" refers to inhibiting a disease; for example, inhibiting a disease, condition, or disorder in an individual who is experiencing or displaying the pathology or symptomology of the disease, condition, or disorder (i.e., arresting further development of the pathology and/or symptomology) or ameliorating the disease; for example, ameliorating a disease, condition, or disorder in an individual who is experiencing or displaying the pathology or symptomology of the disease, condition, or disorder (i.e., reversing the pathology and/or symptomology) such as decreasing the severity of the disease.

The term "prevent," "preventing," or "prevention" as used herein, comprises the prevention of at least one symptom associated with or caused by the state, disease or disorder being prevented.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Combination Therapies
I. Cancer Therapies

Cancer cell growth and survival can be impacted by dysfunction in multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF, FAK, and CDK4/6 kinase inhibitors such as, for example, those described in WO 2006/056399 can be used in combination with the compounds of the present disclosure for treatment of CDK2-associated diseases, disorders or conditions. Other agents such as therapeutic antibodies can be used in combination with the compounds of the present disclosure for treatment of CDK2-associated diseases, disorders or conditions. The one or more additional pharmaceutical agents can be administered to a patient simultaneously or sequentially.

In some embodiments, the CDK2 inhibitor is administered or used in combination with a BCL2 inhibitor or a CDK4/6 inhibitor.

The compounds as disclosed herein can be used in combination with one or more other enzyme/protein/receptor inhibitors therapies for the treatment of diseases, such as cancer and other diseases or disorders described herein. Examples of diseases and indications treatable with combination therapies include those as described herein. Examples of cancers include solid tumors and non-solid tumors, such as liquid tumors, blood cancers. Examples of infections include viral infections, bacterial infections, fungus infections or parasite infections. For example, the compounds of the present disclosure can be combined with one or more inhibitors of the following kinases for the treatment of cancer: Akt1, Akt2, Akt3, BCL2, CDK4/6, TGF-3R, PKA, PKG, PKC, CaM-kinase, phosphorylase kinase, MEKK, ERK, MAPK, mTOR, EGFR, HER2, HER3, HER4, INS-R, IDH2, IGF-1R, IR-R, PDGFαR, PDGFβR, PI3K (alpha, beta, gamma, delta, and multiple or selective), CSF1R, KIT, FLK-II, KDR/FLK-1, FLK-4, flt-1, FGFR1, FGFR2, FGFR3, FGFR4, c-Met, PARP, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the compounds of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR1, FGFR2, FGFR3 or FGFR4, e.g., pemigatinib (INCB54828), INCB62079), an EGFR inhibitor (also known as ErB-1 or HER-1; e.g., erlotinib, gefitinib, vandetanib, orsimertinib, cetuximab, necitumumab, or panitumumab), a VEGFR inhibitor or pathway blocker (e.g. bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g., olaparib, rucaparib, veliparib or niraparib), a JAK inhibitor (JAK1 and/or JAK2; e.g., ruxolitinib or baricitinib; or JAK1; e.g., itacitinib (INCB39110), INCB052793, or INCB054707), an IDO inhibitor (e.g., epacadostat, NLG919, or BMS-986205, MK7162), an LSD1 inhibitor (e.g., GSK2979552, INCB59872 and INCB60003), a TDO inhibitor, a PI3K-delta inhibitor (e.g., parsaclisib (INCB50465) or INCB50797), a PI3K-gamma inhibitor such as PI3K-gamma selective inhibitor, a Pim inhibitor (e.g., INCB53914), a CSF1R inhibitor, a TAM receptor tyrosine kinases (Tyro-3, Axl, and Mer; e.g., INCB081776), an adenosine receptor antagonist (e.g., A2a/A2b receptor antagonist), an HPK1 inhibitor, a chemokine receptor inhibitor (e.g., CCR2 or CCR5 inhibitor), a SHP1/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), c-MET inhibitors (e.g., capmatinib), an anti-CD19 antibody (e.g., tafasitamab), an ALK2 inhibitor (e.g., INCB00928); or combinations thereof.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

Example antibodies for use in combination therapy include, but are not limited to, trastuzumab (e.g., anti-HER2), ranibizumab (e.g., anti-VEGF-A), bevacizumab (AVASTIN™, e.g., anti-VEGF), panitumumab (e.g., anti-EGFR), cetuximab (e.g., anti-EGFR), rituxan (e.g., anti-CD20), and antibodies directed to c-MET.

One or more of the following agents may be used in combination with the compounds of the present disclosure and are presented as a non-limiting list: a cytostatic agent, cisplatin, doxorubicin, taxotere, taxol, etoposide, irinotecan, camptosar, topotecan, paclitaxel, docetaxel, epothilones, tamoxifen, 5-fluorouracil, methotrexate, temozolomide, cyclophosphamide, SCH 66336, R115777, L778,123, BMS 214662, IRESSA™ (gefitinib), TARCEVA™ (erlotinib), antibodies to EGFR, intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath (alemtuzumab), clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, bispecific or multi-specific antibody, antibody drug conjugate, adoptive T cell transfer, Toll receptor agonists, RIG-1 agonists, oncolytic virotherapy and immunomodulating small molecules, including thalidomide or JAK1/2 inhibitor, PI3Kδ inhibitor and the like. The compounds can be administered in combination with one or more anti-cancer drugs, such as a chemotherapeutic agent. Examples of chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

Additional examples of chemotherapeutics include proteasome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, B1853520, and GSK2256098, and their pharmaceutically acceptable salts.

Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

Example suitable CDK4/6 inhibitors include palbociclib, ribociclib, trilaciclib, lerociclib, and abemaciclib, and their pharmaceutically acceptable salts. Other example suitable CDK4/6 inhibitors include compounds, and their pharmaceutically acceptable salts, as disclosed in WO 09/085185, WO 12/129344, WO 11/101409, WO 03/062236, WO 10/075074, and WO 12/061156.

In some embodiments, the compounds of the disclosure can be used in combination with one or more other kinase inhibitors including imatinib, particularly for treating patients resistant to imatinib or other kinase inhibitors.

In some embodiments, the compounds of the disclosure can be used in combination with a chemotherapeutic in the treatment of cancer, and may improve the treatment response as compared to the response to the chemotherapeutic agent alone, without exacerbation of its toxic effects. In some embodiments, the compounds of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining a CDK2 inhibitor of the present disclosure with an additional agent.

The agents can be combined with the present compound in a single or continuous dosage form, or the agents can be administered simultaneously or sequentially as separate dosage forms.

The compounds of the present disclosure can be used in combination with one or more other inhibitors or one or more therapies for the treatment of infections. Examples of infections include viral infections, bacterial infections, fungus infections or parasite infections.

In some embodiments, a corticosteroid such as dexamethasone is administered to a patient in combination with the compounds of the disclosure where the dexamethasone is administered intermittently as opposed to continuously.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fe alpha or Fe gamma receptor-expressing effectors cells to tumor cells. The compounds of the present disclosure can also be combined with macrocyclic peptides that activate host immune responsiveness.

In some further embodiments, combinations of the compounds of the disclosure with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, Giardia, Malaria, *Leishmania, Staphylococcus aureus, Pseudomonas Aeruginosa.*

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, Ebola virus, measles virus, herpes virus (e.g., VZV, HSV-1, HAV-6, HSV-II, and CMV, Epstein Barr virus), flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, chlamydia, rickettsial bacteria, mycobacteria, staphylococci, streptococci, pneumococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, niger*, etc.), Genus Mucorales (*mucor, absidia, rhizophus*), *Sporothrix schenkii, Blastomyces dermatitidis, Paracoccidioides brasiliensis, Coccidioides immitis* and *Histoplasma capsulatum.*

Pathogenic parasites causing infections treatable by methods of the disclosure include, but are not limited to, *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis.*

When more than one pharmaceutical agent is administered to a patient, they can be administered simultaneously, separately, sequentially, or in combination (e.g., for more than two agents).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

II. Immune-Checkpoint Therapies

Compounds of the present disclosure can be used in combination with one or more immune checkpoint inhibitors for the treatment of diseases, such as cancer or infections. Exemplary immune checkpoint inhibitors include inhibitors against immune checkpoint molecules such as CBL-B, CD20, CD28, CD40, CD70, CD122, CD96, CD73, CD47, CDK2, GITR, CSF1R, JAK, PI3K delta, PI3K gamma, TAM, arginase, HPK1, CD137 (also known as 4-1 BB), ICOS, A2AR, B7-H3, B7-H4, BTLA, CTLA-4, LAG3, TIM3, TLR (TLR7/8), TIGIT, CD112R, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the compounds provided herein can be used in combination with one or more agonists of immune checkpoint molecules, e.g., OX40, CD27, GITR, and CD137 (also known as 4-1 BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1 or PD-L1, e.g., an anti-PD-1 or anti-PD-L1 monoclonal antibody. In some embodiments, the anti-PD-1 or anti-PD-L1 antibody is nivolumab, pembrolizumab, atezolizumab, durvalumab, avelumab, cemiplimab, atezolizumab, avelumab, tislelizumab, spartalizumab (PDR001), cetrelimab (JNJ-63723283), toripalimab (JS001), camrelizumab (SHR-1210), sintilimab (IB1308), AB122 (GLS-010), AMP-224, AMP-514/MEDI-0680, BMS936559, JTX-4014, BGB-108, SHR-1210, MED14736, FAZ053, BCD-100, KN035, CS1001, BAT1306, LZM009, AK105, HLX10, SHR-1316, CBT-502 (TQB2450), A167 (KL-A167), STI-A101 (ZKAB001), CK-301, BGB-A333, MSB-2311, HLX20, TSR-042, or LY3300054. In some embodiments, the inhibitor of PD-1 or PD-L1 is one disclosed in U.S. Pat. Nos. 7,488,802, 7,943,743, 8,008,449, 8,168,757, 8,217,149, or 1,308,644; U.S. Pub. Nos. 2017/0145025, 2017/0174671, 2017/0174679, 2017/0320875, 2017/0342060, 2017/0362253, 2018/0016260, 2018/0057486, 2018/77784, 2018/01177870, 2018/0179179, 2018/0179201, 2018/0179202, 2018/0273519, 2019/0040082, 2019/0062345, 2019/0071439, 2019/0127467, 2019/0144439, 2019/0202824, 20119/0225601, 20119/0300524, or 2019/0345170; or POT Pub. Nos. WO 03042402, WO 200811567112, WO 201100894111, WO 20110036959, WO 20111066342, WO 2011159877, WO 20111082400, or WO 2011161699, which are each incorporated herein by reference in their entirety. In some embodiments, the inhibitor of PD-L1 is INCB086550.

In some embodiments, the PD-L1 inhibitor is selected from the compounds in Table A, or a pharmaceutically acceptable salt thereof.

TABLE A

| Cmpd No. | US Publication Appl. No. | Name and Structure |
|---|---|---|
| 1 | US 2018-0179197, Example #24 | (R)-1-((7-cyano-2-(3'-(3-(((R)-3-hydroxypyrrolidin-1-yl)methyl-1,7-naphthyridin-8-ylamino)-2,2'-dimethylbiphenyl-3-yl)benzo[d]oxazol-5-yl)methyl)pyrrolidine-3-carboxylic acid |
| 2 | US 2018-0179201, Example #2 | N-(2-chloro-3'-(8-chloro-6-((2-hydroxyethylamino)methyl)-[1,2,4]triazolo[1,5-a]pyridin-2-yl)-2'-methylbiphenyl-3-yl)-5-((2-hydroxyethylamino)methyl)picolinamide |
| 3 | US 2018-0179197, Example #25 | (S)-1-((7-cyano-2-(3'-(3-(((S)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid |

TABLE A-continued

| Cmpd No. | US Publication Appl. No. | Name and Structure |
|---|---|---|
| 4 | US 2018-0179197, Example #26 | (R)-1-((7-cyano-2-(3'-(3-(((S)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid 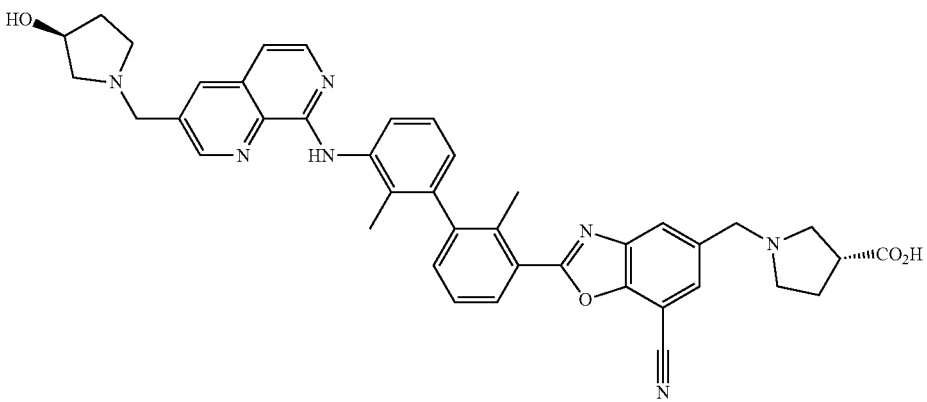 [SMILES: Cc1c(Nc2nccc3cc(CN4CC[C@H](O)C4)cnc23)cccc1-c1cccc(-c2nc3cc(CN4CC[C@@H](C(=O)O)C4)cc(C#N)c3o2)c1C] |
| 5 | US 2018-0179197, Example #28 | (S)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid 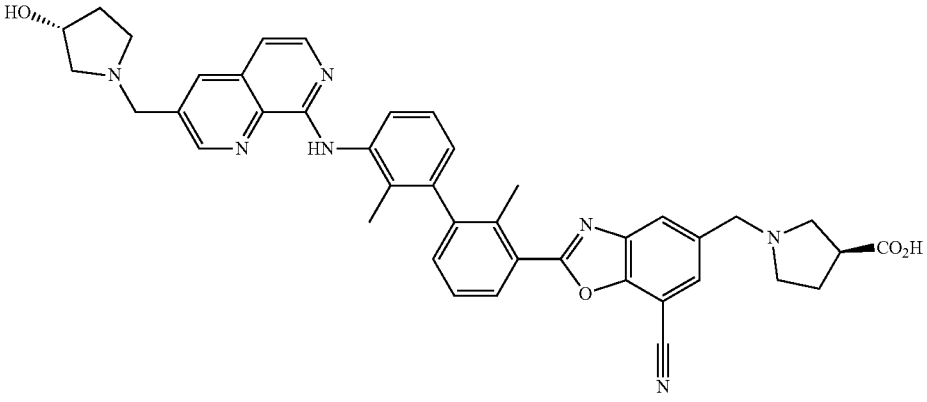 [SMILES: Cc1c(Nc2nccc3cc(CN4CC[C@@H](O)C4)cnc23)cccc1-c1cccc(-c2nc3cc(CN4CC[C@H](C(=O)O)C4)cc(C#N)c3o2)c1C] |
| 6 | US 2018-0179197, Example #236 | 1-((7-cyano-2-(3'-(5-(2-(dimethylamino)acetyl)-5,6-dihydro-4H-pyrrolo[3,4-d]thiazol-2-yl)-2,2'-dimethylbiphenyl-3-yl)benzo[d]oxazol-5-yl)methyl)piperidine-4-carboxylic acid 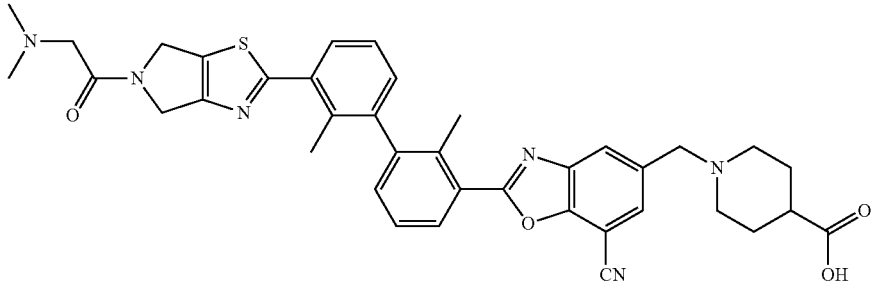 [SMILES: Cc1c(-c2nc3cc(CN4CCC(C(=O)O)CC4)cc(C#N)c3o2)cccc1-c1cccc(-c2nc3c(s2)CN(C(=O)CN(C)C)C3)c1C] |
| 7 | US 2018-0179179, Example #1 | N,N'-(2-chloro-2'-methylbiphenyl-3,3'-diyl)bis(5-((2-hydroxyethylamino)methyl)picolinamide) 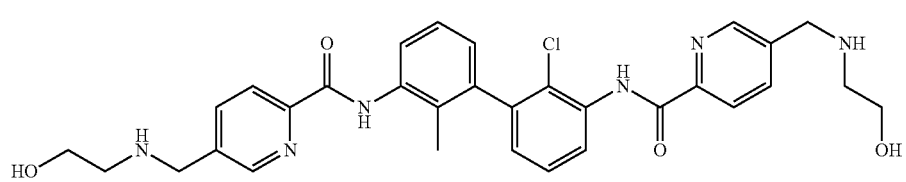 [SMILES: Cc1c(NC(=O)c2ccc(CNCCO)cn2)cccc1-c1cccc(NC(=O)c2ccc(CNCCO)cn2)c1Cl] |

TABLE A-continued

| Cmpd No. | US Publication Appl. No. | Name and Structure |
|---|---|---|
| 8 | US 2018-0179179, Example #9 | (R)-1-((6-(2'-chloro-3'-(5-((3-hydroxypyrrolidin-1-yl)methyl)picolinamido)-2-methylbiphenyl-3-ylcarbamoyl)pyridin-3-yl)methyl)piperidine-4-carboxylic acid |
| 9 | US 2018-0179179, Example #12 | (S)-1-((6-((2'-chloro-2-methyl-3'-(5-(pyrrolidin-1-ylmethyl)picolinamido)-[1,1'-biphenyl]-3-yl)carbamoyl)-4-methylpyridin-3-yl)methyl)piperidine-2-carboxylic acid |
| 10 | US 2018-0179202, Example #52 | trans 4-(2-(2-(2-chloro-3'-(3-(((R)-3-hydroxypyrrolidin-1-yl)methyl)-1,7-naphthyridin-8-ylamino)-2'-methylbiphentl-3-ylcarbamoyl)-1-methyl-6,7-dihydro-1H-imidazo[4,5-c]pyridin-5(4H)-yl)ethyl)cyclohexanecarboxylic acid |
| 11 | US 2018-0179202, Example #56 | cis-4-((2-(2-chloro-3'-(3-(((R)-3-hydroxy-3-methylpyrrolidin-1-yl)methyl)-1,7-naphthyridin-8-ylamino)-2'-methylbiphenyl-3-ylcarbamoyl)-methyl-6,7-dihydro-1H-imidazo[4,5-c]pyridin-5(4H)-yl)methyl)cyclohexanecarboxylic acid |
| 12 | US 2018-0179202, Example #68 | (R)-4-(2-(2-chloro-3'-(7-((3-hydroxypyrrolidin-1-yl)methyl)pyrido[3,2-d]pyrimidin-4-ylamino)-2'-methylbiphenyl-3-ylcarbamoyl)-1-methyl-6,7-dihydro-1H-imidazo[4,5-c]pyridin-5(4H)-yl)-1-methylcyclohexanecarboxylic acid |

TABLE A-continued

| Cmpd No. | US Publication Appl. No. | Name and Structure |
|---|---|---|
| 13 | US 2018-0179202, Example #90 | (R)-1-((8-((2-chloro-3'-(5-(N-ethyl-N-methylglycyl)-5,6-dihydro-4H-pyrrolo[3,4-d]thiazol-2-yl)-2'-methyl-[1,1'-biphenyl]-3-yl)amino)-1,7 naphthyridin-3-yl)methyl)pyrrolidine-3-carboxylic acid |
| 14 | US 2018-0177784, Example #35 | (R)-2-(dimethylamino)-1-(2-(3'-(5-(2-(3-hydroxypyrrolidin-1-yl)acetyl)-5,6-dihydro-4H-pyrrolo[3,4-d]thiazol-2-yl)-2,2'-dimethylbiphenyl-3-yl)-4H-pyrrolo[3,4-d]thiazol-5(6H)-yl)ethanone |
| 15 | US 2018-0177870, Example #37 | trans-4-((2-(2'-chloro-3'-(1,5-dimethyl-4,5,6,7-tetrahydro-1H-imidazo[4,5-c]pyridine-2-carboxamido)-2-methylbiphenyl-3-ylcarbamoyl)-methyl-6,7-dihydro-1H-imidazo[4,5-c]pyridin-5(4H)-yl)methyl)cyclohexane-1-carboxylic acid |

TABLE A-continued

| Cmpd No. | US Publication Appl. No. | Name and Structure |
|---|---|---|
| 16 | US 2018-0177870, Example #100 | trans-4-(2-(2-((2'-chloro-3'-(1,5-dimethyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid |
| 17 | US 2018-0177870, Example #114 | cis-4-((2-((2'-chloro-3'-(1,5-dimethyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid |
| 18 | US 2018-0177870, Example #135 | cis-4-((2-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)carbamoyl-1-methyl-1,4,6,7-tetrahydro-5H-imidazo[4,5-c]pyridin-5-yl)methyl)cyclohexane-1-carboxylic acid |

TABLE A-continued

| Cmpd No. | US Publication Appl. No. | Name and Structure |
|---|---|---|
| 19 | US 2018-0177870, Example #148 | trans-4-(2-(2-((2'-chloro-2-cyano-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid |
| 20 | US 2018-0177870, Example #159 | trans-4-((2-(2-chloro-3'-(5-(2-(ethyl(methyl)amino)acetyl)-5,6-dihydro-4H-pyrrolo[3,4-d]thizol-2-yl)-2'-methylbiphenyl-3-ylcarbamoyl)-1-methyl-6,7-dihydro-1H-imidazo[4,5-c]pyridin-5(4H)-yl)methyl)cyclohexane-1-carboxylic acid |
| 21 | US 2018-0177870, Example #160 | cis-4-((2-(2-chloro-3'-(5-(2-(ethyl(methyl)amino)acetyl)-5-6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)methyl)cyclohexane-1-carboxylic acid |

TABLE A-continued

| Cmpd No. | US Publication Appl. No. | Name and Structure |
|---|---|---|
| 22 | US 2018-0177870, Example #161 | 4-(2-(2-(2-chloro-3'-(5-(2-(ethyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)ethyl)cyclohexane-1-carboxylic acid |
| 23 | US 2018-0177870, Example #162 | 4-(2-(2-(2-chloro-3'-(5-(2-(isopropyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)ethyl)cyclohexane-1-carboxylic acid |
| 24 | US 2019-0300524, Example #16 | (R)-1-((7-cyano-2-(3'-(2-(difluoromethyl)-7-((3-hydroxypyrrolidin-1-yl)methyl)pyrido[3,2-d]pyrimidin-4-ylamino)-2,2'-dimethylbiphenyl-3-yl)benzo[d]oxazol-5-yl)methyl)piperidine-4-carboxylic acid |

TABLE A-continued

| Cmpd No. | US Publication Appl. No. | Name and Structure |
|---|---|---|
| 25 | US 2019-0300524, Example #17 | (R)-1-((7-cyano-2-(3'-(2-(difluoromethyl)-7-(((R)-3-hydroxypyrrolidin-1-yl)methyl)pyrido[3,2-d]pyrimidin-4-ylamino)-2,2'-dimethylphenyl-3-yl)benzo[d]oxazol-5-yl)methyl)pyrrolidine-3-carboxylic acid |
| 26 | US 2019-0300524, Example #18 | (R)-1-((7-cyano-2-(3'-(2-(difluoromethyl)-7-(((R)-3-hydroxypyrrolidin-1-yl)methyl)pyrido[3,2-d]pyrimidin-4-ylamino)-2,2'-dimethylbiphenyl-3-yl)benzo[d]oxazol-5-yl)methyl)-3-methylpyrrolidine-3-carboxylic acid |
| 27 | US 2019-0300524, Example #30 | (R)-1-((7-cyano-2-(3'-(2-(difluoromehtyl)-7-((3-hydroxy-3-methylpyrrolidin-1-yl)methyl)pyrido[3,2-d]pyrimidin-4-ylamino)-2,2'-dimethylbiphenyl-3-yl)benzo[d]oxazol-5-yl)methyl)piperidine-4-carboxylic acid |
| 28 | US 2019-0300524, Example #31 | (S)-1-((7-cyano-2-(3'-(2-(difluoromethyl)-7-((3-hydroxy-3-methylpyrrolidin-1-yl)methyl)pyrido[3,2-d]pyrimidin-4-ylamino)-2,2'-dimethylbiphenyl-3-yl)benzo[d]oxazol-5-yl)methyl)piperidine-4-carboxylic acid |

TABLE A-continued

| Cmpd No. | US Publication Appl. No. | Name and Structure |
|---|---|---|
| 29 | US 2019-0345170, Example #13 | (R)-4-(2-(2-((2,2'-dichloro-3'-(5-(2-hydroxypropyl)-1-methyl-4,5,6,7-tetrahydro-1H-imidazo[4,5-c]pyridine-3-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid |
| 30 | US 2019-0345170, Example #17 | 4,4'-(((((2,2'-dichloro-[1,1'-biphenyl]-3,3'-diyl)bis(azanediyl))bis(carbonyl))bis(1-methyl-1,4,6,7-tertrahydro-5H-imidazo[4,5-c]pyridine-2,5-diyl))bis(ethane-2,1-diyl))bis(bicyclo[2.2.1]heptane-1-carboxylic acid) |

TABLE A-continued

| Cmpd No. | US Publication Appl. No. | Name and Structure |
|---|---|---|
| 31 | US 2019-0345170, Example #18 | 4-((2-((3'-(5-(2-(4-carboxybicyclo[2.2.1]heptan-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic acid |
| 32 | US 2019-0345170, Example #34 | 4,4'-((((((2-chloro-2'-methyl-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethan-2,1-diyl))bis(bicyclo[2.2.1]heptane-1-carboxylic acid) |

TABLE A-continued

| Cmpd No. | US Publication Appl. No. | Name and Structure |
|---|---|---|
| 33 | US 2019-0345170, Example #51 | 4,4'-(((((2-chloro-2'-cyano-[1,1'-biphenyl]-3,3'-diyl)bis(azanediyl))bis(carbonyl))bis(1-methyl-1,4,6,7-tetrahydro-5H-imidazo[4,5-c]pyridine-2,5-diyl))bis(ethane-2,1-diyl))bis(bicyclo[2.2.1]heptane-1-carboxylic acid) |

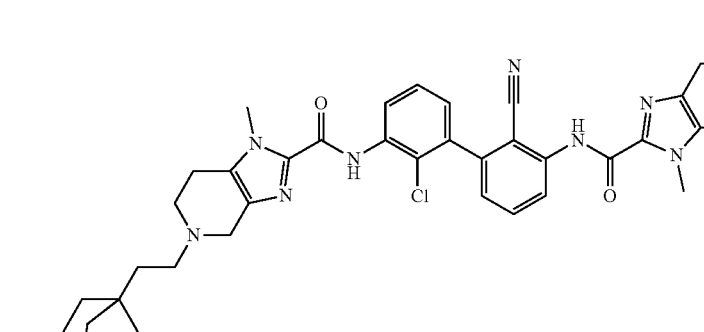

| 34 | US 2021-0094976, Example #1 | (R)-4-(2-(2-((2-chloro-3'-((2-(difluoromethyl)-7-((3-hydroxypyrrolidin-1-yl)methyl)pyrido[3,2-d]pyrimidin-4-yl)amino)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid |

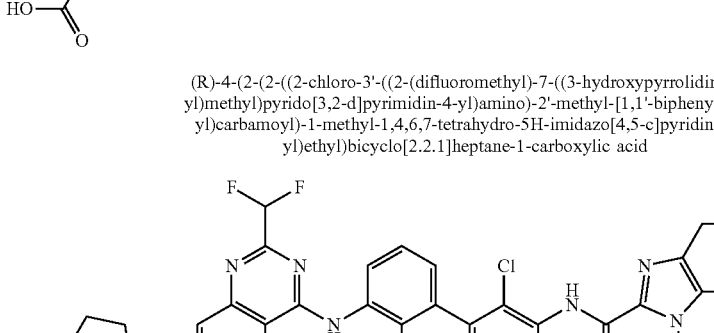

In some embodiments, the antibody is an anti-PD-1 antibody, e.g., an anti-PD-1 monoclonal antibody. In some embodiments, the anti-PD-1 antibody is nivolumab, pembrolizumab, cemiplimab, spartalizumab, camrelizumab, cetrelimab, toripalimab, sintilimab, AB122, AMP-224, JTX-4014, BGB-108, BCD-100, BAT1306, LZM009, AK105, HLX10, or TSR-042. In some embodiments, the anti-PD-1 antibody is nivolumab, pembrolizumab, cemiplimab, spartalizumab, camrelizumab, cetrelimab, toripalimab, or sintilimab. In some embodiments, the anti-PD-1 antibody is pembrolizumab. In some embodiments, the anti-PD-1 antibody is nivolumab. In some embodiments, the anti-PD-1 antibody is cemiplimab. In some embodiments, the anti-PD-1 antibody is spartalizumab. In some embodiments, the anti-PD-1 antibody is camrelizumab. In some embodiments, the anti-PD-1 antibody is cetrelimab. In some embodiments, the anti-PD-1 antibody is toripalimab. In some embodiments, the anti-PD-1 antibody is sintilimab. In some embodiments, the anti-PD-1 antibody is AB122. In some embodiments, the anti-PD-1 antibody is AMP-224. In some embodiments, the anti-PD-1 antibody is JTX-4014. In some embodiments, the anti-PD-1 antibody is BGB-108. In some embodiments, the anti-PD-1 antibody is BCD-100. In some embodiments, the anti-PD-1 antibody is BAT1306. In some embodiments, the anti-PD-1 antibody is LZM009. In some embodiments, the anti-PD-1 antibody is AK105. In some embodiments, the anti-PD-1 antibody is HLX10. In some embodiments, the anti-PD-1 antibody is TSR-042. In some embodiments, the anti-PD-1 monoclonal antibody is nivolumab or pembrolizumab. In some embodiments, the anti-PD-1 monoclonal antibody is MGA012 (INCMGA0012; retifanlimab). In some embodiments, the anti-PD1 antibody is SHR-1210. Other anti-cancer agent(s) include antibody therapeutics such as 4-1 BB (e.g., urelumab, utomilumab). In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, avelumab, durvalumab, tislelizumab, BMS-935559, MED14736, atezolizumab (MPDL3280A; also known as RG7446), avelumab (MSB0010718C), FAZ053, KN035, CS1001, SHR-1316, CBT-502, A167, STI-A101, CK-301, BGB-A333, MSB-2311, HLX20, or LY3300054. In some embodiments, the anti-PD-L1 antibody is atezolizumab, avelumab, durvalumab, or tislelizumab. In some embodiments, the anti-PD-L1 antibody is atezolizumab. In some embodiments, the anti-PD-L1 antibody is avelumab. In some embodiments, the anti-PD-L1 antibody is durvalumab. In some embodiments, the anti-PD-L1 antibody is tislelizumab. In some embodiments, the anti-PD-L1 antibody is BMS-935559. In some embodiments, the anti-PD-L1 antibody is MED14736. In some embodiments, the anti-PD-L1 antibody is FAZ053. In some embodiments, the anti-PD-L1 antibody is KN035. In some embodiments, the anti-PD-L1 antibody is CS1001. In some embodiments, the anti-PD-L1 antibody is SHR-1316. In some embodiments, the anti-PD-L1 antibody is CBT-502. In some embodiments, the anti-PD-L1 antibody is A167. In some embodiments, the anti-PD-L1 antibody is STI-A101. In some embodiments, the anti-PD-L1 antibody is CK-301. In some embodiments, the anti-PD-L1 antibody is BGB-A333. In some embodiments, the anti-PD-L1 antibody is MSB-2311. In some embodiments, the anti-PD-L1 antibody is HLX20. In some embodiments, the anti-PD-L1 antibody is LY3300054.

In some embodiments, the inhibitor of an immune checkpoint molecule is a small molecule that binds to PD-L1, or a pharmaceutically acceptable salt thereof. In some embodiments, the inhibitor of an immune checkpoint molecule is a small molecule that binds to and internalizes PD-L1, or a pharmaceutically acceptable salt thereof. In some embodiments, the inhibitor of an immune checkpoint molecule is a compound selected from those in US 2018/0179201, US 2018/0179197, US 2018/0179179, US 2018/0179202, US 2018/0177784, US 2018/0177870, U.S. Ser. No. 16/369,654 (filed Mar. 29, 2019), and U.S. Ser. No. 62/688,164, or a pharmaceutically acceptable salt thereof, each of which is incorporated herein by reference in its entirety.

In some embodiments, the inhibitor of an immune checkpoint molecule is an inhibitor of KIR, TIGIT, LAIR1, CD160, 2B4 and TGFR beta.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, INCAGN2385, or eftilagimod alpha (IMP321).

In some embodiments, the inhibitor of an immune checkpoint molecule is an inhibitor of CD73. In some embodiments, the inhibitor of CD73 is oleclumab.

In some embodiments, the inhibitor of an immune checkpoint molecule is an inhibitor of TIGIT. In some embodiments, the inhibitor of TIGIT is OMP-31M32.

In some embodiments, the inhibitor of an immune checkpoint molecule is an inhibitor of VISTA. In some embodiments, the inhibitor of VISTA is JNJ-61610588 or CA-170.

In some embodiments, the inhibitor of an immune checkpoint molecule is an inhibitor of B7-H3. In some embodiments, the inhibitor of B7-H3 is enoblituzumab, MGD009, or 8H9.

In some embodiments, the inhibitor of an immune checkpoint molecule is an inhibitor of KIR. In some embodiments, the inhibitor of KIR is lirilumab or IPH4102.

In some embodiments, the inhibitor of an immune checkpoint molecule is an inhibitor of A2aR. In some embodiments, the inhibitor of A2aR is CPI-444.

In some embodiments, the inhibitor of an immune checkpoint molecule is an inhibitor of TGF-beta. In some embodiments, the inhibitor of TGF-beta is trabedersen, galusertinib, or M7824.

In some embodiments, the inhibitor of an immune checkpoint molecule is an inhibitor of PI3K-gamma. In some embodiments, the inhibitor of PI3K-gamma is IPI-549.

In some embodiments, the inhibitor of an immune checkpoint molecule is an inhibitor of CD47. In some embodiments, the inhibitor of CD47 is Hu5F9-G4 or TTI-621.

In some embodiments, the inhibitor of an immune checkpoint molecule is an inhibitor of CD73. In some embodiments, the inhibitor of CD73 is MED19447.

In some embodiments, the inhibitor of an immune checkpoint molecule is an inhibitor of CD70. In some embodiments, the inhibitor of CD70 is cusatuzumab or BMS-936561.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of CD20, e.g., an anti-CD20 antibody. In some embodiments, the anti-CD20 antibody is obinutuzumab or rituximab.

In some embodiments, the agonist of an immune checkpoint molecule is an agonist of OX40, CD27, CD28, GITR, ICOS, CD40, TLR7/8, and CD137 (also known as 4-1 BB).

In some embodiments, the agonist of CD137 is urelumab. In some embodiments, the agonist of CD137 is utomilumab.

In some embodiments, the agonist of an immune checkpoint molecule is an inhibitor of GITR. In some embodiments, the agonist of GITR is TRX518, MK-4166, INCAGN1876, MK-1248, AMG228, BMS-986156, GWN323, MED11873, or MED16469. In some embodiments, the agonist of an immune checkpoint molecule is an agonist of OX40, e.g., OX40 agonist antibody or OX40L fusion protein. In some embodiments, the anti-OX40 antibody is INCAGN01949, MED10562 (tavolimab), MOXR-0916, PF-04518600, GSK3174998, BMS-986178, or 9B12. In some embodiments, the OX40L fusion protein is MED16383.

In some embodiments, the agonist of an immune checkpoint molecule is an agonist of CD40. In some embodiments, the agonist of CD40 is CP-870893, ADC-1013, CDX-1140, SEA-CD40, R07009789, JNJ-64457107, APX-005M, or Chi Lob 7/4.

In some embodiments, the agonist of an immune checkpoint molecule is an agonist of ICOS. In some embodiments, the agonist of ICOS is GSK-3359609, JTX-2011, or MEDI-570.

In some embodiments, the agonist of an immune checkpoint molecule is an agonist of CD28. In some embodiments, the agonist of CD28 is theralizumab.

In some embodiments, the agonist of an immune checkpoint molecule is an agonist of CD27. In some embodiments, the agonist of CD27 is varlilumab.

In some embodiments, the agonist of an immune checkpoint molecule is an agonist of TLR7/8. In some embodiments, the agonist of TLR7/8 is MEDI9197.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor. In some embodiments, the bispecific antibody binds to PD-1 and PD-L1. In some embodiments, the bispecific antibody that binds to PD-1 and PD-L1 is MCLA-136. In some embodiments, the bispecific antibody binds to PD-L1 and CTLA-4. In some embodiments, the bispecific antibody that binds to PD-L1 and CTLA-4 is AK 04.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196. Inhibitors of arginase inhibitors include INCB1158.

As provided throughout, the additional compounds, inhibitors, agents, etc. can be combined with the present compound in a single or continuous dosage form, or they can be administered simultaneously or sequentially as separate dosage forms.

Formulation, Dosage Forms and Administration

When employed as pharmaceuticals, the compounds of the present disclosure can be administered in the form of pharmaceutical compositions. Thus, the present disclosure provides a composition comprising a compound of Formula I, a compound as recited in any of the claims and described herein, or a pharmaceutically acceptable salt thereof, or any of the embodiments thereof, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the present disclosure or a pharmaceutically acceptable salt thereof, in combination with one or more pharmaceutically acceptable carriers or excipients. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel KOOLV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Labeled Compounds and Assay Methods

Another aspect of the present invention relates to labeled compounds of the disclosure (radio-labeled, fluorescent-labeled, etc.) that would be useful not only in imaging techniques but also in assays, both in vitro and in vivo, for localizing and quantitating KRAS protein in tissue samples, including human, and for identifying KRAS ligands by inhibition binding of a labeled compound. Substitution of one or more of the atoms of the compounds of the present disclosure can also be useful in generating differentiated ADME (Adsorption, Distribution, Metabolism and Excretion). Accordingly, the present invention includes KRAS binding assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formula I can be optionally substituted with deuterium atoms, such as —$CD_3$ being substituted for —$CH_3$). In some embodiments, alkyl groups in Formula I can be perdeuterated.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro adenosine receptor labeling and competition assays, compounds that incorporate $^{3}H$, $^{14}C$, $^{82}Br$, $^{125}I$, $^{131}I$ or $^{35}S$ can be useful. For radio-imaging applications $^{11}C$, $^{18}F$, $^{125}I$, $^{123}I$, $^{124}I$, $^{131}I$, $^{75}Br$, $^{76}Br$ or $^{77}Br$ can be useful.

It is understood that a "radio-labeled" or "labeled compound" is a compound that has incorporated at least one radionuclide. In some embodiments, the radionuclide is selected from $^{3}H$, $^{14}C$, $^{125}I$, $^{35}S$ and $^{82}Br$.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the invention can be used in a screening assay to identify and/or evaluate compounds. For example, a newly synthesized or identified compound (i.e., test compound) which is labeled can be evaluated for its ability to bind a KRAS protein by monitoring its concentration variation when contacting with the KRAS, through tracking of the labeling. For example, a test compound (labeled) can be evaluated for its ability to reduce binding of another compound which is known to bind to a KRAS protein (i.e., standard compound). Accordingly, the ability of a test compound to compete with the standard compound for binding to the KRAS protein directly correlates to its binding affinity.

Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, e.g., in the treatment or prevention of diseases or disorders associated with the activity of KRAS, such as cancer or infections, which include one or more containers containing a pharmaceutical composition comprising a therapeutically effective amount of a compound of Formula I or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of KRAS according to at least one assay described herein.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check.

The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 μm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, J. Comb. Chem., 6, 874-883 (2004)]. Typically, the flow rate used with the 30×100 mm column was 60 mL/minute.

pH=10 purifications: Waters XBridge $C_{18}$ 5 μm particle size, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, J. Comb. Chem., 6, 874-883 (2004)]. Typically, the flow rate used with 30×100 mm column was 60 mL/minute."

The following abbreviations may be used herein: AcOH (acetic acid); $Ac_2O$ (acetic anhydride); aq. (aqueous); atm. (atmosphere(s)); Boc (t-butoxycarbonyl); BOP ((benzotriazol-1-yloxy)tris(dimethylamino)phosphonium hexafluorophosphate); br (broad); Cbz (carboxybenzyl); calc. (calculated); d (doublet); dd (doublet of doublets); DBU (1,8-diazabicyclo[5.4.0]undec-7-ene); DCM (dichloromethane); DIAD (N, N'-diisopropyl azidodicarboxylate); DIEA (N,N-diisopropylethylamine); DIPEA (N, N-diisopropylethylamine); DIBAL (diisobutylaluminium hydride); DMF (N, N-dimethylformamide); Et (ethyl); EtOAc (ethyl acetate); FCC (flash column chromatography); g (gram(s)); h (hour(s)); HATU (N, N, N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography-mass spectrometry); LDA (lithium diisopropylamide); m (multiplet); M (molar); mCPBA (3-chloroperoxybenzoic acid); MS (Mass spectrometry); Me (methyl); MeCN (acetonitrile); MeOH (methanol); mg (milligram(s)); min. (minutes(s)); mL (milliliter(s)); mmol (millimole(s)); N (normal); NCS (N-chlorosuccinimide); $NEt_3$ (triethylamine); nM (nanomolar); NMP (N-methylpyrrolidinone); NMR (nuclear magnetic resonance spectroscopy); OTf (trifluoromethanesulfonate); Ph (phenyl); pM (picomolar); PPT (precipitate); RP-HPLC (reverse phase high performance liquid chromatography); r.t. (room temperature), s (singlet); t (triplet or tertiary); TBS (tert-butyldimethylsilyl); tert (tertiary); tt (triplet of triplets); TFA (trifluoroacetic acid); THF (tetrahydrofuran); μg (microgram(s)); μL (microliter(s)); μM (micromolar); wt % (weight percent). Brine is saturated aqueous sodium chloride. In vacuo is under vacuum.

Intermediate 1. 7-Bromo-2,4-dichloro-8-fluoro-6-iodo-3-nitroquinoline

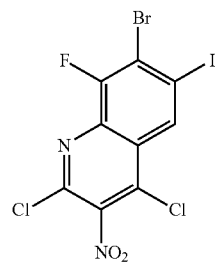 [SMILES: O=[N+]([O-])c1c(Cl)nc2c(F)c(Br)c(I)cc2c1Cl]

Step 1. 2-Amino-4-bromo-3-fluoro-5-iodobenzoic acid

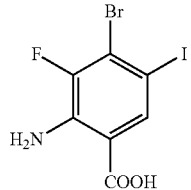 [SMILES: Nc1c(C(=O)O)cc(I)c(Br)c1F]

1-Iodopyrrolidine-2,5-dione (21.15 g, 94 mmol) was added to a solution of 2-amino-4-bromo-3-fluorobenzoic acid (20 g, 85 mmol)) in DMF (200 ml) and then the reaction was stirred at 80° C. for 3 h. The mixture was cooled with ice water and then water (500 mL) was added, the precipitate was filtered and washed with water, dried to provide the desired product as a solid. LC-MS calculated for $C_7H_5BrFINO_2^+$ (M+H)+: m/z=359.9, 361.9; found 359.9, 361.9.

Step 2. 7-Bromo-8-fluoro-6-iodo-2H-benzo[d][1,3]oxazine-2,4(1H)-dione

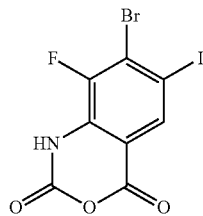 [SMILES: O=c1[nH]c2c(F)c(Br)c(I)cc2c(=O)o1]

Triphosgene (9.07 g, 30.6 mmol) was added to a solution of 2-amino-4-bromo-3-fluoro-5-iodobenzoic acid (22 g, 61.1 mmol) in dioxane (200 ml) and then the reaction was stirred at 80° C. for 2 h. The reaction mixture was cooled with ice water and then filtered. The solid was washed with ethyl acetate to provide the desired product as a solid. LC-MS calculated for $C_8H_3BrFINO_3^+$ (M+H)+: m/z=385.8, 387.8; found 385.8, 387.8.

Step 3. 7-Bromo-8-fluoro-6-iodo-3-nitroquinoline-2,4-diol

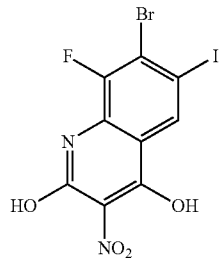 [SMILES: O=[N+]([O-])c1c(O)nc2c(F)c(Br)c(I)cc2c1O]

DIPEA (25.5 ml, 146 mmol) was added to a solution of ethyl 2-nitroacetate (16.33 ml, 146 mmol) and 7-bromo-8-fluoro-6-methyl-2H-benzo[d][1,3]oxazine-2,4(1H)-dione (20 g, 73.0 mmol) in toluene (200 ml) at r.t. and the reaction was stirred at 95° C. for 3 h. The reaction was cooled and then filtered, then washed with small amount of hexanes to provide the desired product. LC-MS calculated for $C_9H_4BrFIN_2O_4^+$ (M+H)+: m/z=428.8, 430.8; found 428.8, 430.8.

Step 4. 7-Bromo-2,4-dichloro-8-fluoro-6-iodo-3-nitroquinoline

DIPEA (8.14 ml, 46.6 mmol) was added to a mixture of 7-bromo-8-fluoro-6-iodo-3-nitroquinoline-2,4-diol (10 g, 23.31 mmol) in POCl$_3$ (10.86 ml, 117 mmol) and then the reaction was stirred at 100° C. for 2 h. The solvent was removed under vacuum and then azeotroped with toluene 3 times to provide the crude material which was purified with flash column. LC-MS calculated for $C_9H_2BrCl_2FIN_2O_2^+$ (M+H)+: m/z=464.8, 466.8; found 464.8, 466.8.

Intermediate 2. tert-Butyl (1R,4R,5S)-5-((7-bromo-6-(2-cyanoethyl)-8-fluoro-3-iodo-2-(methylthio)quinolin-4-yl)(tert-butoxycarbonyl)amino)-2-azabicyclo[2.1.1]hexane-2-carboxylate

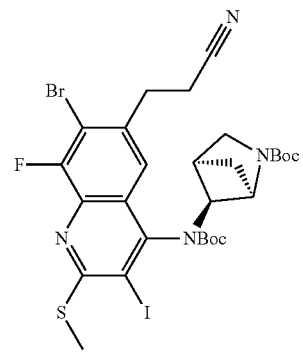

Step 1. tert-Butyl (1R,4R,5S)-5-((7-Bromo-8-fluoro-6-iodo-2-(methylthio)-3-nitroquinolin-4-yl)amino)-2-azabicyclo[2.1.1]hexane-2-carboxylate

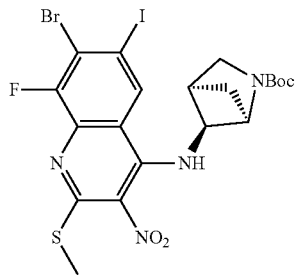

To a solution of 7-bromo-2,4-dichloro-8-fluoro-6-iodo-3-nitroquinoline (25 g, 53.7 mmol, Intermediate 1) and tert-butyl (1R,4R,5S)-5-amino-2-azabicyclo[2.1.1]hexane-2-carboxylate (10.6 g, 53.7 mmol) in NMP (200 ml) was added Hunig's base (14.0 ml, 81 mmol) and the reaction mixture was heated to 60° C. for 1 h. Ice chips and water (100 mL) were added and the suspension was stirred for 15 min. The solids were filtered, rinsed with water, and air dried under vacuum overnight to afford the desired product.

The solid obtained above was suspended in MeCN (200 mL) and cooled to 0° C. A solution of sodium thiomethoxide (11.3 g, 161 mmol) in MeOH (30 ml) was slowly added and the reaction mixture was stirred at this temperature for 1 h. Ice and water were added, and the solid was filtered and air dried. The filtrate was extracted with EtOAc and combined with the solid. The combined product was used without purification. LC-MS calculated for $C_{20}H_{22}BrFIN_4O_4S^+$ (M+H)+: m/z=639.0; found 639.1.

Step 2. tert-Butyl (1R,4R,5S)-5-((7-Bromo-8-fluoro-6-iodo-2-(methylthio)-3-nitroquinolin-4-yl)(tert-butoxycarbonyl)amino)-2-azabicyclo[2.1.1]hexane-2-carboxylate

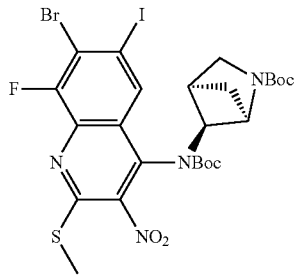

To a solution of tert-butyl (1R,4R,5S)-5-((7-bromo-8-fluoro-6-iodo-2-(methylthio)-3-nitroquinolin-4-yl)amino)-2-azabicyclo[2.1.1]hexane-2-carboxylate (34.3 g, 53.7 mmol) in THF (200 ml) was added triethylamine (18.7 ml, 134 mmol), DMAP (0.66 g, 5.37 mmol), and di-tert-butyl dicarbonate (23.4 g, 107 mmol) sequentially at room temperature, and the reaction mixture was heated to 50° C. for 3 h. The reaction mixture was diluted with EtOAc and washed with saturated NaHCO₃ and brine. The organic layer was dried over MgSO₄, filtered, and concentrated. The product was used without purification. LC-MS calculated for $C_{21}H_{22}BrFIN_4O_6S^+$ (M+H-C₄Ha)+: m/z=683.0; found 683.1.

Step 3. tert-Butyl (1R,4R,5S)-5-((3-Amino-7-bromo-8-fluoro-6-iodo-2-(methylthio)quinolin-4-yl)(tert-butoxycarbonyl)amino)-2-azabicyclo[2.1.1]hexane-2-carboxylate

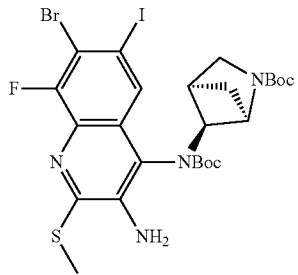

A 1-L flask equipped with a mechanical stirrer was charged with tert-butyl (1R,4R,5S)-5-((7-bromo-8-fluoro-6-iodo-2-(methylthio)-3-nitroquinolin-4-yl)(tert-butoxycarbonyl)amino)-2-azabicyclo[2.1.1]hexane-2-carboxylate (39.7 g, 53.7 mmol), MeOH (75 ml), water (75 ml), and THF (75 ml). Iron (15.0 g, 268 mmol) and ammonium chloride (14.4 g, 268 mmol) were added, and the reaction mixture was stirred at 70° C. overnight. The reaction mixture was diluted with EtOAc and filtered through a pad of celite. The layers were separated and the organic layer was washed with brine, dried over MgSO₄, filtered and concentrated. The product was used without purification. LC-MS calculated for $C_{25}H_{32}BrFIN_4O_4S^+$ (M+H)+: m/z=709.0; found 709.1.

Step 4. tert-Butyl (1R,4R,5S)-5-((3-amino-7-bromo-6-(2-cyanoethyl)-8-fluoro-2-(methylthio)-quinolin-4-yl)(tert-butoxycarbonyl)amino)-2-azabicyclo[2.1.1]hexane-2-carboxylate

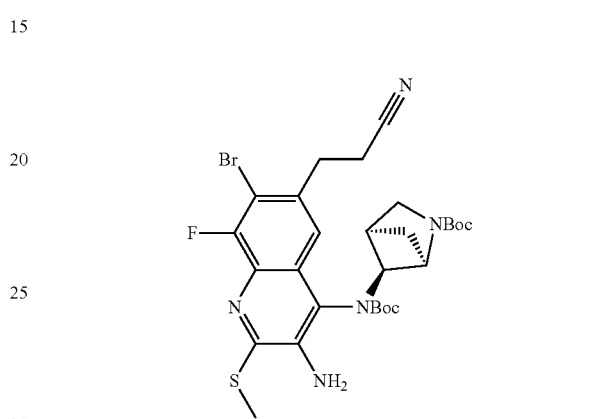

tert-Butyl (1R,4R,5S)-5-((3-amino-7-bromo-8-fluoro-6-iodo-2-(methylthio)quinolin-4-yl)(tert-butoxycarbonyl)amino)-2-azabicyclo[2.1.1]hexane-2-carboxylate (36.7 g, 51.7 mmol), PdOAc₂ (1.16 g, 5.17 mmol), and tri-o-tolylphosphine (3.15 g, 10.4 mmol) were dissolved in DMF (200 ml). Acrylonitrile (6.78 ml, 103 mmol) and triethylamine (14.3 ml, 103 mmol) were added to the reaction mixture in one portion. The headspace was purged with nitrogen and the reaction mixture was stirred at 80° C. for two hours. The reaction mixture was cooled to room temperature and water was added. The resulting precipitate was filtered, washed with water, and air dried.

The resulting solid was taken up in THF (200 ml) and cooled to 0° C. Superhydride (55.8 ml, 55.8 mmol) was added dropwise with LCMS monitoring. Upon completion, MeOH and water were added dropwise at 0° C., then the reaction mixture was warmed to room temperature and stirred for 15 min. The reaction mixture was extracted with EtOAc and the layers were separated. The organic layer was washed with brine, dried over MgSO₄, filtered, and concentrated. The product was used without purification. LC-MS calculated for $C_{28}H_{36}BrFN_5O_4S^+$ (M+H)+: m/z=636.2; found 636.3.

Step 5. tert-Butyl (1R,4R,5S)-5-((7-Bromo-6-(2-cyanoethyl)-8-fluoro-3-iodo-2-(methylthio)quinolin-4-yl)(tert-butoxycarbonyl)amino)-2-azabicyclo[2.1.1]hexane-2-carboxylate To a mixture of tert-butyl (1R,4R,5S)-5-((3-amino-7-bromo-6-(2-cyanoethyl)-8-fluoro-2-(methylthio)quinolin-4-yl)(tert-butoxycarbonyl)amino)-2-azabicyclo[2.1.1]hexane-2-carboxylate (32 g, 50.3 mmol), potassium iodide (41.7 g, 251 mmol), and copper(I) iodide (12.45 g, 65.3 mmol) was added propionic acid (200 ml) and water (50 mL), and the mixture was cooled to −10° C. t-BuONO (50 mL, 377 mmol) was added slowly over 15 minutes to control bubbling. After the addition, the reaction was stirred for 30 minutes. The reaction mixture was poured into cold sodium thiosulfate solution and then extracted with ethyl acetate. The organic layer was washed with NH$_4$OH and saturated NaCl, dried over MgSO$_4$ and concentrated. The product was purified by FCC (0-50% EtOAc/hexanes) to yield the title compound as a brown solid (20 g, 53% over 5 steps). LC-MS calculated for C$_{24}$H$_{26}$BrFIN$_4$O$_4$S$^+$ (M+H-C$_4$H$_8$)$^+$: m/z=691.0; found 691.1.

Intermediate 3. tert-Butyl 5,7-difluoro-3-(4,4,5,5-tetramethyl-1,3,2-dioxaborolan-2-yl)-1H-indole-1-carboxylate

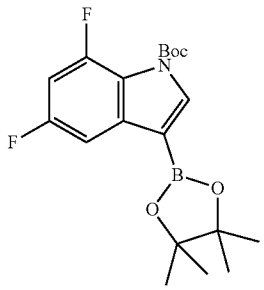 [SMILES: CC(C)(C)OC(=O)n1cc(B2OC(C)(C)C(C)(C)O2)c2cc(F)cc(F)c21]

Step 1. tert-Butyl 3-bromo-5,7-difluoro-1H-indole-1-carboxylate

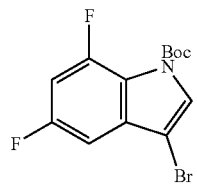 [SMILES: CC(C)(C)OC(=O)n1cc(Br)c2cc(F)cc(F)c21]

To a solution of 5,7-difluoro-1H-indole (300 mg, 1.96 mmol) in DMF (8 ml) at 0° C. was added NBS (384 mg, 2.16 mmol) and the reaction mixture was stirred at this temperature for 30 min. Once the bromination was complete, triethylamine (410 µl, 2.94 mmol), Boc-anhydride (641 mg, 2.94 mmol), and DMAP (24 mg, 0.2 mmol) were added sequentially, and the reaction mixture was allowed to warm to room temperature. After 30 min, the reaction was diluted with EtOAc and quenched with saturated NaHCO$_3$. The reaction mixture was partitioned between water and EtOAc, and the layers were separated. The organic layer was washed with brine, dried over MgSO$_4$, filtered, and concentrated. The residue was purified by flash chromatography (0-10% hexanes/EtOAc) to afford the title compound (531 mg, 82%). LC-MS calculated for C$_9$H$_5$BrF$_2$NO$_2$$^+$ (M+H-C$_4$H$_8$)$^+$: m/z=276.0; found 276.0.

Step 2. tert-Butyl 5,7-difluoro-3-(4,4,5,5-tetramethyl-1,3,2-dioxaborolan-2-yl)-1H-indole-1-carboxylate A mixture of tert-butyl 3-bromo-5,7-difluoro-1H-indole-1-carboxylate (531 mg, 1.60 mmol), 4,4,4',4',5,5,5',5'-octamethyl-2,2'-bi(1,3,2-dioxaborolane) (1.21 g, 4.80 mmol), potassium acetate (471 mg, 4.80 mmol), and PdCl$_2$(dppf)-CH$_2$Cl$_2$ adduct (131 mg, 0.16 mmol) in dioxane (10 ml) was sparged with N$_2$ and heated to 95° C. overnight. The reaction mixture was diluted with EtOAc, filtered, and concentrated. The residue was purified by flash chromatography (0-10% EtOAc/hexanes). LC-MS calculated for C$_{15}$H$_{17}$BF$_2$NO$_4$$^+$ (M+H-C$_4$H$_8$)$^+$: m/z=324.1; found 324.2.

Intermediate 4. tert-Butyl 6-fluoro-5-methyl-3-(4,4,5,5-tetramethyl-1,3,2-dioxaborolan-2-yl)-1H-indole-1-carboxylate

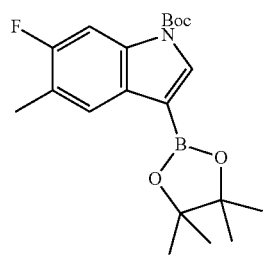

Step 1. tert-Butyl 3-bromo-6-fluoro-5-methyl-1H-indole-1-carboxylate

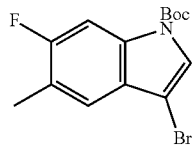

This compound was prepared by a procedure identical to that described for tert-butyl 3-bromo-5,7-difluoro-1H-indole-1-carboxylate (Intermediate 3, Step 1), utilizing 6-fluoro-5-methyl-1H-indole instead of 5,7-difluoro-1H-indole. LC-MS calculated for C$_{14}$H$_{15}$BrFNO$_2$Na$^+$ (M+Na)$^+$: m/z=350.0; found 350.0.

Step 2. tert-Butyl 6-fluoro-5-methyl-3-(4,4,5,5-tetramethyl-1,3,2-dioxaborolan-2-yl)-1H-indole-1-carboxylate To a solution of tert-butyl 3-bromo-6-fluoro-5-methyl-1H-indole-1-carboxylate (187 mg, 0.57 mmol) in THF (4 ml) at −78° C. was added sec-butyllithium (1.4M/hexanes, 0.61 ml, 0.86 mmol), and the reaction mixture was stirred at −78° C. for 15 min. 2-Isopropoxy-4,4,5,5-tetramethyl-1,3,2-dioxaborolane (0.29 ml, 1.43 mmol) was then added and the reaction mixture was allowed to warm to room temperature. The reaction was quenched with saturated NH$_4$Cl and extracted with EtOAc. The layers were separated and the organic layer was dried over MgSO$_4$, filtered, and concentrated. The product was used without purification. LC-MS calculated for C$_{20}$H$_{28}$BFNO$_4$$^+$ (M+H)$^+$: m/z=376.2; found 376.3.

Intermediate 5. tert-Butyl (1R,4R,5S)-5-((7-bromo-6-(2-cyanoethyl)-8-fluoro-3-iodo-2-(methylthio)quinolin-4-yl)amino)-2-azabicyclo[2.1.1]hexane-2-carboxylate

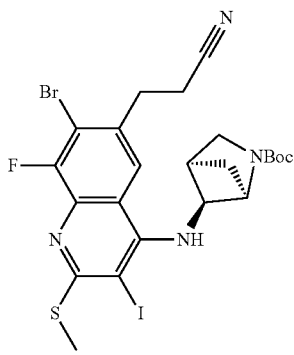 [SMILES: CSc1nc2c(F)c(Br)c(CCC#N)cc2c(N[C@H]2[C@@H]3C[C@H]2N(C(=O)OC(C)(C)C)C3)c1I]

To a solution of tert-butyl (1R,4R,5S)-5-((7-bromo-6-(2-cyanoethyl)-8-fluoro-3-iodo-2-(methylthio)quinolin-4-yl)(tert-butoxycarbonyl)amino)-2-azabicyclo[2.1.1]hexane-2-carboxylate (10.0 g, 13.4 mmol, Intermediate 2) in DCM (134 ml) at room temperature was added TFA (134 mL) and the reaction at room temperature was stirred for 2 h. The reaction mixture was then concentrated and dissolved with THF (134 ml). After that, Boc$_2$O (9.32 ml, 40.1 mmol) and TEA (5.59 ml, 40.1 mmol) were added. The reaction mixture was stirred at room temperature for 1 h. The reaction was then concentrated and purified by flash chromatography (0-60% EtOAc/hexanes) to afford the title compound (6.5 g, 75%). LC-MS calculated for $C_{23}H_{26}BrFIN_4O_2S^+$ (M+H)$^+$: m/z=647.0; found 647.0.

Intermediate 6: tert-Butyl (1R,4R,5S)-5-((7-bromo-8-fluoro-3-iodo-6-methyl-2-(methylthio)quinolin-4-yl)(tert-butoxycarbonyl)amino)-2-azabicyclo[2.1.1]hexane-2-carboxylate

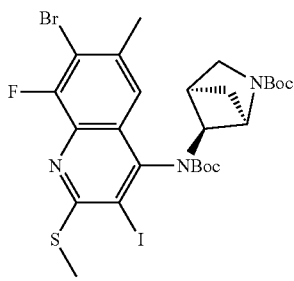

Step 1: tert-Butyl (1R,4R,5S)-5-((3-amino-7-bromo-8-fluoro-6-methyl-2-(methylthio)quinolin-4-yl)(tert-butoxycarbonyl)amino)-2-azabicyclo[2.1.1]hexane-2-carboxylate

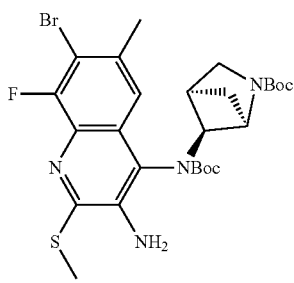

To a mixture of tert-butyl (1R,4R,5S)-5-((3-amino-7-bromo-8-fluoro-6-iodo-2-(methylthio)quinolin-4-yl)(tert-butoxycarbonyl)amino)-2-azabicyclo[2.1.1]hexane-2-carboxylate (10.0 g, 14.1 mmol) (Intermediate 2, Step 3) methylboronic acid (4.22 g, 70.5 mmol), bis(triphenylphosphine)palladium(II) chloride (1.484 g, 2.114 mmol) and Potassium phosphate (8.98 g, 42.3 mmol) were added 1,4-Dioxane (100 ml)/Water (10 ml) and the reaction flask was evacuated, back filled with nitrogen, then stirred at 80 degrees 24 hours. The mixture was diluted with water and extracted with ethyl acetate. The organic layer was washed with water and brine, dried over sodium sulfate and concentrated. The crude product was purified by Biotage (0-50% ethyl acetate in hexanes) to provide the desired product. LC-MS calculated for $C_{26}H_{35}BrFN_4O_4S$ (M+H)$^+$: m/z=597.2; found 597.1.

Step 2: tert-Butyl (1R,4R,5S)-5-((7-bromo-8-fluoro-3-iodo-6-methyl-2-(methylthio)quinolin-4-yl)(tert-butoxycarbonyl)amino)-2-azabicyclo[2.1.1]hexane-2-carboxylate This compound was prepared according to the procedures described in the synthesis of tert-butyl (1R,4R,5S)-5-((7-Bromo-6-(2-cyanoethyl)-8-fluoro-3-iodo-2-(methylthio)quinolin-4-yl)(tert-butoxycarbonyl)amino)-2-azabicyclo[2.1.1]hexane-2-carboxylate (Intermediate 2, Step 5). LC-MS calculated for $C_{26}H_{33}BrFIN_3O_4S$ (M+H)$^+$: m/z=708.0; found 708.2.

Intermediate 7. tert-Butyl (1R,4R,5S)-5-((7-bromo-8-fluoro-3-iodo-6-methyl-2-(methylthio)quinolin-4-yl)amino)-2-azabicyclo[2.1.1]hexane-2-carboxylate

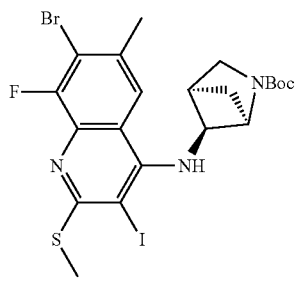

This compound was prepared according to the procedures described in Intermediate 5, using tert-butyl (1R,4R,5S)-5-((7-bromo-8-fluoro-3-iodo-6-methyl-2-(methylthio)quinolin-4-yl)(tert-butoxycarbonyl)amino)-2-azabicyclo[2.1.1]hexane-2-carboxylate (Intermediate 6). LC-MS calculated for $C_{21}H_{25}BrFIN_3O_2S$ (M+H)$^+$: m/z=608.0; found 608.2.

Intermediate 8. Ethyl 7-bromo-2,4-dichloro-8-fluoro-6-iodoquinoline-3-carboxylate

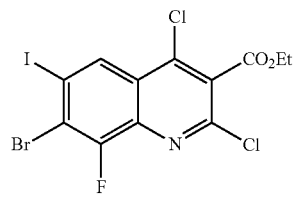 [SMILES: CCOC(=O)c1c(Cl)nc2c(F)c(Br)c(I)cc2c1Cl]

Step 1: Methyl 2-amino-4-bromo-3-fluorobenzoate

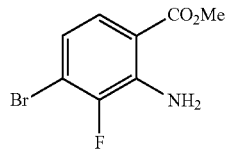 [SMILES: COC(=O)c1ccc(Br)c(F)c1N]

Sulfuric acid (16.7 mL, 313 mmol) was added slowly to a solution of 2-amino-4-bromo-3-fluorobenzoic acid (36.6 g, 156 mmol) in MeOH (300 ml) at r.t. The resulting mixture was heated to 80° C. overnight. The mixture was then cooled to r.t. and slowly quenched with 1 M aqueous NaOH (150 mL). The mixture was stirred at r.t. for 30 min then filtered and dried under air to afford a title compound which was used in the next step without further purification. LC-MS calculated for $C_8H_8BrFNO_2$ (M+H)$^+$: m/z=247.9, 249.9; found 247.9, 249.9.

Step 2: Methyl 2-amino-4-bromo-3-fluoro-5-iodobenzoate

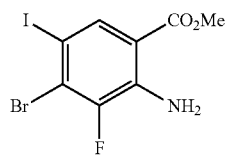

To a solution of methyl 2-amino-4-bromo-3-fluorobenzoate (18.0 g, 72.6 mmol) in DMF (363 ml) was added NIS (29.4 g, 131 mmol). The resultant mixture was stirred 80° C. overnight. After cooling to r.t, ice was added and the mixture was stirred until all ices were dissolvent, filtered, washed with hexanes and dried under air to afford a title compound which was used in the next step without further purification. LC-MS calculated for $C_8H_7BrFINO_2$ (M+H)$^+$: m/z=373.9, 375.9; found 373.9, 375.9.

Step 3: Methyl 4-bromo-2-(3-ethoxy-3-oxopropanamido)-3-fluoro-5-iodobenzoate

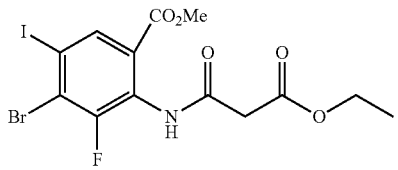 [SMILES: CCOC(=O)CC(=O)Nc1c(C(=O)OC)cc(I)c(Br)c1F]

To a solution of methyl 2-amino-4-bromo-3-fluoro-5-iodobenzoate (10.6 g, 28.3 mmol) and TEA (8.69 mL, 62.4 mmol) in DCM (150 mL) was added dropwise ethyl 3-chloro-3-oxopropanoate (7.26 mL, 56.7 mmol) under air at r.t. The resulting mixture was stirred at r.t. for 2 h and quenched with water. The resulting mixture was extracted with DCM (×2). The organic extracts were combined, dried and concentrated under reduced pressure. Flash column chromatography (0-100% EtOAc:DCM) affords the title compound. LC-MS calculated for $C_{13}H_{13}BrFINO_5$ (M+H)$^+$: m/z=487.9, 489.9; found 487.9, 489.9.

Step 4: Ethyl 7-bromo-8-fluoro-4-hydroxy-6-iodo-2-oxo-1,2-dihydroquinoline-3-carboxylate

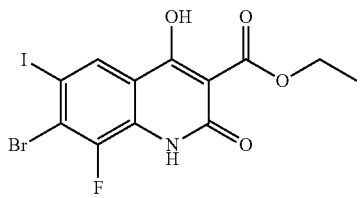 [SMILES: CCOC(=O)c1c(O)c2cc(I)c(Br)c(F)c2[nH]c1=O]

To a solution of methyl 4-bromo-2-(3-ethoxy-3-oxopropanamido)-3-fluoro-5-iodobenzoate (12.3 g, 25.2 mmol) in MeOH (125 mL) was added sodium methoxide in MeOH (25%, 16.6 mL, 52.9 mmol) and. stirred at r.t. for 1 h. The solvent was removed under vacuum, and the crude product was used in the next step without further purification. LC-MS calculated for $C_{12}H_9BrFINO_4$ (M+H)$^+$: m/z=455.9, 457.9; found 455.8, 457.8.

Step 5: Ethyl 7-bromo-2,4-dichloro-8-fluoro-6-iodoquinoline-3-carboxylate

Ethyl 7-bromo-8-fluoro-2,4-dihydroxy-6-iodoquinoline-3-carboxylate (11.0 g, 24.1 mmol) was dissolved in $POCl_3$ (45.0 mL, 110 mmol). The resulting mixture was stirred at 110° C. for 2 h. After cooling to r.t., $POCl_3$ was removed by azeotrope with toluene (3 times).

Flash column chromatography (0-100% DCM:Hexanes) affords the title compound. LC-MS calculated for $C_{12}H_7BrCl_2FINO_2$ (M+H)$^+$: m/z=491.8, 493.8; found 491.8, 493.8.

Intermediate 9. tert-Butyl (2S,4S)-4-amino-2-(2-((tert-butyldimethylsilyl)oxy)ethyl)piperidine-1-carboxylate

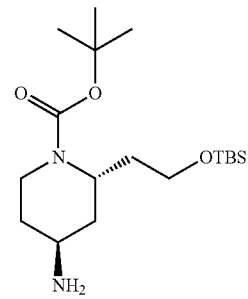 [SMILES: CC(C)(C)OC(=O)N1CC[C@H](N)C[C@H]1CCO[Si](C)(C)C(C)(C)C]

Step 1: tert-Butyl (R)-6-cyano-5-hydroxy-3-oxohexanoate

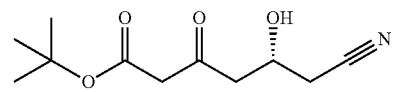 [SMILES: CC(C)(C)OC(=O)CC(=O)C[C@H](O)CC#N]

To a solution of 2.0 M LDA (100 ml, 200 mmol) in anhydrous THF (223 ml) was cooled to −78° C. for 1 h, and then tert-butyl acetate (26.9 mL, 200 mmol) was added dropwise with stirring over 20 min. After an additional 40 minutes maintained at −78° C., a solution of ethyl (R)-4-cyano-3-hydroxybutanoate (10.5 g, 66.8 mmol) was added dropwise. The mixture was allowed to stir at −40° C. for 4 h, and then an appropriate amount of HCl (2 M) was added to the mixture, keeping pH ~6. During this quench, the temperature of the mixture was maintained at −10° C. Upon completion, the temperature of the mixture was cooled to 0° C. The mixture was extracted with ethyl acetate (3×100 mL). The combined organic layer was washed with NaHCO$_3$ (100 mL) and brine (100 mL), dried over anhydrous Na$_2$SO$_4$, and evaporated to provide the material as yellow oil (15.0 g, 99%).

Step 2. tert-Butyl (2S,4R)-2-(2-(tert-butoxy)-2-oxoethyl)-4-hydroxypiperidine-1-carboxylate

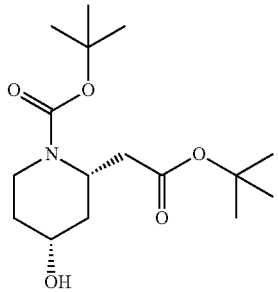 [SMILES: CC(C)(C)OC(=O)C[C@@H]1C[C@H](O)CCN1C(=O)OC(C)(C)C]

A solution of tert-butyl (R)-6-cyano-5-hydroxy-3-oxohexanoate (15.0 g, 66.0 mmol) in acetic acid (110 mL) was treated with platinum (IV) oxide hydrate (0.868 g, 3.30 mmol). The Parr bottle was evacuated and backfilled with H$_2$ three times and stirred under a H$_2$ atmosphere (45 psi, recharged 4 times) at 22° C. for 3 h. The mixture was filtered through Celite and the filter cake was washed with EtOH. The filtrate was concentrated to yield product with a ~9:1 cis:trans diastereomer ratio. The residue was dissolved in methanol (100 mL) then Boc-anhydride (15.3 mL, 66.0 mmol), sodium carbonate (14.0 g, 132 mmol) was added. The reaction mixture was stirred at room temperature overnight. The mixture was filtered and concentrated. The residue was purified with silica gel column to give the desired product (11.7 g, 56%). LCMS (product+Na$^+$) calculated for C$_{16}$H$_{29}$NNaO$_5$ (M+Na)$^+$: m/z=338.2; found: 338.2.

Step 3. tert-Butyl (2S,4S)-4-azido-2-(2-(tert-butoxy)-2-oxoethyl)piperidine-1-carboxylate

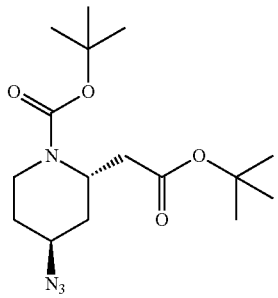 [SMILES: CC(C)(C)OC(=O)C[C@@H]1C[C@@H](N=[N+]=[N-])CCN1C(=O)OC(C)(C)C]

To a solution of tert-butyl (2S,4R)-2-(2-(tert-butoxy)-2-oxoethyl)-4-hydroxypiperidine-1-carboxylate (2.10 g, 6.66 mmol) in DCM (33 mL) at 0° C. was added Ms-Cl (0.67 mL, 8.7 mmol), After stirring for 1 h, The reaction was diluted with water and organic layer was separated and dried over Na$_2$SO$_4$, filtered and concentrated. The resulting residue was dissolved in DMF and sodium azide (1.3 g, 20 mmol) was added and the reaction mixture was heated at 70° C. for 5 h. After cooling to r.t., the reaction was diluted with EtOAc and water. The organic layer was separated and dried over Na$_2$SO$_4$, filtered and concentrated. The residue was purified with silica gel column to give the desired product (1.9 g, 84%). LCMS calculated for (Product-Boc) C$_{11}$H$_{21}$N$_4$O$_2$ (M+H)$^+$: m/z=241.2; found: 241.2.

Step 4. tert-Butyl (2S,4S)-4-azido-2-(2-hydroxyethyl)piperidine-1-carboxylate

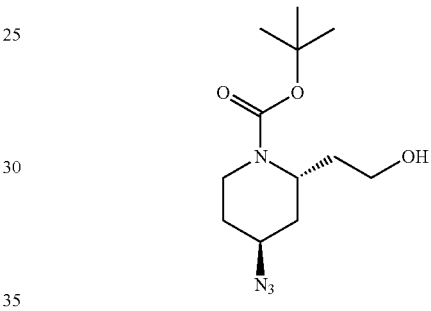

To a solution of tert-butyl (2S,4S)-4-azido-2-(2-(tert-butoxy)-2-oxoethyl)piperidine-1-carboxylate (21.4 g, 62.9 mmol) in DCM (400 mL) at −78° C. was added 1.0 M DIBAL-H in DCM (113 mL, 113 mmol). The resulting mixture was stirred at −78° C. for 2 h. The reaction was quenched with methanol (38.1 mL, 943 mmol) at −78° C. Aqueous Rochelle salt solution (prepared from 126 g (6 wt) of Rochelle salt and 300 mL of water) was added to the solution at ≤10° C. The biphasic mixture was stirred vigorously for ≥1 h at 15-25° C. and separated to give organic layer. The biphasic mixture was separated. The organic layer was washed with aqueous NaCl (×2) at 15-25° C., The organic layer was dried over Na$_2$SO$_4$, filtered and concentrated. and used as is. The residue was dissolved in the methanol (300 mL) and sodium borohydride (1.43 g, 37.7 mmol) was added at 0° C. The reaction mixture was stirred at 0° C. for 1 h. The reaction was quenched with water, methanol was evaporated under reduced pressure. The reaction mixture was extracted with ethyl acetate (2×), the organic layer was washed with brine, dried over Na$_2$SO$_4$, filtered and concentrated. The crude was purified with flash chromatography (eluting with a gradient 0-50% ethyl acetate in hexanes) to give the desired product as colorless oil (14.8 g, 87%). LCMS calculated for (Product-Boc) C$_7$H$_{15}$N$_4$O (M+H)$^+$: m/z=171.1; found: 171.1.

Step 5. tert-Butyl (2S,4S)-4-azido-2-(2-((tert-butyldimethylsilyl)oxy)ethyl)piperidine-1-carboxylate

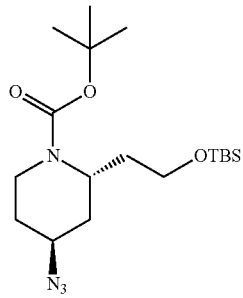 [SMILES: CC(C)(C)OC(=O)N1CC[C@H](N=[N+]=[N-])C[C@H]1CCO[Si](C)(C)C(C)(C)C]

To a solution of tert-butyl (2S,4S)-4-azido-2-(2-hydroxyethyl)piperidine-1-carboxylate (4.0 g, 14.80 mmol) in DMF (74.0 mL was added imidazole (1.51 g, 22.2 mmol) and TBS-Cl (2.90 g, 19.2 mmol). The resulting mixture was stirred at 60° C. for 1 h 15 min. The reaction mixture was diluted with EtOAc and water. The organic layer was washed with water (2×), brine, dried over $Na_2SO_4$, filtered and concentrated. The residue was purified with flash chromatography (0-20% ethyl acetate in hexanes) to give the desired product as colorless oil. (5.3 g, 93%). LCMS calculated for (Product-Boc) $C_{13}H_{29}N_4OSi$ $(M+H)^+$: m/z=285.2; found: 285.2.

Step 6. tert-Butyl (2S,4S)-4-amino-2-(2-((tert-butyldimethylsilyl)oxy)ethyl)piperidine-1-carboxylate

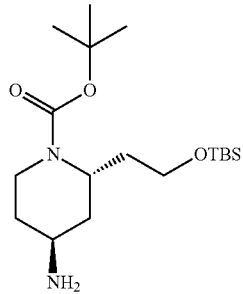 [SMILES: CC(C)(C)OC(=O)N1CC[C@H](N)C[C@H]1CCO[Si](C)(C)C(C)(C)C]

To a solution of tert-butyl (2S,4S)-4-azido-2-(2-((tert-butyldimethylsilyl)oxy)ethyl)-piperidine-1-carboxylate (5.30 g, 13.8 mmol) in methanol (70 mL) was added 10% palladium on carbon (1.47 g, 1.38 mmol). The reaction mixture was evacuated under vacuum and refilled with $H_2$, stirred at r.t. for 2 h. The reaction mixture was filtered through a pad of Celite and washed with methanol. The filtrate was concentrated to give the desired product (4.5 g, 91%). LCMS calculated for (Product-Boc) $C_{13}H_{31}N_2OSi$ $(M+H)^+$: m/z=259.2; found: 259.2.

Intermediate 10. 2-(7-Fluoronaphthalen-1-yl)-4,4,5,5-tetramethyl-1,3,2-dioxaborolane

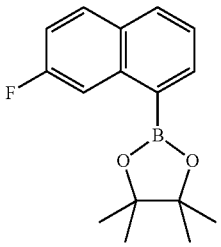 [SMILES: CC1(C)OB(c2cccc3ccc(F)cc23)OC1(C)C]

Step 1. 7-Fluoronaphthalen-1-yl trifluoromethanesulfonate

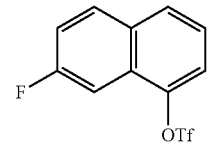

A sample of 7-fluoronaphthalen-1-ol (1.5 g, 9.25 mmol) was dissolved in DCM (31 mL) and treated with triethylamine (1.6 mL, 11.6 mmol). The solution was cooled to 0° C., and then treated dropwise with triflic anhydride (1.7 ml, 10 mmol) over 1 minute. The mixture was stirred for 30 minutes at 0° C., at which point it was quenched with saturated aq. $NaHCO_3$ and diluted with additional DCM. The mixture was extracted, dried over $MgSO_4$, and used in the next step without further purification. The product did not ionize by LCMS and was confirmed by characterization of following reactions.

Step 2. 2-(7-Fluoronaphthalen-1-yl)-4,4,5,5-tetramethyl-1,3,2-dioxaborolane

A sample of 7-fluoronaphthalen-1-yl trifluoromethanesulfonate (2.72 g, 9.24 mmol) was dissolved in 1,4-dioxane (31 mL) and treated with potassium acetate (1.8 g, 18 mmol), bis(pinacolato)diboron (2.9 g, 12 mmol), and [1,1'-bis(diphenylphosphino)ferrocene]dichloropalladium(II), complex with dichloromethane (0.75 g, 0.92 mmol). The solution was warmed to 80° C. and stirred.

After 16 hours, the reaction was cooled to room temperature, diluted with ethyl acetate, filtered to remove solid potassium acetate, and concentrated in vacuo. The crude residue was purified by flash column chromatography in 0-50% DCM/hexanes to give 2-(7-fluoronaphthalen-1-yl)-4,4,5,5-tetramethyl-1,3,2-dioxaborolane (1.5 g, 5.6 mmol, 60% yield). LC-MS calculated for $C_{16}H_{19}BFO_2$ $(M+H)^+$: m/z=273.1; found 273.1.

Intermediate 11. 2-(2,3-Dichloro-5-(methoxymethoxy)phenyl)-4,4,5,5-tetramethyl-1,3,2-dioxaborolane

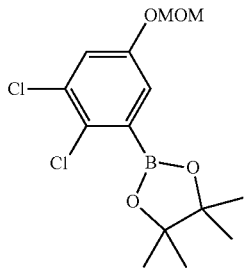

Step 1. 1-Bromo-2,3-dichloro-5-(methoxymethoxy)benzene

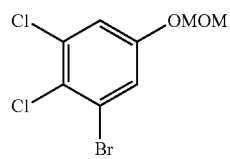

To a solution of 3-bromo-4,5-dichlorophenol (3.3 g, 13.64 mmol) in THF (40.9 ml) at 0° C. was slowly added NaH (600 mg, 15.01 mmol). The reaction mixture was stirred at room temperature for 15 min and cooled down to 0° C. MOM-Cl (0.513 ml, 6.75 mmol) was then added dropwise. The reaction mixture was warmed up and stirred at room temperature for another 30 min. The reaction mixture was quenched by saturated NH$_4$Cl solution, extracted by EtOAc. The organic layers were combined, dried over MgSO$_4$, and concentrated. The resulting white solid was used directly for the next step.

Step 2. 2-(2,3-Dichloro-5-(methoxymethoxy)phenyl)-4,4,5,5-tetramethyl-1,3,2-dioxaborolane Under an atmosphere of nitrogen, to a mixture of 1-bromo-2,3-dichloro-5-(methoxymethoxy)benzene (1.0 g, 3.50 mmol) and 2-Isopropoxy-4,4,5,5-tetramethyl-1,3,2-dioxaborolane (0.856 ml, 4.20 mmol) in THF (18 ml) at −78° C. was added n-butyllithium (2.19 ml, 3.50 mmol). The reaction mixture was stirred at −78° C. for 10 min and warmed to room temperature. The reaction was then quenched by NH$_4$Cl solution and extracted with EtOAc. The organic layers were combined, dried over MgSO$_4$, concentrated and purified by flash column chromatography (eluting with a gradient 0-50% DCM in hexanes) to afford colorless oil (0.6 g, 59% yield). $^1$H NMR (400 MHz, CDCl$_3$) δ 7.22 (d, J=2.8 Hz, 1H), 7.20 (d, J=2.8 Hz, 1H), 5.14 (s, 2H), 3.46 (s, 3H), 1.37 (s, 3H).

Intermediate 12. N,N-Dimethylpent-4-ynamide

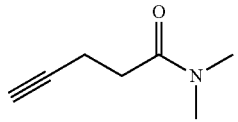

A solution of 4-pentynoic acid (5.0 g, 51.0 mmol) in THF (100 ml) was cooled to 0° C. and oxalyl chloride (5.6 ml, 63.7 mmol) was carefully added. A second solution of DMF (0.40 ml) in DCM (0.60 ml) was added to the above mixture and the reaction was stirred for 30 minutes at 0° C. The ice bath was removed and the mixture was warmed to room temperature. After 2 h, volatiles were removed under reduced pressure and the residue was dissolved in THF (20 mL).

In a second reaction vessel, triethylamine (21 ml, 153 mmol) and dimethylamine (2M/THF, 51 ml, 102 mmol) were cooled to 0° C. The solution from step 1 was added dropwise over 3 minutes at 0° C. Precipitate formation was observed. The reaction solution was warmed to room temperature and stirred for 1 h. At completion, the reaction was quenched with saturated sodium bicarbonate solution. The organics were extracted 3× using DCM, then dried with MgSO$_4$ and concentrated under reduced pressure to give the desired product. LC-MS calculated for C$_7$H$_{12}$NO (M+H)$^+$: m/z=126.1; found 126.1.

Intermediate 13. 2-(3-(Methoxymethoxy)naphthalen-1-yl)-4,4,5,5-tetramethyl-1,3,2-dioxaborolane

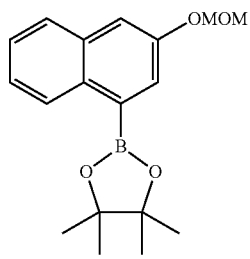

To a solution of 4-(4,4,5,5-tetramethyl-1,3,2-dioxaborolan-2-yl)naphthalen-2-ol (7.0 g, 25.9 mmol) in DCM (130 ml) were added DIPEA (20 ml, 117 mmol) and chloromethyl methyl ether (7.9 ml, 104 mmol). The reaction mixture was stirred at room temperature and progress was monitored by LC-MS. Additional MOM-Cl was added to push reaction to completion (~2 eq). The reaction was quenched with water and extracted with DCM. The organic layer was dried over sodium sulfate and concentrated under reduced pressure. The crude product was purified by flash column chromatography (0-20% ethyl acetate/hexanes) to provide the desired product as an off-white solid. LC-MS calculated for C$_{18}$H$_{24}$BO$_4$ (M+H)$^+$: m/z=315.2; found 315.2.

Intermediate 14. 4-(But-3-yn-2-yl)morpholin-3-one

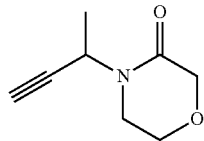

Step 1. N-(But-3-yn-2-yl)-2-(2-chloroethoxy)acetamide

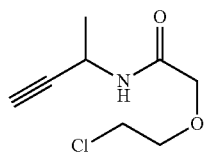

To a solution of but-3-yn-2-amine (0.440 g, 6.37 mmol) and triethylamine (1.776 ml, 12.74 mmol) in THF (10 mL) was added 2-(2-chloroethoxy)acetyl chloride (1 g, 6.37 mmol) at 0° C. The solution was warmed to RT and stirred for 1 h. The reaction was quenched with water and extracted with ethyl acetate. The organic layer was dried over sodium sulfate and concentrated under reduced pressure. The crude product was purified by flash column chromatography to provide the desired product. LC-MS calculated for $C_8H_{13}ClNO_2$ (M+H)$^+$: m/z=190.1; found 190.0.

Step 2. 4-(But-3-yn-2-yl)morpholin-3-one

To a solution of N-(but-3-yn-2-yl)-2-(2-chloroethoxy)acetamide (450 mg, 2.373 mmol) in THF (5 ml) was added sodium hydride (114 mg, 2.85 mmol) at 0° C. The solution was warmed to RT and stirred for 18 h. The reaction was quenched with water and extracted with ethyl acetate. The organic layer was dried over sodium sulfate and concentrated under reduced pressure. The crude product was purified by flash column chromatography to provide the desired product. LC-MS calculated for $C_8H_{12}NO_2$ (M+H)$^+$: m/z=154.1; found 154.0.

Intermediate 15. 4-Isopropyl-1-(prop-2-yn-1-yl)piperazin-2-one

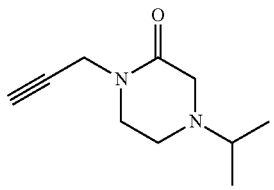

A solution of 1-(prop-2-yn-1-yl)piperazin-2-one hydrochloride (1.32 g, 7.56 mmol), propan-2-one (4.39 g, 76 mmol), triethylamine (2.107 mL, 15.12 mmol), acetic acid (0.865 ml, 15.12 mmol) and sodium cyanoborohydride (1.425 g, 22.68 mmol) in MeOH (2 mL) was stirred at 60° C. for 6 h. The reaction was quenched with water and extracted with ethyl acetate. The organic layer was dried over sodium sulfate and concentrated under reduced pressure. The crude product was purified by flash column chromatography to provide the desired product. LC-MS calculated for $C_{10}H_{17}N_2O$ (M+H)$^+$: m/z=181.1; found 181.1.

Intermediate 16. tert-Butyl (1R,4R,5S)-5-((7-Bromo-6-(2-cyanoethyl)-2-ethoxy-8-fluoro-3-iodoquinolin-4-yl)amino)-2-azabicyclo[2.1.1]hexane-2-carboxylate

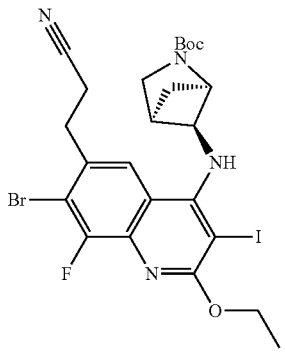 [SMILES: CCOc1nc2c(F)c(Br)c(CCC#N)cc2c(N[C@H]2[C@@H]3C[C@H]2N(C(=O)OC(C)(C)C)C3)c1I]

This compound was prepared according to the procedure described in Intermediate 2 and Intermediate 5, using sodium ethoxide instead of sodium thiomethoxide. LC-MS calculated for $C_{24}H_{28}BrFIN_4O_3$(M+H)$^+$: m/z=645.0; found 645.0.

Intermediate 17. 2-(trimethylsilyl)ethyl (R)-2-ethynylpyrrolidine-1-carboxylate

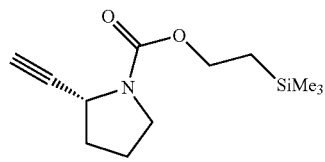 [SMILES: C#C[C@H]1CCCN1C(=O)OCC[Si](C)(C)C]

A solution of tert-butyl (R)-2-ethynylpyrrolidine-1-carboxylate (1.0 g, 5.12 mmol) in 4N HCl in dioxane (10 mL) was stirred at RT for 2 h, then concentrated. To the crude solid were added THF (17.07 ml), triethylamine (2.141 ml, 15.36 mmol) and 1-[2-trimethylsilyl)ethoxycarbonyloxy]pyrrolidin-2,5-dione (1.328 g, 5.12 mmol) and the reaction mixture was stirred at RT for 5 h, then quenched with water and extracted with ethyl acetate. The organic layer was washed with 1 N HCl, 1 N NaOH, water and brine, dried over sodium sulfate and concentrated. The crude product was used in the next step without further purification. LC-MS calculated for $C_{12}H_{22}NO_2Si$ (M+H)$^+$: m/z=240.1; found 240.1.

Intermediate 18. tert-Butyl (1R,4R,5S)-5-(8-(2-cyanoethyl)-7-(2,3-dichlorophenyl)-6-fluoro-4-(methylthio)-2-((R)-1-((2-(trimethylsilyl)ethoxy)carbonyl)pyrrolidin-2-yl)-1H-pyrrolo[3,2-c]quinolin-1-yl)-2-azabicyclo[2.1.1]hexane-2-carboxylate

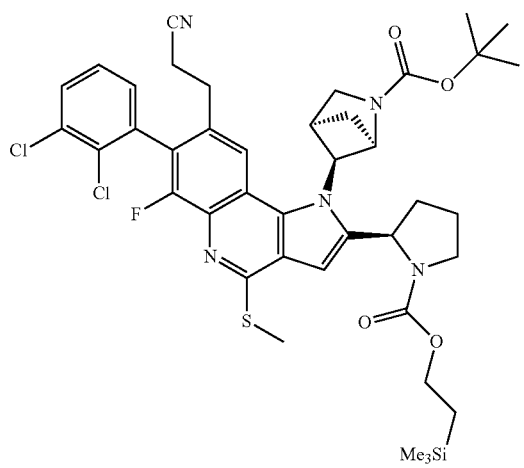 [SMILES: CSc1nc2c(F)c(-c3cccc(Cl)c3Cl)c(CCC#N)cc2c2c1cc([C@H]1CCCN1C(=O)OCC[Si](C)(C)C)n2[C@H]1[C@@H]2C[C@H]1N(C(=O)OC(C)(C)C)C2]

Step 1. tert-butyl (1R,4R,5S)-5-(7-bromo-8-(2-cyanoethyl)-6-fluoro-4-(methylthio)-2-((R)-1-((2-(trimethylsilyl)ethoxy)carbonyl)pyrrolidin-2-yl)-1H-pyrrolo[3,2-c]quinolin-1-yl)-2-azabicyclo[2.1.1]hexane-2-carboxylate

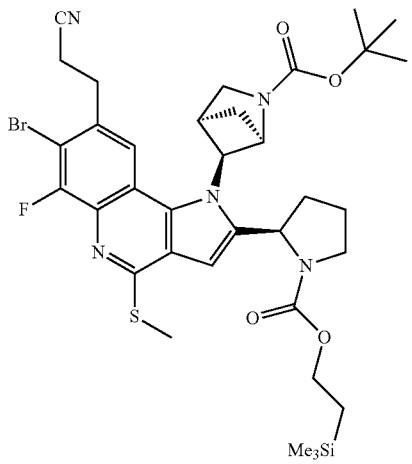 [SMILES: CSc1nc2c(F)c(Br)c(CCC#N)cc2c2c1cc([C@H]1CCCN1C(=O)OCC[Si](C)(C)C)n2[C@H]1[C@@H]2C[C@H]1N(C(=O)OC(C)(C)C)C2]

To a mixture of Intermediate 5 (2.04 g, 3.15 mmol) and Intermediate 17 (1.132 g, 4.73 mmol) were added DMF (10.5 ml) and triethylamine (1.318 ml, 9.45 mmol), followed by bis(triphenylphosphine)palladium(II) dichloride (0.221 g, 0.315 mmol) and copper(I) iodide (0.600 g, 3.15 mmol). The reaction flask was evacuated, back filled with nitrogen, then stirred at 75° C. for 2 h. The reaction mixture was quenched with water and a small amount of 30% aq. ammonium hydroxide, then extracted with ethyl acetate. The organic layer was washed with water and brine, dried over sodium sulfate and concentrated. The crude product was purified by flash chromatography (0-40% acetone in hexanes). This material was dissolved in DMF (10.5 ml) and cesium carbonate (2.054 g, 6.30 mmol) was added. The reaction mixture was heated to 90° C. for 1.5 h, then quenched with water and extracted with ethyl acetate. The organic layer was washed with water and brine, dried over sodium sulfate and concentrated. The crude product was purified by column chromatography (10-30% acetone in hexanes) to provide the desired product (1.07 g, 45%). LC-MS calculated for $C_{35}H_{46}BrFN_5O_4SSi+$ $(M+H)^+$: m/z=758.2/760.2; found 758.0/760.0.

Step 2. tert-butyl (1R,4R,5S)-5-(8-(2-cyanoethyl)-7-(2,3-dichlorophenyl)-6-fluoro-4-(methylthio)-2-((R)-1-((2-(trimethylsilyl)ethoxy)carbonyl)pyrrolidin-2-yl)-1H-pyrrolo[3,2-c]quinolin-1-yl)-2-azabicyclo[2.1.1]hexane-2-carboxylate To a mixture of tert-butyl (1R,4R,5S)-5-(7-bromo-8-(2-cyanoethyl)-6-fluoro-4-(methylthio)-2-((R)-1-((2-(trimethylsilyl)ethoxy)carbonyl)pyrrolidin-2-yl)-1H-pyrrolo[3,2-c]quinolin-1-yl)-2-azabicyclo[2.1.1]hexane-2-carboxylate (471 mg, 0.621 mmol), (2,3-dichlorophenyl)boronic acid (178 mg, 0.931 mmol), potassium fluoride (108 mg, 1.862 mmol) and Pd-132 (44.0 mg, 0.062 mmol) were added 1,4-dioxane (2.4 ml)/water (0.6 ml) and the reaction flask was evacuated, back filled with nitrogen, then stirred at 100° C. for 1 h. The reaction mixture was diluted with DCM and filtered through a plug of Celite. The filtrate was concentrated and the crude product was purified by flash chromatography (0-40% acetone in hexanes) to provide the desired product (416 mg, 81%). LC-MS calculated for $C_{41}H_{49}Cl_2FN_5O_4SSi+$ $(M+H)^+$: m/z=824.3/826.3; found 824.2/826.2.

Intermediate 19. (R)-4-(But-3-yn-2-yl)morpholin-3-one

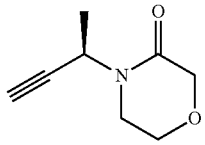

This compound was prepared according to the procedure described in Intermediate 14, using (R)-but-3-yn-2-amine hydrochloride instead of but-3-yn-2-amine. LC-MS calculated for $C_8H_{12}NO_2$ $(M+H)^+$: m/z=154.1; found 154.1.

Intermediate 20. (R)-1-(But-3-yn-2-yl)pyrazin-2(1)-one

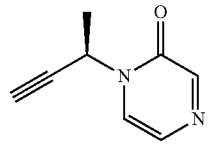

147

Step 1. (S)-But-3-yn-2-yl methanesulfonate

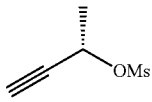

To a stirred DCM solution (100 mL) containing (S)-but-3-yn-2-ol (3.79 g, 54.1 mmol) cooled to 0° C. was added N,N-diisopropylethylamine (18.9 mL, 108 mmol) and methanesulfonyl chloride (4.2 mL, 54.1 mmol) slowly. The reaction was allowed to warm up to ambient temperature. After stirring for 1 h, the reaction was quenched with water and extracted with ethyl acetate. The organic layer was dried over sodium sulfate and concentrated under reduced pressure. The crude product was used directly for next step.

Step 2. (R)-1-(But-3-yn-2-yl)pyrazin-2(1H)-one

To a stirred THF solution (180 mL) containing pyrazine-2(1H)-one (5.20 g, 54.1 mmol) was added potassium tert-butoxide (6.1 g, 54.1 mmol) slowly. After stirring for 0.5 h, a THF solution containing (S)-but-3-yn-2-yl methanesulfonate was added. The slurry was stirred at 60° C. for 48 hours and then quenched with water. The mixture was extracted with ethyl acetate. The organic layer was dried over sodium sulfate and concentrated under reduced pressure. The crude product was purified by flash column chromatography (0-80% ethyl acetate in hexanes) to provide the desired product. LC-MS calculated for $C_8H_9N_2O$ $(M+H)^+$: m/z=149.1; found 149.1. $^1H$ NMR (500 MHz, DMSO-$d_6$) δ 8.04 (d, J=1.2 Hz, 1H), 7.82 (dd, J=4.5, 1.2 Hz, 1H), 7.42 (d, J=4.5 Hz, 1H), 5.62 (qd, J=6.9, 2.5 Hz, 1H), 3.70 (d, J=2.4 Hz, 1H), 1.52 (d, J=6.9 Hz, 3H).

Intermediate 21. 3-Fluoro-N-methyl-5-(4,4,5,5-tetramethyl-1,3,2-dioxaborolan-2-yl)picolinamide

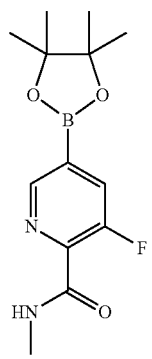 [SMILES: CNC(=O)c1ncc(B2OC(C)(C)C(C)(C)O2)cc1F]

148

Step 1. 5-Bromo-3-fluoro-N-methylpicolinamide

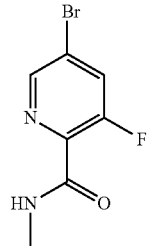

To a solution of 5-bromo-3-fluoropicolinic acid (0.20 g, 0.91 mmol) in DMF (1.50 ml) and DCM (0.30 ml) were added N,N-diisopropylethylamine (0.32 m, 1.82 mmol) and HATU (0.52 g, 1.36 mmol) and the reaction mixture was stirred at r.t. for 15 minutes, then methylamine (2M in THF, 0.68 ml, 1.36 mmol) was added. The reaction solution was stirred for 1 h at r.t. then quenched with 5% aqueous LiCl solution and extracted with ethyl acetate. The aqueous layer was extracted with additional ethyl acetate and the combined organics were washed with water and brine, dried over sodium sulfate and concentrated. The crude product was purified by flash column chromatography eluting with 0-100% ethyl acetate/hexanes. LC-MS calculated for $C_7H_7BrFN_2O^+$ $(M+H)^+$: m/z=233.0/235.0; found 232.9/234.9.

Step 2. 3-Fluoro-N-methyl-5-(4,4,5,5-tetramethyl-1,3,2-dioxaborolan-2-yl)picolinamide To a mixture of 5-bromo-3-fluoro-N-methylpicolinamide (0.10 g, 0.43 mmol), bis(pinacolato)diboron (0.16 g, 0.64 mmol), dichloro[1,1'-bis(diphenylphosphino)ferrocene]palladium (II) dichloromethane adduct (0.070 g, 0.086 mmol), and potassium acetate (0.13 g, 1.29 mmol) was added dioxane (3.43 ml). The reaction vessel was flushed with nitrogen, then sealed and stirred at 100° C. for 1 h. The reaction mixture was diluted with ethyl acetate and SiliaMetS Thiol functionalized silica gel (Silicycle, PN R51030B, 200 mg) then stirred at r.t. for 5 minutes. The slurry was filtered through a plug of Celite. The filtrate was concentrated and the crude product was taken forward without additional purification. LC-MS calculated for $C_{13}H_{19}BFN_2O_3^+$ $(M+H)^+$: m/z=281.1; found 281.1.

Intermediate 22. tert-Butyl (1R,4R,5S)-5-(2-((R)-1-aminoethyl)-8-(2-cyanoethyl)-7-(2,3-dichlorophenyl)-6-fluoro-4-methyl-1H-pyrrolo[3,2-c]quinolin-1-yl)-2-azabicyclo[2.1.1]hexane-2-carboxylate

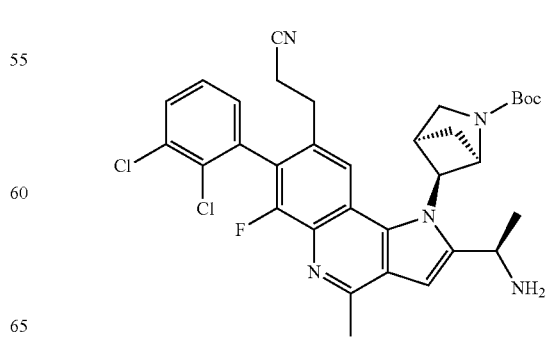

Step 1. 2-(trimethylsilyl)ethyl (R)-but-3-yn-2-ylcarbamate

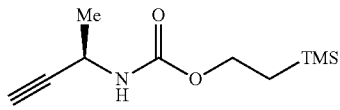

To the reaction mixture of (R)-but-3-yn-2-amine hydrochloride (1.0 g, 9.47 mmol) in acetonitrile (48 ml) was added triethylamine (2.90 ml, 20.84 mmol) and 1-[2-trimethylsilyl) ethoxycarbonyloxy]pyrrolidin-2,5-dione (2.457 g, 9.47 mmol). The reaction mixture was stirred at room temperature for 3 hours. The reaction was then quenched with water and extracted with ethyl acetate. The combined organic layers were washed with 1 N NaOH aqueous solution, 1 N HCl aqueous solution, water and brine, dried over MgSO$_4$ and concentrated. The product was used in the next step directly without further purification. $^1$H NMR (400 MHz, DMSO-d$_6$) δ 7.51 (d, J=8.4 Hz, 1H), 4.38-4.24 (m, 1H), 4.10-4.01 (m, 2H), 3.14-3.10 (m, 1H), 1.28 (d, J=7.0 Hz, 3H), 0.99-0.87 (m, 2H), 0.03 (s, 9H).

Step 2. tert-butyl (1R,4R,5S)-5-(7-bromo-8-(2-cyanoethyl)-6-fluoro-4-(methylthio)-2-((R)-1-(((2-(trimethylsilyl)ethoxy)carbonyl)amino)ethyl)-1H-pyrrolo[3,2-c]quinolin-1-yl)-2-azabicyclo[2.1.1]hexane-2-carboxylate

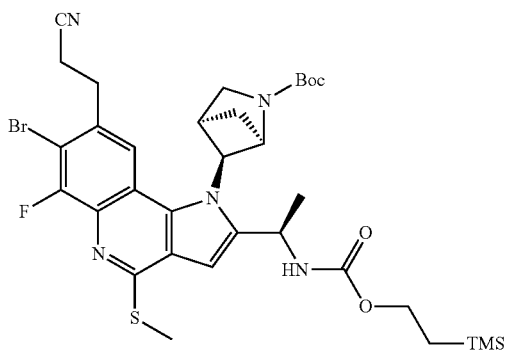 [SMILES: CSc1nc2c(F)c(Br)c(CCC#N)cc2c2c1cc([C@@H](C)NC(=O)OCC[Si](C)(C)C)n2[C@H]1[C@@H]2C[C@H]1N(C(=O)OC(C)(C)C)C2]

Under an atmosphere of nitrogen, the reaction mixture of tert-butyl (1R,4R,5S)-5-((7-bromo-6-(2-cyanoethyl)-8-fluoro-3-iodo-2-(methylthio)quinolin-4-yl)amino)-2-azabicyclo[2.1.1]hexane-2-carboxylate (Intermediate 5, 1.0 g, 1.545 mmol), 2-(trimethylsilyl)ethyl (R)-but-3-yn-2-ylcarbamate (0.494 g, 2.317 mmol), triethylamine (0.646 ml, 4.63 mmol) and copper(I) iodide (0.294 g, 1.545 mmol) was stirred at 70° C. in DMF (7.72 ml) for 2 hours. After cooling down to room temperature, Cs$_2$CO$_3$ (1.510 g, 4.63 mmol) was then added to the reaction mixture. The reaction was then stirred at 95° C. for 30 minutes. Upon completion, the mixture was quenched with water and a small amount of 30% aqueous ammonium hydroxide, then extracted with ethyl acetate. The organic layer was washed with water and brine, dried over magnesium sulfate, concentrated and purified by flash chromatography (0-60% EtOAc in Hexanes) to afford the product (800 mg, 71% yield). LCMS calculated for C$_{33}$H$_{44}$BrFN$_5$O$_4$SSi (M+H)$^+$: m/z=732.2; found 732.2.

Step 3. tert-butyl (1R,4R,5S)-5-(8-(2-cyanoethyl)-7-(2,3-dichlorophenyl)-6-fluoro-4-(methylthio)-2-((R)-1-(((2-(trimethylsilyl)ethoxy)carbonyl)amino)ethyl)-1H-pyrrolo[3,2-c]quinolin-1-yl)-2-azabicyclo[2.1.1] hexane-2-carboxylate

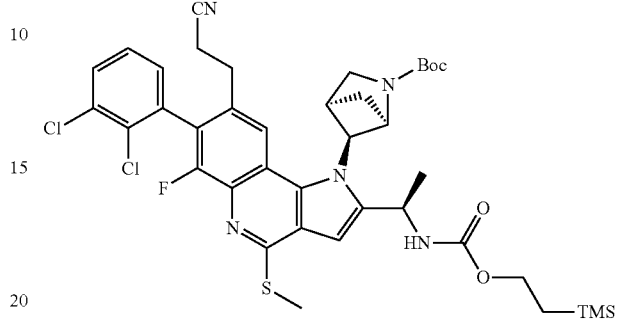

Under the atmosphere of nitrogen, the reaction mixture of tert-butyl (1R,4R,5S)-5-(7-bromo-8-(2-cyanoethyl)-6-fluoro-4-(methylthio)-2-((R)-1-(((2-(trimethylsilyl)ethoxy)carbonyl)amino)ethyl)-1H-pyrrolo[3,2-c]quinolin-1-yl)-2-azabicyclo[2.1.1]hexane-2-carboxylate (800 mg, 1.092 mmol), (2,3-dichlorophenyl)boronic acid (1042 mg, 5.46 mmol), tetrakis(triphenylphosphine)palladium(0) (252 mg, 0.218 mmol) and potassium phosphate, tribasic (1390 mg, 6.55 mmol) in 1,4-dioxane (18.72 ml)/water (3.12 ml) were stirred at 110° C. for 3 hours. After that, the reaction was cooled down to room temperature and more (2,3-dichlorophenyl)boronic acid (1042 mg, 5.46 mmol) was added to the reaction mixture. The reaction mixture was back filled with nitrogen and stirred at 110° C. for another 3 hours. The reaction mixture were then poured in water, extracted with ethyl acetate, concentrated and purified by flash chromatography (0-60% EtOAc in hexanes) to provide the desired product as light yellow solid (700 mg, 80% yield). LCMS calculated for C$_{39}$H$_{47}$Cl$_2$FN$_5$O$_4$SSi (M+H)$^+$: m/z=798.2; found 798.4.

Step 4. tert-butyl (1R,4R,5S)-5-(8-(2-cyanoethyl)-7-(2,3-dichlorophenyl)-6-fluoro-4-methyl-2-((R)-1-(((2-(trimethylsilyl)ethoxy)carbonyl)amino)ethyl)-1H-pyrrolo[3,2-c]quinolin-1-yl)-2-azabicyclo[2.1.1] hexane-2-carboxylate

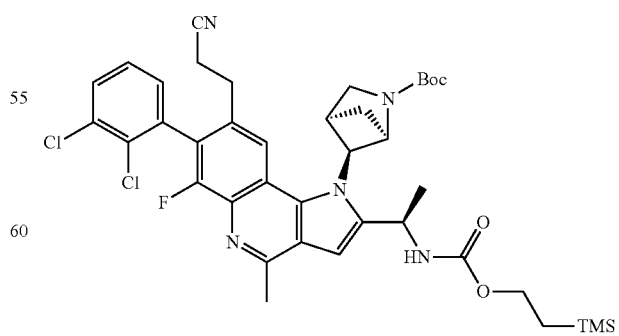

Under the atmosphere of nitrogen, the a mixture of tert-butyl (1R,4R,5S)-5-(8-(2-cyanoethyl)-7-(2,3-dichlorophenyl)-6-fluoro-4-(methylthio)-2-((R)-1-(((2-(trimethylsilyl)ethoxy)carbonyl)amino)ethyl)-1H-pyrrolo[3,2-c]quinolin-1-yl)-2-azabicyclo[2.1.1]hexane-2-carboxylate (700 mg, 0.876 mmol), methylboronic acid (262 mg, 4.38 mmol), tetrakis(triphenylphosphine)palladium(0) (304 mg, 0.263 mmol) and Copper(I) 3-methylsalicylate (564 mg, 2.63 mmol) was added 1,4-dioxane (2.92 ml). The reaction mixture was stirred at 110° C. for 3 hours. The reaction was quenched with water and saturated aq. ammonium hydroxide, then extracted with ethyl acetate. The organic layer was washed with water and brine, dried over sodium sulfate and concentrated. The crude product was purified by flash chromatography (0-80% EtOAc in hexanes) to provide the desired product as light yellow solid (480 mg, 88% yield). LCMS calculated for $C_{39}H_{47}Cl_2FN_5O_4Si$ (M+H)+: m/z=766.3; found 766.4.

Step 5. tert-butyl (1R,4R,5S)-5-(2-((R)-1-aminoethyl)-8-(2-cyanoethyl)-7-(2,3-dichlorophenyl)-6-fluoro-4-methyl-1H-pyrrolo[3,2-c]quinolin-1-yl)-2-azabicyclo[2.1.1]hexane-2-carboxylate To a solution of tert-butyl (1R,4R,5S)-5-(8-(2-cyanoethyl)-7-(2,3-dichlorophenyl)-6-fluoro-4-methyl-2-((R)-1-(((2-(trimethylsilyl)ethoxy)carbonyl)amino)ethyl)-1H-pyrrolo[3,2-c]quinolin-1-yl)-2-azabicyclo[2.1.1]hexane-2-carboxylate (480 mg, 0.626 mmol) in tetrahydrofuran (6.26 ml) was added TBAF (939 μl, 0.939 mmol) and the reaction mixture was heated at 65° C. for 2 hours. After cooling down to room temperature, the reaction was poured into water and extracted with ethyl acetate. The organic layer was washed with water and brine, dried over sodium sulfate and concentrated and used directly for the next step. LCMS calculated for $C_{33}H_{35}Cl_2FN_5O_2$(M+H)+: m/z=622.2; found 622.3.

Intermediate 23. tert-Butyl (1R,4R,5S)-5-(8-(2-cyanoethyl)-7-(2,3-dichlorophenyl)-6-fluoro-4-methyl-2-((R)-1-(methylamino)ethyl)-1H-pyrrolo[3,2-c]quinolin-1-yl)-2-azabicyclo[2.1.1]hexane-2-carboxylate

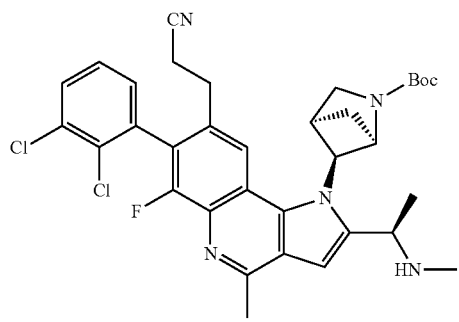 [SMILES: CN[C@H](C)c1cc2c(C)nc3c(F)c(-c4cccc(Cl)c4Cl)c(CCC#N)cc3c2n1[C@H]1[C@@H]2C[C@H]1N(C(=O)OC(C)(C)C)C2]

Step 1. tert-butyl (1R,4R,5S)-5-(8-(2-cyanoethyl)-7-(2,3-dichlorophenyl)-6-fluoro-4-methyl-2-((R)-1-(methyl((2-(trimethylsilyl)ethoxy)carbonyl)amino)ethyl)-1H-pyrrolo[3,2-c]quinolin-1-yl)-2-azabicyclo[2.1.1]hexane-2-carboxylate

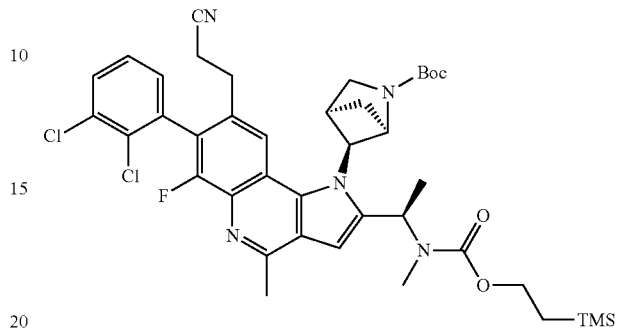

To a solution of tert-butyl (1R,4R,5S)-5-(8-(2-cyanoethyl)-7-(2,3-dichlorophenyl)-6-fluoro-4-methyl-2-((R)-1-(((2-(trimethylsilyl)ethoxy)carbonyl)amino)ethyl)-1H-pyrrolo[3,2-c]quinolin-1-yl)-2-azabicyclo[2.1.1]hexane-2-carboxylate (100 mg, 0.130 mmol, Intermediate 22, Step 4) in DMF (1.304 ml) was added NaH (7.82 mg, 0.196 mmol) at 0° C. After 10 minutes, iodomethane (12.23 μl, 0.196 mmol) was added. The reaction mixture was stirred at room temperature for 1 hour. The reaction mixture was quenched by water and extracted with ethyl acetate. The combined organic layers were washed with water, brine and dried over Na2SO4, filtered and concentrated. The product was used in the next step directly without further purification. LCMS calculated for $C_{40}H_{49}Cl_2FN_5O_4Si$ (M+H)+: m/z=780.3; found 780.3.

Step 2. tert-butyl (1R,4R,5S)-5-(8-(2-cyanoethyl)-7-(2,3-dichlorophenyl)-6-fluoro-4-methyl-2-((R)-1-(methylamino)ethyl)-1H-pyrrolo[3,2-c]quinolin-1-yl)-2-azabicyclo[2.1.1]hexane-2-carboxylate To a solution of tert-butyl (1R,4R,5S)-5-(8-(2-cyanoethyl)-7-(2,3-dichlorophenyl)-6-fluoro-4-methyl-2-((R)-1-(methyl((2-(trimethylsilyl)ethoxy)carbonyl)amino)ethyl)-1H-pyrrolo[3,2-c]quinolin-1-yl)-2-azabicyclo[2.1.1]hexane-2-carboxylate (100 mg, 0.128 mmol) in tetrahydrofuran (1.281 ml) was added TBAF (192 μl, 0.192 mmol) and the reaction mixture was heated at 65° C. for 2 hours, After cooling down to room temperature, the reaction was poured into water and extracted with ethyl acetate. The organic layer was washed with water and brine, dried over sodium sulfate and concentrated and used directly for the next step. LCMS calculated for $C_{34}H_{37}Cl_2FN_5O_2$(M+H)+: m/z=636.2; found 636.3.

Intermediate 24. 4-(but-3-yn-2-yl)-2,6-dimethylpyridazin-3(2H)-one

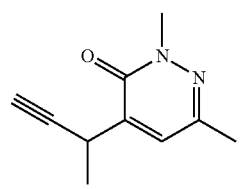

Step 1. 4-bromo-2,6-dimethylpyridazin-3(2H)-one

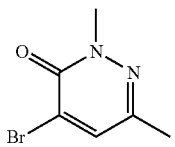

4-bromo-6-methylpyridazin-3(2H)-one (2.0 g, 10.6 mmol) was added to a solution of DMF (50 ml) and cooled to 0° C. Sodium hydride (60% dispersion in mineral oil, 0.55 g, 13.8 mmol) was added in portions. The reaction mixture was stirred at 0° C. for 15 minutes. Iodomethane (2M in MTBE, 6.9 ml, 13.8 mmol) was added dropwise and the reaction mixture was warmed to room temperature and stirred for 30 minutes. The reaction mixture was cooled to 0° C., quenched with saturated aqueous $NH_4Cl$ solution, and diluted with DCM. The layers were separated, and the aqueous layer was extracted with DCM. The combined organic fractions were filtered over a pad of $MgSO_4$, concentrated, and the crude residue was purified by automated flash column chromatography (0-100% Ethyl acetate/hexanes) to afford the desired product (1.4 g, 67%). LC-MS calculated for $C_6H_8BrN_2O^+$ $(M+H)^+$: m/z=203.0; found 203.0.

Step 2. Benzyl 2-(tributylstannyl)acrylate

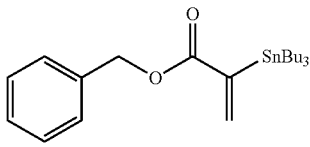

To a 0° C. solution of 4.84 g (30.2 mmol) of benzyl propiolate in 40 ml THF was added 0.7 g (0.6 mmol) of $Pd(PPh_3)_4$ followed by 9.24 g (31.7 mmol) of tributyltin hydride dropwise. After warming and stirring at room temperature overnight, the solvent was removed under reduced pressure. The residue was filtered through a pad of Celite which was then washed with hexanes. The filtrate was concentrated in vacuo and the crude product was purified by automated flash column chromatography (0-15% Ethyl acetate/hexanes) to afford the title compound as a colorless oil (9.5 g, 70%)

Step 3. Benzyl 2-(2,6-dimethyl-3-oxo-2,3-dihydro-pyridazin-4-yl)acrylate

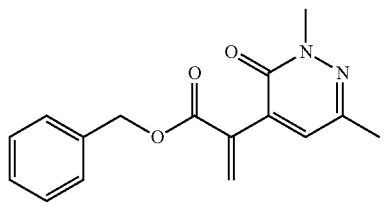 [SMILES: C=C(C(=O)OCc1ccccc1)c1cc(C)nn(C)c1=O]

To a solution of 4-bromo-2,6-dimethylpyridazin-3(2H)-one (from Intermediate 24, Step 1, 1.44 g, 7.09 mmol) in 35 mL THF was added benzyl 2-(tributylstannyl)acrylate (from Intermediate 24, Step 2, 4.16 g, 9.22 mmol), $Pd(PPh_3)_4$ (1.23 g, 1.06 mmol), and copper (1) chloride (0.77 g, 7.80 mmol). The reaction mixture was heated to 60° C. for 6 h, cooled, filtered through a pad of Celite and concentrated. The crude residue was purified by automated flash column chromatography (0-100% Ethyl acetate/DCM) to afford the title compound (1.92 g, 95%). LC-MS calculated for $C_{16}H_{17}N_2O_3^+$ $(M+H)^+$: m/z=285.1; found 285.1.

Step 4. 2-(2,6-dimethyl-3-oxo-2,3-dihydropyridazin-4-yl)propanoic acid

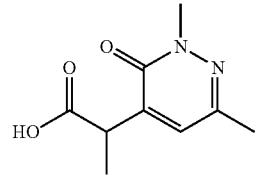

To a vial containing Pd/C (10 wt. %, 1.43 g, 1.35 mmol) under $N_2$ was added a solution of benzyl 2-(2,6-dimethyl-3-oxo-2,3-dihydropyridazin-4-yl)acrylate in 20 mL 1:1 MeOH/ethyl acetate. The suspension was sparged with $H_2$ for 5 minutes and stirred rapidly under 1 atm $H_2$ overnight. The suspension was filtered over a pad of Celite, and the solvent was removed under reduced pressure. The crude material was used in the next step without further purification (1.32 g, 99%). LC-MS calculated for $C_9H_{13}N_2O_3^+$ $(M+H)^+$: m/z=197.1; found 197.1.

Step 5. 2-(2,6-dimethyl-3-oxo-2,3-dihydropyridazin-4-yl)-N-methoxy-N-methylpropanamide

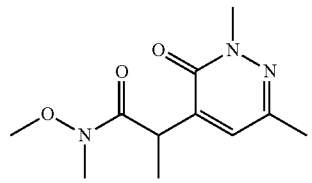

A vial was charged with 2-(2,6-dimethyl-3-oxo-2,3-dihydropyridazin-4-yl)propanoic acid (1.32 g, 6.71 mmol), N,O-dimethylhydroxylamine hydrochloride (0.98 g, 10.1 mmol), DIPEA (2.60 g, 20.1 mmol) and HATU (2.81 g, 7.38 mmol). The reaction mixture was stirred at room temperature for 1 hour. The reaction mixture was quenched with water and diluted with DCM. The layers were separated and the aqueous layer was extracted with DCM. The combined organic fractions were filtered over a pad of $MgSO_4$, concentrated, and purified with automated flash column chromatography (0-10% MeOH/DCM) to afford the desired product (1.6 g, 99%). LC-MS calculated for $C_{11}H_{18}N_3O_3^+$ $(M+H)^+$: m/z=240.1; found 240.1.

Step 6. 2-(2,6-dimethyl-3-oxo-2,3-dihydropyridazin-4-yl)propanal

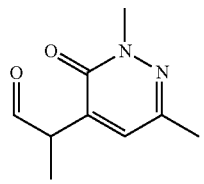

A vial was charged with 2-(2,6-dimethyl-3-oxo-2,3-dihydropyridazin-4-yl)-N-methoxy-N-methylpropanamide (1.86 g, 7.77 mmol) and DCM (20 ml). The reaction mixture was cooled to −78° C. and DIBAL-H (1M in toluene, 8.55 ml, 8.55 mmol) was added dropwise. The reaction mixture was stirred at −78° C. for 30 minutes. The reaction was quenched by slow addition of MeOH (6 ml) at −78° C., stirred at −78° C. for 15 minutes, then warmed slowly to room temperature. Saturated aqueous Rochelle's salt solution and DCM were added, and the biphasic mixture was stirred rapidly for 1 hour. The layers were separated and the aqueous layer extracted with DCM. The combined organic fractions were filtered over a pad of MgSO$_4$, concentrated, and taken to the next step without further purification. LC-MS calculated for C$_9$H$_{13}$N$_2$O$_2$$^+$ (M+H)$^+$: m/z=181.1; found 181.1.

Step 7. 4-(but-3-yn-2-yl)-2,6-dimethylpyridazin-3(2H)-one

A vial was charged with 2-(2,6-dimethyl-3-oxo-2,3-dihydropyridazin-4-yl)propanal (1.48 g, 8.2 mmol), MeOH (20 ml), and K$_2$CO$_3$, (2.27 g, 16.4 mmol). The reaction mixture was cooled to 0° C. Dimethyl (1-diazo-2-oxopropyl)phosphonate (1.73 g, 9.02 mmol) was added dropwise, and the suspension was stirred at 0° C. for 1 hour. The reaction was quenched with water and diluted with DCM. The layers were separated, and the aqueous layer was extracted with DCM. The combined organic fractions were filtered over a bed of MgSO$_4$, concentrated, and purified using automated flash column chromatography (0-100% ethyl acetate/hexanes) to afford the desired product (0.72 g, 50%). LC-MS calculated for C$_{10}$H$_{13}$N$_2$O$^+$ (M+H)$^+$: m/z=177.1; found 177.1.

Example 1. 3-(1-((1R,4R,5S)-2-Azabicyclo[2.1.1]hexan-5-yl)-7-(7-chloro-3-hydroxynaphthalen-1-yl)-6-fluoro-2-methyl-4-(1H-1,2,4-triazol-1-yl)-1H-pyrrolo[3,2-c]quinolin-8-yl)propanenitrile

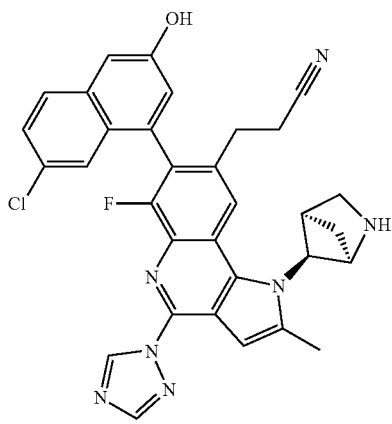 [SMILES: Cc1cc2c(-n3cncn3)nc3c(F)c(-c4cc(O)cc5ccc(Cl)cc45)c(CCC#N)cc3c2n1[C@H]1[C@H]2CN[C@@H]1C2]

Step 1. tert-Butyl (1R,4R,5S)-5-((7-bromo-6-(2-cyanoethyl)-8-fluoro-2-(methylthio)-3-(prop-1-yn-1-yl)quinolin-4-yl)(tert-butoxycarbonyl)amino)-2-azabicyclo[2.1.1]hexane-2-carboxylate

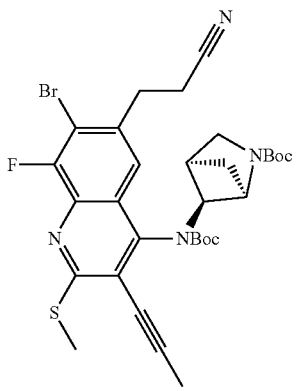

To a mixture of tert-butyl (1R,4R,5S)-5-((7-bromo-6-(2-cyanoethyl)-8-fluoro-3-iodo-2-(methylthio)quinolin-4-yl)(tert-butoxycarbonyl)amino)-2-azabicyclo[2.1.1]hexane-2-carboxylate (5.0 g, 6.7 mmol, Intermediate 2), bis-(triphenylphosphine)palladium(II) chloride (235 mg, 0.33 mmol), and cesium fluoride (3.05 g, 20.0 mmol) in NMP (20 ml) was added tributyl(prop-1-yn-1-yl)stannane (2.24 ml, 7.36 mmol) and the reaction mixture was heated to 105° C. for 45 min. The reaction mixture was diluted with EtOAc and washed with water (×2) and brine. The organic layer was dried over MgSO$_4$, filtered, and concentrated. The residue was purified by flash chromatography (0-40% EtOAc/hexanes) to afford the title compound (2.4 g, 54%). LC-MS calculated for C$_{31}$H$_{37}$BrFN$_4$O$_4$S$^+$ (M+H)$^+$: m/z=659.2; found 659.2.

Step 2. 3-(4-(((1R,4R,5S)-2-Azabicyclo[2.1.1]hexan-5-yl)amino)-7-bromo-8-fluoro-2-(methylthio)-3-(prop-1-yn-1-yl)quinolin-6-yl)propanenitrile

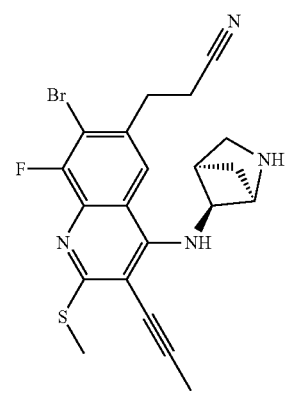 [SMILES: CC#Cc1c(SC)nc2c(F)c(Br)c(CCC#N)cc2c1N[C@H]1[C@H]2CN[C@@H]1C2]

To a solution of tert-butyl (1R,4R,5S)-5-((7-bromo-6-(2-cyanoethyl)-8-fluoro-2-(methylthio)-3-(prop-1-yn-1-yl)quinolin-4-yl)(tert-butoxycarbonyl)amino)-2-azabicyclo[2.1.1]-hexane-2-carboxylate (2.4 g, 3.6 mmol) in DCM (15 ml) was added TFA (15 ml) and the reaction mixture was stirred at room temperature for 3 h. The reaction mixture was concentrated and the residue was azeotroped with MeCN (×3), followed by drying under high vacuum for 1 h. The product was used without purification. LC-MS calculated for $C_{21}H_{21}BrFN_4S^+$ (M+H)⁺: m/z=459.1; found 459.1.

Step 3. tert-butyl (1R,4R,5S)-5-(7-Bromo-8-(2-cyanoethyl)-6-fluoro-2-methyl-4-(methylthio)-1H-pyrrolo[3,2-c]quinolin-1-yl)-2-azabicyclo[2.1.1]hexane-2-carboxylate

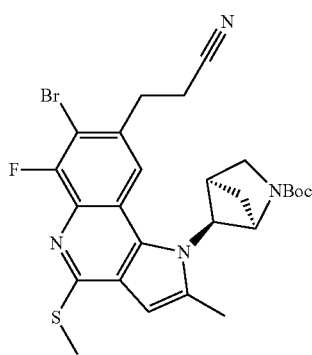 [SMILES: CSc1nc2c(F)c(Br)c(CCC#N)cc2c2c1cc(C)n2[C@H]1[C@@H]2C[C@H]1N(C(=O)OC(C)(C)C)C2]

To a reaction vial containing 3-(4-(((1R,4R,5S)-2-azabicyclo[2.1.1]hexan-5-yl)amino)-7-bromo-8-fluoro-2-(methylthio)-3-(prop-1-yn-1-yl)quinolin-6-yl)propanenitrile (1.67 g, 3.64 mmol) was added 1,3-bis(2,6-diisopropylphenyl-imidazol-2-ylidene)gold(I) chloride (0.23 g, 0.36 mmol) and silver hexafluoroantimonate (1.37 g, 4.00 mmol). The vial was evacuated and backfilled with nitrogen, and THF (15 ml) was added. The reaction mixture was heated to 70° C. for 2 h. After cooling to room temperature, triethylamine (1.52 ml, 10.9 mmol) and boc-anhydride (1.19 g, 5.45 mmol) were added, and the reaction mixture was stirred for 15 minutes. The reaction was quenched with saturated NaHCO₃ and diluted with EtOAc. The mixture was filtered through a pad of Celite and the layers were separated. The organic layer was washed with saturated NaHCO₃ and brine, dried over MgSO₄, filtered and concentrated. The product was purified by flash chromatography (0-50% EtOAc/hexanes) to afford the title compound as a yellow solid (1.28 g, 63% over 3 steps). LC-MS calculated for $C_{26}H_{29}BrFN_4O_2S^+$ (M+H)⁺: m/z=559.1; found 559.3.

Step 4. tert-Butyl (1R,4R,5S)-5-(7-bromo-8-(2-cyanoethyl)-6-fluoro-2-methyl-4-(methylsulfonyl)-1H-pyrrolo[3,2-c]quinolin-1-yl)-2-azabicyclo[2.1.1]hexane-2-carboxylate

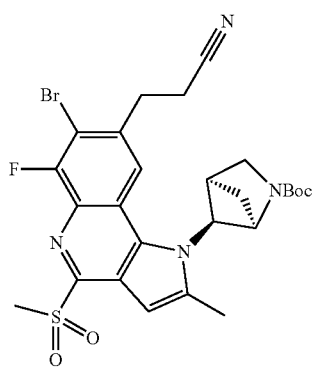 [SMILES: Cc1cc2c(S(C)(=O)=O)nc3c(F)c(Br)c(CCC#N)cc3c2n1[C@H]1[C@@H]2C[C@H]1N(C(=O)OC(C)(C)C)C2]

To a solution of tert-butyl (1R,4R,5S)-5-(7-bromo-8-(2-cyanoethyl)-6-fluoro-2-methyl-4-(methylthio)-1H-pyrrolo[3,2-c]quinolin-1-yl)-2-azabicyclo[2.1.1]hexane-2-carboxylate (207 mg, 0.37 mmol) in DCM (4 ml) was added m-CPBA (207 mg, 0.93 mmol) and the reaction mixture was stirred at room temperature for 1 h. Once complete, the reaction was diluted with DCM, and quenched with saturated Na₂S₂O₃ and saturated NaHCO₃. After stirring for min, the layers were separated and the organic layer was dried over MgSO₄, filtered and concentrated. The product was used without purification. LC-MS calculated for $C_{26}H_{29}BrFN_4O_4S^+$ (M+H)⁺: m/z=591.1; found 591.2.

Step 5. tert-Butyl (1R,4R,5S)-5-(7-bromo-8-(2-cyanoethyl)-6-fluoro-2-methyl-4-(1H-1,2,4-triazol-1-yl)-1H-pyrrolo[3,2-c]quinolin-1-yl)-2-azabicyclo[2.1.1]hexane-2-carboxylate

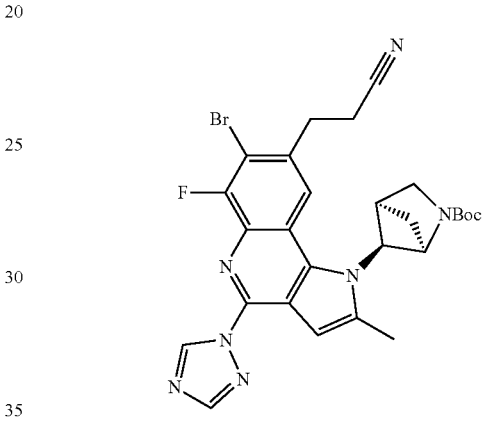

A solution of tert-butyl (1R,4R,5S)-5-(7-bromo-8-(2-cyanoethyl)-6-fluoro-2-methyl-4-(methylsulfonyl)-1H-pyrrolo[3,2-c]quinolin-1-yl)-2-azabicyclo[2.1.1]hexane-2-carboxylate (219 mg, 0.37 mmol), 1H-1,2,4-triazole (128 mg, 1.85 mmol), and cesium carbonate (362 mg, 1.11 mmol) in NMP (3 ml) was heated to 70° C. for 1 h. The reaction mixture was partitioned between water and EtOAc, and the layers were separated. The aqueous layer was extracted with EtOAc and the combined organic layers were washed with brine, dried over MgSO₄, filtered, and concentrated. The product was purified by flash chromatography (0-75% EtOAc/hexanes) to afford the title compound (120 mg, 56% over 2 steps). LC-MS calculated for $C_{27}H_{28}BrFN_7O_2^+$ (M+H)⁺: m/z=580.1; found 580.1.

Step 6. 3-(1-((1R,4R,5S)-2-Azabicyclo[2.1.1]hexan-5-yl)-7-(7-chloro-3-hydroxynaphthalen-1-yl)-6-fluoro-2-methyl-4-(1H-1,2,4-triazol-1-yl)-1H-pyrrolo[3,2-c]quinolin-8-yl)propanenitrile To a mixture of 6-chloro-4-(4,4,5,5-tetramethyl-1,3,2-dioxaborolan-2-yl)naphthalen-2-ol (10.5 mg, 34 μmol, prepared as described in WO 2021142252), Pd(PPh₃)₄ (2.0 mg, 1.7 μmol), and sodium carbonate (9.1 mg, 86 μmol) was added a solution of tert-butyl (1R,4R,5S)-5-(7-bromo-8-(2-cyanoethyl)-6-fluoro-2-methyl-4-(1H-1,2,4-triazol-1-yl)-1H-pyrrolo[3,2-c]quinolin-1-yl)-2-azabicyclo[2.1.1]hexane-2-carboxylate (10 mg, 17 μmol) in dioxane (1 ml). Water (0.3 ml) was added, and the reaction mixture was sparged with N₂ and heated to 100° C. for 1 h. The reaction mixture was filtered through a thiol siliaprep cartridge and concentrated. The residue was stirred in 1:1 DCM/TFA (3 mL) for 30 min, concentrated, and purified by prep HPLC (pH 2). LC-MS calculated for $C_{32}H_{26}ClFN_7O^+$ (M+H)$^+$: m/z=578.2; found 578.3.

Example 2. 3-(1-((1R,4R,5S)-2-Azabicyclo[2.1.1]hexan-5-yl)-7-(5,7-difluoro-1H-indol-3-yl)-6-fluoro-2-methyl-4-((S)-1-((S)-1-methylpyrrolidin-2-yl)ethoxy)-1H-pyrrolo[3,2-c]quinolin-8-yl)propanenitrile

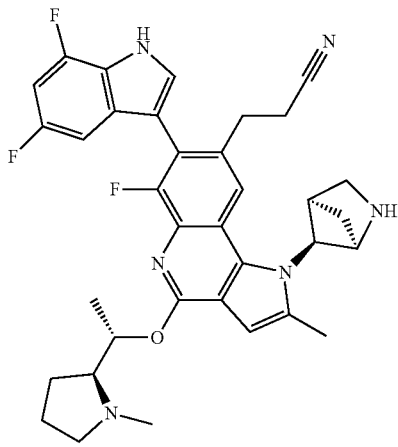 [SMILES: Cc1cc2c(O[C@@H](C)[C@@H]3CCCN3C)nc3c(F)c(-c4c[nH]c5c(F)cc(F)cc45)c(CCC#N)cc3c2n1[C@H]1[C@H]2CN[C@@H]1C2]

Step 1. tert-Butyl (1R,4R,5S)-5-(7-bromo-8-(2-cyanoethyl)-6-fluoro-2-methyl-4-((S)-1-((S)-1-methylpyrrolidin-2-yl)ethoxy)-1H-pyrrolo[3,2-c]quinolin-1-yl)-2-azabicyclo[2.1.1]hexane-2-carboxylate

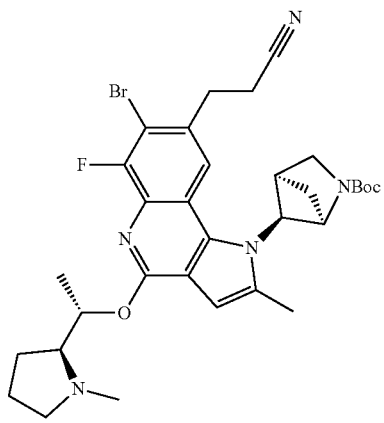 [SMILES: Cc1cc2c(O[C@@H](C)[C@@H]3CCCN3C)nc3c(F)c(Br)c(CCC#N)cc3c2n1[C@H]1[C@@H]2C[C@H]1N(C(=O)OC(C)(C)C)C2]

To a solution of (S)-1-((S)-1-methylpyrrolidin-2-yl)ethan-1-ol (170 µl, 1.32 mmol) in THF (3 ml) at 0° C. was added potassium tert-butoxide (1 M/THF, 1.3 ml, 1.3 mmol), and the reaction mixture was stirred for 5 min. A solution of tert-butyl (1R,4R,5S)-5-(7-bromo-8-(2-cyanoethyl)-6-fluoro-2-methyl-4-(methylsulfonyl)-1H-pyrrolo[3,2-c]quinolin-1-yl)-2-azabicyclo[2.1.1]hexane-2-carboxylate (389 mg, 0.66 mmol, Example 1, Step 4) in THF (1 mL) was then added and the reaction mixture was warmed to room temperature. The reaction mixture was quenched with saturated NH$_4$Cl and extracted with EtOAc. The layers were separated and the organic layer was washed with brine, dried over MgSO$_4$, filtered, and concentrated. The product was purified by flash chromatography (0-100% EtOAc/hexanes followed 0-20% MeOH/DCM) to afford the title compound (244 mg, 58%). LC-MS calculated for $C_{32}H_{40}BrFN_5O_3^+$ (M+H)$^+$: m/z=640.2; found 640.4.

Step 2. 3-(1-((1R,4R,5S)-2-Azabicyclo[2.1.1]hexan-5-yl)-7-(5,7-difluoro-1H-indol-3-yl)-6-fluoro-2-methyl-4-((S)-1-((S)-1-methylpyrrolidin-2-yl)ethoxy)-1H-pyrrolo[3,2-c]quinolin-8-yl)propanenitrile To a mixture of tert-butyl 5,7-difluoro-3-(4,4,5,5-tetramethyl-1,3,2-dioxaborolan-2-yl)-1H-indole-1-carboxylate (26.6 mg, 0.07 mmol), XPhos Pd G2 (1.8 mg, 2.3 µmol), and sodium carbonate (12 mg, 0.1 mmol) was added a solution of tert-butyl (1R,4R,5S)-5-(7-bromo-8-(2-cyanoethyl)-6-fluoro-2-methyl-4-((S)-1-((S)-1-methylpyrrolidin-2-yl)ethoxy)-1H-pyrrolo[3,2-c]quinolin-1-yl)-2-azabicyclo[2.1.1]hexane-2-carboxylate (15 mg, 23 µmol) in dioxane (1 ml). Water (0.3 ml) was added, the reaction mixture was sparged with N$_2$ and heated to 100° C. for 1 h. The reaction mixture was filtered through a thiol siliaprep cartridge and concentrated. The residue was stirred in 1:1 DCM/TFA (3 mL) for 30 min, concentrated, and purified by prep HPLC (pH 2). $^1$H NMR (600 MHz, DMSO-d$_6$) δ 12.22 (d, J=2.6 Hz, 1H), 9.96 (s, 1H), 9.52 (s, 1H), 8.23-8.14 (m, 1H), 8.04 (s, 1H), 7.75 (d, J=2.7 Hz, 1H), 7.10 (ddd, J=11.4, 9.4, 2.2 Hz, 1H), 6.76 (s, 1H), 6.65 (s, 1H), 5.60 (dq, J=9.0, 6.2 Hz, 1H), 5.37 (d, J=3.0 Hz, 1H), 4.97 (s, 1H), 3.91-3.75 (m, 2H), 3.64-3.53 (m, 1H), 3.42 (s, 1H), 3.18 (dq, J=12.4, 6.6 Hz, 1H), 3.06 (d, J=4.7 Hz, 3H), 2.98 (s, 1H), 2.64 (app s, 2H), 2.53 (app s, 2H), 2.51 (app p, J=1.9 Hz, 3H), 2.30 (dq, J=13.2, 8.0, 6.5 Hz, 2H), 2.10 (dt, J=13.3, 6.8 Hz, 1H), 1.93 (ddt, J=25.4, 12.8, 7.2 Hz, 2H), 1.60 (d, J=9.1 Hz, 1H), 1.50 (d, J=6.1 Hz, 3H). LC-MS calculated for $C_{35}H_{36}F_3N_6O^+$ (M+H)$^+$: m/z=613.3; found 613.4.

Example 3. 3-(1-((1R,4R,5S)-2-Azabicyclo[2.1.1]hexan-5-yl)-6-fluoro-7-(6-fluoro-5-methyl-1H-indol-3-yl)-2-methyl-4-((S)-1-((S)-1-methylpyrrolidin-2-yl)ethoxy)-1H-pyrrolo[3,2-c]quinolin-8-yl)propanenitrile

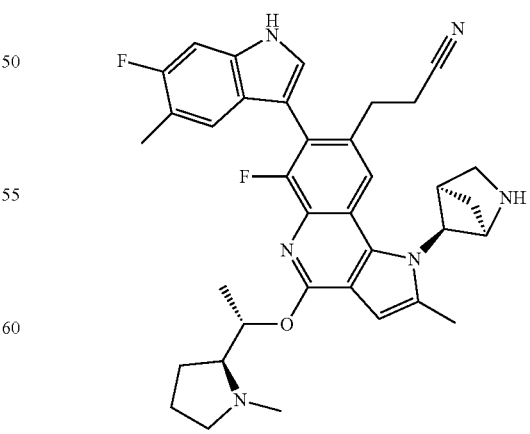

This compound was prepared according to the procedure described in Example 2, Step 2, utilizing tert-butyl 6-fluoro- 5-methyl-3-(4,4,5,5-tetramethyl-1,3,2-dioxaborolan-2-yl)-1H-indole-1-carboxylate (Intermediate 4) instead of tert-butyl 5,7-difluoro-3-(4,4,5,5-tetramethyl-1,3,2-dioxaborolan-2-yl)-1H-indole-1-carboxylate. LC-MS calculated for $C_{36}H_{39}F_2N_6O^+$ (M+H)$^+$: m/z=609.3; found 609.3.

Example 4. 3-(2-(3-(Azetidin-1-yl)-3-oxopropyl)-1-((1R,4R,5S)-2-azabicyclo[2.1.1]hexan-5-yl)-7-(2,3-dichlorophenyl)-6-fluoro-4-((S)-1-((S)-1-methylpyrrolidin-2-yl)ethoxy)-1H-pyrrolo[3,2-c]quinolin-8-yl)propanenitrile

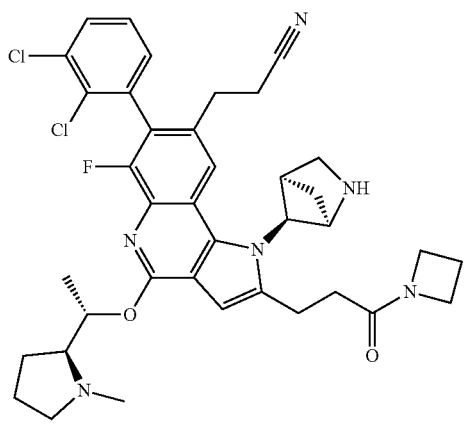 [SMILES: C[C@H](Oc1nc2c(F)c(-c3cccc(Cl)c3Cl)c(CCC#N)cc2c2c1cc(CCC(=O)N1CCC1)n2[C@H]1[C@H]2CN[C@@H]1C2)[C@@H]1CCCN1C]

Step 1. tert-Butyl (1R,4R,5S)-5-((7-bromo-6-(2-cyanoethyl)-8-fluoro-3-(5-methoxy-5-oxopent-1-yn-1-yl)-2-(methylthio)quinolin-4-yl)amino)-2-azabicyclo[2.1.1]hexane-2-carboxylate

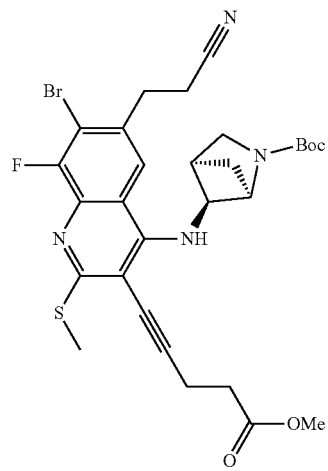 [SMILES: COC(=O)CCC#Cc1c(SC)nc2c(F)c(Br)c(CCC#N)cc2c1N[C@H]1[C@@H]2C[C@H]1N(C(=O)OC(C)(C)C)C2]

The reaction mixture of tert-butyl (1R,4R)-5-((7-bromo-6-(2-cyanoethyl)-8-fluoro-3-iodo-2-(methylthio)quinolin-4-yl)amino)-2-azabicyclo[2.1.1]hexane-2-carboxylate (2.3 g, 3.55 mmol, Intermediate 5), methyl pent-4-ynoate (1.3 ml, 10.66 mmol), tetrakis(triphenylphosphine)palladium(0) (0.4 g, 0.355 mmol), CuI (0.13 g, 0.711 mmol) and DIPEA (3.1 ml, 17.76 mmol) in DMF (18.0 ml) was sparged with N$_2$ and heated at 60° C. for 1 h. Once completed, the reaction mixture was cooled down to room temperature and poured into water. The aqueous layer was extracted with EA, washed with brine, concentrated and purified by flash chromatography (0-100% EtOAc/hexanes) to afford the title compound (2.0 g, 89% yield). LC-MS calculated for $C_{29}H_{33}BrFN_4O_4S^+$ (M+H)$^+$: m/z=631.1; found 631.3.

Step 2. tert-Butyl (1R,4R,5S)-5-(7-bromo-8-(2-cyanoethyl)-6-fluoro-2-(3-methoxy-3-oxopropyl)-4-(methylthio)-1H-pyrrolo[3,2-c]quinolin-1-yl)-2-azabicyclo[2.1.1]hexane-2-carboxylate

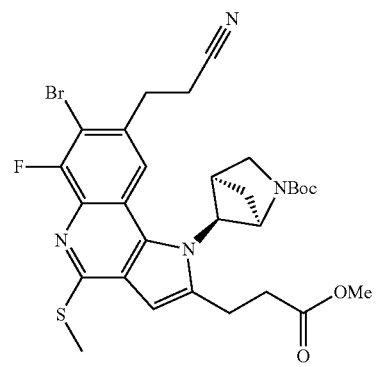 [SMILES: COC(=O)CCc1cc2c(SC)nc3c(F)c(Br)c(CCC#N)cc3c2n1[C@H]1[C@@H]2C[C@H]1N(C(=O)OC(C)(C)C)C2]

To a reaction vial containing tert-butyl (1R,4R)-5-((7-bromo-6-(2-cyanoethyl)-8-fluoro-3-(5-methoxy-5-oxopent-1-yn-1-yl)-2-(methylthio)quinolin-4-yl)amino)-2-azabicyclo[2.1.1]hexane-2-carboxylate (2.0 g, 3.17 mmol) was added 1,3-bis(2,6-diisopropylphenyl-imidazol-2-ylidene) gold(I) chloride (0.39 g, 0.63 mmol) and silver hexafluoroantimonate (1.30 g, 3.8 mmol). The vial was evacuated and backfilled with nitrogen, and THF (30 ml) was added. The reaction mixture was heated to 70° C. for 1.5 h. After cooling to room temperature, triethylamine (1.5 ml, 10.8 mmol) and boc-anhydride (1.2 g, 5.5 mmol) were added, and the reaction mixture was stirred for 15 minutes. The reaction was quenched with saturated NaHCO$_3$ and diluted with EtOAc. The mixture was filtered through a pad of celite and the layers were separated. The organic layer was washed with saturated NaHCO$_3$ and brine, dried over MgSO$_4$, filtered and concentrated. The product was purified by flash chromatography (0-10% MeOH/DCM) to afford the title compound (1.8 g, 90% yield). LC-MS calculated for $C_{29}H_{33}BrFN_4O_4S^+$ (M+H)$^+$: m/z=631.1; found 631.3.

Step 3. tert-Butyl (1R,4R,5S)-5-(2-(3-(azetidin-1-yl)-3-oxopropyl)-7-bromo-8-(2-cyanoethyl)-6-fluoro-4-(methylthio)-1H-pyrrolo[3,2-c]quinolin-1-yl)-2-azabicyclo[2.1.1]hexane-2-carboxylate

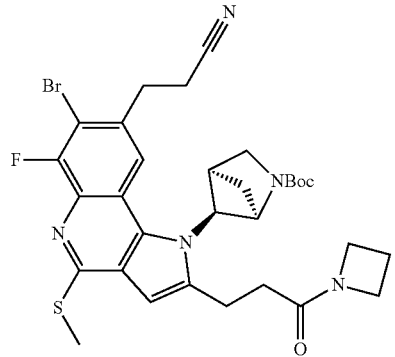 [SMILES: CSc1nc2c(F)c(Br)c(CCC#N)cc2c2c1cc(CCC(=O)N1CCC1)n2[C@H]1[C@@H]2C[C@H]1N(C(=O)OC(C)(C)C)C2]

To a solution of tert-butyl (1R,4R,5S)-5-(7-bromo-8-(2-cyanoethyl)-6-fluoro-2-(3-methoxy-3-oxopropyl)-4-(methylthio)-1H-pyrrolo[3,2-c]quinolin-1-yl)-2-azabicyclo[2.1.1]hexane-2-carboxylate (1.8 g, 2.85 mmol) in THF/MeOH (1/1, a total of 30 ml) was added aqueous LiOH solution (2.0M, 15 mL). The reaction mixture was stirred at 45° C. for 3 h. Once completed, the reaction was concentrated to remove the organic solvents. The aqueous residue was then acidified by 1 N HCl solution. The corresponding carboxylic acid intermediate was precipitated out, which was filtered and dried to afford the carboxylic acid intermediate.

To a reaction vial containing the above obtained carboxylic acid intermediate was added triethylamine (0.865 g, 8.55 mmol), azetidine (0.488 g, 8.55 mmol) and PyBOP (2.225 g, 4.28 mmol) in THF (60 ml). The vial was evacuated and backfilled with nitrogen and was heated to 60° C. for 1 h. The reaction mixture was poured into water and extracted with ethyl acetate. The organic layers was separated, concentrated to give the title compound which was used directly without further purification. LC-MS calculated for $C_{31}H_{36}BrFN_5O_3S^+$ $(M+H)^+$: m/z=656.2; found 656.1.

Step 4. tert-butyl (1R,4R,5S)-5-(2-(3-(azetidin-1-yl)-3-oxopropyl)-7-bromo-8-(2-cyanoethyl)-6-fluoro-4-((S)-1-((S)-1-methylpyrrolidin-2-yl)ethoxy)-1H-pyrrolo[3,2-c]quinolin-1-yl)-2-azabicyclo[2.1.1]hexane-2-carboxylate

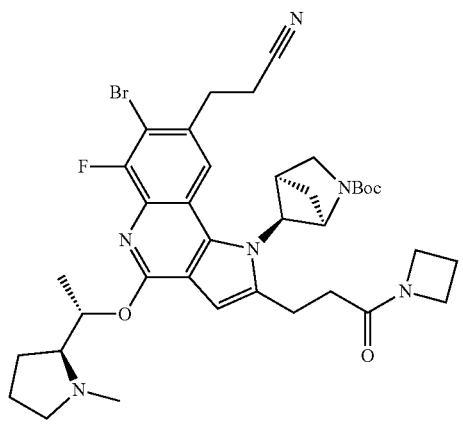 [SMILES: C[C@H](Oc1nc2c(F)c(Br)c(CCC#N)cc2c2c1cc(CCC(=O)N1CCC1)n2[C@H]1[C@@H]2C[C@H]1N(C(=O)OC(C)(C)C)C2)[C@@H]1CCCN1C]

To a solution of tert-butyl (1R,4R,5S)-5-(2-(3-(azetidin-1-yl)-3-oxopropyl)-7-bromo-8-(2-cyanoethyl)-6-fluoro-4-(methylthio)-1H-pyrrolo[3,2-c]quinolin-1-yl)-2-azabicyclo[2.1.1]hexane-2-carboxylate (1.3 g, 2.0 mmol) in ethyl acetate (10 ml) was added m-CPBA (0.56 g, 2.51 mmol) and the reaction mixture was stirred at room temperature for 1 h. Once complete, the reaction was quenched with saturated $Na_2S_2O_3$ solution. The organic layers were separated, dried over $MgSO_4$, filtered and concentrated to afford tert-butyl (1R,4R,5S)-5-(2-(3-(azetidin-1-yl)-3-oxopropyl)-7-bromo-8-(2-cyanoethyl)-6-fluoro-4-(methylsulfinyl)-1H-pyrrolo[3,2-c]quinolin-1-yl)-2-azabicyclo[2.1.1]hexane-2-carboxylate intermediate.

To a solution of (S)-1-((S)-1-methylpyrrolidin-2-yl)ethan-1-ol (1.0 g, 8.0 mmol) in THF (80 ml) at 0° C. was added potassium tert-butoxide (8.0 ml, 8.0 mmol), and the reaction mixture was stirred for 5 min. A solution of above obtained intermediate in THF (20 mL) was then added. The reaction mixture was warmed to room temperature and stirred for another 1 h. The reaction was quenched with saturated $NH_4Cl$ and extracted with EtOAc. The organic layers were combined and concentrated and purified by flash chromatography (0-10% MeOH/DCM) to afford the title compound (0.88 g, 60% over 2 steps). LC-MS calculated for $C_{37}H_{47}BrFN_6O_4^+$ $(M+H)^+$: m/z=737.3; found 737.3.

Step 5. 3-(2-(3-(azetidin-1-yl)-3-oxopropyl)-1-((1R,4R,5S)-2-azabicyclo[2.1.1]hexan-5-yl)-7-(2,3-dichlorophenyl)-6-fluoro-4-((S)-1-((S)-1-methylpyrrolidin-2-yl)ethoxy)-1H-pyrrolo[3,2-c]quinolin-8-yl)propanenitrile To a mixture of (2,3-dichlorophenyl)boronic acid (23.3 mg, 0.12 mmol), Pd(PPh₃)₄ (9.4 mg, 8.1 μmol), and potassium carbonate (16.9 mg, 0.12 μmol) was added a solution of tert-butyl (1R,4R,5S)-5-(7-bromo-8-(2-cyanoethyl)-6-fluoro-2-methyl-4-(1H-1,2,4-triazol-1-yl)-1H-pyrrolo[3,2-c]quinolin-1-yl)-2-azabicyclo[2.1.1]hexane-2-carboxylate (30 mg, 41 μmol) in dioxane (1 ml). Water (0.3 ml) was added, and the reaction mixture was sparged with $N_2$ and heated to 100° C. for 2 h. The reaction mixture was filtered through a thiol siliaprep cartridge and concentrated. The residue was stirred in 1:1 DCM/TFA (3 mL) for 30 min, concentrated, and purified by prep HPLC (pH 2). LC-MS calculated for $C_{38}H_{42}Cl_2FN_6O_2^+$ $(M+H)^+$: m/z=703.3; found 703.3.

Example 5: 3-((1-((1R,4R,5S)-2-Azabicyclo[2.1.1]hexan-5-yl)-6-fluoro-7-(3-hydroxynaphthalen-1-yl)-8-methyl-4-((S)-1-((S)-1-methylpyrrolidin-2-yl)ethoxy)-1H-pyrrolo[3,2-c]quinolin-2-yl)methyl)oxazolidin-2-one

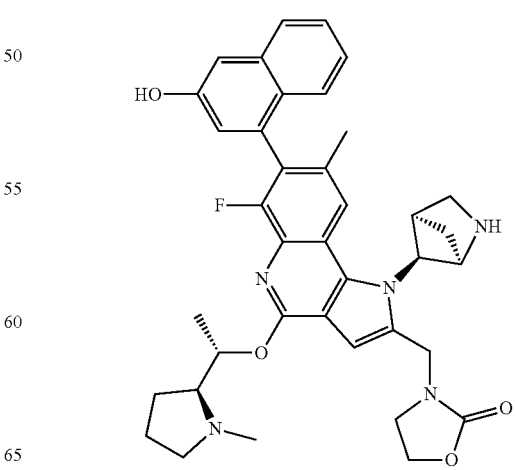

Step 1: tert-Butyl (1R,4R,5S)-5-(7-bromo-6-fluoro-8-methyl-4-(methylthio)-2-((2-oxooxazolidin-3-yl)methyl)-1H-pyrrolo[3,2-c]quinolin-1-yl)-2-azabicyclo[2.1.1]hexane-2-carboxylate

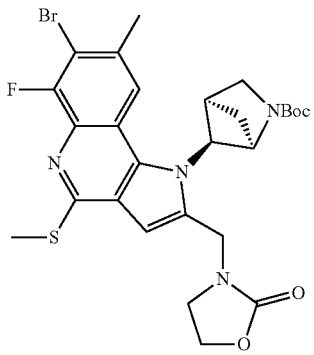 [SMILES: CSc1nc2c(F)c(Br)c(C)cc2c2c1cc(CN1CCOC1=O)n2[C@H]1[C@@H]2C[C@H]1N(C(=O)OC(C)(C)C)C2]

This compound was prepared according to the procedures described in Example 4, Step 1-2, using tert-butyl (1R,4R,5S)-5-((7-bromo-8-fluoro-3-iodo-6-methyl-2-(methylthio)quinolin-4-yl)amino)-2-azabicyclo[2.1.1]hexane-2-carboxylate (Intermediate 7) and 3-(prop-2-yn-1-yl)oxazolidin-2-one. LC-MS calculated for $C_{27}H_{31}BrFN_4O_4S$ (M+H)$^+$: m/z=605.1; found 605.1.

Step 2: tert-Butyl (1R,4R,5S)-5-(7-bromo-6-fluoro-8-methyl-4-((S)-1-((S)-1-methylpyrrolidin-2-yl)ethoxy)-2-((2-oxooxazolidin-3-yl)methyl)-1H-pyrrolo[3,2-c]quinolin-1-yl)-2-azabicyclo[2.1.1]hexane-2-carboxylate

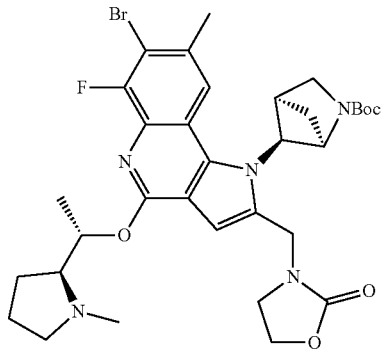 [SMILES: Cc1cc2c(nc(O[C@@H](C)[C@@H]3CCCN3C)c3cc(CN4CCOC4=O)n([C@H]4[C@@H]5C[C@H]4N(C(=O)OC(C)(C)C)C5)c32)c(F)c1Br]

This compound was prepared according to the procedure described in Example 4, step 4 using tert-butyl (1R,4R,5S)-5-(7-bromo-6-fluoro-8-methyl-4-(methylthio)-2-((2-oxooxazolidin-3-yl)methyl)-1H-pyrrolo[3,2-c]quinolin-1-yl)-2-azabicyclo[2.1.1]hexane-2-carboxylate instead of tert-butyl (1R,4R,5S)-5-(2-(3-(azetidin-1-yl)-3-oxopropyl)-7-bromo-8-(2-cyanoethyl)-6-fluoro-4-(methylthio)-1H-pyrrolo[3,2-c]quinolin-1-yl)-2-azabicyclo[2.1.1]hexane-2-carboxylate. LC-MS calculated for $C_{33}H_{42}BrFN_5O_5$(M+H)$^+$: m/z=686.2; found 686.1.

Step 3: 3-((1-(((1R,4R,5S)-2-Azabicyclo[2.1.1]hexan-5-yl)-6-fluoro-7-(3-hydroxynaphthalen-1-yl)-8-methyl-4-((S)-1-((S)-1-methylpyrrolidin-2-yl)ethoxy)-1H-pyrrolo[3,2-c]quinolin-2-yl)methyl)oxazolidin-2-one A mixture of tert-butyl (1R,4R,5S)-5-(7-bromo-6-fluoro-8-methyl-4-((S)-1-((S)-1-methylpyrrolidin-2-yl)ethoxy)-2-((2-oxooxazolidin-3-yl)methyl)-1H-pyrrolo[3,2-c]quinolin-1-yl)-2-azabicyclo[2.1.1]hexane-2-carboxylate (15 mg, 0.022 mmol), 2-(3-(methoxymethoxy)naphthalen-1-yl)-4,4,5,5-tetramethyl-1,3,2-dioxaborolane (10.30 mg, 0.033 mmol), XPhos Pd G2 (1.719 mg, 2.185 µmol), sodium carbonate (6.95 mg, 0.066 mmol) in Dioxane (1 ml) and Water (0.2 ml) was sparged with $N_2$ and heated to 100° C. for 0.5 h. After cooling to r.t., the reaction mixture diluted with DCM, dried over $MgSO_4$, then filtered and concentrated. The residue was stirred in 1:1 DCM/TFA (3 mL) for 30 min, concentrated, and purified by prep HPLC (pH 2). LC-MS calculated for $C_{38}H_{41}FN_5O_4$(M+H)$^+$: m/z=650.3; found 650.3.

Example 6: 8-(1-(((1R,4R,5S)-2-Azabicyclo[2.1.1]hexan-5-yl)-6-fluoro-2,8-dimethyl-4-((S)-1-((S)-1-methylpyrrolidin-2-yl)ethoxy)-1H-pyrrolo[3,2-c]quinolin-7-yl)-1-naphthonitrile

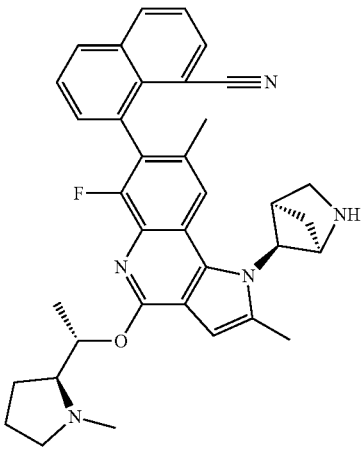 [SMILES: Cc1cc2c(nc(O[C@@H](C)[C@@H]3CCCN3C)c3cc(C)n([C@H]4[C@H]5CN[C@@H]4C5)c32)c(F)c1-c1cccc2cccc(C#N)c12]

Step 1: tert-Butyl (1R,4R,5S)-5-(7-bromo-6-fluoro-2,8-dimethyl-4-((S)-1-((S)-1-methylpyrrolidin-2-yl)ethoxy)-1H-pyrrolo[3,2-c]quinolin-1-yl)-2-azabicyclo[2.1.1]hexane-2-carboxylate

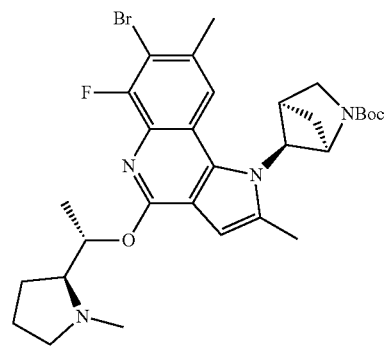 [SMILES: Cc1cc2c(nc(O[C@@H](C)[C@@H]3CCCN3C)c3cc(C)n([C@H]4[C@@H]5C[C@H]4N(C(=O)OC(C)(C)C)C5)c32)c(F)c1Br]

This compound was prepared according to the procedure described in Example 2 starting with tert-butyl (1R,4R,5S)-5-((7-bromo-8-fluoro-3-iodo-6-methyl-2-(methylthio)quinolin-4-yl)(tert-butoxycarbonyl)amino)-2-azabicyclo[2.1.1]hexane-2-carboxylate (Intermediate 6). LC-MS calculated for $C_{30}H_{39}BrFN_4O_3$ (M+H)$^+$: m/z=601.2; found 601.1.

Step 2: 8-(1-((1R,4R,5S)-2-Azabicyclo[2.1.1]hexan-5-yl)-6-fluoro-2,8-dimethyl-4-((S)-1-((S)-1-methylpyrrolidin-2-yl)ethoxy)-1H-pyrrolo[3,2-c]quinolin-7-yl)-1-naphthonitrile A mixture of tert-butyl (1R,4R,5S)-5-(7-bromo-6-fluoro-2,8-dimethyl-4-((S)-1-((S)-1-methylpyrrolidin-2-yl)ethoxy)-1H-pyrrolo[3,2-c]quinolin-1-yl)-2-azabicyclo[2.1.1]hexane-2-carboxylate (15 mg, 0.025 mmol), 8-(4,4,5,5-tetramethyl-1,3,2-dioxaborolan-2-yl)-1-naphthonitrile (10.44 mg, 0.037 mmol), XPhos Pd G2 (1.962 mg, 2.494 μmol), sodium carbonate (7.93 mg, 0.075 mmol), dioxane (1 ml) and Water (0.2 ml) was sparged with N$_2$ and heated to 100° C. for 0.5 h. After cooling to r.t., the reaction mixture diluted with DCM, dried over MgSO$_4$, then filtered and concentrated. The residue was stirred in 1:1 DCM/TFA (3 mL) for 30 min, concentrated, and purified by prep HPLC (pH 2). LC-MS calculated for $C_{36}H_{37}FN_5O$ (M+H)$^+$: m/z=574.3; found 574.2.

Example 7. 1-((2S,4S)-1-Acetyl-2-(cyanomethyl)piperidin-4-yl)-7-(8-cyanonaphthalen-1-yl)-6-fluoro-4-((S)-1-((S)-1-methylpyrrolidin-2-yl)ethoxy)-1H-pyrazolo[4,3-c]quinoline-8-carbonitrile

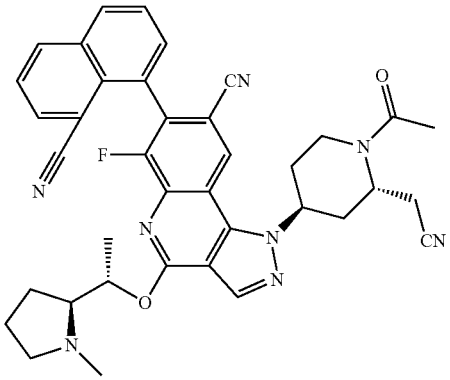 [SMILES: CC(=O)N1CC[C@H](n2ncc3c(O[C@@H](C)[C@@H]4CCCN4C)nc4c(F)c(-c5cccc6cccc(C#N)c56)c(C#N)cc4c32)C[C@H]1CC#N]

Step 1. Ethyl 7-bromo-4-(((2S,4S)-1-(tert-butoxycarbonyl)-2-(2-((tert-butyldimethylsilyl)oxy)ethyl)piperidin-4-yl)amino)-2-chloro-8-fluoro-6-iodoquinoline-3-carboxylate

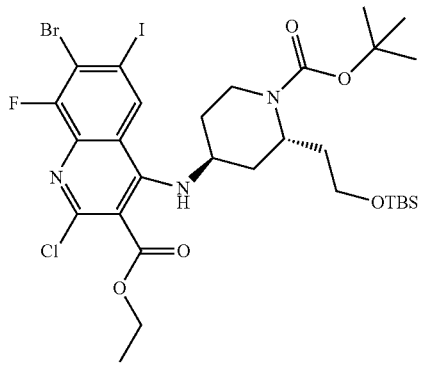 [SMILES: CCOC(=O)c1c(Cl)nc2c(F)c(Br)c(I)cc2c1N[C@H]1CCN(C(=O)OC(C)(C)C)[C@H](CCO[Si](C)(C)C(C)(C)C)C1]

To a solution of ethyl 7-bromo-2,4-dichloro-8-fluoro-6-iodoquinoline-3-carboxylate (Intermediate 8, 10.0 g, 20.3 mmol) in THF (100 mL) was added tert-Butyl (2S,4S)-4-amino-2-(2-((tert-butyldimethylsilyl)oxy)ethyl)piperidine-1-carboxylate (Intermediate 9, 10.9 g, 30.4 mmol) and DIEA (7.09 ml, 40.6 mmol). The resulting mixture was stirred at 65° C. for 5 h. After cooling to room temperature, ethyl acetate and water were added. The organic layer was washed with water (2×) and brine, dried over Na$_2$SO$_4$, filtered and concentrated. The residue was purified with flash chromatography (eluting with 0%-100% ethyl acetate in hexanes) to give the desired product. LC-MS calculated for $C_{30}H_{44}BrClFIN_3O_5Si$ (M+H)$^+$: m/z=814.1, 816.1; found 814.0, 816.0.

Step 2. tert-Butyl (2S,4S)-4-((7-bromo-2-chloro-8-fluoro-3-(hydroxymethyl)-6-iodoquinolin-4-yl)amino)-2-(2-((tert-butyldimethylsilyl)oxy)ethyl)piperidine-1-carboxylate

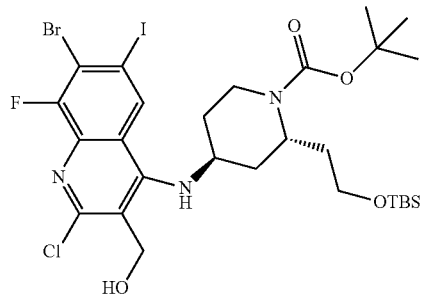 [SMILES: CC(C)(C)OC(=O)N1CC[C@H](Nc2c(CO)c(Cl)nc3c(F)c(Br)c(I)cc23)C[C@H]1CCO[Si](C)(C)C(C)(C)C]

To a solution of ethyl 7-bromo-4-(((2S,4S)-1-(tert-butoxycarbonyl)-2-(2-((tert-butyldimethylsilyl)oxy)ethyl)piperidin-4-yl)amino)-2-chloro-8-fluoro-6-iodoquinoline-3-carboxylate (16.2 g, 19.9 mmol) in toluene (100 ml) at −0° C. was added 1.0 M DIBAL-H in DCM (60 mL, 60 mmol). The resulting mixture was slowly warmed to r.t. and stirred for additional 1 h. The resultant mixture was quenched with methanol (8.04 mL, 199 mmol). Aqueous Rochelle salt solution (prepared from 88 g (6 wt) of Rochelle salt and 200 mL of water) was added to the solution at r.t. and the resultant mixture was stirred overnight. The biphasic mixture was separated. The organic layer was washed with brine, dried over Na$_2$SO$_4$, filtered and concentrated. The crude was used as is. LC-MS calculated for $C_{21}H_{42}BrClFIN_3O_4Si$ (M+H)$^+$: m/z=772.1, 774.1; found 772.1, 774.1.

Step 3. tert-butyl (2S,4S)-4-((7-bromo-2-chloro-8-fluoro-3-formyl-6-iodoquinolin-4-yl)amino)-2-(2-((tert-butyldimethylsilyl)oxy)ethyl)piperidine-1-carboxylate

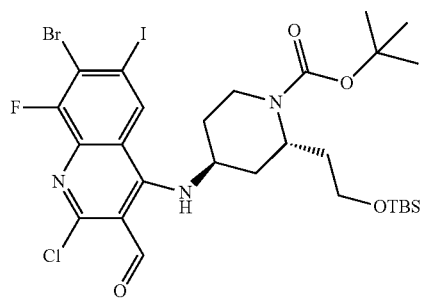 [SMILES: CC(C)(C)OC(=O)N1CC[C@H](Nc2c(C=O)c(Cl)nc3c(F)c(Br)c(I)cc23)C[C@H]1CCO[Si](C)(C)C(C)(C)C]

To a solution of tert-butyl (2S,4S)-4-((7-bromo-2-chloro-8-fluoro-3-(hydroxymethyl)-6-iodoquinolin-4-yl)amino)-2-(2-((tert-butyldimethylsilyl)oxy)ethyl)piperidine-1-carboxylate (17 g, 22 mmol) in DCM (100 mL) was added slowly a solution DMP (14 g, 33 mmol) in DCM (100 mL). The resulting reaction mixture was stirred at r.t. for 1 h, quenched with satd. NaHCO$_3$ and extracted with EtOAc. The combined organic extracts were dried and concentrated under reduced pressure to afford the crude product which was used in the next step without further purification. LC-MS calculated for $C_{28}H_{40}BrClFIN_3O_4Si$ (M+H)$^+$: m/z=770.1, 772.1; found 770.0, 772.1.

Step 4. tert-butyl (2S,4S)-4-((7-bromo-2-chloro-8-fluoro-3-((E)-(hydroxyimino)methyl)-6-iodoquinolin-4-yl)amino)-2-(2-((tert-butyldimethylsilyl)oxy)ethyl)piperidine-1-carboxylate

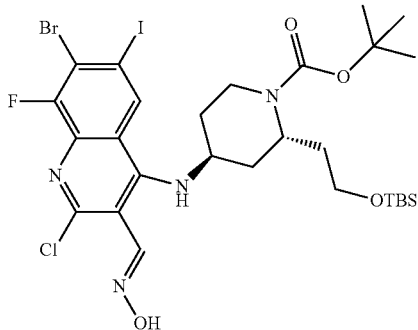 [SMILES: CC(C)(C)OC(=O)N1CC[C@H](Nc2c(/C=N/O)c(Cl)nc3c(F)c(Br)c(I)cc23)C[C@H]1CCO[Si](C)(C)C(C)(C)C]

To a mixture of tert-butyl (2S,4S)-4-((7-bromo-2-chloro-8-fluoro-3-formyl-6-iodoquinolin-4-yl)amino)-2-(2-((tert-butyldimethylsilyl)oxy)ethyl)piperidine-1-carboxylate (16.0 g, 20.8 mmol) and hydroxylamine hydrochloride (4.33 g, 62.3 mmol) in EtOH (100 mL) was added pyridine (10.1 mL, 125 mmol). The reaction mixture was stirred at 50° C. for overnight. The solvent was evaporated in vacuo. The residue was diluted with EtOAc and water and the layers were separated. The aqueous layer was extracted with EtOAc. The combined organic layers were washed with brine, dried over Na$_2$SO$_4$, and concentrated in vacuo. The residue was purified with column chromatography on silica gel (0-100% EtOAc:DCM) to give the desired product. LC-MS calculated for $C_{28}H_{41}BrClFIN_4O_4Si$ (M+H)$^+$: m/z=785.1, 787.1; found 785.1, 787.0.

Step 5. tert-butyl (2S,4S)-4-(7-bromo-4-chloro-6-fluoro-8-iodo-1H-pyrazolo[4,3-c]quinolin-1-yl)-2-(2-((tert-butyldimethylsilyl)oxy)ethyl)piperidine-1-carboxylate

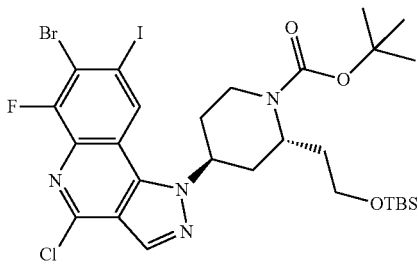 [SMILES: CC(C)(C)OC(=O)N1CC[C@H](n2ncc3c(Cl)nc4c(F)c(Br)c(I)cc4c32)C[C@H]1CCO[Si](C)(C)C(C)(C)C]

To a solution of (tert-butyl (2S,4S)-4-((7-bromo-2-chloro-8-fluoro-3-((E)-(hydroxyimino)methyl)-6-iodoquinolin-4-yl)amino)-2-(2-((tert-butyldimethylsilyl)oxy)ethyl)piperidine-1-carboxylate (6.7 g, 8.5 mmol) and 2-aminopyridine (1.61 g, 17.1 mmol)) in DCM (60 mL) was added Ms-Cl (1.33 mL, 17.1 mmol) at 0° C. The resulting mixture was slowly warmed to r.t. and stirred overnight. The reaction was diluted with water. The organic layer was washed with brine, dried and concentrated under reduced pressure. The crude product was used in the next step without further purification. LC-MS calculated for $C_{28}H_{39}BrClFIN_4O_3Si$ (M+H)$^+$: m/z=767.1, 769.1; found 767.1, 769.1.

Step 6. tert-butyl (2S,4S)-4-(7-bromo-6-fluoro-8-iodo-4-(methylthio)-1H-pyrazolo[4,3-c]quinolin-1-yl)-2-(2-((tert-butyldimethylsilyl)oxy)ethyl)piperidine-1-carboxylate

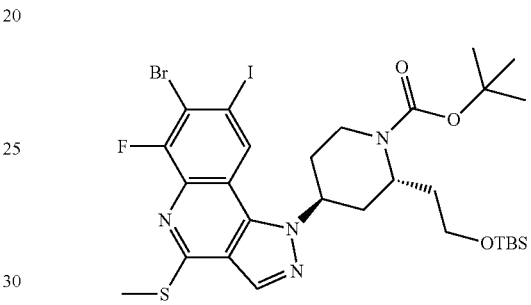

Sodium thiomethoxide (1.92 g, 27.3 mmol) was added to a mixture of tert-butyl (2S,4S)-4-(7-bromo-4-chloro-6-fluoro-8-iodo-1H-pyrazolo[4,3-c]quinolin-1-yl)-2-(2-((tert-butyldimethylsilyl)oxy)ethyl)piperidine-1-carboxylate (7.0 g, 9.1 mmol) in MeOH (45.6 mL)/DCM (45.6 mL) and then stirred at r.t. for 1 h. The mixture was diluted with sat'd NH$_4$Cl and extracted with EtOAc. The combined organic layers were dried and concentrated. The crude product was used in the next step without further purification. LC-MS calculated for $C_{29}H_{42}BrFIN_4O_3SSi$ (M+H)$^+$: m/z=779.1, 781.1; found 779.1, 781.1.

Step 7. tert-butyl (2S,4S)-4-(7-bromo-6-fluoro-8-iodo-4-(methylthio)-1H-pyrazolo[4,3-c]quinolin-1-yl)-2-(2-hydroxyethyl)piperidine-1-carboxylate

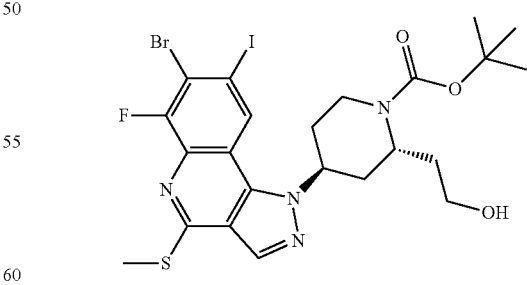

To a solution of tert-butyl (2S,4S)-4-(7-bromo-6-fluoro-8-iodo-4-(methylthio)-1H-pyrazolo[4,3-c]quinolin-1-yl)-2-(2-((tert-butyldimethylsilyl)oxy)ethyl)piperidine-1-carboxylate (7.5 g, 9.6 mmol) in THF (95 mL) was added 1.0 M TBAF in THF (11.5 mL, 11.5 mmol). The resulting mixture was stirred at 60° C. for 1 h. After cooling to r.t., the reaction mixture was diluted with water and ethyl acetate. The organic layer was separated and washed with brine, dried over Na₂SO₄ and concentrated. The crude was used as is. LC-MS calculated for C₂₃H₂₈BrFIN₄O₃S (M+H)⁺: m/z=665.0, 667.0; found 664.9, 666.9.

Step 8. tert-butyl (2S,4S)-4-(7-bromo-6-fluoro-8-iodo-4-(methylthio)-1H-pyrazolo[4,3-c]quinolin-1-yl)-2-(cyanomethyl)piperidine-1-carboxylate

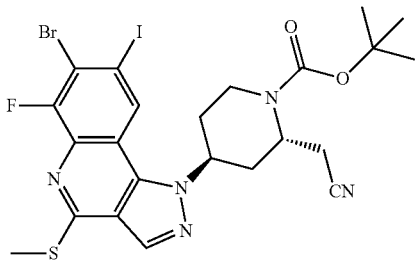 [SMILES: CSc1nc2c(F)c(Br)c(I)cc2c2c1cnn2[C@H]1CCN(C(=O)OC(C)(C)C)[C@H](CC#N)C1]

To a solution of tert-butyl (2S,4S)-4-(7-bromo-6-fluoro-8-iodo-4-(methylthio)-1H-pyrazolo[4,3-c]quinolin-1-yl)-2-(2-hydroxyethyl)piperidine-1-carboxylate (5.50 g, 8.27 mmol) in DCM (100 ml) was added a solution of dess-martinperiodinane (5.26 g, 12.4 mmol) in DCM (50 mL). The resulting mixture was stirred for 1 h. To the reaction flask was added saturated NaHCO₃ and stirred for 10 min. The organic layer was separated and dried over Na₂SO₄ and concentrated. The crude was dissolved in THF (100 mL) and ammonium hydroxide (18.6 mL, 134 mmol) was added to the reaction flask, followed by iodine (2.14 g, 8.43 mmol). The resulting mixture was stirred at r.t. for 1 h, The reaction solution was quenched with sat'd NaS₂O₃ solution. The organic layer was separated. The aqueous layer was extracted with DCM. The combine organic extracts were washed with brine dried over Na₂SO₄ and concentrated. The residue was purified with flash chromatography (0-100% EtOAc:DCM) to give the desired product. LC-MS calculated for C₂₃H₂₅BrFIN₅O₂S (M+H)⁺: m/z=660.0, 662.0; found 660.0, 662.0.

Step 9. tert-butyl (2S,4S)-4-(7-bromo-6-fluoro-8-iodo-4-((S)-1-((S)-1-methylpyrrolidin-2-yl)ethoxy)-1H-pyrazolo[4,3-c]quinolin-1-yl)-2-(cyanomethyl)piperidine-1-carboxylate

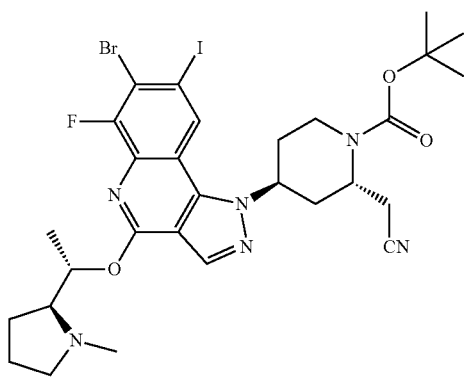 [SMILES: C[C@H](Oc1nc2c(F)c(Br)c(I)cc2c2c1cnn2[C@H]1CCN(C(=O)OC(C)(C)C)[C@H](CC#N)C1)[C@@H]1CCCN1C]

To a solution of tert-butyl (2S,4S)-4-(7-bromo-6-fluoro-8-iodo-4-(methylthio)-1H-pyrazolo[4,3-c]quinolin-1-yl)-2-(cyanomethyl)piperidine-1-carboxylate (130 mg, 0.197 mmol) in EtOAc (2 mL) at 0° C. was added m-CPBA (67.9 mg, 0.295 mmol). The reaction mixture was slowly warmed to r.t. and stirred for 1 h. The reaction was quenched by adding sat'd Na₂S₂O₃, diluted with ethyl acetate and washed with saturated NaHCO₃, brine, dried and concentrated. The crude was dissolve in THF (2 mL) and was added a separately prepared solution of LiHMDS (455 µL, 0.455 mmol), (S)-1-((S)-1-methylpyrrolidin-2-yl)ethan-1-ol (58.8 mg, 0.455 mmol) in THF (2 mL) (30 min stir). The resulting mixture was stirred at 70° C. for 2 h. The reaction mixture was diluted with water and extracted with EtOAc. The organic extracts were dried and concentrated and the crude was used in the next step directly. LC-MS calculated for C₂₈H₃₆BrFIN₆O₃(M+H)⁺: m/z=741.1, 743.1; found 741.3, 743.3.

Step 10. 2-((2S,4S)-1-acetyl-4-(7-bromo-6-fluoro-8-iodo-4-((S)-1-((S)-1-methylpyrrolidin-2-yl)ethoxy)-1H-pyrazolo[4,3-c]quinolin-1-yl)piperidin-2-yl)acetonitrile

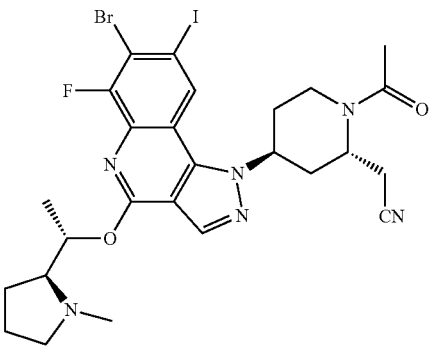 [SMILES: CC(=O)N1CC[C@H](n2ncc3c(O[C@@H](C)[C@@H]4CCCN4C)nc4c(F)c(Br)c(I)cc4c32)C[C@H]1CC#N]

To a solution of tert-butyl (2S,4S)-4-(7-bromo-6-fluoro-8-iodo-4-((S)-1-((S)-1-methylpyrrolidin-2-yl)ethoxy)-1H-pyrazolo[4,3-c]quinolin-1-yl)-2-(cyanomethyl)piperidine-1-carboxylate (150 mg, 0.202 mmol) in dioxane (1 mL) was added HCl (4M in dioxane) (0.5 mL, 2 mmol). The reaction mixture was stirred at r.t. for 2 h and concentrated. To the residue was dissolved in DCM (1 mL) and DIEA (720 µL, 4.13 mmol) was added. The resultant mixture was cool to 0° C. and then acetyl chloride (1M in DCM) (413 µL, 0.413 mmol) was added dropwise. The resulting mixture was stirred at 0° C. for 20 min and concentrated. Flash column chromatography (0-20% MeOH:DCM) affords the title compound. LC-MS calculated for C₂₆H₃₀BrFIN₆O₂(M+H)⁺: m/z=683.1, 685.1; found 683.3, 685.2.

Step 11. 1-((2S,4S)-1-acetyl-2-(cyanomethyl)piperidin-4-yl)-7-(8-cyanonaphthalen-1-yl)-6-fluoro-4-((S)-1-((S)-1-methylpyrrolidin-2-yl)ethoxy)-1H-pyrazolo[4,3-c]quinoline-8-carbonitrile A solution of 2-((2S,4S)-1-acetyl-4-(7-bromo-6-fluoro-8-iodo-4-((S)-1-((S)-1-methylpyrrolidin-2-yl)ethoxy)-1H-pyrazolo[4,3-c]quinolin-1-yl)piperidin-2-yl)acetonitrile (38 mg, 0.055 mmol), Zn(CN)₂ (5.4 mg, 0.046 mmol), Pd(dppf)Cl₂.DCM (7.5 mg, 9.2 µmol) and potassium acetate (9.0 mg, 0.092 mmol) in DMA (1 mL) was flushed with N₂ for ca. 2 min and then stirred at 100° C. for 2 h. The resultant mixture was quenched with water and extracted with EtOAc. The organic extracts were dried and concentrated. To the residue was added 8-(4,4,5,5-tetramethyl-1,3,2-dioxaborolan-2-yl)-1-naphthonitrile (26 mg, 0.092 mmol), SPhos Pd G4 (7.3 mg, 9.2 μmol), $K_3PO_4$ (29.3 mg, 0.138 mmol) and dioxane (1 mL)/water (0.2 mL). The resultant mixture was flushed with $N_2$ for ca. 2 min. stirred at 100° C. for 2 h. The resulting mixture was filtered through a thiocartridge and purified using prep-LCMS (XBridge C18 column, eluting with a gradient of acetonitrile/water containing 0.1% TFA, at flow rate of 60 mL/min) to afford the desired product as two peaks.

Diastereomer 1. Peak 1. LC-MS calculated for $C_{38}H_{36}FN_8O_2(M+H)^+$: m/z=655.3; found 655.3.

Diastereomer 2. Peak 2. LC-MS calculated for $C_{38}H_{36}FN_8O_2(M+H)^+$: m/z=655.3; found 655.3.

Example 8: 8-(1-((1R,4R,5S)-2-Azabicyclo[2.1.1]hexan-5-yl)-6-fluoro-8-methyl-4-((S)-1-((S)-1-methylpyrrolidin-2-yl)ethoxy)-2-((3-oxomorpholino)methyl)-1H-pyrrolo[3,2-c]quinolin-7-yl)-1-naphthonitrile

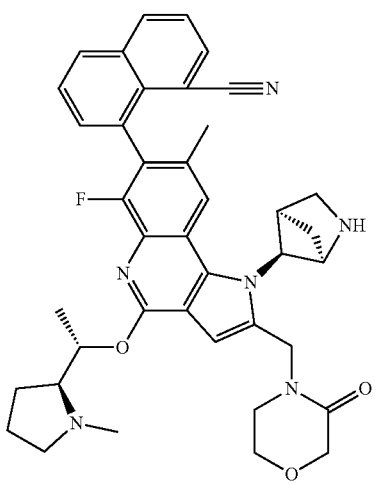 [SMILES: Cc1cc2c(nc(O[C@@H](C)[C@@H]3CCCN3C)c3cc(CN4CCOCC4=O)n([C@H]4[C@H]5CN[C@@H]4C5)c32)c(F)c1-c1cccc2cccc(C#N)c12]

Step 1: tert-Butyl (1R,4R,5S)-5-(7-bromo-6-fluoro-8-methyl-4-(methylthio)-2-((3-oxomorpholino)methyl)-1H-pyrrolo[3,2-c]quinolin-1-yl)-2-azabicyclo[2.1.1]hexane-2-carboxylate

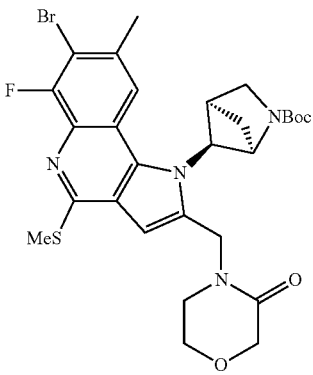 [SMILES: CSc1nc2c(F)c(Br)c(C)cc2c2c1cc(CN1CCOCC1=O)n2[C@H]1[C@@H]2C[C@H]1N(C(=O)OC(C)(C)C)C2]

This compound was prepared according to the procedures described in Example 4, Step 1-2, using tert-butyl (1R,4R,5S)-5-((7-bromo-8-fluoro-3-iodo-6-methyl-2-(methylthio)quinolin-4-yl)amino)-2-azabicyclo[2.1.1]hexane-2-carboxylate (Intermediate 7) and 4-(prop-2-yn-1-yl)morpholin-3-one. LC-MS calculated for $C_{28}H_{33}BrFN_4O_4S$ $(M+H)^+$: m/z=619.1; found 619.1.

Step 2: tert-Butyl (1R,4R,5S)-5-(7-bromo-6-fluoro-8-methyl-4-((S)-1-((S)-1-methylpyrrolidin-2-yl)ethoxy)-2-((3-oxomorpholino)methyl)-1H-pyrrolo[3,2-c]quinolin-1-yl)-2-azabicyclo[2.1.1]hexane-2-carboxylate

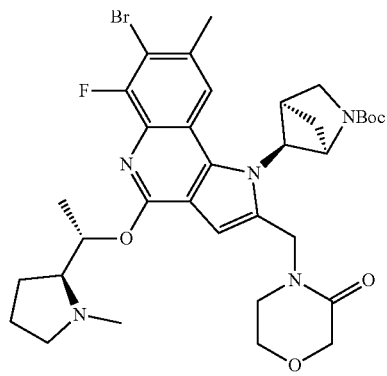 [SMILES: Cc1cc2c(nc(O[C@@H](C)[C@@H]3CCCN3C)c3cc(CN4CCOCC4=O)n([C@H]4[C@@H]5C[C@H]4N(C(=O)OC(C)(C)C)C5)c32)c(F)c1Br]

This compound was prepared according to the procedure described in Example 4, step 4, using tert-butyl (1R,4R,5S)-5-(7-bromo-6-fluoro-8-methyl-4-(methylthio)-2-((3-oxomorpholino)methyl)-1H-pyrrolo[3,2-c]quinolin-1-yl)-2-azabicyclo[2.1.1]hexane-2-carboxylate. LC-MS calculated for $C_{34}H_{44}BrFN_5O_5(M+H)^+$: m/z=700.3; found 700.2.

Step 3: 8-(1-((1R,4R,5S)-2-Azabicyclo[2.1.1]hexan-5-yl)-6-fluoro-8-methyl-4-((S)-1-((S)-1-methylpyrrolidin-2-yl)ethoxy)-2-((3-oxomorpholino)methyl)-1H-pyrrolo[3,2-c]quinolin-7-yl)-1-naphthonitrile This compound was prepared according to the procedure described in Example 6, step 2, using tert-butyl (1R,4R,5S)-5-(7-bromo-6-fluoro-8-methyl-4-((S)-1-((S)-1-methylpyrrolidin-2-yl)ethoxy)-2-((3-oxomorpholino)methyl)-1H-pyrrolo[3,2-c]quinolin-1-yl)-2-azabicyclo[2.1.1]hexane-2-carboxylate. Two diastereomers were obtained.

Diastereomer 1. Peak 1. LC-MS calculated for $C_{40}H_{42}FN_6O_3(M+H)^+$: m/z=673.3; found 673.4.

Diastereomer 2. Peak 2. LC-MS calculated for $C_{40}H_{42}FN_6O_3(M+H)^+$: m/z=673.3; found 673.4.

Example 9: 3-(7-(Benzo[b]thiophen-3-yl)-1-((1R, 4R,5S)-2-azabicyclo[2.1.1]hexan-5-yl)-6-fluoro-4-((S)-1-((S)-1-methylpyrrolidin-2-yl)ethoxy)-2-((2-oxopyrrolidin-1-yl)methyl)-1H-pyrrolo[3,2-c]quinolin-8-yl)propanenitrile

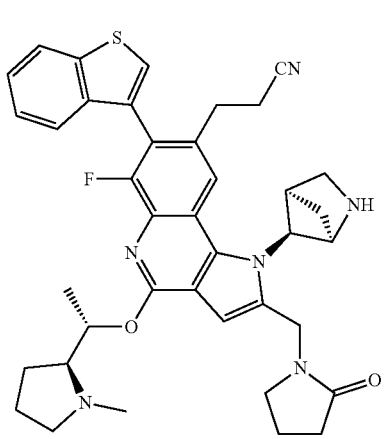 [SMILES: C[C@H](Oc1nc2c(F)c(-c3csc4ccccc34)c(CCC#N)cc2c2c1cc(CN1CCCC1=O)n2[C@H]1[C@H]2CN[C@@H]1C2)[C@@H]1CCCN1C]

Step 1: tert-Butyl (1R,4R,5S)-5-((7-bromo-6-(2-cyanoethyl)-8-fluoro-2-(methylthio)-3-(3-(2-oxopyrrolidin-1-yl)prop-1-yn-1-yl)quinolin-4-yl)(tert-butoxycarbonyl)amino)-2-azabicyclo[2.1.1]hexane-2-carboxylate

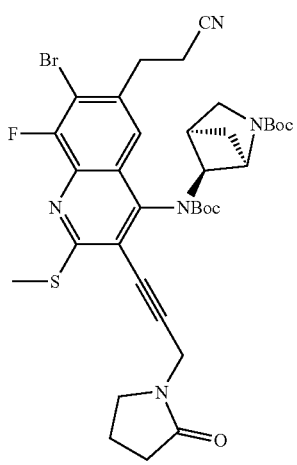

This compound was prepared according to the procedure described in Example 4, Step 1, using tert-butyl (1R,4R,5S)-5-((7-bromo-6-(2-cyanoethyl)-8-fluoro-3-iodo-2-(methylthio)quinolin-4-yl)(tert-butoxycarbonyl)amino)-2-azabicyclo[2.1.1]hexane-2-carboxylate (Intermediate 2) as starting material and 1-(prop-2-yn-1-yl)pyrrolidin-2-one instead of methyl pent-4-ynoate. LC-MS calculated for $C_{35}H_{42}BrFN_5O_5S$ (M+H)$^+$: m/z=742.2, 744.2; found 742.2, 744.2.

Step 2: 3-(4-(((1R,4R,5S)-2-Azabicyclo[2.1.1]hexan-5-yl)amino)-7-bromo-8-fluoro-2-(methylthio)-3-(3-(2-oxopyrrolidin-1-yl)prop-1-yn-1-yl)quinolin-6-yl)propanenitrile

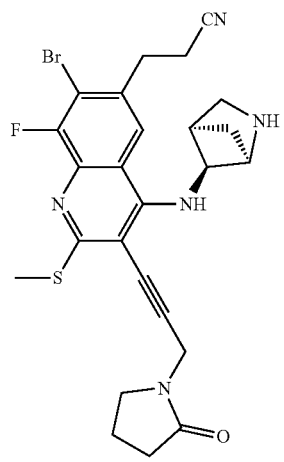 [SMILES: CSc1nc2c(F)c(Br)c(CCC#N)cc2c(N[C@H]2[C@H]3CN[C@@H]2C3)c1C#CCN1CCCC1=O]

This compound was prepared according to the procedure described in Example 1, Step 2. LC-MS calculated for $C_{25}H_{26}BrFN_5OS$ (M+H)$^+$: m/z=542.1, 544.1; found 542.1, 544.1.

Step 3: tert-Butyl (1R,4R,5S)-5-(7-bromo-8-(2-cyanoethyl)-6-fluoro-4-(methylthio)-2-((2-oxopyrrolidin-1-yl)methyl)-1H-pyrrolo[3,2-c]quinolin-1-yl)-2-azabicyclo[2.1.1]hexane-2-carboxylate

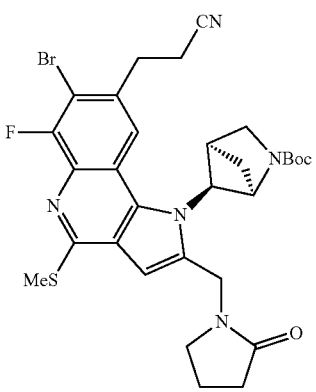 [SMILES: CSc1nc2c(F)c(Br)c(CCC#N)cc2c2c1cc(CN1CCCC1=O)n2[C@H]1[C@@H]2C[C@H]1N(C(=O)OC(C)(C)C)C2]

This compound was prepare according to the procedure described in Example 1, Step 3. LC-MS calculated for $C_{30}H_{34}BrFN_5O_3S$ (M+H)$^+$: m/z=642.2, 644.2; found 642.2, 644.2.

Step 4: tert-Butyl (1R,4R,5S)-5-(7-(benzo[b]thiophen-3-yl)-8-(2-cyanoethyl)-6-fluoro-4-(methylthio)-2-((2-oxopyrrolidin-1-yl)methyl)-1H-pyrrolo[3,2-c]quinolin-1-yl)-2-azabicyclo[2.1.1]hexane-2-carboxylate

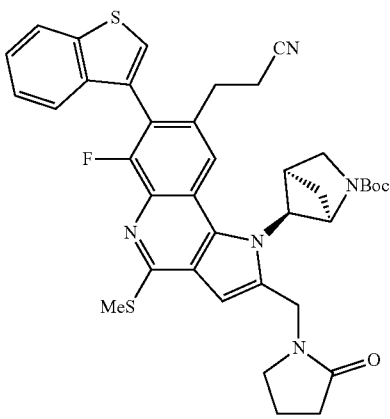 [SMILES: CSc1nc2c(F)c(-c3csc4ccccc34)c(CCC#N)cc2c2c1cc(CN1CCCC1=O)n2[C@H]1[C@@H]2C[C@H]1N(C(=O)OC(C)(C)C)C2]

A sample of tert-butyl (1R,4R,5S)-5-(7-bromo-8-(2-cyanoethyl)-6-fluoro-4-(methylthio)-2-((2-oxopyrrolidin-1-yl)methyl)-1H-pyrrolo[3,2-c]quinolin-1-yl)-2-azabicyclo[2.1.1]hexane-2-carboxylate (200 mg, 0.311 mmol) was dissolved in 1,4-dioxane (2.5 mL) and water (0.6 mL) and stirred at room temperature. The solution was treated with $K_2CO_3$ (129 mg, 0.934 mmol) and benzo[b]thiophen-3-ylboronic acid (139 mg, 0.778 mmol). The solution was de-gassed by bubbling with nitrogen and sonication for 5 minutes. Finally, the solution was treated with Pd XPhos G2 (37 mg, 0.047 mmol) and stirred at 65° C.

After 90 mins, LCMS indicated complete conversion to the product. The reaction was cooled to RT, quenched with satd. aq. $NH_4Cl$ and diluted with EtOAc. The layers were separated, and the aqueous layer was extracted with additional EtOAc. The combined organic layers were dried over $MgSO_4$, filtered, and concentrated in vacuo.

The crude material was purified by flash column chromatography (0-100% EtOAc/hexanes) to give tert-butyl (1R,4R,5S)-5-(7-(benzo[b]thiophen-3-yl)-8-(2-cyanoethyl)-6-fluoro-4-(methylthio)-2-((2-oxopyrrolidin-1-yl)methyl)-1H-pyrrolo[3,2-c]quinolin-1-yl)-2-azabicyclo[2.1.1]hexane-2-carboxylate (213 mg, 0.306 mmol, 98% yield).

LC-MS calculated for $C_{38}H_{39}FN_5O_3S_2$ (M+H)$^+$: m/z=696.3; found 696.3.

Step 5: tert-Butyl (1R,4R,5S)-5-(7-(benzo[b]thiophen-3-yl)-8-(2-cyanoethyl)-6-fluoro-4-(methylsulfinyl)-2-((2-oxopyrrolidin-1-yl)methyl)-1H-pyrrolo[3,2-c]quinolin-1-yl)-2-azabicyclo[2.1.1]hexane-2-carboxylate

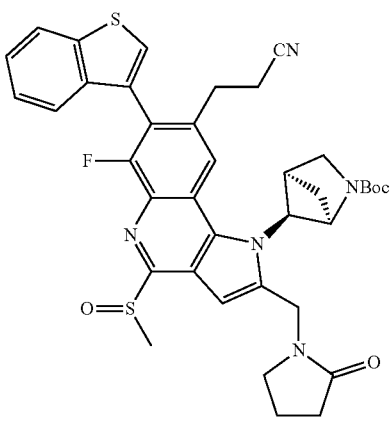 [SMILES: CS(=O)c1nc2c(F)c(-c3csc4ccccc34)c(CCC#N)cc2c2c1cc(CN1CCCC1=O)n2[C@H]1[C@@H]2C[C@H]1N(C(=O)OC(C)(C)C)C2]

A sample of tert-butyl (1R,4R,5S)-5-(7-(benzo[b]thiophen-3-yl)-8-(2-cyanoethyl)-6-fluoro-4-(methylthio)-2-((2-oxopyrrolidin-1-yl)methyl)-1H-pyrrolo[3,2-c]quinolin-1-yl)-2-azabicyclo[2.1.1]hexane-2-carboxylate (100 mg, 0.144 mmol) was dissolved in DCM (1.4 mL) and stirred at 0° C. The solution was treated with m-CPBA (35 mg, 75% w/w, 0.15 mmol).

After 45 min, LCMS showed complete conversion to the desired product, with some over-oxidation to the corresponding sulfone. The reaction was quenched with saturated. aq. $NaHCO_3$ and diluted with DCM. The layers were separated, and the aqueous layer was extracted with additional DCM. The combined organic layers were dried over $MgSO_4$, filtered, and concentrated in vacuo to give tert-butyl (1R,4R,5S)-5-(7-(benzo[b]thiophen-3-yl)-8-(2-cyanoethyl)-6-fluoro-4-(methylsulfinyl)-2-((2-oxopyrrolidin-1-yl)methyl)-1H-pyrrolo[3,2-c]quinolin-1-yl)-2-azabicyclo[2.1.1]hexane-2-carboxylate (97 mg, 0.136 mmol, 95% yield).

LC-MS calculated for $C_{38}H_{39}FN_5O_4S_2$ (M+H)$^+$: m/z=712.2; found 712.3.

Step 6: 3-(7-(Benzo[b]thiophen-3-yl)-1-((1R,4R,5S)-2-azabicyclo[2.1.1]hexan-5-yl)-6-fluoro-4-((S)-1-((S)-1-methylpyrrolidin-2-yl)ethoxy)-2-((2-oxopyrrolidin-1-yl)methyl)-1H-pyrrolo[3,2-c]quinolin-8-yl)propanenitrile A sample of tert-butyl (1R,4R,5S)-5-(7-(benzo[b]thiophen-3-yl)-8-(2-cyanoethyl)-6-fluoro-4-(methylsulfinyl)-2-((2-oxopyrrolidin-1-yl)methyl)-1H-pyrrolo[3,2-c]quinolin-1-yl)-2-azabicyclo[2.1.1]hexane-2-carboxylate (20 mg, 0.028 mmol) was suspended in toluene and treated with (S)-1-((S)-1-methylpyrrolidin-2-yl)ethan-1-ol (7 mg, 0.056 mmol). The mixture was concentrated in vacuo and azeotroped with toluene twice more. Afterwards, the flask was backfilled with nitrogen gas. The residue was dissolved in anhydrous THF (0.3 mL). Lastly, potassium tert-butoxide (73.0 μL, 0.037 mmol) (1M in THF) was added dropwise, and the solution was stirred at 22° C.

After 15 minutes, LCMS showed the reaction was complete. The reaction was quenched with saturated aq. $NH_4Cl$ and diluted with DCM. The layers were separated, and the aqueous layer was extracted with additional DCM. The combined organic fractions were dried over $MgSO_4$, filtered, and concentrated in vacuo.

LC-MS calculated for $C_{44}H_{50}FN_6O_4S$ (M+H)$^+$: m/z=777.4; found 777.4.

The crude intermediate was dissolved in DCM (0.5 mL) and treated with trifluoroacetic acid (0.5 mL). The mixture was stirred for 30 minutes, at which point LCMS indicated complete conversion to the desired product.

The solution was concentrated in vacuo, then purified by HPLC (pH=2 method) to give 3-(7-(benzo[b]thiophen-3-yl)-1-((1R,4R,5S)-2-azabicyclo[2.1.1]hexan-5-yl)-6-fluoro-4-((S)-1-((S)-1-methylpyrrolidin-2-yl)ethoxy)-2-((2-oxopyrrolidin-1-yl)methyl)-1H-pyrrolo[3,2-c]quinolin-8-yl)propanenitrile as two diastereomers (Peak 1: 1.4 mg, 2.1 μmol, 7% yield; Peak 2: 2.5 mg, 3.7 μmol, 13% yield).

Diastereomer 1. Peak 1. LC-MS calculated for $C_{39}H_{42}FN_6O_2S$ (M+H)$^+$: m/z=677.3; found 677.3.

Diastereomer 2. Peak 2. LC-MS calculated for $C_{39}H_{42}FN_6O_2S$ (M+H)$^+$: m/z=677.3; found 677.4.

Example 10: 3-(1-((1R,4R,5S)-2-Azabicyclo[2.1.1]hexan-5-yl)-4-(((S)-1-(dimethylamino)propan-2-yl)oxy)-6-fluoro-7-(7-fluoronaphthalen-1-yl)-2-((2-oxopyrrolidin-1-yl)methyl)-1H-pyrrolo[3,2-c]quinolin-8-yl)propanenitrile

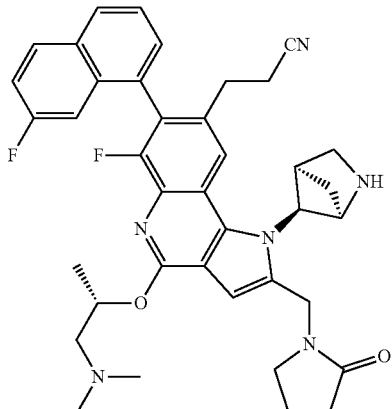

Step 1: tert-Butyl (1R,4R,5S)-5-(8-(2-cyanoethyl)-6-fluoro-7-(7-fluoronaphthalen-1-yl)-4-(methylthio)-2-((2-oxopyrrolidin-1-yl)methyl)-1H-pyrrolo[3,2-c]quinolin-1-yl)-2-azabicyclo[2.1.1]hexane-2-carboxylate

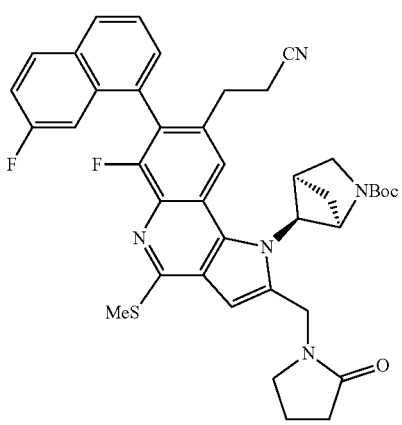 [SMILES: CSc1nc2c(F)c(-c3cccc4ccc(F)cc34)c(CCC#N)cc2c2c1cc(CN1CCCC1=O)n2[C@H]1[C@@H]2C[C@H]1N(C(=O)OC(C)(C)C)C2]

This compound was prepared according to the procedure described in Example 9, Step 4, using 2-(7-fluoronaphthalen-1-yl)-4,4,5,5-tetramethyl-1,3,2-dioxaborolane (Intermediate 10) instead of benzo[b]thiophen-3-ylboronic acid. LC-MS calculated for $C_{40}H_{40}F_2N_5O_3S$ (M+H)$^+$: m/z=708.3; found 708.3.

Step 2: tert-Butyl (1R,4R,5S)-5-(8-(2-cyanoethyl)-6-fluoro-7-(7-fluoronaphthalen-1-yl)-4-(methylsulfinyl)-2-((2-oxopyrrolidin-1-yl)methyl)-1H-pyrrolo[3,2-c]quinolin-1-yl)-2-azabicyclo[2.1.1]hexane-2-carboxylate

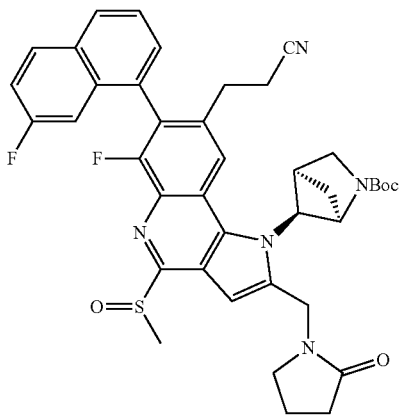 [SMILES: CS(=O)c1nc2c(F)c(-c3cccc4ccc(F)cc34)c(CCC#N)cc2c2c1cc(CN1CCCC1=O)n2[C@H]1[C@@H]2C[C@H]1N(C(=O)OC(C)(C)C)C2]

This compound was prepared according to the procedure described in Example 9, Step 5, using tert-butyl (1R,4R,5S)-5-(8-(2-cyanoethyl)-6-fluoro-7-(7-fluoronaphthalen-1-yl)-4-(methylthio)-2-((2-oxopyrrolidin-1-yl)methyl)-1H-pyrrolo[3,2-c]quinolin-1-yl)-2-azabicyclo[2.1.1]hexane-2-carboxylate as starting material. LC-MS calculated for $C_{40}H_{40}F_2N_5O_4S$ (M+H)$^+$: m/z=724.3; found 724.3.

Step 3: 3-(1-((1R,4R,5S)-2-azabicyclo[2.1.1]hexan-5-yl)-4-(((S)-1-(dimethylamino)propan-2-yl)oxy)-6-fluoro-7-(7-fluoronaphthalen-1-yl)-2-((2-oxopyrrolidin-1-yl)methyl)-1H-pyrrolo[3,2-c]quinolin-8-yl)propanenitrile This compound was prepared according to the procedure described in Example 9, Step 6, using tert-butyl (1R,4R,5S)-5-(8-(2-cyanoethyl)-6-fluoro-7-(7-fluoronaphthalen-1-yl)-4-(methylsulfinyl)-2-((2-oxopyrrolidin-1-yl)methyl)-1H-pyrrolo[3,2-c]quinolin-1-yl)-2-azabicyclo[2.1.1]hexane-2-carboxylate as starting material and (S)-1-(dimethylamino)propan-2-ol in place of (S)-1-((S)-1-methylpyrrolidin-2-yl)ethan-1-ol. The title compound was isolated as four diastereomers.

Diastereomer 1. Peak 1 (1.1 mg, 1.7 µmol, 6% yield). LC-MS calculated for $C_{39}H_{41}F_2N_6O_2$ (M+H)$^+$: m/z=663.3; found 663.4.

Diastereomer 2. Peak 2 (1.7 mg, 2.6 µmol, 9% yield). LC-MS calculated for $C_{39}H_{41}F_2N_6O_2$ (M+H)$^+$: m/z=663.3; found 663.4.

Diastereomer 3. Peak 3 (0.9 mg, 1.4 µmol, 5% yield). LC-MS calculated for $C_{39}H_{41}F_2N_6O_2$ (M+H)$^+$: m/z=663.3; found 663.3.

Diastereomer 4. Peak 4 (1.4 mg, 2.1 µmol, 8% yield). LC-MS calculated for $C_{39}H_{41}F_2N_6O_2$ (M+H)$^+$: m/z=663.3; found 663.4.

Example 11: 8-(1-(((1R,4R,5S)-2-Azabicyclo[2.1.1]
hexan-5-yl)-8-(2-cyanoethyl)-6-fluoro-2-methyl-4-
((S)-1-((S)-1-methylpyrrolidin-2-yl)ethoxy)-1H-
pyrrolo[3,2-c]quinolin-7-yl)-1-naphthonitrile

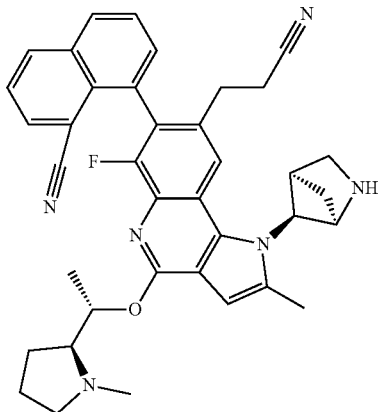 [SMILES: Cc1cc2c(O[C@@H](C)[C@@H]3CCCN3C)nc3c(F)c(-c4cccc5cccc(C#N)c45)c(CCC#N)cc3c2n1[C@H]1[C@H]2CN[C@@H]1C2]

To a mixture of 8-(4,4,5,5-tetramethyl-1,3,2-dioxaborolan-2-yl)-1-naphthonitrile (84 mg, 0.30 mmol), Pd(amphos)Cl₂ (14 mg, 0.02 mmol), tert-butyl (1R,4R,5S)-5-(7-bromo-8-(2-cyanoethyl)-6-fluoro-4-((S)-1-((S)-1-methylpyrrolidin-2-yl)ethoxy)-1H-pyrrolo[3,2-c]quinolin-1-yl)-2-azabicyclo[2.1.1]hexane-2-carboxylate (129 mg, 0.20 mmol) (Example 2, Step 1), and potassium phosphate (128 mg, 0.60 mmol) was added 1,4-dioxane (0.81 ml) and water (0.20 ml). The reaction mixture was sparged with N₂ and heated to 100° C. for 1 h.

Upon completion, the reaction was diluted with water and EtOAc. The layers were separated, and the aqueous layer was extracted with additional EtOAc. The combined organic fractions were washed with brine, dried over MgSO₄, filtered, and concentrated in vacuo. tert-Butyl (1R,4R,5S)-5-(8-(2-cyanoethyl)-7-(8-cyanonaphthalen-1-yl)-6-fluoro-2-methyl-4-((S)-1-((S)-1-methylpyrrolidin-2-yl)ethoxy)-1H-pyrrolo[3,2-c]quinolin-1-yl)-2-azabicyclo[2.1.1]hexane-2-carboxylate was isolated by flash column chromatography eluting with 0-30% MeOH/DCM. Further purification by prep HPLC (pH 10) gave the Boc-protected product as two peaks.

Diastereomer 1. Peak 1. LC-MS calculated for C₄₃H₄₆FN₆O₃ (M+H)⁺: m/z=713.4; found 713.4.

Diastereomer 2. Peak 2. LC-MS calculated for C₄₃H₄₆FN₆O₃ (M+H)⁺: m/z=713.4; found 713.4.

After concentration in vacuo, the residue of each peak was individually stirred in 2:1 DCM/TFA (3 mL) for 30 min, concentrated, and purified by prep HPLC (pH 2). The title compound was isolated as two diastereomers.

Diastereomer 1. Peak 1. LC-MS calculated for C₃₈H₃₈FN₆O (M+H)⁺: m/z=613.3; found 613.6.

Diastereomer 2. Peak 2. LC-MS calculated for C₃₈H₃₈FN₆O (M+H)⁺: m/z=613.3; found 613.6.

Example 12: 3-(1-(((1R,4R,5S)-2-Azabicyclo[2.1.1]
hexan-5-yl)-7-(2,3-dichloro-5-hydroxyphenyl)-6-
fluoro-2-methyl-4-((S)-1-((S)-1-methylpyrrolidin-2-
yl)ethoxy)-1H-pyrrolo[3,2-c]quinolin-8-yl)
propanenitrile

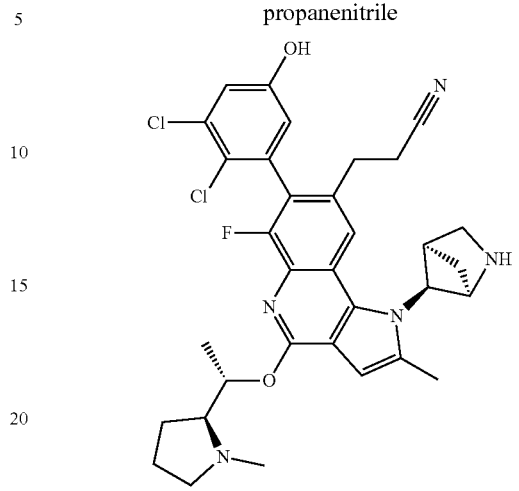

This compound was prepared according to the procedure described in Example 2, Step 2, utilizing 2-(2,3-dichloro-5-(methoxymethoxy)phenyl)-4,4,5,5-tetramethyl-1,3,2-dioxaborolane (Intermediate 11) instead of tert-butyl 5,7-difluoro-3-(4,4,5,5-tetramethyl-1,3,2-dioxa-borolan-2-yl)-1H-indole-1-carboxylate. The title compound was isolated as four diastereomers.

Diastereomer 1. Peak 1. LC-MS calculated for C₃₃H₃₅Cl₂FN₅O₂ (M+H)⁺: m/z=622.2, 624.2; found 622.2, 624.2.

Diastereomer 2. Peak 2. LC-MS calculated for C₃₃H₃₅Cl₂FN₅O₂ (M+H)⁺: m/z=622.2, 624.2; found 622.2, 624.2.

Diastereomer 3. Peak 3. LC-MS calculated for C₃₃H₃₅Cl₂FN₅O₂ (M+H)⁺: m/z=622.2, 624.2; found 622.2, 624.2.

Diastereomer 4. Peak 4. LC-MS calculated for C₃₃H₃₅Cl₂FN₅O₂ (M+H)⁺: m/z=622.2, 624.2; found 622.2, 624.1.

Example 13: 3-(1-(((1R,4R,5S)-2-Azabicyclo[2.1.1]
hexan-5-yl)-8-(2-cyanoethyl)-6-fluoro-4-((3-fluoro-
1-methylazetidin-3-yl)methoxy)-7-(3-hydroxynaph-
thalen-1-yl)-1H-pyrrolo[3,2-c]quinolin-2-yl)-N,N-
dimethylpropanamide

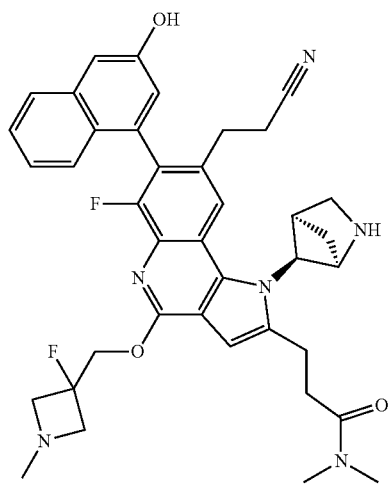 [SMILES: CN1CC(F)(COc2nc3c(F)c(-c4cc(O)cc5ccccc45)c(CCC#N)cc3c3c2cc(CCC(=O)N(C)C)n3[C@H]2[C@H]3CN[C@@H]2C3)C1]

183

Step 1. tert-Butyl (1R,4R,5S)-5-((7-bromo-6-(2-cyanoethyl)-3-(5-(dimethylamino)-5-oxopent-1-yn-1-yl)-8-fluoro-2-(methylthio)quinolin-4-yl)(tert-butoxycarbonyl)amino)-2-azabicyclo[2.1.1]hexane-2-carboxylate

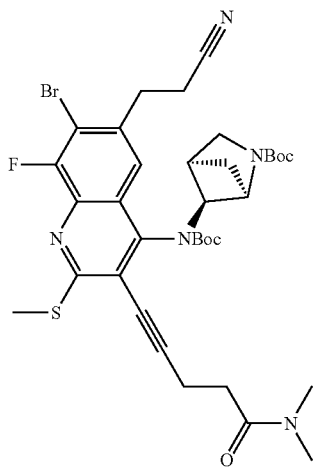

The reaction mixture of tert-butyl (1R,4R,5S)-5-((7-bromo-6-(2-cyanoethyl)-8-fluoro-3-iodo-2-(methylthio)quinolin-4-yl)(tert-butoxycarbonyl)amino)-2-azabicyclo[2.1.1]hexane-2-carboxylate (6.2 g, 8.33 mmol) (Intermediate 2), N,N-dimethylpent-4-ynamide (5.2 g, 41.7 mmol) (Intermediate 12), bis(triphenylphosphine)palladium(II) chloride (1.2 g, 1.67 mmol), CuI (2.4 g, 12.5 mmol) and TEA (23 ml, 167 mmol) in DMF (42 ml) was sparged with $N_2$ and heated at 95° C. for 1 h.

Once completed, the reaction was cooled to room temperature and poured into a solution of 5% LiCl in water. The aqueous layer was extracted with EtOAc, washed with brine, concentrated under reduced pressure and purified by flash column chromatography (0-20% MeOH/DCM) to afford the title compound (3.7 g, 60% yield). LC-MS calculated for $C_{35}H_{44}BrFN_5O_5S$ (M+H)$^+$: m/z=744.2, 746.2; found 744.3, 746.3.

Step 2. 5-(4-(((1R,4R,5S)-2-Azabicyclo[2.1.1]hexan-5-yl)amino)-7-bromo-6-(2-cyanoethyl)-8-fluoro-2-(methylthio)quinolin-3-yl)-N,N-dimethylpent-4-ynamide

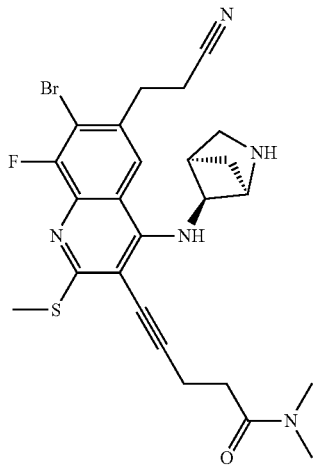 [SMILES: CSc1nc2c(F)c(Br)c(CCC#N)cc2c(N[C@H]2[C@H]3CN[C@@H]2C3)c1C#CCCC(=O)N(C)C]

184

This compound was prepared according to the procedure described in Example 1, Step 2 with tert-butyl (1R,4R,5S)-5-((7-bromo-6-(2-cyanoethyl)-3-(5-(dimethylamino)-5-oxopent-1-yn-1-yl)-8-fluoro-2-(methylthio)quinolin-4-yl)(tert-butoxycarbonyl)amino)-2-azabicyclo[2.1.1]hexane-2-carboxylate replacing tert-butyl (1R,4R,5S)-5-((7-bromo-6-(2-cyanoethyl)-8-fluoro-2-(methylthio)-3-(prop-1-yn-1-yl)quinolin-4-yl)(tert-butoxycarbonyl)amino)-2-azabicyclo[2.1.1]-hexane-2-carboxylate as starting material. LC-MS calculated for $C_{25}H_{28}BrFN_5OS$ (M+H)$^+$: m/z=544.1, 546.1; found 544.1, 546.1.

Step 3. tert-Butyl (1R,4R,5S)-5-(7-bromo-8-(2-cyanoethyl)-2-(3-(dimethylamino)-3-oxopropyl)-6-fluoro-4-(methylthio)-1H-pyrrolo[3,2-c]quinolin-1-yl)-2-azabicyclo[2.1.1]hexane-2-carboxylate

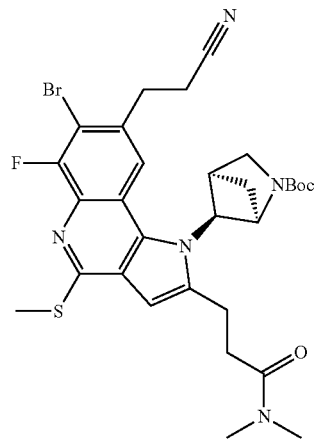 [SMILES: CSc1nc2c(F)c(Br)c(CCC#N)cc2c2c1cc(CCC(=O)N(C)C)n2[C@H]1[C@@H]2C[C@H]1N(C(=O)OC(C)(C)C)C2]

This compound was prepared according to the procedure described in Example 1, Step 3 with 5-(4-(((1R,4R,5S)-2-azabicyclo[2.1.1]hexan-5-yl)amino)-7-bromo-6-(2-cyanoethyl)-8-fluoro-2-(methylthio)quinolin-3-yl)-N,N-dimethylpent-4-ynamide replacing 3-(4-(((1R,4R,5R)-2-azabicyclo[2.1.1]hexan-5-yl)amino)-7-bromo-8-fluoro-2-(methylthio)-3-(prop-1-yn-1-yl)quinolin-6-yl)propanenitrile as starting material. LC-MS calculated for $C_{30}H_{36}BrFN_5O_3S$ (M+H)$^+$: m/z=644.2, 646.2; found 644.1, 646.1.

Step 4. tert-Butyl (1R,4R,5S)-5-(8-(2-cyanoethyl)-2-(3-(dimethylamino)-3-oxopropyl)-6-fluoro-7-(3-(methoxymethoxy)naphthalen-1-yl)-4-(methylthio)-1H-pyrrolo[3,2-c]quinolin-1-yl)-2-azabicyclo[2.1.1]hexane-2-carboxylate

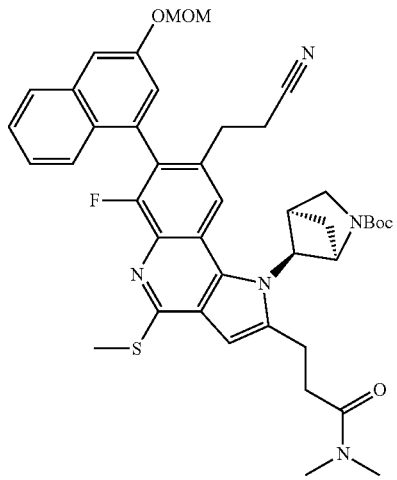

A mixture of tert-butyl (1R,4R,5S)-5-(7-bromo-8-(2-cyanoethyl)-2-(3-(dimethylamino)-3-oxopropyl)-6-fluoro-4-(methylthio)-1H-pyrrolo[3,2-c]quinolin-1-yl)-2-azabicyclo[2.1.1]hexane-2-carboxylate (3.6 g, 5.60 mmol), 2-(3-(methoxymethoxy)naphthalen-1-yl)-4,4,5,5-tetramethyl-1,3,2-dioxaborolane (2.6 g, 8.40 mmol) (Intermediate 13), XPhos Pd G2 (220 mg, 0.28 mmol), and sodium carbonate (1.78 g, 16.8 mmol) in 1,4-dioxane (31 ml) and water (6.2 ml) was sparged with $N_2$ and heated to 100° C. for 1 h.

After cooling to room temperature, the reaction mixture was diluted with EtOAc and water. The organic layer was washed with brine, concentrated under reduced pressure and purified by flash column chromatography (0-20% MeOH/DCM) to afford the title compound (2.7 g, 63% yield). LC-MS calculated for $C_{42}H_{47}FN_5O_5S$ (M+H)$^+$: m/z=752.3; found 752.2.

Step 5. tert-Butyl (1R,4R,5S)-5-(8-(2-cyanoethyl)-2-(3-(dimethylamino)-3-oxopropyl)-6-fluoro-7-(3-(methoxymethoxy)naphthalen-1-yl)-4-(methylsulfinyl)-1H-pyrrolo[3,2-c]quinolin-1-yl)-2-azabicyclo[2.1.1]hexane-2-carboxylate

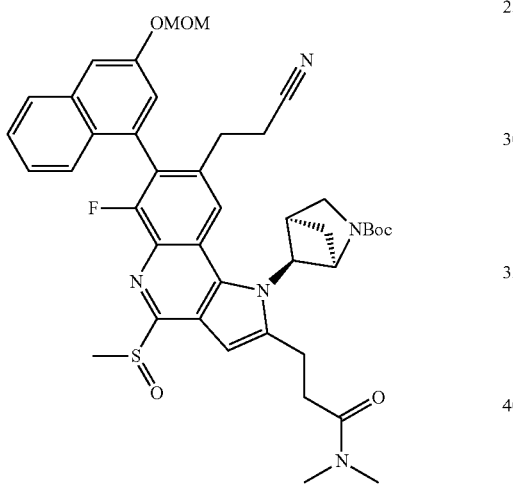

This compound was prepared according to the procedure described in Example 9, Step 5 with tert-butyl (1R,4R,5S)-5-(8-(2-cyanoethyl)-2-(3-(dimethylamino)-3-oxopropyl)-6-fluoro-7-(3-(methoxymethoxy)naphthalen-1-yl)-4-(methylthio)-1H-pyrrolo[3,2-c]quinolin-1-yl)-2-azabicyclo[2.1.1]hexane-2-carboxylate replacing tert-butyl (1R,4R,5S)-5-(7-(benzo[b]thiophen-3-yl)-8-(2-cyanoethyl)-6-fluoro-4-(methylthio)-2-((2-oxopyrrolidin-1-yl)methyl)-1H-pyrrolo[3,2-c]quinolin-1-yl)-2-azabicyclo[2.1.1]hexane-2-carboxylate as starting material. LC-MS calculated for $C_{42}H_{47}FN_5O_6S$ (M+H)$^+$: m/z=768.3; found 768.5.

Step 6. 3-(1-((1R,4R,5S)-2-Azabicyclo[2.1.1]hexan-5-yl)-8-(2-cyanoethyl)-6-fluoro-4-((3-fluoro-1-methylazetidin-3-yl)methoxy)-7-(3-hydroxynaphthalen-1-yl)-1H-pyrrolo[3,2-c]quinolin-2-yl)-N,N-dimethylpropanamide To a solution of (3-fluoro-1-methylazetidin-3-yl)methanol (11 µl, 0.10 mmol) in THF (0.50 ml) at 0° C. was added potassium tert-butoxide (1 M/THF, 0.08 ml, 0.08 mmol), and the reaction mixture was stirred for 5 min. A solution of tert-butyl (1R,4R,5S)-5-(8-(2-cyanoethyl)-2-(3-(dimethylamino)-3-oxopropyl)-6-fluoro-7-(3-(methoxymethoxy)naphthalen-1-yl)-4-(methylsulfinyl)-1H-pyrrolo[3,2-c]quinolin-1-yl)-2-azabicyclo[2.1.1]hexane-2-carboxylate (40 mg, 0.052 mmol) in THF (0.50 mL) was then added and the reaction mixture was warmed to room temperature.

After 30 min, full conversion of starting material was confirmed by LC-MS and the reaction mixture was cooled to 0° C. HCl (4M/1,4-dioxane, 0.39 ml, 1.56 mmol) was slowly added to the solution. The reaction mixture was stirred at room temperature for 10 min before warming to 50° C. After 1 h of stirring complete deprotection was observed by LC-MS and the desired product was isolated by prep HPLC (pH 2). The title compound was isolated as two diastereomers.

Diastereomer 1. Peak 1. LC-MS calculated for $C_{39}H_{41}F_2N_6O_3$ (M+H)$^+$: m/z=679.3; found 679.3.

Diastereomer 2. Peak 2. LC-MS calculated for $C_{39}H_{41}F_2N_6O_3$ (M+H)$^+$: m/z=679.3; found 679.3.

Example 14: 3-(1-((1R,4R,5S)-2-Azabicyclo[2.1.1]hexan-5-yl)-6-fluoro-7-(3-hydroxynaphthalen-1-yl)-2-methyl-4-(5-methylpyrazin-2-yl)-1H-pyrrolo[3,2-c]quinolin-8-yl)propanenitrile

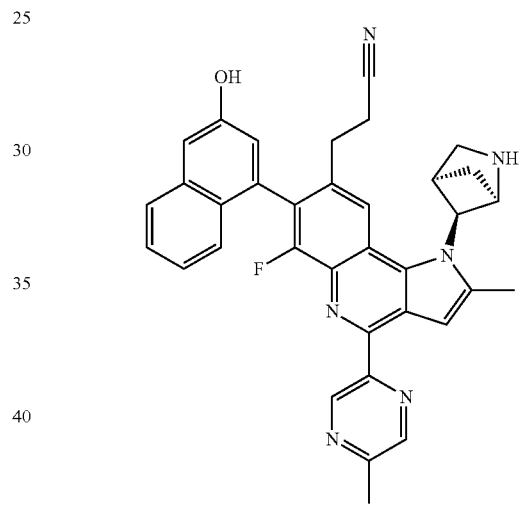

Step 1. tert-Butyl (1R,4R,5S)-5-(8-(2-cyanoethyl)-6-fluoro-7-(3-(methoxymethoxy)naphthalen-1-yl)-2-methyl-4-(methylthio)-1H-pyrrolo[3,2-c]quinolin-1-yl)-2-azabicyclo[2.1.1]hexane-2-carboxylate

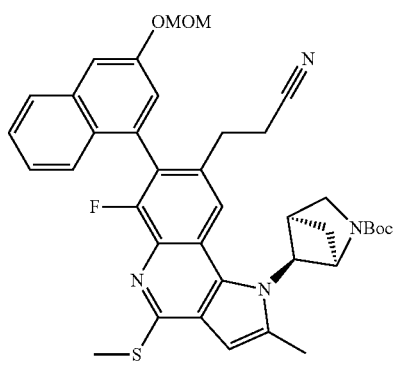

This compound was prepared according to the procedure described in Example 13, Step 4 with tert-butyl (1R,4R,5S)-5-(7-Bromo-8-(2-cyanoethyl)-6-fluoro-2-methyl-4-(methylthio)-1H-pyrrolo[3,2-c]quinolin-1-yl)-2-azabicyclo[2.1.1]hexane-2-carboxylate (Example 1, Step 3) replacing tert-butyl (1R,4R,5S)-5-(7-bromo-8-(2-cyanoethyl)-2-(3-(dimethylamino)-3-oxopropyl)-6-fluoro-4-(methylthio)-1H-pyrrolo[3,2-c]quinolin-1-yl)-2-azabicyclo[2.1.1]hexane-2-carboxylate as starting material. LC-MS calculated for $C_{38}H_{40}FN_4O_4S$ (M+H)$^+$: m/z=667.3; found 667.2.

Step 2. 3-(1-((1R,4R,5S)-2-Azabicyclo[2.1.1]hexan-5-yl)-6-fluoro-7-(3-hydroxynaphthalen-1-yl)-2-methyl-4-(5-methylpyrazin-2-yl)-1H-pyrrolo[3,2-c]quinolin-8-yl)propanenitrile To a mixture of tert-butyl (1R,4R,5S)-5-(8-(2-cyanoethyl)-6-fluoro-7-(3-(methoxymethoxy)naphthalen-1-yl)-2-methyl-4-(methylthio)-1H-pyrrolo[3,2-c]quinolin-1-yl)-2-azabicyclo[2.1.1]hexane-2-carboxylate (17 mg, 0.025 mmol), (5-methylpyrazin-2-yl)boronic acid (8.79 mg, 0.064 mmol, Tetrakis(triphenylphosphine)-palladium(0) (5.89 mg, 5.10 μmol), Copper(1)3-methylsalicylate (19.70 mg, 0.092 mmol), Dioxane (1.0 mL) was added. The reaction mixture was sparged with $N_2$ and heated to 120° C. for 20 hrs. The reaction mixture was filtered through a thiol siliaprep cartridge and concentrated. The residue was stirred in 1:1 DCM/TFA (3 mL) for 30 min, concentrated, and purified by prep HPLC (pH 2). The title compound was isolated as two diastereomers.

Diastereomer 1. Peak 1. LC-MS calculated for $C_{35}H_{30}FN_6O$ (M+H)$^+$: m/z=569.2; found 569.3.
Diastereomer 2. Peak 2. LC-MS calculated for $C_{35}H_{30}FN_6O$ (M+H)$^+$: m/z=569.2; found 569.3.

Example 15: 3-(1-((1R,4R,5S)-2-Azabicyclo[2.1.1]hexan-5-yl)-6-fluoro-7-(7-fluoronaphthalen-1-yl)-4-methyl-2-((4-methyl-2-oxopiperazin-1-yl)methyl)-1H-pyrrolo[3,2-c]quinolin-8-yl)propanenitrile

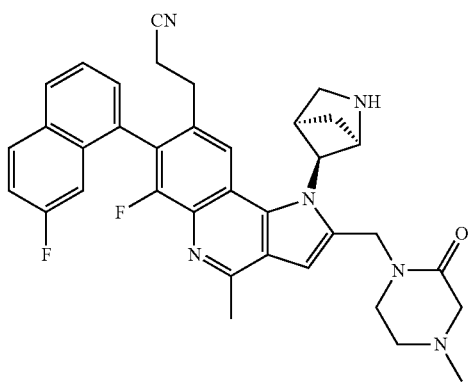 [SMILES: Cc1nc2c(F)c(-c3cccc4ccc(F)cc34)c(CCC#N)cc2c2c1cc(CN1CCN(C)CC1=O)n2[C@H]1[C@H]2CN[C@@H]1C2]

Step 1: tert-Butyl (1R,4R,5S)-5-(2-((4-((benzyloxy)carbonyl)-2-oxopiperazin-1-yl)methyl)-8-(2-cyanoethyl)-6-fluoro-7-(7-fluoronaphthalen-1-yl)-4-(methylthio)-1H-pyrrolo[3,2-c]quinolin-1-yl)-2-azabicyclo[2.1.1]hexane-2-carboxylate

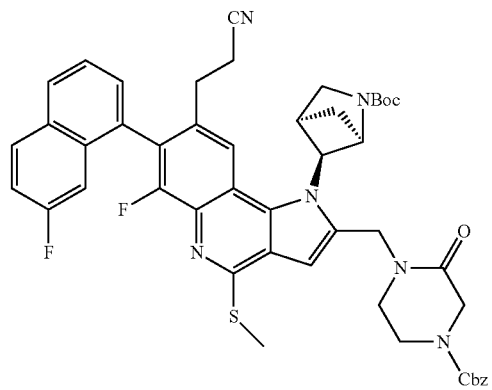 [SMILES: CSc1nc2c(F)c(-c3cccc4ccc(F)cc34)c(CCC#N)cc2c2c1cc(CN1CCN(C(=O)OCc3ccccc3)CC1=O)n2[C@H]1[C@@H]2C[C@H]1N(C(=O)OC(C)(C)C)C2]

This compound was prepared according to the procedure described in Example 10, Step 1, using benzyl 3-oxo-4-(prop-2-yn-1-yl)piperazine-1-carboxylate instead of 1-(prop-2-yn-1-yl)pyrrolidin-2-one. LC-MS calculated for $C_{48}H_{47}F_2N_6O_5S$ (M+H)$^+$: m/z=857.3; found 857.3.

Step 2: tert-Butyl (1R,4R,5S)-5-(2-((4-((benzyloxy)carbonyl)-2-oxopiperazin-1-yl)methyl)-8-(2-cyanoethyl)-6-fluoro-7-(7-fluoronaphthalen-1-yl)-4-methyl-1H-pyrrolo[3,2-c]quinolin-1-yl)-2-azabicyclo[2.1.1]hexane-2-carboxylate

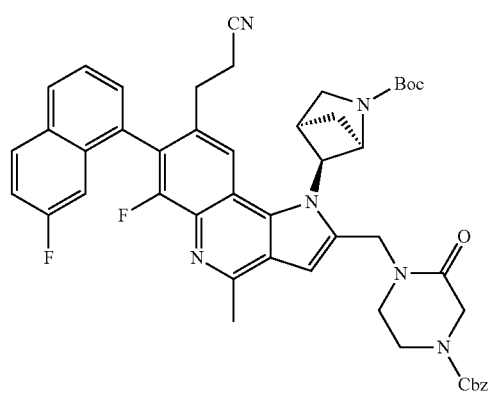 [SMILES: Cc1nc2c(F)c(-c3cccc4ccc(F)cc34)c(CCC#N)cc2c2c1cc(CN1CCN(C(=O)OCc3ccccc3)CC1=O)n2[C@H]1[C@@H]2C[C@H]1N(C(=O)OC(C)(C)C)C2]

This compound was prepared according to the procedure described in Example 14, Step 2, using trimethylboroxine instead of (5-methylpyrazin-2-yl)boronic acid. LC-MS calculated for $C_{48}H_{47}F_2N_6O_5$ (M+H)$^+$: m/z=825.4; found 825.4.

Step 3: tert-Butyl (1R,4R,5S)-5-(8-(2-cyanoethyl)-6-fluoro-7-(7-fluoronaphthalen-1-yl)-4-methyl-2-((2-oxopiperazin-1-yl)methyl)-1H-pyrrolo[3,2-c]quinolin-1-yl)-2-azabicyclo[2.1.1]hexane-2-carboxylate

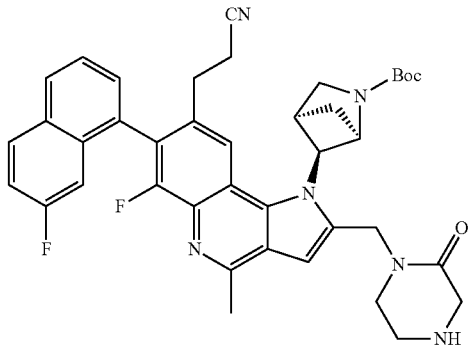 [SMILES: Cc1nc2c(F)c(-c3cccc4ccc(F)cc34)c(CCC#N)cc2c2c1cc(CN1CCNCC1=O)n2[C@H]1[C@@H]2C[C@H]1N(C(=O)OC(C)(C)C)C2]

A mixture of tert-butyl (1R,4R,5S)-5-(2-((4-((benzyloxy)carbonyl)-2-oxopiperazin-1-yl)methyl)-8-(2-cyanoethyl)-6-fluoro-7-(7-fluoronaphthalen-1-yl)-4-methyl-1H-pyrrolo[3,2-c]quinolin-1-yl)-2-azabicyclo[2.1.1]hexane-2-carboxylate (0.243 g, 0.294 mmol) and Pd(OH)$_2$ (150 mg) in MeOH (5 mL) was stirred under H$_2$ at RT for 6 h. The reaction mixture was concentrated under reduced pressure. The crude product was purified by flash column chromatography to provide the desired product. LC-MS calculated for $C_{40}H_{41}F_2N_6O_3$ (M+H)$^+$: m/z=691.3; found 691.3.

Step 4: 3-(1-((1R,4R,5S)-2-Azabicyclo[2.1.1]hexan-5-yl)-6-fluoro-7-(7-fluoronaphthalen-1-yl)-4-methyl-2-((4-methyl-2-oxopiperazin-1-yl)methyl)-1H-pyrrolo[3,2-c]quinolin-8-yl)propanenitrile A solution of tert-butyl (1R,4R,5S)-5-(8-(2-cyanoethyl)-6-fluoro-7-(7-fluoronaphthalen-1-yl)-4-methyl-2-((2-oxopiperazin-1-yl)methyl)-1H-pyrrolo[3,2-c]quinolin-1-yl)-2-azabicyclo[2.1.1]hexane-2-carboxylate (30 mg, 0.043 mmol), formaldehyde solution (0.1 mL, 37 wt. % in H$_2$O), 0.1 mL AcOH and sodium cyanoborohydride (13.65 mg, 0.217 mmol) in MeOH (2 mL) was stirred at RT for 1 h. The reaction mixture was concentrated. The residue was stirred in 1:1 DCM/TFA (3 mL) for 30 min, concentrated, and purified by prep HPLC (pH 2) to give the desired product. LC-MS calculated for $C_{36}H_{35}F_2N_6O$ (M+H)$^+$: m/z=605.3; found 605.5.

Example 16: 3-(1-((1R,4R,5S)-2-azabicyclo[2.1.1]hexan-5-yl)-7-(2,3-dichloro-5-hydroxyphenyl)-4-ethoxy-6-fluoro-2-((4-isopropyl-2-oxopiperazin-1-yl)methyl)-1H-pyrrolo[3,2-c]quinolin-8-yl)propanenitrile

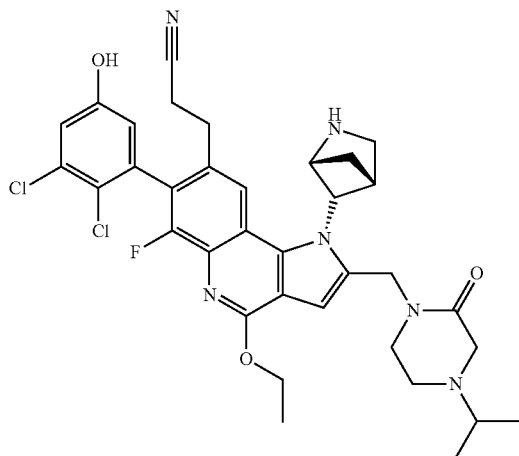

Step 1: tert-Butyl (1R,4R,5S)-5-(7-bromo-8-(2-cyanoethyl)-4-ethoxy-6-fluoro-2-((4-isopropyl-2-oxopiperazin-1-yl)methyl)-1H-pyrrolo[3,2-c]quinolin-1-yl)-2-azabicyclo[2.1.1]hexane-2-carboxylate

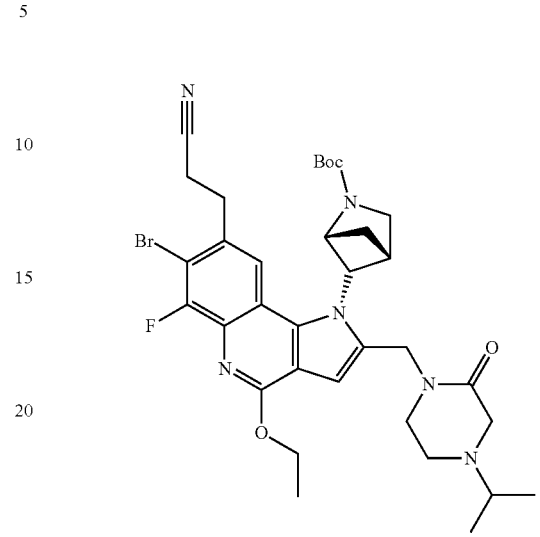

This compound was prepared according to the procedure described in Example 4, Step 2, using 4-isopropyl-1-(prop-2-yn-1-yl)piperazin-2-one (Intermediate 15) and tert-Butyl (1R,4R,5S)-5-((7-Bromo-6-(2-cyanoethyl)-2-ethoxy-8-fluoro-3-iodoquinolin-4-yl)amino)-2-azabicyclo[2.1.1]hexane-2-carboxylate (Intermediate 16) instead of methyl pent-4-ynoate and tert-butyl (1R,4R)-5-((7-bromo-6-(2-cyanoethyl)-8-fluoro-3-iodo-2-(methylthio)quinolin-4-yl)amino)-2-azabicyclo[2.1.1]hexane-2-carboxylate. LC-MS calculated for $C_{34}H_{43}BrFN_6O_4$ (M+H)$^+$: m/z=697.2; found 697.2.

Step 2: 3-(1-((1R,4R,5S)-2-azabicyclo[2.1.1]hexan-5-yl)-7-(2,3-dichloro-5-hydroxyphenyl)-4-ethoxy-6-fluoro-2-((4-isopropyl-2-oxopiperazin-1-yl)methyl)-1H-pyrrolo[3,2-c]quinolin-8-yl)propanenitrile This compound was prepared according to the procedure described in Example 12, using tert-butyl 5-(7-bromo-8-(2-cyanoethyl)-4-ethoxy-6-fluoro-2-((4-isopropyl-2-oxopiperazin-1-yl)methyl)-1H-pyrrolo[3,2-c]quinolin-1-yl)-2-azabicyclo[2.1.1]hexane-2-carboxylate. LC-MS calculated for $C_{35}H_{38}Cl_2FN_6O_3$ (M+H)$^+$: m/z=679.2; found 679.5.

Example 17: 3-(1-((1R,4R,5S)-2-Azabicyclo[2.1.1]
hexan-5-yl)-4-(3-(dimethylamino)-3-methylazetidin-
1-yl)-6-fluoro-7-(7-fluoronaphthalen-1-yl)-2-((3-
oxomorpholino)methyl)-1H-pyrrolo[3,2-c]quinolin-
8-yl)propanenitrile

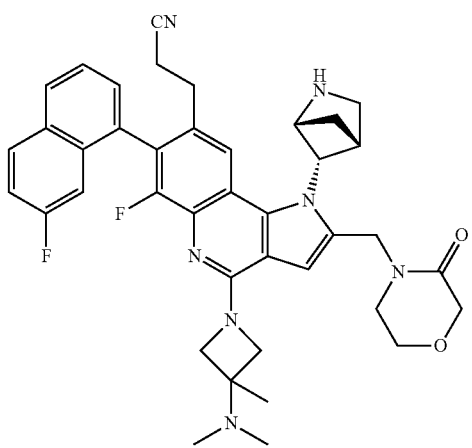 [SMILES: CN(C)C1(C)CN(c2nc3c(F)c(-c4cccc5ccc(F)cc45)c(CCC#N)cc3c3c2cc(CN2CCOCC2=O)n3[C@H]2[C@H]3CN[C@@H]2C3)C1]

Step 1: tert-Butyl (1R,4R,5S)-5-(8-(2-cyanoethyl)-
6-fluoro-7-(7-fluoronaphthalen-1-yl)-4-(methylsulfi-
nyl)-2-((3-oxomorpholino)methyl)-1H-pyrrolo[3,2-
c]quinolin-1-yl)-2-azabicyclo[2.1.1]hexane-2-
carboxylate

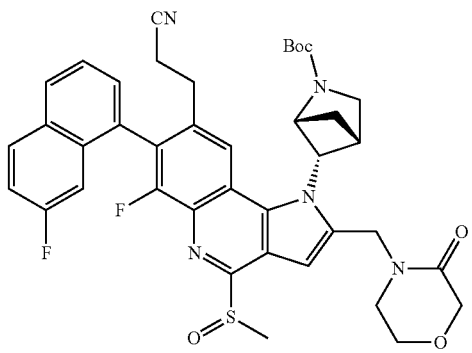 [SMILES: CS(=O)c1nc2c(F)c(-c3cccc4ccc(F)cc34)c(CCC#N)cc2c2c1cc(CN1CCOCC1=O)n2[C@H]1[C@@H]2C[C@H]1N(C(=O)OC(C)(C)C)C2]

This compound was prepared according to the procedure described in Example 10, Step 2, using 4-(prop-2-yn-1-yl)morpholin-3-one instead of 1-(prop-2-yn-1-yl)pyrrolidin-2-one. LC-MS calculated for $C_{40}H_{40}F_2N_5O_5S$ (M+H)$^+$: m/z=740.3; found 740.3.

Step 2: 3-(1-((1R,4R,5S)-2-Azabicyclo[2.1.1]hexan-
5-yl)-4-(3-(dimethylamino)-3-methylazetidin-1-yl)-
6-fluoro-7-(7-fluoronaphthalen-1-yl)-2-((3-oxomor-
pholino)methyl)-1H-pyrrolo[3,2-c]quinolin-8-yl)
propanenitrile A solution of tert-butyl (1R,4R,5S)-5-(8-(2-cyanoethyl)-6-fluoro-7-(7-fluoronaphthalen-1-yl)-4-(methylsulfinyl)-2-((3-oxomorpholino)methyl)-1H-pyrrolo[3,2-c]quinolin-1-yl)-2-azabicyclo[2.1.1]hexane-2-carboxylate (25 mg, 0.034 mmol), N,N,3-trimethylazetidin-3-amine dihydrochloride (25.3 mg, 0.135 mmol) and N,N-diisopropylethylamine (29.5 μL, 0.169 mmol) in NMP (1 mL) was stirred at 120° C. for 3 h. The reaction mixture was concentrated. The residue was stirred in 1:1 DCM/TFA (3 mL) for 30 min, concentrated, and purified by prep HPLC (pH 2) to give the desired product. LC-MS calculated for $C_{40}H_{42}F_2N_7O_2$ (M+H)$^+$: m/z=690.3; found 690.4.

Example 18: 3-(1-((1R,4R,5S)-2-azabicyclo[2.1.1]
hexan-5-yl)-4-ethoxy-6-fluoro-7-(3-hydroxynaphtha-
len-1-yl)-2-(1-(3-oxomorpholino)ethyl)-1H-pyrrolo
[3,2-c]quinolin-8-yl)propanenitrile

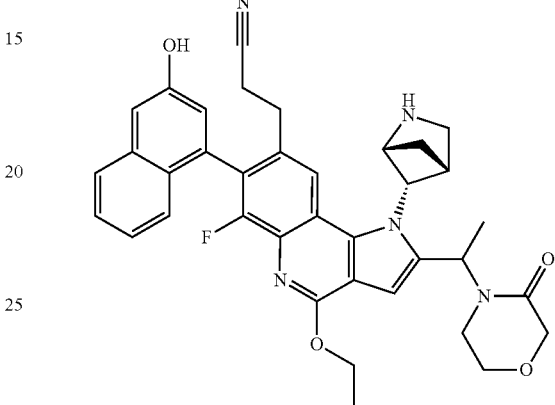

This compound was prepared according to the procedure described in Example 4, Step 2, using 4-(but-3-yn-2-yl)morpholin-3-one (Intermediate 14) and 4-(4,4,5,5-tetramethyl-1,3,2-dioxaborolan-2-yl)naphthalen-2-ol instead of 4-isopropyl-1-(prop-2-yn-1-yl)piperazin-2-one and 2-(2,3-dichloro-5-(methoxymethoxy)phenyl)-4,4,5,5-tetramethyl-1,3,2-dioxaborolane. The compound was isolated as a mixture of diastereomers. LC-MS calculated for $C_{37}H_{37}FN_5O_4$ (M+H)$^+$: m/z=634.3; found 634.3.

Example 19: 3-(1-((endo)-2-Azabicyclo[2.1.1]
hexan-5-yl)-6-fluoro-7-(3-hydroxynaphthalen-1-yl)-
4-((S)-1-((S)-1-methylpyrrolidin-2-yl)ethoxy)-2-
(pyridin-3-yl)-1H-pyrrolo[3,2-c]quinolin-8-yl)
propanenitrile

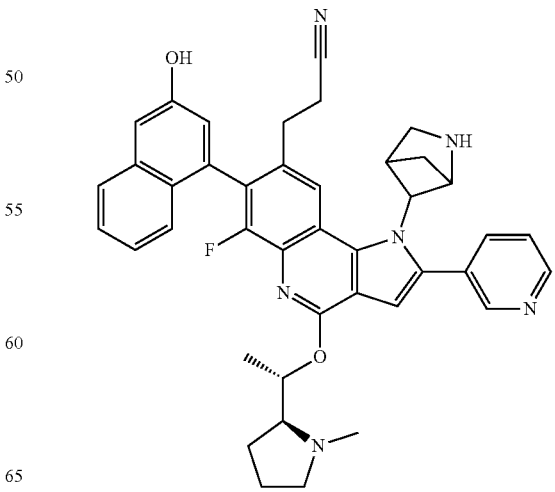

Step 1: tert-Butyl (endo)-5-((7-bromo-2-chloro-8-fluoro-6-iodo-3-nitroquinolin-4-yl)amino)-2-azabicyclo[2.1.1]hexane-2-carboxylate

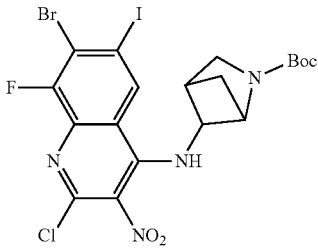 [SMILES: CC(C)(C)OC(=O)N1CC2CC1C2Nc1c([N+](=O)[O-])c(Cl)nc2c(F)c(Br)c(I)cc12]

To a solution of 7-bromo-2,4-dichloro-8-fluoro-6-iodo-3-nitroquinoline (15 g, 32.5 mmol, Intermediate 1) and tert-butyl (endo)-5-amino-2-azabicyclo[2.1.1]hexane-2-carboxylate (6.76 g, 34.1 mmol) in MeCN (325 ml) was added Hunig's base (6.80 ml, 39.0 mmol) and the reaction mixture was heated to 60° C. for 1 h. Ice chips and water (100 mL) were added and the suspension was stirred for 15 min. The solids were filtered, rinsed with water, and air dried under vacuum overnight to afford the desired product. LC-MS calculated for $C_{19}H_{19}BrClFIN_4O_4$ (M+H)$^+$: m/z=626.9; found 626.9.

Step 2: tert-Butyl (endo)-5-((7-bromo-8-fluoro-6-iodo-2-((S)-1-((S)-1-methylpyrrolidin-2-yl)ethoxy)-3-nitroquinolin-4-yl)amino)-2-azabicyclo[2.1.1]hexane-2-carboxylate

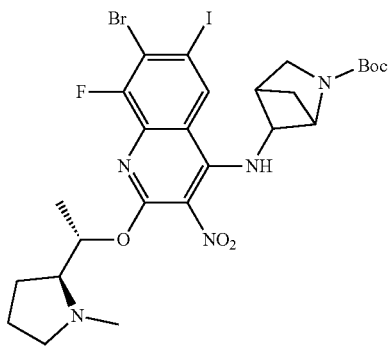 [SMILES: C[C@H](Oc1nc2c(F)c(Br)c(I)cc2c(NC2C3CC2N(C(=O)OC(C)(C)C)C3)c1[N+](=O)[O-])[C@@H]1CCCN1C]

This compound was prepared according to the procedure described in Example 2, Step 1, utilizing tert-butyl (endo)-5-((7-bromo-2-chloro-8-fluoro-6-iodo-3-nitroquinolin-4-yl)amino)-2-azabicyclo[2.1.1]hexane-2-carboxylate instead of tert-butyl (1R,4R,5S)-5-(7-bromo-8-(2-cyanoethyl)-6-fluoro-2-methyl-4-(methylsulfonyl)-1H-pyrrolo[3,2-c]quinolin-1-yl)-2-azabicyclo[2.1.1]hexane-2-carboxylate.
LC-MS calculated for $C_{26}H_{33}BrFIN_5O_5$ (M+H)$^+$: m/z=720.1; found 720.0.

Step 3: tert-Butyl (endo)-5-((7-bromo-8-fluoro-6-iodo-2-((S)-1-((S)-1-methylpyrrolidin-2-yl)ethoxy)-3-nitroquinolin-4-yl)(tert-butoxycarbonyl)amino)-2-azabicyclo[2.1.1]hexane-2-carboxylate

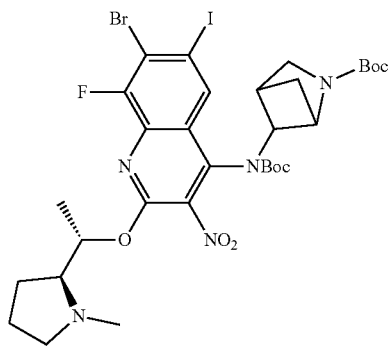 [SMILES: C[C@H](Oc1nc2c(F)c(Br)c(I)cc2c(N(C(=O)OC(C)(C)C)C2C3CC2N(C(=O)OC(C)(C)C)C3)c1[N+](=O)[O-])[C@@H]1CCCN1C]

This compound was prepared according to the procedure described in Intermediate 2, Step 2 utilizing tert-butyl (endo)-5-((7-bromo-8-fluoro-6-iodo-2-((S)-1-((S)-1-methylpyrrolidin-2-yl)ethoxy)-3-nitroquinolin-4-yl)amino)-2-azabicyclo[2.1.1]hexane-2-carboxylate instead of tert-butyl (1R,4R,5S)-5-((7-bromo-8-fluoro-6-iodo-2-(methylthio)-3-nitroquinolin-4-yl)amino)-2-azabicyclo[2.1.1]hexane-2-carboxylate. LC-MS calculated for $C_{31}H_{41}BrFIN_5O_7$ (M+H)$^+$: m/z=820.1; found 820.1.

Step 4: tert-Butyl (endo)-5-((3-amino-7-bromo-8-fluoro-6-iodo-2-((S)-1-((S)-1-methylpyrrolidin-2-yl)ethoxy)quinolin-4-yl)(tert-butoxycarbonyl)amino)-2-azabicyclo[2.1.1]hexane-2-carboxylate

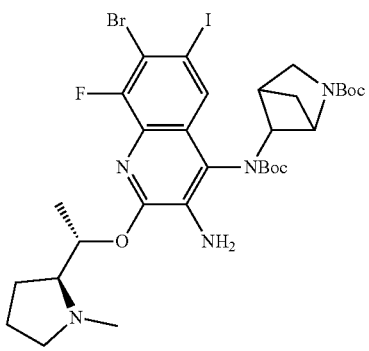 [SMILES: C[C@H](Oc1nc2c(F)c(Br)c(I)cc2c(N(C(=O)OC(C)(C)C)C2C3CC2N(C(=O)OC(C)(C)C)C3)c1N)[C@@H]1CCCN1C]

This compound was prepared according to the procedure described in Intermediate 2, Step 3 utilizing tert-butyl (endo)-5-((7-bromo-8-fluoro-6-iodo-2-((S)-1-((S)-1-methylpyrrolidin-2-yl)ethoxy)-3-nitroquinolin-4-yl)(tert-butoxycarbonyl)amino)-2-azabicyclo[2.1.1]hexane-2-carboxylate instead of tert-butyl (1R,4R,5S)-5-((7-bromo-8-fluoro-6-iodo-2-(methylthio)-3-nitroquinolin-4-yl)(tert-butoxycarbonyl)amino)-2-azabicyclo[2.1.1]hexane-2-carboxylate.
LC-MS calculated for $C_{31}H_{43}BrFIN_5O_5$ (M+H)$^+$: m/z=790.2; found 790.0.

Step 5: tert-Butyl (endo)-5-((3-amino-7-bromo-6-(2-cyanoethyl)-8-fluoro-2-((S)-1-((S)-1-methylpyrrolidin-2-yl)ethoxy)quinolin-4-yl)(tert-butoxycarbonyl)amino)-2-azabicyclo[2.1.1]hexane-2-carboxylate

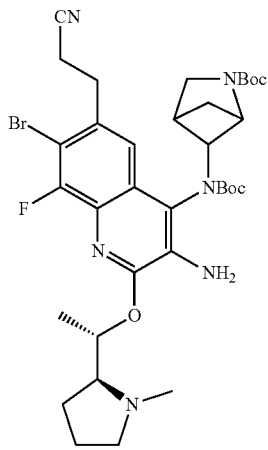 [SMILES: C[C@H](Oc1nc2c(F)c(Br)c(CCC#N)cc2c(N(C(=O)OC(C)(C)C)C2C3CC2N(C(=O)OC(C)(C)C)C3)c1N)[C@@H]1CCCN1C]

This compound was prepared according to the procedure described in Intermediate 2, Step 4 utilizing tert-butyl (endo)-5-((3-amino-7-bromo-8-fluoro-6-iodo-2-((S)-1-((S)-1-methylpyrrolidin-2-yl)ethoxy)quinolin-4-yl)(tert-butoxycarbonyl)amino)-2-azabicyclo[2.1.1]hexane-2-carboxylate instead of tert-Butyl (1R,4R,5S)-5-((3-amino-7-bromo-8-fluoro-6-iodo-2-(methylthio)quinolin-4-yl)(tert-butoxycarbonyl)amino)-2-azabicyclo[2.1.1]hexane-2-carboxylate. LC-MS calculated for $C_{34}H_{47}BrFN_6O_5$ $(M+H)^+$: m/z=717.3; found 717.2.

Step 6: tert-Butyl (endo)-5-((7-bromo-6-(2-cyanoethyl)-8-fluoro-2-((S)-1-((S)-1-methylpyrrolidin-2-yl)ethoxy)quinolin-4-yl)(tert-butoxycarbonyl)amino)-2-azabicyclo[2.1.1]hexane-2-carboxylate

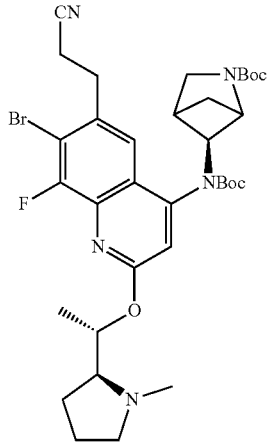

To a mixture tert-butyl (endo)-5-((3-amino-7-bromo-6-(2-cyanoethyl)-8-fluoro-2-((S)-1-((S)-1-methylpyrrolidin-2-yl)ethoxy)quinolin-4-yl)(tert-butoxycarbonyl)amino)-2-azabicyclo[2.1.1]hexane-2-carboxylate (1.82 g, 2.54 mmol) in acetic acid (19 ml) and water (7 mL) at 0° C. was added t-BuONO (1.5 mL, 12.7 mmol) dropwise over 5 minutes to control bubbling. After the addition, the reaction was stirred at room temperature for 1 h. The reaction mixture was partitioned between water (100 mL) and EtOAc (100 mL) and the layers separated. The organic layer was washed with saturated NaCl, dried over MgSO₄ and concentrated. The product was used without purification. LC-MS calculated for $C_{34}H_{46}BrFN_5O_5^+$ $(M+H)^+$: m/z=702.3; found 702.3.

Step 7: tert-Butyl (endo)-5-((7-bromo-6-(2-cyanoethyl)-8-fluoro-2-((S)-1-((S)-1-methylpyrrolidin-2-yl)ethoxy)quinolin-4-yl)amino)-2-azabicyclo[2.1.1]hexane-2-carboxylate

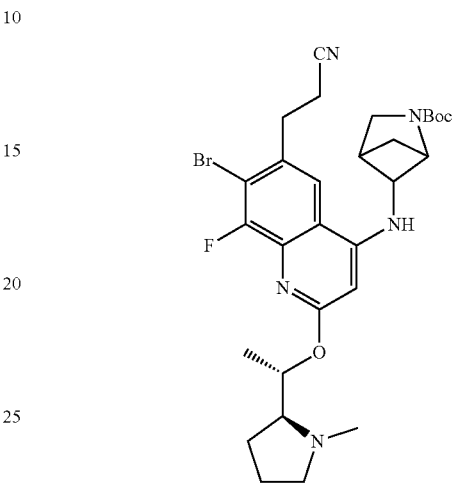

This compound was prepared according to the procedure described in Intermediate 5, utilizing tert-butyl (endo)-5-((7-bromo-6-(2-cyanoethyl)-8-fluoro-2-((S)-1-((S)-1-methylpyrrolidin-2-yl)ethoxy)quinolin-4-yl)(tert-butoxycarbonyl)amino)-2-azabicyclo[2.1.1]hexane-2-carboxylate instead of tert-butyl (1R,4R,5S)-5-((7-bromo-6-(2-cyanoethyl)-8-fluoro-3-iodo-2-(methylthio)quinolin-4-yl)(tert-butoxycarbonyl)amino)-2-azabicyclo[2.1.1]hexane-2-carboxylate. LC-MS calculated for $C_{29}H_{38}BrFN_5O_3^+$ $(M+H)^+$: m/z=602.2; found 602.3.

Step 8: tert-Butyl (endo)-5-((6-(2-cyanoethyl)-8-fluoro-7-(3-(methoxymethoxy)naphthalen-1-yl)-2-((S)-1-((S)-1-methylpyrrolidin-2-yl)ethoxy)quinolin-4-yl)amino)-2-azabicyclo[2.1.1]hexane-2-carboxylate

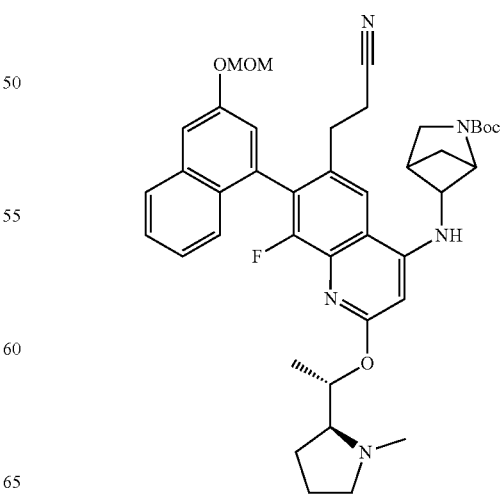

A mixture of tert-butyl (endo)-5-((7-bromo-6-(2-cyanoethyl)-8-fluoro-2-((S)-1-((S)-1-methylpyrrolidin-2-yl)ethoxy)quinolin-4-yl)amino)-2-azabicyclo[2.1.1]hexane-2-carboxylate (770 mg, 1.28 mmol), 2-(3-(methoxymethoxy)naphthalen-1-yl)-4,4,5,5-tetramethyl-1,3,2-dioxaborolane (422 mg, 1.34 mmol) (Intermediate 13), tetrakis(triphenylphosphine)palladium(0) (148 mg, 0.13 mmol), and sodium carbonate (406 mg, 3.83 mmol) in 1,4-dioxane (7 ml) and water (1.7 ml) was sparged with $N_2$ and heated to 80° C. for 15 h. After cooling to room temperature, the reaction mixture was diluted with EtOAc and water. The organic layer was washed with brine, concentrated under reduced pressure and purified by flash column chromatography (0-100% EtOAc/Hexanes) to afford the title compound (397 mg, 44% yield). LC-MS calculated for $C_{41}H_{49}FN_5O_5$ (M+H)$^+$: m/z=710.4; found 710.4.

Step 9: tert-Butyl (endo)-5-((6-(2-cyanoethyl)-8-fluoro-3-iodo-7-(3-(methoxymethoxy)naphthalen-1-yl)-2-((S)-1-((S)-1-methylpyrrolidin-2-yl)ethoxy)quinolin-4-yl)amino)-2-azabicyclo[2.1.1]hexane-2-carboxylate

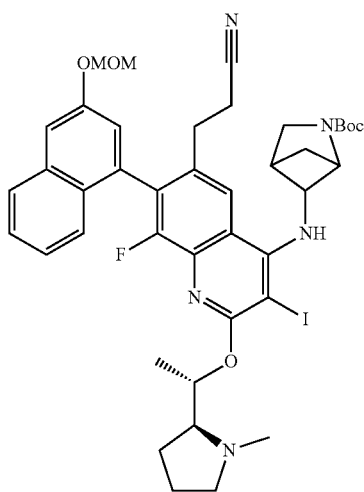

To a solution of tert-butyl (endo)-5-((6-(2-cyanoethyl)-8-fluoro-7-(3-(methoxymethoxy)naphthalen-1-yl)-2-((S)-1-((S)-1-methylpyrrolidin-2-yl)ethoxy)quinolin-4-yl)amino)-2-azabicyclo[2.1.1]hexane-2-carboxylate (397 mg, 0.559 mmol) in DCM (7.99 ml) was added silver trifluoroacetate (185 mg, 0.839 mmol), and the mixture was cooled to 0° C. Iodine monochloride (559 μl, 0.559 mmol) was added and the reaction mixture was stirred for 30 min at 0° C. The reaction was quenched with saturated sodium thiosulfate and extracted with EtOAc. The layers were separated and the organic layer was washed with brine, dried over magnesium sulfate, filtered, and concentrated. The crude residue was purified by flash chromatography (0-5% MeOH/DCM) to afford the title compound (233.5 mg, 0.279 mmol, 50.0% yield). LC-MS calculated for $C_{41}H_{48}FIN_5O_5$ (M+H)$^+$: m/z=836.3; found 836.2.

Step 10: tert-Butyl (endo)-5-((6-(2-cyanoethyl)-8-fluoro-7-(3-(methoxymethoxy)naphthalen-1-yl)-2-((S)-1-((S)-1-methylpyrrolidin-2-yl)ethoxy)-3-(pyridin-3-ylethynyl)quinolin-4-yl)amino)-2-azabicyclo[2.1.1]hexane-2-carboxylate

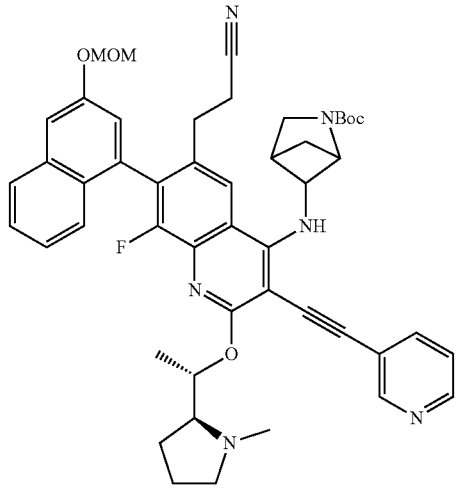

This compound was prepared according to the procedure described in Example 13, Step 1 utilizing tert-butyl (endo)-5-((6-(2-cyanoethyl)-8-fluoro-3-iodo-7-(3-(methoxymethoxy)naphthalen-1-yl)-2-((S)-1-((S)-1-methylpyrrolidin-2-yl)ethoxy)quinolin-4-yl)amino)-2-azabicyclo[2.1.1]hexane-2-carboxylate and 3-ethynylpyridine instead of tert-butyl (1R,4R,5S)-5-((7-bromo-6-(2-cyanoethyl)-8-fluoro-3-iodo-2-(methylthio)quinolin-4-yl)(tert-butoxycarbonyl)amino)-2-azabicyclo[2.1.1]hexane-2-carboxylate and N,N-dimethylpent-4-ynamide, respectively. LC-MS calculated for $C_{48}H_{52}FN_6O_5$ (M+H)$^+$: m/z=811.4; found 811.3.

Step 11: 3-(1-((endo)-2-Azabicyclo[2.1.1]hexan-5-yl)-6-fluoro-7-(3-hydroxynaphthalen-1-yl)-4-((S)-1-((S)-1-methylpyrrolidin-2-yl)ethoxy)-2-(pyridin-3-yl)-1H-pyrrolo[3,2-c]quinolin-8-yl)propanenitrile To a reaction vial tert-butyl (endo)-5-((6-(2-cyanoethyl)-8-fluoro-7-(3-(methoxymethoxy)naphthalen-1-yl)-2-((S)-1-((S)-1-methylpyrrolidin-2-yl)ethoxy)-3-(pyridin-3-ylethynyl)quinolin-4-yl)amino)-2-azabicyclo[2.1.1]hexane-2-carboxylate (255 mg, 0.314 mmol) was added 1,3-bis(2,6-diisopropylphenyl-imidazol-2-ylidene)gold(I) chloride (39.1 mg, 0.063 mmol) and silver hexafluoroantimonate (324 mg, 0.943 mmol). The vial was evacuated and back-filled with nitrogen, and THF (6.29 ml) was added. The reaction mixture was heated to 70° C. for 8 h, then passed through a thiol plug, and concentrated. The crude residue was dissolved EtOH (2.5 mL) and 4 N HCl in dioxane (1.0 mL), and stirred for 1 h, which point the reaction was quenched aqueous sodium bicarbonate (5 mL) and partitioned between water (50 mL) and DCM (50 mL). The layers were separated and the organic layer dried over sodium sulfate, filtered, and concentrated. The crude material was purified by prep HPLC (pH 2). LC-MS calculated for $C_{41}H_{40}FN_6O_2$ (M+H)$^+$: m/z=667.3; found 667.3.

Example 20. 3-(2-(3-(azetidin-1-yl)-3-oxopropyl)-1-((1R,4R,5S)-2-azabicyclo[2.1.1]hexan-5-yl)-7-(7,8-difluoronaphthalen-1-yl)-6-fluoro-4-((S)-1-((S)-1-methylpyrrolidin-2-yl)ethoxy)-1H-pyrrolo[3,2-c]quinolin-8-yl)propanenitrile

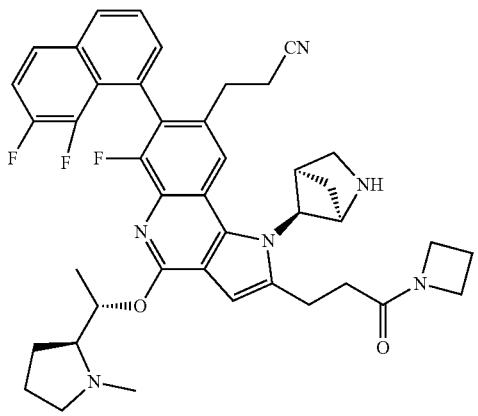 [SMILES: C[C@H](Oc1nc2c(F)c(-c3cccc4ccc(F)c(F)c34)c(CCC#N)cc2c2c1cc(CCC(=O)N1CCC1)n2[C@H]1[C@H]2CN[C@@H]1C2)[C@@H]1CCCN1C]

This compound was prepared starting from tert-butyl (1R,4R,5S)-5-(2-(3-(azetidin-1-yl)-3-oxopropyl)-7-bromo-8-(2-cyanoethyl)-6-fluoro-4-((S)-1-((S)-1-methylpyrrolidin-2-yl)ethoxy)-1H-pyrrolo[3,2-c]quinolin-1-yl)-2-azabicyclo[2.1.1]hexane-2-carboxylate (Example 4, Step 4) via the following protocol: In a 1 dram vial tert-butyl (1R,4R,5S)-5-(2-(3-(azetidin-1-yl)-3-oxopropyl)-7-bromo-8-(2-cyanoethyl)-6-fluoro-4-((S)-1-((S)-1-methylpyrrolidin-2-yl)ethoxy)-1H-pyrrolo[3,2-c]quinolin-1-yl)-2-azabicyclo[2.1.1]hexane-2-carboxylate (20 mg, 0.027 mmol), 2-(7,8-difluoronaphthalen-1-yl)-4,4,5,5-tetramethyl-1,3,2-dioxaborolane (15.73 mg, 0.054 mmol), and XPhos Pd-G4 (4.67 mg, 5.42 µmol) were dissolved in 1 mL of 4:1 dioxane/0.5M aq. $K_3PO_4$ open to air. The vial headspace was purged with nitrogen and the mixture stirred at 80° C. for 1 h. At this time, the mixture was diluted with MeOH and purified by prep-LCMS (XBridge C18 column, eluting with a gradient of acetonitrile/water containing 0.1% TFA, at flow rate of 60 mL/min), yielding two peaks that were combined and lyophilized. The lyophilized powder was treated with TFA (0.4 mL) for 30 min and then diluted with MeOH (4.5 mL) and again purified by prep-LCMS to afford the desired product as two peaks.

Diastereomer 1. Peak 1. LC-MS calculated for $C_{42}H_{44}F_3N_6O_2$ (M+H)$^+$: m/z=721.3; found 721.3.

Diastereomer 2. Peak 2. LC-MS calculated for $C_{42}H_{44}F_3N_6O_2$ (M+H)$^+$: m/z=721.3; found 721.3.

Example 21. 3-(2-(3-(azetidin-1-yl)-3-oxopropyl)-1-((1R,4R,5S)-2-azabicyclo[2.1.1]hexan-5-yl)-7-(6,7-difluoronaphthalen-1-yl)-6-fluoro-4-((S)-1-((S)-1-methylpyrrolidin-2-yl)ethoxy)-1H-pyrrolo[3,2-c]quinolin-8-yl)propanenitrile

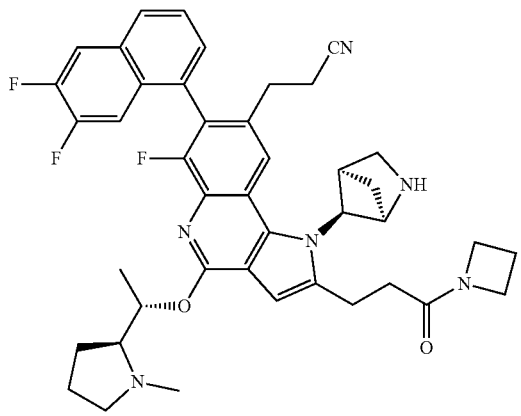 [SMILES: C[C@H](Oc1nc2c(F)c(-c3cccc4cc(F)c(F)cc34)c(CCC#N)cc2c2c1cc(CCC(=O)N1CCC1)n2[C@H]1[C@H]2CN[C@@H]1C2)[C@@H]1CCCN1C]

This compound was prepared starting using protocols outlined in Example 20, replacing 2-(7,8-difluoronaphthalen-1-yl)-4,4,5,5-tetramethyl-1,3,2-dioxaborolane with 2-(6,7-difluoronaphthalen-1-yl)-4,4,5,5-tetramethyl-1,3,2-dioxaborolane.

Diastereomer 1. Peak 1. LC-MS calculated for $C_{42}H_{44}F_3N_6O_2$ (M+H)$^+$: m/z=721.3; found 721.3.

Diastereomer 2. Peak 2. LC-MS calculated for $C_{42}H_{44}F_3N_6O_2$ (M+H)$^+$: m/z=721.3; found 721.3.

Example 22. 3-(1-((1R,4R,5S)-2-azabicyclo[2.1.1]hexan-5-yl)-6-fluoro-7-(7-fluoro-3-hydroxynaphthalen-1-yl)-2-methyl-4-((S)-1-((S)-1-methylpyrrolidin-2-yl)ethoxy)-1H-pyrrolo[3,2-c]quinolin-8-yl)propanenitrile

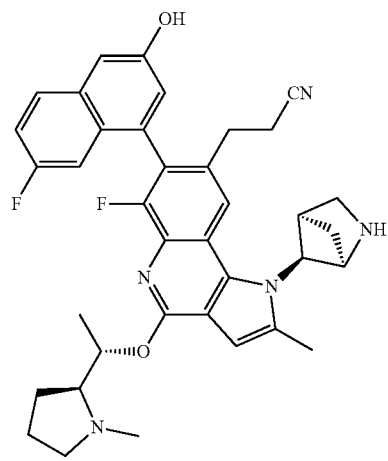 [SMILES: Cc1cc2c(O[C@@H](C)[C@@H]3CCCN3C)nc3c(F)c(-c4cc(O)cc5ccc(F)cc45)c(CCC#N)cc3c2n1[C@H]1[C@H]2CN[C@@H]1C2]

201

Step 1. 6-fluoronaphthalen-1-amine

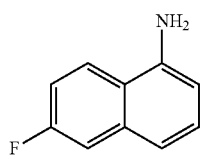

Part A: In a 40 mL vial 6-fluoro-1-naphthoic acid (0.500 g, 2.63 mmol, 1.0 equiv.) was dissolved in toluene (10 ml) open to air. Molecular sieves (3 Å, 3 g) were added followed by tert-butanol (2.5 mL), DIPEA (2.3 mL, 13.15 mmol, 5.0 equiv.), and diphenylphosphoryl azide (DPPA, 0.85 mL, 3.94 mmol, 1.5 equiv.). The headspace was purged with nitrogen and the mixture was sealed and heated to 110° C. overnight. The mixture was filtered through Celite® and volatiles were removed in vacuo. The residue was purified by automated FCC (0-30% EtOAc/heptane) to yield tert-butyl (6-fluoronaphthalen-1-yl)carbamate as a white solid (575 mg, 2.20 mmol, 84%).

Part B: tert-butyl (6-fluoronaphthalen-1-yl)carbamate (575 mg, 2.20 mmol, prepared in Part A) was dissolved in neat TFA (20 mL) and stirred at RT for 30 min. Volatiles were removed in vacuo and the residue was treated with saturated $NaHCO_3$ solution (30 mL) and extracted into DCM (3×15 mL). Organic extracts were combined, washed with brine (10 mL), dried over $MgSO_4$, and dried in vacuo to yield 6-fluoronaphthalen-1-amine as a white solid that was used in the subsequent step without further purification (339 mg, 2.10 mmol, 95%).

Step 2. 2,4-dibromo-6-fluoronaphthalen-1-amine

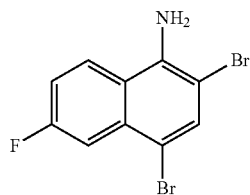 [SMILES: Nc1c(Br)cc(Br)c2cc(F)ccc12]

To a solution of 6-fluoronaphthalen-1-amine (3.28 g, 20.35 mmol) in acetic acid (100 mL) open to air was added bromine (2.29 ml, 44.4 mmol) at RT, and the reaction was stirred at 85° C. for 1.5 h. After cooling to RT, the reaction mixture (slurry) was filtered over a fritted funnel, the filter cake washed copiously with 1 N NaOH and then water, and dried on the filter to give the title compound as an off-white solid (6.32 g, 19.81 mmol, 97%). LCMS calculated for $C_{10}H_7Br_2FN$ $(M+H)^+$: m/z=317.9, 319.9, 321.9 (1:2:1); found: 317.8, 319.9, 321.9.

202

Step 3. 5-bromo-7-fluoronaphtho[1,2-d][1,2,3]oxa-diazole

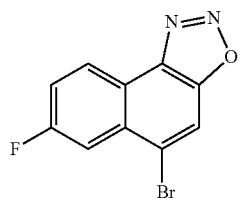 [SMILES: Fc1ccc2c(c1)c(Br)cc1onnc12]

In a 250 mL round-bottomed flask, 2,4-dibromo-6-fluoronaphthalen-1-amine (6.32 g, 19.81 mmol) was dissolved in an acetic acid (75 ml)/propionic acid (15 mL) mixture and stirred open to air at 0° C. Sodium nitrite (1.709 g, 11 24.77 mmol) was added to the reaction mixture portionwise over 2 min. The mixture was allowed to warm to RT and stirred for 1 hour. At this time, the mixture was poured into ice water (350 mL) with stirring and the precipitate was collected by filtration and washed with cold water. The material was dried on the filter, yielding 5.15 g of the oxadiazole as a light orange powder (19.28 mmol, 97%). LCMS calculated for $C_{10}H5BrFN_2O$ $(M+H)^+$: m/z=267.0, 269.0; found: 266.9, 268.9.

Step 4. 4-bromo-6-fluoronaphthalen-2-ol

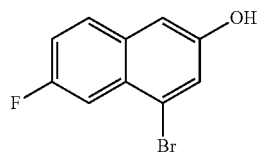 [SMILES: Oc1cc(Br)c2cc(F)ccc2c1]

In a 250 mL round-bottomed flask, 5-bromo-7-fluoronaphtho[1,2-d][1,2,3]oxadiazole (5.15 g, 19.28 mmol) was dissolved in ethanol (100 ml) open to air. Sodium borohydride (1.459 g, 38.6 mmol) was added to the reaction mixture portionwise over 10 min at 0° C. Following complete addition, the reaction allowed to warm to RT and stirred for an additional 3 h. Water (100 mL) was then added and the reaction mixture was extracted with DCM (3×100 mL). Organic layers were combined and the product was extracted into 1 N NaOH (100 mL). The NaOH solution was added dropwise to a rapidly stirring solution of 1 N HCl (200 mL, pre-chilled on ice) to precipitate the desired product. Solids were filtered and dried under vacuum to yield the title compound as an off-white solid (3.68 g, 15.27 mmol, 79%). $^1$H NMR (500 MHz, DMSO-$d_6$) δ 10.17 (s, 1H), 7.87 (dd, J=9.1, 5.7 Hz, 1H), 7.64 (dd, J=10.9, 2.6 Hz, 1H), 7.53 (d, J=2.2 Hz, 1H), 7.41 (td, J=8.7, 2.6 Hz, 1H), 7.27 (d, J=2.3 Hz, 1H). $^{19}$F NMR (471 MHz, DMSO-$d_6$) δ −116.42.

Step 5. 6-fluoro-4-(4,4,5,5-tetramethyl-1,3,2-dioxaborolan-2-yl)naphthalen-2-ol

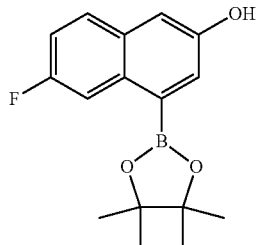

In a 40 mL vial, 4-bromo-6-fluoronaphthalen-2-ol (300 mg, 1.245 mmol), bis(pinacolato)diboron (411 mg, 1.618 mmol), Pd(dppf)Cl$_2$·CH$_2$Cl$_2$ (102 mg, 0.124 mmol), and potassium acetate (244 mg, 2.489 mmol) were dissolved in dioxane (5 ml). The mixture was capped under nitrogen and stirred at 80° C. for 4 h. The reaction mixture was diluted with EtOAc, filtered, and concentrated. Crude material was dissolved in DCM and purified by FCC (0-50% EtOAc/hexanes) to yield the title compound as a white solid. LCMS calculated for C$_{16}$H$_{19}$BFO$_3$ (M+H)$^+$: m/z=289.1; found 289.0.

Step 6. 3-(1-((1R,4R,5S)-2-azabicyclo[2.1.1]hexan-5-yl)-6-fluoro-7-(7-fluoro-3-hydroxynaphthalen-1-yl)-2-methyl-4-((S)-1-((S)-1-methylpyrrolidin-2-yl)ethoxy)-1H-pyrrolo[3,2-c]quinolin-8-yl)propanenitrile This compound was prepared starting using protocols outlined in Example 20, replacing 2-(7,8-difluoronaphthalen-1-yl)-4,4,5,5-tetramethyl-1,3,2-dioxaborolane with 6-fluoro-4-(4,4,5,5-tetramethyl-1,3,2-dioxaborolan-2-yl)naphthalen-2-ol and tert-butyl (1R,4R,5S)-5-(2-(3-(azetidin-1-yl)-3-oxopropyl)-7-bromo-8-(2-cyanoethyl)-6-fluoro-4-((S)-1-((S)-1-methylpyrrolidin-2-yl)ethoxy)-1H-pyrrolo[3,2-c]quinolin-1-yl)-2-azabicyclo[2.1.1]hexane-2-carboxylate with tert-Butyl (1R,4R,5S)-5-(7-bromo-8-(2-cyanoethyl)-6-fluoro-2-methyl-4-((S)-1-((S)-1-methylpyrrolidin-2-yl)ethoxy)-1H-pyrrolo[3,2-c]quinolin-1-yl)-2-azabicyclo[2.1.1]hexane-2-carboxylate (Example 2, Step 1).

Diastereomer 1. Peak 1. LC-MS calculated for C$_{37}$H$_{38}$F$_2$N$_5$O$_2$ (M+H)$^+$: m/z=622.3; found 622.2.
Diastereomer 2. Peak 2. LC-MS calculated for C$_{37}$H$_{38}$F$_2$N$_5$O$_2$ (M+H)$^+$: m/z=622.3; found 622.2. 1H NMR (500 MHz, DMSO-d$_6$) δ 10.11 (s, 1H), 9.8 (s, 1H), 9.5 (s, 1H), 8.09 (s, 1H), 7.94 (dd, J=9.2, 5.8 Hz, 1H), 7.43-7.34 (m, 2H), 7.17 (d, J=2.4 Hz, 1H), 6.90 (s, 1H), 6.66 (s, 1H), 5.58 (dt, J=12.5, 6.3 Hz, 1H), 5.41-5.37 (m, 1H), 5.09-5.04 (m, 1H), 3.89-3.80 (m, 2H), 3.57-3.42 (m, 3H), 3.24 (m, 1H) 3.04 (s, 3H), 2.97 (s, 2H), 2.74-2.63 (m, 2H), 2.55 (s, 3H), 2.29 (d, J=8.6 Hz, 2H), 1.90 (q, J=12.8, 7.3 Hz, 3H), 1.61 (d, J=9.1 Hz, 1H), 1.49 (d, J=6.1 Hz, 3H). $^{19}$F NMR (471 MHz, DMSO-d$_6$) δ −117.63, −123.48.

Example 23a and Example 23b. 1-(1-((2S,4S)-1-Acetyl-2-(cyanomethyl)piperidin-4-yl)-8-chloro-6-fluoro-4-((S)-1-((S)-1-methylpyrrolidin-2-yl)ethoxy)-1H-pyrazolo[4,3-c]quinolin-7-yl)isoquinoline-8-carbonitrile

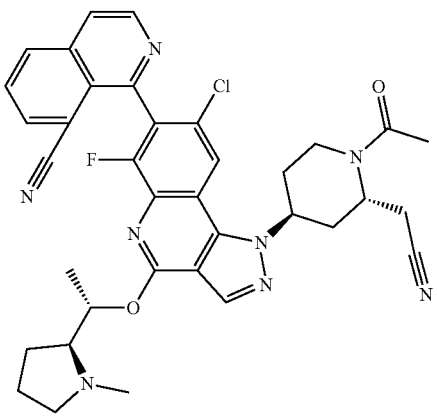 [SMILES: CC(=O)N1CC[C@H](n2ncc3c(O[C@@H](C)[C@@H]4CCCN4C)nc4c(F)c(-c5nccc6cccc(C#N)c56)c(Cl)cc4c32)C[C@H]1CC#N]

Step 1. ethyl 2-amino-4-bromo-3-fluorobenzoate

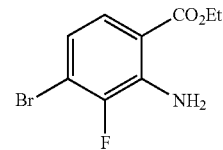 [SMILES: CCOC(=O)c1ccc(Br)c(F)c1N]

To a solution of 2-amino-4-bromo-3-fluorobenzoic acid (22.7 g, 92 mmol) in ethanol (184 ml) was added sulfuric acid (9.82 ml, 184 mmol) slowly. The resulting mixture was heated to reflux for 2 days. After cooling to room temperature, the reaction mixture was diluted with water and adjusted to pH 7 with 6 M NaOH (22 mL). The organic solvent was removed in vacuo. The resulting mixture was diluted with ethyl acetate and water. The organic layer was washed with 0.5 N NaOH solution, brine, dried over Na$_2$SO$_4$, filtered and concentrated under vacuum to give the desired product (23.2 g, 96%). LCMS calculated for C$_9$H$_{10}$BrFNO$_2$ (M+H)$^+$ m/z=262.0, 264.0; found 262.0, 264.0.

Step 2. ethyl 2-amino-3-fluoro-4-(4,4,5,5-tetramethyl-1,3,2-dioxaborolan-2-yl)benzoate

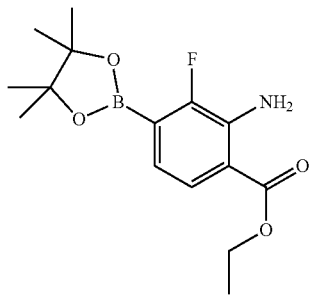 [SMILES: CCOC(=O)c1ccc(B2OC(C)(C)C(C)(C)O2)c(F)c1N]

A mixture of ethyl 2-amino-4-bromo-3-fluorobenzoate (21.8 g, 83 mmol), bis(pinacolato)diboron (25.3 g, 100 mmol), dichloro[1,1'-bis(diphenylphosphino)ferrocene]palladium (II) dichloromethane adduct (6.79 g, 8.32 mmol) and potassium acetate (17.96 g, 183 mmol) in dioxane (416 ml) was stirred at 100° C. under nitrogen atmosphere for 5 h. The crude mixture was filtered through Celite® and washed with ethyl acetate. The filtrate was concentrated. The residue was purified by flash chromatography to give the desired product (24 g, 93%). LCMS calculated for $C_{15}H_{22}BFNO_4$ $(M+H)^+$ m/z=310.2; found 310.1.

Step 3. 8-cyanoisoquinoline 2-oxide

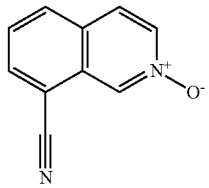 [SMILES: N#Cc1cccc2cc[n+]([O-])cc12]

To a solution of isoquinoline-8-carbonitrile (3.70 g, 24.00 mmol) in $CH_2Cl_2$ (240 ml) was added m-CPBA (7.10 g, 28.8 mmol) at 0° C. The reaction mixture was stirred at 0° C. for 2 h. The reaction mixture was diluted with saturated $NaHCO_3$ solution. The aqueous layer was extracted with DCM (3×). The combined organic layers were dried over $Na_2SO_4$, filtered and concentrated. The crude was purified by flash chromatography (eluting with a gradient 0-100% ethyl acetate in hexanes) to give the desired product (3.2 g, 78%). LC-MS calculated for $C_{10}HN_2O$ $(M)^+$: m/z=170.1; found 170.1.

Step 4. 1-chloroisoquinoline-8-carbonitrile

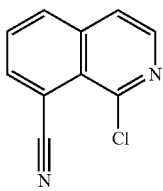 [SMILES: N#Cc1cccc2ccnc(Cl)c12]

To a solution of 8-cyanoisoquinoline 2-oxide (5.30 g, 31.1 mmol) and 2,6-lutidine (7.26 ml, 62.3 mmol) in $CH_2Cl_2$ (62.3 ml) was added $POCl_3$ (5.81 ml, 62.3 mmol). The reaction mixture was stirred at room temperature for 2 h. The reaction mixture was quenched with addition of saturated $NaHCO_3$ (80 mL). The organic layer was dried with $MgSO_4$ and concentrated to give a crude product. The crude product was triturated with ethyl acetate in hexanes to give the desired product as white solid (4.0 g, 68%). LC-MS calculated for $C_{10}H_6ClN_2$ $(M+H)^+$: m/z=189.0; found 189.0.

Step 5. ethyl 2-amino-4-(8-cyanoisoquinolin-1-yl)-3-fluorobenzoate

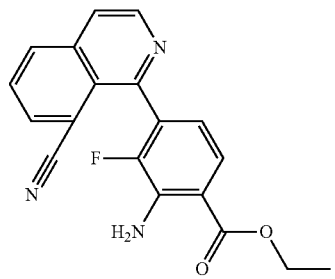 [SMILES: CCOC(=O)c1ccc(-c2nccc3cccc(C#N)c23)c(F)c1N]

A mixture of 1-chloroisoquinoline-8-carbonitrile (6.60 g, 35.0 mmol), ethyl 2-amino-3-fluoro-4-(4,4,5,5-tetramethyl-1,3,2-dioxaborolan-2-yl)benzoate (11.4 g, 36.7 mmol), SPhos Pd G4 (1.39 g, 1.75 mmol) and tripotassium phosphate hydrate (17.7 g, 77 mmol) in 1,4-dioxane (120 mL) and water (24 mL) was stirred at 80° C. for 2 h. The solution was diluted with ethyl acetate and water. The organic layer was concentrated. The crude was used in the next step without purification. LC-MS calculated for $C_{19}H_{15}FN_3O_2$ $(M+H)^+$: m/z=336.1; found 336.1.

Step 6. ethyl 2-amino-5-chloro-4-(8-cyanoisoquinolin-1-yl)-3-fluorobenzoate

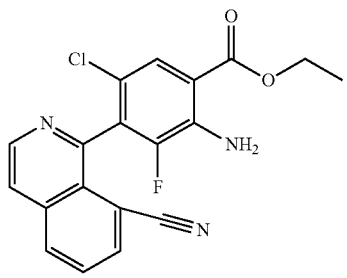 [SMILES: CCOC(=O)c1cc(Cl)c(-c2nccc3cccc(C#N)c23)c(F)c1N]

To a solution of ethyl 2-amino-4-(8-cyanoisoquinolin-1-yl)-3-fluorobenzoate (11.7 g, 34.9 mmol) in DMF (116 ml) was added NCS (5.12 g, 38.4 mmol) at room temperature. The mixture was heated at 80° C. for 15 h. The reaction mixture was cooled to room temperature and diluted with water. The precipitate was collected with filtration and washed with water and ethyl acetate/hexane (1:2). The filtrate was extracted with ethyl acetate. The organic layer was concentrated. The solid was collected with filtration and washed with ethyl acetate/hexane (1:2) to give the desired product (10.2 g, 79%). LC-MS calculated for $C_{19}H_{14}ClFN_3O_2$ $(M+H)^+$: m/z=370.1; found 370.1.

Step 7. ethyl 5-chloro-4-(8-cyanoisoquinolin-1-yl)-2-(3-ethoxy-3-oxopropanamido)-3-fluorobenzoate

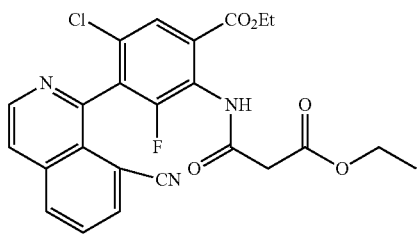 [SMILES: CCOC(=O)CC(=O)Nc1c(C(=O)OCC)cc(Cl)c(-c2nccc3cccc(C#N)c23)c1F]

To a solution of ethyl 2-amino-5-chloro-4-(8-cyanoisoquinolin-1-yl)-3-fluorobenzoate (10.3 g, 27.9 mmol) and TEA (5.05 ml, 36.2 mmol) in DCM (280 mL) was added ethyl 3-chloro-3-oxopropanoate (3.92 ml, 30.6 mmol) dropwise at 0° C. The resulting mixture was stirred at 0° C. and monitored by LC-MS. Another equivalent of ethyl 3-chloro-3-oxopropanoate (3.92 ml, 30.6 mmol) was added dropwise and stirred for 1 h. The reaction was diluted with water and DCM. The organic layer was separated and dried over $Na_2SO_4$, filtered and concentrated. The residue was purified with flash chromatography to give the desired product (9.5 g, 70%). LC-MS calculated for $C_{24}H_{20}ClFN_3O_5$ (M+H)$^+$: m/z=484.1; found 484.1.

Step 8. ethyl 6-chloro-7-(8-cyanoisoquinolin-1-yl)-8-fluoro-2,4-dihydroxyquinoline-3-carboxylate

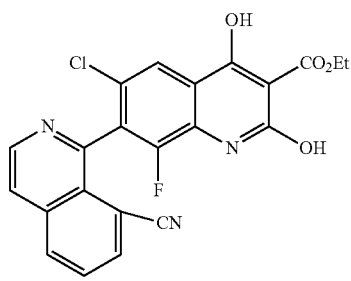 [SMILES: CCOC(=O)c1c(O)nc2c(F)c(-c3nccc4cccc(C#N)c34)c(Cl)cc2c1O]

A solution of sodium ethoxide (21%/EtOH, 19.9 ml, 53.3 mmol) was added dropwise to a solution of ethyl 5-chloro-4-(8-cyanoisoquinolin-1-yl)-2-(3-ethoxy-3-oxopropanamido)-3-fluorobenzoate (8.6 g, 17.8 mmol) in EtOH (80 ml). The resulting mixture was stirred at room temp for 2 h. To the reaction flask was added 1 N HCl to adjust pH to 3. The solvent was removed under vacuum. The resulting precipitate was collected and washed with ethyl acetate to give the desired product as white solid (7.4 g, 95%). LC-MS calculated for $C_{22}H_{14}ClFN_3O_4$ (M+H)$^+$: m/z=438.1; found 438.1.

Step 9. Ethyl 2,4,6-trichloro-7-(8-cyanoisoquinolin-1-yl)-8-fluoroquinoline-3-carboxylate

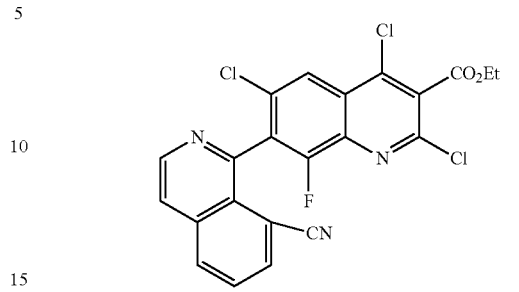

To reaction flask was added ethyl 6-chloro-7-(8-cyanoisoquinolin-1-yl)-8-fluoro-2,4-dihydroxyquinoline-3-carboxylate (7.4 g, 16.9 mmol) and $POCl_3$ (31.5 ml, 338 mmol), The resulting mixture was stirred at 110° C. for 2 h. $POCl_3$ was removed by azeotrope with toluene (3 times), and the residue was diluted with DCM and saturated $NaHCO_3$ solution. The organic layer was separated and dried over $Na_2SO_4$, filtered and concentrated. The crude was triturated with ethyl acetate/hexane (1:1) to give the desired product as white solid (7.24 g, 90%). LC-MS calculated for $C_{22}H_{12}Cl_3FN_3O_2$ (M+H)$^+$: m/z=474.0, 476.0; found 474.0, 476.0.

Step 10. ethyl 4-(((2S,4S)-1-(tert-butoxycarbonyl)-2-(2-((tert-butyldimethylsilyl)oxy)ethyl)piperidin-4-yl)amino)-2,6-dichloro-7-(8-cyanoisoquinolin-1-yl)-8-fluoroquinoline-3-carboxylate

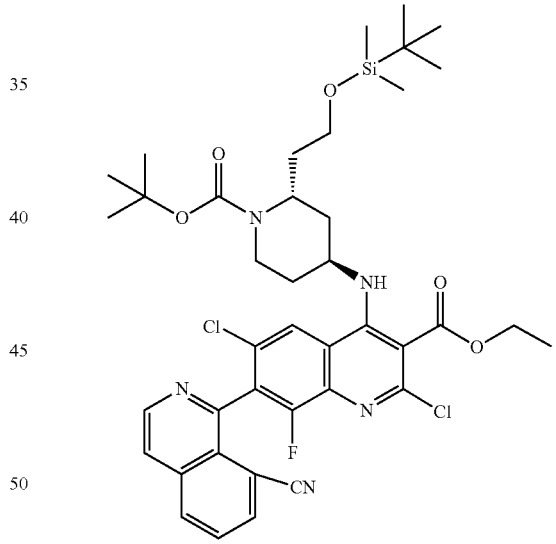

To a solution of ethyl 2,4,6-trichloro-7-(8-cyanoisoquinolin-1-yl)-8-fluoroquinoline-3-carboxylate (7.24 g, 15.25 mmol) in DMF (100 ml) was added tert-butyl (2S,4S)-4-amino-2-(2-((tert-butyldimethylsilyl)oxy)ethyl)piperidine-1-carboxylate (Intermediate 9, 6.56 g, 18.30 mmol) and DIEA (5.3 ml, 30.5 mmol). The resulting mixture was stirred at 65° C. overnight. The reaction mixture was diluted with ethyl acetate and water. The organic layer was washed with water and brine, dried over $Na_2SO_4$, filtered and concentrated. The crude was purified with silica gel column (eluted with a gradient 0-30% ethyl acetate in hexanes) to give the desired product as light yellow foam (11.5 g, 95%). LC-MS calculated for $C_{40}H_{49}Cl_2FN_5O_5Si$ (M+H)$^+$: m/z=796.3, 798.3; found 796.3, 798.3.

Step 11. tert-butyl (2S,4S)-2-(2-((tert-butyldimethylsilyl)oxy)ethyl)-4-((2,6-dichloro-7-(8-cyanoisoquinolin-1-yl)-8-fluoro-3-(hydroxymethyl)quinolin-4-yl)amino)piperidine-1-carboxylate

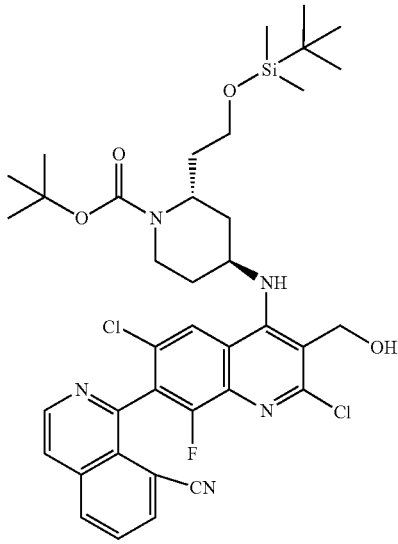 [SMILES: CC(C)(C)OC(=O)N1CC[C@H](Nc2c(CO)c(Cl)nc3c(F)c(-c4nccc5cccc(C#N)c45)c(Cl)cc23)C[C@H]1CCO[Si](C)(C)C(C)(C)C]

To a solution of ethyl 4-(((2S,4S)-1-(tert-butoxycarbonyl)-2-(2-((tert-butyldimethylsilyl)oxy)ethyl)piperidin-4-yl)amino)-2,6-dichloro-7-(8-cyanoisoquinolin-1-yl)-8-fluoroquinoline-3-carboxylate (2.45 g, 3.07 mmol) in toluene (30.7 ml) at −78° C. was added 1.0 M DIBAL-H in DCM (9.84 ml, 9.84 mmol). The resulting mixture was allowed to warm to −20° C. over 2 h period, quenched with methanol (1.3 mL). Aqueous Rochelle salt (prepared from 14.7 g (6 wt) of Rochelle salt and 50 mL of water was added to the solution at ≤10° C. The biphasic mixture was stirred vigorously for ≥1 h at 15-25° C. and separated to give organic layer. The organic layer was dried over $Na_2SO_4$, filtered and concentrated. The product was used without purification. LC-MS calculated for $C_{38}H_{47}Cl_2FN_5O_4Si$ $(M+H)^+$: m/z=754.3, 756.3; found 754.3, 756.3.

Step 12. tert-butyl (2S,4S)-2-(2-((tert-butyldimethylsilyl)oxy)ethyl)-4-((2,6-dichloro-7-(8-cyanoisoquinolin-1-yl)-8-fluoro-3-formylquinolin-4-yl)amino)piperidine-1-carboxylate

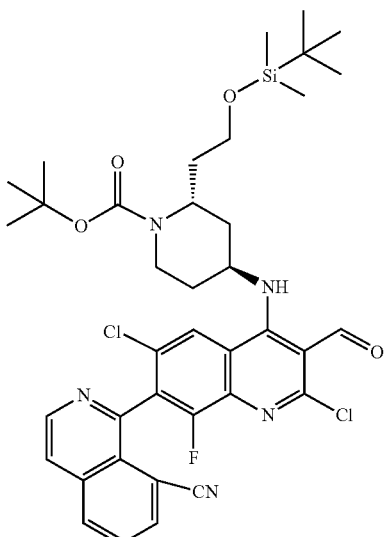

To a solution of tert-butyl (2S,4S)-2-(2-((tert-butyldimethylsilyl)oxy)ethyl)-4-((2,6-dichloro-7-(8-cyanoisoquinolin-1-yl)-8-fluoro-3-(hydroxymethyl)quinolin-4-yl)amino)piperidine-1-carboxylate (2.32 g, 3.07 mmol) in DCM (23 ml) and acetonitrile (7.7 ml) was added acetic acid (0.53 ml, 9.22 mmol) and IBX (2.58 g, 9.22 mmol). The resulting mixture was stirred at 38° C. for 22 h. The reaction mixture was filtered and washed with DCM. The filtrate was concentrated and purified by silica gel column (eluted with a gradient 0-20% ethyl acetate in hexs) to give the desired products as two peaks.

Diastereomer 1 (1.05 g, 45%). Peak 1. LC-MS calculated for $C_{38}H_{45}Cl_2FN_5O_4Si$ $(M+H)^+$: m/z=752.3, 754.3; found 752.3, 754.3.

Diastereomer 2 (1.05 g, 45%). Peak 2. LC-MS calculated for $C_{38}H_{45}Cl_2FN_5O_4Si$ $(M+H)^+$: m/z=752.3, 754.3; found 752.3, 754.3.

Step 13. tert-butyl (2S,4S)-2-(2-((tert-butyldimethylsilyl)oxy)ethyl)-4-((2,6-dichloro-7-(8-cyanoisoquinolin-1-yl)-8-fluoro-3-((E)-(hydroxyimino)methyl)quinolin-4-yl)amino)piperidine-1-carboxylate

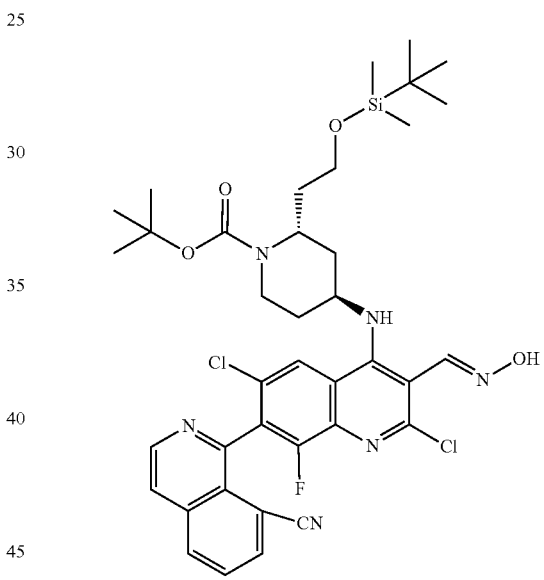

To a mixture of tert-butyl (2S,4S)-2-(2-((tert-butyldimethylsilyl)oxy)ethyl)-4-((2,6-dichloro-7-(8-cyanoisoquinolin-1-yl)-8-fluoro-3-formylquinolin-4-yl)amino)piperidine-1-carboxylate (0.85 g, 1.13 mmol) (diasteromer 1 from Step 12) in DCM (11 ml) and EtOH (11 ml) was added hydroxylamine hydrochloride (0.26 g, 3.73 mmol) and pyridine (0.30 ml, 3.73 mmol). The reaction mixture was stirred at 40° C. for 16 hours. The solvent was evaporated in vacuo. The residue was diluted with DCM and water and the layers were separated. The aqueous layer was extracted with DCM. The combined organic layers were washed with aqueous $CuSO_4$, brine, dried over $MgSO_4$, filtered and concentrated in vacuo. The residue was purified with column chromatography on silica gel to give the desired product (0.5 g, 57%). LC-MS calculated for $C_{38}H_{46}Cl_2FN_6O_4Si$ $(M+H)^+$: m/z=767.3, 769.3; found 767.3, 769.3.

Diastereomer 2 was prepared in similar way as Diastereomer 1 using peak 2 from last step. LC-MS calculated for $C_{38}H_{46}Cl_2FN_6O_4Si$ $(M+H)^+$: m/z=767.3, 769.3; found 767.3, 769.3.

Step 14. tert-butyl (2S,4S)-2-(2-((tert-butyldimethylsilyl)oxy)ethyl)-4-(4,8-dichloro-7-(8-cyanoisoquinolin-1-yl)-6-fluoro-1H-pyrazolo[4,3-c]quinolin-1-yl)piperidine-1-carboxylate

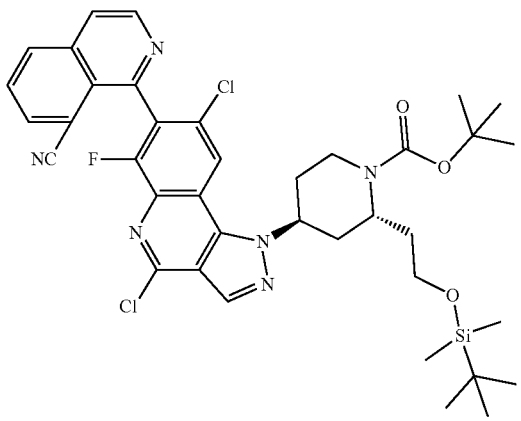 [SMILES: CC(C)(C)OC(=O)N1CC[C@H](n2ncc3c(Cl)nc4c(F)c(-c5nccc6cccc(C#N)c56)c(Cl)cc4c32)C[C@H]1CCO[Si](C)(C)C(C)(C)C]

To a solution of (tert-butyl (2S,4S)-2-(2-((tert-butyldimethylsilyl)oxy)ethyl)-4-((2,6-dichloro-7-(8-cyanoisoquinolin-1-yl)-8-fluoro-3-((E)-(hydroxyimino)methyl)quinolin-4-yl)amino)piperidine-1-carboxylate (486 mg, 0.633 mmol) (Diastereomer 1 from Step 13) in $CH_2Cl_2$ (5 mL) was added 2-aminopyridine (113 mg, 1.20 mmol) and MsCl (84 µl, 1.08 mmol) at 0° C. The resulting mixture was stirred at 0° C. for 2 hours, then warmed to room temperature overnight. The reaction mixture was diluted with water. The organic layer was washed with brine, dried over $MgSO_4$, filtered and concentrated. The residue was used without purification. LC-MS calculated for $C_{38}H_{44}Cl_2FN_6O_3Si$ $(M+H)^+$: m/z=749.3, 751.3; found 749.3, 751.3.

Diastereomer 2 was prepared in similar way as Diastereomer 1 using peak 2 from Step 13. LC-MS calculated for $C_{38}H_{44}Cl_2FN_6O_3Si$ $(M+H)^+$: m/z=749.3, 751.3; found 749.3, 751.3.

Step 15. tert-butyl (2S,4S)-2-(2-((tert-butyldimethylsilyl)oxy)ethyl)-4-(8-chloro-7-(8-cyanoisoquinolin-1-yl)-6-fluoro-4-(methylthio)-1H-pyrazolo[4,3-c]quinolin-1-yl)piperidine-1-carboxylate

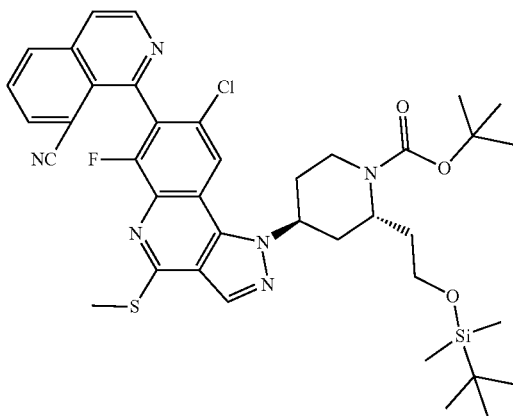

Sodium thiomethoxide (133 mg, 1.901 mmol) was added to a mixture of tert-butyl (2S,4S)-2-(2-((tert-butyldimethylsilyl)oxy)ethyl)-4-(4,8-dichloro-7-(8-cyanoisoquinolin-1-yl)-6-fluoro-1H-pyrazolo[4,3-c]quinolin-1-yl)piperidine-1-carboxylate (475 mg, 0.634 mmol) (Diastereomer 1 from last step) in MeOH (6.3 ml)/1,4-dioxane (6.3 ml) and the reaction mixture was stirred at 90° C. for 18 h. The mixture was diluted with saturated $NH_4Cl$ and extracted with EtOAc. The combined organic layers were dried over $MgSO_4$, filtered, concentrated, and the product was used without purification. LC-MS calculated for $C_{39}H_{47}ClFN_6O_3SSi$ $(M+H)^+$: m/z=761.3; found 761.3.

Diastereomer 2 was prepared in similar way as Diastereomer 1 using peak 2 from last step. LC-MS calculated for $C_{39}H_{47}ClFN_6O_3SSi$ $(M+H)^+$: m/z=761.3; found 761.3.

Step 16. tert-butyl (2S,4S)-4-(8-chloro-7-(8-cyanoisoquinolin-1-yl)-6-fluoro-4-(methylthio)-1H-pyrazolo[4,3-c]quinolin-1-yl)-2-(2-hydroxyethyl)piperidine-1-carboxylate

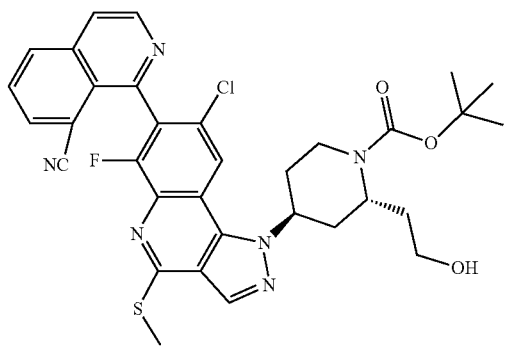 [SMILES: CSc1nc2c(F)c(-c3nccc4cccc(C#N)c34)c(Cl)cc2c2c1cnn2[C@H]1CCN(C(=O)OC(C)(C)C)[C@H](CCO)C1]

To a solution of tert-butyl (2S,4S)-2-(2-((tert-butyldimethylsilyl)oxy)ethyl)-4-(8-chloro-7-(8-cyanoisoquinolin-1-yl)-6-fluoro-4-(methylthio)-1H-pyrazolo[4,3-c]quinolin-1-yl)piperidine-1-carboxylate (482 mg, 0.633 mmol) (Diastereomer 1 from last step) in THF (6.33 ml) was added 1.0 M TBAF in THF (633 µl, 0.63 mmol). The resulting mixture was stirred at 60° C. for 1 h. After cooling to rt, the reaction mixture was diluted with water and ethyl acetate. The organic layer was separated and washed with brine, dried over $Na_2SO_4$, filtered and concentrated. The residue was purified with flash chromatography to give the desired product (0.39 g, 95%). LC-MS calculated for $C_{33}H_{33}ClFN_6O_3S$ $(M+H)^+$: m/z=647.2; found 647.2.

Diastereomer 2 was prepared in similar way as Diastereomer 1 using peak 2 from last step. LC-MS calculated for $C_{33}H_{33}ClFN_6O_3S$ $(M+H)^+$: m/z=647.2; found 647.2.

Step 17. tert-Butyl (2S,4S)-4-(8-chloro-7-(8-cya-noisoquinolin-1-yl)-6-fluoro-4-(methylthio)-1H-pyrazolo[4,3-c]quinolin-1-yl)-2-(cyanomethyl)piperidine-1-carboxylate

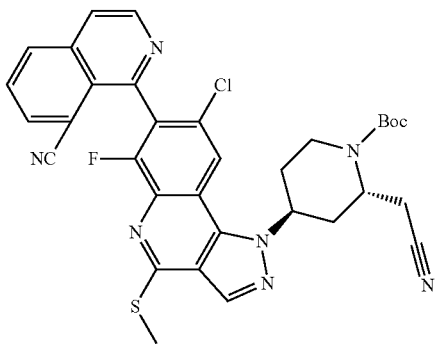 [SMILES: CSc1nc2c(F)c(-c3nccc4cccc(C#N)c34)c(Cl)cc2c2c1cnn2[C@H]1CCN(C(=O)OC(C)(C)C)[C@H](CC#N)C1]

To a solution of tert-butyl (2S,4S)-4-(8-chloro-7-(8-cyanoisoquinolin-1-yl)-6-fluoro-4-(methylthio)-1H-pyrazolo[4,3-c]quinolin-1-yl)-2-(2-hydroxyethyl)piperidine-1-carboxylate (392 mg, 0.61 mmol) in DCM (6.0 ml) was added Dess-Martin periodinane (283 mg, 0.67 mmol).

The resulting mixture was stirred for 1 h. To the reaction flask was added saturated $NaHCO_3$ and stirred for 10 min. The organic layer was separated and dried over $Na_2SO_4$, filtered and concentrated. The crude was dissolved in THF (20 mL), then ammonium hydroxide (1.37 ml, 9.81 mmol) was added to reaction flask, followed by iodine (157 mg, 0.618 mmol). The resulting mixture was stirred at rt for 2 h. The reaction solution was diluted with ethyl acetate and sat. $NaS_2O_3$ solution. The organic layer was separated and washed with brine, dried over $Na_2SO_4$, filtered and concentrated. The residue was purified with flash chromatography to give the desired product (0.32 g, 82%) LC-MS calculated for $C_{33}H_{30}ClFN_7O_2S$ $(M+H)^+$: m/z=642.2; found 642.2.

Diastereomer 2 was prepared in similar way as Diastereomer 1 using peak 2 from last step. LC-MS calculated for $C_{33}H_{30}ClFN_7O_2S$ $(M+H)^+$: m/z=642.2; found 642.2.

Step 18. 1-(8-chloro-1-((2S,4S)-2-(cyanomethyl)piperidin-4-yl)-6-fluoro-4-((S)-1-((S)-1-methylpyrrolidin-2-yl)ethoxy)-1H-pyrazolo[4,3-c]quinolin-7-yl)isoquinoline-8-carbonitrile

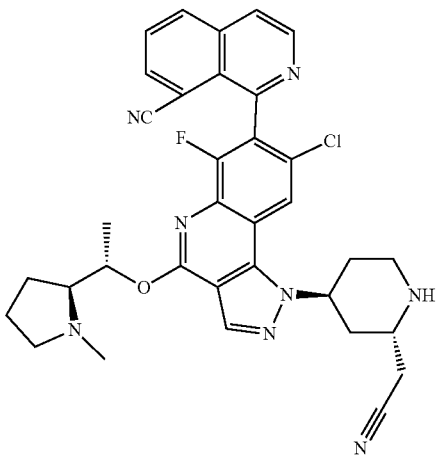 [SMILES: C[C@H](Oc1nc2c(F)c(-c3nccc4cccc(C#N)c34)c(Cl)cc2c2c1cnn2[C@H]1CCN[C@H](CC#N)C1)[C@@H]1CCCN1C]

m-CPBA (77%, 43.9 mg, 0.25 mmol) was added to a solution of tert-butyl (2S,4S)-4-(8-chloro-7-(8-cyanoisoquinolin-1-yl)-6-fluoro-4-(methylthio)-1H-pyrazolo[4,3-c]quinolin-1-yl)-2-(cyanomethyl)piperidine-1-carboxylate (142 mg, 0.22 mmol) in $CH_2Cl_2$ (2.2 ml) at 0° C. and then the reaction was stirred at this temperature for 20 min. The reaction was quenched by adding saturated $Na_2S_2O_3$. The reaction mixture was diluted with ethyl acetate and the layers were separated. The organic layer was washed with saturated $NaHCO_3$ solution, brine, filtered and concentrated. The crude was used in the next step directly.

LiHMDS (318 µl, 0.318 mmol) was added to a solution of (S)-1-((S)-1-methylpyrrolidin-2-yl)ethan-1-ol (41.0 mg, 0.32 mmol) in THF (1 mL). The resulting mixture was stirred at rt for 30 min. The first solution was added to a solution of tert-butyl (2S,4S)-4-(8-chloro-7-(8-cyanoisoquinolin-1-yl)-6-fluoro-4-(methylsulfinyl)-1H-pyrazolo[4,3-c]quinolin-1-yl)-2-(cyanomethyl)piperidine-1-carboxylate (95 mg, 0.14 mmol) in THF (2.0 ml) and then the reaction was stirred at 60° C. for 2 h. The reaction mixture was diluted with ethyl acetate and water. The organic layer was separated and dried over $Na_2SO_4$, filtered and concentrated. The residue was treated with 1:1 DCM/TFA (2 mL) for 1 h. The solvent was evaporated in vacuo. The residue was purified with prep-LCMS (XBridge C18 column, eluting with a gradient of acetonitrile/water containing 0.1% TFA, at flow rate of 60 mL/min) to give the desired product as two peaks (60 mg, 58%). LC-MS calculated for $C_{34}H_{33}ClFN_8O$ $(M+H)^+$: m/z=623.2; found 623.2.

Diastereomer 2 was prepared in similar way as Diastereomer 1 using peak 2 from last step. LC-MS calculated for $C_{34}H_{33}ClFN_8O$ $(M+H)^+$: m/z=623.2; found 623.2.

Step 19. 1-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-1H-pyrazolo[4,3-c]quinolin-7-yl)isoquinoline-8-carbonitrile To a solution of 1-(8-chloro-1-((2S,4S)-2-(cyanomethyl)piperidin-4-yl)-6-fluoro-4-((S)-1-((S)-1-methylpyrrolidin-2-yl)ethoxy)-1H-pyrazolo[4,3-c]quinolin-7-yl)isoquinoline-8-carbonitrile bis(2,2,2-trifluoroacetate) (7.0 mg, 8.2 µmol) in DCM (1.0 ml) was added acetyl chloride (0.5M/DCM, 19.7 µl, 9.87 µmol) and DIPEA (5.8 µl, 33 µmol). The resulting mixture was stirred at rt for 1 h. The solvent was removed in vacuo. The residue was dissolved in methanol and 1 N HCl (0.1 mL) and purified using prep-LCMS (XBridge C18 column, eluting with a gradient of acetonitrile/water containing 0.1% TFA, at flow rate of 60 mL/min) to afford the desired diastereomer 1.

Diastereomer 2 was synthesized in similar way using 1-(8-chloro-1-((2S,4S)-2-(cyanomethyl)piperidin-4-yl)-6-fluoro-4-((S)-1-((S)-1-methylpyrrolidin-2-yl)ethoxy)-1H-pyrazolo[4,3-c]quinolin-7-yl)isoquinoline-8-carbonitrile bis (2,2,2-trifluoroacetate) (peak2 from last step).

Example 23a. Diastereomer 1. Peak 1. LCMS calculated for $C_{36}H_{35}ClFN_8O_2$ (M+H)+m/z=665.3; found 665.3.

Example 23b. Diastereomer 2. Peak 2. LCMS calculated for $C_{36}H_{35}ClFN_8O_2$ $(M+H)^+$: m/z=665.3; found 665.3.

Example 24a and Example 24b. 8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-1H-pyrrolo[3,2-c]quinolin-7-yl)-1-naphthonitrile

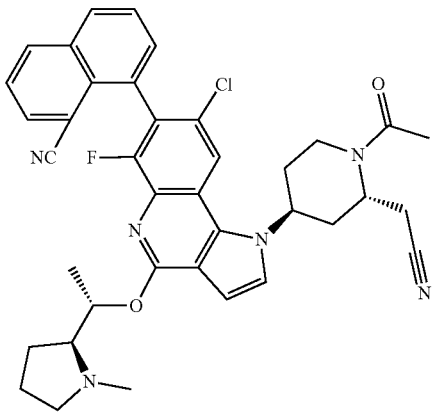 [SMILES: CC(=O)N1CC[C@H](n2ccc3c(O[C@@H](C)[C@@H]4CCCN4C)nc4c(F)c(-c5cccc6cccc(C#N)c56)c(Cl)cc4c32)C[C@H]1CC#N]

Step 1: methyl 2-amino-4-bromo-5-chloro-3-fluorobenzoate

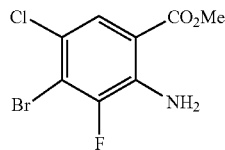 [SMILES: COC(=O)c1cc(Cl)c(Br)c(F)c1N]

Sulfuric acid (7.76 ml, 146 mmol) was added slowly to a solution of 2-amino-4-bromo-5-chloro-3-fluorobenzoic acid (19.5 g, 72.8 mmol) in MeOH (146 ml) at r.t. The resulting mixture was heated to 80° C. overnight. The mixture was then cooled to r.t. and slowly poured into sat'd NaHCO$_3$. The mixture was stirred at r.t. for 30 min then extracted with EtOAc. The organic layer was dried over MgSO$_4$, filtered, concentrated, and used in the next step without further purification. LC-MS calculated for C$_8$H$_7$BrClFNO$_2$ (M+H)$^+$: m/z=281.9, 283.9; found 281.9, 283.9.

Step 2: ethyl 7-bromo-6-chloro-8-fluoro-4-hydroxy-2-oxo-1,2-dihydroquinoline-3-carboxylate

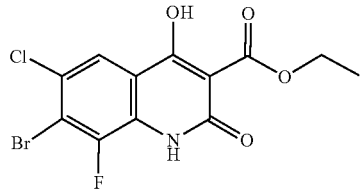 [SMILES: CCOC(=O)c1c(O)c2cc(Cl)c(Br)c(F)c2[nH]c1=O]

Ethyl 3-chloro-3-oxopropanoate (9.60 ml, 75.0 mmol) was added dropwise to a solution of methyl 2-amino-4-bromo-5-chloro-3-fluorobenzoate (19.25 g, 68.1 mmol) and TEA (14.25 ml, 102 mmol) in DCM (150 mL) at rt. After stirring for 1 h, additional ethyl 3-chloro-3-oxopropanoate (1.745 ml, 13.63 mmol) added. After stirring for another 1 h, the reaction was quenched with water then extracted with ethyl acetate. The organic layer was dried, filtered, then concentrated. The concentrated residue was redissolved in EtOH (150 ml) and sodium ethoxide in ethanol (53.4 ml, 143 mmol) was added. The reaction mixture was stirred at r.t. for 1 h. The reaction mixture was poured into water (1 L) and acidified to pH~3. The resulting precipitate was collected via filtration to give the desired product (18.39 g, 74.0%). LC-MS calculated for C$_{12}$H$_9$BrClFNO$_4$ (M+H)$^+$: m/z=363.9, 365.9; found 363.9, 365.9.

Step 3: ethyl 7-bromo-2,4,6-trichloro-8-fluoroquinoline-3-carboxylate

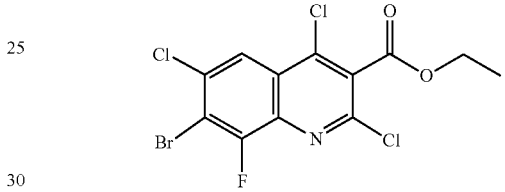

Ethyl 7-bromo-6-chloro-8-fluoro-2,4-dihydroxyquinoline-3-carboxylate (2.0 g, 5.49 mmol) was dissolved in POCl$_3$ (10.2 ml, 110 mmol), and DIPEA (1.92 ml, 10.97 mmol) was added. The resulting mixture was stirred at 100° C. for 2 h. After cooling to r.t., the reaction was quenched by slowly pouring into rapidly stirred ice water (~ 250 mL), stirred for 30 min then collected solids via filtration to yield the desired product as a brown solid (1.66 g, 75%). LC-MS calculated for C$_{12}$H$_7$BrCl$_3$FNO$_2$ (M+H)$^+$: m/z=399.9, 401.9, 403.9; found 399.9, 401.9, 403.9.

Step 4. ethyl 7-bromo-4-(((2S,4S)-1-(tert-butoxycarbonyl)-2-(2-((tert-butyldimethylsilyl)oxy)ethyl)piperidin-4-yl)amino)-2,6-dichloro-8-fluoroquinoline-3-carboxylate

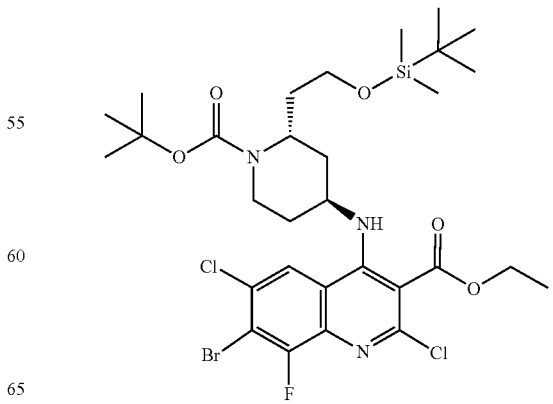

To a solution of ethyl 7-bromo-2,4,6-trichloro-8-fluoro-quinoline-3-carboxylate (8.7 g, 21.7 mmol) in DMF (80 ml) was added tert-butyl (2S,4S)-4-amino-2-(2-((tert-butyldimethylsilyl)oxy)ethyl)piperidine-1-carboxylate (Intermediate 9, 9.33 g, 26.0 mmol) and DIEA (7.6 ml, 43.3 mmol). The resulting mixture was stirred at 65° C. for 5 h. After cooling to room temperature, ethyl acetate and water were added. The organic layer was washed with water (2×) and brine, dried over Na$_2$SO$_4$, filtered and concentrated. The residue was purified with flash chromatography (eluting with 0%-25% ethyl acetate in hexanes) to give the desired product as foam (14.6 g, 93%). LC-MS calculated for C$_{30}$H$_{44}$BrCl$_2$FN$_3$O$_5$Si (M+H)$^+$: m/z=722.2, 724.2; found 722.2, 724.2.

Step 5. tert-butyl (2S,4S)-4-((7-bromo-2,6-dichloro-8-fluoro-3-(hydroxymethyl)quinolin-4-yl)amino)-2-(2-((tert-butyldimethylsilyl)oxy)ethyl)piperidine-1-carboxylate

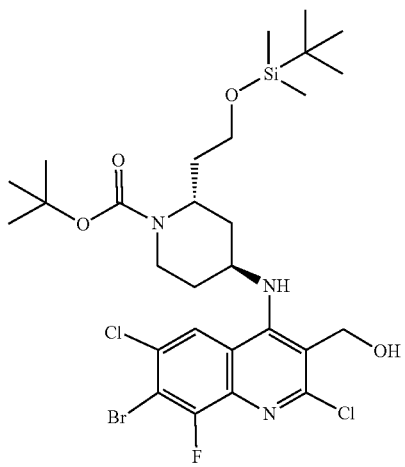 [SMILES: CC(C)(C)OC(=O)N1CC[C@H](Nc2c(CO)c(Cl)nc3c(F)c(Br)c(Cl)cc23)C[C@H]1CCO[Si](C)(C)C(C)(C)C]

To a solution of ethyl 7-bromo-4-(((2S,4S)-1-(tert-butoxycarbonyl)-2-(2-((tert-butyldimethylsilyl)oxy)ethyl)piperidin-4-yl)amino)-2,6-dichloro-8-fluoroquinoline-3-carboxylate (14.6 g, 20.18 mmol) in toluene (200 ml) at −78° C. was added 1.0 M DIBAL-H in DCM (60.5 ml, 60.5 mmol). The resulting mixture was stirred at −78° C. for 40 min and warm to 0° C. for 1.5 h and quenched with methanol (6.8 ml, 167 mmol). Aqueous Rochelle salt solution (prepared from 88 g (6 wt) of Rochelle salt and 200 mL of water) was added to the solution at ≤10° C. The biphasic mixture was stirred vigorously for ≥1 h at 15-25° C. and separated to give organic layer. The biphasic mixture was separated. The organic layer was washed with brine, dried over Na$_2$SO$_4$, filtered and concentrated. The crude was used as is. LC-MS calculated for C$_{28}$H$_{42}$BrCl$_2$FN$_3$O$_4$Si (M+H)$^+$: m/z=680.1, 682.1; found 680.1, 682.1.

Step 6. tert-butyl (2S,4S)-4-((7-bromo-2,6-dichloro-8-fluoro-3-formylquinolin-4-yl)amino)-2-(2-((tert-butyldimethylsilyl)oxy)ethyl)piperidine-1-carboxylate

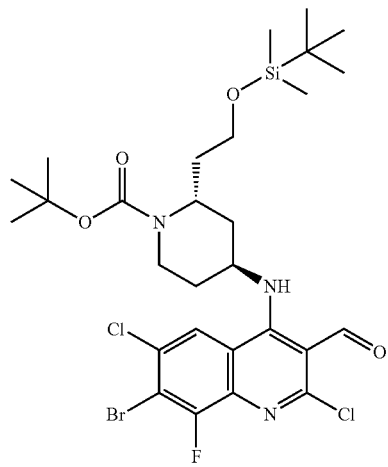 [SMILES: CC(C)(C)OC(=O)N1CC[C@H](Nc2c(C=O)c(Cl)nc3c(F)c(Br)c(Cl)cc23)C[C@H]1CCO[Si](C)(C)C(C)(C)C]

To a solution of tert-butyl (2S,4S)-4-((7-bromo-2,6-dichloro-8-fluoro-3-(hydroxymethyl)quinolin-4-yl)amino)-2-(2-((tert-butyldimethylsilyl)oxy)ethyl)piperidine-1-carboxylate (13.0 g, 19.07 mmol) in DCM (150 ml) and acetonitrile (50 ml) was added IBX (16.02 g, 57.2 mmol) and acetic acid (3.28 ml, 57.2 mmol). The resulting reaction mixture was stirred at 35° C. for 16 h. The reaction mixture was filtered and the filtrate was concentrated. The resulting residue was triturated with EtOAc, the resulting precipitate was collected via filtration, dried under vacuum to give the desired product as light yellow solid (9.4 g, 73% over 2 steps). LC-MS calculated for C$_{28}$H$_{40}$BrCl$_2$FN$_3$O$_4$Si (M+H)$^+$: m/z=678.1, 680.1; found 678.1, 680.1.

Step 7. tert-butyl (2S,4S)-4-((7-bromo-6-chloro-8-fluoro-3-formyl-2-(methylthio)quinolin-4-yl)amino)-2-(2-((tert-butyldimethylsilyl)oxy)ethyl)piperidine-1-carboxylate

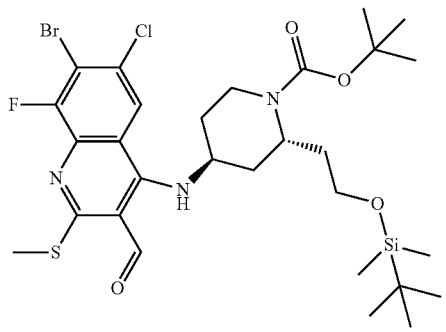 [SMILES: CSc1nc2c(F)c(Br)c(Cl)cc2c(N[C@H]2CCN(C(=O)OC(C)(C)C)[C@H](CCO[Si](C)(C)C(C)(C)C)C2)c1C=O]

Sodium thiomethoxide (0.947 g, 13.51 mmol) was added to a mixture of tert-butyl (2S,4S)-4-((7-bromo-2,6-dichloro-8-fluoro-3-formylquinolin-4-yl)amino)-2-(2-((tert-butyldimethylsilyl)oxy)ethyl)piperidine-1-carboxylate (3.06 g, 4.50 mmol) in MeOH (45.0 ml)/DCM (45.0 ml) and then stirred at rt for 1 h. The mixture was diluted with sat'd NH₄Cl and extracted with EtOAc. The combined organic layers were dried over MgSO₄, filtered, concentrated, and the residue was purified by silica gel column (eluting with a gradient of 0-15% hexane/EtOAc) to give the desire product as white solid (3.05 g, 98%). LC-MS calculated for $C_{29}H_{43}BrClFN_3O_4SSi$ (M+H)⁺: m/z=690.2, 692.2; found 690.2, 692.2.

Step 8. tert-butyl (2S,4S)-4-((7-bromo-6-chloro-8-fluoro-3-((E)-2-methoxyvinyl)-2-(methylthio)quinolin-4-yl)amino)-2-(2-((tert-butyldimethylsilyl)oxy)ethyl)piperidine-1-carboxylate

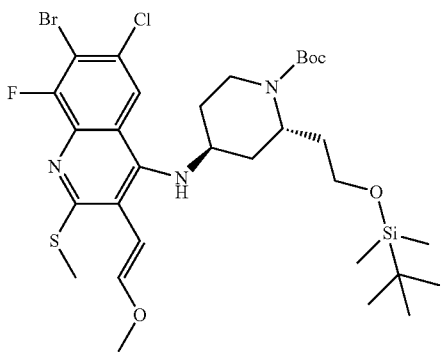 [SMILES: CO/C=C/c1c(SC)nc2c(F)c(Br)c(Cl)cc2c1N[C@H]1CCN(C(=O)OC(C)(C)C)[C@H](CCO[Si](C)(C)C(C)(C)C)C1]

To a solution of (methoxymethyl)triphenylphosphonium chloride (451 mg, 1.32 mmol) in toluene (3 mL) was added potassium tert-butoxide (1 M/THF, 1.5 mL, 1.5 mmol) at rt under an atmosphere of nitrogen. After stirring for 30 minutes, a solution of tert-butyl (2S,4S)-4-((7-bromo-6-chloro-8-fluoro-3-formyl-2-(methylthio)quinolin-4-yl)amino)-2-(2-((tert-butyldimethylsilyl)oxy)ethyl)piperidine-1-carboxylate (350 mg, 0.506 mmol) in THF (1.0 mL) was cannulated into the reaction flask. The resulting solution was stirred at rt for 1 h. The reaction was quenched with 1 N HCl and diluted with ethyl acetate. Aqueous layer was extracted with ethyl acetate once. The combined organic solutions were washed with brine, dried over Na₂SO₄, filtered and concentrated. The residue was purified with silica gel chromatography (eluting with a gradient of 0-20% ethyl acetate in hexanes) to give the desired product (0.32 g, 88%). LC-MS calculated for $C_{31}H_{47}BrClFN_3O_4SSi$ (M+H)⁺: m/z=718.2, 720.2; found 718.3, 720.3.

Step 9. tert-butyl (2S,4S)-4-(7-bromo-8-chloro-6-fluoro-4-(methylthio)-1H-pyrrolo[3,2-c]quinolin-1-yl)-2-(2-hydroxyethyl)piperidine-1-carboxylate

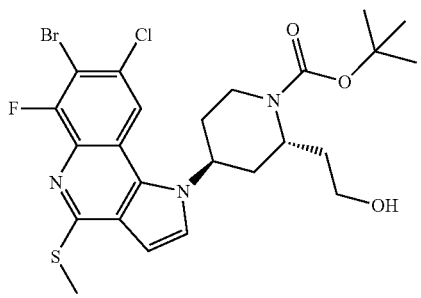 [SMILES: CSc1nc2c(F)c(Br)c(Cl)cc2c2c1ccn2[C@H]1CCN(C(=O)OC(C)(C)C)[C@H](CCO)C1]

To a flask was added tert-butyl (2S,4S)-4-((7-bromo-6-chloro-8-fluoro-3-((E)-2-methoxyvinyl)-2-(methylthio)quinolin-4-yl)amino)-2-(2-((tert-butyldimethylsilyl)oxy)ethyl)piperidine-1-carboxylate (320 mg, 0.445 mmol), 4.0 M HCl in dioxane (2.25 ml, 8.90 mmol), and ethanol (3.0 ml). The reaction mixture was stirred at 70° C. for 1 h. The solvent was removed in vacuo. The residue was dissolved in methanol. Boc-anhydride (155 μl, 0.667 mmol) and TEA (248 μl, 1.780 mmol) were added and the reaction mixture was stirred for 2 h. The solvent was removed and the crude product was purified by column chromatography on silica gel to give the desired product (198 mg, 78%). LC-MS calculated for $C_{24}H_{29}BrClFN_3O_3S$ (M+H)⁺: m/z=572.1, 574.1; found 572.1, 574.1.

Step 10. tert-butyl (2S,4S)-4-(7-bromo-8-chloro-6-fluoro-4-(methylthio)-1H-pyrrolo[3,2-c]quinolin-1-yl)-2-(cyanomethyl)piperidine-1-carboxylate

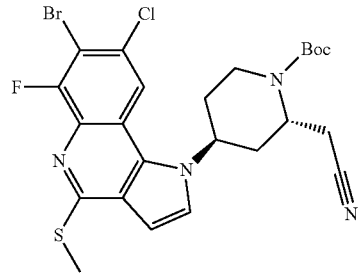 [SMILES: CSc1nc2c(F)c(Br)c(Cl)cc2c2c1ccn2[C@H]1CCN(C(=O)OC(C)(C)C)[C@H](CC#N)C1]

To a solution of tert-butyl (2S,4S)-4-(7-bromo-8-chloro-6-fluoro-4-(methylthio)-1H-pyrrolo[3,2-c]quinolin-1-yl)-2-(2-hydroxyethyl)piperidine-1-carboxylate (215 mg, 0.375 mmol) in CH₂Cl₂ (3.8 ml) was added Dess-Martin periodinane (175 mg, 0.413 mmol). The resulting mixture was stirred for 1 h. To the reaction flask was added saturated NaHCO₃ and stirred for 10 min. The organic layer was separated and dried over Na₂SO₄, filtered and concentrated. The crude was dissolved in THF (4 mL), ammonium hydroxide (845 μl, 6.08 mmol) was added to reaction flask, followed by iodine (97 mg, 0.383 mmol). The resulting mixture was stirred at rt for 3 h. The reaction solution was diluted with ethyl acetate and sat. NaS₂O₃ solution. The organic layer was separated and washed with brine, dried over Na₂SO₄, filtered and concentrated. The residue was purified with flash chromatography to give the desired product (0.19 g, 89%). LC-MS calculated for $C_{24}H_{26}BrClFN_4O_2S$ (M+H)⁺: m/z=567.1, 569.1; found 567.1, 569.1.

Step 11. tert-butyl (2S,4S)-4-(7-bromo-8-chloro-6-fluoro-4-((S)-1-((S)-1-methylpyrrolidin-2-yl)ethoxy)-1H-pyrrolo[3,2-c]quinolin-1-yl)-2-(cyanomethyl)piperidine-1-carboxylate

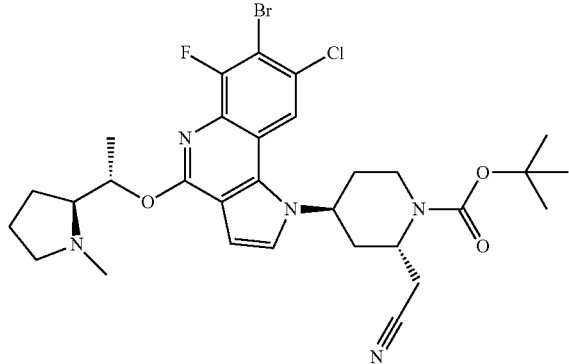 [SMILES: C[C@H](Oc1nc2c(F)c(Br)c(Cl)cc2c2c1ccn2[C@H]1CCN(C(=O)OC(C)(C)C)[C@H](CC#N)C1)[C@@H]1CCCN1C]

m-CPBA (68.1 mg, 0.395 mmol) was added to a solution of tert-butyl (2S,4S)-4-(7-bromo-8-chloro-6-fluoro-4-(methylthio)-1H-pyrrolo[3,2-c]quinolin-1-yl)-2-(cyanomethyl)piperidine-1-carboxylate (195 mg, 0.343 mmol) in $CH_2Cl_2$ (3.4 ml) at 0° C. and then the reaction was stirred at this temperature for 20 min. The reaction was quenched by adding saturated $Na_2S_2O_3$ solution, diluted with ethyl acetate and washed with saturated $NaHCO_3$, brine, filtered, dried and concentrated and the crude was used in the next step directly.

LiHMDS (776 µl, 0.776 mmol) was added to a solution of (S)-1-((S)-1-methylpyrrolidin-2-yl)ethan-1-ol (100 mg, 0.776 mmol) in THF (1 mL). The resulting mixture was stirred at rt for 30 min. The first solution was added to a solution of tert-butyl (2S,4S)-4-(7-bromo-8-chloro-6-fluoro-4-(methylsulfinyl)-1H-pyrrolo[3,2-c]quinolin-1-yl)-2-(cyanomethyl)piperidine-1-carboxylate (206 mg, 0.353 mmol) in THF (2.0 ml) and then the reaction was stirred at 60° C. for 2 h. The reaction mixture was diluted with ethyl acetate and water. The organic layer was dried over $Na_2SO_4$, filtered and concentrated. The residue was purified with silica gel column to give the desired product (131 mg, 57%). LCMS calculated for $C_{30}H_{37}BrClFN_5O_3$ $(M+H)^+$ m/z=648.2, 650.2; found 648.2, 650.2.

Step 12. 8-(8-chloro-1-((2S,4S)-2-(cyanomethyl)piperidin-4-yl)-6-fluoro-4-((S)-1-((S)-1-methylpyrrolidin-2-yl)ethoxy)-1H-pyrrolo[3,2-c]quinolin-7-yl)-1-naphthonitrile

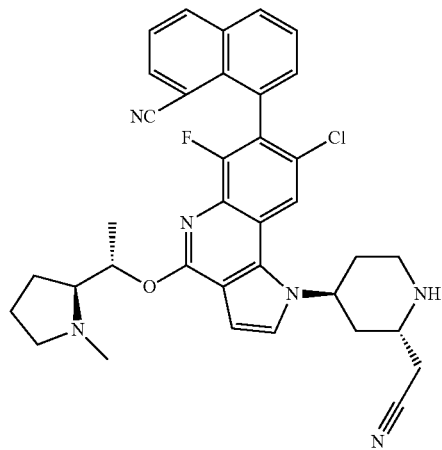 [SMILES: C[C@H](Oc1nc2c(F)c(-c3cccc4cccc(C#N)c34)c(Cl)cc2c2c1ccn2[C@H]1CCN[C@H](CC#N)C1)[C@@H]1CCCN1C]

A microwave vial was charged with tert-butyl (2S,4S)-4-(7-bromo-8-chloro-6-fluoro-4-((S)-1-((S)-1-methylpyrrolidin-2-yl)ethoxy)-1H-pyrrolo[3,2-c]quinolin-1-yl)-2-(cyanomethyl)piperidine-1-carboxylate (99 mg, 0.153 mmol), 8-(4,4,5,5-tetramethyl-1,3,2-dioxaborolan-2-yl)-1-naphthonitrile (42.6 mg, 0.153 mmol), methanesulfonato(2-dicyclohexylphosphino-2',6'-dimethoxy-1,1'-biphenyl)(2'-methylamino-1,1'-biphenyl-2-yl)palladium(II) dichloromethane adduct (12.1 mg, 0.015 mmol), potassium phosphate (64.8 mg, 0.305 mmol) and 1,4-dioxane (1.4 ml)/water (0.14 ml). The reaction mixture was purged with $N_2$ and heated at 75° C. for 2 h. The reaction mixture was diluted with ethyl acetate and water. The organic layer was separated, dried over $Na_2SO_4$, filtered and concentrated. The resulting residue was dissolved in DCM (1 ml) and TFA (1 ml). After stirring for 1 h, the solvent was removed in vacuo, the residue was purified with prep-LCMS (XBridge C18 column, eluting with a gradient of acetonitrile/water containing 0.1% TFA, at flow rate of 60 mL/min) to give the desired product as two peaks (30 mg, 32%).

Diastereomer 1. Peak 1. LC-MS calculated for $C_{36}H_{35}ClFN_6O$ $(M+H)^+$: m/z=621.3; found 621.3.

Diastereomer 2. Peak 2. LC-MS calculated for $C_{36}H_{35}ClFN_6O$ $(M+H)^+$: m/z=621.3; found 621.3.

Step 13. 8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-1H-pyrrolo[3,2-c]quinolin-7-yl)-1-naphthonitrile To a solution of 8-(8-chloro-1-((2S,4S)-2-(cyanomethyl)piperidin-4-yl)-6-fluoro-4-((S)-1-((S)-1-methylpyrrolidin-2-yl)ethoxy)-1H-pyrrolo[3,2-c]quinolin-7-yl)-1-naphthonitrile bis(2,2,2-trifluoroacetate) (10.0 mg, 12 µmol) in DMF (1.0 ml) was added 1.0 M acetyl chloride in DCM (14.1 µl, 0.014 mmol) and DIPEA (8.2 µl, 0.047 mmol). The resulting mixture was stirred at rt for 1 h. The reaction was diluted with methanol and 1 N HCl (0.1 mL) and purified using prep-LCMS (XBridge C18 column, eluting with a gradient of acetonitrile/water containing 0.1% TFA, at flow rate of 60 mL/min) to afford the desired diastereomer 1.

Diastereomer 2 was synthesized in similar way using 8-(8-chloro-1-((2S,4S)-2-(cyanomethyl)piperidin-4-yl)-6-fluoro-4-((S)-1-((S)-1-methylpyrrolidin-2-yl)ethoxy)-1H-pyrrolo[3,2-c]quinolin-7-yl)-1-naphthonitrile bis(2,2,2-trifluoroacetate) (peak2 from last step).

Example 24a. Diastereomer 1. Peak 1. LCMS calculated for $C_{38}H_{37}ClFN_6O_2$ (M+H)+m/z=663.3; found 663.3.

Example 24b. Diastereomer 2. Peak 2. LCMS calculated for $C_{38}H_{37}ClFN_6O_2$ (M+H)+m/z=663.3; found 663.3.

Example 25. 8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-1H-pyrazolo[4,3-c]quinolin-7-yl)-1-naphthonitrile

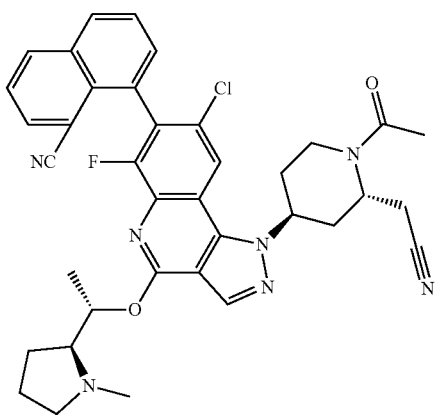 [SMILES: CC(=O)N1CC[C@H](n2ncc3c(O[C@@H](C)[C@@H]4CCCN4C)nc4c(F)c(-c5cccc6cccc(C#N)c56)c(Cl)cc4c32)C[C@H]1CC#N]

Step 1. ethyl 2-amino-4-(8-cyanonaphthalen-1-yl)-3-fluorobenzoate

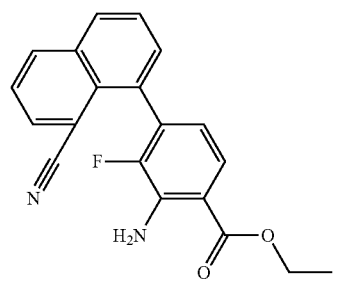 [SMILES: CCOC(=O)c1ccc(-c2cccc3cccc(C#N)c23)c(F)c1N]

The title compound was synthesized according to the procedure described for Example 23a and 23b in Step 5, utilizing 8-bromo-1-naphthonitrile instead of 1-chloroisoquinoline-8-carbonitrile. LCMS calculated for $C_{20}H_{16}FN_2O_2$ (M+H)$^+$ m/z=335.1; found 335.1.

Step 2. ethyl 2-amino-5-chloro-4-(8-cyanonaphthalen-1-yl)-3-fluorobenzoate

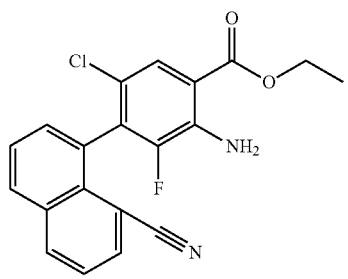 [SMILES: CCOC(=O)c1cc(Cl)c(-c2cccc3cccc(C#N)c23)c(F)c1N]

The title compound was synthesized according to the procedure described for Example 23a and 23b in step 6, utilizing ethyl 2-amino-4-(8-cyanonaphthalen-1-yl)-3-fluorobenzoate instead of ethyl 2-amino-4-(8-cyanoisoquinolin-1-yl)-3-fluorobenzoate. LCMS calculated for $C_{20}H_{15}ClFN_2O_2$ (M+H)$^+$ m/z=369.1; found 369.1.

Step 3. ethyl 5-chloro-4-(8-cyanonaphthalen-1-yl)-2-(3-ethoxy-3-oxopropanamido)-3-fluorobenzoate

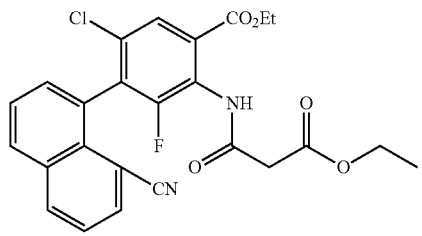 [SMILES: CCOC(=O)CC(=O)Nc1c(C(=O)OCC)cc(Cl)c(-c2cccc3cccc(C#N)c23)c1F]

This compound was prepared according to the procedure described in Example 23a and 23b, in Step 7 replacing ethyl 2-amino-5-chloro-4-(8-cyanoisoquinolin-1-yl)-3-fluorobenzoate with ethyl 2-amino-5-chloro-4-(8-cyanonaphthalen-1-yl)-3-fluorobenzoate. LC-MS calculated for $C_{25}H_{21}ClFN_2O_5$ (M+H)$^+$: m/z=483.1; found 483.1.

Step 4. ethyl 6-chloro-7-(8-cyanonaphthalen-1-yl)-8-fluoro-2,4-dihydroxyquinoline-3-carboxylate

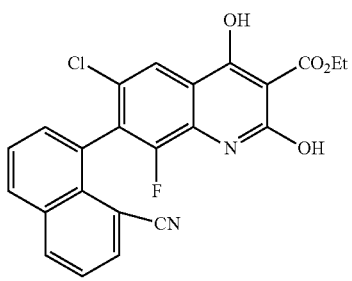

This compound was prepared according to the procedure described in Example 23a and 23b, in Step 8 replacing ethyl 5-chloro-4-(8-cyanoisoquinolin-1-yl)-2-(3-ethoxy-3-oxopropanamido)-3-fluorobenzoate with ethyl 5-chloro-4-(8-cyanonaphthalen-1-yl)-2-(3-ethoxy-3-oxopropanamido)-3-fluorobenzoate. LC-MS calculated for $C_{23}H_{15}ClFN_2O_4$ (M+H)$^+$: m/z=437.1; found 437.1.

Step 5. ethyl 2,4,6-trichloro-7-(8-cyanonaphthalen-1-yl)-8-fluoroquinoline-3-carboxylate

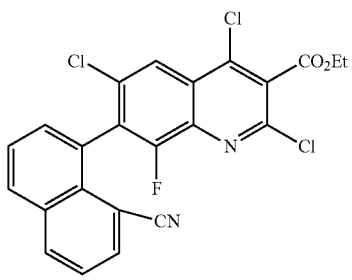 [SMILES: CCOC(=O)c1c(Cl)nc2c(F)c(-c3cccc4cccc(C#N)c34)c(Cl)cc2c1Cl]

This compound was prepared according to the procedure described in Example 23a and 23b, in Step 9 replacing ethyl 6-chloro-7-(8-cyanoisoquinolin-1-yl)-8-fluoro-2,4-dihydroxyquinoline-3-carboxylate with ethyl 6-chloro-7-(8-cyanonaphthalen-1-yl)-8-fluoro-2,4-dihydroxyquinoline-3-carboxylate. LC-MS calculated for $C_{23}H_{13}Cl_3FN_2O_2$ (M+H)$^+$: m/z=473.0, 475.0; found 473.1, 475.1.

Step 6. ethyl 4-(((2S,4S)-1-(tert-butoxycarbonyl)-2-(2-((tert-butyldimethylsilyl)oxy)ethyl)piperidin-4-yl)amino)-2,6-dichloro-7-(8-cyanonaphthalen-1-yl)-8-fluoroquinoline-3-carboxylate

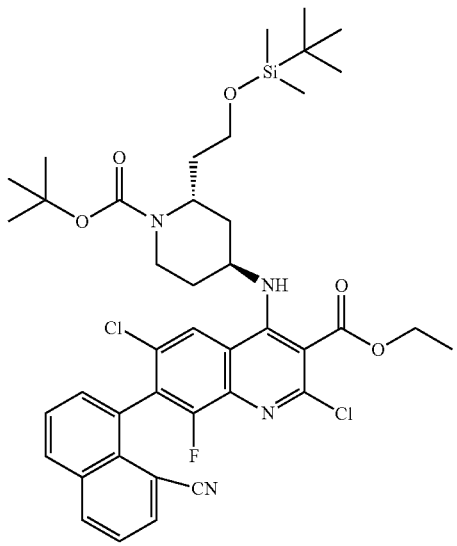 [SMILES: CCOC(=O)c1c(Cl)nc2c(F)c(-c3cccc4cccc(C#N)c34)c(Cl)cc2c1N[C@H]1CCN(C(=O)OC(C)(C)C)[C@H](CCO[Si](C)(C)C(C)(C)C)C1]

This compound was prepared according to the procedure described in Example 23a and 23b, in Step 10 replacing ethyl 2,4,6-trichloro-7-(8-cyanoisoquinolin-1-yl)-8-fluoroquinoline-3-carboxylate with ethyl 2,4,6-trichloro-7-(8-cyanonaphthalen-1-yl)-8-fluoroquinoline-3-carboxylate. LC-MS calculated for $C_{41}H_{50}Cl_2FN_4O_5Si$ (M+H)$^+$: m/z=795.3, 797.3; found 795.5, 797.5.

Step 7. tert-butyl (2S,4S)-2-(2-((tert-butyldimethylsilyl)oxy)ethyl)-4-((2,6-dichloro-7-(8-cyanonaphthalen-1-yl)-8-fluoro-3-(hydroxymethyl)quinolin-4-yl)amino)piperidine-1-carboxylate

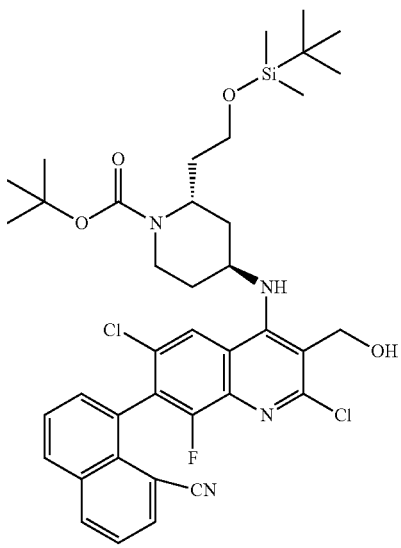 [SMILES: CC(C)(C)OC(=O)N1CC[C@H](Nc2c(CO)c(Cl)nc3c(F)c(-c4cccc5cccc(C#N)c45)c(Cl)cc23)C[C@H]1CCO[Si](C)(C)C(C)(C)C]

This compound was prepared according to the procedure described in Example 23a and 23b, in Step 11 replacing ethyl 4-(((2S,4S)-1-(tert-butoxycarbonyl)-2-(2-((tert-butyldimethylsilyl)oxy)ethyl)piperidin-4-yl)amino)-2,6-dichloro-7-(8-cyanoisoquinolin-1-yl)-8-fluoroquinoline-3-carboxylate with ethyl 4-(((2S,4S)-1-(tert-butoxycarbonyl)-2-(2-((tert-butyldimethylsilyl)oxy)ethyl)piperidin-4-yl)amino)-2,6-dichloro-7-(8-cyanonaphthalen-1-yl)-8-fluoroquinoline-3-carboxylate. LC-MS calculated for $C_{39}H_{48}Cl_2FN_4O_4Si$ (M+H)$^+$: m/z=753.3, 755.3; found 753.4, 755.5.

Step 8. tert-butyl (2S,4S)-2-(2-((tert-butyldimethylsilyl)oxy)ethyl)-4-((2,6-dichloro-7-(8-cyanonaphthalen-1-yl)-8-fluoro-3-formylquinolin-4-yl)amino)piperidine-1-carboxylate

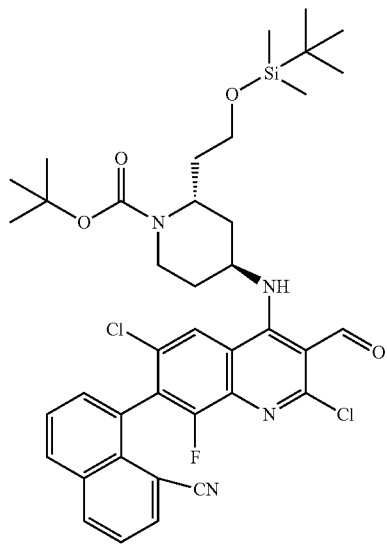 [SMILES: CC(C)(C)OC(=O)N1CC[C@H](Nc2c(C=O)c(Cl)nc3c(F)c(-c4cccc5cccc(C#N)c45)c(Cl)cc23)C[C@H]1CCO[Si](C)(C)C(C)(C)C]

This compound was prepared according to the procedure described in Example 23a and 23b, in Step 12 replacing tert-butyl (2S,4S)-2-(2-((tert-butyldimethylsilyl)oxy)ethyl)-4-((2,6-dichloro-7-(8-cyanoisoquinolin-1-yl)-8-fluoro-3-(hydroxymethyl)quinolin-4-yl)amino)piperidine-1-carboxylate with tert-butyl (2S,4S)-2-(2-((tert-butyldimethylsilyl)oxy)ethyl)-4-((2,6-dichloro-7-(8-cyanonaphthalen-1-yl)-8-fluoro-3-(hydroxymethyl)quinolin-4-yl)amino)piperidine-1-carboxylate. LC-MS calculated for $C_{39}H_{46}Cl_2FN_4O_4Si$ (M+H)$^+$: m/z=751.3, 753.3; found 751.4, 753.4.

Step 9. tert-butyl (2S,4S)-2-(2-((tert-butyldimethyl-silyl)oxy)ethyl)-4-((2,6-dichloro-7-(8-cyanonaphtha-len-1-yl)-8-fluoro-3-((E)-(hydroxyimino)methyl) quinolin-4-yl)amino)piperidine-1-carboxylate

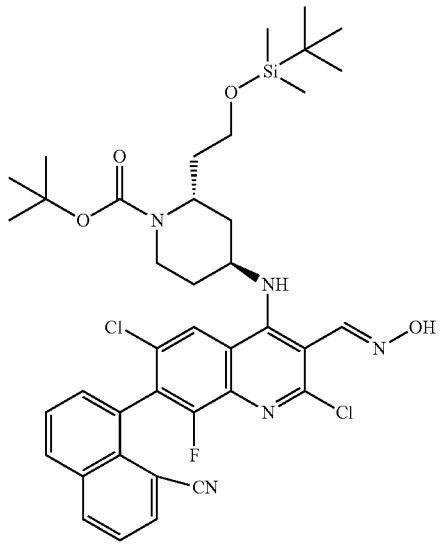 [SMILES: CC(C)(C)OC(=O)N1CC[C@H](Nc2c(/C=N/O)c(Cl)nc3c(F)c(-c4cccc5cccc(C#N)c45)c(Cl)cc23)C[C@H]1CCO[Si](C)(C)C(C)(C)C]

This compound was prepared according to the procedure described in Example 23a and 23b, in Step 13 replacing tert-butyl (2S,4S)-2-(2-((tert-butyldimethylsilyl)oxy)ethyl)-4-((2,6-dichloro-7-(8-cyanoisoquinolin-1-yl)-8-fluoro-3-formylquinolin-4-yl)amino)piperidine-1-carboxylate with tert-butyl (2S,4S)-2-(2-((tert-butyldimethylsilyl)oxy)ethyl)-4-((2,6-dichloro-7-(8-cyanonaphthalen-1-yl)-8-fluoro-3-formylquinolin-4-yl)amino)piperidine-1-carboxylate.
LC-MS calculated for $C_{39}H_{47}Cl_2FN_5O_4Si$ (M+H)$^+$: m/z=766.3, 768.3; found 766.4, 768.4.

Step 10. tert-butyl (2S,4S)-2-(2-((tert-butyldimeth-ylsilyl)oxy)ethyl)-4-(4,8-dichloro-7-(8-cyanonaph-thalen-1-yl)-6-fluoro-1H-pyrazolo[4,3-c]quinolin-1-yl)piperidine-1-carboxylate

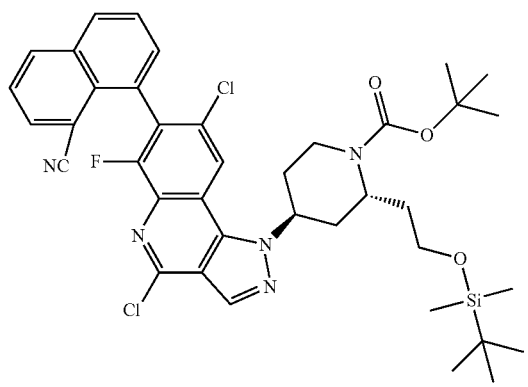 [SMILES: CC(C)(C)OC(=O)N1CC[C@H](n2ncc3c(Cl)nc4c(F)c(-c5cccc6cccc(C#N)c56)c(Cl)cc4c32)C[C@H]1CCO[Si](C)(C)C(C)(C)C]

This compound was prepared according to the procedure described in Example 23a and 23b, in Step 14 replacing (tert-butyl (2S,4S)-2-(2-((tert-butyldimethylsilyl)oxy) ethyl)-4-((2,6-dichloro-7-(8-cyanoisoquinolin-1-yl)-8-fluoro-3-((E)-(hydroxyimino)methyl)quinolin-4-yl)amino) piperidine-1-carboxylate with tert-butyl (2S,4S)-2-(2-((tert-butyldimethylsilyl)oxy)ethyl)-4-((2,6-dichloro-7-(8-cyanonaphthalen-1-yl)-8-fluoro-3-((E)-(hydroxyimino) methyl)quinolin-4-yl)amino)piperidine-1-carboxylate.
LC-MS calculated for $C_{39}H_{45}Cl_2FN_5O_3Si$ (M+H)$^+$: m/z=748.3, 750.3; found 748.4, 750.4.

Step 11. tert-butyl (2S,4S)-2-(2-((tert-butyldimeth-ylsilyl)oxy)ethyl)-4-(8-chloro-7-(8-cyanonaphthalen-1-yl)-6-fluoro-4-(methylthio)-1H-pyrazolo[4,3-c] quinolin-1-yl)piperidine-1-carboxylate

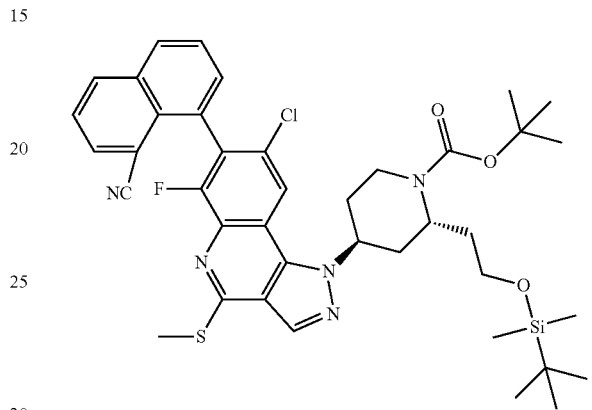

This compound was prepared according to the procedure described in in Example 23a and 23b, in Step 15 replacing tert-butyl (2S,4S)-2-(2-((tert-butyldimethylsilyl)oxy)ethyl)-4-(4,8-dichloro-7-(8-cyanoisoquinolin-1-yl)-6-fluoro-1H-pyrazolo[4,3-c]quinolin-1-yl)piperidine-1-carboxylate with tert-butyl (2S,4S)-2-(2-((tert-butyldimethylsilyl)oxy)ethyl)-4-(4,8-dichloro-7-(8-cyanonaphthalen-1-yl)-6-fluoro-1H-pyrazolo[4,3-c]quinolin-1-yl)piperidine-1-carboxylate. LC-MS calculated for $C_{40}H_{48}ClFN_5O_3SSi$ (M+H)$^+$: m/z=760.3; found 760.3.

Step 12. tert-butyl (2S,4S)-4-(8-chloro-7-(8-cyanon-aphthalen-1-yl)-6-fluoro-4-(methylthio)-1H-pyrazolo [4,3-c]quinolin-1-yl)-2-(2-hydroxyethyl)piperidine-1-carboxylate

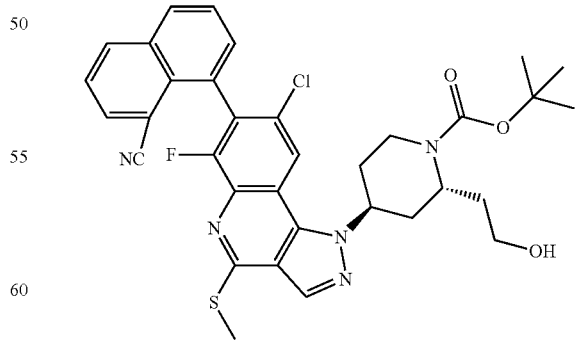

This compound was prepared according to the procedure described in Example 23a and 23b, in Step 16 replacing tert-butyl (2S,4S)-2-(2-((tert-butyldimethylsilyl)oxy)ethyl)-4-(8-chloro-7-(8-cyanoisoquinolin-1-yl)-6-fluoro-4-(methylthio)-1H-pyrazolo[4,3-c]quinolin-1-yl)piperidine-1-carboxylate with tert-butyl (2S,4S)-2-(2-((tert-butyldimethylsilyl)oxy)ethyl)-4-(8-chloro-7-(8-cyanonaphthalen-1-yl)-6-fluoro-4-(methylthio)-1H-pyrazolo[4,3-c]quinolin-1-yl)piperidine-1-carboxylate. LC-MS calculated for $C_{34}H_{34}ClFN_5O_3S$ (M+H)$^+$: m/z=646.2; found 646.2.

Step 13. tert-butyl (2S,4S)-4-(8-chloro-7-(8-cyanonaphthalen-1-yl)-6-fluoro-4-(methylthio)-1H-pyrazolo[4,3-c]quinolin-1-yl)-2-(cyanomethyl)piperidine-1-carboxylate

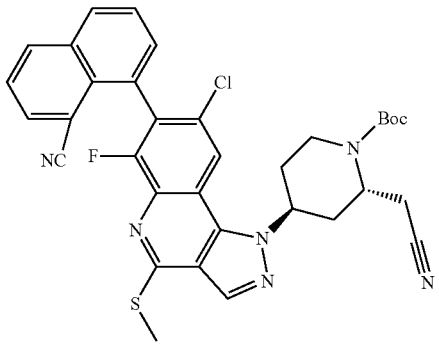 [SMILES: CSc1nc2c(F)c(-c3cccc4cccc(C#N)c34)c(Cl)cc2c2c1cnn2[C@H]1CCN(C(=O)OC(C)(C)C)[C@H](CC#N)C1]

This compound was prepared according to the procedure described in Example 23a and 23b, in Step 17 replacing tert-butyl (2S,4S)-4-(8-chloro-7-(8-cyanoisoquinolin-1-yl)-6-fluoro-4-(methylthio)-1H-pyrazolo[4,3-c]quinolin-1-yl)-2-(2-hydroxyethyl)piperidine-1-carboxylate with tert-butyl (2S,4S)-4-(8-chloro-7-(8-cyanonaphthalen-1-yl)-6-fluoro-4-(methylthio)-1H-pyrazolo[4,3-c]quinolin-1-yl)-2-(2-hydroxyethyl)piperidine-1-carboxylate. LC-MS calculated for $C_{34}H_{31}ClFN_6O_2S$ (M+H)$^+$: m/z=641.2; found 641.2.

Step 14. 8-(8-chloro-1-((2S,4S)-2-(cyanomethyl)piperidin-4-yl)-6-fluoro-4-((S)-1-((S)-1-methylpyrrolidin-2-yl)ethoxy)-1H-pyrazolo[4,3-c]quinolin-7-yl)-1-naphthonitrile

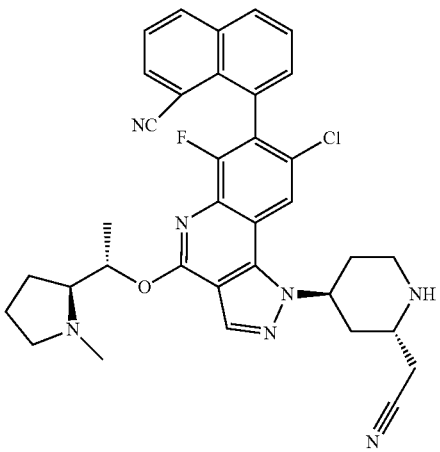 [SMILES: C[C@H](Oc1nc2c(F)c(-c3cccc4cccc(C#N)c34)c(Cl)cc2c2c1cnn2[C@H]1CCN[C@H](CC#N)C1)[C@@H]1CCCN1C]

This compound was prepared according to the procedure described in Example 23a and 23b, in Step 18 replacing of tert-butyl (2S,4S)-4-(8-chloro-7-(8-cyanoisoquinolin-1-yl)-6-fluoro-4-(methylthio)-1H-pyrazolo[4,3-c]quinolin-1-yl)-2-(cyanomethyl)piperidine-1-carboxylate with tert-butyl (2S,4S)-4-(8-chloro-7-(8-cyanonaphthalen-1-yl)-6-fluoro-4-(methylthio)-1H-pyrazolo[4,3-c]quinolin-1-yl)-2-(cyanomethyl)piperidine-1-carboxylate. LC-MS calculated for $C_{35}H_{34}ClFN_7O$ (M+H)$^+$: m/z=622.2; found 622.2.

Step 15. 8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-1H-pyrazolo[4,3-c]quinolin-7-yl)-1-naphthonitrile The title compounds was synthesized according to the procedure described for Example 23a and 23b, in Step 19 replacing of 1-(8-chloro-1-((2S,4S)-2-(cyanomethyl)piperidin-4-yl)-6-fluoro-4-((S)-1-((S)-1-methylpyrrolidin-2-yl)ethoxy)-1H-pyrazolo[4,3-c]quinolin-7-yl)isoquinoline-8-carbonitrile bis(2,2,2-trifluoroacetate) with 8-(8-chloro-1-((2S,4S)-2-(cyanomethyl)piperidin-4-yl)-6-fluoro-4-((S)-1-((S)-1-methylpyrrolidin-2-yl)ethoxy)-1H-pyrazolo[4,3-c]quinolin-7-yl)-1-naphthonitrile bis(2,2,2-trifluoroacetate).
LCMS calculated for $C_{37}H_{36}ClFN_7O_2$ (M+H)$^+$ m/z=664.3 found 664.3. $^1$H NMR (500 MHz, DMSO, mixture of rotamers) δ 9.79 (s, 1H), 8.54-8.49 (m, 3H), 8.34 (d, J=8.1 Hz, 1H), 8.16 (d, J=7.1 Hz, 1H), 7.88 (t, J=7.7 Hz, 1H), 7.81-7.70 (m, 2H), 5.81-5.73 (m, 1H), 5.49 (m, 1H), 5.20 (m, 0.5H), 4.67 (m, 1H), 4.03 (d, J=14.0 Hz, 0.5H), 3.87-3.81 (m, 1H), 3.69-3.60 (m, 2H), 3.58-3.52 (m, 1H), 3.27-3.07 (m, 5H), 2.36-2.04 (m, 9H), 1.91 (m, 2H), 1.53 (d, J=6.0 Hz, 3H).

Example 26: 3-(1-((1R,4R,5S)-2-Azabicyclo[2.1.1]hexan-5-yl)-6-fluoro-7-(7-fluoro-3-hydroxynaphthalen-1-yl)-2-methyl-4-(1H-1,2,4-triazol-1-yl)-1H-pyrrolo[3,2-c]quinolin-8-yl)propanenitrile

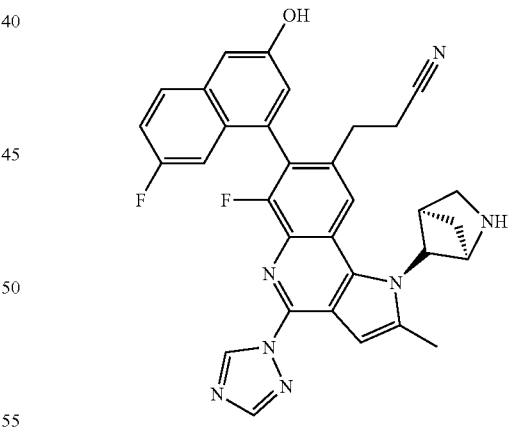

To a mixture of 6-fluoro-4-(4,4,5,5-tetramethyl-1,3,2-dioxaborolan-2-yl)naphthalen-2-ol (10.5 mg, 34 µmol, prepared as described in Example 22), Pd(PPh$_3$)$_4$ (2.0 mg, 1.7 µmol), and sodium carbonate (9.1 mg, 86 µmol) was added a solution of tert-butyl (1R,4R,5S)-5-(7-bromo-8-(2-cyanoethyl)-6-fluoro-2-methyl-4-(1H-1,2,4-triazol-1-yl)-1H-pyrrolo[3,2-c]quinolin-1-yl)-2-azabicyclo[2.1.1]hexane-2-carboxylate (10 mg, 17 µmol, Example 1, Step 5) in dioxane (1 ml). Water (0.3 ml) was added, and the reaction mixture was sparged with N$_2$ and heated to 100° C. for 1 h. The reaction mixture was filtered through a thiol siliaprep cartridge and concentrated. The residue was stirred in 1:1 DCM/TFA (3 mL) for 30 min, concentrated, and purified by prep HPLC (pH 2). LC-MS calculated for $C_{32}H_{26}F_2N_7O^+$ (M+H)$^+$: m/z=562.2; found 562.6. $^1$H NMR (600 MHz, DMSO-d$_6$) δ 9.54 (s, 1H), 8.46 (s, 1H), 8.25 (s, 1H), 7.97 (dd, J=9.2, 5.8 Hz, 1H), 7.45-7.40 (m, 1H), 7.39 (d, J=2.4 Hz, 1H), 7.34 (s, 1H), 7.24 (d, J=2.4 Hz, 1H), 6.94 (d, J=10.7 Hz, 1H), 5.53 (s, 1H), 5.07 (s, 1H), 3.93-3.87 (m, 2H), 3.42 (s, 1H), 3.08-3.01 (m, 1H), 2.98 (s, 1H), 2.82-2.71 (m, 3H), 2.63 (s, 3H), 2.36-2.30 (m, 1H), 1.60 (d, J=9.1 Hz, 1H).

Example 27. 3-(1-((1R,4R,5S)-2-Azabicyclo[2.1.1]hexan-5-yl)-6-fluoro-7-(7-fluoronaphthalen-1-yl)-2-methyl-4-((S)-1-((S)-1-methylpyrrolidin-2-yl)ethoxy)-1H-pyrrolo[3,2-c]quinolin-8-yl)propanenitrile

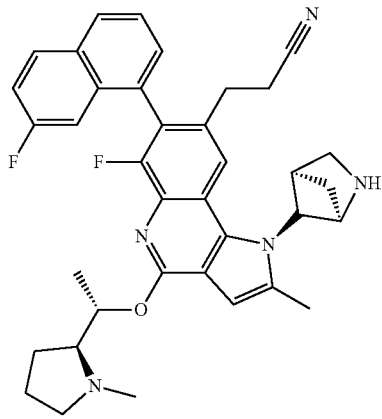

This compound was prepared according to the procedure described in Example 2, Step 2, utilizing 2-(7-fluoronaphthalen-1-yl)-4,4,5,5-tetramethyl-1,3,2-dioxaborolane (Intermediate 10) instead of tert-butyl 5,7-difluoro-3-(4,4,5,5-tetramethyl-1,3,2-dioxa-borolan-2-yl)-1H-indole-1-carboxylate. LC-MS calculated for $C_{37}H_{38}F_2N_5O^+$ (M+H)$^+$: m/z=606.3; found 606.3.

Example 28. (2R)-2-(l-((1R,4R,5S)-2-Azabicyclo[2.1.1]hexan-5-yl)-8-(2-cyanoethyl)-7-(2,3-dichlorophenyl)-6-fluoro-4-(1H-1,2,4-triazol-1-yl)-1H-pyrrolo[3,2-c]quinolin-2-yl)-N,N-dimethylpyrrolidine-1-carboxamide

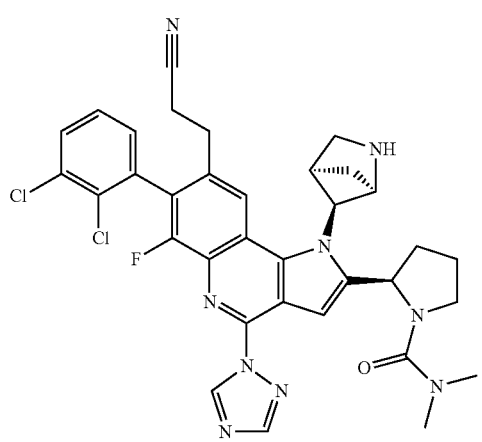 [SMILES: CN(C)C(=O)N1CCC[C@@H]1c1cc2c(-n3cncn3)nc3c(F)c(-c4cccc(Cl)c4Cl)c(CCC#N)cc3c2n1[C@H]1[C@H]2CN[C@@H]1C2]

Step 1. tert-butyl (1R,4R,5S)-5-((7-bromo-6-(2-cyanoethyl)-8-fluoro-2-(methylthio)-3-(((R)-1-((2-(trimethylsilyl)ethoxy)carbonyl)pyrrolidin-2-yl)ethynyl)quinolin-4-yl)amino)-2-azabicyclo[2.1.1]hexane-2-carboxylate

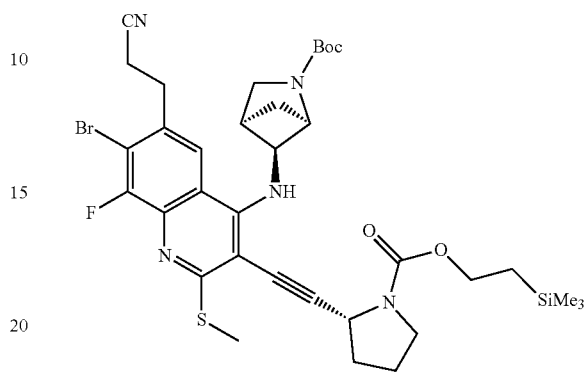

To a mixture of tert-butyl (1R,4R,5S)-5-((7-bromo-6-(2-cyanoethyl)-8-fluoro-3-iodo-2-(methylthio)quinolin-4-yl)amino)-2-azabicyclo[2.1.1]hexane-2-carboxylate (Intermediate 5, 1.0 g, 1.545 mmol) and Intermediate 17 (0.481 g, 2.008 mmol) were added DMF (7.7 ml) and triethylamine (0.646 ml, 4.63 mmol), followed by bis(triphenylphosphine)palladium(II) chloride (0.108 g, 0.154 mmol) and copper(I) iodide (0.294 g, 1.545 mmol). The reaction flask was evacuated, back filled with nitrogen, then stirred at 75° C. for 2 h. The reaction mixture was quenched with water and a small amount of 30% aq ammonium hydroxide, then extracted with ethyl acetate. The organic layer was washed with water and brine, dried over sodium sulfate and concentrated. The crude product was purified by flash column chromatography to provide the desired product (834 mg, 71%). LC-MS calculated for $C_{35}H_{46}BrFN_5O_4SSi$ (M+H)$^+$: m/z=758.0/760.0; found 758.0/760.0.

Step 2. tert-butyl (1R,4R,5S)-5-(7-bromo-8-(2-cyanoethyl)-6-fluoro-4-(methylthio)-2-((R)-1-((2-(trimethylsilyl)ethoxy)carbonyl)pyrrolidin-2-yl)-1H-pyrrolo[3,2-c]quinolin-1-yl)-2-azabicyclo[2.1.1]hexane-2-carboxylate

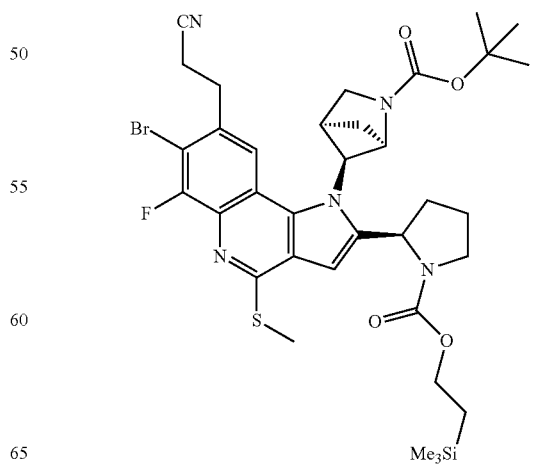

To a solution of tert-butyl (1R,4R,5S)-5-((7-bromo-6-(2-cyanoethyl)-8-fluoro-2-(methylthio)-3-(((R)-1-((2-(trimethylsilyl)ethoxy)carbonyl)pyrrolidin-2-yl)ethynyl)quinolin-4-yl)amino)-2-azabicyclo[2.1.1]hexane-2-carboxylate (834 mg, 1.10 mmol) in DMF (5.5 ml) was added cesium carbonate (1.07 g, 3.30 mmol) and the reaction mixture was heated to 90° C. for 2 h. The reaction was quenched with water and extracted with ethyl acetate. The organic layer was washed with water and brine, dried over sodium sulfate and concentrated. The crude product was purified by flash column chromatography to provide the desired product (532 mg, 64%). LC-MS calculated for $C_{35}H_{46}BrFN_5O_4SSi$ (M+H): m/z=758.0/760.0; found 758.0/760.0.

Step 3. tert-butyl (1R,4R,5S)-5-(7-bromo-8-(2-cyanoethyl)-6-fluoro-4-(1H-1,2,4-triazol-1-yl)-2-((R)-1-((2-(trimethylsilyl)ethoxy)carbonyl)pyrrolidin-2-yl)-1H-pyrrolo[3,2-c]quinolin-1-yl)-2-azabicyclo[2.1.1]hexane-2-carboxylate

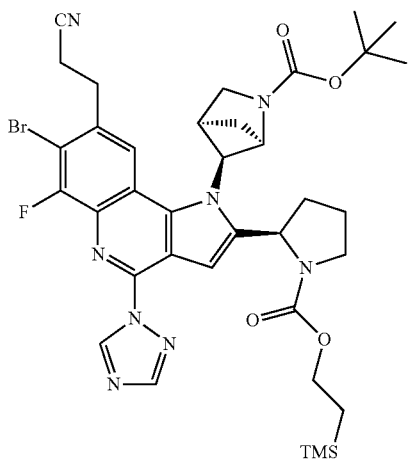 [SMILES: CC(C)(C)OC(=O)N1C[C@H]2C[C@@H]1[C@H]2n1c([C@H]2CCCN2C(=O)OCC[Si](C)(C)C)cc2c(-n3cncn3)nc3c(F)c(Br)c(CCC#N)cc3c21]

To a solution of tert-butyl (1R,4R,5S)-5-(7-bromo-8-(2-cyanoethyl)-6-fluoro-4-(methylthio)-2-((R)-1-((2-(trimethylsilyl)ethoxy)carbonyl)pyrrolidin-2-yl)-1H-pyrrolo[3,2-c]quinolin-1-yl)-2-azabicyclo[2.1.1]hexane-2-carboxylate (532 mg, 0.701 mmol) in DCM (3.5 ml) was added m-CPBA (173 mg, 0.771 mmol) and the reaction mixture was stirred at RT for 30 min, then quenched with sat. sodium bicarbonate. The mixture was diluted with water and extracted with DCM. The organic layer was dried over sodium sulfate and concentrated. The crude product was dissolved in DMF (3 mL) and 1H-1,2,4-triazole (58.1 mg, 0.841 mmol) and cesium carbonate (685 mg, 2.103 mmol) were added. The reaction mixture was heated to 80° C. for 30 min, then quenched with water and extracted with ethyl acetate. The organic layer was washed with water and brine, dried over sodium sulfate and concentrated. The crude product was used in the next step without further purification (505 mg, 92%). LC-MS calculated for $C_{36}H_{45}BrFN_8O_4Si$ (M+H)$^+$: m/z=779.2/781.2; found 779.2/781.2.

Step 4. tert-butyl (1R,4R,5S)-5-(7-bromo-8-(2-cyanoethyl)-2-((R)-1-(dimethylcarbamoyl)pyrrolidin-2-yl)-6-fluoro-4-(1H-1,2,4-triazol-1-yl)-1H-pyrrolo[3,2-c]quinolin-1-yl)-2-azabicyclo[2.1.1]hexane-2-carboxylate

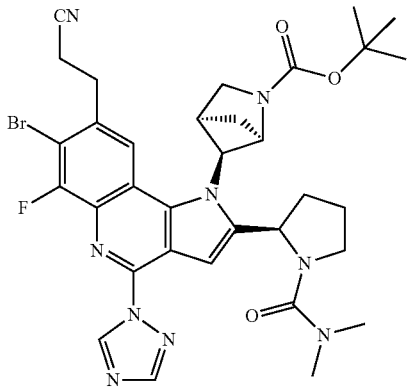 [SMILES: CN(C)C(=O)N1CCC[C@@H]1c1cc2c(-n3cncn3)nc3c(F)c(Br)c(CCC#N)cc3c2n1[C@H]1[C@@H]2C[C@H]1N(C(=O)OC(C)(C)C)C2]

To a solution of tert-butyl (1R,4R,5S)-5-(7-bromo-8-(2-cyanoethyl)-6-fluoro-4-(1H-1,2,4-triazol-1-yl)-2-((R)-1-((2-(trimethylsilyl)ethoxy)carbonyl)pyrrolidin-2-yl)-1H-pyrrolo[3,2-c]quinolin-1-yl)-2-azabicyclo[2.1.1]hexane-2-carboxylate (755 mg, 0.968 mmol) in Tetrahydrofuran (4.84 ml) was added TBAF (1162 μl, 1.162 mmol) and the reaction mixture was heated to 65° C. for 2 h. To an aliquot of this solution (150 mg, 0.236 mmol) were added triethylamine (99 μl, 0.708 mmol) and dimethylcarbamoyl chloride (28.2 μl, 0.307 mmol) and the reaction mixture was stirred at RT for 30 min, then quenched with water and extracted with ethyl acetate. The organic layer was washed with water and brine, dried over sodium sulfate and concentrated. The crude product was purified by flash column chromatography to provide the desired product (65 mg, 39%). LC-MS calculated for $C_{33}H_{38}BrFN_9O_3$ (M+H)$^+$: m/z=706.2/708.2; found 706.2/708.2. Step 5. (2R)-2-(1-((1R,4R,5S)-2-azabicyclo[2.1.1]hexan-5-yl)-8-(2-cyanoethyl)-7-(2,3-dichlorophenyl)-6-fluoro-4-(1H-1,2,4-triazol-1-yl)-1H-pyrrolo[3,2-c]quinolin-2-yl)-N,N-dimethylpyrrolidine-1-carboxamide To a mixture of tert-butyl (1R,4R,5S)-5-(7-bromo-8-(2-cyanoethyl)-2-((R)-1-(dimethylcarbamoyl)pyrrolidin-2-yl)-6-fluoro-4-(1H-1,2,4-triazol-1-yl)-1H-pyrrolo[3,2-c]quinolin-1-yl)-2-azabicyclo[2.1.1]hexane-2-carboxylate (65 mg, 0.092 mmol), (2,3-dichlorophenyl)boronic acid (35.1 mg, 0.184 mmol), tetrakis(triphenylphosphine)palladium(0) (10.63 mg, 9.20 μmol) and sodium carbonate (29.2 mg, 0.276 mmol) were added 1,4-Dioxane (0.800 ml)/Water (0.200 ml) and the reaction flask was evacuated, back filled with nitrogen, then stirred at 100° C. overnight. The reaction mixture was diluted with DCM and filtered through a plug of Celite. The filtrate was concentrated and the residue was dissolved in 1:1 DCM/TFA (1 mL). After standing for 30 mins, the mixture was diluted with MeOH and purified by prep HPLC (pH 2) to provide the desired product. LC-MS calculated for $C_{34}H_{33}Cl_2FN_9O$ (M+H)$^+$: m/z=672.2; found 672.2.

Example 29. Methyl (2R)-2-(1-((1R,4R,5S)-2-azabicyclo[2.1.1]hexan-5-yl)-7-(2-chloro-3-methylphenyl)-8-(2-cyanoethyl)-6-fluoro-4-(1H-1,2,4-triazol-1-yl)-1H-pyrrolo[3,2-c]quinolin-2-yl)pyrrolidine-1-carboxylate

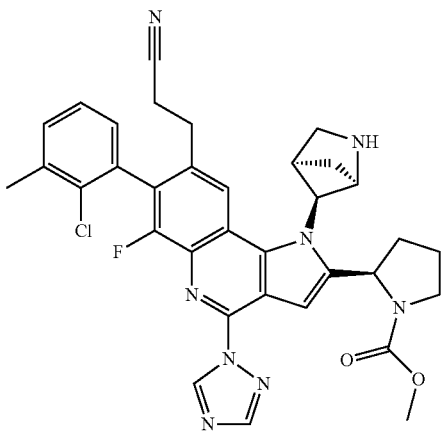 [SMILES: COC(=O)N1CCC[C@@H]1c1cc2c(-n3cncn3)nc3c(F)c(-c4cccc(C)c4Cl)c(CCC#N)cc3c2n1[C@H]1[C@H]2CN[C@@H]1C2]

Step 1. tert-butyl (1R,4R,5S)-5-(7-(2-chloro-3-methylphenyl)-8-(2-cyanoethyl)-6-fluoro-4-(1H-1,2,4-triazol-1-yl)-2-((R)-1-((2-(trimethylsilyl)ethoxy)carbonyl)pyrrolidin-2-yl)-1H-pyrrolo[3,2-c]quinolin-1-yl)-2-azabicyclo[2.1.1]hexane-2-carboxylate

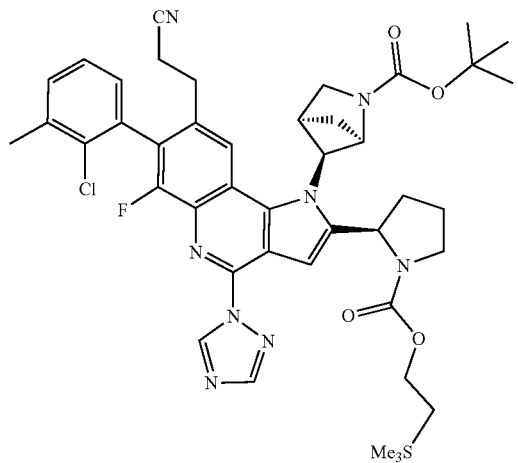

To a mixture of tert-butyl (1R,4R,5S)-5-(7-bromo-8-(2-cyanoethyl)-6-fluoro-4-(1H-1,2,4-triazol-1-yl)-2-((R)-1-((2-(trimethylsilyl)ethoxy)carbonyl)pyrrolidin-2-yl)-1H-pyrrolo[3,2-c]quinolin-1-yl)-2-azabicyclo[2.1.1]hexane-2-carboxylate (Example 28, Step 3; 227 mg, 0.291 mmol), (2-chloro-3-methylphenyl)boronic acid (74.4 mg, 0.437 mmol), tetrakis(triphenylphosphine)palladium(0) (33.6 mg, 0.029 mmol) and sodium carbonate (93 mg, 0.873 mmol) were added 1,4-Dioxane (1.2 ml)/Water (0.300 ml) and the reaction flask was evacuated, back filled with nitrogen, then stirred at 100° C. overnight. The mixture was diluted with DCM and filtered through a plug of Celite. The filtrate was concentrated and the crude residue was purified by flash column chromatography to provide the desired product (111 mg, 46%). LC-MS calculated for $C_{43}H_{51}ClFN_8O_4Si$ (M+H)$^+$: m/z=825.3; found 825.3.

Step 2. methyl (2R)-2-(1-((1R,4R,5S)-2-azabicyclo[2.1.1]hexan-5-yl)-7-(2-chloro-3-methylphenyl)-8-(2-cyanoethyl)-6-fluoro-4-(1H-1,2,4-triazol-1-yl)-1H-pyrrolo[3,2-c]quinolin-2-yl)pyrrolidine-1-carboxylate To a solution of tert-butyl (1R,4R,5S)-5-(7-(2-chloro-3-methylphenyl)-8-(2-cyanoethyl)-6-fluoro-4-(1H-1,2,4-triazol-1-yl)-2-((R)-1-((2-(trimethylsilyl)ethoxy)carbonyl)pyrrolidin-2-yl)-1H-pyrrolo[3,2-c]quinolin-1-yl)-2-azabicyclo[2.1.1]hexane-2-carboxylate (111 mg, 0.134 mmol) in THF (0.672 ml) was added TBAF (161 µl, 0.161 mmol) and the reaction mixture was heated to 65° C. for 2 hr, then cooled to RT. Triethylamine (56.2 µl, 0.403 mmol) and methyl chloroformate (15.62 µl, 0.202 mmol) were added and the reaction mixture was stirred at RT for 30 min, then quenched with water and extracted with ethyl acetate. The organic layer was washed with water and brine, dried over sodium sulfate and concentrated. The crude product was dissolved in 1:1 DCM/TFA (2 mL) and stirred at RT for 30 mins, then diluted with MeOH and purified by prep HPLC (pH 2) to provide the desired product. LC-MS calculated for $C_{34}H_{33}ClFN_8O_2$ (M+H)$^+$: m/z=639.2; found 639.2.

Example 30. Methyl (1S,3R,5S)-3-(1-((1R,4R,5S)-2-azabicyclo[2.1.1]hexan-5-yl)-8-(2-cyanoethyl)-7-(2,3-dichlorophenyl)-4-(6-(dimethylcarbamoyl)pyridin-3-yl)-6-fluoro-1H-pyrrolo[3,2-c]quinolin-2-yl)-2-azabicyclo[3.1.0]hexane-2-carboxylate

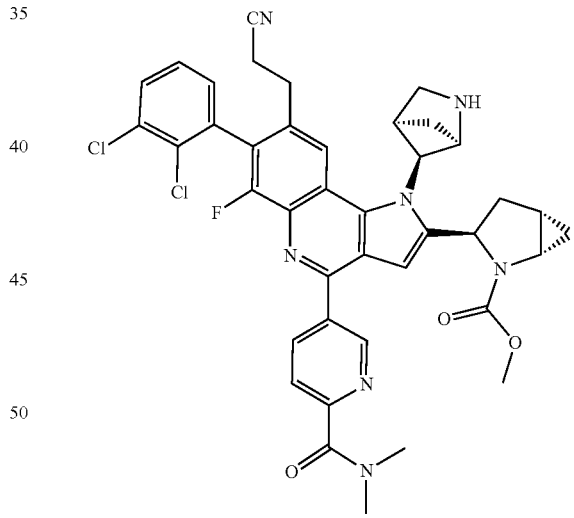

Step 1. tert-Butyl (1S,3R,5S)-3-(hydroxymethyl)-2-azabicyclo[3.1.0]hexane-2-carboxylate

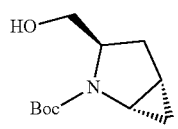

To a solution of (1S,3R,5S)-2-(tert-butoxycarbonyl)-2-azabicyclo[3.1.0]hexane-3-carboxylic acid (4.9 g, 21.56 mmol) in THF (71.9 ml) at 0° C. were added triethylamine (3.61 ml, 25.9 mmol) and isobutyl chloroformate (2.83 ml, 21.56 mmol) and the reaction mixture was warmed up to r.t. and stirred for 1 h. The reaction was then filtered and the solid washed with THF. The filtrate was cooled to 0° C. and a solution of sodium borohydride (1.631 g, 43.1 mmol) in water (~5 mL) was added dropwise. The reaction mixture was stirred at r.t. for 30 min, then quenched with 1N HCl and extracted with ethyl acetate. The organic layer was washed with water and brine, dried over sodium sulfate and concentrated. The crude product was used in the next step without further purification (4.6 g, 100%). LC-MS calculated for $C_7H_{12}NO_3+(M+H-C_4H_8)^+$: m/z=158.1; found 158.1.

Step 2. tert-Butyl (1S,3R,5S)-3-formyl-2-azabicyclo[3.1.0]hexane-2-carboxylate

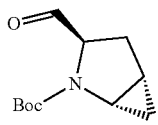 [SMILES: CC(C)(C)OC(=O)N1[C@@H](C=O)C[C@@H]2C[C@@H]21]

To a −78° C. solution of oxalyl chloride (2.077 ml, 23.73 mmol) in DCM (60 mL) was added a solution of DMSO (3.37 ml, 47.5 mmol) in DCM (4 mL) dropwise. The reaction mixture was stirred at −78° C. for 45 min, then a solution of tert-butyl (1S,3R,5S)-3-(hydroxymethyl)-2-azabicyclo[3.1.0]hexane-2-carboxylate (4.6 g, 21.57 mmol) in DCM (5 mL) was added dropwise. The reaction mixture was stirred at −78° C. for 2 h, then triethylamine (9.02 ml, 64.7 mmol) was added slowly. The reaction mixture was stirred at −78° C. for 1 h, then warmed up to r.t and stirred for an additional 1 h. The reaction was then quenched with 1 N HCl and extracted with DCM. The organic layer was washed with water and brine, dried over sodium sulfate and concentrated. The crude product was used in the next step without further purification. LC-MS calculated for $C_7H_{10}NO_3+(M+H-C_4H_8)^+$: m/z=156.1; found 156.1.

Step 3. tert-Butyl (1S,3R,5S)-3-ethynyl-2-azabicyclo[3.1.0]hexane-2-carboxylate

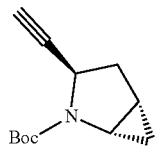

To a solution of tert-butyl (1S,3R,5S)-3-formyl-2-azabicyclo[3.1.0]hexane-2-carboxylate (4.6 g, 21.77 mmol) in MeOH (72.6 ml) at 0° C. were added potassium carbonate (6.02 g, 43.5 mmol) and dimethyl (1-diazo-2-oxopropyl)phosphonate (3.27 ml, 21.77 mmol) dropwise. The reaction mixture was allowed to warm to r.t. overnight, then concentrated. The crude residue was partitioned between water and ethyl acetate. The organic layer was washed with water and brine, dried over sodium sulfate and concentrated. The crude product was purified by flash column chromatography (0-50% acetone in hexanes) to provide the desired product (3.46 g, 77%). LC-MS calculated for $C_8H_{10}NO_2+(M+H-C_4H_8)^+$: m/z=152.1; found 152.1.

Step 4. Methyl (1S,3R,5S)-3-ethynyl-2-azabicyclo[3.1.0]hexane-2-carboxylate

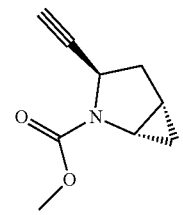

A solution of tert-butyl (1S,3R,5S)-3-ethynyl-2-azabicyclo[3.1.0]hexane-2-carboxylate (1 g, 4.82 mmol) in HCl (4N in dioxane, 2.412 ml, 9.65 mmol) was stirred at r.t. for 30 min, then diluted with THF (16.08 ml) and cooled to 0° C. Triethylamine (3.36 ml, 24.12 mmol) and methyl chloroformate (0.448 ml, 5.79 mmol) were added and the reaction mixture was warmed to r.t. and stirred for 1 h, then quenched with water and extracted with ethyl acetate. The organic layer was washed with water and brine, dried over sodium sulfate and concentrated. The crude product was used in the next step without further purification (797 mg, 100%). LC-MS calculated for $C_9H_{12}NO_2+(M+H)^+$: m/z=166.1; found 166.1.

Step 5. tert-Butyl (1R,4R,5S)-5-(7-bromo-8-(2-cyanoethyl)-6-fluoro-2-((1S,3R,5S)-2-(methoxycarbonyl)-2-azabicyclo[3.1.0]hexan-3-yl)-4-(methylthio)-1H-pyrrolo[3,2-c]quinolin-1-yl)-2-azabicyclo[2.1.1]hexane-2-carboxylate

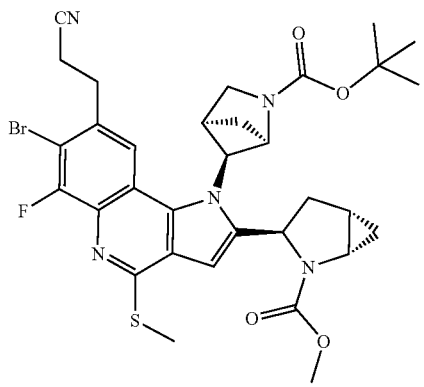 [SMILES: COC(=O)N1[C@@H](c2cc3c(SC)nc4c(F)c(Br)c(CCC#N)cc4c3n2[C@H]2[C@@H]3C[C@H]2N(C(=O)OC(C)(C)C)C3)C[C@@H]2C[C@@H]21]

To a mixture of Intermediate 5 (1.5 g, 2.317 mmol) and methyl (1S,3R,5S)-3-ethynyl-2-azabicyclo[3.1.0]hexane-2-carboxylate (0.574 g, 3.48 mmol) were added DMF (5.79 ml) and triethylamine (0.969 ml, 6.95 mmol), followed by tetrakis(triphenylphosphine)palladium(0) (0.268 g, 0.232 mmol) and copper(I) iodide (0.441 g, 2.317 mmol). The reaction flask was evacuated, back filled with nitrogen, then stirred at 70° C. for 2 h. Cesium carbonate (1.510 g, 4.63 mmol) was then added and the reaction mixture was heated to 80° C. for 2 h. The reaction was quenched with water and a small amount of sat. aq. ammonium hydroxide, then diluted with ethyl acetate and filtered through a plug of Celite. The filtrate layers were separated and the organic layer was washed with water and brine, dried over sodium sulfate and concentrated. The crude product was purified by flash column chromatography (0-60% acetone in hexanes) to provide the desired product (924 mg, 58%). LC-MS calculated for $C_{32}H_{36}BrFN_5O_4S^+$ $(M+H)^+$: m/z=684.2/686.2; found 684.2/686.2.

Step 6. tert-Butyl (1R,4R,5S)-5-(8-(2-cyanoethyl)-7-(2,3-dichlorophenyl)-6-fluoro-2-((1S,3R,5S)-2-(methoxycarbonyl)-2-azabicyclo[3.1.0]hexan-3-yl)-4-(methylthio)-1H-pyrrolo[3,2-c]quinolin-1-yl)-2-azabicyclo[2.1.1]hexane-2-carboxylate

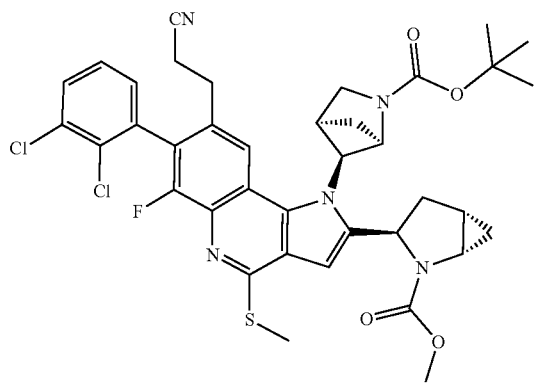 [SMILES: COC(=O)N1[C@@H](c2cc3c(SC)nc4c(F)c(-c5cccc(Cl)c5Cl)c(CCC#N)cc4c3n2[C@H]2[C@@H]3C[C@H]2N(C(=O)OC(C)(C)C)C3)C[C@@H]2C[C@@H]21]

To a mixture of tert-butyl (1R,4R,5S)-5-(7-bromo-8-(2-cyanoethyl)-6-fluoro-2-((1 S,3R,5S)-2-(methoxycarbonyl)-2-azabicyclo[3.1.0]hexan-3-yl)-4-(methylthio)-1H-pyrrolo[3,2-c]quinolin-1-yl)-2-azabicyclo[2.1.1]hexane-2-carboxylate (924 mg, 1.350 mmol), (2,3-dichlorophenyl)boronic acid (309 mg, 1.620 mmol), potassium fluoride (235 mg, 4.05 mmol) and Pd-132 (96 mg, 0.135 mmol) were added 1,4-dioxane (3.60 ml)/water (0.900 ml) and the reaction flask was evacuated, back filled with nitrogen, then stirred at 100° C. for 2 h. The reaction mixture was diluted with DCM and filtered through a plug of Celite. The filtrate was concentrated and the crude product was purified by flash column chromatography (0-65% acetone in hexanes) to provide the desired product. LC-MS calculated for $C_{38}H_{39}Cl_2FN_5O_4S^+$ $(M+H)^+$: m/z=750.2/752.2; found 750.2/752.2.

Step 7. Methyl (1S,3R,5S)-3-(1-((1R,4R,5S)-2-azabicyclo[2.1.1]hexan-5-yl)-8-(2-cyanoethyl)-7-(2,3-dichlorophenyl)-4-(6-(dimethylcarbamoyl)pyridin-3-yl)-6-fluoro-1H-pyrrolo[3,2-c]quinolin-2-yl)-2-azabicyclo[3.1.0]hexane-2-carboxylate To a mixture of tert-butyl (1R,4R,5S)-5-(8-(2-cyanoethyl)-7-(2,3-dichlorophenyl)-6-fluoro-2-((1 S,3R,5S)-2-(methoxycarbonyl)-2-azabicyclo[3.1.0]hexan-3-yl)-4-(methylthio)-1H-pyrrolo[3,2-c]quinolin-1-yl)-2-azabicyclo[2.1.1]hexane-2-carboxylate (592 mg, 0.789 mmol), N,N-dimethyl-5-(4,4,5,5-tetramethyl-1,3,2-dioxaborolan-2-yl)picolinamide (436 mg, 1.577 mmol), tetrakis(triphenylphosphine)palladium(0) (91 mg, 0.079 mmol) and copper(I) 3-methylsalicylate (508 mg, 2.366 mmol) was added 1,4-dioxane (1.971 ml) and the reaction flask was evacuated, back filled with nitrogen, then stirred at 100° C. for 3 h. The reaction was quenched with water and sat. aq. ammonium hydroxide, then diluted with ethyl acetate and filtered through a plug of Celite. The layers of the filtrate were separated and the organic layer was washed with water and brine, dried over sodium sulfate and concentrated. The crude product was purified by flash column chromatography (0-80% acetone in hexanes). The purified product was dissolved in 1:1 TFA/DCM (10 mL) and stirred at r.t. for 1 h, then concentrated. The crude residue was diluted with acetonitrile and purified by prep HPLC (pH 2) to provide the desired product. LC-MS calculated for $C_{40}H_{37}Cl_2FN_7O_3^+$ $(M+H)^+$: m/z=752.2/754.2; found 752.2/754.2. $^1$H NMR (600 MHz, DMSO) δ 9.48 (s, 1H), 9.16 (s, 1H), 8.47 (d, J=7.3 Hz, 1H), 8.21 (s, 1H), 8.14 (s, 1H), 7.85 (dd, J=8.1, 1.3 Hz, 1H), 7.83 (d, J=8.1 Hz, 1H), 7.59 (t, J=7.9 Hz, 1H), 7.51 (d, J=6.6 Hz, 1H), 6.82 (s, 1H), 5.60 (s, 1H), 5.14 (d, J=7.7 Hz, 1H), 4.89 (d, J=4.9 Hz, 1H), 3.91 (s, 1H), 3.73 (s, 3H), 3.54 (dd, J=8.1, 3.9 Hz, 2H), 3.43 (s, 1H), 3.07 (s, 3H), 3.05 (s, 3H), 2.96-2.82 (m, 2H), 2.70 (dt, J=15.5, 7.1 Hz, 1H), 2.58 (dd, J=12.1, 9.1 Hz, 1H), 2.33 (d, J=8.4 Hz, 1H), 2.11-1.99 (bs, 1H), 1.61 (d, J=8.9 Hz, 2H), 0.94 (dt, J=9.8, 5.1 Hz, 1H), 0.67 (s, 1H).

Example 31. 3-(1-((1R,4R,5S)-2-Azabicyclo[2.1.1]hexan-5-yl)-7-(2,3-dichlorophenyl)-6-fluoro-4-methyl-2-(5-oxo-1,2,3,5-tetrahydroindolizin-3-yl)-1H-pyrrolo[3,2-c]quinolin-8-yl)propanenitrile

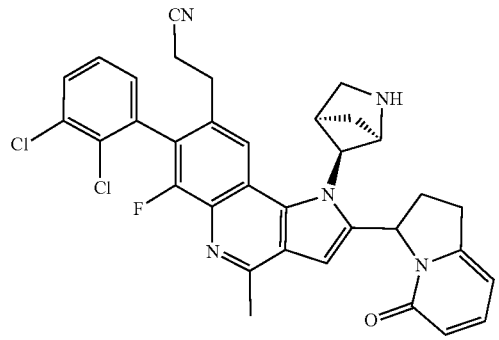 [SMILES: Cc1nc2c(F)c(-c3cccc(Cl)c3Cl)c(CCC#N)cc2c2c1cc(C1CCc3cccc(=O)n31)n2[C@H]1[C@H]2CN[C@@H]1C2]

Step 1: N-methoxy-N-methyl-5-oxo-1,2,3,5-tetrahydroindolizine-3-carboxamide

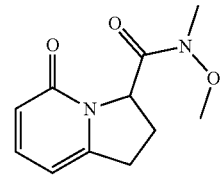 [SMILES: CON(C)C(=O)C1CCc2cccc(=O)n21]

A vial was charged with commercially available 5-oxo-1,2,3,5-tetrahydroindolizine-3-carboxylic acid (250 mg, 1.395 mmol), N,O-dimethylhydroxylamine hydrochloride (204 mg, 2.093 mmol), DMF (7 ml), and DIEA (0.675 ml, 3.86 mmol). The reaction mixture was stirred at room temperature for 5 min, then HATU (562 mg, 1.479 mmol) was added. The reaction mixture was stirred at room temperature for 1 h. The reaction mixture was quenched with water and extracted into DCM. The combined organic Step 4. tert-butyl (1R,4R,5S)-5-(8-(2-cyanoethyl)-7-(2,3-dichlorophenyl)-6-fluoro-4-(methylthio)-2-(-5-oxo-1,2,3,5-tetrahydroindolizin-3-yl)-1H-pyrrolo[3,2-c]quinolin-1-yl)-2-azabicyclo[2.1.1]hexane-2-carboxylate

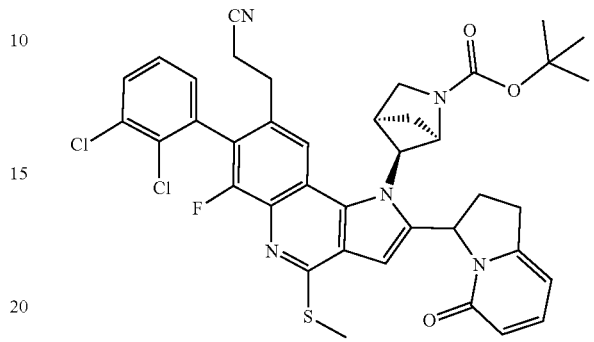

This compound was prepared in an analogous fashion to Intermediate 18, with 3-ethynyl-2,3-dihydroindolizin-5(1H)-one replacing 2-(trimethylsilyl)ethyl (R)-2-ethynylpyrrolidine-1-carboxylate. LCMS calculated for $C_{39}H_{37}Cl_2FN_5O_3S^+$ $(M+H)^+$: m/z=744.2/746.2; found 744.2/746.2.

Step 5. 3-(1-((1R,4R,5S)-2-azabicyclo[2.1.1]hexan-5-yl)-7-(2,3-dichlorophenyl)-6-fluoro-4-methyl-2-(5-oxo-1,2,3,5-tetrahydroindolizin-3-yl)-1H-pyrrolo[3,2-c]quinolin-8-yl)propanenitrile To a solution of tert-butyl (1R,4R,5S)-5-(8-(2-cyanoethyl)-7-(2,3-dichlorophenyl)-6-fluoro-4-(methylthio)-2-(5-oxo-1,2,3,5-tetrahydroindolizin-3-yl)-1H-pyrrolo[3,2-c]quinolin-1-yl)-2-azabicyclo[2.1.1]hexane-2-carboxylate (20 mg, 0.027 mmol) in DCM (0.269 ml) at 0° C. was added m-CPBA (7.22 mg, 0.032 mmol) and the reaction mixture was stirred at r.t. for 30 min, then quenched with sat. sodium bicarbonate and extracted with DCM. The organic layer was dried over sodium sulfate and concentrated. The crude product was dissolved in THF (0.8 mL) and cooled to 0° C. Methylmagnesium bromide (3M in diethyl ether, 8.95 µl, 0.027 mmol) was added dropwise and the reaction mixture was stirred at 0° C. for 1 h, then quenched with sat. ammonium chloride and extracted with ethyl acetate. The organic layer was washed with water and brine, dried over sodium sulfate and concentrated. The crude product was allowed to stand in 1:1 DCM/TFA (1 mL) for 15 min, then diluted with MeOH and purified by prep HPLC (pH 2) to provide the desired product. LCMS calculated for $C_{34}H_{29}Cl_2FN_5O^+$ $(M+H)^+$: m/z=612.2/614.2; found 612.2/614.2. A single isomer was isolated after purification. The stereochemistry at the pyrrole 2-position was not determined.

fractions were dried over magnesium sulfate, filtered, and concentrated. The crude residue was purified by flash column chromatography (0-20% MeOH in DCM) to afford the product as a white crystalline solid (0.249 g, 80% yield). LCMS calculated for $C_{11}H_{15}N_2O_3+(M+H)^+$: m/z=223.1; found 223.1.

Step 2:
5-oxo-1,2,3,5-tetrahydroindolizine-3-carbaldehyde

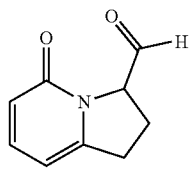 [SMILES: O=CC1CCc2cccc(=O)n21]

To a cooled (−45° C.) THF (11.2 mL) solution of N-methoxy-N-methyl-5-oxo-1,2,3,5-tetrahydroindolizine-3-carboxamide (0.25 g) was added a 1 M solution of lithium aluminum hydride in THF (1.34 mL) over 10 minutes. The reaction mixture was stirred at −45° C. for 30 minutes, 0° C. for 90 minutes then cooled to −45° C., and a solution of potassium hydrogen sulfate (0.305 g) in water (1.0 mL) was added. The mixture was warmed to room temperature, filtered, and concentrated. The crude material was taken to the next step without further purification (0.2 g, 100% yield). LCMS calculated for $C_9H_{10}NO_2$ $(M+H)^+$: m/z=164.1; found 164.1.

Step 3: 3-ethynyl-2,3-dihydroindolizin-5(1H)-one

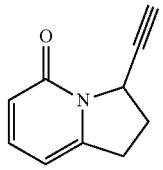

To a cooled (0° C.) solution of 5-oxo-1,2,3,5-tetrahydroindolizine-3-carbaldehyde (0.215 g, 1.32 mmol) in methanol (6.6 ml) was added potassium carbonate (0.364 g, 2.64 mmol) followed directly by dimethyl (1-diazo-2-oxopropyl)phosphonate (0.217 ml, 1.45 mmol). The reaction solution was stirred at 0° C. for 2 hours. The reaction was quenched with water and extracted with DCM. The combined organic fractions were dried over magnesium sulfate then concentrated. The crude material was purified by flash column chromatography (0-20% MeOH in DCM) to afford the desired product (0.114 g, 54% yield). LCMS calculated for $C_{10}H_{10}NO$ $(M+H)^+$: m/z=160.1; found 160.1

Example 32. Methyl (2R)-2-(1-((1R,4R,5S)-2-azabicyclo[2.1.1]hexan-5-yl)-8-(2-cyanoethyl)-7-(2,3-dichlorophenyl)-4-(6-(dimethylcarbamoyl)pyridin-3-yl)-6-fluoro-1H-pyrrolo[3,2-c]quinolin-2-yl)pyrrolidine-1-carboxylate

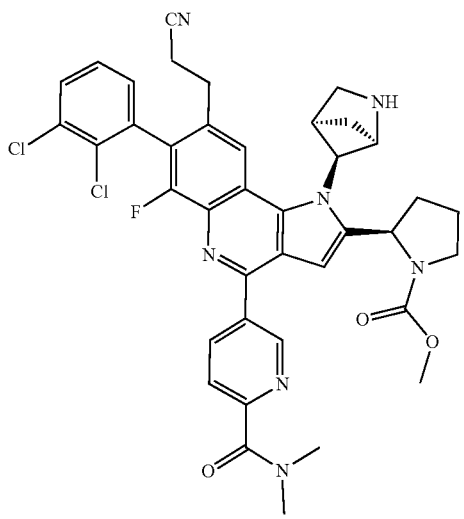 [SMILES: COC(=O)N1CCC[C@@H]1c1cc2c(-c3ccc(C(=O)N(C)C)nc3)nc3c(F)c(-c4cccc(Cl)c4Cl)c(CCC#N)cc3c2n1[C@H]1[C@H]2CN[C@@H]1C2]

Step 1. tert-butyl (1R,4R,5S)-5-(8-(2-cyanoethyl)-7-(2,3-dichlorophenyl)-4-(6-(dimethylcarbamoyl)pyridin-3-yl)-6-fluoro-2-((R)-1-((2-(trimethylsilyl)ethoxy)carbonyl)pyrrolidin-2-yl)-1H-pyrrolo[3,2-c]quinolin-1-yl)-2-azabicyclo[2.1.1]hexane-2-carboxylate

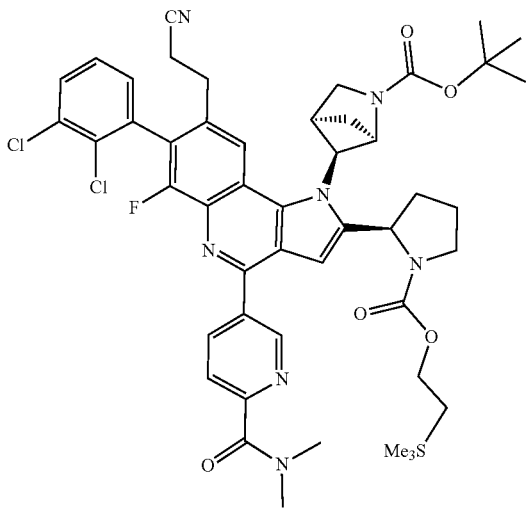

To a mixture of Intermediate 18 (416 mg, 0.504 mmol), N,N-dimethyl-5-(4,4,5,5-tetramethyl-1,3,2-dioxaborolan-2-yl)picolinamide (279 mg, 1.009 mmol), tetrakis(triphenylphosphine) palladium(0) (58.3 mg, 0.050 mmol) and Copper(I) 3-methylsalicylate (325 mg, 1.513 mmol) was added 1,4-dioxane (2.5 ml) and the reaction flask was evacuated, back filled with nitrogen, then stirred at 100° C. overnight. The reaction was quenched with water and sat. aq. ammonium hydroxide, then extracted with ethyl acetate. The organic layer was washed with water and brine, dried over sodium sulfate and concentrated. The crude product was purified by flash chromatography (0-7% MeOH in DCM) to provide the desired product (465 mg, 99%). LC-MS calculated for $C_{48}H_{55}Cl_2FN_7O_5Si^+$ (M+H)$^+$: m/z=926.3/928.3; found 926.3/928.3.

Step 2. Methyl (2R)-2-(1-((1R,4R,5S)-2-azabicyclo[2.1.1]hexan-5-yl)-8-(2-cyanoethyl)-7-(2,3-dichlorophenyl)-4-(6-(dimethylcarbamoyl)pyridin-3-yl)-6-fluoro-1H-pyrrolo[3,2-c]quinolin-2-yl)pyrrolidine-1-carboxylate To a solution of tert-butyl (1R,4R,5S)-5-(8-(2-cyanoethyl)-7-(2,3-dichlorophenyl)-4-(6-(dimethylcarbamoyl)pyridin-3-yl)-6-fluoro-2-((R)-1-((2-(trimethylsilyl)ethoxy)carbonyl)pyrrolidin-2-yl)-1H-pyrrolo[3,2-c]quinolin-1-yl)-2-azabicyclo[2.1.1]hexane-2-carboxylate (465 mg, 0.502 mmol) in THF (2.5 ml) was added TBAF (1 M in THF, 602 µl, 0.602 mmol) and the reaction mixture was heated to 65° C. for 1 h, then cooled to 0° C. To the reaction mixture were added triethylamine (210 µl, 1.506 mmol) and methyl chloroformate (58.3 µl, 0.753 mmol) and the reaction mixture was stirred at r.t. for 30 min, then quenched with water and extracted with ethyl acetate. The organic layer was washed with water and brine, dried over sodium sulfate and concentrated. The crude product was purified by flash chromatography (0-100% acetone in hexanes) to provide the desired intermediate. This was allowed to stand in 1:1 TFA/DCM (1 mL) for 15 min, then diluted with MeOH and purified by prep HPLC (pH 2) to provide the desired product. LC-MS calculated for $C_{39}H_{37}Cl_2FN_7O_3^+$ (M+H)$^+$: m/z=740.2/742.2; found 740.2/742.2. $^1$H NMR (600 MHz, DMSO) δ 9.79-9.61 (m, 1H), 9.15 (s, 1H), 8.47 (t, J=6.9 Hz, 1H), 8.31-8.08 (m, 2H), 7.89-7.75 (m, 2H), 7.59 (t, J=7.9 Hz, 1H), 7.50 (d, J=6.5 Hz, 1H), 6.67 (s, 1H), 5.67 (s, 1H), 5.17 (t, J=8.5 Hz, 1H), 4.90 (dd, J=13.3, 5.7 Hz, 1H), 4.01-3.90 (m, 2H), 3.72-3.60 (m, 4H), 3.52-3.38 (m, 2H), 3.07 (s, 3H), 3.04 (s, 3H), 2.94-2.80 (m, 2H), 2.71 (dt, J=15.2, 7.1 Hz, 1H), 2.40-2.32 (m, 2H), 1.94-1.80 (m, 2H), 1.75-1.57 (m, 2H).

Example 33. Methyl (2R)-2-(1-((1R,4R,5S)-2-azabicyclo[2.1.1]hexan-5-yl)-8-(2-cyanoethyl)-7-(2,3-dichlorophenyl)-6-fluoro-4-(6-(methylcarbamoyl)pyridin-3-yl)-1H-pyrrolo[3,2-c]quinolin-2-yl)pyrrolidine-1-carboxylate

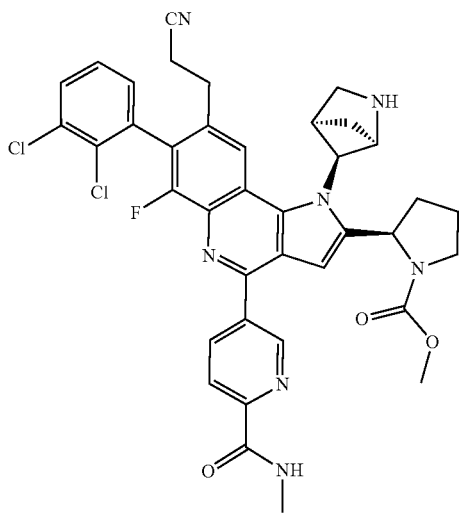 [SMILES: CNC(=O)c1ccc(-c2nc3c(F)c(-c4cccc(Cl)c4Cl)c(CCC#N)cc3c3c2cc([C@H]2CCCN2C(=O)OC)n3[C@H]2[C@H]3CN[C@@H]2C3)cn1]

This compound was prepared in an analogous fashion to Example 32, with N-methyl-5-(4,4,5,5-tetramethyl-1,3,2-dioxaborolan-2-yl)picolinamide replacing N,N-dimethyl-5-(4,4,5,5-tetramethyl-1,3,2-dioxaborolan-2-yl)picolinamide in Step 2. LC-MS calculated for $C_{38}H_{35}Cl_2FN_7O_3^+$ (M+H)$^+$: m/z=726.2/728.2; found 726.2/728.2. $^1$H NMR (600 MHz, DMSO) δ 9.17 (d, J=1.7 Hz, 1H), 8.48 (dd, J=8.1, 2.1 Hz, 1H), 8.20 (s, 1H), 7.87-7.76 (m, 2H), 7.58 (t, J=7.9 Hz, 1H), 7.49 (d, J=7.6 Hz, 1H), 6.68 (s, 1H), 5.63 (s, 1H), 5.18 (d, J=8.1 Hz, 1H), 4.93 (s, 1H), 3.98 (s, 1H), 3.70 (m, 5H), 3.47 (q, J=9.8 Hz, 2H), 3.08 (s, 5H), 2.88 (dq, J=12.7, 5.6 Hz, 2H), 2.77-2.68 (m, 1H), 2.37 (d, J=8.4 Hz, 2H), 1.89 (s, 2H), 1.66 (d, J=9.2 Hz, 1H).

Example 34. 3-(1-((1R,4R,5S)-2-Azabicyclo[2.1.1]hexan-5-yl)-7-(2-chloro-3-fluorophenyl)-2-((R)-1-(cyclopropanecarbonyl)pyrrolidin-2-yl)-6-fluoro-4-methyl-1H-pyrrolo[3,2-c]quinolin-8-yl)propanenitrile

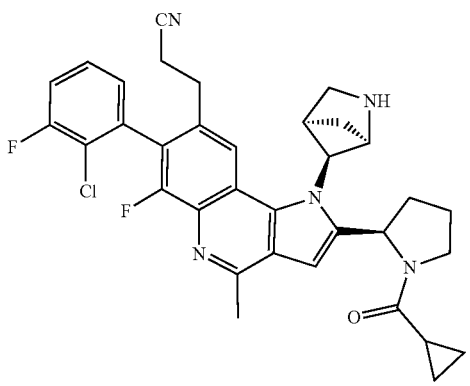 [SMILES: Cc1nc2c(F)c(-c3cccc(F)c3Cl)c(CCC#N)cc2c2c1cc([C@H]1CCCN1C(=O)C1CC1)n2[C@H]1[C@H]2CN[C@@H]1C2]

Step 1. tert-butyl (1R,4R,5S)-5-(7-(2-chloro-3-fluorophenyl)-8-(2-cyanoethyl)-6-fluoro-4-(methylthio)-2-((R)-1-((2-(trimethylsilyl)ethoxy)carbonyl)pyrrolidin-2-yl)-1H-pyrrolo[3,2-c]quinolin-1-yl)-2-azabicyclo[2.1.1]hexane-2-carboxylate

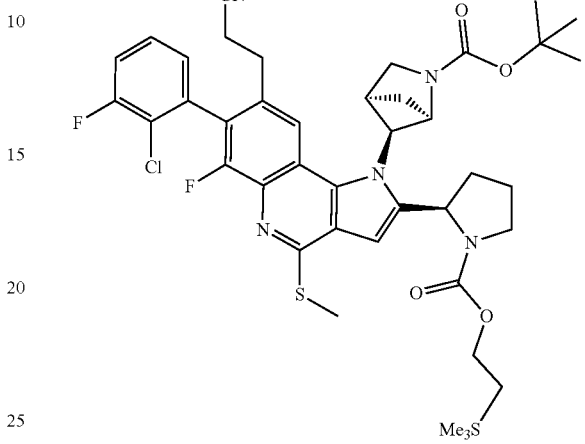

This compound was prepared in an analogous fashion to Intermediate 18, with (2-chloro-3-fluorophenyl)boronic acid replacing (2,3-dichlorophenyl)boronic acid in Step 2. LC-MS calculated for $C_{41}H_{49}ClF_2N_5O_4SSi^+$ (M+H)$^+$: m/z=808.2; found 808.2.

Step 2. tert-butyl (1R,4R,5S)-5-(7-(2-chloro-3-fluorophenyl)-8-(2-cyanoethyl)-2-((R)-1-(cyclopropanecarbonyl)pyrrolidin-2-yl)-6-fluoro-4-(methylthio)-1H-pyrrolo[3,2-c]quinolin-1-yl)-2-azabicyclo[2.1.1]hexane-2-carboxylate

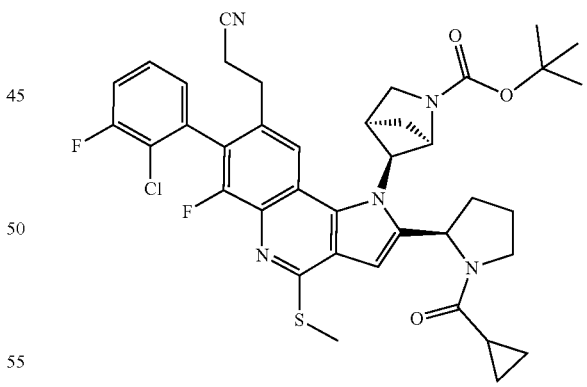

To a solution of tert-butyl (1R,4R,5S)-5-(7-(2-chloro-3-fluorophenyl)-8-(2-cyanoethyl)-6-fluoro-4-(methylthio)-2-((R)-1-((2-(trimethylsilyl)ethoxy)carbonyl)pyrrolidin-2-yl)-1H-pyrrolo[3,2-c]quinolin-1-yl)-2-azabicyclo[2.1.1]hexane-2-carboxylate (434 mg, 0.537 mmol) in THF (2.7 ml) was added TBAF (1 M in THF, 644 μl, 0.644 mmol) and the reaction mixture was stirred at 65° C. for 1 h. The mixture was then cooled to r.t. and triethylamine (224 μl, 1.610 mmol) and cyclopropanecarbonyl chloride (48.8 μl, 0.537 mmol) were added. The reaction mixture was stirred at r.t. for 30 min, then quenched with water and extracted with ethyl acetate. The organic layer was washed with water and brine, dried over sodium sulfate and concentrated. The crude product was purified by column chromatography (30-100% acetone in hexanes) to provide the desired product (335 mg, 85%). LC-MS calculated for $C_{39}H_{41}ClF_2N_5O_3S^+$ (M+H)$^+$: m/z=732.2; found 732.2.

Step 3. 3-(1-((1R,4R,5S)-2-azabicyclo[2.1.1]hexan-5-yl)-7-(2-chloro-3-fluorophenyl)-2-((R)-1-(cyclopropanecarbonyl)pyrrolidin-2-yl)-6-fluoro-4-methyl-1H-pyrrolo[3,2-c]quinolin-8-yl)propanenitrile To a solution of tert-butyl (1R,4R,5S)-5-(7-(2-chloro-3-fluorophenyl)-8-(2-cyanoethyl)-2-((R)-1-(cyclopropanecarbonyl)pyrrolidin-2-yl)-6-fluoro-4-(methylthio)-1H-pyrrolo[3,2-c]quinolin-1-yl)-2-azabicyclo[2.1.1]hexane-2-carboxylate (335 mg, 0.457 mmol) in DCM (2.287 ml) at 0° C. was added m-CPBA (103 mg, 0.595 mmol) and the reaction mixture was stirred at r.t. for 30 min, then quenched with sat. sodium bicarbonate and extracted with DCM. The organic layer was dried over sodium sulfate and concentrated. To the crude product was added THF (2.5 mL) and the mixture was cooled to 0° C. Methylmagnesium bromide (3 M in diethyl ether, 305 µl, 0.915 mmol) was added dropwise and the reaction mixture was allowed to stir at 0° C. for 30 min, then quenched with sat. aq. ammonium chloride. The mixture was extracted with ethyl acetate and the organic layer was washed with water and brine, dried over sodium sulfate and concentrated. The crude product was dissolved in DCM/TFA (1:1; 2 mL), then stirred at r.t. for 30 min, diluted with MeOH and purified by prep HPLC (pH 10 then pH 2) to provide the desired product. LC-MS calculated for $C_{34}H_{33}ClF_2N_5O^+$ (M+H)$^+$: m/z=600.2; found 600.2. $^1$H NMR (600 MHz, DMSO) δ 8.18 (d, J=6.7 Hz, 1H), 7.59 (dd, J=7.9, 3.9 Hz, 2H), 7.49-7.40 (m, 1H), 6.40 (s, 1H), 5.34 (d, J=7.2 Hz, 1H), 4.90 (s, 1H), 4.39-4.20 (m, 1H), 3.98 (s, 1H), 3.73 (s, 1H), 3.59-3.46 (m, 2H), 2.87 (d, J=6.3 Hz, 2H), 2.82-2.69 (m, 7H), 2.30 (s, 1H), 1.96 (s, 2H), 1.86 (s, 2H), 1.25-1.17 (m, 1H), 0.81 (m, 4H).

Example 35. 8-(2-((R)-1-Acetylpyrrolidin-2-yl)-1-((1R,4R,5S)-2-azabicyclo[2.1.1]hexan-5-yl)-6-fluoro-8-methyl-4-(2-methylpyridin-4-yl)-1H-pyrrolo[3,2-c]quinolin-7-yl)-1,2,3,4-tetrahydronaphthalene-1-carbonitrile

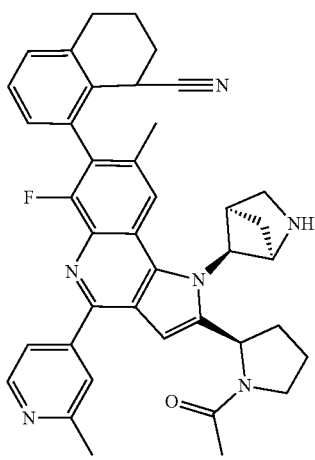 [SMILES: CC(=O)N1CCC[C@@H]1c1cc2c(-c3ccnc(C)c3)nc3c(F)c(-c4cccc5c4C(C#N)CCC5)c(C)cc3c2n1[C@H]1[C@H]2CN[C@@H]1C2]

Step 1. (R)-1-(2-Ethynylpyrrolidin-1-yl)ethan-1-one

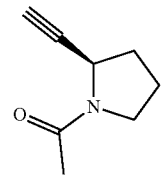

Acetic anhydride (1.72 ml, 18.2 mmol) was added dropwise to a solution of (R)-2-ethynylpyrrolidine hydrochloride (2 g, 15.2 mmol) and triethylamine (4.66 ml, 33.4 mmol) in DCM (20 ml) at 0° C., and the resulting mixture was stirred at 0° C. for 30 minutes. The reaction was quenched with water and extracted with ethyl acetate. The organic layer was washed with 1 N HCl, 1 N NaOH, water and brine, dried over sodium sulfate and concentrated. The crude product was used in the next step without further purification. LC-MS calculated for $C_8H_{12}NO$ (M+H)$^+$: m/z=138.2; found 138.2.

Step 2. tert-Butyl (1R,4R,5S)-5-((3-(((R)-1-acetylpyrrolidin-2-yl)ethynyl)-7-bromo-8-fluoro-6-methyl-2-(methylthio)quinolin-4-yl)amino)-2-azabicyclo[2.1.1]hexane-2-carboxylate A mixture of tert-butyl (1R,4R,5S)-5-((7-bromo-8-fluoro-3-iodo-6-methyl-2-(methylthio)quinolin-4-yl)amino)-2-azabicyclo[2.1.1]hexane-2-carboxylate (intermediate 7, 700 mg, 1.151 mmol), (R)-1-(2-ethynylpyrrolidin-1-yl)ethan-1-one (316 mg, 2.301 mmol), bis(triphenylphosphine)palladium(II) chloride (162 mg, 0.230 mmol), copper(I) iodide (219 mg, 1.151 mmol), and DIPEA (2.010 ml, 11.51 mmol) in DMF (15 ml) was stirred at 70° C. for 2 hours. Upon completion, the reaction mixture was diluted with ethyl acetate, washed subsequently with water (3 times) and brine. The organic phase was dried over anhydrous sodium sulfate, filtered and concentrated. The crude was purified with flash chromatography (eluting with a gradient 0-100% ethyl acetate in hexanes) to give the product (700 mg, 98% yield). LC-MS calculated for $C_{29}H_{35}BrFN_4O_3S$ (M+H)$^+$: m/z=617.2; found 617.1.

Step 3. tert-Butyl (1R,4R,5S)-5-(2-((R)-1-acetylpyr-rolidin-2-yl)-7-bromo-6-fluoro-8-methyl-4-(methyl-thio)-1H-pyrrolo[3,2-c]quinolin-1-yl)-2-azabicyclo[2.1.1]hexane-2-carboxylate

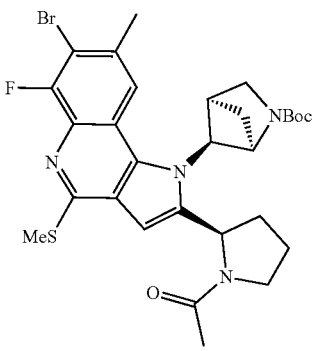 [SMILES: CSc1nc2c(F)c(Br)c(C)cc2c2c1cc([C@H]1CCCN1C(C)=O)n2[C@H]1[C@@H]2C[C@H]1N(C(=O)OC(C)(C)C)C2]

A mixture of tert-butyl (1R,4R,5S)-5-((3-(((R)-1-acetylpyrrolidin-2-yl)ethynyl)-7-bromo-8-fluoro-6-methyl-2-(methylthio)quinolin-4-yl)amino)-2-azabicyclo[2.1.1]hexane-2-carboxylate (600 mg, 0.972 mmol) and Cs$_2$CO$_3$ (950 mg, 2.91 mmol) in DMF (12 ml) was stirred at 100° C. for 1 h. After cooling to room temperature, the reaction mixture was diluted with ethyl acetate, washed subsequently with water (3 times) and brine. The organic phase was dried over anhydrous sodium sulfate, filtered and concentrated to give the crude product (600 mg, 100% yield), which was used in the next step without further purification. LC-MS calculated for C$_{28}$H$_{35}$BrFN$_4$O$_3$S (M+H)$^+$: m/z=617.2; found 617.1.

Step 4. tert-Butyl (1R,4R,5S)-5-(2-((R)-1-acetylpyr-rolidin-2-yl)-7-(8-cyano-5,6,7,8-tetrahydronaphtha-len-1-yl)-6-fluoro-8-methyl-4-(methylthio)-1H-pyr-rolo[3,2-c]quinolin-1-yl)-2-azabicyclo[2.1.1]hexane-2-carboxylate

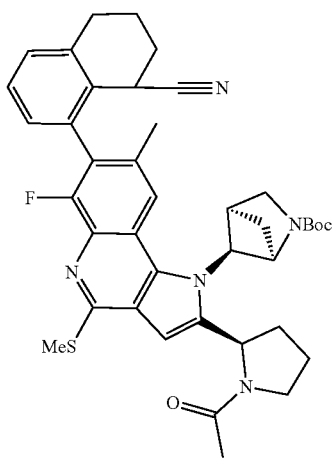 [SMILES: CSc1nc2c(F)c(-c3cccc4c3C(C#N)CCC4)c(C)cc2c2c1cc([C@H]1CCCN1C(C)=O)n2[C@H]1[C@@H]2C[C@H]1N(C(=O)OC(C)(C)C)C2]

A mixture of tert-butyl (1R,4R,5S)-5-(2-((R)-1-acetylpyr-rolidin-2-yl)-7-bromo-6-fluoro-8-methyl-4-(methylthio)-1H-pyrrolo[3,2-c]quinolin-1-yl)-2-azabicyclo[2.1.1]hexane-2-carboxylate (125 mg, 0.202 mmol), bis(di-tert-butyl(4-dimethylaminophenyl)phosphine)dichlorop-alladium(II) (43.0 mg, 0.061 mmol), 8-(4,4,5,5-tetramethyl-1,3,2-dioxaborolan-2-yl)-1,2,3,4-tetrahydronaphthalene-1-carbonitrile (172 mg, 0.607 mmol), and K$_3$PO$_4$ (129 mg, 0.607 mmol) in dioxane (5 ml) and water (1 ml) was stirred at 100° C. for 1 h. The reaction was cooled to room temperature and solvent was removed in vacuo, and the residue was purified by flash chromatography (eluting with a gradient 0~100% ethyl acetate in hexanes) to give the desired product (100 mg, 71% yield). LC-MS calculated for C$_{40}$H$_{45}$FN$_5$O$_3$S (M+H)$^+$: m/z=694.3; found 694.3.

Step 5: 8-(2-((R)-1-Acetylpyrrolidin-2-yl)-1-((1R,4R,5S)-2-azabicyclo[2.1.1]hexan-5-yl)-6-fluoro-8-methyl-4-(2-methylpyridin-4-yl)-1H-pyrrolo[3,2-c]quinolin-7-yl)-1,2,3,4-tetrahydronaphthalene-1-carbonitrile A mixture of tert-butyl (1R,4R,5S)-5-(2-((R)-1-acetylpyr-rolidin-2-yl)-7-(8-cyano-5,6,7,8-tetrahydronaphthalen-1-yl)-6-fluoro-8-methyl-4-(methylthio)-1H-pyrrolo[3,2-c]quinolin-1-yl)-2-azabicyclo[2.1.1]hexane-2-carboxylate (100 mg, 0.144 mmol), 2-methyl-4-(4,4,5,5-tetramethyl-1,3,2-dioxaborolan-2-yl)pyridine (95 mg, 0.432 mmol), Copper(I) 3-methylsalicylate (111 mg, 0.519 mmol), and Pd(PPh$_3$)$_4$ (50.0 mg, 0.043 mmol) in dioxane (5 ml) was stirred at 105° C. for 2 h. After cooling to room temperature, the reaction mixture was filtered through Celite, and the filtrate was concentrated in vacuo. The residue was dissolved in TFA (2 ml) and DCM (2 ml) and stirred at room temperature for 30 min. The reaction mixture was diluted with CH$_3$CN, which was then purified by prep-LCMS (XBridge C18 column, eluting with a gradient of acetonitrile/water containing 0.1% TFA, at flow rate of 60 mL/min) to afford the product as a TFA salt in the form of a white amorphous powder.

Diastereomer 1. Peak 1. LC-MS calculated for C$_{40}$H$_{40}$FN$_6$O (M+H)$^+$: m/z=639.3; found 639.3.

Diastereomer 2. Peak 2. LC-MS calculated for C$_{40}$H$_{40}$FN$_6$O (M+H)$^+$: m/z=639.3; found 639.3. This is the desired peak. $^1$H NMR (600 MHz, DMSO-d$_6$) δ 9.30 (s, 1H), 8.81 (d, J=5.5 Hz, 1H), 8.20 (s, 1H), 8.18 (s, 1H), 8.05-7.96 (m, 2H), 7.46 (t, J=7.6 Hz, 1H), 7.35 (d, J=7.7 Hz, 1H), 7.14 (d, J=7.3 Hz, 1H), 6.64 (s, 1H), 5.62 (d, J=2.9 Hz, 1H), 5.24 (d, J=8.1 Hz, 1H), 4.62 (d, J=6.0 Hz, 1H), 3.96 (dt, J=6.4, 3.2 Hz, 1H), 3.89 (t, J=4.3 Hz, 1H), 3.83 (t, J=9.2 Hz, 1H), 3.77 (s, 1H), 3.55 (td, J=10.0, 7.0 Hz, 1H), 3.46-3.40 (m, 1H), 3.06-2.87 (m, 2H), 2.73 (s, 3H), 2.41-2.35 (m, 4H), 2.34-2.25 (m, 1H), 2.15 (s, 3H), 2.13-2.09 (m, 1H) 2.05-1.78 (m, 5H), 1.75-1.67 (m, 1H), 1.58 (d, J=9.2 Hz, 1H).

Diastereomer 3. Peak 3. LC-MS calculated for C$_{40}$H$_{40}$FN$_6$O (M+H)$^+$: m/z=639.3; found 639.3.

Example 36: 5-(1-((1R,4R,5S)-2-Azabicyclo[2.1.1]hexan-5-yl)-7-(3-chloro-2-methylphenyl)-8-(2-cyanoethyl)-6-fluoro-2-((R)-1-(2-oxopyrazin-1(2H)-yl)ethyl)-1H-pyrrolo[3,2-c]quinolin-4-yl)-N-methylpicolinamide

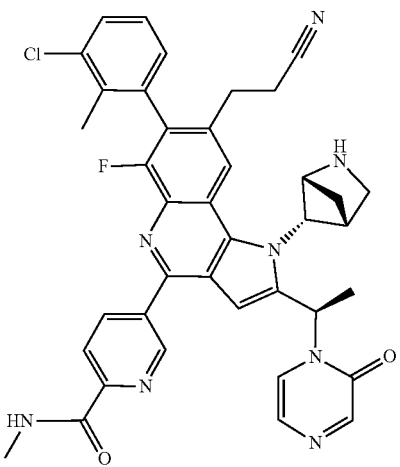 [SMILES: CNC(=O)c1ccc(-c2nc3c(F)c(-c4cccc(Cl)c4C)c(CCC#N)cc3c3c2cc([C@@H](C)n2ccncc2=O)n3[C@H]2[C@H]3CN[C@@H]2C3)cn1]

Step 1: tert-Butyl (1R,4R,5S)-5-((7-bromo-6-(2-cyanoethyl)-8-fluoro-2-(methylthio)-3-((R)-3-(2-oxopyrazin-1(2H)-yl)but-1-yn-1-yl)quinolin-4-yl)amino)-2-azabicyclo[2.1.1]hexane-2-carboxylate

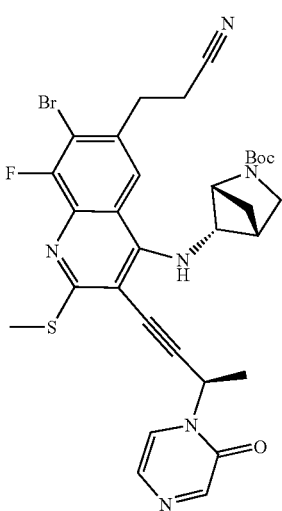 [SMILES: CSc1nc2c(F)c(Br)c(CCC#N)cc2c(N[C@H]2[C@@H]3C[C@H]2N(C(=O)OC(C)(C)C)C3)c1C#C[C@@H](C)n1ccncc1=O]

A mixture of tert-Butyl (1R,4R,5S)-5-((7-bromo-6-(2-cyanoethyl)-8-fluoro-3-iodo-2-(methylthio)quinolin-4-yl)amino)-2-azabicyclo[2.1.1]hexane-2-carboxylate (2.70 g, 4.17 mmol, Intermediate 5), (R)-1-(but-3-yn-2-yl)pyrazin-2(1H)-one (1.24 g, 8.34 mmol, intermediate 20), tetrakis(triphenylphosphine)palladium(0) (0.96 g, 0.83 mmol), CuI (0.32 g, 1.67 mmol) and N,N-diisopropylethylamine (7.3 mL, 41.7 mmol) in DMF (21.0 mL) was sparged with $N_2$ and heated to 70° C. for 1 h. Once completed, the reaction mixture was cooled down to room temperature and poured into water. The aqueous layer was extracted with ethyl acetate, washed with brine, concentrated and purified by flash chromatography (0-100% EtOAc/hexanes) to afford the title compound. LC-MS calculated for $C_{31}H_{33}BrFN_6O_3S$ (M+H)$^+$: m/z=667.1; found 667.1.

Step 2: tert-Butyl (1R,4R,5S)-5-(7-bromo-8-(2-cyanoethyl)-6-fluoro-4-(methylthio)-2-((R)-1-(2-oxopyrazin-1(2H)-yl)ethyl)-1H-pyrrolo[3,2-c]quinolin-1-yl)-2-azabicyclo[2.1.1]hexane-2-carboxylate

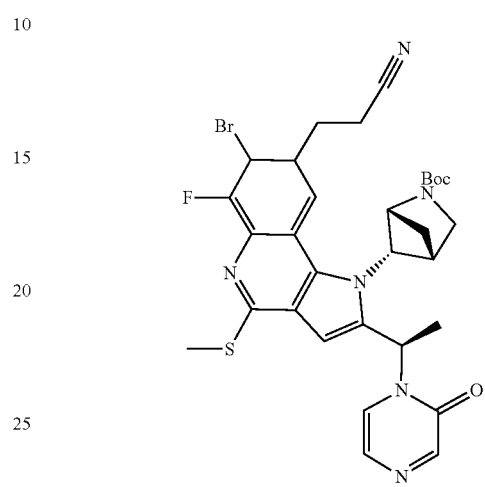

A mixture of tert-butyl (1R,4R,5S)-5-((7-bromo-6-(2-cyanoethyl)-8-fluoro-2-(methylthio)-3-((R)-3-(2-oxopyrazin-1(2H)-yl)but-1-yn-1-yl)quinolin-4-yl)amino)-2-azabicyclo[2.1.1]hexane-2-carboxylate (2.00 g, 3.00 mmol) and cesium carbonate (2.93 g, 9.00 mmol) in DMA (6.0 mL) was heated at 100° C. for 0.5 h. Once completed, the reaction mixture was cooled to room temperature and poured into water. The aqueous layer was extracted with EA, washed with brine, concentrated and purified by flash chromatography (0-100% EtOAc/hexanes) to afford the title compound. LC-MS calculated for $C_{31}H_{33}BrFN_6O_3S$ (M+H)$^+$: m/z=667.1; found 667.2.

Step 3: tert-Butyl (1R,4R,5S)-5-(7-(3-chloro-2-methylphenyl)-8-(2-cyanoethyl)-6-fluoro-4-(methylthio)-2-((R)-1-(2-oxopyrazin-1(2H)-yl)ethyl)-1H-pyrrolo[3,2-c]quinolin-1-yl)-2-azabicyclo[2.1.1]hexane-2-carboxylate

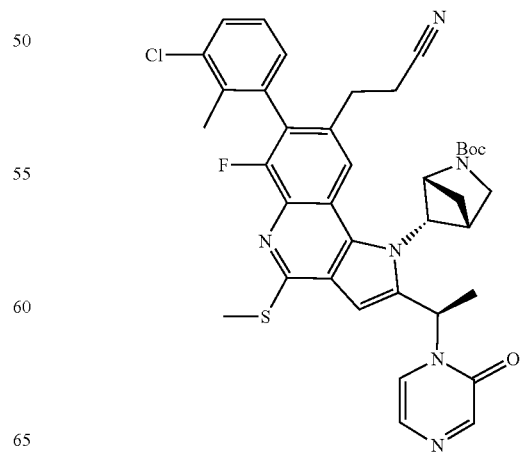

A mixture of tert-butyl (1R,4R,5S)-5-(7-bromo-8-(2-cyanoethyl)-6-fluoro-4-(methylthio)-2-((R)-1-(2-oxopyrazin-1(2H)-yl)ethyl)-1H-pyrrolo[3,2-c]quinolin-1-yl)-2-azabicyclo[2.1.1]hexane-2-carboxylate (173 mg, 0.26 mmol), (3-chloro-2-methylphenyl)boronic acid (88 mg, 0.52 mmol), tetrakis(triphenylphosphine)palladium(0) (45 mg, 0.039 mmol), potassium phosphate (220 mg, 1.04 mmol) in dioxane (1.2 mL) and water (0.12 mL) was sparged with $N_2$ and heated at 100° C. for 2 h. Once completed, the reaction mixture was cooled down to room temperature and poured into water. The aqueous layer was extracted with EA, washed with brine, concentrated and purified by flash chromatography (0-100% EtOAc/hexanes) to afford the title compound. LC-MS calculated for $C_{38}H_{39}ClFN_6O_3S$ (M+H)$^+$: m/z=713.2; found 713.3.

Step 4: 5-(1-((1R,4R,5S)-2-Azabicyclo[2.1.1]hexan-5-yl)-7-(3-chloro-2-methylphenyl)-8-(2-cyanoethyl)-6-fluoro-2-((R)-1-(2-oxopyrazin-1(2H)-yl)ethyl)-1H-pyrrolo[3,2-c]quinolin-4-yl)-N-methylpicolinamide A mixture of tert-butyl (1R,4R,5S)-5-(7-(3-chloro-2-methylphenyl)-8-(2-cyanoethyl)-6-fluoro-4-(methylthio)-2-((R)-1-(2-oxopyrazin-1(2H)-yl)ethyl)-1H-pyrrolo[3,2-c]quinolin-1-yl)-2-azabicyclo[2.1.1]hexane-2-carboxylate (50 mg, 0.070 mmol), N-methyl-5-(4,4,5,5-tetramethyl-1,3,2-dioxaborolan-2-yl)picolinamide (74 mg, 0.28 mmol), tetrakis(triphenylphosphine)-palladium(0) (41 mg, 0.035 mmol), copper(I) 3-methylsalicylate (68 mg, 0.32 mmol) in dioxane (0.35 mL) was sparged with $N_2$ and heated to 120° C. for 1 h. Once completed, the reaction mixture was filtered through celite and concentrated. To the residue was added a drop of MeCN and a 2 M HCl in dioxane solution (2 mL). The mixture was stirred for 30 mins, and purified by prep HPLC (pH 2). The title compound was isolated as a pair of atropisomers. $^1$H NMR was collected on the TFA salts of a mixture of two atropisomers. $^1$H NMR (600 MHz, DMSO-d$_6$) δ 9.51 (br, 2H), 9.31 (dd, J=5.8, 2.2 Hz, 1H), 9.08 (dd, J=5.8, 2.2 Hz, 1H), 8.90 (m, 1H), 8.88 (m, 1H), 8.68 (td, J=8.6, 2.3 Hz, 1H), 8.47 (td, J=8.6, 2.3 Hz, 1H), 8.34 (br, 2H), 8.31 (d, J=8.1 Hz, 1H), 8.25-8.16 (m, 5H), 7.98 (m, 1H), 7.65-7.60 (m, 2H), 7.58 (dd, J=8.5, 4.5 Hz, 1H), 7.52 (d, J=4.2 Hz, 1H), 7.47-7.39 (m, 2H), 7.36-7.29 (m, 2H), 7.26 (d, J=7.5 Hz, 1H), 7.01-6.91 (m, 1H), 6.40 (dd, J=10.5 Hz, 1H), 6.30 (m, 1H), 6.09 (m, 1H), 5.74 (m, 1H), 5.26 (m, 1H), 5.16 (m, 1H), 4.95 (m, 1H), 4.02 (m, 1H), 3.81 (m, 1H), 3.40 (m, 2H), 3.04 (m, 2H), 2.89-2.63 (m, 12H), 2.18 (m, 3H), 2.13 (m, 2H), 2.06 (m, 3H) 1.85 (m, 3H), 1.79 (m, 3H), 1.52 (d, J=9.2 Hz, 2H).

Atropisomer 1. Peak 1. LC-MS calculated for $C_{39}H_{35}ClFN_8O_2$ (M+H)$^+$: m/z=701.3; found 701.2.

Atropisomer 2. Peak 2. LC-MS calculated for $C_{39}H_{35}ClFN_8O_2$ (M+H)$^+$: m/z=701.3; found 701.2.

Example 37: 3-(1-((1R,4R,5S)-2-Azabicyclo[2.1.1]hexan-5-yl)-6-fluoro-7-(7-fluoronaphthalen-1-yl)-4-(6-(2-hydroxypropan-2-yl)pyridin-3-yl)-2-((R)-1-(2-oxopyrazin-1(2H)-yl)ethyl)-1H-pyrrolo[3,2-c]quinolin-8-yl)propanenitrile

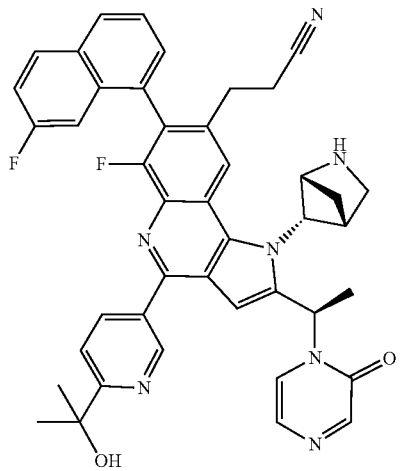 [SMILES: C[C@H](c1cc2c(-c3ccc(C(C)(C)O)nc3)nc3c(F)c(-c4cccc5ccc(F)cc45)c(CCC#N)cc3c2n1[C@H]1[C@H]2CN[C@@H]1C2)n1ccncc1=O]

Step 1: tert-Butyl (1R,4R,5S)-5-(8-(2-cyanoethyl)-6-fluoro-7-(7-fluoronaphthalen-1-yl)-4-(methylthio)-2-((R)-1-(2-oxopyrazin-1(2H)-yl)ethyl)-1H-pyrrolo[3,2-c]quinolin-1-yl)-2-azabicyclo[2.1.1]hexane-2-carboxylate

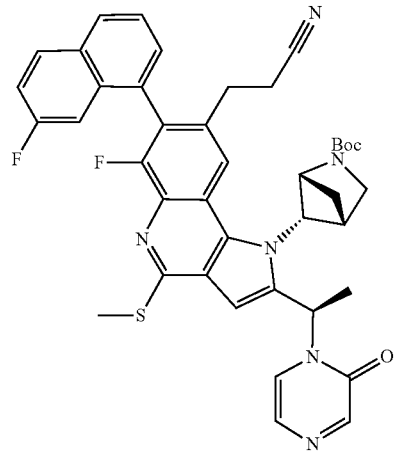 [SMILES: CSc1nc2c(F)c(-c3cccc4ccc(F)cc34)c(CCC#N)cc2c2c1cc([C@@H](C)n1ccncc1=O)n2[C@H]1[C@@H]2C[C@H]1N(C(=O)OC(C)(C)C)C2]

This compound was prepared according to the procedure described in Example 36, Step 3, using 2-(7-fluoronaphthalen-1-yl)-4,4,5,5-tetramethyl-1,3,2-dioxaborolane instead of (3-chloro-2-methylphenyl)boronic acid. LC-MS calculated for $C_{41}H_{39}F_2N_6O_3S$ (M+H)$^+$: m/z=733.3; found 733.2.

Step 2: 3-(1-((1R,4R,5S)-2-Azabicyclo[2.1.1]hexan-5-yl)-6-fluoro-7-(7-fluoronaphthalen-1-yl)-4-(6-(2-hydroxypropan-2-yl)pyridin-3-yl)-2-((R)-1-(2-oxopyrazin-1(2H)-yl)ethyl)-1H-pyrrolo[3,2-c]quinolin-8-yl)propanenitrile This compound was prepared according to the procedure described in Example 36, Step 4, using tert-butyl (1R,4R, 5S)-5-(8-(2-cyanoethyl)-6-fluoro-7-(7-fluoronaphthalen-1-yl)-4-(methylthio)-2-((R)-1-(2-oxopyrazin-1(2H)-yl)ethyl)-1H-pyrrolo[3,2-c]quinolin-1-yl)-2-azabicyclo[2.1.1]hexane-2-carboxylate instead of tert-butyl (1R,4R,5S)-5-(7-(3-chloro-2-methylphenyl)-8-(2-cyanoethyl)-6-fluoro-4-(methylthio)-2-((R)-1-(2-oxopyrazin-1(2H)-yl)ethyl)-1H-pyrrolo[3,2-c]quinolin-1-yl)-2-azabicyclo[2.1.1]hexane-2-carboxylate and 5-(4,4,5,5-tetramethyl-1,3,2-dioxaborolan-2-yl)-2-(2-((trimethylsilyl)oxy)propan-2-yl)pyridine instead of N-methyl-5-(4,4,5,5-tetramethyl-1,3,2-dioxaborolan-2-yl)picolinamide. The title compound was isolated as a mixture of two atropisomers. LC-MS calculated for $C_{43}H_{38}F_2N_7O_2$ (M+H)$^+$: m/z=722.3; found 722.2. $^1$H NMR was collected on the TFA salts of a mixture of two atropisomers. $^1$H NMR (500 MHz, DMSO-d$_6$) δ 9.45 (br, 2H), 9.21 (d, J=5.3 Hz, 1H), 9.19 (br, 2H), 9.03 (d, J=5.3 Hz, 1H), 8.49 (t, J=6.6 Hz, 1H), 8.35-8.15 (m, 7H), 8.08 (m, 1H), 7.94 (d, J=8.0 Hz, 1H), 7.85 (d, J=7.9 Hz, 1H), 7.76-7.65 (m, 4H), 7.61 (d, J=6.6 Hz, 1H), 7.58-7.49 (m, 4H), 7.32 (m, 1H), 7.14 (d, J=10.2 Hz, 1H), 7.09 (d, J=9.4 Hz, 1H), 7.06-6.94 (m, 1H), 6.88 (d, J=10.2 Hz, 1H), 6.46 (d, J=3.0 Hz, 1H), 6.33 (m, 1H), 6.12 (m, 1H), 5.74 (m, 1H), 5.38-5.24 (m, 1H), 5.18 (d, J=12.1 Hz, 1H), 5.15-4.95 (m, 1H), 4.01 (m, 1H), 3.95-3.80 (m, 1H), 3.59 (br, 2H), 3.40 (m, 2H), 3.04 (m, 2H), 2.95-2.66 (m, 8H), 2.16 (m, 2H), 1.89 (m, 3H), 1.80 (m, 3H), 1.55 (s, 6H), 1.52 (m, 2H), 1.50 (s, 6H).

Example 38: 3-(1-((1R,4R,5S)-2-Azabicyclo[2.1.1]hexan-5-yl)-7-(3-chloro-2-methylphenyl)-6-fluoro-4-(5-methylpyrazin-2-yl)-2-((R)-1-(2-oxopyrazin-1(2H)-yl)ethyl)-1H-pyrrolo[3,2-c]quinolin-8-yl)propanenitrile

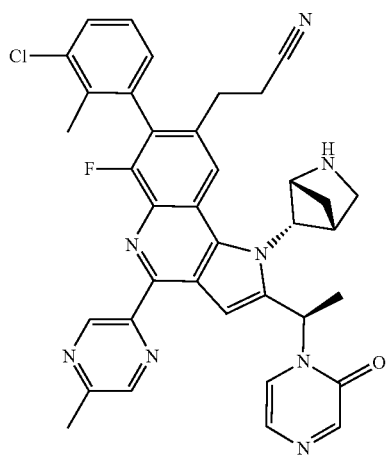 [SMILES: Cc1cnc(-c2nc3c(F)c(-c4cccc(Cl)c4C)c(CCC#N)cc3c3c2cc([C@@H](C)n2ccncc2=O)n3[C@H]2[C@H]3CN[C@@H]2C3)cn1]

This compound was prepared according to the procedure described in Example 36, Step 4, using 2-methyl-5-(4,4,5,5-tetramethyl-1,3,2-dioxaborolan-2-yl)pyrazine instead of N-methyl-5-(4,4,5,5-tetramethyl-1,3,2-dioxaborolan-2-yl)picolinamide. The title compound was isolated as a pair of atropisomers.

Atropisomer 1. Peak 1. LC-MS calculated for $C_{37}H_{33}ClFN_8O$ (M+H)$^+$: m/z=659.2; found 659.2.

Atropisomer 2. Peak 2. LC-MS calculated for $C_{37}H_{33}ClFN_8O$ (M+H)$^+$: m/z=659.2; found 659.2.

Example 39. Methyl (2R)-2-(1-((1R,4R,5S)-2-azabicyclo[2.1.1]hexan-5-yl)-8-(2-cyanoethyl)-7-(2,3-dichlorophenyl)-6-fluoro-4-(5-fluoro-6-(methylcarbamoyl)pyridin-3-yl)-1H-pyrrolo[3,2-c]quinolin-2-yl)pyrrolidine-1-carboxylate

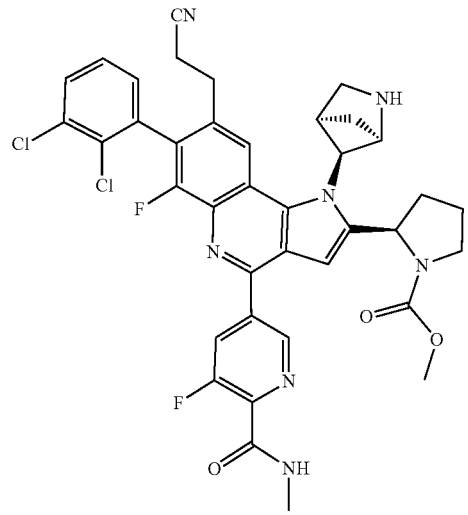 [SMILES: CNC(=O)c1ncc(-c2nc3c(F)c(-c4cccc(Cl)c4Cl)c(CCC#N)cc3c3c2cc([C@H]2CCCN2C(=O)OC)n3[C@H]2[C@H]3CN[C@@H]2C3)cc1F]

Step 1. tert-Butyl (1R,4R,5S)-5-(7-bromo-8-(2-cyanoethyl)-6-fluoro-4-(methylthio)-2-((R)-pyrrolidin-2-yl)-1H-pyrrolo[3,2-c]quinolin-1-yl)-2-azabicyclo[2.1.1]hexane-2-carboxylate

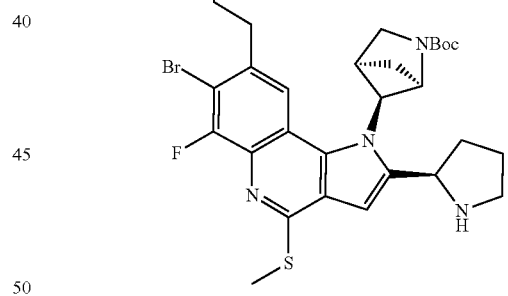

To a solution of tert-butyl (1R,4R,5S)-5-((7-bromo-6-(2-cyanoethyl)-8-fluoro-2-(methylthio)-3-(((R)-1-((2-(trimethylsilyl)ethoxy)carbonyl)pyrrolidin-2-yl)ethynyl)quinolin-4-yl)amino)-2-azabicyclo[2.1.1]hexane-2-carboxylate (5.63 g, 7.42 mmol, Example 28, Step 1) in DMF (37.1 ml) was added cesium carbonate (7.25 g, 22.26 mmol) and the reaction mixture was heated to 90° C. for 2 h. Upon complete cyclization as observed by LCMS, cesium fluoride (4.51 g, 29.7 mmol) was added and the reaction mixture was heated to 90° C. After 3 h, the reaction was diluted with DCM and 5% aqueous LiCl solution. The organics were washed three times with 5% aqueous LiCl solution and then brine, dried over magnesium sulfate and concentrated. The crude material was taken forward without additional purification. LC-MS calculated for $C_{29}H_{34}BrFN_5O_2S^+$ (M+H)$^+$: m/z=614.2/616.2; found 614.2/616.2.

Step 2. tert-Butyl (1R,4R,5S)-5-(7-bromo-8-(2-cyanoethyl)-6-fluoro-2-((R)-1-(methoxycarbonyl)pyrrolidin-2-yl)-4-(methylthio)-1H-pyrrolo[3,2-c]quinolin-1-yl)-2-azabicyclo[2.1.1]hexane-2-carboxylate

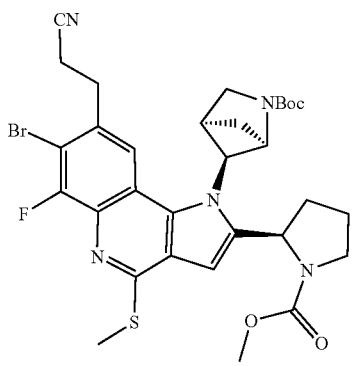 [SMILES: COC(=O)N1CCC[C@@H]1c1cc2c(SC)nc3c(F)c(Br)c(CCC#N)cc3c2n1[C@H]1[C@@H]2C[C@H]1N(C(=O)OC(C)(C)C)C2]

To a solution of tert-butyl (1R,4R,5S)-5-(7-bromo-8-(2-cyanoethyl)-6-fluoro-4-(methylthio)-2-((R)-pyrrolidin-2-yl)-1H-pyrrolo[3,2-c]quinolin-1-yl)-2-azabicyclo[2.1.1] hexane-2-carboxylate (2.5 g, 4.07 mmol) in THF (20.3 ml) at 0° C. were added N,N-diisopropylethylamine (4.26 ml, 24.4 mmol) and methyl carbonochloridate (0.63 ml, 8.14 mmol). The reaction solution was stirred at r.t. for 30 min, then quenched with water and extracted with ethyl acetate. The organic layer was washed with water and brine, dried over sodium sulfate and concentrated. The desired product was isolated by flash column chromatography eluting with a gradient of 0-60% acetone/hexanes. LC-MS calculated for $C_{31}H_{36}BrFN_5O_4S^+$ (M+H)$^+$: m/z=672.2/674.2; found 672.1/674.1.

Step 3. tert-Butyl (1R,4R,5S)-5-(8-(2-cyanoethyl)-7-(2,3-dichlorophenyl)-6-fluoro-2-((R)-1-(methoxycarbonyl)pyrrolidin-2-yl)-4-(methylthio)-1H-pyrrolo[3,2-c]quinolin-1-yl)-2-azabicyclo[2.1.1]hexane-2-carboxylate

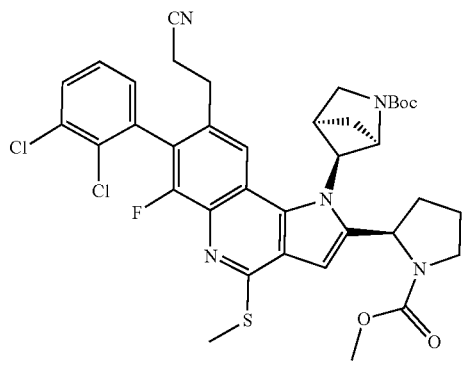 [SMILES: COC(=O)N1CCC[C@@H]1c1cc2c(SC)nc3c(F)c(-c4cccc(Cl)c4Cl)c(CCC#N)cc3c2n1[C@H]1[C@@H]2C[C@H]1N(C(=O)OC(C)(C)C)C2]

To a mixture of tert-butyl (1R,4R,5S)-5-(7-bromo-8-(2-cyanoethyl)-6-fluoro-2-((R)-1-(methoxycarbonyl)pyrrolidin-2-yl)-4-(methylthio)-1H-pyrrolo[3,2-c]quinolin-1-yl)-2-azabicyclo[2.1.1]hexane-2-carboxylate (2.03 g, 3.02 mmol), (2,3-dichlorophenyl)boronic acid (1.15 g, 6.04 mmol), potassium fluoride (0.526 g, 9.05 mmol) and Pd-132 (214 mg, 0.302 mmol) were added 1,4-dioxane (12.1 ml)/water (3.02 ml) and the reaction flask was evacuated, back filled with nitrogen, then stirred at 100° C. for 1 h. The reaction mixture was diluted with DCM and filtered through a plug of Celite. The filtrate was concentrated and the crude product was purified by flash chromatography (0-80% acetone/hexanes) to provide the desired product (1.90 g, 85%). LC-MS calculated for $C_{37}H_{39}Cl_2FN_5O_4S^+$ (M+H)$^+$: m/z=738.2/740.2; found 738.1/740.1.

Step 4. Methyl (2R)-2-(1-((1R,4R,5S)-2-azabicyclo[2.1.1]hexan-5-yl)-8-(2-cyanoethyl)-7-(2,3-dichlorophenyl)-6-fluoro-4-(5-fluoro-6-(methylcarbamoyl)pyridin-3-yl)-1H-pyrrolo[3,2-c]quinolin-2-yl)pyrrolidine-1-carboxylate To a mixture of tert-butyl (1R,4R,5S)-5-(8-(2-cyanoethyl)-7-(2,3-dichlorophenyl)-6-fluoro-2-((R)-1-(methoxycarbonyl)pyrrolidin-2-yl)-4-(methylthio)-1H-pyrrolo[3,2-c]quinolin-1-yl)-2-azabicyclo[2.1.1]hexane-2-carboxylate (20 mg, 0.027 mmol), Intermediate 21 (27 mg, 0.135 mmol), tetrakis(triphenylphosphine)palladium(0) (3.1 mg, 2.71 µmol) and copper(I) 3-methylsalicylate (17 mg, 0.081 mmol) was added 1,4-dioxane (0.22 ml) and the reaction flask was evacuated, back filled with nitrogen, then stirred at 100° C. overnight. The reaction mixture was quenched with water and saturated aq. ammonium hydroxide, then extracted with ethyl acetate. The organic layer was washed with water and brine, dried over sodium sulfate and concentrated. The crude product was stirred in 1:1 TFA/DCM (1 ml) for 30 min, then concentrated. The desired product was purified by prep HPLC (pH 2). LC-MS calculated for $C_{38}H_{34}Cl_2F_2N_7O_3^+$ (M+H)$^+$: m/z=744.2/746.2; found 744.1/746.1.

Example 40. Methyl (2R)-2-(1-((1R,4R,5S)-2-azabicyclo[2.1.1]hexan-5-yl)-8-(2-cyanoethyl)-7-(2,3-dichlorophenyl)-6-fluoro-4-(6-(2-hydroxypropan-2-yl)pyridin-3-yl)-1H-pyrrolo[3,2-c]quinolin-2-yl)pyrrolidine-1-carboxylate

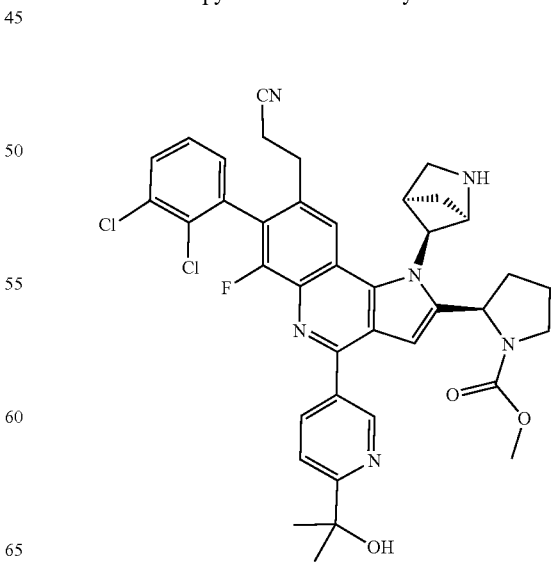

Step 1. tert-Butyl (1R,4R,5S)-5-(8-(2-cyanoethyl)-7-(2,3-dichlorophenyl)-6-fluoro-4-(6-(2-hydroxypropan-2-yl)pyridin-3-yl)-2-((R)-1-((2-(trimethylsilyl)ethoxy)carbonyl)pyrrolidin-2-yl)-1H-pyrrolo[3,2-c]quinolin-1-yl)-2-azabicyclo[2.1.1]hexane-2-carboxylate

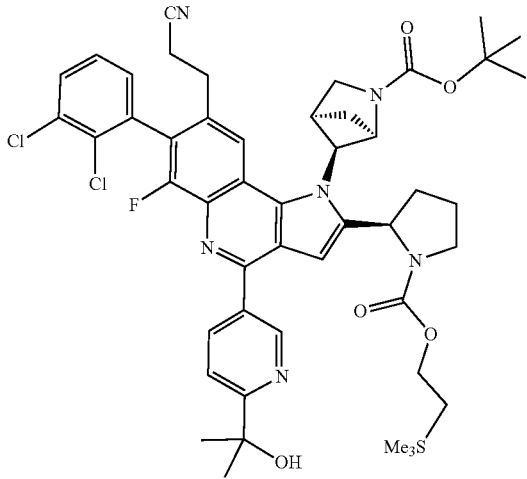

To a mixture of Intermediate 18 (380 mg, 0.46 mmol), 5-(4,4,5,5-tetramethyl-1,3,2-dioxaborolan-2-yl)-2-(2-((trimethylsilyl)oxy)propan-2-yl)pyridine (232 mg, 0.69 mmol), tetrakis(triphenylphosphine) palladium(0) (53 mg, 0.046 mmol) and copper(I) 3-methylsalicylate (297 mg, 1.38 mmol) was added 1,4-dioxane (3.7 ml) and the reaction flask was evacuated, back filled with nitrogen, then stirred at 100° C. overnight. The reaction was quenched with water and saturated aq. ammonium hydroxide, then extracted with ethyl acetate. The organic layer was washed with water and brine, dried over sodium sulfate and concentrated. The crude product was purified by flash chromatography (0-7% MeOH/DCM) to provide the desired product. LC-MS calculated for $C_{48}H_{56}Cl_2FN_6O_5Si^+$ (M+H)$^+$: m/z=913.3/915.3; found 913.4/915.3.

Step 2. tert-Butyl (1R,4R,5S)-5-(8-(2-cyanoethyl)-7-(2,3-dichlorophenyl)-6-fluoro-4-(6-(2-hydroxypropan-2-yl)pyridin-3-yl)-2-((R)-pyrrolidin-2-yl)-1H-pyrrolo[3,2-c]quinolin-1-yl)-2-azabicyclo[2.1.1]hexane-2-carboxylate

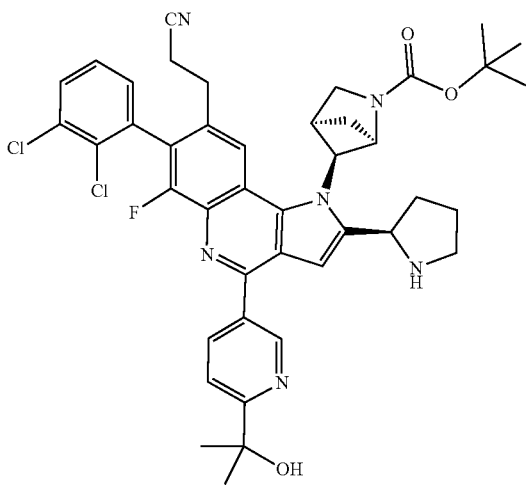 [SMILES: CC(C)(C)OC(=O)N1C[C@H]2C[C@@H]1[C@H]2n1c([C@H]2CCCN2)cc2c(-c3ccc(C(C)(C)O)nc3)nc3c(F)c(-c4cccc(Cl)c4Cl)c(CCC#N)cc3c21]

To a solution of tert-butyl (1R,4R,5S)-5-(8-(2-cyanoethyl)-7-(2,3-dichlorophenyl)-6-fluoro-4-(6-(2-hydroxypropan-2-yl)pyridin-3-yl)-2-((R)-1-((2-(trimethylsilyl)ethoxy)carbonyl)pyrrolidin-2-yl)-1H-pyrrolo[3,2-c]quinolin-1-yl)-2-azabicyclo[2.1.1]hexane-2-carboxylate (306 mg, 0.34 mmol) in DMF (1.67 ml) was added cesium fluoride (203 mg, 1.34 mmol) and the reaction mixture was heated to 90° C. After 1 h, the reaction was diluted with DCM and 5% aqueous LiCl solution. The organics were washed three times with 5% aqueous LiCl solution and then brine, dried over magnesium sulfate and concentrated. The crude material was taken forward without additional purification. LC-MS calculated for $C_{42}H_{44}Cl_2FN_6O_3^+$ (M+H)$^+$: m/z=769.3/771.3; found 769.3/771.3.

Step 3. Methyl (2R)-2-(1-((1R,4R,5S)-2-azabicyclo[2.1.1]hexan-5-yl)-8-(2-cyanoethyl)-7-(2,3-dichlorophenyl)-6-fluoro-4-(6-(2-hydroxypropan-2-yl)pyridin-3-yl)-1H-pyrrolo[3,2-c]quinolin-2-yl)pyrrolidine-1-carboxylate To a solution of tert-butyl (1R,4R,5S)-5-(8-(2-cyanoethyl)-7-(2,3-dichlorophenyl)-6-fluoro-4-(6-(2-hydroxypropan-2-yl)pyridin-3-yl)-2-((R)-pyrrolidin-2-yl)-1H-pyrrolo[3,2-c]quinolin-1-yl)-2-azabicyclo[2.1.1]hexane-2-carboxylate (25 mg, 0.032 mmol) in THF (0.16 ml) cooled to 0° C. were added N,N-diisopropylethylamine (0.045 ml, 0.325 mmol) and methyl carbonochloridate (3.76 µl, 0.049 mmol). The reaction solution was stirred at r.t. for 30 min, then quenched with water and extracted with ethyl acetate. The organic layer was washed with water and brine, dried over sodium sulfate and concentrated. The crude product was stirred in 1:1 TFA/DCM (1 ml) for 30 min, then concentrated. The desired product was purified by prep HPLC (pH 2). LC-MS calculated for $C_{39}H_{38}Cl_2FN_6O_3^+$ (M+H)$^+$: m/z=727.2/729.2; found 727.3/729.3. $^1$H NMR (TFA salt, 600 MHz, DMSO-d$_6$) δ 9.53-9.40 (m, 1H), 9.10 (d, J=2.2 Hz, 1H), 8.54-8.48 (m, 1H), 8.23-8.19 (m, 2H), 8.02 (d, J=8.4 Hz, 1H), 7.85 (dd, J=8.1, 1.5 Hz, 1H), 7.59 (t, J=7.9 Hz, 1H), 7.54-7.46 (m, 1H), 6.71-6.64 (m, 1H), 5.65 (s, 1H), 5.17 (t, J=7.9 Hz, 1H), 4.92 (dd, J=15.7, 6.0 Hz, 1H), 4.04-3.91 (m, 1H), 3.74-3.59 (m, 5H), 3.55-3.38 (m, 2H), 3.10-3.03 (m, 1H), 2.96-2.81 (m, 2H), 2.75-2.64 (m, 1H), 2.42-2.29 (m, 2H), 1.93-1.80 (m, 2H), 1.75-1.59 (m, 2H), 1.57 (s, 6H).

261

Example 41. Ethyl (2R)-2-(1-((1R,4R,5S)-2-azabicyclo[2.1.1]hexan-5-yl)-8-(2-cyanoethyl)-7-(2,3-dichlorophenyl)-6-fluoro-4-(6-(2-hydroxypropan-2-yl)pyridin-3-yl)-1H-pyrrolo[3,2-c]quinolin-2-yl)pyrrolidine-1-carboxylate

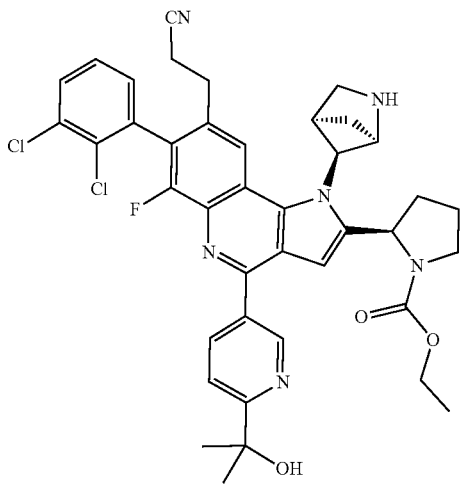 [SMILES: CCOC(=O)N1CCC[C@@H]1c1cc2c(-c3ccc(C(C)(C)O)nc3)nc3c(F)c(-c4cccc(Cl)c4Cl)c(CCC#N)cc3c2n1[C@H]1[C@H]2CN[C@@H]1C2]

This compound was prepared in an analogous fashion to Example 40, with ethyl carbonochloridate replacing methyl carbonochloridate in Step 3. LC-MS calculated for $C_{40}H_{40}Cl_2FN_6O_3^+$ (M+H)$^+$: m/z=741.3/743.2; found 741.4/743.4. $^1$H NMR (TFA salt, rotamers, 600 MHz, DMSO-$d_6$) δ 9.38-9.26 (m, 1H), 9.08 (s, 1H), 8.47-8.39 (m, 1H), 8.21-8.11 (m, 2H), 7.97 (dd, J=10.9, 8.2 Hz, 1H), 7.85 (dd, J=8.1, 1.5 Hz, 1H), 7.59 (t, J=7.9 Hz, 1H), 7.50 (t, J=7.9 Hz, 1H), 6.63 (s, 1H), 5.64 (s, 1H), 5.15 (d, J=8.1 Hz, 1H), 4.98-4.88 (m, 2H), 4.22-4.05 (m, 2H), 4.02-3.92 (m, 1H), 3.71-3.57 (m, 2H), 3.55-3.37 (m, 2H), 3.10-3.02 (m, 1H), 2.95-2.82 (m, 2H), 2.72-2.63 (m, 1H), 2.44-2.31 (m, 2H), 1.96-1.80 (m, 2H), 1.72-1.59 (m, 2H), 1.55 (s, 6H), 1.27 (t, J=7.0 Hz, 2H), 1.17 (t, J=7.1 Hz, 1H).

Example 42. 3-(1-((1R,4R,5S)-2-Azabicyclo[2.1.1]hexan-5-yl)-7-(2,3-dichlorophenyl)-2-((R)-1-(3,3-difluoroazetidine-1-carbonyl)pyrrolidin-2-yl)-6-fluoro-4-(methyl-d)-1H-pyrrolo[3,2-c]quinolin-8-yl)propanenitrile

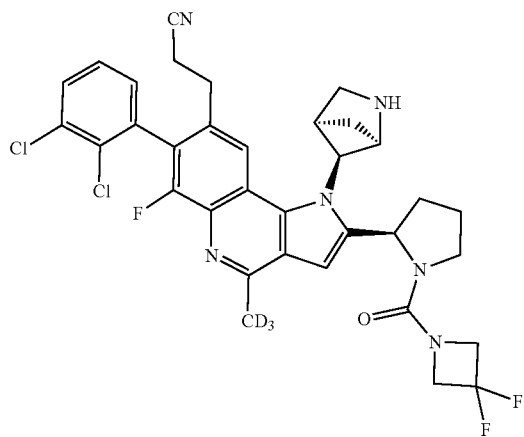 [SMILES: [2H]C([2H])([2H])c1nc2c(F)c(-c3cccc(Cl)c3Cl)c(CCC#N)cc2c2c1cc([C@H]1CCCN1C(=O)N1CC(F)(F)C1)n2[C@H]1[C@H]2CN[C@@H]1C2]

262

Step 1. tert-Butyl (1R,4R,5S)-5-(7-bromo-8-(2-cyanoethyl)-2-((R)-1-(3,3-difluoroazetidine-1-carbonyl)pyrrolidin-2-yl)-6-fluoro-4-(methylthio)-1H-pyrrolo[3,2-c]quinolin-1-yl)-2-azabicyclo[2.1.1]hexane-2-carboxylate

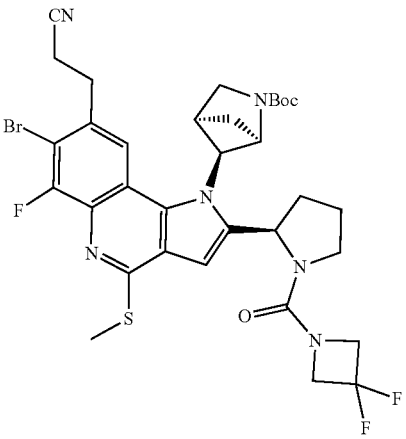 [SMILES: CSc1nc2c(F)c(Br)c(CCC#N)cc2c2c1cc([C@H]1CCCN1C(=O)N1CC(F)(F)C1)n2[C@H]1[C@@H]2C[C@H]1N(C(=O)OC(C)(C)C)C2]

To solution of tert-butyl (1R,4R,5S)-5-(7-bromo-8-(2-cyanoethyl)-6-fluoro-4-(methylthio)-2-((R)-pyrrolidin-2-yl)-1H-pyrrolo[3,2-c]quinolin-1-yl)-2-azabicyclo[2.1.1]hexane-2-carboxylate (1.51 g, 2.46 mmol, Example 39, Step 1) and N,N-diisopropylethylamine (1.29 ml, 7.37 mmol) in THF (12.3 ml) at 0° C. was added triphosgene (0.292 g, 0.983 mmol). The reaction was stirred at r.t. for 1 h, at which point 3,3-difluoroazetidine hydrochloride (0.382 g, 2.95 mmol) and N,N-diisopropylethylamine (1.29 ml, 7.37 mmol) were added. The reaction mixture was stirred at 50° C. for 30 min. The reaction was then quenched with water and extracted with ethyl acetate. The organic layer was washed with water and brine, dried over sodium sulfate and concentrated. The crude product was purified by flash column chromatography eluting with 0-70% acetone/hexanes. LC-MS calculated for $C_{33}H_{37}BrF_3N_6O_3S^+$ (M+H)$^+$: m/z=733.2/735.2; found 733.1/735.1.

Step 2. tert-Butyl (1R,4R,5S)-5-(7-bromo-8-(2-cyanoethyl)-2-((R)-1-(3,3-difluoroazetidine-1-carbonyl)pyrrolidin-2-yl)-6-fluoro-4-(methylsulfinyl)-1H-pyrrolo[3,2-c]quinolin-1-yl)-2-azabicyclo[2.1.1]hexane-2-carboxylate

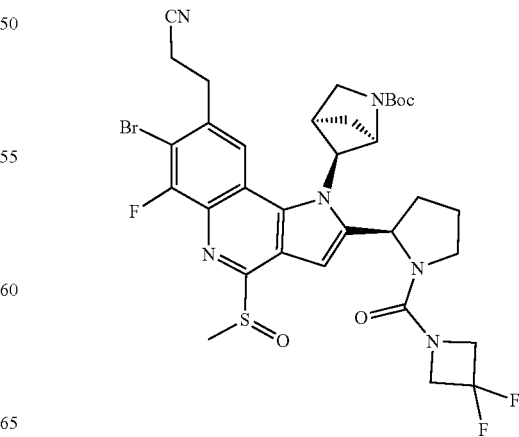

To a solution of tert-butyl (1R,4R,5S)-5-(7-bromo-8-(2-cyanoethyl)-2-((R)-1-(3,3-difluoroazetidine-1-carbonyl)pyrrolidin-2-yl)-6-fluoro-4-(methylthio)-1H-pyrrolo[3,2-c]quinolin-1-yl)-2-azabicyclo[2.1.1]hexane-2-carboxylate (1.12 g, 1.53 mmol) in ethyl acetate (30.5 ml) at 0° C. was added m-CPBA (0.790 g, 2.29 mmol) and the reaction mixture was stirred at r.t. for 30 min, then quenched with saturated sodium bicarbonate and extracted with ethyl acetate. The organic layer was dried over sodium sulfate and concentrated. The crude product was taken forward without additional purification. LC-MS calculated for $C_{33}H_{37}BrF_3N_6O_4S^+$ $(M+H)^+$: m/z=749.2/751.2; found 749.2/751.1.

Step 3. tert-butyl (1R,4R,5S)-5-(7-bromo-8-(2-cyanoethyl)-2-((R)-1-(3,3-difluoroazetidine-1-carbonyl)pyrrolidin-2-yl)-6-fluoro-4-(methyl-d$_3$)-1H-pyrrolo[3,2-c]quinolin-1-yl)-2-azabicyclo[2.1.1]hexane-2-carboxylate

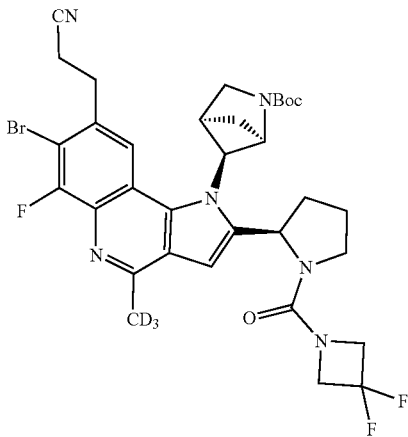 [SMILES: [2H]C([2H])([2H])c1nc2c(F)c(Br)c(CCC#N)cc2c2c1cc([C@H]1CCCN1C(=O)N1CC(F)(F)C1)n2[C@H]1[C@@H]2C[C@H]1N(C(=O)OC(C)(C)C)C2]

To a solution of tert-butyl (1R,4R,5S)-5-(7-bromo-8-(2-cyanoethyl)-2-((R)-1-(3,3-difluoroazetidine-1-carbonyl)pyrrolidin-2-yl)-6-fluoro-4-(methylsulfinyl)-1H-pyrrolo[3,2-c]quinolin-1-yl)-2-azabicyclo[2.1.1]hexane-2-carboxylate (1.14 g, 1.52 mmol) in THF (7.6 mL) at 0° C. was added (methyl-d$_3$)magnesium iodide (1 M in diethyl ether, 1.98 ml, 1.98 mmol) dropwise. The reaction mixture was stirred at 0° C. for 30 min. An additional equivalent of (methyl-d$_3$) magnesium iodide solution was added. After 30 min, full starting material conversion was observed and the reaction was quenched with saturated aq. ammonium chloride. The mixture was extracted with ethyl acetate and the organic layer was washed with water and brine, dried over sodium sulfate and concentrated. The crude product was purified by flash column chromatography eluting with 0-70% ethyl acetate/hexanes. LC-MS calculated for $C_{33}H_{34}D_3BrF_3N_6O_3+(M+H)^+$: m/z=704.2/706.2; found 704.2/706.2.

Step 4. 3-(1-((1R,4R,5S)-2-Azabicyclo[2.1.1]hexan-5-yl)-7-(2,3-dichlorophenyl)-2-((R)-1-(3,3-difluoroazetidine-1-carbonyl)pyrrolidin-2-yl)-6-fluoro-4-(methyl-d$_3$)-1H-pyrrolo[3,2-c]quinolin-8-yl)propanenitrile To a mixture of tert-butyl (1R,4R,5S)-5-(7-bromo-8-(2-cyanoethyl)-2-((R)-1-(3,3-difluoroazetidine-1-carbonyl)pyrrolidin-2-yl)-6-fluoro-4-(methyl-d$_3$)-1H-pyrrolo[3,2-c]quinolin-1-yl)-2-azabicyclo[2.1.1]hexane-2-carboxylate (0.150 g, 0.213 mmol), (2,3-dichlorophenyl)boronic acid (0.081 g, 0.426 mmol), potassium fluoride (0.037 g, 0.639 mmol) and Pd-132 (15 mg, 0.021 mmol) were added 1,4-dioxane (0.85 ml)/water (0.21 ml) and the reaction flask was evacuated, back filled with nitrogen, then stirred at 100° C. for 2 h. The reaction mixture was diluted with ethyl acetate and SiliaMetS Thiol functionalized silica gel (Silicycle, PN R51030B, 200 mg) then stirred at r.t. for 5 minutes. The slurry was filtered through a plug of Celite. The filtrate was diluted with water. The mixture was extracted with ethyl acetate and the organic layer was washed with water and brine, dried over sodium sulfate and concentrated. The crude product was isolated by prep HPLC (pH 10). Following concentration by EZ-2 evaporator the product was stirred in 1:1 TFA/DCM (3 ml) for 30 min, then concentrated. The desired product was purified by prep HPLC (pH 2). LC-MS calculated for $C_{34}H_{29}D_3Cl_2F_3N_6O^+$ $(M+H)^+$: m/z=670.2/672.2; found 670.3/672.3. $^1$H NMR (TFA salt, 600 MHz, DMSO-d$_6$) δ 9.48-9.37 (m, 1H), 8.23-8.11 (m, 2H), 7.86 (dd, J=8.2, 1.5 Hz, 1H), 7.59 (t, J=7.9 Hz, 1H), 7.47 (dd, J=7.6, 1.5 Hz, 1H), 6.96 (s, 1H), 5.64-5.57 (m, 1H), 5.29-5.22 (m, 1H), 4.87 (d, J=6.0 Hz, 1H), 4.60-4.48 (m, 4H), 4.00-3.94 (m, 1H), 3.82-3.75 (m, 1H), 3.65-3.57 (m, 1H), 3.47-3.38 (m, 2H), 3.09-3.01 (m, 1H), 2.92-2.81 (m, 2H), 2.72-2.63 (m, 1H), 2.37-2.27 (m, 2H), 1.98-1.90 (m, 1H), 1.78-1.67 (m, 2H), 1.62-1.57 (m, 1H).

Example 43. 3-(1-((1R,4R,5S)-2-Azabicyclo[2.1.1]hexan-5-yl)-7-(2,3-dichlorophenyl)-2-((R)-1-(3,3-difluoroazetidine-1-carbonyl)pyrrolidin-2-yl)-6-fluoro-1H-pyrrolo[3,2-c]quinolin-8-yl)propanenitrile

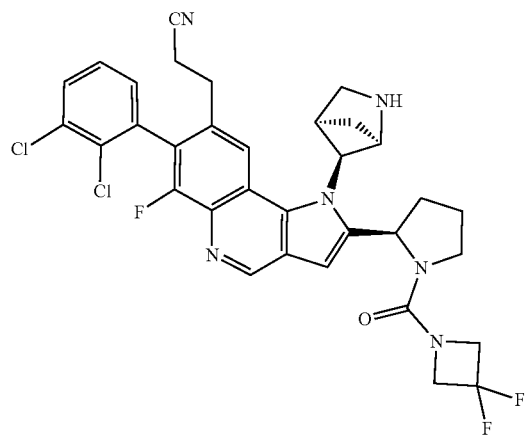 [SMILES: N#CCCc1cc2c(ncc3cc([C@H]4CCCN4C(=O)N4CC(F)(F)C4)n([C@H]4[C@H]5CN[C@@H]4C5)c32)c(F)c1-c1cccc(Cl)c1Cl]

265

Step 1. tert-Butyl (1R,4R,5S)-5-(7-bromo-8-(2-cyanoethyl)-2-((R)-1-(3,3-difluoroazetidine-1-carbonyl)pyrrolidin-2-yl)-6-fluoro-4-(methylthio)-1H-pyrrolo[3,2-c]quinolin-1-yl)-2-azabicyclo[2.1.1]hexane-2-carboxylate

266

Step 2. tert-Butyl (1R,4R,5S)-5-(8-(2-cyanoethyl)-7-(2,3-dichlorophenyl)-2-((R)-1-(3,3-difluoroazetidine-1-carbonyl)pyrrolidin-2-yl)-6-fluoro-4-(methylthio)-1H-pyrrolo[3,2-c]quinolin-1-yl)-2-azabicyclo[2.1.1]hexane-2-carboxylate

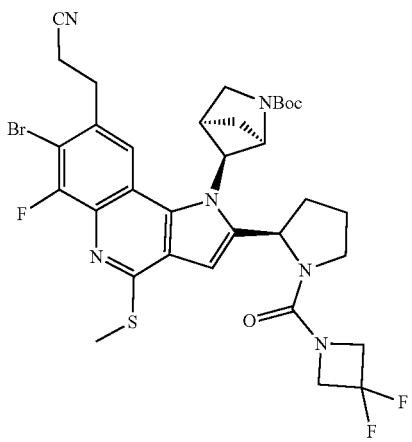 [SMILES: CSc1nc2c(F)c(Br)c(CCC#N)cc2c2c1cc([C@H]1CCCN1C(=O)N1CC(F)(F)C1)n2[C@H]1[C@@H]2C[C@H]1N(C(=O)OC(C)(C)C)C2]

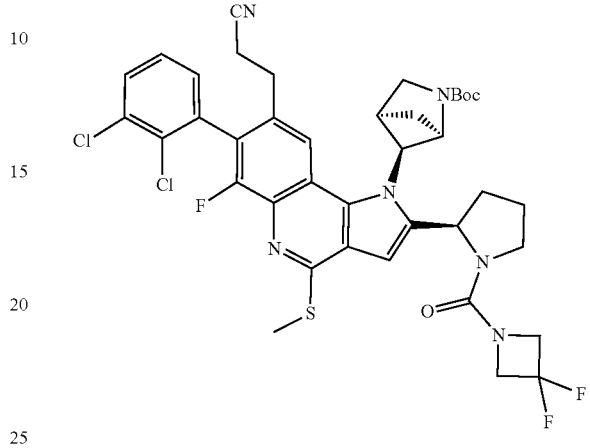

This compound was prepared in an analogous fashion to Example 39, Step 3, with tert-butyl (1R,4R,5S)-5-(7-bromo-8-(2-cyanoethyl)-2-((R)-1-(3,3-difluoroazetidine-1-carbonyl)pyrrolidin-2-yl)-6-fluoro-4-(methylthio)-1H-pyrrolo[3,2-c]quinolin-1-yl)-2-azabicyclo[2.1.1]hexane-2-carboxylate replacing tert-butyl (1R,4R,5S)-5-(7-bromo-8-(2-cyanoethyl)-6-fluoro-2-((R)-1-(methoxycarbonyl)pyrrolidin-2-yl)-4-(methylthio)-1H-pyrrolo[3,2-c]quinolin-1-yl)-2-azabicyclo[2.1.1]hexane-2-carboxylate. LC-MS calculated for $C_{39}H_{40}Cl_2F_3N_6O_3S^+$ (M+H)$^+$: m/z=799.2/801.2; found 799.2/801.2.

Step 3. 3-(1-((1R,4R,5S)-2-Azabicyclo[2.1.1]hexan-5-yl)-7-(2,3-dichlorophenyl)-2-((R)-1-(3,3-difluoroazetidine-1-carbonyl)pyrrolidin-2-yl)-6-fluoro-1H-pyrrolo[3,2-c]quinolin-8-yl)propanenitrile To a solution of tert-butyl (1R,4R,5S)-5-(7-bromo-8-(2-cyanoethyl)-6-fluoro-4-(methylthio)-2-((R)-1-((2-(trimethylsilyl)ethoxy)carbonyl)pyrrolidin-2-yl)-1H-pyrrolo[3,2-c]quinolin-1-yl)-2-azabicyclo[2.1.1]hexane-2-carboxylate (2.24 g, 2.95 mmol, Example 39, Step 1 in DMF (14.8 mL) was added cesium fluoride (1.79 g, 11.8 mmol) and the reaction mixture was heated to 90° C. for 1 h. The reaction solution was then diluted with DCM and 5% aqueous LiCl solution. The organics were washed three times with 5% aqueous LiCl solution, then brine, dried over magnesium sulfate and concentrated. The residue was dissolved in THF (14.8 mL) and cooled to 0° C. N,N-Diisopropylethylamine (1.55 ml, 8.86 mmol) was added followed by triphosgene (0.350 g, 1.18 mmol) and the reaction was stirred at r.t. for 1 h. Then 3,3-difluoroazetidine hydrochloride (0.459 g, 3.54 mmol) and N,N-diisopropylethylamine (1.55 mL, 8.86 mmol) were added and the reaction mixture was stirred at 50° C. for 30 min. Upon completion, the reaction was then quenched with water and extracted with ethyl acetate. The organic layer was washed with water and brine, dried over sodium sulfate and concentrated. The crude product was purified by column chromatography eluting with 0-70% acetone/hexanes. LC-MS calculated for $C_{33}H_{37}BrF_3N_6O_3S^+$ (M+H)$^+$: m/z=733.2/735.2; found 733.1/735.1.

To a solution of tert-butyl (1R,4R,5S)-5-(8-(2-cyanoethyl)-7-(2,3-dichlorophenyl)-2-((R)-1-(3,3-difluoroazetidine-1-carbonyl)pyrrolidin-2-yl)-6-fluoro-4-(methylthio)-1H-pyrrolo[3,2-c]quinolin-1-yl)-2-azabicyclo[2.1.1]hexane-2-carboxylate (30 mg, 0.038 mmol) in ethyl acetate (0.75 mL) at 0° C. was added m-CPBA (32 mg, 0.094 mmol) and the reaction mixture was stirred at r.t. for 30 min, then quenched with saturated sodium bicarbonate and extracted with ethyl acetate. The organic layer was dried over sodium sulfate and concentrated. The residue was dissolved in acetic acid (0.75 mL) and zinc (30 mg, 0.459 mmol) was added. The mixture was heated to 70° C. for 16 h. The reaction mixture was diluted with DCM, filtered through a Celite plug and concentrated. The crude product was stirred in 1:1 TFA/DCM (1 mL) for 30 min, then concentrated. The desired product was purified by prep HPLC (pH 2). LC-MS calculated for $C_{33}H_{30}Cl_2F_3N_6O^+$ (M+H)$^+$: m/z=653.2/655.2; found 653.2/655.1.

Example 44: 3-(1-((1R,4R,5S)-2-Azabicyclo[2.1.1]hexan-5-yl)-7-(3-chloro-2-methylphenyl)-6-fluoro-4-(5-methylpyrazin-2-yl)-2-((R)-1-(3-oxomorpholino)ethyl)-1H-pyrrolo[3,2-c]quinolin-8-yl)propanenitrile

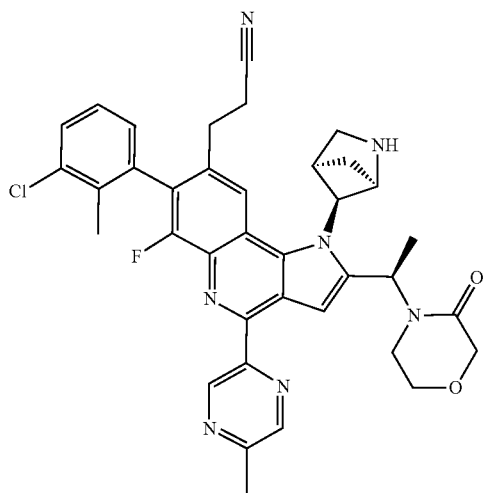 [SMILES: Cc1cnc(-c2nc3c(F)c(-c4cccc(Cl)c4C)c(CCC#N)cc3c3c2cc([C@@H](C)N2CCOCC2=O)n3[C@H]2[C@H]3CN[C@@H]2C3)cn1]

Step 1: tert-Butyl (1R,4R,5S)-5-((7-bromo-6-(2-cyanoethyl)-8-fluoro-2-(methylthio)-3-((R)-3-(3-oxomorpholino)but-1-yn-1-yl)quinolin-4-yl)amino)-2-azabicyclo[2.1.1]hexane-2-carboxylate

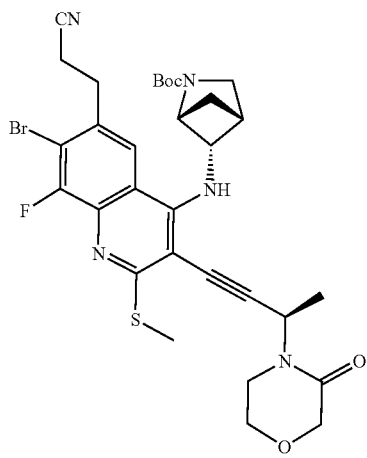 [SMILES: CSc1nc2c(F)c(Br)c(CCC#N)cc2c(N[C@H]2[C@@H]3C[C@H]2N(C(=O)OC(C)(C)C)C3)c1C#C[C@@H](C)N1CCOCC1=O]

A solution of tert-butyl (1R,4R,5S)-5-((7-bromo-6-(2-cyanoethyl)-8-fluoro-3-iodo-2-(methylthio)quinolin-4-yl)amino)-2-azabicyclo[2.1.1]hexane-2-carboxylate (Intermediate 5, 3 g, 4.63 mmol), (R)-4-(but-3-yn-2-yl)morpholin-3-one (Intermediate 19, 1.42 g, 9.27 mmol), DIPEA (8.09 mL, 46.3 mmol), Pd(PPh$_3$)$_4$ (1.07 g, 0.927 mmol), and copper(I) iodide (0.353 g, 1.854 mmol) in DMF (25 mL) was stirred at 70° C. for 1 h. The reaction was then concentrated and purified by flash chromatography to afford the title compound. LC-MS calculated for $C_{31}H_{36}BrFN_5O_4S^+$ (M+H)$^+$: m/z=672.2; found 672.2.

Step 2: tert-Butyl (1R,4R,5S)-5-(7-bromo-8-(2-cyanoethyl)-6-fluoro-4-(methylthio)-2-((R)-1-(3-oxomorpholino)ethyl)-1H-pyrrolo[3,2-c]quinolin-1-yl)-2-azabicyclo[2.1.1]hexane-2-carboxylate

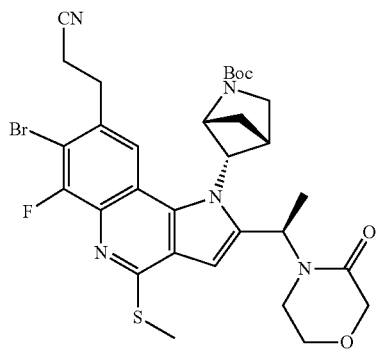 [SMILES: CSc1nc2c(F)c(Br)c(CCC#N)cc2c2c1cc([C@@H](C)N1CCOCC1=O)n2[C@H]1[C@@H]2C[C@H]1N(C(=O)OC(C)(C)C)C2]

A solution of tert-butyl (1R,4R,5S)-5-((7-bromo-6-(2-cyanoethyl)-8-fluoro-2-(methylthio)-3-((R)-3-(3-oxomorpholino)but-1-yn-1-yl)quinolin-4-yl)amino)-2-azabicyclo[2.1.1]hexane-2-carboxylate (3.2 g, 4.76 mmol) and cesium carbonate (4.65 g, 14.27 mmol) in DMF (50 mL) was stirred at 70° C. for 1 h. The reaction was then concentrated and purified by flash chromatography to afford the title compound. LC-MS calculated for $C_{31}H_{36}BrFN_5O_4S^+$ (M+H)$^+$: m/z=672.2; found 672.2.

Step 3: tert-Butyl (1R,4R,5S)-5-(7-(3-chloro-2-methylphenyl)-8-(2-cyanoethyl)-6-fluoro-4-(methylthio)-2-((R)-1-(3-oxomorpholino)ethyl)-1H-pyrrolo[3,2-c]quinolin-1-yl)-2-azabicyclo[2.1.1]hexane-2-carboxylate

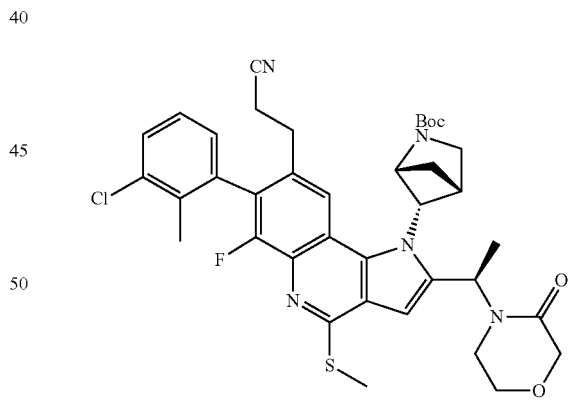

A solution of tert-butyl (1R,4R,5S)-5-(7-bromo-8-(2-cyanoethyl)-6-fluoro-4-(methylthio)-2-((R)-1-(3-oxomorpholino)ethyl)-1H-pyrrolo[3,2-c]quinolin-1-yl)-2-azabicyclo[2.1.1]hexane-2-carboxylate (2.16 g, 3.21 mmol), (3-chloro-2-methylphenyl)boronic acid (1.09 g, 6.42 mmol), Pd(PPh$_3$)$_4$ (0.742 g, 0.642 mmol) and potassium phosphate (1.70 g, 8.03 mmol) in 1,4-dioxane (20 mL) and water (4 mL) was stirred at 80° C. for 30 min. The reaction was then concentrated and purified by flash chromatography to afford the title compound. LC-MS calculated for $C_{38}H_{42}ClFN_5O_4S^+$ (M+H)$^+$: m/z=718.3; found 718.3.

Step 4: 3-(1-((1R,4R,5S)-2-Azabicyclo[2.1.1]hexan-5-yl)-7-(3-chloro-2-methylphenyl)-6-fluoro-4-(5-methylpyrazin-2-yl)-2-((R)-1-(3-oxomorpholino)ethyl)-1H-pyrrolo[3,2-c]quinolin-8-yl)propanenitrile A solution of tert-butyl (1R,4R,5S)-5-(7-(3-chloro-2-methylphenyl)-8-(2-cyanoethyl)-6-fluoro-4-(methylthio)-2-((R)-1-(3-oxomorpholino)ethyl)-1H-pyrrolo[3,2-c]quinolin-1-yl)-2-azabicyclo[2.1.1]hexane-2-carboxylate (1.25 g, 1.74 mmol), Pd(PPh$_3$)$_4$ (1.00 g, 0.870 mmol), copper(I) 3-methylsalicylate (1.87 g, 8.70 mmol) and 2-methyl-5-(4,4,5,5-tetramethyl-1,3,2-dioxaborolan-2-yl)pyrazine (1.92 g, 8.70 mmol) in 1,4-dioxane (10 mL) was stirred at 120° C. for 1 h. The reaction mixture was filtered through a thiol siliaprep cartridge and concentrated. The residue was stirred in 1:1 DCM/TFA (30 mL) for 30 min, concentrated and purified by prep HPLC (pH 2). LC-MS calculated for C$_{37}$H$_{36}$ClFN$_7$O$_2$$^+$ (M+H)$^+$: m/z=664.3; found 664.4. $^1$H NMR (500 MHz, DMF-d$_7$) δ 9.71 (d, J=1.5 Hz, 1H), 8.81 (d, J=1.5 Hz, 1H), 8.63 (s, 1H), 7.84 (s, 1H), 7.65 (m, 1H), 7.49 (m, 2H), 6.38 (q, J=6.3 Hz, 1H), 5.07 (m, 1H), 4.63 (d, J=5.9 Hz, 1H), 4.21 (d, J=16.5 Hz, 1H), 4.16 (d, J=16.5 Hz, 1H), 3.82 (m, 1H), 3.76 (m, 1H), 3.59 (m, 1H), 3.12 (m, 1H), 3.10 (m, 1H), 2.96 (m, 2H), 2.91 (m, 1H), 2.67 (s, 3H), 2.60 (m, 1H), 2.52 (d, J=8.6 Hz, 1H), 2.19 (s, 3H), 1.94 (d, J=7.0 Hz, 1H), 1.69 (d, J=6.7 Hz, 3H), 1.36 (d, J=8.6 Hz, 1H), 1.22 (d, J=7.0 Hz, 1H).

Example 45. 5-(1-((1R,4R,5S)-2-Azabicyclo[2.1.1]hexan-5-yl)-8-(2-cyanoethyl)-6-fluoro-7-(7-fluoronaphthalen-1-yl)-2-((R)-1-(3-oxomorpholino)ethyl)-1H-pyrrolo[3,2-c]quinolin-4-yl)-N-methylpicolinamide

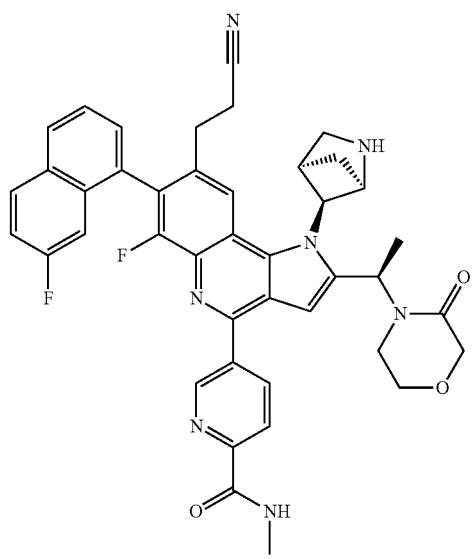 [SMILES: CNC(=O)c1ccc(-c2nc3c(F)c(-c4cccc5ccc(F)cc45)c(CCC#N)cc3c3c2cc([C@@H](C)N2CCOCC2=O)n3[C@H]2[C@H]3CN[C@@H]2C3)cn1]

This compound was prepared according to the procedure described in Example 44, using 2-(7-fluoronaphthalen-1-yl)-4,4,5,5-tetramethyl-1,3,2-dioxaborolane instead of (3-chloro-2-methylphenyl)boronic acid in Step 3, and N-methyl-5-(4,4,5,5-tetramethyl-1,3,2-dioxaborolan-2-yl)picolinamide instead of 2-methyl-5-(4,4,5,5-tetramethyl-1,3,2-dioxaborolan-2-yl)pyrazine in Step 4. LC-MS calculated for C$_{42}$H$_{38}$F$_2$N$_7$O$_3$ (M+H)$^+$: m/z=726.3; found 726.4. $^1$H NMR (TFA salt, mixture of atropisomers, rotamers, 600 MHz, DMSO-d$_6$) δ 9.53 (m, 1H), 9.25 (m, 1H), 8.89 (m, 1H), 8.61 (m, 1H), 8.43-8.14 (m, 4H), 7.77-7.48 (m, 3H), 7.26-6.80 (m, 2H), 5.98-5.75 (m, 1H), 5.71-5.40 (m, 1H), 5.24-4.91 (m, 1H), 4.26 (m, 2H), 4.10-2.99 (m, 5H), 2.98-2.53 (m, 7H), 2.49-1.92 (m, 3H), 1.71-1.49 (m, 4H).

Example 46. 3-(1-((1R,4R,5S)-2-Azabicyclo[2.1.1]hexan-5-yl)-6-fluoro-7-(7-fluoronaphthalen-1-yl)-4-(6-(2-hydroxypropan-2-yl)pyridin-3-yl)-2-((R)-1-(3-oxomorpholino)ethyl)-1H-pyrrolo[3,2-c]quinolin-8-yl)propanenitrile

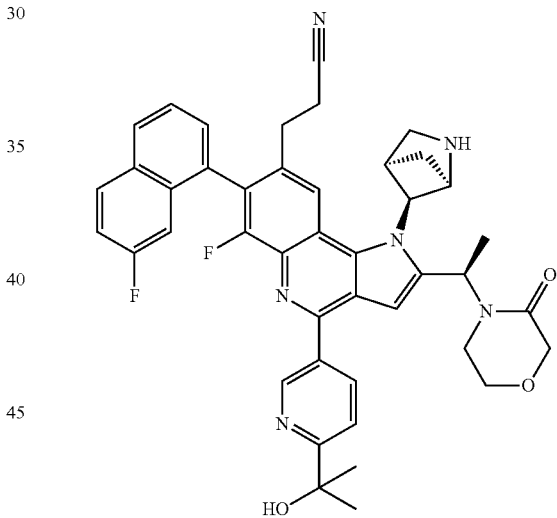

This compound was prepared according to the procedure described in Example 44, using 2-(7-fluoronaphthalen-1-yl)-4,4,5,5-tetramethyl-1,3,2-dioxaborolane instead of (3-chloro-2-methylphenyl)boronic acid in Step 3, and 5-(4,4,5,5-tetramethyl-1,3,2-dioxaborolan-2-yl)-2-(2-((trimethylsilyl)oxy)propan-2-yl)pyridine instead of 2-methyl-5-(4,4,5,5-tetramethyl-1,3,2-dioxaborolan-2-yl)pyrazine in Step 4. LC-MS calculated for C$_{43}$H$_{41}$F$_2$N$_6$O$_3$ (M+H)$^+$: m/z=727.3; found 727.4. $^1$H NMR (TFA salt, mixture of atropisomers, rotamers, 600 MHz, DMSO-d$_6$) δ 9.54 (m, 1H), 9.15 (m, 1H), 8.51-8.14 (m, 4H), 7.93 (m, 1H), 7.76-7.48 (m, 3H), 7.26-6.82 (m, 2H), 5.99-5.78 (m, 1H), 5.69-5.36 (m, 1H), 5.25-4.90 (m, 1H), 4.24 (m, 2H), 4.11-2.98 (m, 5H), 2.98-2.54 (m, 4H), 2.48-1.90 (m, 3H), 1.73-1.38 (m, 10H).

Example 47. 3-(1-((1R,4R,5S)-2-Azabicyclo[2.1.1]
hexan-5-yl)-6-fluoro-7-(7-fluoronaphthalen-1-yl)-4-
(5-methylpyrazin-2-yl)-2-((R)-1-(3-oxomorpholino)
ethyl)-1H-pyrrolo[3,2-c]quinolin-8-yl)propanenitrile

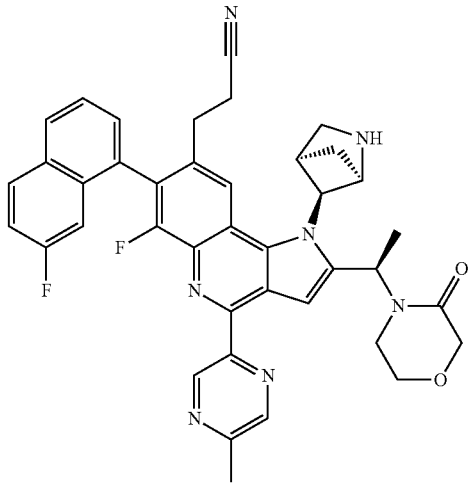 [SMILES: Cc1cnc(-c2nc3c(F)c(-c4cccc5ccc(F)cc45)c(CCC#N)cc3c3c2cc([C@@H](C)N2CCOCC2=O)n3[C@H]2[C@H]3CN[C@@H]2C3)cn1]

This compound was prepared according to the procedure described in Example 44, using 2-(7-fluoronaphthalen-1-yl)-4,4,5,5-tetramethyl-1,3,2-dioxaborolane instead of (3-chloro-2-methylphenyl)boronic acid in Step 3. LC-MS calculated for $C_{40}H_{36}F_2N_7O_2$ $(M+H)^+$: m/z=684.3; found 684.4. $^1$H NMR (TFA salt, mixture of atropisomers, rotamers, 600 MHz, DMSO-$d_6$) δ 9.59 (m, 1H), 9.49 (m, 0.7H), 9.20 (m, 0.3H), 8.82 (m, 1H), 8.40-8.30 (m, 1.5H), 8.27-8.16 (m, 2.5H), 7.87-7.61 (m, 4H), 7.55 (m, 1H), 7.16 (m, 0.5H), 6.92 (m, 0.5H), 5.93 (m, 0.7H), 5.77 (m, 0.3H), 5.67 (m, 0.3H), 5.44 (m, 0.7H), 5.21-4.89 (m, 1H), 4.35-4.12 (m, 2.3H), 4.05-3.38 (m, 3.3H), 3.14-1.86 (m, 11H), 1.74-1.46 (m, 4.4H).

Example 48. Methyl (1R,3R,5R)-3-(1-((1R,4R,5S)-2-azabicyclo[2.1.1]hexan-5-yl)-8-(2-cyanoethyl)-7-(2,3-dichlorophenyl)-4-(6-(dimethylcarbamoyl)pyridin-3-yl)-6-fluoro-1H-pyrrolo[3,2-c]quinolin-2-yl)-2-azabicyclo[3.1.0]hexane-2-carboxylate

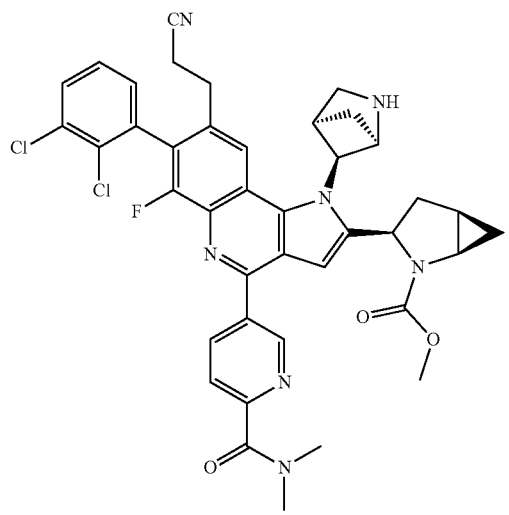 [SMILES: COC(=O)N1[C@@H](c2cc3c(-c4ccc(C(=O)N(C)C)nc4)nc4c(F)c(-c5cccc(Cl)c5Cl)c(CCC#N)cc4c3n2[C@H]2[C@H]3CN[C@@H]2C3)C[C@H]2C[C@H]21]

This compound was prepared in an analogous fashion to Example 30, using 2-(tert-butyl) 3-ethyl (1R,3R,5R)-2-azabicyclo[3.1.0]hexane-2,3-dicarboxylate instead of 2-(tert-butyl) 3-ethyl (1 S,3R,5S)-2-azabicyclo[3.1.0]hexane-2,3-dicarboxylate in Step 1. LC-MS calculated for $C_{40}H_{37}Cl_2FN_7O_3^+$ $(M+H)^+$: m/z=752.2/754.2; found 752.2/754.2. $^1$H NMR (600 MHz, DMSO-$d_6$) δ 9.91-9.76 (m, 1H), 9.15-9.06 (m, 1H), 8.42 (t, J=8.0 Hz, 1H), 8.22 (d, J=7.5 Hz, 1H), 8.07 (s, 1H), 7.84 (t, J=8.9 Hz, 2H), 7.64-7.56 (m, 1H), 7.50 (d, J=6.6 Hz, 1H), 6.53 (d, J=3.4 Hz, 1H), 5.66 (d, J=10.5 Hz, 1H), 5.41 (d, J=10.7 Hz, 1H), 4.86 (d, J=6.1 Hz, 1H), 3.93-3.77 (m, 2H), 3.75 (s, 1H), 3.67 (d, J=4.0 Hz, 1H), 3.49-3.26 (m, 1H), 3.10-3.05 (m, 4H), 3.04 (d, J=1.9 Hz, 3H), 2.91 (dt, J=12.6, 6.6 Hz, 2H), 2.87-2.79 (m, 1H), 2.73 (td, J=15.7, 7.4 Hz, 1H), 2.31 (s, 1H), 2.14-1.98 (m, 1H), 1.71-1.56 (m, 2H), 1.19 (t, J=7.3 Hz, 1H), 0.71-0.61 (m, 1H), 0.60-0.41 (m, 1H).

Example 49. 3-(1-((1R,4R,5S)-2-Azabicyclo[2.1.1]hexan-5-yl)-2-((1R,3R,5R)-2-(cyclopropanecarbonyl)-2-azabicyclo[3.1.0]hexan-3-yl)-7-(2,3-dichlorophenyl)-6-fluoro-4-methyl-1H-pyrrolo[3,2-c]quinolin-8-yl)propanenitrile

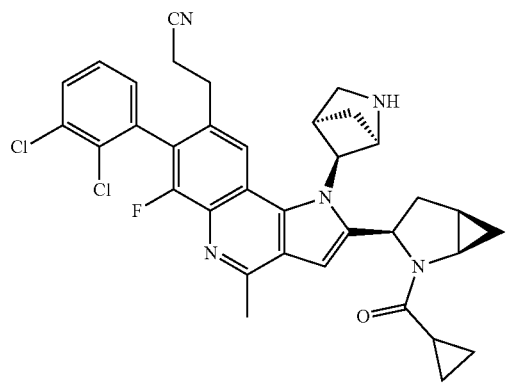 [SMILES: Cc1nc2c(F)c(-c3cccc(Cl)c3Cl)c(CCC#N)cc2c2c1cc([C@H]1C[C@H]3C[C@H]3N1C(=O)C1CC1)n2[C@H]1[C@H]2CN[C@@H]1C2]

Step 1. tert-Butyl (1R,3R,5R)-3-(hydroxymethyl)-2-azabicyclo[3.1.0]hexane-2-carboxylate

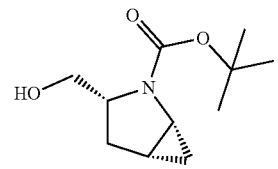

To a solution of 2-(tert-butyl) 3-ethyl (1R,3R,5R)-2-azabicyclo[3.1.0]hexane-2,3-dicarboxylate (4.243 g, 16.62 mmol) in Tetrahydrofuran (83 ml) at 0° C. was added LAH (0.757 g, 19.94 mmol, 2M in THF) and the reaction mixture was stirred at r.t. for 1 h, then cooled to 0° C. The reaction was quenched by the successive addition of 760 μL water, 760 μL 15% NaOH and 2.3 mL water. After stirring at r.t. for 30 min, the mixture was diluted with DCM and filtered through a plug of Celite. The filtrate was concentrated. The crude product was used in the next step without further purification (2.78 g, 79%). LC-MS calculated for $C_{11}H_{20}NO_3^+$ $(M+H)^+$: m/z=214.1; found 214.2.

Step 2. tert-Butyl (1R,3R,5R)-3-formyl-2-azabicyclo[3.1.0]hexane-2-carboxylate

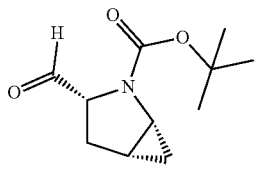

To a solution of oxalyl chloride (1.372 mL, 15.67 mmol) in DCM (60 mL) at −78° C. was added DMSO (1.112 mL, 15.67 mmol) dropwise and the reaction mixture was stirred at −78° C. for 45 min, then a solution of tert-butyl (1R,3R,5R)-3-(hydroxymethyl)-2-azabicyclo[3.1.0]hexane-2-carboxylate (2.78 g, 13 mmol) from the previous step in DCM (5 mL) was added dropwise. Stirring was continued for an additional 45 min, at which point triethylamine (5.46 mL, 39.2 mmol) was added. After an additional 45 min at −78° C., the reaction mixture was transferred to an ice bath and stirred for 15 min, then quenched with water and extracted with DCM. The organic layer was washed with 1 N HCl, water and brine, dried over sodium sulfate and concentrated. The crude product was used in the next step without further purification (2.5 g, 91%). LC-MS calculated for $C_{11}H_{18}NO_3+(M+H)^+$: m/z=212.1; found 212.2.

Step 3. tert-Butyl (1R,3R,5R)-3-ethynyl-2-azabicyclo[3.1.0]hexane-2-carboxylate

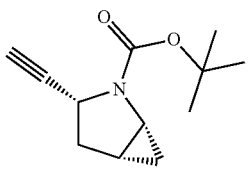

To a solution of tert-butyl (1R,3R,5R)-3-formyl-2-azabicyclo[3.1.0]hexane-2-carboxylate (2.498 g, 11.82 mmol) in MeOH (60 mL) at 0° C. were added potassium carbonate (3.27 g, 23.65 mmol) and Dimethyl (1-diazo-2-oxopropyl) phosphonate (1.775 mL, 11.82 mmol) and the reaction mixture was stirred at r.t. for 2 h, then concentrated. The residue was partitioned between water and ethyl acetate and the organic layer was washed with water and brine, dried over sodium sulfate and concentrated. The crude product was used in the next step without further purification. LC-MS calculated for $C_{12}H_{18}NO_2+(M+H)^+$: m/z=208.1; found 208.2.

Step 4. 2-(Trimethylsilyl)ethyl (1R,3R,5R)-3-ethynyl-2-azabicyclo[3.1.0]hexane-2-carboxylate

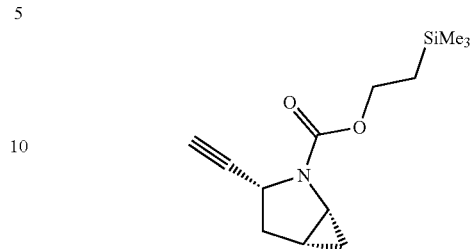

A solution of tert-butyl (1R,3R,5R)-3-ethynyl-2-azabicyclo[3.1.0]hexane-2-carboxylate (2.451 g, 11.82 mmol) in 4N HCl in dioxane (20 mL) was stirred at r.t. for 2 h, then concentrated. The residue was dissolved in Acetonitrile (40 mL) and triethylamine (8.24 mL, 59.1 mmol) was added. After 5 mins, 1-[2-Trimethylsilyl)ethoxycarbonyloxy]pyrrolidin-2,5-dione (3.07 g, 11.82 mmol) was added as a solid and the reaction mixture was stirred overnight. The reaction was quenched with water and extracted with ethyl acetate. The organic layer was washed with water and brine, dried over sodium sulfate and concentrated. The crude product was purified by column chromatography (0-50% ethyl acetate in hexanes) to provide the desired product (1.94, 65%). LC-MS calculated for $C_{13}H_{22}NO_2Si^+$ $(M+H)^+$: m/z=252.1; found 252.2.

Step 5. tert-Butyl (1R,4R,5S)-5-((7-bromo-6-(2-cyanoethyl)-8-fluoro-2-(methylthio)-3-(((1R,3R,5R)-2-((2-(trimethylsilyl)ethoxy)carbonyl)-2-azabicyclo[3.1.0]hexan-3-yl)ethynyl)quinolin-4-yl)amino)-2-azabicyclo[2.1.1]hexane-2-carboxylate

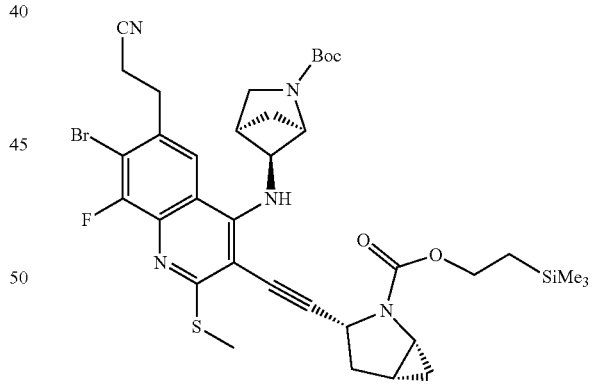

To a mixture of Intermediate 5 (2.9 g, 4.48 mmol) and 2-(trimethylsilyl)ethyl (1R,3R,5R)-3-ethynyl-2-azabicyclo[3.1.0]hexane-2-carboxylate (1.689 g, 6.72 mmol) were added DMF (15 mL) and triethylamine (1.873 mL, 13.44 mmol), followed by bis(triphenylphosphine)palladium(II) chloride (0.314 g, 0.448 mmol) and copper(I) iodide (0.853 g, 4.48 mmol). The reaction flask was evacuated, back filled with nitrogen, then stirred at 70° C. for 2 h. The reaction mixture was quenched with water and a small amount of 30% aq. ammonium hydroxide, then extracted with ethyl acetate. The organic layer was washed with water and brine, dried over sodium sulfate and concentrated. The crude product was purified by column chromatography (0-40% acetone in hexanes) to provide the desired product (2.54 g, 73%). LC-MS calculated for $C_{36}H_{46}BrFN_5O_4SSi^+$ (M+H)$^+$: m/z=770.2/772.2; found 770.0/772.0.

Step 6. tert-Butyl (1R,4R,5S)-5-(7-bromo-8-(2-cyanoethyl)-6-fluoro-4-(methylthio)-2-((1R,3R,5R)-2-((2-(trimethylsilyl)ethoxy)carbonyl)-2-azabicyclo[3.1.0]hexan-3-yl)-1H-pyrrolo[3,2-c]quinolin-1-yl)-2-azabicyclo[2.1.1]hexane-2-carboxylate

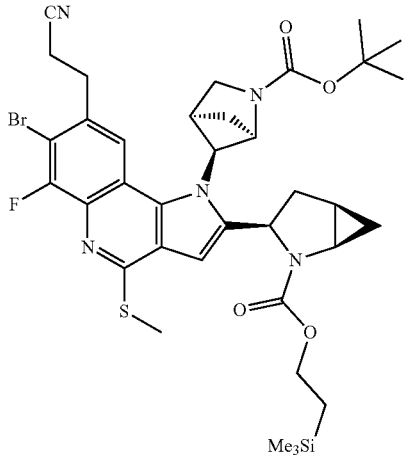 [SMILES: CSc1nc2c(F)c(Br)c(CCC#N)cc2c2c1cc([C@H]1C[C@H]3C[C@H]3N1C(=O)OCC[Si](C)(C)C)n2[C@H]1[C@@H]2C[C@H]1N(C(=O)OC(C)(C)C)C2]

To a solution of tert-butyl (1R,4R,5S)-5-((7-bromo-6-(2-cyanoethyl)-8-fluoro-2-(methylthio)-3-(((1R,3R,5R)-2-((2-(trimethylsilyl)ethoxy)carbonyl)-2-azabicyclo[3.1.0]hexan-3-yl)ethynyl)quinolin-4-yl)amino)-2-azabicyclo[2.1.1]hexane-2-carboxylate (2.537 g, 3.29 mmol) in DMF (15 ml) was added cesium carbonate (2.145 g, 6.58 mmol) and the reaction mixture was heated to 90° C. for 2 h. The reaction was quenched with water and extracted with ethyl acetate. The organic layer was washed with water and brine, dried over sodium sulfate and concentrated. The crude product was purified by column chromatography (0-40% acetone in hexanes) to provide the desired product (1.7 g, 67%). LC-MS calculated for $C_{36}H_{46}BrFN_5O_4SSi^+$ (M+H)$^+$: m/z=770.2/772.2; found 770.0/772.0.

Step 7. tert-Butyl (1R,4R,5S)-5-(8-(2-cyanoethyl)-7-(2,3-dichlorophenyl)-6-fluoro-4-(methylthio)-2-((1R,3R,5R)-2-((2-(trimethylsilyl)ethoxy)carbonyl)-2-azabicyclo[3.1.0]hexan-3-yl)-1H-pyrrolo[3,2-c]quinolin-1-yl)-2-azabicyclo[2.1.1]hexane-2-carboxylate

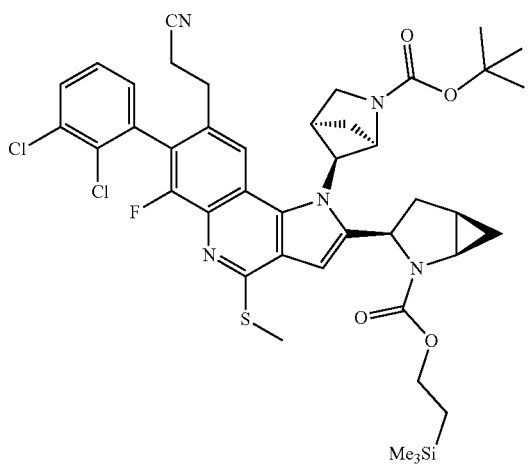 [SMILES: CSc1nc2c(F)c(-c3cccc(Cl)c3Cl)c(CCC#N)cc2c2c1cc([C@H]1C[C@H]3C[C@H]3N1C(=O)OCC[Si](C)(C)C)n2[C@H]1[C@@H]2C[C@H]1N(C(=O)OC(C)(C)C)C2]

To a mixture of tert-butyl (1R,4R,5S)-5-(7-bromo-8-(2-cyanoethyl)-6-fluoro-4-(methylthio)-2-((1R,3R,5R)-2-((2-(trimethylsilyl)ethoxy)carbonyl)-2-azabicyclo[3.1.0]hexan-3-yl)-1H-pyrrolo[3,2-c]quinolin-1-yl)-2-azabicyclo[2.1.1]hexane-2-carboxylate (1.699 g, 2.204 mmol), (2,3-dichlorophenyl)boronic acid (0.631 g, 3.31 mmol), potassium fluoride (0.384 g, 6.61 mmol) and Pd-132 (0.156 g, 0.220 mmol) were added 1,4-Dioxane (6 mL)/Water (1.5 mL) and the reaction flask was evacuated, back filled with nitrogen, then stirred at 100° C. for 1 h. The reaction mixture was diluted with DCM and filtered through a plug of Celite. The filtrate was concentrated and the crude product was purified by column chromatography (0-40% acetone in hexanes) to provide the desired product (1.72 g, 93%). LC-MS calculated for $C_{42}H_{49}Cl_2FN_5O_4SSi^+$ (M+H)$^+$: m/z=836.3/838.3; found 836.2/838.2.

Step 8. tert-Butyl (1R,4R,5S)-5-(8-(2-cyanoethyl)-2-((1R,3R,5R)-2-(cyclopropanecarbonyl)-2-azabicyclo[3.1.0]hexan-3-yl)-7-(2,3-dichlorophenyl)-6-fluoro-4-(methylthio)-1H-pyrrolo[3,2-c]quinolin-1-yl)-2-azabicyclo[2.1.1]hexane-2-carboxylate

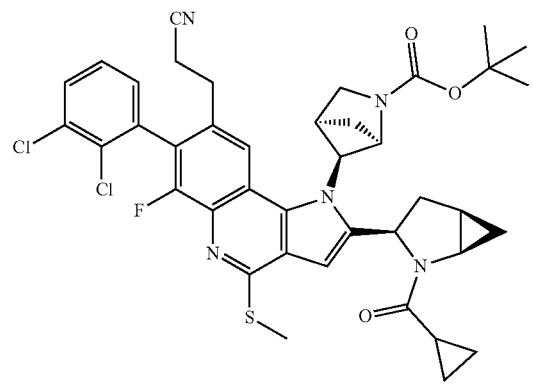 [SMILES: CSc1nc2c(F)c(-c3cccc(Cl)c3Cl)c(CCC#N)cc2c2c1cc([C@H]1C[C@H]3C[C@H]3N1C(=O)C1CC1)n2[C@H]1[C@@H]2C[C@H]1N(C(=O)OC(C)(C)C)C2]

To a solution of tert-butyl (1R,4R,5S)-5-(8-(2-cyanoethyl)-7-(2,3-dichlorophenyl)-6-fluoro-4-(methylthio)-2-((1R,3R,5R)-2-((2-(trimethylsilyl)ethoxy)carbonyl)-2-azabicyclo[3.1.0]hexan-3-yl)-1H-pyrrolo[3,2-c]quinolin-1-yl)-2-azabicyclo[2.1.1]hexane-2-carboxylate (1.72 g, 2.055 mmol) in Tetrahydrofuran (10 mL) was added TBAF (1M in THF, 2.466 mL, 2.466 mmol) and the reaction mixture was stirred at 65° C. for 1 h, then cooled to r.t. Triethylamine (0.859 mL, 6.17 mmol) and cyclopropanecarbonyl chloride (0.279 mL, 3.08 mmol) were added and the reaction mixture was stirred at r.t. for 30 min, then quenched with water and extracted with ethyl acetate. The organic layer was washed with water and brine, dried over sodium sulfate and concentrated. The crude product was purified by column chromatography (0-100% acetone in hexanes) to provide the desired product. LC-MS calculated for $C_{40}H_{41}Cl_2FN_5O_3S^+$ (M+H)$^+$: m/z=760.2/762.2; found 760.2/762.2.

Step 9. tert-Butyl (1R,4R,5S)-5-(8-(2-cyanoethyl)-2-((1R,3R,5R)-2-(cyclopropanecarbonyl)-2-azabicyclo[3.1.0]hexan-3-yl)-7-(2,3-dichlorophenyl)-6-fluoro-4-(methylsulfinyl)-1H-pyrrolo[3,2-c]quinolin-1-yl)-2-azabicyclo[2.1.1]hexane-2-carboxylate

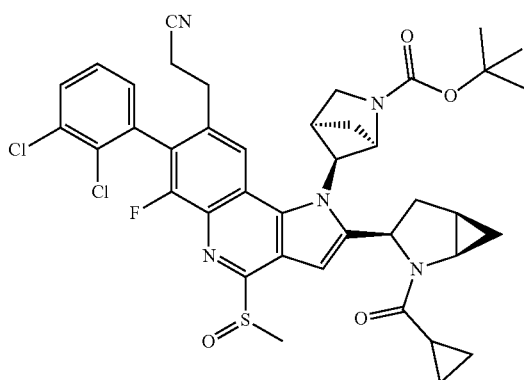

To a solution of tert-butyl (1R,4R,5S)-5-(8-(2-cyanoethyl)-2-((1R,3R,5R)-2-(cyclopropanecarbonyl)-2-azabicyclo[3.1.0]hexan-3-yl)-7-(2,3-dichlorophenyl)-6-fluoro-4-(methylthio)-1H-pyrrolo[3,2-c]quinolin-1-yl)-2-azabicyclo[2.1.1]hexane-2-carboxylate (925 mg, 1.216 mmol) in DCM (6 mL) at 0° C. was added m-CPBA (327 mg, 1.459 mmol, 77% w/w in water) and the reaction mixture was stirred at r.t. for 30 min, then quenched with sat. sodium bicarbonate and extracted with DCM. The organic layer was dried over sodium sulfate and concentrated. The crude product was purified by column chromatography (0-100% acetone in hexanes) to provide the desired product (703 mg, 74%). LC-MS calculated for $C_{40}H_{41}Cl_2FN_5O_4S^+$ (M+H)$^+$: m/z=776.2/778.2; found 776.2/778.2.

Step 10. 3-(1-((1R,4R,5S)-2-Azabicyclo[2.1.1]hexan-5-yl)-2-((1R,3R,5R)-2-(cyclopropanecarbonyl)-2-azabicyclo[3.1.0]hexan-3-yl)-7-(2,3-dichlorophenyl)-6-fluoro-4-methyl-1H-pyrrolo[3,2-c]quinolin-8-yl)propanenitrile Tert-butyl (1R,4R,5S)-5-(8-(2-cyanoethyl)-2-((1R,3R,5R)-2-(cyclopropanecarbonyl)-2-azabicyclo[3.1.0]hexan-3-yl)-7-(2,3-dichlorophenyl)-6-fluoro-4-(methylsulfinyl)-1H-pyrrolo[3,2-c]quinolin-1-yl)-2-azabicyclo[2.1.1]hexane-2-carboxylate (403 mg, 0.519 mmol) was dissolved in Tetrahydrofuran (2.59 ml) and cooled to −20° C. Methylmagnesium bromide (3M in diethyl ether, 346 μl, 1.038 mmol) was added and the reaction mixture was stirred at −20° C. for 1 h, then quenched with sat. ammonium chloride and extracted with ethyl acetate. The organic layer was washed with water and brine, dried over sodium sulfate and concentrated. The crude product was allowed to stand in 1:1 DCM/TFA (2 mL) for 15 min, then diluted with MeOH and purified by prep HPLC (pH 2) to provide the desired product. LC-MS calculated for $C_{35}H_{33}Cl_2FN_5O^+$ (M+H)$^+$: m/z=628.2/630.2; found 628.2/630.2. $^1$H NMR (500 MHz, DMSO-d$_6$) δ 9.76 (s, 1H), 8.15 (s, 1H), 8.03 (s, 1H), 7.85 (d, J=8.0 Hz, 1H), 7.58 (t, J=7.8 Hz, 1H), 7.46 (d, J=7.5 Hz, 1H), 6.52 (s, 1H), 5.62 (s, 1H), 5.51 (d, J=10.7 Hz, 1H), 4.81 (d, J=5.9 Hz, 1H), 4.14 (t, J=2.5 Hz, 1H), 3.90 (s, 1H), 3.47 (s, 1H), 3.35 (s, 1H), 3.03 (dt, J=14.0, 6.6 Hz, 1H), 2.95-2.76 (m, 5H), 2.71 (dt, J=15.1, 7.2 Hz, 1H), 2.35-2.29 (m, 1H), 2.27 (d, J=9.1 Hz, 1H), 1.97 (dd, J=12.9, 2.6 Hz, 1H), 1.79 (dq, J=12.2, 6.5 Hz, 1H), 1.58 (d, J=9.2 Hz, 1H), 1.24 (s, 1H), 1.00-0.89 (m, 3H), 0.88-0.80 (m, 1H), 0.76 (q, J=6.8 Hz, 1H), 0.66 (dt, J=7.4, 3.5 Hz, 1H).

Example 50: 3-(1-((1R,4R,5S)-2-Azabicyclo[2.1.1]hexan-5-yl)-7-(2,3-dichlorophenyl)-6-fluoro-4-(6-(2-hydroxypropan-2-yl)pyridin-3-yl)-2-((R)-1-(2-oxopyrazin-1(2H)-yl)ethyl)-1H-pyrrolo[3,2-c]quinolin-8-yl)propanenitrile

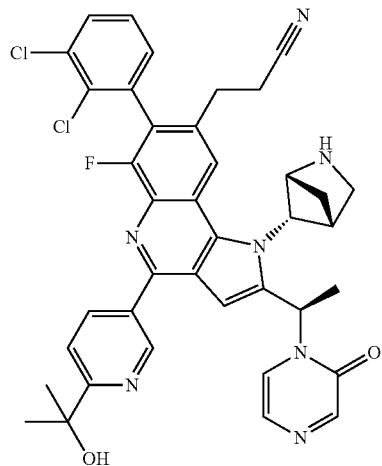 [SMILES: C[C@H](c1cc2c(-c3ccc(C(C)(C)O)nc3)nc3c(F)c(-c4cccc(Cl)c4Cl)c(CCC#N)cc3c2n1[C@H]1[C@H]2CN[C@@H]1C2)n1ccncc1=O]

Step 1: tert-Butyl (1R,4R,5S)-5-((7-bromo-6-(2-cyanoethyl)-8-fluoro-2-(methylthio)-3-((R)-3-(2-oxopyrazin-1(2H)-yl)but-1-yn-1-yl)quinolin-4-yl)amino)-2-azabicyclo[2.1.1]hexane-2-carboxylate

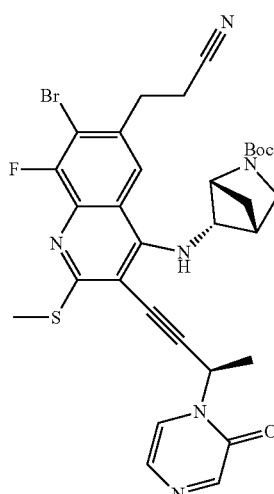

A mixture of tert-Butyl (1R,4R,5S)-5-((7-bromo-6-(2-cyanoethyl)-8-fluoro-3-iodo-2-(methylthio)quinolin-4-yl)amino)-2-azabicyclo[2.1.1]hexane-2-carboxylate (2.70 g, 4.17 mmol, Intermediate 5), (R)-1-(but-3-yn-2-yl)pyrazin-2(1H)-one (1.24 g, 8.34 mmol, intermediate 20), tetrakis(triphenylphosphine)palladium(0) (0.96 g, 0.83 mmol), CuI (0.32 g, 1.67 mmol) and N,N-diisopropylethylamine (7.3 mL, 41.7 mmol) in DMF (21.0 mL) was sparged with N₂ and heated to 70° C. for 1 h. Once completed, the reaction mixture was cooled down to room temperature and poured into water. The aqueous layer was extracted with ethyl acetate, washed with brine, concentrated and purified by flash chromatography (0-100% EtOAc/hexanes) to afford the title compound. LC-MS calculated for $C_{31}H_{33}BrFN_6O_3S$ (M+H)⁺: m/z=667.1; found 667.1.

Step 2: tert-Butyl (1R,4R,5S)-5-(7-bromo-8-(2-cyanoethyl)-6-fluoro-4-(methylthio)-2-((R)-1-(2-oxopyrazin-1(2H)-yl)ethyl)-1H-pyrrolo[3,2-c]quinolin-1-yl)-2-azabicyclo[2.1.1]hexane-2-carboxylate

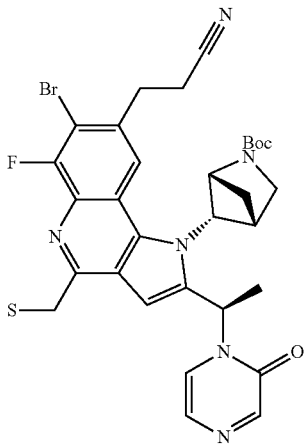

A mixture of tert-butyl (1R,4R,5S)-5-((7-bromo-6-(2-cyanoethyl)-8-fluoro-2-(methylthio)-3-((R)-3-(2-oxopyrazin-1(2H)-yl)but-1-yn-1-yl)quinolin-4-yl)amino)-2-azabicyclo[2.1.1]hexane-2-carboxylate (2.00 g, 3.00 mmol) and cesium carbonate (2.93 g, 9.00 mmol) in DMA (6.0 mL) was heated at 100° C. for 0.5 h. Once completed, the reaction mixture was cooled to room temperature and poured into water. The aqueous layer was extracted with EA, washed with brine, concentrated and purified by flash chromatography (0-100% EtOAc/hexanes) to afford the title compound. LC-MS calculated for $C_{31}H_{33}BrFN_6O_3S$ (M+H)⁺: m/z=667.1; found 667.2.

Step 3: tert-Butyl (1R,4R,5S)-5-(8-(2-cyanoethyl)-7-(2,3-dichlorophenyl)-6-fluoro-4-(methylthio)-2-((R)-1-(2-oxopyrazin-1(2H)-yl)ethyl)-1H-pyrrolo[3,2-c]quinolin-1-yl)-2-azabicyclo[2.1.1]hexane-2-carboxylate

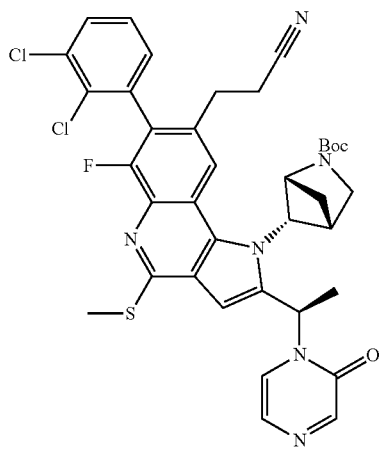 [SMILES: CSc1nc2c(F)c(-c3cccc(Cl)c3Cl)c(CCC#N)cc2c2c1cc([C@@H](C)n1ccncc1=O)n2[C@H]1[C@@H]2C[C@H]1N(C(=O)OC(C)(C)C)C2]

A mixture of tert-butyl (1R,4R,5S)-5-(7-bromo-8-(2-cyanoethyl)-6-fluoro-4-(methylthio)-2-((R)-1-(2-oxopyrazin-1(2H)-yl)ethyl)-1H-pyrrolo[3,2-c]quinolin-1-yl)-2-azabicyclo[2.1.1]hexane-2-carboxylate (150 mg, 0.23 mmol), (2,3-dichlorophenyl)boronic acid (64 mg, 0.34 mmol), bis(di-tert-butyl(4-dimethylaminophenyl)phosphine) dichloropalladium(II) (13 mg, 0.022 mmol), potassium fluoride (191 mg, 0.90 mmol) in dioxane (0.70 mL) and water (0.07 mL) was sparged with N₂ and heated at 100° C. for 1 h. Once completed, the reaction mixture was cooled down to room temperature and poured into water. The aqueous layer was extracted with EA, washed with brine, concentrated and purified by flash chromatography (0-100% EtOAc/hexanes) to afford the title compound. LC-MS calculated for $C_{37}H_{36}Cl_2FN_6O_3S$ (M+H)⁺: m/z=733.2; found 733.1.

Step 4: 3-(1-((1R,4R,5S)-2-Azabicyclo[2.1.1]hexan-5-yl)-7-(2,3-dichlorophenyl)-6-fluoro-4-(6-(2-hydroxypropan-2-yl)pyridin-3-yl)-2-((R)-1-(2-oxopyrazin-1(2H)-yl)ethyl)-1H-pyrrolo[3,2-c]quinolin-8-yl)propanenitrile A mixture of tert-butyl (1R,4R,5S)-5-(8-(2-cyanoethyl)-7-(2,3-dichlorophenyl)-6-fluoro-4-(methylthio)-2-((R)-1-(2-oxopyrazin-1(2H)-yl)ethyl)-1H-pyrrolo[3,2-c]quinolin-1-yl)-2-azabicyclo[2.1.1]hexane-2-carboxylate (73 mg, 0.10 mmol), 5-(4,4,5,5-tetramethyl-1,3,2-dioxaborolan-2-yl)-2-(2-((trimethylsilyl)oxy)propan-2-yl)pyridine (100 mg, 0.30 mmol), tetrakis(triphenylphosphine)palladium(0) (58 mg, 0.050 mmol), copper(I) 3-methylsalicylate (75 mg, 0.35 mmol) in dioxane (0.50 mL) was sparged with N₂ and heated to 120° C. for 1 h. Once completed, the reaction mixture was filtered through celite and concentrated. To the residue was added a drop of MeCN and a 2 M HCl in dioxane solution (2 mL). The mixture was stirred for 30 mins, and purified by prep HPLC (pH 2).

Atropisomer 1. Peak 1. LC-MS calculated for $C_{39}H_{35}Cl_2FN_7O_2$ (M+H)⁺: m/z=722.2; found 722.2.

Atropisomer 2. Peak 2. LC-MS calculated for $C_{39}H_{35}Cl_2FN_7O_2$ (M+H)⁺: m/z=722.2; found 722.2. ¹H NMR (TFA salt, mixture of rotamers, 500 MHz, DMSO-d₆) δ 9.60 (br, 0.6H), 9.27 (br, 0.4H), 9.21 (m, 0.6H), 9.00 (m, 0.4H), 8.51 (m, 0.6H), 8.38 (br, 0.6H), 8.14 (br, 0.4H), 8.28 (m, 0.4H), 8.25-8.18 (m, 2H), 8.02-7.93 (m, 0.8H), 7.91-7.81 (m, 1.6H), 7.63-7.47 (m, 3H), 7.28 (d, J=4.4 Hz, 0.6H), 6.96 (d, J=4.4 Hz, 0.6H), 6.42 (s, 0.4H), 6.29 (m, 0.6H), 6.10 (m, 0.4H), 5.72 (s, 0.4H), 5.26 (m, 0.6H), 5.14 (s, 0.6H), 5.05 (br, 1H), 4.95 (m, 0.4H), 4.00 (m, 0.4H), 3.80 (m, 0.6H), 3.54 (m, 0.4H), 3.42 (m, 0.4H), 3.06 (m, 0.6H), 2.95-2.64 (m, 4H), 2.37 (m, 0.4H), 2.13 (m, 0.6H), 1.95 (m, 0.4H), 1.86 (d, J=6.3 Hz, 1.8H), 1.77 (d, J=6.9 Hz, 1.2H), 1.57-1.48 (m, 7.2H).

Example 51. Methyl (2R,4S)-2-(1-((1R,4R,5S)-2-azabicyclo[2.1.1]hexan-5-yl)-8-(2-cyanoethyl)-7-(2,3-dichlorophenyl)-6-fluoro-4-(6-(2-hydroxypropan-2-yl)pyridin-3-yl)-1H-pyrrolo[3,2-c]quinolin-2-yl)-4-fluoropyrrolidine-1-carboxylate

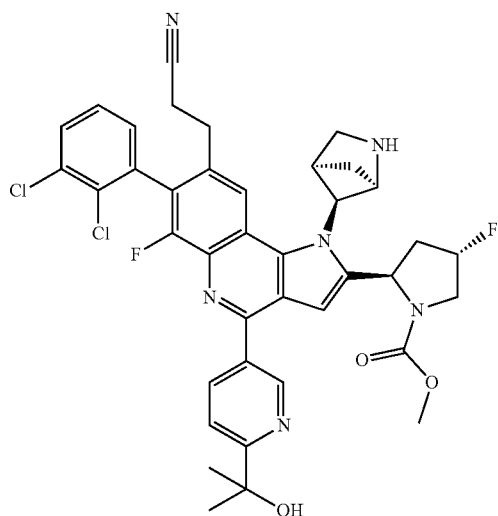 [SMILES: COC(=O)N1C[C@@H](F)C[C@@H]1c1cc2c(-c3ccc(C(C)(C)O)nc3)nc3c(F)c(-c4cccc(Cl)c4Cl)c(CCC#N)cc3c2n1[C@H]1[C@H]2CN[C@@H]1C2]

Step 1. tert-Butyl (2R,4S)-4-fluoro-2-(hydroxymethyl)pyrrolidine-1-carboxylate

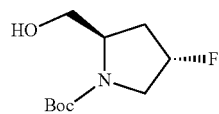

To a 0° C. solution of (2R,4S)-1-(tert-butoxycarbonyl)-4-fluoropyrrolidine-2-carboxylic acid (4.36 g, 18.69 mmol) and triethylamine (2.87 ml, 20.56 mmol) in THF (93 ml) was added isobutyl chloroformate (2.70 ml, 20.56 mmol) and the reaction mixture was stirred at r.t. for 1 hr, then filtered. The solid was washed with THF. The filtrate was cooled to 0° C. and a solution of sodium borohydride in water (10 mL) was added. The reaction mixture was stirred at r.t. for 30 min, then quenched with water and extracted with ethyl acetate. The organic layer was washed with water and brine, dried over sodium sulfate and concentrated. The crude product was used in the next step without further purification (2.3 g, 56%). LC-MS calculated for $C_6H_{11}FNO_3^+$ $(M+H-C_4H_8)^+$: m/z=164.1; found 164.0.

Step 2. tert-Butyl (2R,4S)-4-fluoro-2-formylpyrrolidine-1-carboxylate

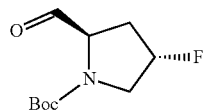 [SMILES: CC(C)(C)OC(=O)N1C[C@@H](F)C[C@@H]1C=O]

To a solution of oxalyl chloride (1.800 ml, 20.57 mmol) in DCM (62.3 ml) at −78° C. was added DMSO (2.92 ml, 41.1 mmol) dropwise and the reaction mixture was stirred at −78° C. for 45 mins, then a solution of tert-butyl (2R,4S)-4-fluoro-2-(hydroxymethyl)pyrrolidine-1-carboxylate (4.1 g, 18.70 mmol) in DCM (3 mL) was added and stirring was continued at −78° C. for an additional 2 h. Triethylamine (7.82 ml, 56.1 mmol) was then added and the reaction mixture was stirred at −78° for 15 mins, then warmed up to 0° C. and stirred an additional 1 h. The reaction mixture was quenched with 1 N HCl and extracted with DCM. The organic layer was washed with water and brine, dried over sodium sulfate and concentrated. The crude product was used in the next step without further purification (4.0 g, 98%). LC-MS calculated for $C_6H_9FNO_3^+$ $(M+H-C_4H_8)^+$: m/z=162.1; found 162.0.

Step 3. tert-Butyl (2R,4S)-2-ethynyl-4-fluoropyrrolidine-1-carboxylate

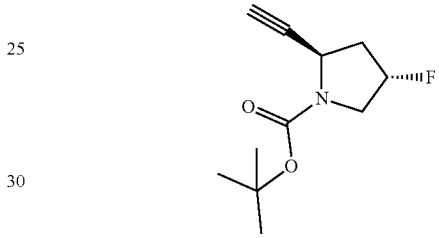

To a 0° C. solution of tert-butyl (2R,4S)-4-fluoro-2-formylpyrrolidine-1-carboxylate (3.2 g, 14.73 mmol) in MeOH (73.7 ml) were added potassium carbonate (4.07 g, 29.5 mmol) and dimethyl (1-diazo-2-oxopropyl)phosphonate (2.211 ml, 14.73 mmol) and the reaction mixture was stirred at r.t. for 2 h, then concentrated. The residue was partitioned between water and ethyl acetate and the organic layer was washed with water and brine, dried over sodium sulfate and concentrated. The crude product was purified by Biotage (0-50% acetone in hexanes) to provide the desired product (1.51 g, 48%). LC-MS calculated for $C_7H_9FNO_2^+$ $(M+H-C_4H_8)^+$: m/z=158.1; found 158.0.

Step 4. Methyl (2R,4S)-2-ethynyl-4-fluoropyrrolidine-1-carboxylate

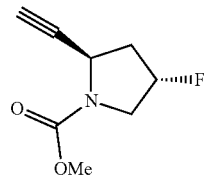

A solution of tert-butyl (2R,4S)-2-ethynyl-4-fluoropyrrolidine-1-carboxylate (500 mg, 2.345 mmol) in 4N HCl in dioxane (5 mL) was stirred at r.t. for 1 h, then concentrated. The residue was dissolved in DCM (4.7 ml) and cooled to 0° C. Triethylamine (1634 μl, 11.72 mmol) and methyl chloroformate (218 μl, 2.81 mmol) were added. The reaction mixture was stirred at r.t. for 1 h, then quenched with water and extracted with ethyl acetate. The organic layer was washed with brine, dried over sodium sulfate and concentrated. The crude product was used in the next step without further purification (377 mg, 94%). LC-MS calculated for $C_8H_{11}FNO_2^+$ (M+H)$^+$: m/z=172.1; found 172.1.

Step 5. tert-Butyl (1R,4R,5S)-5-(7-bromo-8-(2-cyanoethyl)-6-fluoro-2-((2R,4S)-4-fluoro-1-(methoxycarbonyl)pyrrolidin-2-yl)-4-(methylthio)-1H-pyrrolo[3,2-c]quinolin-1-yl)-2-azabicyclo[2.1.1]hexane-2-carboxylate

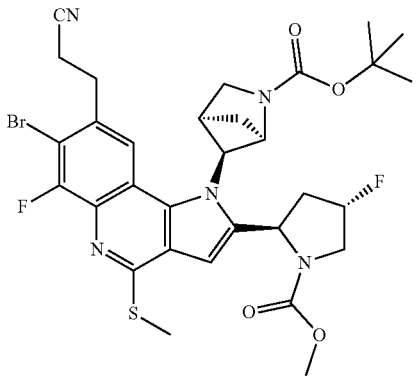 [SMILES: COC(=O)N1C[C@@H](F)C[C@@H]1c1cc2c(SC)nc3c(F)c(Br)c(CCC#N)cc3c2n1[C@H]1[C@@H]2C[C@H]1N(C(=O)OC(C)(C)C)C2]

To a mixture of Intermediate 5 (1.3 g, 2.008 mmol) and methyl (2R,4S)-2-ethynyl-4-fluoropyrrolidine-1-carboxylate (0.447 g, 2.61 mmol) were added DMF (5.02 ml) and triethylamine (0.840 ml, 6.02 mmol), followed by tetrakis(triphenylphosphine)palladium(0) (0.232 g, 0.201 mmol) and copper(I) iodide (0.382 g, 2.008 mmol). The reaction flask was evacuated, back filled with nitrogen, then stirred at 70° C. for 2 h. Cesium carbonate (1.309 g, 4.02 mmol) was then added and the reaction mixture was heated to 80° C. for 2 h. The reaction was quenched with water and a small amount of sat. aq. ammonium hydroxide, then diluted with ethyl acetate and filtered through a plug of Celite. The filtrate layers were separated and the organic layer was washed with water and brine, dried over sodium sulfate and concentrated. The crude product was purified by flash column chromatography (0-60% acetone in hexanes) to provide the desired product (486 mg, 35%). LC-MS calculated for $C_{31}H_{35}BrF_2N_5O_4S^+$ (M+H)$^+$: m/z=690.2/692.2; found 690.0/692.0.

Step 6. tert-Butyl (1R,4R,5S)-5-(8-(2-cyanoethyl)-7-(2,3-dichlorophenyl)-6-fluoro-2-((2R,4S)-4-fluoro-1-(methoxycarbonyl)pyrrolidin-2-yl)-4-(methylthio)-1H-pyrrolo[3,2-c]quinolin-1-yl)-2-azabicyclo[2.1.1]hexane-2-carboxylate

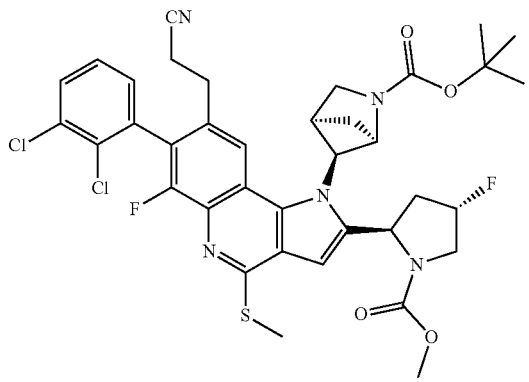 [SMILES: COC(=O)N1C[C@@H](F)C[C@@H]1c1cc2c(SC)nc3c(F)c(-c4cccc(Cl)c4Cl)c(CCC#N)cc3c2n1[C@H]1[C@@H]2C[C@H]1N(C(=O)OC(C)(C)C)C2]

To a mixture of tert-butyl (1R,4R,5S)-5-(7-bromo-8-(2-cyanoethyl)-6-fluoro-2-((2R,4S)-4-fluoro-1-(methoxycarbonyl)pyrrolidin-2-yl)-4-(methylthio)-1H-pyrrolo[3,2-c]quinolin-1-yl)-2-azabicyclo[2.1.1]hexane-2-carboxylate (486 mg, 0.704 mmol), (2,3-dichlorophenyl)boronic acid (161 mg, 0.844 mmol), potassium fluoride (123 mg, 2.111 mmol) and Pd-132 (49.8 mg, 0.070 mmol) were added 1,4-dioxane (1.407 ml)/water (0.352 ml) and the reaction flask was evacuated, back filled with nitrogen, then stirred at 100° C. for 2 h. The reaction mixture was diluted with DCM and filtered through a plug of Celite. The filtrate was concentrated and the crude product was purified by flash column chromatography (0-65% acetone in hexanes) to provide the desired product (368 mg, 69%). LC-MS calculated for $C_{37}H_{38}Cl_2F_2N_5O_4S^+$ (M+H)$^+$: m/z=756.2/758.2; found 756.2/758.2.

Step 7. Methyl (2R,4S)-2-(1-((1R,4R,5S)-2-azabicyclo[2.1.1]hexan-5-yl)-8-(2-cyanoethyl)-7-(2,3-dichlorophenyl)-6-fluoro-4-(6-(2-hydroxypropan-2-yl)pyridin-3-yl)-1H-pyrrolo[3,2-c]quinolin-2-yl)-4-fluoropyrrolidine-1-carboxylate To a mixture of tert-butyl (1R,4R,5S)-5-(8-(2-cyanoethyl)-7-(2,3-dichlorophenyl)-6-fluoro-2-((2R,4S)-4-fluoro-1-(methoxycarbonyl)pyrrolidin-2-yl)-4-(methylthio)-1H-pyrrolo[3,2-c]quinolin-1-yl)-2-azabicyclo[2.1.1]hexane-2-carboxylate (353 mg, 0.467 mmol), 5-(4,4,5,5-tetramethyl-1,3,2-dioxaborolan-2-yl)-2-(2-((trimethylsilyl)oxy)propan-2-yl)pyridine (313 mg, 0.933 mmol), tetrakis(triphenylphosphine)palladium(0) (53.9 mg, 0.047 mmol) and Copper(I) 3-methylsalicylate (300 mg, 1.400 mmol) was added 1,4-Dioxane (1.5 ml) and the reaction flask was evacuated, back filled with nitrogen, then stirred at 100° C. for 3 h. The reaction was quenched with water and sat. aq. ammonium hydroxide, then diluted with ethyl acetate and filtered through a plug of Celite. The layers of the filtrate were separated and the organic layer was washed with water and brine, dried over sodium sulfate and concentrated. The crude product was purified by flash column chromatography (0-80% acetone in hexanes). The purified product was dissolved in 1:1 TFA/DCM (20 mL) and stirred at r.t. for 1 hr, then concentrated. The crude product was diluted with acetonitrile and purified by prep HPLC (pH 2) to provide the desired product. LC-MS calculated for $C_{39}H_{37}Cl_2F_2N_6O_3^+$ (M+H)$^+$: m/z=745.2/747.2; found 745.2/747.2.

285

Example 52. Methyl (2R,5R)-2-(1-((1R,4R,5S)-2-azabicyclo[2.1.1]hexan-5-yl)-8-(2-cyanoethyl)-7-(2,3-dichlorophenyl)-6-fluoro-4-(6-(2-hydroxypropan-2-yl)pyridin-3-yl)-1H-pyrrolo[3,2-c]quinolin-2-yl)-5-methylpyrrolidine-1-carboxylate

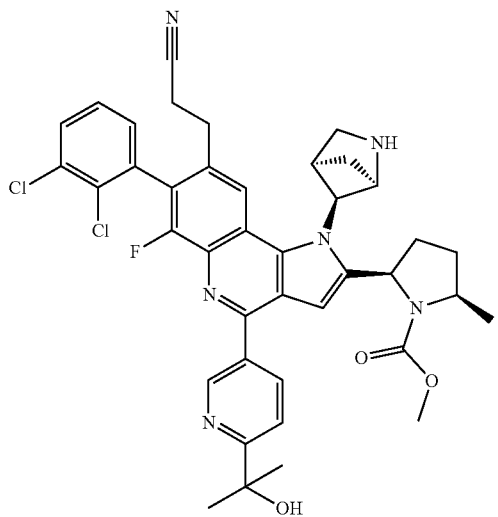 [SMILES: COC(=O)N1[C@H](C)CC[C@@H]1c1cc2c(-c3ccc(C(C)(C)O)nc3)nc3c(F)c(-c4cccc(Cl)c4Cl)c(CCC#N)cc3c2n1[C@H]1[C@H]2CN[C@@H]1C2]

Step 1. tert-Butyl (2R,5R)-2-(hydroxymethyl)-5-methylpyrrolidine-1-carboxylate

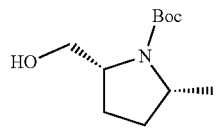

To a solution of (2R,5R)-1-(tert-butoxycarbonyl)-5-methylpyrrolidine-2-carboxylic acid (5.015 g, 21.87 mmol) in THF (109 ml) at 0° C. were added triethylamine (3.35 ml, 24.06 mmol) and isobutyl chloroformate (3.16 ml, 24.06 mmol) and the reaction mixture was stirred at r.t. for 1 h, then filtered. The solid was washed with THF and the filtrate was cooled to 0° C. A solution of sodium borohydride (1.655 g, 43.7 mmol) in water (~10 mL) was then added dropwise and the reaction mixture was stirred at 0° C. for 30 min, then quenched with water and extracted with ethyl acetate. The organic layer was washed with water and brine, dried over sodium sulfate and concentrated. The crude product was used in the next step without further purification. LC-MS calculated for $C_7H_{14}NO_3^+$ (M+H-$C_4H_8$)$^+$: m/z=160.1; found 160.1.

Step 2. tert-Butyl (2R,5R)-2-formyl-5-methylpyrrolidine-1-carboxylate

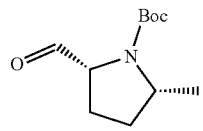

286

To a solution of oxalyl chloride (2.106 ml, 24.06 mmol) in DCM (80 mL) at −78° C. was added a solution of DMSO (3.42 ml, 48.1 mmol) in DCM (3.5 mL) dropwise and the reaction mixture was stirred at −78° C. for 45 min, then a solution of tert-butyl (2R,5R)-2-(hydroxymethyl)-5-methylpyrrolidine-1-carboxylate (4.71 g, 21.88 mmol) in DCM (10 mL) was added dropwise and the stirring was continued for an additional 45 min at −78° C. Triethylamine (9.15 ml, 65.6 mmol) was then added dropwise and stirring was continued at −78° C. for 30 min, then warmed up to 0° C. and stirred for 30 min. The reaction was quenched with 1 N HCl and extracted with DCM. The organic layer was washed with water and brine, dried over sodium sulfate and concentrated. The crude product was used in the next step without further purification. LC-MS calculated for $C_7H_{12}NO_3^+$ (M+H-$C_4H_8$)$^+$: m/z=158.1; found 158.1.

Step 3. tert-Butyl (2R,5R)-2-ethynyl-5-methylpyrrolidine-1-carboxylate Boc

To a 0° C. solution of tert-butyl (2R,5R)-2-formyl-5-methylpyrrolidine-1-carboxylate (4.67 g, 21.90 mmol) in MeOH (109 ml) were added potassium carbonate (6.05 g, 43.8 mmol) and dimethyl (1-diazo-2-oxopropyl)phosphonate (3.29 ml, 21.90 mmol) and the reaction mixture was stirred at r.t. overnight, then concentrated. The residue was partitioned between water and ethyl acetate and the layers were separated. The organic layer was washed with water and brine, dried over sodium sulfate and concentrated. The crude product was used in the next step without further purification. LC-MS calculated for $C_8H_{12}NO_2^+$ (M+H-$C_4H_8$)$^+$: m/z=154.1; found 154.1.

Step 4. 2-(trimethylsilyl)ethyl (2R,5R)-2-ethynyl-5-methylpyrrolidine-1-carboxylate

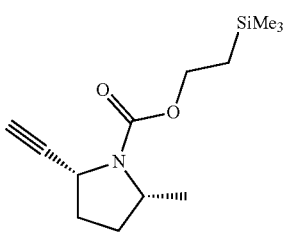 [SMILES: C#C[C@H]1CC[C@@H](C)N1C(=O)OCC[Si](C)(C)C]

A solution of tert-butyl (2R,5R)-2-ethynyl-5-methylpyrrolidine-1-carboxylate (4.5 g, 21.50 mmol) in 4N HCl in dioxane (5 mL) was stirred at r.t. for 1 h, then concentrated. The residue was suspended in acetonitrile (108 ml) and triethylamine (14.98 ml, 108 mmol) was added. After 5 min at r.t., 1-[2-trimethylsilyl)ethoxycarbonyloxy]pyrrolidin-2,5-dione (5.58 g, 21.50 mmol) was added as a solid in one portion and the reaction mixture was stirred at r.t. for 2 h, then quenched with water and extracted with ethyl acetate. The organic layer was washed with water and brine, dried over sodium sulfate and concentrated. The crude product was purified by flash column chromatography (0-50% ethyl acetate in hexanes) to provide the desired product (3.95 g, 72% over 5 steps). LC-MS calculated for $C_{13}H_{24}NO_2Si^+$ (M+H)$^+$: m/z=254.1; found 254.1.

Step 5. tert-Butyl (1R,4R,5S)-5-(7-bromo-8-(2-cyanoethyl)-6-fluoro-2-((2R,5R)-5-methyl-1-((2-(trimethylsilyl)ethoxy)carbonyl)pyrrolidin-2-yl)-4-(methylthio)-1H-pyrrolo[3,2-c]quinolin-1-yl)-2-azabicyclo[2.1.1]hexane-2-carboxylate

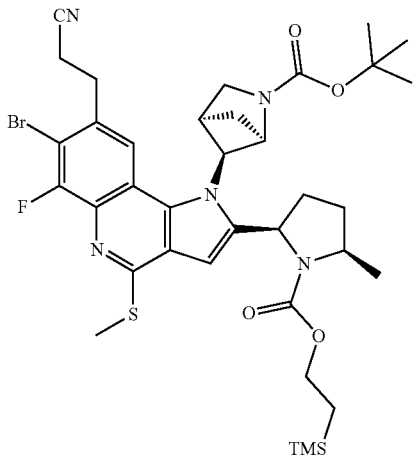 [SMILES: CSc1nc2c(F)c(Br)c(CCC#N)cc2c2c1cc([C@H]1CC[C@@H](C)N1C(=O)OCC[Si](C)(C)C)n2[C@H]1[C@@H]2C[C@H]1N(C(=O)OC(C)(C)C)C2]

To a solution of Intermediate 5 (1.8 g, 2.78 mmol) in DMF (12 ml) was added 2-(trimethylsilyl)ethyl (2R,5R)-2-ethynyl-5-methylpyrrolidine-1-carboxylate (1.3 g, 5.01 mmol), TEA (3.0 mL, 22.2 mmol), bis(triphenylphosphine)palladium(II) chloride (0.39 g, 0.556 mmol), and CuI (0.58 g, 3.06 mmol). The head space of the reaction vessel was purged with $N_2$ for 5 min. The reaction mixture was heated to 80° C. for 2 h, after which point the crude reaction mixture was cooled to r.t. and $Cs_2CO_3$ (4.5 g, 13.9 mmol) was added. The reaction mixture was heated back up to 80° C. and stirred for additional 1 h. The reaction mixture was poured into water and the aqueous layer was extracted with EtOAc, washed with brine, dried over sodium sulfate, filtered, and concentrated. The crude product was purified by flash column chromatography to provide the desired product (1.3 g, 61%). LC-MS calculated for $C_{36}H_{48}BrFN_5O_4SSi$ (M+H)$^+$: m/z=772.2/774.2; found 772.2/774.2.

Step 6. tert-Butyl (1R,4R,5S)-5-(7-bromo-8-(2-cyanoethyl)-6-fluoro-2-((2R,5R)-1-(methoxycarbonyl)-5-methylpyrrolidin-2-yl)-4-(methylthio)-1H-pyrrolo[3,2-c]quinolin-1-yl)-2-azabicyclo[2.1.1]hexane-2-carboxylate

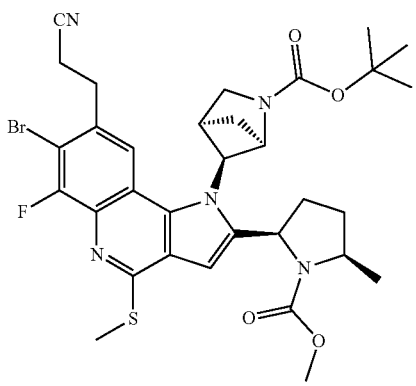 [SMILES: COC(=O)N1[C@H](C)CC[C@@H]1c1cc2c(SC)nc3c(F)c(Br)c(CCC#N)cc3c2n1[C@H]1[C@@H]2C[C@H]1N(C(=O)OC(C)(C)C)C2]

To a solution of tert-butyl (1R,4R,5S)-5-(7-bromo-8-(2-cyanoethyl)-6-fluoro-2-((2R,5R)-5-methyl-1-((2-(trimethylsilyl)ethoxy)carbonyl)pyrrolidin-2-yl)-4-(methylthio)-1H-pyrrolo[3,2-c]quinolin-1-yl)-2-azabicyclo[2.1.1]hexane-2-carboxylate (1.3 g, 1.68 mmol) in THF (10 mL) was added TBAF (2.0 mL, 2.02 mmol, 1 M in THF) at 0° C. The reaction mixture was heated to 60° C. and stirred for 30 min. The reaction mixture was cooled back down to r.t. After that, $Et_3N$ (0.59 mL, 4.21 mmol) was added followed by methyl chloroformate (240 mg, 2.52 mmol). The reaction mixture was allowed to stir at r.t. for additional 20 min. Water was added and the aqueous layer was extracted with EtOAc. The organic layer was washed with brine, dried over sodium sulfate, filtered, and concentrated. The crude product was purified by flash column chromatography to provide the desired product (0.80 g, 76%). LC-MS calculated for $C_{32}H_{38}BrFN_5O_4S$ (M+H)$^+$: m/z=686.2/688.2; found 686.2/688.2.

Step 7. tert-Butyl (1R,4R,5S)-5-(8-(2-cyanoethyl)-7-(2,3-dichlorophenyl)-6-fluoro-2-((2R,5R)-1-(methoxycarbonyl)-5-methylpyrrolidin-2-yl)-4-(methylthio)-1H-pyrrolo[3,2-c]quinolin-1-yl)-2-azabicyclo[2.1.1]hexane-2-carboxylate

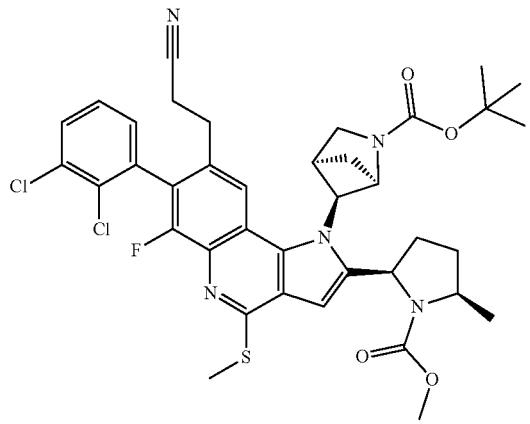 [SMILES: COC(=O)N1[C@H](C)CC[C@@H]1c1cc2c(SC)nc3c(F)c(-c4cccc(Cl)c4Cl)c(CCC#N)cc3c2n1[C@H]1[C@@H]2C[C@H]1N(C(=O)OC(C)(C)C)C2]

To a mixture of tert-butyl (1R,4R,5S)-5-(7-bromo-8-(2-cyanoethyl)-6-fluoro-2-((2R,5R)-1-(methoxycarbonyl)-5-methylpyrrolidin-2-yl)-4-(methylthio)-1H-pyrrolo[3,2-c]quinolin-1-yl)-2-azabicyclo[2.1.1]hexane-2-carboxylate (803 mg, 1.17 mmol), (2,3-dichlorophenyl)boronic acid (446 mg, 2.34 mmol), potassium fluoride (204 mg, 3.51 mmol) and Pd-132 (124 mg, 0.175 mmol) were added 1,4-dioxane (7 mL)/water (1.5 mL) and the reaction flask was evacuated, back filled with nitrogen, then stirred at 100° C. for 1 h. The reaction mixture was diluted with DCM and filtered through a plug of Celite. The filtrate was concentrated and the crude product was purified by flash column chromatography (0-40% acetone in hexanes) to provide the desired product (498 mg, 57%). LC-MS calculated for $C_{38}H_{41}Cl_2FN_5O_4S^+$ (M+H)$^+$: m/z=752.2; found 752.2.

Step 8. tert-Butyl (1R,4R,5S)-5-(8-(2-cyanoethyl)-7-(2,3-dichlorophenyl)-6-fluoro-4-(6-(2-hydroxypropan-2-yl)pyridin-3-yl)-2-((2R,5R)-1-(methoxycarbonyl)-5-methylpyrrolidin-2-yl)-1H-pyrrolo[3,2-c]quinolin-1-yl)-2-azabicyclo[2.1.1]hexane-2-carboxylate

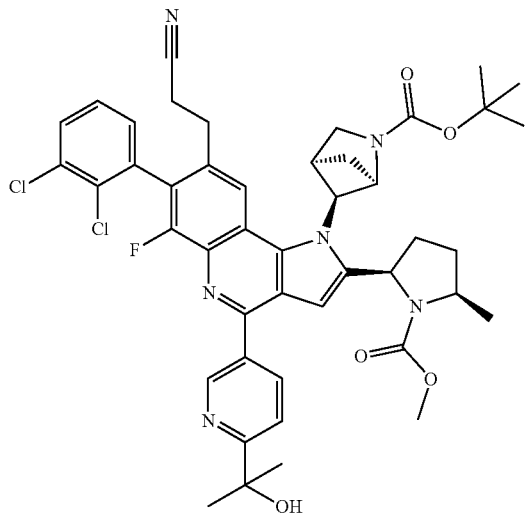 [SMILES: COC(=O)N1[C@H](C)CC[C@@H]1c1cc2c(-c3ccc(C(C)(C)O)nc3)nc3c(F)c(-c4cccc(Cl)c4Cl)c(CCC#N)cc3c2n1[C@H]1[C@@H]2C[C@H]1N(C(=O)OC(C)(C)C)C2]

To a mixture of tert-butyl (1R,4R,5S)-5-(8-(2-cyanoethyl)-7-(2,3-dichlorophenyl)-6-fluoro-2-((2R,5R)-1-(methoxycarbonyl)-5-methylpyrrolidin-2-yl)-4-(methylthio)-1H-pyrrolo[3,2-c]quinolin-1-yl)-2-azabicyclo[2.1.1]hexane-2-carboxylate (498 mg, 0.662 mmol), 5-(4,4,5,5-tetramethyl-1,3,2-dioxaborolan-2-yl)-2-(2-((trimethylsilyl)oxy)propan-2-yl)pyridine (666 mg, 1.99 mmol), tetrakis(triphenylphosphine)palladium(0) (382 mg, 0.331 mmol) and copper(I) 3-methylsalicylate (568 mg, 2.65 mmol) was added 1,4-dioxane (7 ml) and the reaction flask was evacuated, back filled with nitrogen, then stirred at 100° C. for 3 h. The reaction mixture was quenched with water and sat. aq. ammonium hydroxide, then extracted with ethyl acetate. The organic layer was washed with water and brine, dried over sodium sulfate and concentrated. The crude product was purified by flash column chromatography (0-15% MeOH in DCM) to provide the desired product (398 mg, 72%). LC-MS calculated for $C_{45}H_{48}Cl_2FN_6O_5$ $(M+H)^+$: m/z=841.3; found 841.3.

Step 9. Methyl (2R,5R)-2-(1-((1R,4R,5S)-2-azabicyclo[2.1.1]hexan-5-yl)-8-(2-cyanoethyl)-7-(2,3-dichlorophenyl)-6-fluoro-4-(6-(2-hydroxypropan-2-yl)pyridin-3-yl)-1H-pyrrolo[3,2-c]quinolin-2-yl)-5-methylpyrrolidine-1-carboxylate To a solution of tert-butyl (1R,4R,5S)-5-(8-(2-cyanoethyl)-7-(2,3-dichlorophenyl)-6-fluoro-4-(6-(2-hydroxypropan-2-yl)pyridin-3-yl)-2-((2R,5R)-1-(methoxycarbonyl)-5-methylpyrrolidin-2-yl)-1H-pyrrolo[3,2-c]quinolin-1-yl)-2-azabicyclo[2.1.1]hexane-2-carboxylate (398 mg, 0.473 mmol) in $CH_3CN$ (4 mL) was added TFA (4 mL). The mixture was allowed to stir at r.t. for 2 h. After that, the mixture was diluted with more $CH_3CN$ and purified by prep HPLC (pH 10) followed by prep HPLC (pH 2). LC-MS calculated for $C_{40}H_{40}Cl_2FN_6O_3+(M+H)^+$: m/z=741.3; found 741.3. $^1H$ NMR (TFA salt, 600 MHz, DMSO-$d_6$) δ 9.24 (s, 1H), 9.05 (s, 1H), 8.35 (d, J=8.2 Hz, 1H), 8.24-8.10 (m, 2H), 7.94 (d, J=8.3 Hz, 1H), 7.85 (dd, J=8.1, 1.5 Hz, 1H), 7.59 (t, J=7.9 Hz, 1H), 7.49 (d, J=7.6 Hz, 1H), 6.70 (s, 1H), 5.63 (s, 1H), 5.20-5.12 (m, 1H), 4.96-4.84 (s, 1H), 3.97-3.87 (m, 2H), 3.75-3.56 (m, 3H), 3.52-3.40 (m, 1H), 3.10-3.03 (m, 1H), 2.93-2.81 (m, 3H), 2.72-2.61 (m, 1H), 2.51-2.31 (m, 3H), 2.14-1.99 (m, 1H), 1.91-1.78 (m, 1H), 1.63-1.57 (m, 1H), 1.54 (s, 6H), 1.38 (d, J=6.0 Hz, 3H).

Example 53. Methyl (2R)-2-(1-((1R,4R,5S)-2-azabicyclo[2.1.1]hexan-5-yl)-3-chloro-8-(2-cyanoethyl)-7-(2,3-dichlorophenyl)-6-fluoro-4-(6-(2-hydroxypropan-2-yl)pyridin-3-yl)-1H-pyrrolo[3,2-c]quinolin-2-yl)pyrrolidine-1-carboxylate

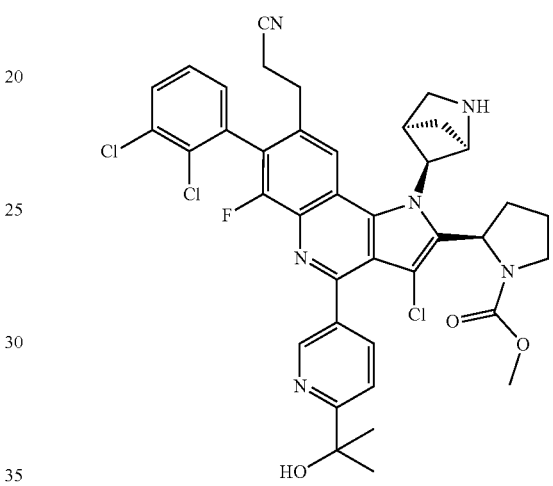

Step 1. tert-Butyl (1R,4R,5S)-5-(8-(2-cyanoethyl)-7-(2,3-dichlorophenyl)-6-fluoro-4-(6-(2-hydroxypropan-2-yl)pyridin-3-yl)-2-((R)-1-(methoxycarbonyl)pyrrolidin-2-yl)-1H-pyrrolo[3,2-c]quinolin-1-yl)-2-azabicyclo[2.1.1]hexane-2-carboxylate

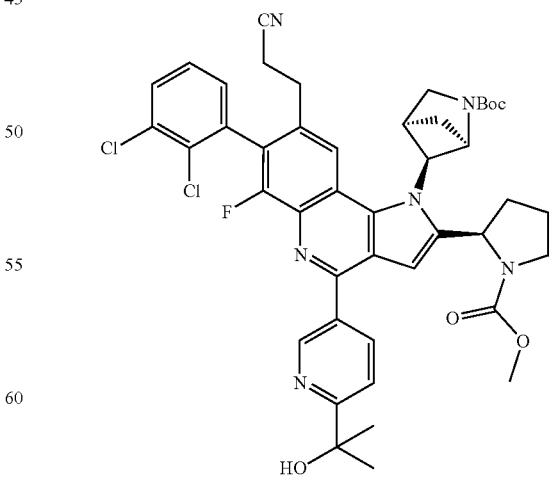

To a mixture of tert-butyl (1R,4R,5S)-5-(8-(2-cyanoethyl)-7-(2,3-dichlorophenyl)-6-fluoro-2-((R)-1-(methoxycarbonyl)pyrrolidin-2-yl)-4-(methylthio)-1H-pyrrolo[3,2-c]

quinolin-1-yl)-2-azabicyclo[2.1.1]hexane-2-carboxylate (2.06 g, 2.79 mmol, Example 39, Step 3), 5-(4,4,5,5-tetramethyl-1,3,2-dioxaborolan-2-yl)-2-(2-((trimethylsilyl)oxy) propan-2-yl)pyridine (2.81 g, 8.37 mmol), tetrakis(triphenylphosphine)palladium(0) (322 mg, 0.28 mmol) and copper(I) 3-methylsalicylate (1.80 g, 8.37 mmol) was added 1,4-dioxane (28 ml) and the reaction flask was evacuated, back filled with nitrogen, then stirred at 100° C. overnight. The reaction mixture was quenched with water and saturated aq. ammonium hydroxide, then extracted with ethyl acetate. The organic layer was washed with water and brine, dried over sodium sulfate and concentrated. The crude product was purified by column chromatography eluting with 0-100% acetone/hexanes. LC-MS calculated for $C_{44}H_{46}Cl_2FN_6O_5$ $(M+H)^+$: m/z=827.3/829.3; found 827.4/829.3.

Step 2. Methyl (2R)-2-(1-((1R,4R,5S)-2-azabicyclo[2.1.1]hexan-5-yl)-3-chloro-8-(2-cyanoethyl)-7-(2,3-dichlorophenyl)-6-fluoro-4-(6-(2-hydroxypropan-2-yl)pyridin-3-yl)-1H-pyrrolo[3,2-c]quinolin-2-yl)pyrrolidine-1-carboxylate To a solution of tert-butyl (1R,4R,5S)-5-(8-(2-cyanoethyl)-7-(2,3-dichlorophenyl)-6-fluoro-4-(6-(2-hydroxypropan-2-yl)pyridin-3-yl)-2-((R)-1-(methoxycarbonyl)pyrrolidin-2-yl)-1H-pyrrolo[3,2-c]quinolin-1-yl)-2-azabicyclo[2.1.1]hexane-2-carboxylate (2.70 g, 3.26 mmol) in DMF (33 ml) was added N-chlorosuccinimide (0.436 g, 3.26 mmol) and the reaction mixture was heated to 65° C. for 2 h. At completion, the reaction was quenched with the addition of ethyl acetate and water. The organic layer was washed with water and brine, dried over sodium sulfate and concentrated. The crude product was stirred in 1:1 TFA/DCM (1 ml) for 30 min, then concentrated. The desired product was purified by prep HPLC (pH 2). LC-MS calculated for $C_{39}H_{37}Cl_3FN_6O_3^+$ $(M+H)^+$: m/z=761.2/763.2; found 761.1/763.1.

Example 54a and 54b: 4-(1-((1R,4R,5S)-2-Azabicyclo[2.1.1]hexan-5-yl)-8-(2-cyanoethyl)-7-(2,3-dichlorophenyl)-6-fluoro-2-((R)-1-(2-oxopyrazin-1(2H)-yl)ethyl)-1H-pyrrolo[3,2-c]quinolin-4-yl)-2-fluoro-N-methylbenzamide

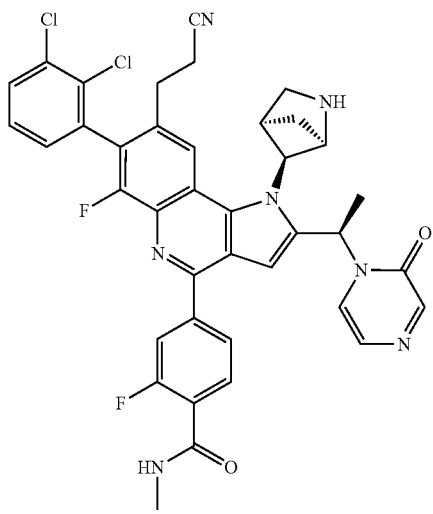 [SMILES: CNC(=O)c1ccc(-c2nc3c(F)c(-c4cccc(Cl)c4Cl)c(CCC#N)cc3c3c2cc([C@@H](C)n2ccncc2=O)n3[C@H]2[C@H]3CN[C@@H]2C3)cc1F]

Step 1: tert-Butyl (1R,4R,5S)-5-((7-bromo-6-(2-cyanoethyl)-8-fluoro-2-(methylthio)-3-((R)-3-(2-oxopyrazin-1(2H)-yl)but-1-yn-1-yl)quinolin-4-yl)amino)-2-azabicyclo[2.1.1]hexane-2-carboxylate

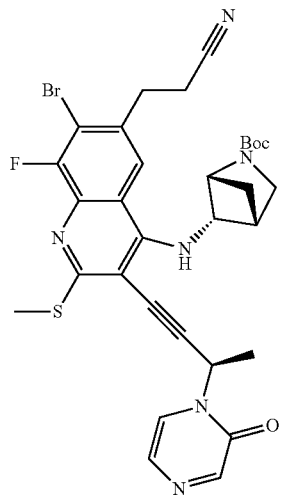 [SMILES: CSc1nc2c(F)c(Br)c(CCC#N)cc2c(N[C@H]2[C@@H]3C[C@H]2N(C(=O)OC(C)(C)C)C3)c1C#C[C@@H](C)n1ccncc1=O]

A mixture of tert-butyl (1R,4R,5S)-5-((7-bromo-6-(2-cyanoethyl)-8-fluoro-3-iodo-2-(methylthio)quinolin-4-yl)amino)-2-azabicyclo[2.1.1]hexane-2-carboxylate (2.70 g, 4.17 mmol, Intermediate 5), (R)-1-(but-3-yn-2-yl)pyrazin-2(1H)-one (1.24 g, 8.34 mmol, Intermediate 20), tetrakis(triphenylphosphine)palladium(0) (0.96 g, 0.83 mmol), CuI (0.32 g, 1.67 mmol) and N,N-diisopropylethylamine (7.3 mL, 41.7 mmol) in DMF (21.0 mL) was sparged with $N_2$ and heated to 70° C. for 1 h. Once completed, the reaction mixture was cooled down to room temperature and poured into water. The aqueous layer was extracted with ethyl acetate, washed with brine, concentrated and purified by flash chromatography (0-100% EtOAc/hexanes) to afford the title compound. LC-MS calculated for $C_{31}H_{33}BrFN_6O_3S$ $(M+H)^+$: m/z=667.1; found 667.1.

Step 2: tert-Butyl (1R,4R,5S)-5-(7-bromo-8-(2-cyanoethyl)-6-fluoro-4-(methylthio)-2-((R)-1-(2-oxopyrazin-1(2H)-yl)ethyl)-1H-pyrrolo[3,2-c]quinolin-1-yl)-2-azabicyclo[2.1.1]hexane-2-carboxylate

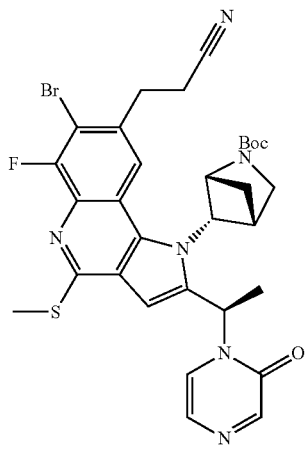 [SMILES: CSc1nc2c(F)c(Br)c(CCC#N)cc2c2c1cc([C@@H](C)n1ccncc1=O)n2[C@H]1[C@@H]2C[C@H]1N(C(=O)OC(C)(C)C)C2]

A mixture of tert-butyl (1R,4R,5S)-5-((7-bromo-6-(2-cyanoethyl)-8-fluoro-2-(methylthio)-3-((R)-3-(2-oxopyrazin-1(2H)-yl)but-1-yn-1-yl)quinolin-4-yl)amino)-2-azabicyclo[2.1.1]hexane-2-carboxylate (2.00 g, 3.00 mmol) and cesium carbonate (2.93 g, 9.00 mmol) in DMA (6.0 mL) was heated at 100° C. for 0.5 h. Once completed, the reaction mixture was cooled to room temperature and poured into water. The aqueous layer was extracted with ethyl acetate, washed with brine, concentrated and purified by flash chromatography (0-100% EtOAc/hexanes) to afford the title compound. LC-MS calculated for $C_{31}H_{33}BrFN_6O_3S$ $(M+H)^+$: m/z=667.1; found 667.2.

Step 3: tert-butyl (1R,4R,5S)-5-(8-(2-cyanoethyl)-7-(2,3-dichlorophenyl)-6-fluoro-4-(methylthio)-2-((R)-1-(2-oxopyrazin-1(2H)-yl)ethyl)-1H-pyrrolo[3,2-c]quinolin-1-yl)-2-azabicyclo[2.1.1]hexane-2-carboxylate

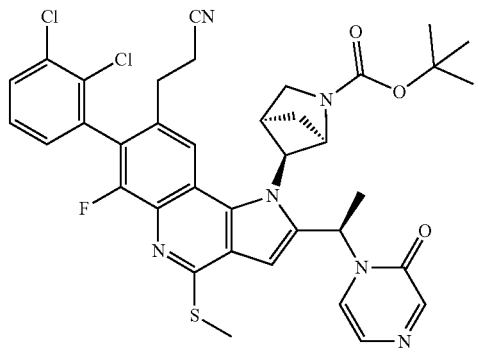 [SMILES: CSc1nc2c(F)c(-c3cccc(Cl)c3Cl)c(CCC#N)cc2c2c1cc([C@@H](C)n1ccncc1=O)n2[C@H]1[C@@H]2C[C@H]1N(C(=O)OC(C)(C)C)C2]

A mixture of tert-butyl (1R,4R,5S)-5-(7-bromo-8-(2-cyanoethyl)-6-fluoro-4-(methylthio)-2-((R)-1-(2-oxopyrazin-1(2H)-yl)ethyl)-1H-pyrrolo[3,2-c]quinolin-1-yl)-2-azabicyclo[2.1.1]hexane-2-carboxylate (1 g, 1.498 mmol), (2,3-dichlorophenyl)boronic acid (0.429 g, 2.247 mmol), Pd(amphos)Cl$_2$ (0.106 g, 0.150 mmol), potassium fluoride (0.348 g, 5.99 mmol) in dioxane (15 ml) and water (3.00 ml) was sparged with N$_2$ and heated at 100° C. for 2 h. Once completed, the reaction mixture was cooled down to room temperature and poured into water. The aqueous layer was extracted with EtOAc, washed with brine, dried over Na$_2$SO$_4$, concentrated and purified by flash chromatography (0-100% EtOAc/hexanes) to afford the title compound. LC-MS calculated for $C_{37}H_{36}Cl_2FN_6O_3S$ $(M+H)^+$: m/z=733.2; found 733.2.

Step 4: 4-(1-((1R,4R,5S)-2-azabicyclo[2.1.1]hexan-5-yl)-8-(2-cyanoethyl)-7-(2,3-dichlorophenyl)-6-fluoro-2-((R)-1-(2-oxopyrazin-1(2H)-yl)ethyl)-1H-pyrrolo[3,2-c]quinolin-4-yl)-2-fluoro-N-methylbenzamide To a vial was added tert-butyl (1R,4R,5S)-5-(8-(2-cyanoethyl)-7-(2,3-dichlorophenyl)-6-fluoro-4-(methylthio)-2-((R)-1-(2-oxopyrazin-1(2H)-yl)ethyl)-1H-pyrrolo[3,2-c]quinolin-1-yl)-2-azabicyclo[2.1.1]hexane-2-carboxylate (400 mg, 0.545 mmol), copper(I) 3-methylsalicylate (351 mg, 1.636 mmol), tetrakis (63.0 mg, 0.055 mmol) and (3-fluoro-4-(methylcarbamoyl)phenyl)boronic acid (537 mg, 2.73 mmol). Dioxane (4 ml) and water (2 ml) were added. The head space was flushed with nitrogen and the vial was sealed. The vessel was heated to 120° C. for 2 h, upon which time LCMS analysis indicated full SM conversion.

The crude mixture was diluted with EtOAc and aqueous NH$_4$OH. The organic layer was separated and washed with water and brine before being dried over Na$_2$SO$_4$ and concentrated. The residue was purified by flash chromatography (0-40% AcOEt in DCM) to give the product.

The intermediate was dissolved in MeCN (2 mL) and HCl (4M in dioxane) (2 mL, 8.00 mmol). The mixture was stirred at room temperature of 20 min, then diluted with acetonitrile/water and purified using prep-LCMS (XBridge C18 column, eluting with a gradient of acetonitrile/water containing 0.1% TFA, at flow rate of 60 mL/min) to afford the desired products as a TFA salt. The product was isolated as a pair of atropisomers. $^1$H NMR was collected on the TFA salts of a mixture of two atropisomers. $^1$H NMR (600 MHz, DMSO-d$_6$) δ 9.61 (br, 1H), 9.31 (br, 1H), 8.52 (m, 1H), 8.42-8.35 (m, 3H), 8.23-8.19 (m, 3H), 8.02-7.93 (m, 4H), 7.90 (dd, J=8.0, 1.3 Hz, 2H), 7.63-7.56 (m, 4H), 7.45 (s, 2H), 7.30 (d, J=4.5 Hz, 2H), 6.96 (d, J=3.6 Hz, 1H), 6.91 (d, J=4.5 Hz, 1H), 6.32-6.28 (m, 3H), 6.1 (d, J=7.5 Hz, 1H), 5.74 (m, 1H), 5.26 (d, J=6.6 Hz, 1H), 5.15-5.13 (m, 2H), 4.94 (m, 1H), 4.02 (m, 1H), 3.79 (m, 1H), 3.10-3.04 (m, 1H), 2.94-2.63 (m, 17H), 2.13 (dd, J=9.3, 2.3 Hz, 1H), 1.95 (d, J=9.0 Hz, 1H), 1.85 (d, J=6.0 Hz, 3H), 1.78 (d, J=6.7 Hz, 3H), 1.64 (d, J=8.6 Hz, 1H), 1.53 (d, J=9.2 Hz, 1H).

Example 54a. atropisomer 1. Peak 1. LCMS calculated for $C_{39}H_{32}Cl_2F_2N_7O_2$ $(M+H)^+$: m/z=738.2; found 738.2.

Example 54b. atropisomer 2. Peak 2 (desired product). LCMS calculated for $C_{39}H_{32}Cl_2F_2N_7O_2$ $(M+H)^+$: m/z=738.2; found 738.2.

Example 55: Methyl ((1R)-1-(1-((1R,4R,5S)-2-azabicyclo[2.1.1]hexan-5-yl)-8-(2-cyanoethyl)-7-(2,3-dichlorophenyl)-6-fluoro-4-methyl-1H-pyrrolo[3,2-c]quinolin-2-yl)ethyl)carbamate

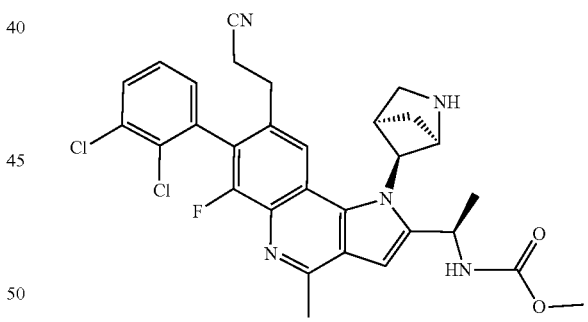

To a solution of tert-butyl (1R,4R,5S)-5-(2-((R)-1-aminoethyl)-8-(2-cyanoethyl)-7-(2,3-dichlorophenyl)-6-fluoro-4-methyl-1H-pyrrolo[3,2-c]quinolin-1-yl)-2-azabicyclo[2.1.1]hexane-2-carboxylate (Intermediate 22, 20 mg, 0.032 mmol) in tetrahydrofuran (0.321 ml) at 0° C. was added triethylamine (22.39 μl, 0.161 mmol) and methyl chloroformate (7.46 μl, 0.096 mmol). The reaction mixture was stirred at room temperature for 30 minutes. Upon completion, the reaction was concentrated in vacuo. The residue was dissolved in TFA (1 ml), and the solution was stirred at room temperature for 10 minutes to remove the Boc protecting group. The reaction was then diluted with acetonitrile, which was purified prep-LCMS (XBridge C18 column, eluting with a gradient of acetonitrile/water containing 0.1% TFA, at flow rate of 60 mL/min) to afford the product as a TFA salt in the form of a white amorphous powder. LC-MS calculated for $C_{30}H_{29}Cl_2FN_5O_2$ (M+H)⁺: m/z=580.2; found 580.3. ¹H NMR (600 MHz, DMSO-d₆) 9.21 (s, 1H), 8.14-8.07 (m, 2H), 8.02 (s, 1H), 7.83 (d, J=7.8 Hz, 1H), 7.57 (t, J=7.8 Hz, 1H), 7.46 (d, J=7.8 Hz, 1H), 6.80 (s, 1H), 5.57 (s, 1H), 4.91-4.79 (m, 2H), 3.96-3.87 (m, 1H), 3.66 (s, 3H), 3.64-3.55 (m, 1H), 3.46-3.38 (m, 1H), 3.07-2.97 (m, 1H), 2.91-2.83 (m, 2H), 2.82 (s, 3H), 2.97-2.69 (m, 1H), 2.31 (d, J=8.5 Hz, 1H), 1.57 (d, J=8.5 Hz, 1H), 1.39 (d, J=6.8 Hz, 3H), Example 56: N-((1R)-1-(1-((1R,4R,5S)-2-Azabicyclo[2.1.1]hexan-5-yl)-8-(2-cyanoethyl)-7-(2,3-dichlorophenyl)-6-fluoro-4-methyl-1H-pyrrolo[3,2-c]quinolin-2-yl)ethyl)-2,2-difluoroacetamide

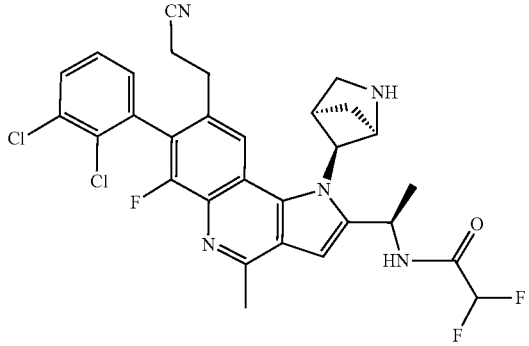 [SMILES: Cc1nc2c(F)c(-c3cccc(Cl)c3Cl)c(CCC#N)cc2c2c1cc([C@@H](C)NC(=O)C(F)F)n2[C@H]1[C@H]2CN[C@@H]1C2]

To a solution of tert-butyl (1R,4R,5S)-5-(2-((R)-1-aminoethyl)-8-(2-cyanoethyl)-7-(2,3-dichlorophenyl)-6-fluoro-4-methyl-1H-pyrrolo[3,2-c]quinolin-1-yl)-2-azabicyclo[2.1.1]hexane-2-carboxylate (Intermediate 22, 20 mg, 0.032 mmol) in tetrahydrofuran (0.321 ml) was added triethylamine (44.8 µl, 0.321 mmol) and 2,2-difluoroacetic anhydride (28.0 mg, 0.161 mmol). The reaction mixture was stirred at room temperature for 30 minutes. Upon completion, the reaction was quenched with water and extracted with ethyl acetate. The organic layer was washed with water and brine and concentrated. The residue was dissolved in TFA (1 ml), and the solution was stirred at room temperature for 10 minutes to remove the Boc protecting group. The reaction was then diluted with acetonitrile, which was purified prep-LCMS (XBridge C18 column, eluting with a gradient of acetonitrile/water containing 0.1% TFA, at flow rate of 60 mL/min) to afford the product as a TFA salt in the form of a white amorphous powder. LC-MS calculated for $C_{30}H_{27}Cl_2F_3N_5O$ (M+H)⁺: m/z=600.2; found 600.2.

Example 57: (2S)—N-((1R)-1-(1-((1R,4R,5S)-2-Azabicyclo[2.1.1]hexan-5-yl)-8-(2-cyanoethyl)-7-(2,3-dichlorophenyl)-6-fluoro-4-methyl-1H-pyrrolo[3,2-c]quinolin-2-yl)ethyl)tetrahydrofuran-2-carboxamide

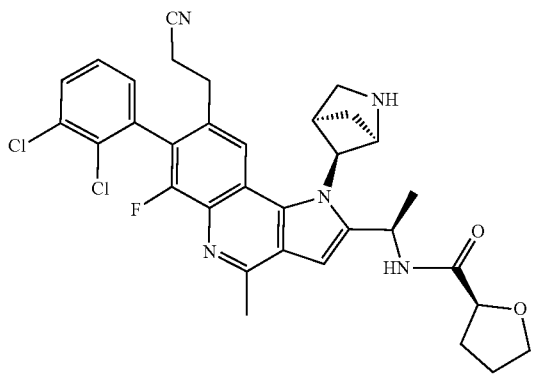 [SMILES: Cc1nc2c(F)c(-c3cccc(Cl)c3Cl)c(CCC#N)cc2c2c1cc([C@@H](C)NC(=O)[C@@H]1CCCO1)n2[C@H]1[C@H]2CN[C@@H]1C2]

To a solution of tert-butyl (1R,4R,5S)-5-(8-(2-cyanoethyl)-7-(2,3-dichlorophenyl)-6-fluoro-4-methyl-2-((R)-1-(methylamino)ethyl)-1H-pyrrolo[3,2-c]quinolin-1-yl)-2-azabicyclo[2.1.1]hexane-2-carboxylate (Intermediate 22, 20 mg, 0.031 mmol) and triethylamine (21.90 µl, 0.157 mmol) in acetonitrile (0.628 ml) was added (S)-tetrahydrofuran-2-carboxylic acid (7.30 mg, 0.063 mmol) and HATU (23.89 mg, 0.063 mmol). The reaction mixture was stirred at room temperature for 1 hour. Upon completion, the reaction was quenched by saturated sodium bicarbonate solution. The reaction mixture was extracted by ethyl acetate. The combined organic layer were dried over sodium sulfate, filtered and concentrated. The residue was dissolved in TFA (1 ml), and the solution was stirred at room temperature for 10 minutes to remove the Boc protecting group. The reaction was then diluted with acetonitrile, which was purified prep-LCMS (XBridge C18 column, eluting with a gradient of acetonitrile/water containing 0.1% TFA, at flow rate of 60 mL/min) to afford the product as a TFA salt in the form of a white amorphous powder. LC-MS calculated for $C_{33}H_{33}Cl_2FN_5O_2$ (M+H)⁺: m/z=620.2; found 620.2.

Example 58: N-((1R)-1-(1-((1R,4R,5S)-2-Azabicyclo[2.1.1]hexan-5-yl)-8-(2-cyanoethyl)-7-(2,3-dichlorophenyl)-6-fluoro-4-methyl-1H-pyrrolo[3,2-c]quinolin-2-yl)ethyl)cyclopropanesulfonamide

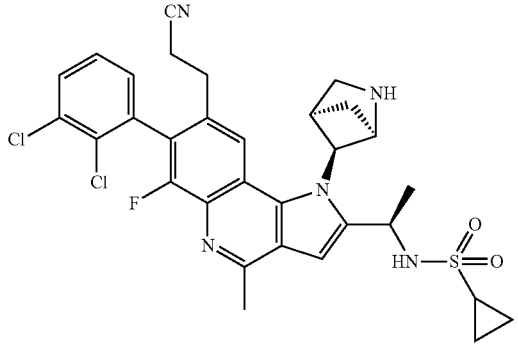 [SMILES: Cc1nc2c(F)c(-c3cccc(Cl)c3Cl)c(CCC#N)cc2c2c1cc([C@@H](C)NS(=O)(=O)C1CC1)n2[C@H]1[C@H]2CN[C@@H]1C2]

To a solution of tert-butyl (1R,4R,5S)-5-(2-((R)-1-aminoethyl)-8-(2-cyanoethyl)-7-(2,3-dichlorophenyl)-6-fluoro-4-methyl-1H-pyrrolo[3,2-c]quinolin-1-yl)-2-azabicyclo[2.1.1]hexane-2-carboxylate (Intermediate 22, 20 mg, 0.032 mmol) in tetrahydrofuran (0.643 ml) was added triethylamine (22.39 µl, 0.161 mmol) and cyclopropanesulfonyl chloride (13.55 mg, 0.096 mmol). The reaction mixture was stirred at room temperature for 30 minutes. Upon completion, the reaction was concentrated in vacuo. The residue was dissolved in TFA (1 ml), and the solution was stirred at room temperature for 10 minutes to remove the Boc protecting group. The reaction was then diluted with acetonitrile, which was purified prep-LCMS (XBridge C18 column, eluting with a gradient of acetonitrile/water containing 0.1% TFA, at flow rate of 60 mL/min) to afford the product as a TFA salt in the form of a white amorphous powder. LC-MS calculated for $C_{31}H_{31}Cl_2FN_5O_2S$ (M+H)⁺: m/z=626.2; found 626.2.

Example 59: N-((1R)-1-(1-((1R,4R,5S)-2-Azabicyclo[2.1.1]hexan-5-yl)-8-(2-cyanoethyl)-7-(2,3-dichlorophenyl)-6-fluoro-4-methyl-1H-pyrrolo[3,2-c]quinolin-2-yl)ethyl)thiazole-4-carboxamide

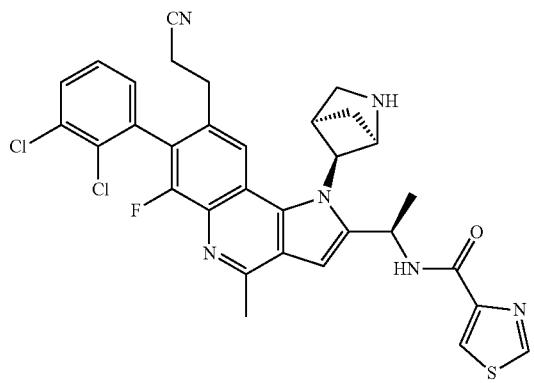 [SMILES: Cc1nc2c(F)c(-c3cccc(Cl)c3Cl)c(CCC#N)cc2c2c1cc([C@@H](C)NC(=O)c1cscn1)n2[C@H]1[C@H]2CN[C@@H]1C2]

To a solution of tert-butyl (1R,4R,5S)-5-(2-((R)-1-aminoethyl)-8-(2-cyanoethyl)-7-(2,3-dichlorophenyl)-6-fluoro-4-methyl-1H-pyrrolo[3,2-c]quinolin-1-yl)-2-azabicyclo[2.1.1]hexane-2-carboxylate (Intermediate 22, 20 mg, 0.032 mmol) in acetonitrile (0.643 ml) was added triethylamine (22.39 μl, 0.161 mmol) and thiazole-4-carboxylic acid (8.30 mg, 0.064 mmol). The reaction mixture was stirred at room temperature for 30 minutes. Upon completion, the reaction was quenched by saturated sodium bicarbonate solution. The reaction mixture was extracted by ethyl acetate. The combined organic layers were dried over sodium sulfate, filtered and concentrated. The residue was dissolved in TFA (1 ml), and the solution was stirred at room temperature for 10 minutes to remove the Boc protecting group. The reaction was then diluted with acetonitrile, which was purified prep-LCMS (XBridge C18 column, eluting with a gradient of acetonitrile/water containing 0.1% TFA, at flow rate of 60 mL/min) to afford the product as a TFA salt in the form of a white amorphous powder. LC-MS calculated for $C_{32}H_{28}Cl_2FN_6OS$ (M+H)$^+$: m/z=633.1; found 633.2.

Example 60: N-((1R)-1-(1-((1R,4R,5S)-2-Azabicyclo[2.1.1]hexan-5-yl)-8-(2-cyanoethyl)-7-(2,3-dichlorophenyl)-6-fluoro-4-methyl-1H-pyrrolo[3,2-c]quinolin-2-yl)ethyl)-N-methylcyclopropanecarboxamide

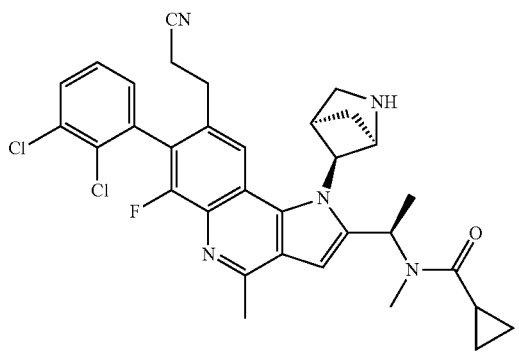 [SMILES: Cc1nc2c(F)c(-c3cccc(Cl)c3Cl)c(CCC#N)cc2c2c1cc([C@@H](C)N(C)C(=O)C1CC1)n2[C@H]1[C@H]2CN[C@@H]1C2]

To a solution of tert-butyl (1R,4R,5S)-5-(8-(2-cyanoethyl)-7-(2,3-dichlorophenyl)-6-fluoro-4-methyl-2-((R)-1-(methylamino)ethyl)-1H-pyrrolo[3,2-c]quinolin-1-yl)-2-azabicyclo[2.1.1]hexane-2-carboxylate (Intermediate 23, 20 mg, 0.031 mmol) in tetrahydrofuran (0.628 ml) was added triethylamine (21.90 μl, 0.157 mmol) and cyclopropanecarbonyl chloride (6.57 mg, 0.063 mmol). The reaction mixture was stirred at room temperature for 30 minutes. Upon completion, the reaction was concentrated in vacuo. The residue was dissolved in TFA (1 mL), and the solution was stirred at room temperature for 10 minutes to remove the Boc protecting group. The reaction was then diluted with acetonitrile, which was purified prep-LCMS (XBridge C18 column, eluting with a gradient of acetonitrile/water containing 0.1% TFA, at flow rate of 60 mL/min) to afford the product as a TFA salt in the form of a white amorphous powder. LC-MS calculated for $C_{33}H_{33}Cl_2FN_5O$ (M+H)$^+$: m/z=604.2; found 604.3.

Example 61. N-((1R)-1-(1-((1R,4R,5S)-2-Azabicyclo[2.1.1]hexan-5-yl)-8-(2-cyanoethyl)-7-(2,3-dichlorophenyl)-6-fluoro-4-(1-hydroxyethyl)-1H-pyrrolo[3,2-c]quinolin-2-yl)ethyl)-1-methylcyclopropane-1-carboxamide

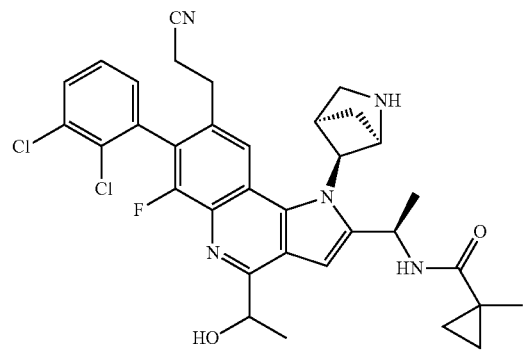 [SMILES: CC(O)c1nc2c(F)c(-c3cccc(Cl)c3Cl)c(CCC#N)cc2c2c1cc([C@@H](C)NC(=O)C1(C)CC1)n2[C@H]1[C@H]2CN[C@@H]1C2]

Step 1. tert-Butyl (1R,4R,5S)-5-(2-((R)-1-aminoethyl)-8-(2-cyanoethyl)-7-(2,3-dichlorophenyl)-6-fluoro-4-(methylthio)-1H-pyrrolo[3,2-c]quinolin-1-yl)-2-azabicyclo[2.1.1]hexane-2-carboxylate

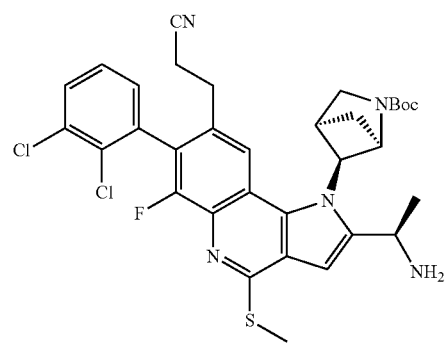 [SMILES: CSc1nc2c(F)c(-c3cccc(Cl)c3Cl)c(CCC#N)cc2c2c1cc([C@@H](C)N)n2[C@H]1[C@@H]2C[C@H]1N(C(=O)OC(C)(C)C)C2]

To a solution of tert-butyl (1R,4R,5S)-5-(8-(2-cyanoethyl)-7-(2,3-dichlorophenyl)-6-fluoro-4-(methylthio)-2-((R)-1-(((2-(trimethylsilyl)ethoxy)carbonyl)amino)ethyl)-

1H-pyrrolo[3,2-c]quinolin-1-yl)-2-azabicyclo[2.1.1]hexane-2-carboxylate (250 mg, 0.31 mmol, Intermediate 22, Step 3) in DMF (1.60 mL) was added cesium fluoride (190 mg, 1.25 mmol) and the reaction mixture was heated at 90° C. for 1 hour. After cooling to room temperature, the reaction was diluted with DCM and 5% aqueous LiCl solution. The organics were washed three times with 5% aqueous LiCl solution and then brine, dried over sodium sulfate and concentrated. The crude material was taken forward without additional purification. LCMS calculated for $C_{33}H_{35}Cl_2FN_5O_2S$ (M+H)$^+$: m/z=654.2/656.2; found 654.1/656.1.

Step 2. tert-Butyl (1R,4R,5S)-5-(8-(2-cyanoethyl)-7-(2,3-dichlorophenyl)-6-fluoro-2-((R)-1-(1-methyl-cyclopropane-1-carboxamido)ethyl)-4-(methylthio)-1H-pyrrolo[3,2-c]quinolin-1-yl)-2-azabicyclo[2.1.1]hexane-2-carboxylate

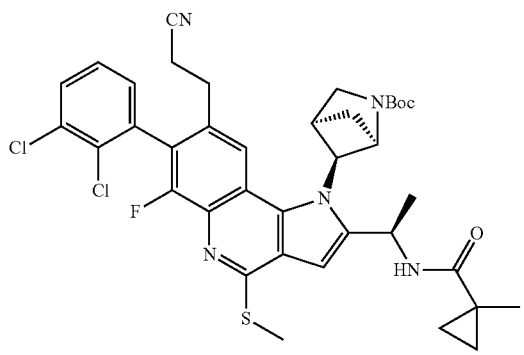 [SMILES: CSc1nc2c(F)c(-c3cccc(Cl)c3Cl)c(CCC#N)cc2c2c1cc([C@@H](C)NC(=O)C1(C)CC1)n2[C@H]1[C@@H]2C[C@H]1N(C(=O)OC(C)(C)C)C2]

To a solution of tert-butyl (1R,4R,5S)-5-(2-((R)-1-amino-ethyl)-8-(2-cyanoethyl)-7-(2,3-dichlorophenyl)-6-fluoro-4-(methylthio)-1H-pyrrolo[3,2-c]quinolin-1-yl)-2-azabicyclo[2.1.1]hexane-2-carboxylate (250 mg, 0.38 mmol) and triethylamine (0.27 mL, 1.91 mmol) in acetonitrile (3.82 mL) was added 1-methylcyclopropane-1-carboxylic acid (76 mg, 0.76 mmol) and HATU (290 mg, 0.76 mmol). The reaction mixture was stirred at room temperature for 1 hour. Upon completion, the reaction was poured into water. The reaction mixture was extracted by ethyl acetate. The combined organic layers were dried over sodium sulfate, filtered and concentrated. The desired product was isolated by flash column chromatography eluting with a gradient of 0-70% acetone/n-heptane as a yellowish brown solid (164 mg, 58% yield). LCMS calculated for $C_{38}H_{41}Cl_2FN_5O_3S$ (M+H)$^+$: m/z=736.2/738.2; found 736.2/738.2.

Step 3. tert-Butyl (1R,4R,5S)-5-(8-(2-cyanoethyl)-7-(2,3-dichlorophenyl)-6-fluoro-2-((R)-1-(1-methyl-cyclopropane-1-carboxamido)ethyl)-4-(prop-1-en-2-yl)-1H-pyrrolo[3,2-c]quinolin-1-yl)-2-azabicyclo[2.1.1]hexane-2-carboxylate

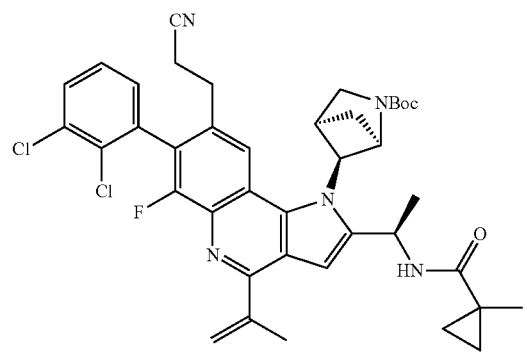

To a solution of tert-butyl (1R,4R,5S)-5-(8-(2-cyano-ethyl)-7-(2,3-dichlorophenyl)-6-fluoro-2-((R)-1-(1-methyl-cyclopropane-1-carboxamido)ethyl)-4-(methylthio)-1H-pyrrolo[3,2-c]quinolin-1-yl)-2-azabicyclo[2.1.1]hexane-2-carboxylate (164 mg, 0.22 mmol) in dioxane (2.23 mL) was added copper(I) 3-methylsalicylate (143 mg, 0.67 mmol), tetrakis(triphenylphosphine) palladium(0) (26 mg, 0.022 mmol), and 4,4,5,5-tetramethyl-2-(prop-1-en-2-yl)-1,3,2-dioxaborolane (0.21 mL, 1.11 mmol). The headspace was purged with nitrogen and the vessel was sealed and heated to 100° C. for 3 h. The reaction mixture was quenched with water and saturated aq. ammonium hydroxide, then extracted with ethyl acetate. The organic layer was washed with water and brine, dried over sodium sulfate and concentrated. The desired product was isolated by flash column chromatography eluting with a gradient of 0-80% acetone/n-heptane as a yellowish brown solid (145 mg, 89% yield). LCMS calculated for $C_{40}H_{43}Cl_2FN_5O_3$ (M+H)$^+$: m/z=730.3/732.3; found 730.2/732.2.

Step 4. tert-Butyl (1R,4R,5S)-5-(4-acetyl-8-(2-cyanoethyl)-7-(2,3-dichlorophenyl)-6-fluoro-2-((R)-1-(1-methylcyclopropane-1-carboxamido)ethyl)-1H-pyrrolo[3,2-c]quinolin-1-yl)-2-azabicyclo[2.1.1]hexane-2-carboxylate

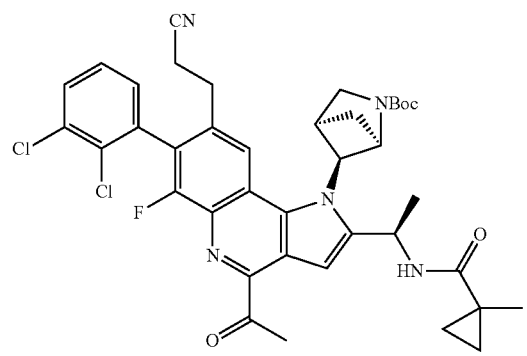 [SMILES: C=C(C)c1nc2c(F)c(-c3cccc(Cl)c3Cl)c(CCC#N)cc2c2c1cc([C@@H](C)NC(=O)C1(C)CC1)n2[C@H]1[C@@H]2C[C@H]1N(C(=O)OC(C)(C)C)C2]

A vial was charged with tert-butyl (1R,4R,5S)-5-(8-(2-cyanoethyl)-7-(2,3-dichlorophenyl)-6-fluoro-2-((R)-1-(1- methylcyclopropane-1-carboxamido)ethyl)-4-(prop-1-en-2-yl)-1H-pyrrolo[3,2-c]quinolin-1-yl)-2-azabicyclo[2.1.1]hexane-2-carboxylate (145 mg, 0.20 mmol), a stir bar, THF (1.59 mL) and water (0.40 mL). To this suspension was added potassium osmate dihydrate (0.7 mg, 1.98 μmol). The reaction was stirred for five minutes then sodium periodate (212 mg, 0.99 mmol) was added. After 1 h, full conversion of starting material was detected by LCMS. The reaction mixture was diluted with water and DCM. The organic layer was washed with water and brine, dried over sodium sulfate and concentrated. The desired product was isolated by flash column chromatography eluting with a gradient of 0-80% acetone/n-heptane. LCMS calculated for $C_{39}H_{41}Cl_2FN_5O_4$ $(M+H)^+$: m/z=732.2/734.2; found 732.4/734.4.

Step 5. N-((1R)-1-(1-(((1R,4R,5S)-2-Azabicyclo[2.1.1]hexan-5-yl)-8-(2-cyanoethyl)-7-(2,3-dichlorophenyl)-6-fluoro-4-(1-hydroxyethyl)-1H-pyrrolo[3,2-c]quinolin-2-yl)ethyl)-1-methylcyclopropane-1-carboxamide To a solution of tert-butyl (1R,4R,5S)-5-(4-acetyl-8-(2-cyanoethyl)-7-(2,3-dichlorophenyl)-6-fluoro-2-((R)-1-(1-methylcyclopropane-1-carboxamido)ethyl)-1H-pyrrolo[3,2-c]quinolin-1-yl)-2-azabicyclo[2.1.1]hexane-2-carboxylate (30 mg, 0.041 mmol) in DCM (0.15 mL) and formic acid/triethylamine complex (0.03 mL, 5:2) was added RuCl(p-cymene)[(R,R)-Ts-DPEN] (1.8 mg, 2.87 μmol). The mixture was stirred for 16 h at room temperature. The crude material was stirred in 1:1 TFA/DCM (0.5 ml) for 30 min, then concentrated. The desired product was purified by prep HPLC (pH 2). LC-MS calculated for $C_{34}H_{35}Cl_2FN_5O_2^+$ $(M+H)^+$: m/z=634.2/636.2; found 634.5/636.3. $^1$H NMR (600 MHz, DMSO) δ 9.23 (s, 1H), 8.10 (s, 1H), 8.06 (s, 1H), 7.84 (dd, J=8.2, 1.5 Hz, 1H), 7.57 (t, J=7.9 Hz, 1H), 7.46 (dd, J=7.6, 1.6 Hz, 1H), 6.70 (s, 1H), 5.53 (s, 1H), 5.49 (d, J=11.0 Hz, 1H), 5.12 (q, J=6.6 Hz, 1H), 4.85 (d, J=6.0 Hz, 1H), 4.03-3.97 (m, 1H), 3.90-3.85 (m, 1H), 3.55-3.49 (m, 1H), 3.41-3.35 (m, 1H), 3.05-2.98 (m, 1H), 2.91-2.77 (m, 3H), 2.65 (dt, J=15.7, 7.2 Hz, 1H), 2.28 (d, J=9.0 Hz, 1H), 1.94 (dd, J=13.0, 2.6 Hz, 1H), 1.85-1.77 (m, 1H), 1.61 (s, 3H), 1.56-1.50 (m, 4H), 1.23-1.17 (m, 1H), 0.91-0.79 (m, 3H), 0.69-0.62 (m, 2H).

Example 62. 3-(1-((1R,4R,5S)-2-Azabicyclo[2.1.1]hexan-5-yl)-7-(2,3-dichlorophenyl)-6-fluoro-4-(1-hydroxyethyl)-2-((1R,3R,5R)-2-(1-methylcyclopropane-1-carbonyl)-2-azabicyclo[3.1.0]hexan-3-yl)-1H-pyrrolo[3,2-c]quinolin-8-yl)propanenitrile

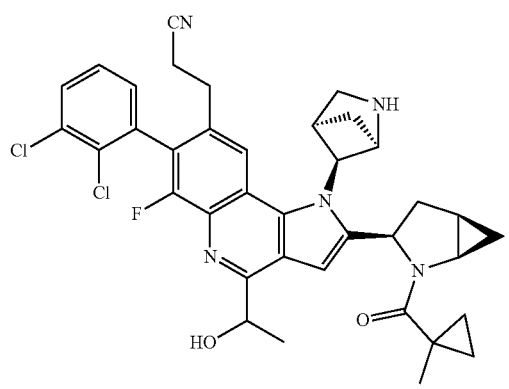 [SMILES: CC(O)c1nc2c(F)c(-c3cccc(Cl)c3Cl)c(CCC#N)cc2c2c1cc([C@H]1C[C@H]3C[C@H]3N1C(=O)C1(C)CC1)n2[C@H]1[C@H]2CN[C@@H]1C2]

Step 1. tert-Butyl (1R,4R,5S)-5-(2-((1R,3R,5R)-2-azabicyclo[3.1.0]hexan-3-yl)-8-(2-cyanoethyl)-7-(2,3-dichlorophenyl)-6-fluoro-4-(methylthio)-1H-pyrrolo[3,2-c]quinolin-1-yl)-2-azabicyclo[2.1.1]hexane-2-carboxylate

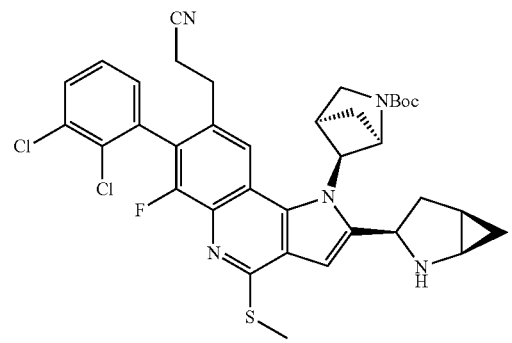 [SMILES: CSc1nc2c(F)c(-c3cccc(Cl)c3Cl)c(CCC#N)cc2c2c1cc([C@H]1C[C@H]3C[C@H]3N1)n2[C@H]1[C@@H]2C[C@H]1N(C(=O)OC(C)(C)C)C2]

This compound was prepared in an analogous fashion to Example 61, Step 1, with tert-butyl (1R,4R,5S)-5-(8-(2-cyanoethyl)-7-(2,3-dichlorophenyl)-6-fluoro-4-(methylthio)-2-((1R,3R,5R)-2-((2-(trimethylsilyl)ethoxy)carbonyl)-2-azabicyclo[3.1.0]hexan-3-yl)-1H-pyrrolo[3,2-c]quinolin-1-yl)-2-azabicyclo[2.1.1]hexane-2-carboxylate replacing tert-butyl (1R,4R,5S)-5-(8-(2-cyanoethyl)-7-(2,3-dichlorophenyl)-6-fluoro-4-(methylthio)-2-((R)-1-(((2-(trimethylsilyl)ethoxy)carbonyl)amino)ethyl)-1H-pyrrolo[3,2-c]quinolin-1-yl)-2-azabicyclo[2.1.1]hexane-2-carboxylate. LC-MS calculated for $C_{36}H_{37}Cl_2FN_5O_2S^+$ $(M+H)^+$: m/z=692.2/694.2; found 692.1/694.1.

Step 2. tert-Butyl (1R,4R,5S)-5-(8-(2-cyanoethyl)-7-(2,3-dichlorophenyl)-6-fluoro-2-((1R,3R,5R)-2-(1-methylcyclopropane-1-carbonyl)-2-azabicyclo[3.1.0]hexan-3-yl)-4-(methylthio)-1H-pyrrolo[3,2-c]quinolin-1-yl)-2-azabicyclo[2.1.1]hexane-2-carboxylate

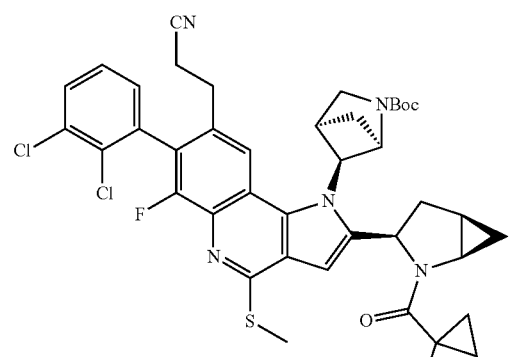

To a solution of tert-butyl (1R,4R,5S)-5-(2-((1R,3R,5R)-2-azabicyclo[3.1.0]hexan-3-yl)-8-(2-cyanoethyl)-7-(2,3-dichlorophenyl)-6-fluoro-4-(methylthio)-1H-pyrrolo[3,2-c]quinolin-1-yl)-2-azabicyclo[2.1.1]hexane-2-carboxylate (200 mg, 0.29 mmol) and triethylamine (0.20 mL, 1.44 mmol) in acetonitrile (2.9 mL) was added 1-methylcyclopropane-1-carboxylic acid (58 mg, 0.58 mmol) and HATU (220 mg, 0.58 mmol). The reaction mixture was stirred at room temperature for 1 hour. Upon completion, the reaction was poured into water. The reaction mixture was extracted by ethyl acetate. The combined organic layers were dried over sodium sulfate, filtered and concentrated. The desired product was isolated by flash column chromatography eluting with a gradient of 0-70% acetone/n-heptane as a yellowish brown solid (142 mg, 64% yield). LCMS calculated for $C_{41}H_{43}Cl_2FN_5O_3S$ (M+H)$^+$: m/z=774.2/776.2; found 774.3/776.3.

Step 3. tert-Butyl (1R,4R,5S)-5-(8-(2-cyanoethyl)-7-(2,3-dichlorophenyl)-6-fluoro-2-((1R,3R,5R)-2-(1-methylcyclopropane-1-carbonyl)-2-azabicyclo[3.1.0]hexan-3-yl)-4-(prop-1-en-2-yl)-1H-pyrrolo[3,2-c]quinolin-1-yl)-2-azabicyclo[2.1.1]hexane-2-carboxylate

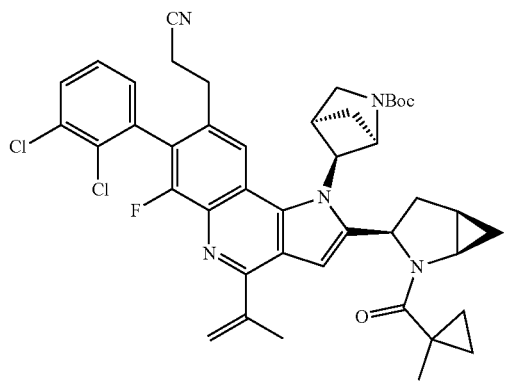

To a solution of tert-butyl (1R,4R,5S)-5-(8-(2-cyanoethyl)-7-(2,3-dichlorophenyl)-6-fluoro-2-((1R,3R,5R)-2-(1-methylcyclopropane-1-carbonyl)-2-azabicyclo[3.1.0]hexan-3-yl)-4-(methylthio)-1H-pyrrolo[3,2-c]quinolin-1-yl)-2-azabicyclo[2.1.1]hexane-2-carboxylate (142 mg, 0.18 mmol) in dioxane (1.83 mL) was added copper(I) 3-methylsalicylate (118 mg, 0.55 mmol), tetrakis(triphenylphosphine)palladium(0) (21 mg, 0.018 mmol), and 4,4,5,5-tetramethyl-2-(prop-1-en-2-yl)-1,3,2-dioxaborolane (0.17 mL, 0.92 mmol). The headspace was purged with nitrogen and the vessel was sealed and heated to 100° C. for 3 h. The reaction mixture was quenched with water and saturated aq. ammonium hydroxide, then extracted with ethyl acetate. The organic layer was washed with water and brine, dried over sodium sulfate and concentrated. The desired product was isolated by flash column chromatography eluting with a gradient of 0-80% acetone/n-heptane as a yellowish brown solid (78 mg, 55% yield). LCMS calculated for $C_{43}H_{45}Cl_2FN_5O_3$ (M+H)$^+$: m/z=768.3/770.3; found 768.2/770.2.

Step 4. tert-Butyl (1R,4R,5S)-5-(4-acetyl-8-(2-cyanoethyl)-7-(2,3-dichlorophenyl)-6-fluoro-2-((1R,3R,5R)-2-(1-methylcyclopropane-1-carbonyl)-2-azabicyclo[3.1.0]hexan-3-yl)-1H-pyrrolo[3,2-c]quinolin-1-yl)-2-azabicyclo[2.1.1]hexane-2-carboxylate

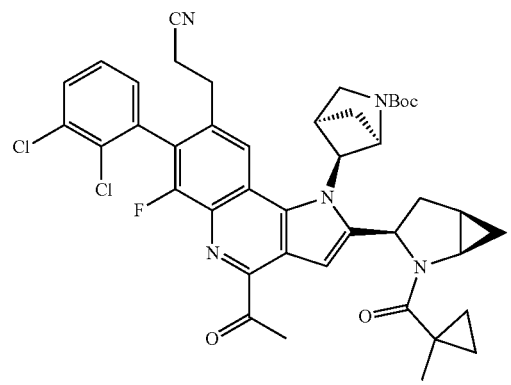 [SMILES: C=C(C)c1nc2c(F)c(-c3cccc(Cl)c3Cl)c(CCC#N)cc2c2c1cc([C@H]1C[C@H]3C[C@H]3N1C(=O)C1(C)CC1)n2[C@H]1[C@@H]2C[C@H]1N(C(=O)OC(C)(C)C)C2]

A vial was charged with tert-butyl (1R,4R,5S)-5-(8-(2-cyanoethyl)-7-(2,3-dichlorophenyl)-6-fluoro-2-((1R,3R,5R)-2-(1-methylcyclopropane-1-carbonyl)-2-azabicyclo[3.1.0]hexan-3-yl)-4-(prop-1-en-2-yl)-1H-pyrrolo[3,2-c]quinolin-1-yl)-2-azabicyclo[2.1.1]hexane-2-carboxylate (78 mg, 0.10 mmol), a stir bar, THF (0.81 mL) and water (0.20 mL). To this suspension was added potassium osmate dihydrate (0.4 mg, 1.02 μmol). The reaction was stirred for five minutes then sodium periodate (109 mg, 0.51 mmol) was added. After 1 h, full conversion of starting material was detected by LCMS. The reaction mixture was diluted with water and DCM. The organic layer was washed with water and brine, dried over sodium sulfate and concentrated. The desired product was isolated by flash column chromatography eluting with a gradient of 0-80% acetone/n-heptane. LCMS calculated for $C_{42}H_{43}Cl_2FN_5O_4$ (M+H)$^+$: m/z=770.3/772.3; found 770.5/772.4.

Step 5. 3-(1-((1R,4R,5S)-2-Azabicyclo[2.1.1]hexan-5-yl)-7-(2,3-dichlorophenyl)-6-fluoro-4-(1-hydroxyethyl)-2-((1R,3R,5R)-2-(1-methylcyclopropane-1-carbonyl)-2-azabicyclo[3.1.0]hexan-3-yl)-1H-pyrrolo[3,2-c]quinolin-8-yl)propanenitrile To a solution of tert-butyl (1R,4R,5S)-5-(4-acetyl-8-(2-cyanoethyl)-7-(2,3-dichlorophenyl)-6-fluoro-2-((1R,3R,5R)-2-(1-methylcyclopropane-1-carbonyl)-2-azabicyclo[3.1.0]hexan-3-yl)-1H-pyrrolo[3,2-c]quinolin-1-yl)-2-azabicyclo[2.1.1]hexane-2-carboxylate (29 mg, 0.038 mmol) in DCM (0.13 mL) and formic acid/triethylamine complex (0.03 mL, 5:2) was added RuCl(p-cymene)[(R,R)-Ts-DPEN] (1.7 mg, 2.63 μmol). The mixture was stirred for 16 h at room temperature. The crude material was stirred in 1:1 TFA/DCM (0.5 ml) for 30 min, then concentrated. The desired product was purified by prep HPLC (pH 2). LC-MS calculated for $C_{37}H_{37}Cl_2FN_5O_2^+$ (M+H)$^+$: m/z=672.2/674.2; found 672.4/674.4.

Example 63. 3-(1-((1R,4R,5S)-2-Azabicyclo[2.1.1]hexan-5-yl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-(1-hydroxyethyl)-1H-pyrrolo[3,2-c]quinolin-8-yl)propanenitrile

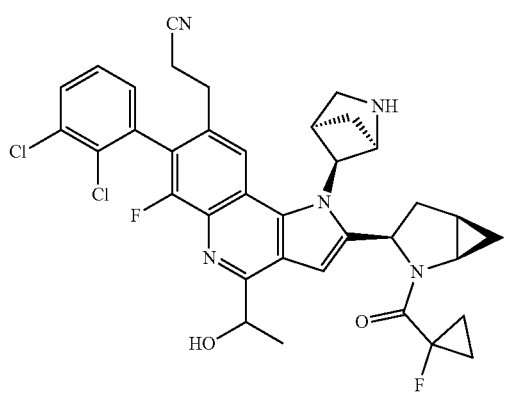 [SMILES: CC(O)c1nc2c(F)c(-c3cccc(Cl)c3Cl)c(CCC#N)cc2c2c1cc([C@H]1C[C@H]3C[C@H]3N1C(=O)C1(F)CC1)n2[C@H]1[C@H]2CN[C@@H]1C2]

Step 1. (1R,3R,5R)-3-Ethynyl-2-azabicyclo[3.1.0]hexane hydrochloride

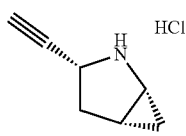

To a solution of tert-butyl (1R,3R,5R)-3-ethynyl-2-azabicyclo[3.1.0]hexane-2-carboxylate (Example 49, step 3; 4.88 g, 23.5 mmol) in THF (80 mL) was added 4N HCl in dioxane (18 mL). The solution was stirred at room temperature for 8-16 h until full starting material conversion was observed as detected by LCMS, then concentrated to near dryness. The crude solid was slurried in ether, collected by filtration, then air dried (2.48 g, 73% yield). LCMS calculated for $C_7H_{10}N$ (M+H)$^+$: m/z=108.1; found 108.1.

Step 2. ((1R,3R,5R)-3-Ethynyl-2-azabicyclo[3.1.0]hexan-2-yl)(1-fluorocyclopropyl)methanone

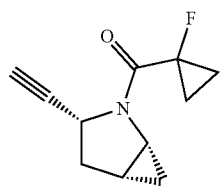

To a solution of (1R,3R,5R)-3-ethynyl-2-azabicyclo[3.1.0]hexane hydrochloride (2.48 g, 17.3 mmol) and triethylamine (12 mL, 86 mmol) in acetonitrile (90 mL) was added 1-fluorocyclopropane-1-carboxylic acid (3.59 g, 34.5 mmol) and HATU (13.1 g, 34.5 mmol). The reaction mixture was stirred at room temperature for 1 hour. Upon completion, the reaction was poured into water. The reaction mixture was extracted by ethyl acetate. The combined organic layers were dried over sodium sulfate, filtered and concentrated. The desired product was isolated by flash column chromatography eluting with a gradient of 0-50% acetone/hexanes as a colorless oil (2.71 g, 81% yield). LCMS calculated for $C_{11}H_{13}FNO$ (M+H)$^+$: m/z=194.1; found 194.1.

Step 3. tert-Butyl (1R,4R,5S)-5-(7-bromo-8-(2-cyanoethyl)-6-fluoro-2-((1R,3R,5R)-2-(1-fluorocyclopropane-1-carbonyl)-2-azabicyclo[3.1.0]hexan-3-yl)-4-(methylthio)-1H-pyrrolo[3,2-c]quinolin-1-yl)-2-azabicyclo[2.1.1]hexane-2-carboxylate

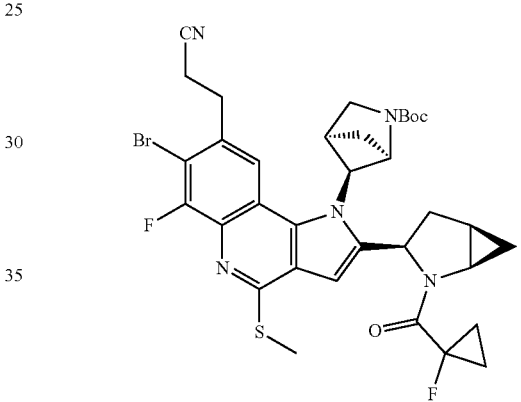

To a mixture of Intermediate 5 (2.5 g, 3.86 mmol) and ((1R,3R,5R)-3-ethynyl-2-azabicyclo[3.1.0]hexan-2-yl)(1-fluorocyclopropyl)methanone (970 mg, 5.02 mmol) were added DMF (19.3 mL) and triethylamine (5.38 mL, 38.6 mmol), followed by bis(triphenylphosphine)palladium(II) chloride (270 mg, 0.386 mmol) and copper(I) iodide (736 mg, 3.86 mmol). The head space of the reaction flask flushed with nitrogen, then stirred at 75° C. for 2 h. Cesium carbonate (6.29 g, 19.3 mmol) was then added and the reaction mixture was heated to 55° C. for 16 h. The reaction was quenched with water and a small amount of sat. aq. ammonium hydroxide, then diluted with ethyl acetate and filtered through a plug of Celite. The filtrate layers were separated and the organic layer was washed with water and brine, dried over sodium sulfate and concentrated. The crude product was purified by flash column chromatography (0-60% acetone in n-heptane) to provide the desired product (1.86 g, 68%). LC-MS calculated for $C_{34}H_{37}BrF_2N_5O_3S^+$ (M+H)$^+$: m/z=712.2/714.2; found 712.3/714.3.

Step 4. tert-Butyl (1R,4R,5S)-5-(8-(2-cyanoethyl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-(methylthio)-1H-pyrrolo[3,2-c]quinolin-1-yl)-2-azabicyclo[2.1.1]hexane-2-carboxylate

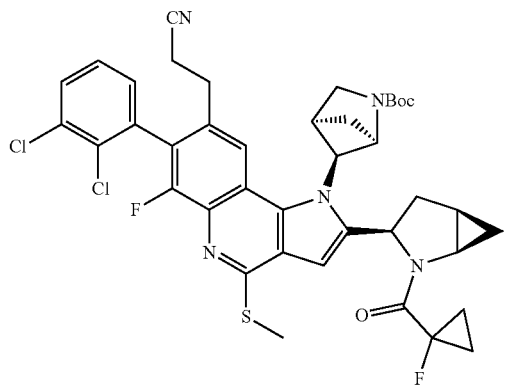 [SMILES: CSc1nc2c(F)c(-c3cccc(Cl)c3Cl)c(CCC#N)cc2c2c1cc([C@H]1C[C@H]3C[C@H]3N1C(=O)C1(F)CC1)n2[C@H]1[C@@H]2C[C@H]1N(C(=O)OC(C)(C)C)C2]

To a mixture of tert-butyl (1R,4R,5S)-5-(7-bromo-8-(2-cyanoethyl)-6-fluoro-2-((1R,3R,5R)-2-(1-fluorocyclopropane-1-carbonyl)-2-azabicyclo[3.1.0]hexan-3-yl)-4-(methylthio)-1H-pyrrolo[3,2-c]quinolin-1-yl)-2-azabicyclo[2.1.1]hexane-2-carboxylate (3.92 g, 5.50 mmol), (2,3-dichlorophenyl)boronic acid (1.36, 7.15 mmol), potassium fluoride (959 mg, 16.5 mmol) and Pd-132 (389 mg, 0.55 mmol) were added 1,4-dioxane (44 mL)/water (11 mL) and the reaction flask was evacuated, back filled with nitrogen, then stirred at 90° C. for 1 h. The reaction mixture was diluted with ethyl acetate, washed with water and brine, dried over sodium sulfate, and then concentrated. The crude product was purified by flash column chromatography (0-70% acetone/n-heptane) to provide the desired product (3.76 g, 88%). LC-MS calculated for $C_{40}H_{40}Cl_2F_2N_5O_3S^+$ (M+H)$^+$: m/z=778.2/780.2; found 778.4/780.3.

Step 5. tert-Butyl (1R,4R,5S)-5-(8-(2-cyanoethyl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-(prop-1-en-2-yl)-1H-pyrrolo[3,2-c]quinolin-1-yl)-2-azabicyclo[2.1.1]hexane-2-carboxylate

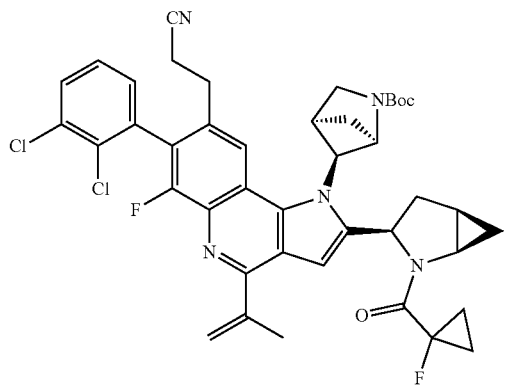 [SMILES: C=C(C)c1nc2c(F)c(-c3cccc(Cl)c3Cl)c(CCC#N)cc2c2c1cc([C@H]1C[C@H]3C[C@H]3N1C(=O)C1(F)CC1)n2[C@H]1[C@@H]2C[C@H]1N(C(=O)OC(C)(C)C)C2]

To a solution of tert-butyl (1R,4R,5S)-5-(8-(2-cyanoethyl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-(methylthio)-1H-pyrrolo[3,2-c]quinolin-1-yl)-2-azabicyclo[2.1.1]hexane-2-carboxylate (3.76 g, 4.83 mmol) in dioxane (48 mL) was added copper(I) 3-methylsalicylate (3.11 g, 14.5 mmol), tetrakis(triphenylphosphine)palladium (0) (558 mg, 0.48 mmol), and 4,4,5,5-tetramethyl-2-(prop-1-en-2-yl)-1,3,2-dioxaborolane (4.54 mL, 24.1 mmol). The headspace was purged with nitrogen and the vessel was sealed and heated to 100° C. for 3 h. The reaction mixture was quenched with water and saturated aq. ammonium hydroxide, then extracted with ethyl acetate. The organic layer was washed with water and brine, dried over sodium sulfate and concentrated. The desired product was isolated by flash column chromatography eluting with a gradient of 0-80% acetone/n-heptane as a yellowish brown solid (2.84 g, 76% yield). LCMS calculated for $C_{42}H_{42}Cl_2F_2N_5O_3$ (M+H)$^+$: m/z=772.3/774.3; found 772.2/774.2.

Step 6. tert-Butyl (1R,4R,5S)-5-(4-acetyl-8-(2-cyanoethyl)-7-(2,3-dichlorophenyl)-6-fluoro-2-((1R,3R,5R)-2-(1-fluorocyclopropane-1-carbonyl)-2-azabicyclo[3.1.0]hexan-3-yl)-1H-pyrrolo[3,2-c]quinolin-1-yl)-2-azabicyclo[2.1.1]hexane-2-carboxylate

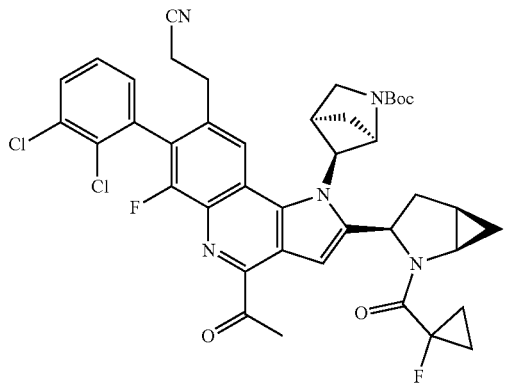 [SMILES: CC(=O)c1nc2c(F)c(-c3cccc(Cl)c3Cl)c(CCC#N)cc2c2c1cc([C@H]1C[C@H]3C[C@H]3N1C(=O)C1(F)CC1)n2[C@H]1[C@@H]2C[C@H]1N(C(=O)OC(C)(C)C)C2]

A round bottom flask was charged with tert-butyl (1R,4R,5S)-5-(8-(2-cyanoethyl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-(prop-1-en-2-yl)-1H-pyrrolo[3,2-c]quinolin-1-yl)-2-azabicyclo[2.1.1]hexane-2-carboxylate (2.84 g, 3.68 mmol), a stir bar, THF (30 mL) and water (7.4 mL). To this suspension was added potassium osmate dihydrate (14 mg, 0.037 mmol). The reaction was stirred for five minutes then sodium periodate (3.93 g, 18.4 mmol) was added. After 1 h, full conversion of starting material was detected by LCMS. The reaction mixture was diluted with water and DCM. The organic layer was washed with water and brine, dried over sodium sulfate and concentrated. The desired product was isolated by flash column chromatography eluting with a gradient of 0-80% acetone/n-heptane. LCMS calculated for $C_{41}H_{40}Cl_2F_2N_5O_4$ (M+H)$^+$: m/z=774.2/776.2; found 774.1/776.2.

Step 7. tert-Butyl (1R,4R,5S)-5-(8-(2-cyanoethyl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-(1-hydroxyethyl)-1H-pyrrolo[3,2-c]quinolin-1-yl)-2-azabicyclo[2.1.1]hexane-2-carboxylate

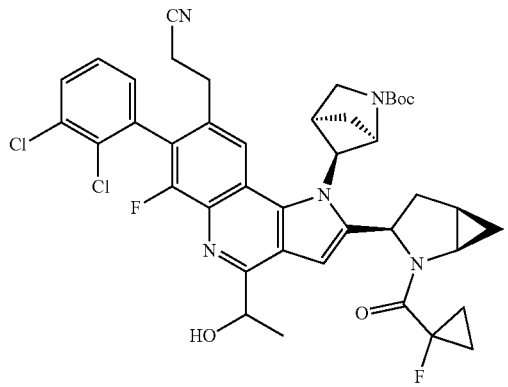

To a solution of tert-butyl (1R,4R,5S)-5-(4-acetyl-8-(2-cyanoethyl)-7-(2,3-dichlorophenyl)-6-fluoro-2-((1R,3R,5R)-2-(1-fluorocyclopropane-1-carbonyl)-2-azabicyclo[3.1.0]hexan-3-yl)-1H-pyrrolo[3,2-c]quinolin-1-yl)-2-azabicyclo[2.1.1]hexane-2-carboxylate (2.81 g, 3.63 mmol) in DCM (6.05 mL) and formic acid/triethylamine complex (1.21 mL, 5:2) was added RuCl(p-cymene)[(R,R)-Ts-DPEN] (231 mg, 0.36 mmol). The mixture was stirred for 24 h at room temperature. Upon full conversion of starting material as detected by LCMS, saturated aqueous sodium bicarbonate was added and the organics were extracted with DCM. The organics were washed with water and brine, dried over sodium sulfate and concentrated. The desired product was isolated by flash column chromatography eluting with a gradient of 0-100% acetone/n-heptane (1.86 g, 66% yield). LCMS calculated for $C_{41}H_{42}Cl_2F_2N_5O_4$ $(M+H)^+$: m/z=776.3/778.3; found 776.3/778.3.

Step 8. 3-(1-((1R,4R,5S)-2-Azabicyclo[2.1.1]hexan-5-yl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-(1-hydroxyethyl)-1H-pyrrolo[3,2-c]quinolin-8-yl)propanenitrile A solution of tert-butyl (1R,4R,5S)-5-(8-(2-cyanoethyl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-(1-hydroxyethyl)-1H-pyrrolo[3,2-c]quinolin-1-yl)-2-azabicyclo[2.1.1]hexane-2-carboxylate (1.86 g, 2.4 mmol) in 1:1 TFA/DCM (10 ml) was stirred for 30 min at room temperature, then concentrated. The desired product was purified by prep HPLC (pH 2). LC-MS calculated for $C_{36}H_{34}Cl_2F_2N_5O_2^+$ $(M+H)^+$: m/z=676.2/678.2; found 676.3/678.2. $^1$H NMR (600 MHz, DMSO-$d_6$) δ 9.28 (s, 1H), 8.11 (s, 1H), 8.06 (s, 1H), 7.84 (dd, J=8.1, 1.5 Hz, 1H), 7.58 (t, J=7.9 Hz, 1H), 7.46 (dd, J=7.6, 1.5 Hz, 1H), 6.77 (s, 1H), 5.64 (d, J=10.8 Hz, 1H), 5.56 (s, 1H), 5.15 (q, J=6.7 Hz, 1H), 4.85 (d, J=6.0 Hz, 1H), 4.13-4.07 (m, 1H), 3.93-3.88 (m, 1H), 3.54-3.48 (m, 1H), 3.42-3.36 (m, 1H), 3.06-2.98 (m, 1H), 2.92-2.79 (m, 3H), 2.66 (dt, J=15.6, 7.2 Hz, 1H), 2.29 (d, J=9.0 Hz, 1H), 1.96 (dd, J=12.9, 2.7 Hz, 1H), 1.86-1.79 (m, 1H), 1.62-1.50 (m, 2H), 1.52 (d, J=6.5 Hz, 3H), 1.50-1.41 (m, 2H), 1.28-1.18 (m, 1H), 0.80 (dt, J=8.9, 6.0 Hz, 1H), 0.71-0.64 (m, 1H).

Example 64. 3-(1-((1R,4R,5S)-2-Azabicyclo[2.1.1]hexan-5-yl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-methyl-1H-pyrrolo[3,2-c]quinolin-8-yl)propanenitrile

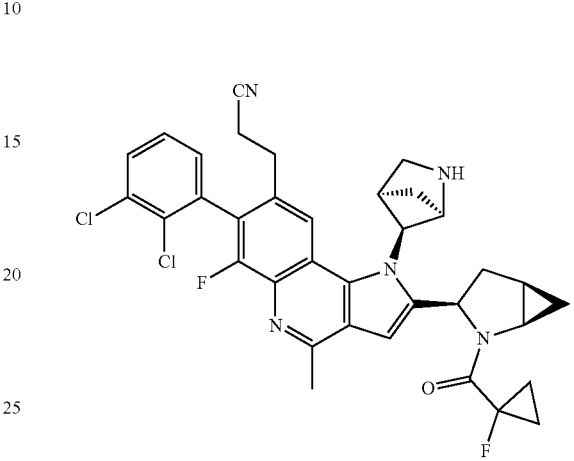

Step 1. tert-Butyl (1R,4R,5S)-5-(8-(2-cyanoethyl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-methyl-1H-pyrrolo[3,2-c]quinolin-1-yl)-2-azabicyclo[2.1.1]hexane-2-carboxylate

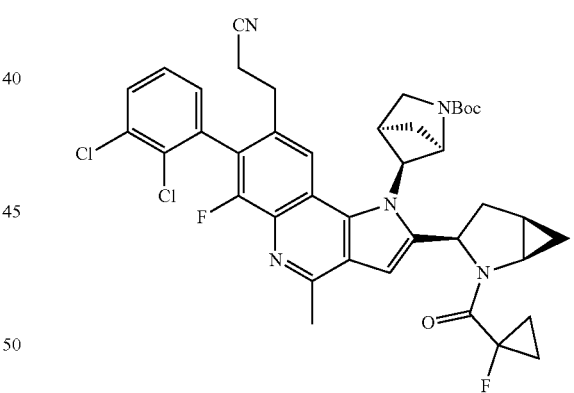

This compound was prepared in an analogous fashion to Example 63, with methylboronic acid replacing 4,4,5,5-tetramethyl-2-(prop-1-en-2-yl)-1,3,2-dioxaborolane in Step 5. LC-MS calculated for $C_{40}H_{40}Cl_2F_2N_5O_3^+$ $(M+H)^+$: m/z=746.2/748.2; found 746.2/748.2.

Step 2. 3-(1-((1R,4R,5S)-2-Azabicyclo[2.1.1]hexan-5-yl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-methyl-1H-pyrrolo[3,2-c]quinolin-8-yl)propanenitrile A solution of tert-butyl (1R,4R,5S)-5-(8-(2-cyanoethyl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-methyl-1H-pyrrolo[3,2-c]quinolin-1-yl)-2-azabicyclo[2.1.1]hexane-2-carboxylate (19 mg, 0.026 mmol) in 1:1 TFA/DCM (0.5 mL) was stirred at room temperature for 30 min, then concentrated. The desired product was purified by prep HPLC (pH 2). LC-MS calculated for $C_{35}H_{32}Cl_2F_2N_5O^+$ (M+H)$^+$: m/z=646.2/648.2; found 646.1/648.1.

Example 65. N-((1R)-1-(1-((1R,4R,5S)-2-Azabicyclo[2.1.1]hexan-5-yl)-8-(2-cyanoethyl)-7-(2,3-dichlorophenyl)-6-fluoro-4-(1-hydroxyethyl)-1H-pyrrolo[3,2-c]quinolin-2-yl)ethyl)-1-fluorocyclopropane-1-carboxamide

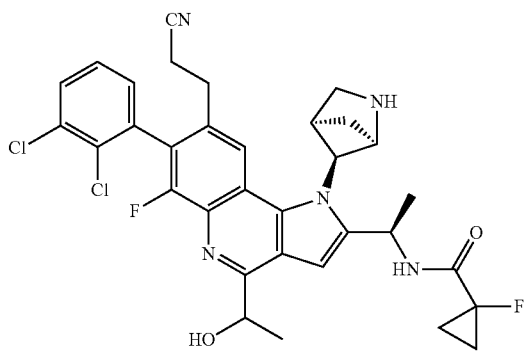 [SMILES: CC(O)c1nc2c(F)c(-c3cccc(Cl)c3Cl)c(CCC#N)cc2c2c1cc([C@@H](C)NC(=O)C1(F)CC1)n2[C@H]1[C@H]2CN[C@@H]1C2]

Step 1. tert-Butyl (1R,4R,5S)-5-(8-(2-cyanoethyl)-7-(2,3-dichlorophenyl)-6-fluoro-4-(prop-1-en-2-yl)-2-((R)-1-(((2-(trimethylsilyl)ethoxy)carbonyl)amino)ethyl)-1H-pyrrolo[3,2-c]quinolin-1-yl)-2-azabicyclo[2.1.1]hexane-2-carboxylate

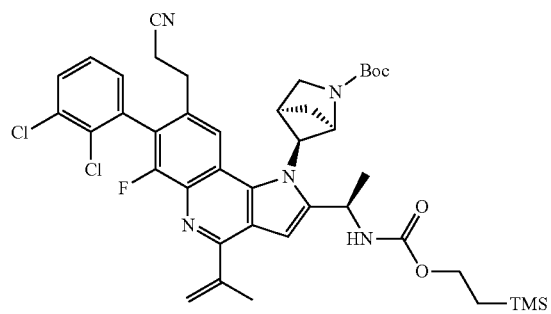 [SMILES: C=C(C)c1nc2c(F)c(-c3cccc(Cl)c3Cl)c(CCC#N)cc2c2c1cc([C@@H](C)NC(=O)OCC[Si](C)(C)C)n2[C@H]1[C@@H]2C[C@H]1N(C(=O)OC(C)(C)C)C2]

To a solution of tert-butyl (1R,4R,5S)-5-(8-(2-cyanoethyl)-7-(2,3-dichlorophenyl)-6-fluoro-4-(methylthio)-2-((R)-1-(((2-(trimethylsilyl)ethoxy)carbonyl)amino)ethyl)-1H-pyrrolo[3,2-c]quinolin-1-yl)-2-azabicyclo[2.1.1]hexane-2-carboxylate (1.0 g, 1.25 mmol, Intermediate 22, Step 3) in dioxane (12.5 mL) was added copper(I) 3-methylsalicylate (806 mg, 3.76 mmol), tetrakis(triphenylphosphine)palladium(0) (145 mg, 0.13 mmol), and 4,4,5,5-tetramethyl-2-(prop-1-en-2-yl)-1,3,2-dioxaborolane (0.71 mL, 3.76 mmol). The headspace was purged with nitrogen and the vessel was sealed and heated to 100° C. for 3 h. The reaction mixture was quenched with water and saturated aq. ammonium hydroxide, then extracted with ethyl acetate. The organic layer was washed with water and brine, dried over sodium sulfate and concentrated. The desired product was isolated by flash column chromatography eluting with a gradient of 0-80% acetone/n-heptane as a yellowish brown solid (858 mg, 86% yield). LCMS calculated for $C_{4}H_{49}Cl_2FN_5O_4Si$ (M+H)$^+$: m/z=792.3/794.3; found 792.2/794.2.

Step 2. tert-Butyl (1R,4R,5S)-5-(4-acetyl-8-(2-cyanoethyl)-7-(2,3-dichlorophenyl)-6-fluoro-2-((R)-1-(((2-(trimethylsilyl)ethoxy)carbonyl)amino)ethyl)-1H-pyrrolo[3,2-c]quinolin-1-yl)-2-azabicyclo[2.1.1]hexane-2-carboxylate

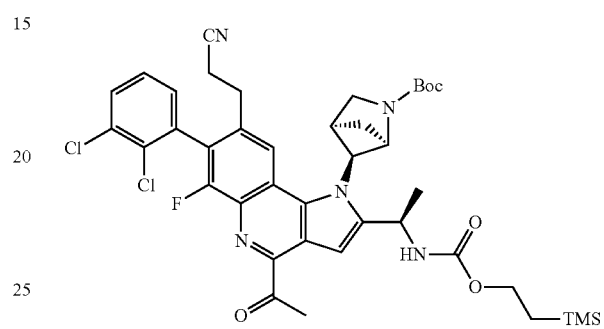

A vial was charged with tert-butyl (1R,4R,5S)-5-(8-(2-cyanoethyl)-7-(2,3-dichlorophenyl)-6-fluoro-4-(prop-1-en-2-yl)-2-((R)-1-(((2-(trimethylsilyl)ethoxy)carbonyl)amino)ethyl)-1H-pyrrolo[3,2-c]quinolin-1-yl)-2-azabicyclo[2.1.1]hexane-2-carboxylate (858 mg, 1.08 mmol), a stir bar, THF (8.66 mL) and water (2.16 mL). To this suspension was added potassium osmate dihydrate (4.0 mg, 10.8 μmol). The reaction was stirred for five minutes then sodium periodate (1.16 g, 5.41 mmol) was added. After 1 h, full conversion of starting material was detected by LCMS. The reaction mixture was diluted with water and DCM. The organic layer was washed with water and brine, dried over sodium sulfate and concentrated. The desired product was isolated by flash column chromatography eluting with a gradient of 0-80% acetone/n-heptane (667 mg, 78% yield). LCMS calculated for $C_{40}H_{47}Cl_2FN_5O_5Si$ (M+H)$^+$: m/z=794.3/796.3; found 794.2/796.2.

Step 3. tert-Butyl (1R,4R,5S)-5-(4-acetyl-2-((R)-1-aminoethyl)-8-(2-cyanoethyl)-7-(2,3-dichlorophenyl)-6-fluoro-1H-pyrrolo[3,2-c]quinolin-1-yl)-2-azabicyclo[2.1.1]hexane-2-carboxylate

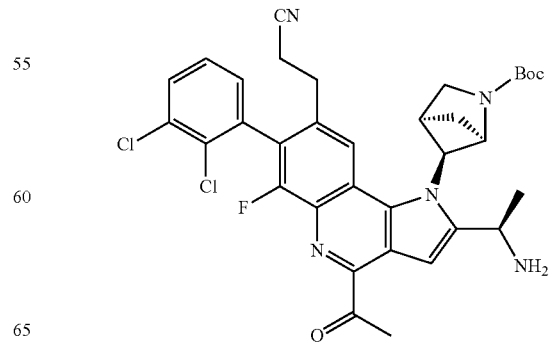

To a solution of tert-butyl (1R,4R,5S)-5-(4-acetyl-8-(2-cyanoethyl)-7-(2,3-dichlorophenyl)-6-fluoro-2-((R)-1-(((2-(trimethylsilyl)ethoxy)carbonyl)amino)ethyl)-1H-pyrrolo[3,2-c]quinolin-1-yl)-2-azabicyclo[2.1.1]hexane-2-carboxylate (667 mg, 0.84 mmol) in DMF (4.2 mL) was added cesium fluoride (510 mg, 3.36 mmol) and the reaction mixture was heated at 90° C. for 1 hour. After cooling to room temperature, the reaction was diluted with DCM and 5% aqueous LiCl solution. The organics were washed three times with 5% aqueous LiCl solution and then brine, dried over sodium sulfate and concentrated. The crude material was taken forward without additional purification. LCMS calculated for $C_{34}H_{35}Cl_2FN_5O_3$ (M+H)$^+$: m/z=650.2/652.2; found 650.2/652.2.

Step 4. tert-Butyl (1R,4R,5S)-5-(4-acetyl-8-(2-cyanoethyl)-7-(2,3-dichlorophenyl)-6-fluoro-2-((R)-1-(1-fluorocyclopropane-1-carboxamido)ethyl)-1H-pyrrolo[3,2-c]quinolin-1-yl)-2-azabicyclo[2.1.1]hexane-2-carboxylate

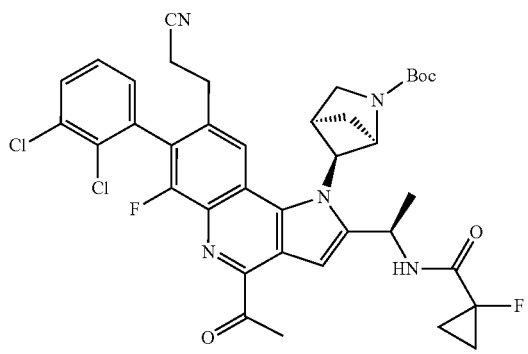 [SMILES: CC(=O)c1nc2c(F)c(-c3cccc(Cl)c3Cl)c(CCC#N)cc2c2c1cc([C@@H](C)NC(=O)C1(F)CC1)n2[C@H]1[C@@H]2C[C@H]1N(C(=O)OC(C)(C)C)C2]

To a solution of tert-butyl (1R,4R,5S)-5-(4-acetyl-2-((R)-1-aminoethyl)-8-(2-cyanoethyl)-7-(2,3-dichlorophenyl)-6-fluoro-1H-pyrrolo[3,2-c]quinolin-1-yl)-2-azabicyclo[2.1.1]hexane-2-carboxylate (350 mg, 0.54 mmol) and triethylamine (0.38 mL, 2.69 mmol) in acetonitrile (5.4 mL) was added 1-fluorocyclopropane-1-carboxylic acid (112 mg, 1.08 mmol) and HATU (409 mg, 1.08 mmol). The reaction mixture was stirred at room temperature for 1 hour. Upon completion, the reaction was poured into water. The reaction mixture was extracted by ethyl acetate. The combined organic layers were dried over sodium sulfate, filtered and concentrated. The desired product was isolated by flash column chromatography eluting with a gradient of 0-80% acetone/hexanes (205 mg, 52% yield). LCMS calculated for $C_{38}H_{38}Cl_2F_2N_5O_4$ (M+H)$^+$: m/z=736.2/738.2; found 736.2/738.1.

Step 5. tert-Butyl (1R,4R,5S)-5-(8-(2-cyanoethyl)-7-(2,3-dichlorophenyl)-6-fluoro-2-((R)-1-(1-fluorocyclopropane-1-carboxamido)ethyl)-4-(1-hydroxyethyl)-1H-pyrrolo[3,2-c]quinolin-1-yl)-2-azabicyclo[2.1.1]hexane-2-carboxylate

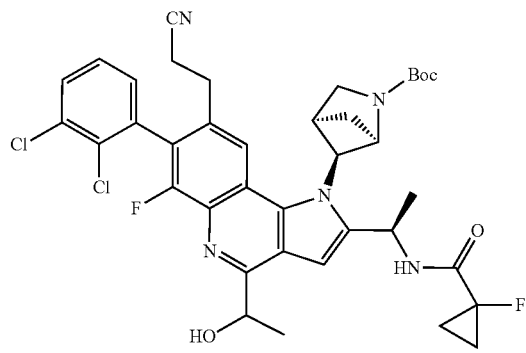 [SMILES: CC(O)c1nc2c(F)c(-c3cccc(Cl)c3Cl)c(CCC#N)cc2c2c1cc([C@@H](C)NC(=O)C1(F)CC1)n2[C@H]1[C@@H]2C[C@H]1N(C(=O)OC(C)(C)C)C2]

To a solution of tert-butyl (1R,4R,5S)-5-(4-acetyl-8-(2-cyanoethyl)-7-(2,3-dichlorophenyl)-6-fluoro-2-((R)-1-(1-fluorocyclopropane-1-carboxamido)ethyl)-1H-pyrrolo[3,2-c]quinolin-1-yl)-2-azabicyclo[2.1.1]hexane-2-carboxylate (205 mg, 0.28 mmol) in DCM (4.6 mL) and formic acid/triethylamine complex (0.93 mL, 5:2) was added RuCl(p-cymene)[(R,R)-Ts-DPEN] (18 mg, 0.028 mmol). The mixture was stirred for 16 h at room temperature. Upon full conversion of starting material as detected by LCMS, saturated aqueous sodium bicarbonate was added and the organics were extracted with DCM. The organics were washed with water and brine, dried over sodium sulfate and concentrated. The desired product was isolated by prep HPLC (pH 10) (106 mg, 52% yield). LCMS calculated for $C_{38}H_{40}Cl_2F_2N_5O_4$ (M+H)$^+$: m/z=738.2/740.2; found 738.2/740.2.

Step 6. N-((1R)-1-(1-((1R,4R,5S)-2-Azabicyclo[2.1.1]hexan-5-yl)-8-(2-cyanoethyl)-7-(2,3-dichlorophenyl)-6-fluoro-4-(1-hydroxyethyl)-1H-pyrrolo[3,2-c]quinolin-2-yl)ethyl)-1-fluorocyclopropane-1-carboxamide A solution of tert-butyl (1R,4R,5S)-5-(8-(2-cyanoethyl)-7-(2,3-dichlorophenyl)-6-fluoro-2-((R)-1-(1-fluorocyclopropane-1-carboxamido)ethyl)-4-(1-hydroxyethyl)-1H-pyrrolo[3,2-c]quinolin-1-yl)-2-azabicyclo[2.1.1]hexane-2-carboxylate (106 mg, 0.14 mmol) in 1:1 TFA/DCM (0.6 mL) for 30 min, then concentrated. The desired product was purified by prep HPLC (pH 2). LC-MS calculated for $C_{33}H_{32}Cl_2F_2N_5O_2^+$ (M+H)$^+$: m/z=638.2/640.2; found 638.3/640.3. $^1$H NMR (600 MHz, DMSO) δ 9.46 (s, 1H), 9.32 (d, J=7.5 Hz, 1H), 8.16 (s, 1H), 8.09 (s, 1H), 7.84 (dd, J=8.1, 1.6 Hz, 1H), 7.58 (t, J=7.8 Hz, 1H), 7.49 (dd, J=7.8, 1.5 Hz, 1H), 7.09 (s, 1H), 5.62 (s, 1H), 5.28-5.19 (m, 2H), 4.86 (d, J=6.0 Hz, 1H), 3.97-3.91 (m, 1H), 3.64 (t, J=8.4 Hz, 1H), 3.42 (t, J=9.1 Hz, 1H), 3.10-2.95 (m, 1H), 2.92-2.72 (m, 2H), 2.72-2.63 (m, 1H), 2.33 (d, J=8.8 Hz, 1H), 1.62-1.53 (m, 4H), 1.51 (d, J=6.9 Hz, 3H), 1.50-1.39 (m, 2H), 1.34-1.23 (m, 2H).

Example 66. N-((1R)-1-(1-(((1R,4R,5S)-2-azabicyclo[2.1.1]hexan-5-yl)-8-(2-cyanoethyl)-7-(2,3-dichlorophenyl)-6-fluoro-4-(1-hydroxyethyl)-1H-pyrrolo[3,2-c]quinolin-2-yl)ethyl)-1-fluorocyclobutane-1-carboxamide

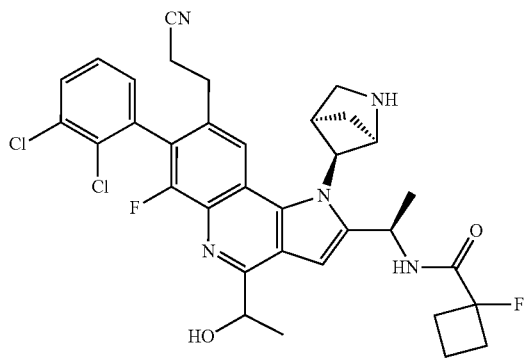 [SMILES: CC(O)c1nc2c(F)c(-c3cccc(Cl)c3Cl)c(CCC#N)cc2c2c1cc([C@@H](C)NC(=O)C1(F)CCC1)n2[C@H]1[C@H]2CN[C@@H]1C2]

This compound was prepared in an analogous fashion to Example 67, with 1-fluorocyclobutane-1-carboxylic acid replacing 1-fluorocyclopropane-1-carboxylic acid in Step 4. LC-MS calculated for $C_{34}H_{34}Cl_2F_2N_5O_2^+$ (M+H)$^+$: m/z=652.2/654.2; found 652.1/654.2.

Example 67. 3-(1-(((1R,4R,5S)-2-azabicyclo[2.1.1]hexan-5-yl)-7-(3-chloro-2-methylphenyl)-2-(1-(2,6-dimethyl-3-oxo-2,3-dihydropyridazin-4-yl)ethyl)-6-fluoro-4-methyl-1H-pyrrolo[3,2-c]quinolin-8-yl)propanenitrile

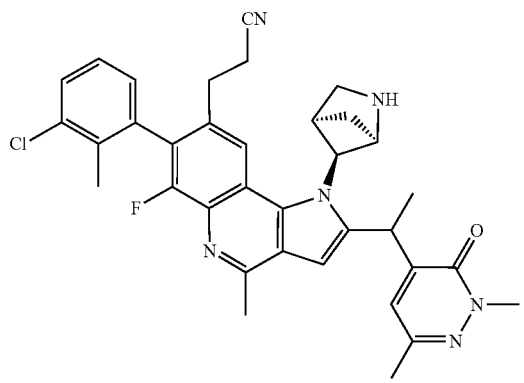 [SMILES: Cc1cc(C(C)c2cc3c(C)nc4c(F)c(-c5cccc(Cl)c5C)c(CCC#N)cc4c3n2[C@H]2[C@H]3CN[C@@H]2C3)c(=O)n(C)n1]

Step 1. tert-butyl (1R,4R,5S)-5-((3-amino-7-(3-chloro-2-methylphenyl)-6-(2-cyanoethyl)-8-fluoro-2-(methylthio)quinolin-4-yl)(tert-butoxycarbonyl)amino)-2-azabicyclo[2.1.1]hexane-2-carboxylate

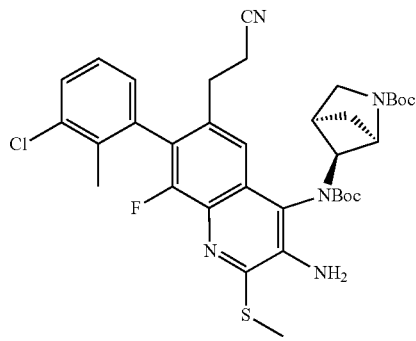 [SMILES: CSc1nc2c(F)c(-c3cccc(Cl)c3C)c(CCC#N)cc2c(N(C(=O)OC(C)(C)C)[C@H]2[C@@H]3C[C@H]2N(C(=O)OC(C)(C)C)C3)c1N]

To a mixture of tert-butyl (1R,4R,5S)-5-((3-amino-7-bromo-6-(2-cyanoethyl)-8-fluoro-2-(methylthio)-quinolin-4-yl)(tert-butoxycarbonyl)amino)-2-azabicyclo[2.1.1]hexane-2-carboxylate (from Intermediate 2, step 4, 14.37 g, 22.57 mmol), Pd(PPh$_3$)$_4$ (2.61 g, 2.26 mmol), and potassium phosphate (14.37 g, 67.7 mmol) in dioxane (100 ml) and water (20 ml) was added (3-chloro-2-methylphenyl)boronic acid (7.69 g, 45.1 mmol). The reaction mixture was heated to 100° C. for 1 hour. The reaction mixture was cooled to room temperature and water and DCM were added. The layers were separated and the aqueous layer was extracted with DCM. The combined organic fractions were filtered over a plug of MgSO$_4$, and concentrated. The crude residue was purified by automated flash column chromatography (0-100% EtOAc/hexanes) to afford the title compound (11.1 g, 72%). LC-MS calculated for $C_{35}H_{42}ClFN_5O_4S^+$ (M+H)$^+$: m/z=682.3; found 682.4.

Step 2. tert-butyl (1R,4R,5S)-5-((3-amino-7-(3-chloro-2-methylphenyl)-6-(2-cyanoethyl)-8-fluoro-2-methylquinolin-4-yl)(tert-butoxycarbonyl)amino)-2-azabicyclo[2.1.1]hexane-2-carboxylate

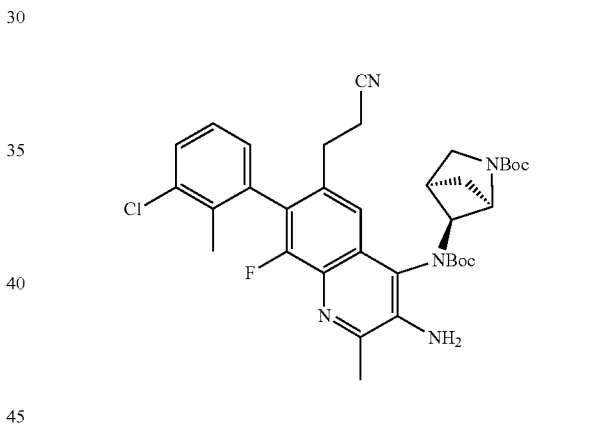

To a solution of tert-butyl (1R,4R,5S)-5-((3-amino-7-(3-chloro-2-methylphenyl)-6-(2-cyanoethyl)-8-fluoro-2-(methylthio)quinolin-4-yl)(tert-butoxycarbonyl)amino)-2-azabicyclo[2.1.1]hexane-2-carboxylate (11.1 g, 16.3 mmol), methylboronic acid (3.51 g, 58.6 mmol), Pd(PPh$_3$)$_4$ (3.76 g, 3.25 mmol) in dioxane (100 ml) was added copper(I) 3-methylsalicylate (12.6 g, 58.6 mmol). The reaction mixture was stirred at 110° C. for 1 hour. The reaction mixture was cooled to room temperature and quenched with saturated aqueous NH$_4$OH solution and diluted with DCM. The layers were separated and the organic layer was extracted with DCM. The combined organic fractions were filtered over a plug of MgSO$_4$, and concentrated. The crude residue was purified by automated flash column chromatography (0-100% EtOAc/hexanes) to afford the title compound (8.34 g, 79%). LC-MS calculated for $C_{35}H_{42}ClFN_5O_4^+$ (M+H)$^+$: m/z=650.3; found 650.4.

Step 3. tert-butyl (1R,4R,5S)-5-((7-(3-chloro-2-methylphenyl)-6-(2-cyanoethyl)-8-fluoro-3-iodo-2-methylquinolin-4-yl)amino)-2-azabicyclo[2.1.1]hexane-2-carboxylate

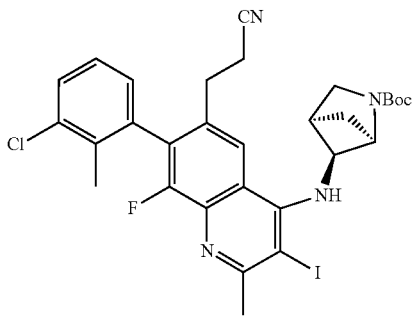 [SMILES: Cc1nc2c(F)c(-c3cccc(Cl)c3C)c(CCC#N)cc2c(N[C@H]2[C@@H]3C[C@H]2N(C(=O)OC(C)(C)C)C3)c1I]

To a −20° C. solution of tert-butyl (1R,4R,5S)-5-((3-amino-7-(3-chloro-2-methylphenyl)-6-(2-cyanoethyl)-8-fluoro-2-methylquinolin-4-yl)(tert-butoxycarbonyl)amino)-2-azabicyclo[2.1.1]hexane-2-carboxylate (8.34 g, 12.83 mmol) in acetonitrile (130 ml) was added sulfuric acid (50% v/v, 3.44 ml, 32.1 mmol) dropwise. A concentrated aqueous solution of sodium nitrite (1.77 g, 25.7 mmol) was added dropwise, keeping the reaction mixture temperature between −20° C. and −15° C. After addition the reaction mixture was stirred rapidly at −20° C. A concentrated aqueous solution of potassium iodide (8.52 g, 51.3 mmol) was added dropwise, keeping the reaction mixture temperature between −20° C. and −15° C. After addition, the reaction mixture was quenched with saturated aqueous sodium thiosulfate solution and saturated aqueous sodium bicarbonate solution, and diluted with DCM. The layers were separated and the organic layer was extracted with DCM. The combined organic fractions were filtered over a plug of MgSO₄, and concentrated. To the crude residue was added DCM (100 ml) and TFA (100 ml) at room temperature. The reaction mixture was stirred at room temperature for 1 hour. The reaction mixture was concentrated. DCM (100 ml) was added to the crude residue and the solution was concentrated again. The crude residue was dissolved into THF (100 ml), and triethylamine (18.7 ml, 107 mmol) and Boc₂O (2.8 g, 12.85 mmol) were added. The reaction mixture was stirred for 1 hour. The reaction mixture was quenched with saturated aqueous sodium bicarbonate solution, and diluted with DCM. The layers were separated and the organic layer was extracted with DCM. The combined organic fractions were filtered over a plug of MgSO₄, and concentrated. The crude residue was purified by automated flash column chromatography (0-100% ethyl acetate/hexanes) to afford the desired material (2.8 g, 40%). LC-MS calculated for $C_{30}H_{32}ClFIN_4O_2^+$ (M+H)⁺: m/z=661.1; found 661.2.

Step 4. 3-(1-((1R,4R,5S)-2-azabicyclo[2.1.1]hexan-5-yl)-7-(3-chloro-2-methylphenyl)-2-(1-(2,6-dimethyl-3-oxo-2,3-dihydropyridazin-4-yl)ethyl)-6-fluoro-4-methyl-1H-pyrrolo[3,2-c]quinolin-8-yl)propanenitrile To a solution of tert-butyl (1R,4R,5S)-5-((7-(3-chloro-2-methylphenyl)-6-(2-cyanoethyl)-8-fluoro-3-iodo-2-methylquinolin-4-yl)amino)-2-azabicyclo[2.1.1]hexane-2-carboxylate (40 mg, 0.061 mmol) in DMF (0.3 ml) was added 4-(but-3-yn-2-yl)-2,6-dimethylpyridazin-3(2H)-one (Intermediate 24, 21.3 mg, 0.121 mmol), copper(I) iodide (4.61 mg, 0.024 mmol), Pd(PPh₃)₄ (14 mg, 0.012 mmol), and DIPEA (0.1 ml, 0.6 mmol). The reaction mixture was sparged with N₂ for 1 minute then heated to 55° C. for 1 hour. The reaction mixture was cooled to room temperature and Cs₂CO₃ (100 mg, 0.3 mmol) was added. The reaction mixture was then heated to 90° C. for 1 hour. The reaction mixture was cooled to room temperature then quenched with saturated aqueous NH₄OH solution and diluted with DCM. The layers were separated and the aqueous layer was extracted with DCM. The combined organic fractions were filtered over a plug of MgSO₄ and concentrated. The crude residue was dissolved into DCM (0.3 ml) and TFA (0.3 ml) and stirred for 1 hour. The reaction mixture was concentrated and diluted with MeCN, filtered, and purified by prep-HPLC (pH 2). LC-MS calculated for $C_{35}H_{35}ClFN_6O^+$ (M+H)⁺: m/z=609.3; found 609.3.

Example 68: N-((1R)-1-(1-((1R,4R,5S)-2-azabicyclo[2.1.1]hexan-5-yl)-8-(2-cyanoethyl)-7-(2,3-dichlorophenyl)-6-fluoro-4-methyl-1H-pyrrolo[3,2-c]quinolin-2-yl)ethyl)pyrimidine-4-carboxamide

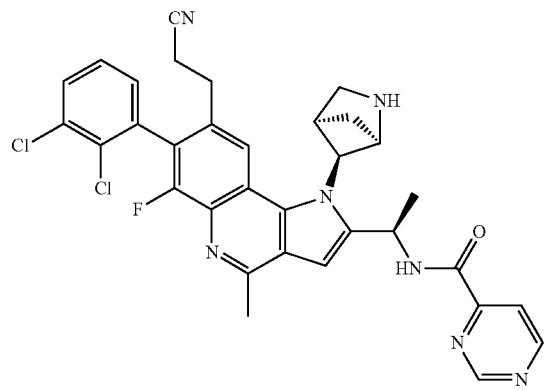 [SMILES: Cc1nc2c(F)c(-c3cccc(Cl)c3Cl)c(CCC#N)cc2c2c1cc([C@@H](C)NC(=O)c1ccncn1)n2[C@H]1[C@H]2CN[C@@H]1C2]

To a solution of tert-butyl (1R,4R,5S)-5-(2-((R)-1-aminoethyl)-8-(2-cyanoethyl)-7-(2,3-dichlorophenyl)-6-fluoro-4-methyl-1H-pyrrolo[3,2-c]quinolin-1-yl)-2-azabicyclo[2.1.1]hexane-2-carboxylate (Intermediate 22, 600 mg, 0.964 mmol), pyrimidine-4-carboxylic acid (239 mg, 1.928 mmol), HATU (733 mg, 1.928 mmol) in Acetonitrile (9.64 ml) was added triethylamine (672 μl, 4.82 mmol). The reaction mixture was stirred at room temperature for 1 h. Upon completion, the reaction was quenched by saturated sodium bicarbonate solution. The reaction mixture was extracted by ethyl acetate. The combined organic layers were dried over sodium sulfate, filtered and concentrated. The residue was dissolved in DCM/TFA solution (1:1 ratio, a total of 20 ml), and the solution was stirred at room temperature for 2 hours to remove the Boc protecting group. The reaction was then concentrated and diluted with acetonitrile, which was purified prep-LCMS (XBridge C18 column, eluting with a gradient of acetonitrile/water containing 0.1% TFA, at flow rate of 60 mL/min) to afford the product as a TFA salt in the form of a white amorphous powder. LC-MS calculated for $C_{33}H_{29}Cl_2FN_7O$ (M+H)⁺: m/z=628.2; found 628.2. ¹H NMR (600 MHz, DMSO-d₆) 9.79 (d, J=7.5 Hz, 1H), 9.48 (s, 1H), 9.45-9.34 (m, 1H), 9.16 (d, J=5.0 Hz, 1H), 8.19 (s, 1H), 8.11 (d, J=5.0 Hz, 1H), 7.85 (dd, J=8.0, 1.0 Hz, 1H), 7.59 (t, J=8.0 Hz, 1H), 7.49 (dd, J=8.0, 1.0 Hz, 1H), 6.98 (s, 1H), 5.68 (s, 1H), 5.40-5.32 (m, 1H), 4.88 (d, J=6.0

Hz, 1H), 4.05-3.98 (m, 1H), 3.73-3.65 (m, 1H), 3.53-3.44 (m, 1H), 3.09-3.01 (m, 1H), 2.95-2.79 (m, 5H), 2.72-2.66 (m, 1H), 2.34 (d, J=8.9 Hz, 1H), 1.62 (d, J=8.9 Hz, 1H), 1.60 (d, J=7.0 Hz, 3H).

Example 69: N-((1R)-1-(1-((1R,4R,5S)-2-azabicyclo[2.1.1]hexan-5-yl)-8-(2-cyanoethyl)-7-(2,3-dichlorophenyl)-6-fluoro-4-methyl-1H-pyrrolo[3,2-c]quinolin-2-yl)ethyl)pyridazine-3-carboxamide

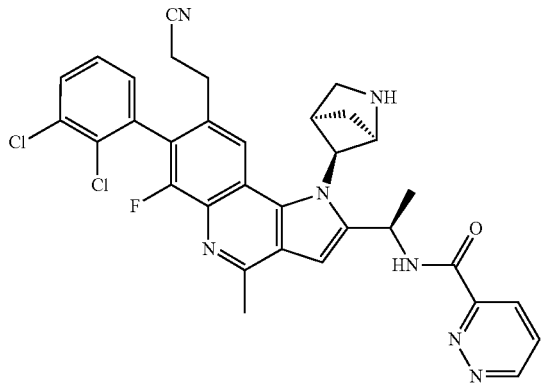 [SMILES: Cc1nc2c(F)c(-c3cccc(Cl)c3Cl)c(CCC#N)cc2c2c1cc([C@@H](C)NC(=O)c1cccnn1)n2[C@H]1[C@H]2CN[C@@H]1C2]

To a solution of tert-butyl (1R,4R,5S)-5-(2-((R)-1-aminoethyl)-8-(2-cyanoethyl)-7-(2,3-dichlorophenyl)-6-fluoro-4-methyl-1H-pyrrolo[3,2-c]quinolin-1-yl)-2-azabicyclo[2.1.1]hexane-2-carboxylate (Intermediate 22, 100 mg, 0.161 mmol), pyridazine-3-carboxylic acid (39.9 mg, 0.321 mmol), HATU (122 mg, 0.321 mmol) in Acetonitrile (1.606 ml) was added triethylamine (112 µl, 0.803 mmol). The reaction mixture was stirred at room temperature for 1 h. Upon completion, the reaction was quenched by saturated sodium bicarbonate solution. The reaction mixture was extracted by ethyl acetate. The combined organic layers were dried over sodium sulfate, filtered and concentrated. The residue was dissolved in DCM/TFA solution (1:1 ratio, a total of 5 ml), and the solution was stirred at room temperature for 2 hours to remove the Boc protecting group. The reaction was then concentrated and diluted with acetonitrile, which was purified prep-LCMS (XBridge C18 column, eluting with a gradient of acetonitrile/water containing 0.1% TFA, at flow rate of 60 mL/min) to afford the product as a TFA salt in the form of a white amorphous powder. LC-MS calculated for $C_{33}H_{29}Cl_2FN_7O$ (M+H)$^+$: m/z=628.2; found 628.3.

Example 70: N-((1R)-1-(1-((1R,4R,5S)-2-azabicyclo[2.1.1]hexan-5-yl)-8-(2-cyanoethyl)-7-(2,3-dichlorophenyl)-6-fluoro-4-methyl-1H-pyrrolo[3,2-c]quinolin-2-yl)ethyl)-3,3-difluoroazetidine-1-carboxamide

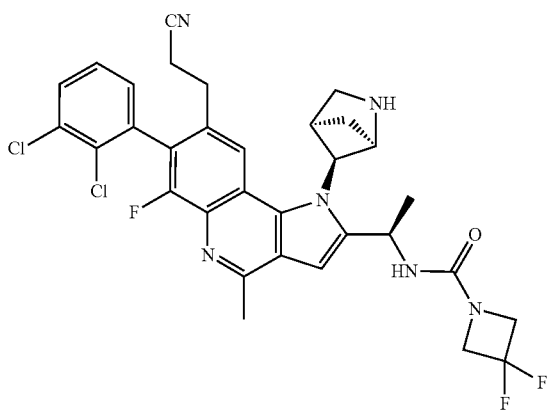 [SMILES: Cc1nc2c(F)c(-c3cccc(Cl)c3Cl)c(CCC#N)cc2c2c1cc([C@@H](C)NC(=O)N1CC(F)(F)C1)n2[C@H]1[C@H]2CN[C@@H]1C2]

To a solution of tert-butyl (1R,4R,5S)-5-(2-((R)-1-aminoethyl)-8-(2-cyanoethyl)-7-(2,3-dichlorophenyl)-6-fluoro-4-methyl-1H-pyrrolo[3,2-c]quinolin-1-yl)-2-azabicyclo[2.1.1]hexane-2-carboxylate (Intermediate 22, 20 mg, 0.032 mmol) and DIPEA (5.61 µl, 0.032 mmol) in Tetrahydrofuran (0.643 ml) was added triphosgene (5.72 mg, 0.019 mmol) and the reaction was stirred at 0° C. for 30 minutes. After that, 3,3-difluoroazetidine hydrochloride (4.16 mg, 0.032 mmol) was added. The reaction mixture was then stirred at room temperature for 1 h. Upon completion, the reaction was quenched by saturated sodium bicarbonate solution. The reaction mixture was extracted by ethyl acetate. The combined organic layers were dried over sodium sulfate, filtered and concentrated. The residue was dissolved in TFA solution (1 ml), and the solution was stirred at room temperature for 30 minutes to remove the Boc protecting group. The reaction was then concentrated and diluted with acetonitrile, which was purified prep-LCMS (XBridge C18 column, eluting with a gradient of acetonitrile/water containing 0.1% TFA, at flow rate of 60 mL/min) to afford the product as a TFA salt in the form of a white amorphous powder. LC-MS calculated for $C_{32}H_{30}Cl_2F_3N_6O$ (M+H)$^+$: m/z=641.2; found 641.3.

Example 71: 3-(1-((1R,4R,5S)-2-azabicyclo[2.1.1]hexan-5-yl)-7-(2,3-dichlorophenyl)-6-fluoro-4-methyl-2-((R)-1-((1-methyl-1H-pyrazol-4-yl)amino)ethyl)-1H-pyrrolo[3,2-c]quinolin-8-yl)propanenitrile

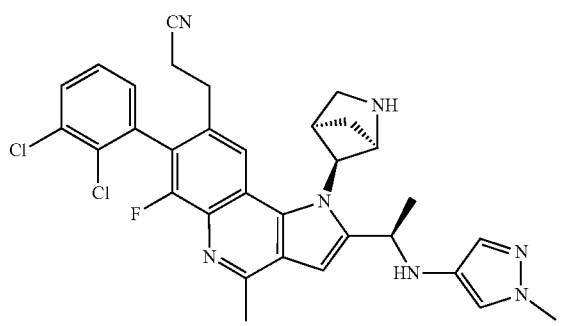 [SMILES: Cc1nc2c(F)c(-c3cccc(Cl)c3Cl)c(CCC#N)cc2c2c1cc([C@@H](C)Nc1cnn(C)c1)n2[C@H]1[C@H]2CN[C@@H]1C2]

A reaction mixture of tert-butyl (1R,4R,5S)-5-(2-((R)-1-aminoethyl)-8-(2-cyanoethyl)-7-(2,3-dichlorophenyl)-6-fluoro-4-methyl-1H-pyrrolo[3,2-c]quinolin-1-yl)-2-azabicyclo[2.1.1]hexane-2-carboxylate (Intermediate 22, 20 mg, 0.032 mmol), 1-Methyl-4-iodo-1H-pyrazole (13.36 mg, 0.064 mmol), tBuBrettPhos Pd G3 (2.74 mg, 3.21 µmol), tBuBrettPhos (1.557 mg, 3.21 µmol) and sodium tert-butoxide (4.63 mg, 0.048 mmol) in Dioxane (0.643 ml) was sparged with N$_2$ and heated to 100° C. for 5 hours. Upon completion, the reaction was quenched by saturated sodium bicarbonate solution. The reaction mixture was extracted by ethyl acetate. The combined organic layers were dried over sodium sulfate, filtered and concentrated. The residue was dissolved in TFA solution (1 ml), and the solution was stirred at room temperature for 30 minutes to remove the Boc protecting group. The reaction was then concentrated and diluted with acetonitrile, which was purified prep-LCMS (XBridge C18 column, eluting with a gradient of acetonitrile/water containing 0.1% TFA, at flow rate of 60 mL/min) to afford the product as a TFA salt in the form of a white amorphous powder. LC-MS calculated for $C_{32}H_{31}Cl_2FN_7$ (M+H)$^+$: m/z=602.2; found 602.3.

321

Example 72. 5-(1-(((1R,4R,5S)-2-Azabicyclo[2.1.1]hexan-5-yl)-8-(2-cyanoethyl)-7-(2,3-dichlorophenyl)-6-fluoro-2-((R)-1-(1-fluorocyclopropane-1-carbonyl)pyrrolidin-2-yl)-1H-pyrrolo[3,2-c]quinolin-4-yl)-N,N-dimethylpicolinamide

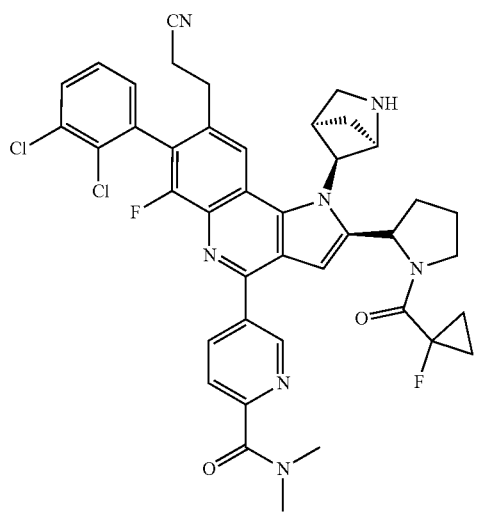

Step 1: (R)-(2-Ethynylpyrrolidin-1-yl)(1-fluorocyclopropyl)methanone

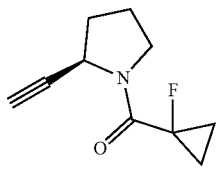

To a solution of (R)-2-ethynylpyrrolidine hydrochloride (5 g, 38.0 mmol), 1-fluorocyclopropane-1-carboxylic acid (7.91 g, 76 mmol), HATU (28.9 g, 76 mmol) in acetonitrile (190 ml) was added triethylamine (26.5 ml, 190 mmol). The reaction was stirred at room temperature for 30 minutes. The reaction was quenched with water and extracted with ethyl acetate. The organic layer was washed with water and brine, dried over sodium sulfate and concentrated. The crude product was purified by column chromatography eluting with 0-50% acetone/hexanes to give the desired product. LC-MS calculated for $C_{10}H_{13}FNO^+$ (M+H)$^+$: m/z=182.1; found 182.1.

322

Step 2: tert-Butyl (1R,4R,5S)-5-(7-bromo-8-(cyanoethyl)-6-fluoro-2-((R)-1-(1-fluorocyclopropane-1-carbonyl)pyrrolidin-2-yl)-4-(methylthio)-1H-pyrrolo[3,2-c]quinolin-1-yl)-2-azabicyclo[2.1.1]hexane-2-carboxylate

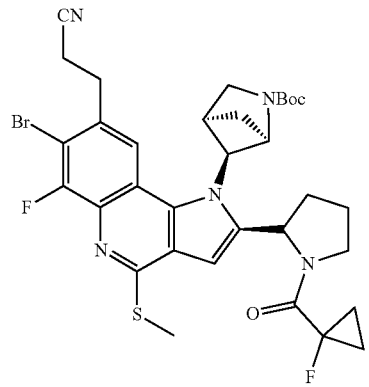

To a mixture of tert-butyl (1R,4R,5S)-5-((7-bromo-6-(2-cyanoethyl)-8-fluoro-3-iodo-2-(methylthio)quinolin-4-yl)amino)-2-azabicyclo[2.1.1]hexane-2-carboxylate (Intermediate 5, 2.0 g, 3.09 mmol), (R)-(2-ethynylpyrrolidin-1-yl)(1-fluorocyclopropyl)methanone (0.728 g, 4.02 mmol), bis(triphenylphosphine)palladium(II) chloride (0.217 g, 0.309 mmol), copper(I) iodide (0.588 g, 3.09 mmol), and triethylamine (4.3 ml, 30.9 mmol), DMF (20 ml) was added. The reaction flask was evacuated, back filled with nitrogen, then stirred at 75° C. for 2 h. Then $Cs_2CO_3$ (5.03 g, 15.45 mmol) was added and stirred at 100° C. for 12 hrs. After cooling to room temperature, the reaction mixture was diluted with ethyl acetate, washed subsequently with water (3 times) and brine. The organic phase was dried over anhydrous sodium sulfate, filtered and concentrated. The crude was purified with flash chromatography (eluting with a gradient 0-100% ethyl acetate in hexanes) to give the product (1.1 g, 50% yield). LC-MS calculated for $C_{33}H_{37}BrF_2N_5O_3S^+$ (M+H)$^+$: m/z=700.2/702.2; found 700.1/702.2.

Step 3: tert-Butyl (1R,4R,5S)-5-(8-(2-cyanoethyl)-7-(2,3-dichlorophenyl)-6-fluoro-2-((R)-1-(1-fluorocyclopropane-1-carbonyl)pyrrolidin-2-yl)-4-(methylthio)-1H-pyrrolo[3,2-c]quinolin-1-yl)-2-azabicyclo[2.1.1]hexane-2-carboxylate

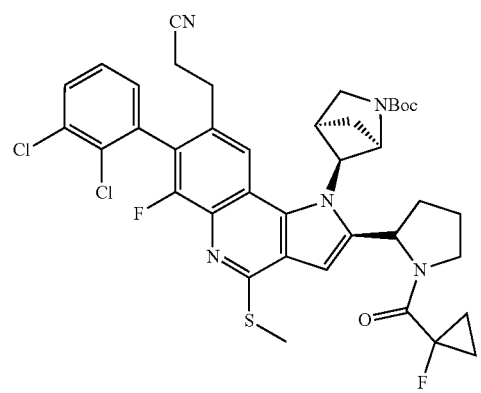

To a mixture of tert-butyl (1R,4R,5S)-5-(7-bromo-8-(cyanoethyl)-6-fluoro-2-((R)-1-(1-fluorocyclopropane-1-carbonyl)pyrrolidin-2-yl)-4-(methylthio)-1H-pyrrolo[3,2-c]quinolin-1-yl)-2-azabicyclo[2.1.1]hexane-2-carboxylate (1.1 g, 1.57 mmol), (2,3-dichlorophenyl)boronic acid (389 mg, 2.041 mmol), potassium fluoride (274 mg, 4.71 mmol) and Pd-132 (111 mg, 0.157 mmol) were added 1,4-dioxane (12.5 ml)/water (3.2 ml) and the reaction flask was evacuated, back filled with nitrogen, then stirred at 90° C. for 2 h. The reaction mixture was diluted with EtOAc and filtered through a plug of Celite. The filtrate was concentrated and the crude product was purified by flash column chromatography (0-65% ethyl acetate in hexanes) to provide the desired product (0.861 g, 71.5% yield). LC-MS calculated for $C_{39}H_{40}Cl_2F_2N_5O_3S^+$ (M+H)$^+$: m/z=766.2/768.2; found 766.2/768.2.

Step 4: 5-(1-((1R,4R,5S)-2-Azabicyclo[2.1.1]hexan-5-yl)-8-(2-cyanoethyl)-7-(2,3-dichlorophenyl)-6-fluoro-2-((R)-1-(1-fluorocyclopropane-1-carbonyl)pyrrolidin-2-yl)-1H-pyrrolo[3,2-c]quinolin-4-yl)-N,N-dimethylpicolinamide To a mixture of tert-butyl (1R,4R,5S)-5-(8-(2-cyanoethyl)-7-(2,3-dichlorophenyl)-6-fluoro-2-((R)-1-(1-fluorocyclopropane-1-carbonyl)pyrrolidin-2-yl)-4-(methylthio)-1H-pyrrolo[3,2-c]quinolin-1-yl)-2-azabicyclo[2.1.1]hexane-2-carboxylate (861 mg, 1.123 mmol), N,N-dimethyl-5-(4,4,5,5-tetramethyl-1,3,2-dioxaborolan-2-yl)picolinamide (620 mg, 2.246 mmol), tetrakis(triphenylphosphine)palladium(0) (130 mg, 0.112 mmol) and copper(I) 3-methylsalicylate (723 mg, 3.37 mmol) was added 1,4-dioxane (7.5 ml) and the reaction flask was evacuated, back filled with nitrogen, then stirred at 100° C. overnight. The reaction was quenched with water and sat. aq. ammonium hydroxide, then diluted with ethyl acetate and filtered through a plug of Celite. The layers of the filtrate were separated and the organic layer was washed with water and brine, dried over sodium sulfate and concentrated. The crude product was purified by flash column chromatography (0-80% EtOAc in hexanes). The purified product was dissolved in 1:1 TFA/DCM (10 mL) and stirred at r.t. for 1 h, then concentrated. The crude residue was diluted with acetonitrile and purified by prep HPLC (pH 2) to provide the desired product. LC-MS calculated for $C_{41}H_{38}Cl_2F_2N_7O_2^+$ (M+H)$^+$: m/z=768.2/770.2; found 768.3/770.3. $^1$H NMR (500 MHz, DMSO) δ 9.28 (s, 1H), 9.14 (d, J=2.1 Hz, 1H), 8.46 (dd, J=8.1, 2.2 Hz, 1H), 8.21 (s, 1H), 8.11 (s, 1H), 7.86 (dd, J=8.1, 1.6 Hz, 1H), 7.82 (d, J=8.0 Hz, 1H), 7.59 (t, J=7.9 Hz, 1H), 7.50 (dd, J=7.6, 1.5 Hz, 1H), 6.60 (s, 1H), 5.66 (s, 1H), 5.39 (d, J=7.3 Hz, 1H), 4.91 (d, J=6.0 Hz, 1H), 4.12-4.09 (m, 1H), 4.02-3.96 (m, 1H), 3.86-3.75 (m, 2H), 3.45-3.42 (m, 1H), 3.07 (s, 3H), 3.06-3.02 (m, 4H), 2.96-2.83 (m, 2H), 2.74-2.65 (m, 1H), 2.43-2.32 (m, 2H), 2.01-1.97 (m, 1H), 1.91-1.84 (m, 1H), 1.80-1.75 (m, 1H), 1.60 (d, J=9.2 Hz, 1H), 1.48-1.35 (m, 2H), 1.32-1.19 (m, 2H).

Example 73: methyl (2R)-2-(1-((1R,4R,5S)-2-Azabicyclo[2.1.1]hexan-5-yl)-8-(2-cyanoethyl)-7-(2,3-dichlorophenyl)-4-(4-((dimethylamino)methyl)-2,3-difluorophenyl)-6-fluoro-1H-pyrrolo[3,2-c]quinolin-2-yl)pyrrolidine-1-carboxylate

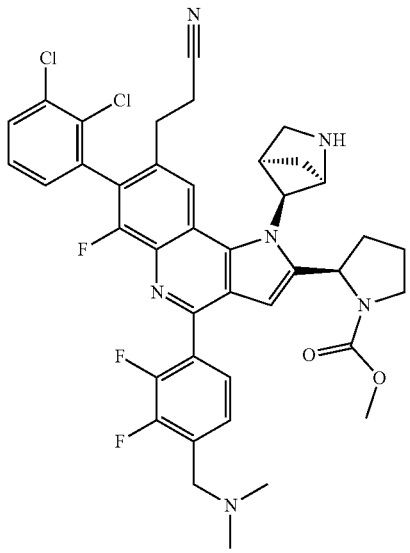 [SMILES: COC(=O)N1CCC[C@@H]1c1cc2c(-c3ccc(CN(C)C)c(F)c3F)nc3c(F)c(-c4cccc(Cl)c4Cl)c(CCC#N)cc3c2n1[C@H]1[C@H]2CN[C@@H]1C2]

Step 1: tert-butyl (1R,4R,5S)-5-(8-(2-cyanoethyl)-7-(2,3-dichlorophenyl)-4-(2,3-difluoro-4-(methoxycarbonyl)phenyl)-6-fluoro-2-((R)-1-(methoxycarbonyl)pyrrolidin-2-yl)-1H-pyrrolo[3,2-c]quinolin-1-yl)-2-azabicyclo[2.1.1]hexane-2-carboxylate

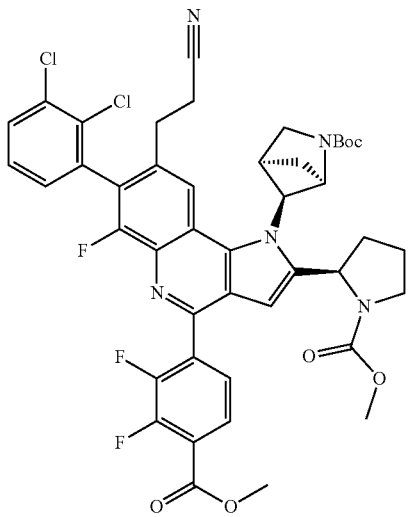 [SMILES: COC(=O)c1ccc(-c2nc3c(F)c(-c4cccc(Cl)c4Cl)c(CCC#N)cc3c3c2cc([C@H]2CCCN2C(=O)OC)n3[C@H]2[C@@H]3C[C@H]2N(C(=O)OC(C)(C)C)C3)c(F)c1F]

This compound was prepared by a procedure identical to that described for Methyl (2R)-2-(1-((1R,4R,5S)-2-azabicyclo[2.1.1]hexan-5-yl)-8-(2-cyanoethyl)-7-(2,3-dichlorophenyl)-6-fluoro-4-(5-fluoro-6-(methylcarbamoyl)pyridin-3-yl)-1H-pyrrolo[3,2-c]quinolin-2-yl)pyrrolidine-1-carboxylate (Example 39). LC-MS calculated for $C_{44}H_{41}Cl_2F_3N_5O_6$ (M+H)$^+$: m/z=862.2; found 862.2.

Step 2: tert-butyl (1R,4R,5S)-5-(8-(2-cyanoethyl)-7-(2,3-dichlorophenyl)-4-(2,3-difluoro-4-(hydroxymethyl)phenyl)-6-fluoro-2-((R)-1-(methoxycarbonyl)pyrrolidin-2-yl)-1H-pyrrolo[3,2-c]quinolin-1-yl)-2-azabicyclo[2.1.1]hexane-2-carboxylate

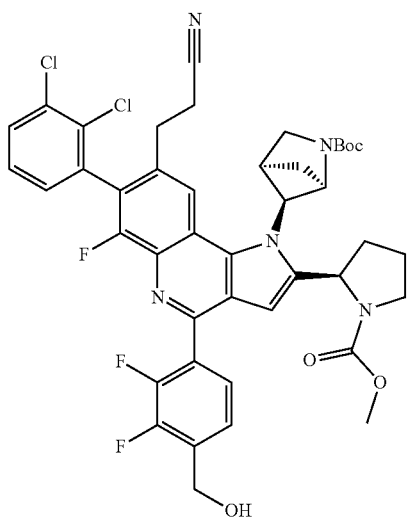 [SMILES: COC(=O)N1CCC[C@@H]1c1cc2c(-c3ccc(CO)c(F)c3F)nc3c(F)c(-c4cccc(Cl)c4Cl)c(CCC#N)cc3c2n1[C@H]1[C@@H]2C[C@H]1N(C(=O)OC(C)(C)C)C2]

To a solution of tert-butyl (1R,4R,5S)-5-(8-(2-cyanoethyl)-7-(2,3-dichlorophenyl)-4-(2,3-difluoro-4-(methoxycarbonyl)phenyl)-6-fluoro-2-((R)-1-(methoxycarbonyl)pyrrolidin-2-yl)-1H-pyrrolo[3,2-c]quinolin-1-yl)-2-azabicyclo[2.1.1]hexane-2-carboxylate (900 mg, 1.043 mmol) in THF (10 ml) was added lithium borohydride (1043 μl, 2.086 mmol). The reaction was stirred at r.t. overnight. The reaction mixture was quenched with 1 M HCl solution, diluted with water, then extracted with ethyl acetate twice. The organic layer was washed with water and brine, dried over sodium sulfate and concentrated. The crude product was purified by Biotage (0-10% Methanol in DCM) to provide the desired product. LC-MS calculated for $C_{43}H_{41}Cl_2F_3N_5O_5$ (M+H)$^+$: m/z=834.2; found 834.3.

Step 3: methyl (2R)-2-(1-((1R,4R,5S)-2-azabicyclo[2.1.1]hexan-5-yl)-8-(2-cyanoethyl)-7-(2,3-dichloropheny)-4-(4-((dimethylamino)methyl)-2,3-difluorophenyl)-6-fluoro-1H-pyrrolo[3,2-c]quinolin-2-yl)pyrrolidine-1-carboxylate To a solution of tert-butyl (1R,4R,5S)-5-(8-(2-cyanoethyl)-7-(2,3-dichlorophenyl)-4-(2,3-difluoro-4-(hydroxymethyl)phenyl)-6-fluoro-2-((R)-1-(methoxycarbonyl)pyrrolidin-2-yl)-1H-pyrrolo[3,2-c]quinolin-1-yl)-2-azabicyclo[2.1.1]hexane-2-carboxylate (140 mg, 0.168 mmol) in DCM (5 ml) was added methanesulfonyl chloride (19.60 μl, 0.252 mmol) and TEA (46.8 μl, 0.335 mmol) at 0° C. The reaction was stirred at 0° C. for 30 min, then a solution of dimethylamine (2.0M) in THF (419 μl, 0.839 mmol) and TEA (46.8 μl, 0.335 mmol) were added. The reaction mixture continue to stir at r.t. for 2 h. The reaction mixture was quenched with water, extracted with DCM. The organic layer was washed with brine, dried over sodium sulfate and concentrated. The residue was stirred in 1:1 DCM/TFA (4 mL) for 30 min, concentrated, and purified by prep HPLC (pH 2). LC-MS calculated for $C_{40}H_{38}Cl_2F_3N_6O_2$ (M+H)$^+$: m/z=761.7; found 761.2.

Example A. GDP-GTP Exchange Assay

The inhibitor potency of the exemplified compounds was determined in a fluorescence based guanine nucleotide exchange assay, which measures the exchange of bodipy-GDP (fluorescently labeled GDP) for GppNHp (Non-hydrolyzable GTP analog) to generate the active state of KRAS in the presence of SOS1 (guanine nucleotide exchange factor). Inhibitors were serially diluted in DMSO and a volume of 0.1 μL was transferred to the wells of a black low volume 384-well plate. 5 μL/well volume of bodipy-loaded KRAS G12D diluted to 2.5 nM in assay buffer (25 mM Hepes pH 7.5, 50 mM NaCl, 10 mM MgCl$_2$ and 0.01% Brij-35) was added to the plate and pre-incubated with inhibitor for 4 hours at ambient temperature. Appropriate controls (enzyme with no inhibitor or with a G12D inhibitor) were included on the plate. The exchange was initiated by the addition of a 5 μL/well volume containing 1 mM GppNHp and 300 nM SOS1 in assay buffer. The 10 μL/well reaction concentration of the bodipy-loaded KRAS G12D, GppNHp, and SOS1 were 2.5 nM, 500 uM, and 150 nM, respectively. The reaction plates were incubated at ambient temperature for 2 hours, a time estimated for complete GDP-GTP exchange in the absence of inhibitor. For the KRAS G12V mutant, similar guanine nucleotide exchange assays were used with 2.5 nM as final concentration for the bodipy loaded KRAS proteins and 3 hours incubation after adding GppNHp-SOS1 mixture. A cyclic peptide described to selectively bind G12D mutant (Sakamoto et al., BBRC 484.3 (2017), 605-611) or internal compounds with confirmed binding were used as positive controls in the assay plates. Fluorescence intensities were measured on a PheraStar plate reader instrument (BMG Labtech) with excitation at 485 nm and emission at 520 nm.

Either GraphPad prism or Genedata Screener SmartFit was used to analyze the data. The IC$_{50}$ values were derived by fitting the data to a four parameter logistic equation producing a sigmoidal dose-response curve with a variable Hill coefficient.

The KRAS_G12D and KRAS_G12V exchange assay IC$_{50}$ data are provided in Table 1 below. The symbol "†" indicates IC$_{50}$≤100 nM, "††" indicates IC$_{50}$>100 nM but ≤1 μM; and "†††" indicates IC$_{50}$ is >1 μM but ≤5 μM, "††††" indicates IC$_{50}$ is >5 μM but ≤10 μM. "NA" indicates IC$_{50}$ not available.

TABLE 1

| Ex. No. | G12D_exchange | G12V_exchange |
|---|---|---|
| 1 | † | † |
| 2 | † | † |
| 3 | † | † |
| 4 | † | † |
| 5 | † | † |
| 6 | † | † |
| 7 | † | † |
| 8 | † | † |
| 9 | † | † |
| 10 | † | † |
| 11 | † | † |
| 12 | † | † |
| 13 | † | † |
| 14 | † | † |
| 15 | † | †† |
| 16 | † | † |
| 17 | † | † |
| 18 | † | † |
| 19 | † | † |
| 20 | † | † |

TABLE 1-continued

| Ex. No. | G12D_exchange | G12V_exchange |
|---|---|---|
| 21 | † | † |
| 22 | † | † |
| 23a | † | † |
| 24a | † | † |
| 25 | † | † |
| 26 | † | † |
| 27 | † | † |
| 28 | † | †† |
| 29 | † | † |
| 30 | † | † |
| 31 | † | † |
| 32 | † | † |
| 33 | † | † |
| 34 | † | †† |
| 35 | † | † |
| 36 | † | † |
| 37 | † | † |
| 38 | † | † |
| 39 | † | † |
| 40 | † | † |
| 41 | † | † |
| 42 | † | † |
| 43 | † | † |
| 44 | † | † |
| 45 | † | † |
| 46 | † | † |
| 47 | † | † |
| 48 | † | † |
| 49 | † | † |
| 50 | † | † |
| 51 | † | † |
| 52 | † | † |
| 53 | † | † |
| 54b | † | † |
| 55 | † | † |
| 56 | † | † |
| 57 | † | † |
| 58 | † | † |
| 59 | † | † |
| 60 | † | †† |
| 61 | † | † |
| 62 | † | † |
| 63 | † | † |
| 64 | † | †† |
| 65 | † | † |
| 66 | † | † |
| 67 | † | † |
| 68 | † | † |
| 69 | † | † |
| 70 | † | † |
| 71 | † | † |
| 72 | † | † |
| 73 | † | † |

Example B: Luminescent Viability Assay

MIA PaCa-2 (KRAS G12C; ATCCO®CRL-1420), NCI-H358 (KRAS G12C; ATCO CRL-5807), A427 (KRAS G12D; ATCO HTB53), HPAFII (KRAS G12D; ATCC® CRL-1997), YAPC (KRAS G12V; DSMZ ACC382), SW480 (KRAS G12V; ATCC® CRL-228) and NCI-H838 (KRAS WT; ATCC® CRL-5844) cells are cultured in RPMI 1640 media supplemented with 10% FIBS (Gibco/Life Technologies). Eight hundred cells per well in RPMI 1640 media supplemented with 2% FBS are seeded into white, clear bottomed 384-well Costar tissue culture plates containing 50 nL dots of test compounds (final concentration is a 1:500 dilution, with a final concentration in 0.2% DMSO). Plates are incubated for 3 days at 370° C., 5% $CO_2$. At the end of the assay, 25 ul/well of CellTiter-Glo reagent (Promega) is added. Luminescence is read after 15 minutes with a PHERAstar (BMG). Data are analyzed in Genedata Screener using SmartFit for $IC_{50}$ values.

Example C: Cellular pERK HTRF Assay

MIA PaCa-2 (KRAS G12C; ATCC® CRL-1420), NCI-H358 (KRAS G12C; ATCC® CRL-5807), A427 (KRAS G12D; ATCC® HTB53), HPAFII (KRAS G12D; ATCC® CRL-1997), YAPC (KRAS G12V; DSMZ ACC382), SW480 (KRAS G12V; ATCC® CRL-228) and NCI-H838 (KRAS WT; ATCC® CRL-5844) cells are purchased from ATCC and maintained in RPMI 1640 media supplemented with 10% FBS (Gibco/Life Technologies). The cells are plated at 5000 cells per well (8 uL) into Greiner 384-well low volume, flat-bottom, and tissue culture treated white plates and incubated overnight at 370° C., 5% $CO_2$. The next morning, test compound stock solutions are diluted in media at 3× the final concentration and 4 uL are added to the cells, with a final concentration of 0.1% of DMSO. The cells are incubated with the test compounds for 4 hours (G12C and G12V) or 2 hrs (G12D) at 37° C., 5% $CO_2$. Four uL of 4× lysis buffer with blocking reagent (Cisbio) are added to each well and plates are rotated gently (300 rpm) for 30 minutes at room temperature. Four uL per well of Cisbio anti Phospho-ERK 1/2 d2 is mixed with anti Phospho-ERK 1/2 Cryptate (1:1), and added to each well, incubated overnight in the dark at room temperature. Plates are read on the Pherastar plate reader at 665 nm and 620 nm wavelengths. Data are analyzed in Genedata Screener using SmartFit for $IC_{50}$ values.

Example D: Whole Blood pERK1/2 HTRF Assay

MIA PaCa-2 cells (KRAS G12C; ATCC® CRL-1420), HPAF-II (KRAS G12D; ATCC® CRL-1997) and YAPC (KRAS G12V; DSMZ ACC382) are maintained in RPMI 1640 with 10% FBS (Gibco/Life Technologies). For MIA PaCa-2 assay, cells are seeded into 96 well tissue culture plates (Corning #3596) at 25000 cells per well in 100 uL media and cultured for 2 days at 37° C., 5% $CO_2$ before the assay. For HPAF-II and YAPC assay, cells are seeded in 96 well tissue culture plates at 50000 cells per well in 100 uL media and cultured for 1 day before the assay. Whole Blood are added to the 1 uL dots of compounds (prepared in DMSO) in 96 well plates and mixed gently by pipetting up and down so that the concentration of the compound in blood is 1× of desired concentration, in 0.5% DMSO. The media is aspirated from the cells and 50 uL per well of whole blood with test compound is added and incubated for 4 hours for MIA PaCa and YAPC assay; or 2 hours for HPAF-II assay, respectively at 37° C., 5% $CO_2$. After dumping the blood, the plates are gently washed twice by adding PBS to the side of the wells and dumping the PBS from the plate onto a paper towel, tapping the plate to drain well. Fifty ul/well of 1× lysis buffer #1 (Cisbio) with blocking reagent (Cisbio) and Benzonase nuclease (Sigma Cat #E1014-5KU, 1:10000 final concentration) is then added and incubated at room temperature for 30 minutes with shaking (250 rpm). Following lysis, 16 µL of lysate is transferred into 384-well Greiner small volume white plate using an Assist Plus (Integra Biosciences, NH). Four uL of 1:1 mixture of anti Phospho-ERK 1/2 d2 and anti Phospho-ERK 1/2 Cryptate (Cisbio) is added to the wells using the Assist Plus and incubated at room temperature overnight in the dark. Plates are read on the Pherastar plate reader at 665 nm and 620 nm wavelengths. Data are analyzed in Genedata Screener using SmartFit for $IC_{50}$ values.

Example E: Ras Activation Elisa

The 96-Well Ras Activation ELISA Kit (Cell Biolabs Inc; #STA441) uses the Raf1 RBD (Rho binding domain) bound to a 96-well plate to selectively pull down the active form of Ras from cell lysates. The captured GTP-Ras is then detected by a pan-Ras antibody and HRP-conjugated secondary antibody.

MIA PaCa-2 (KRAS G12C; ATCC® CRL-1420), NCI-H358 (KRAS G12C; ATCC® CRL-5807), A427 (KRAS G12D; ATCC® HTB53), HPAFII (KRAS G12D; ATCC® CRL-1997), YAPC (KRAS G12V; DSMZ ACC382), SW480 (KRAS G12V; ATCC® CRL-228) and NCI-H838 (KRAS WT; ATCC® CRL-5844) cells are maintained in RPMI 1640 with 10% FBS (Gibco/Life Technologies). The cells are seeded into 96 well tissue culture plates (Corning #3596) at 25000 cells per well in 100 uL media and cultured for 2 days at 37° C., 5% $CO_2$ so that they are approximately 80% confluent at the start of the assay. The cells are treated with compounds for either 4 hours or overnight at 37° C., 5% $CO_2$. At the time of harvesting, the cells are washed with PBS, drained well and then lysed with 50 µL of the 1× Lysis buffer (provided by the kit) plus added Halt Protease and Phosphatase inhibitors (1:100) for 1 hour on ice.

The Raf-1 RBD is diluted 1:500 in Assay Diluent (provided in kit) and 100 µL of the diluted Raf-1 RBD is added to each well of the Raf-1 RBD Capture Plate. The plate is covered with a plate sealing film and incubated at room temperature for 1 hour on an orbital shaker. The plate is washed 3 times with 250 µL 1× Wash Buffer per well with thorough aspiration between each wash. 50 µL of Ras lysate sample (10-100 µg) is added per well in duplicate. A "no cell lysate" control is added in a couple of wells for background determination. 50 µL of Assay Diluent is added to all wells immediately to each well and the plate is incubated at room temperature for 1 hour on an orbital shaker. The plate is washed 5 times with 250 µL 1× Wash Buffer per well with thorough aspiration between each wash. 100 µL of the diluted Anti-pan-Ras Antibody is added to each well and the plate is incubated at room temperature for 1 hour on an orbital shaker. The plate is washed 5 times as previously. 100 µL of the diluted Secondary Antibody, HRP Conjugate is added to each well and the plate is incubated at room temperature for 1 hour on an orbital shaker. The plate is washed 5 times as previously and drained well. 100 µL of Chemiluminescent Reagent (provided in the kit) is added to each well, including the blank wells. The plate is incubated at room temperature for 5 minutes on an orbital shaker before the luminescence of each microwell is read on a plate luminometer. The % inhibition is calculated relative to the DMSO control wells after a background level of the "no lysate control" is subtracted from all the values. $IC_{50}$ determination is performed by fitting the curve of inhibitor percent inhibition versus the log of the inhibitor concentration using the GraphPad Prism 7 software.

Example F: Inhibition of RAS-RAF and PI3K-AKT Pathways

The cellular potency of compounds was determined by measuring phosphorylation of KRAS downstream effectors extracellular-signal-regulated kinase (ERK), ribosomal S6 kinase (RSK), AKT (also known as protein kinase B, PKB) and downstream substrate S6 ribosomal protein.

To measure phosphorylated extracellular-signal-regulated kinase (ERK), ribosomal S6 kinase (RSK), AKT and S6 ribosomal protein, cells (details regarding the cell lines and types of data produced are further detailed in Table 2) were seeded overnight in Corning 96-well tissue culture treated plates in RPMI medium with 10% FBS at 4×104 cells/well. The following day, cells were incubated in the presence or absence of a concentration range of test compounds for 4 hours at 37° C., 5% $CO_2$. Cells were washed with PBS and lysed with 1× lysis buffer (Cisbio) with protease and phosphatase inhibitors (Thermo Fisher, 78446). Ten or twenty µg of total protein lysates was subjected to SDS-PAGE and immunoblot analysis using following antibodies: phospho-ERK1/2-Thr202/Tyr204 (#9101 L), total-ERK1/2 (#9102L), phosphor-AKT-Ser473 (#4060L), phospho-p90RSK-Ser380 (#11989S) and phospho-S6 ribosomal protein-Ser235/Ser236 (#2211 S) are from Cell Signaling Technologies (Danvers, MA).

TABLE 2

| Cell Line | Histology | KRAS alteration | Readout |
|---|---|---|---|
| H358 | Lung | G12C | pERK, pAKT, p-S6, p-p90RSK |
| MIA PaCa-2 | Pancreas | G12C | pERK, pAKT, p-S6, p-p90RSK |
| HPAF II | Pancreas | G12D | pERK, pAKT, p-S6, p-p90RSK |
| A427 | Lung | G12D | pERK, pAKT, p-S6, p-p90RSK |
| AGS | Stomach | G12D | pERK, pAKT, p-S6, p-p90RSK |
| PaTu 8988s | Pancreas | G12V | pERK, pAKT, p-S6, p-p90RSK |
| H441 | Lung | G12V | pERK, pAKT, p-S6, p-p90RSK |
| YAPC | Pancreas | G12V | pERK, pAKT, p-S6, p-p90RSK |
| SW480 | Colorectal | G12V | pERK, pAKT, p-S6, p-p90RSK |

Example G: In Vivo Efficacy Studies

MIA-PaCa-2 (KRAS G12C), H358 (KRAS G12C), HPAF-II (KRAS G12D), AGS (KRAS G12D), SW480 (KRAS G12V) or YAPC(KRAS G12V) human cancer cells are obtained from the American Type Culture Collection and maintained in RPMI media supplemented with 10% FBS. For efficacy studies experiments, 5×106 cells are inoculated subcutaneously into the right hind flank of 6- to 8-week-old BALB/c nude mice (Charles River Laboratories, Wilmington, MA, USA). When tumor volumes are approximately 150-250 mm3, mice are randomized by tumor volume and compounds are orally administered. Tumor volume is calculated using the formula (L×W2)/2, where L and W refer to the length and width dimensions, respectively. Tumor growth inhibition is calculated using the formula (1−(VT/VC))×100, where VT is the tumor volume of the treatment group on the last day of treatment, and VC is the tumor volume of the control group on the last day of treatment. Two-way analysis of variance with Dunnett's multiple comparisons test is used to determine statistical differences between treatment groups (GraphPad Prism). Mice are housed at 10-12 animals per cage, and are provided enrichment and exposed to 12-hour light/dark cycles. Mice whose tumor volumes exceeded limits (10% of body weight) are humanely euthanized by $CO_2$ inhalation. Animals are maintained in a barrier facility fully accredited by the Association for Assessment and Accreditation of Laboratory Animal Care, International. All of the procedures are conducted in accordance with the US Public Service Policy on Human Care and Use of Laboratory Animals and with Incyte Animal Care and Use Committee Guidelines.

Example H: Caco2 Assay

Caco-2 cells are grown at 37° C. in an atmosphere of 5% $CO_2$ in DMEM growth medium supplemented with 10% (v/v) fetal bovine serum, 1% (v/v) nonessential amino acids, penicillin (100 U/mL), and streptomycin (100 µg/mL). Confluent cell monolayers are subcultured every 7 days or 4 days for Caco-2 by treatment with 0.05% trypsin containing 1 µM EDTA. Caco-2 cells are seeded in 96-well Transwell plates. The seeding density for Caco-2 cells is 14,000 cells/well. DMEM growth medium is replaced every other day after seeding. Cell monolayers are used for transport assays between 22 and 25 days for Caco-2 cells.

Cell culture medium is removed and replaced with HBSS. To measure the TEER, the HBSS is added into the donor compartment (apical side) and receiver compartment (basolateral side). The TEER is measured by using a REMS Autosampler to ensure the integrity of the cell monolayers. Caco-2 cell monolayers with TEER values ≥300 Ω·cm² are used for transport experiments. To determine the $P_{app}$ in the absorptive direction (A-B), solution of test compound (50 µM) in HBSS is added to the donor compartment (apical side), while HBSS solution with 4% BSA is added to the receiver compartment (basolateral side). The apical volume was 0.075 mL, and the basolateral volume is 0.25 mL. The incubation period is 120 minutes at 37° C. in an atmosphere of 5% $CO_2$. At the end of the incubation period, samples from the donor and receiver sides are removed and an equal volume of acetonitrile is added for protein precipitation. The supernatants are collected after centrifugation (3000 rpm, Allegra X-14R Centrifuge from Beckman Coulter, Indianapolis, IN) for LCMS analysis. The permeability value is determined according to the equation:

$$P_{app}(\text{cm/s}) = (F * VD)/(SA * MD),$$

where the flux rate (F, mass/time) is calculated from the slope of cumulative amounts of compound of interest on the receiver side, SA is the surface area of the cell membrane, VD is the donor volume, and MD is the initial amount of the solution in the donor chamber.

The Caco-2 data are provided in Tables 3 and 4 below. The symbol "+" indicates a Caco-2 value of ≤0.5, "++" indicates a Caco-2 value of >0.5 but ≤1; and "+++" indicates a Caco-2 value of >1. "NA" indicates $IC_{50}$ not available.

TABLE 3

| Ex. No. | Caco-2 |
| --- | --- |
| 1 | ++ |
| 2 | + |
| 3 | + |
| 4 | + |
| 5 | + |
| 6 | ++ |
| 7 | +++ |
| 8 | + |
| 9 | + |
| 10 | + |
| 11 | + |
| 12 | + |
| 13 | NA |
| 14 | ++ |
| 15 | ++ |
| 16 | + |
| 17 | + |
| 18 | + |
| 19 | + |
| 20 | + |
| 21 | + |
| 22 | + |
| 23 | ++ |
| 24 | + |
| 25 | +++ |
| 26 | + |
| 27 | + |

TABLE 4

| Ex. No. | Caco-2 |
| --- | --- |
| 28 | +++ |
| 29 | +++ |
| 30 | +++ |
| 31 | + |
| 32 | ++ |
| 33 | ++ |
| 34 | + |
| 35 | ++ |
| 36 | +++ |
| 37 | +++ |
| 38 | +++ |
| 39 | ++ |
| 40 | ++ |
| 41 | +++ |
| 42 | ++ |
| 43 | +++ |
| 44 | +++ |
| 45 | +++ |
| 46 | +++ |
| 47 | +++ |
| 48 | ++ |
| 49 | +++ |
| 50 | +++ |
| 51 | +++ |
| 52 | +++ |
| 53 | +++ |
| 54b | +++ |
| 55 | +++ |
| 56 | +++ |
| 57 | +++ |
| 58 | ++ |
| 59 | +++ |
| 60 | +++ |
| 61 | ++ |
| 62 | +++ |
| 63 | +++ |
| 64 | +++ |
| 65 | +++ |
| 66 | +++ |
| 67 | +++ |
| 68 | +++ |
| 69 | +++ |
| 70 | +++ |
| 71 | +++ |
| 72 | +++ |
| 73 | +++ |

Example I: Human Whole Blood Stability

The whole blood stability of the exemplified compounds is determined by LC-MS/MS. The 96-Well Flexi-Tier™ Block (Analytical Sales & Services, Inc, Flanders, NJ) is used for the incubation plate containing 1.0 mL glass vials with 0.5 mL of blood per vial (pooled gender, human whole blood sourced from BIOIVT, Hicksville, NY or similar). Blood is pre-warmed in water bath to 37° C. for 30 minutes. 96-deep well analysis plate is prepared with the addition of 100 µL ultrapure water/well. 50 µL chilled ultrapure water/well is added to 96-deep well sample collection plate and covered with a sealing mat. 1 µL of 0.5 mM compound working solution (DMSO:water) is added to the blood in incubation plate to reach final concentrations of 1 µM, mixed by pipetting thoroughly and 50 µL is transferred 50 into the T=0 wells of the sample collection plate. Blood is allowed to sit in the water for 2 minutes and then 400 µL stop solution/well is added (acetonitrile containing an internal standard). The incubation plate is placed in the Incu-Shaker $CO_2$ Mini incubator (Benchmark Scientific, Sayreville, NJ) at 37° C. with shaking at 150 rpm. At 1, 2 and 4-hr, the blood samples are mixed thoroughly by pipetting and 50 µL is transferred into the corresponding wells of the sample collection plate. Blood is allowed to sit in the water for 2 minutes and then 400 µL of stop solution/well is added. The collection plate is sealed and vortexed at 1700 rpm for 3 minutes (VX-2500 Multi-Tube Vortexer, VWR International, Radnor, PA), and samples are then centrifuged in the collection plate at 3500 rpm for 10 minutes (Allegra X-14R Centrifuge Beckman Coulter, Indianapolis, IN). 100 µL of supernatant/well is transferred from the sample collection plate into the corresponding wells of the analysis plate. The final plate is vortexed at 1700 rpm for 1 minute and analyze samples by LC-MS/MS. The peak area ratio of the 1, 2, and 4 hr samples relative to T=0 is used to determine the percent remaining. The natural log of the percent remaining versus time is used determine a slope to calculate the compounds half-life in blood ($t_{1/2}$=0.693/slope).

Example J: In Vitro Intrinsic Clearance Protocol

For in vitro metabolic stability experiments, test compounds are incubated with human liver microsomes at 37° C. The incubation mixture contains test compounds (1 µM), NADPH (2 mM), and human liver microsomes (0.5 mg protein/mL) in 100 mM phosphate buffer (pH 7.4). The mixture is pre-incubated for 2 min at 37° C. before the addition of NADPH. Reactions are commenced upon the addition of NADPH and quenched with ice-cold methanol at 0, 10, 20, and 30 min. Terminated incubation mixtures are analyzed using LC-MS/MS system. The analytical system consisted of a Shimadzu LC-30AD binary pump system and SIL-30AC autosampler (Shimadzu Scientific Instruments, Columbia, MD) coupled with a Sciex Triple Quad 6500+ mass spectrometer from Applied Biosystems (Foster City, CA). Chromatographic separation of test compounds and internal standard is achieved using a Hypersil Gold $C_{18}$ column (50×2.1 mm, 5 µM, 175 Å) from ThermoFisher Scientific (Waltham, MA). Mobile phase A consists of 0.1% formic acid in water, and mobile phase B consists of 0.1% formic acid in acetonitrile. The total LC-MS/MS runtime can be 2.75 minutes with a flow rate of 0.75 mL/min. Peak area integrations and peak area ratio calculations are performed using Analyst software (version 1.6.3) from Applied Biosystems.

The in vitro intrinsic clearance, $CL_{int,\ in\ vitro}$, is calculated from the $t_{1/2}$ of test compound disappearance as $CL_{int,\ in\ vitro}$=(0.693/$t_{1/2}$)×(1/$C_{protein}$), where $C_{protein}$ is the protein concentration during the incubation, and $t_{1/2}$ is determined by the slope (k) of the log-linear regression analysis of the concentration versus time profiles; thus, $t_{1/2}$=ln2/k. The $CL_{int,\ in\ vitro}$ values are scaled to the in vivo values for human by using physiologically based scaling factors, hepatic microsomal protein concentrations (45 mg protein/g liver), and liver weights (21 g/kg body weight). The equation $CL_{int}$=$CL_{int,\ in\ vitro}$×(mg protein/g liver weight)×(g liver weight/kg body weight) is used. The in vivo hepatic clearance ($CL_H$) is then calculated by using $CL_{int}$ and hepatic blood flow, Q (20 mL·min$^{-1}$·kg$^{-1}$ in humans) in the well-stirred liver model disregarding all binding from $CL_H$=(Q×$CL_{int}$)/(Q+$CL_{int}$). The hepatic extraction ratio was calculated as $CL_H$ divided by Q.

Example K: In Vivo Pharmacokinetics Protocol

For in vivo pharmacokinetic experiments, test compounds are administered to male Sprague Dawley rats or male and female Cynomolgus monkeys intravenously or via oral gavage. For intravenous (IV) dosing, test compounds are dosed at 0.5 to 1 mg/kg using a formulation of 10% dimethylacetamide (DMAC) in acidified saline via IV bolus for rat and 5 min or 10 min IV infusion for monkey. For oral (PO) dosing, test compounds are dosed at 1.0 to 3.0 mg/kg using 5% DMAC in 0.5% methylcellulose in citrate buffer (pH 2.5). Blood samples are collected at predose and various time points up to 24 hours postdose. All blood samples are collected using EDTA as the anticoagulant and centrifuged to obtain plasma samples. The plasma concentrations of test compounds are determined by LC-MS methods. The measured plasma concentrations are used to calculate PK parameters by standard noncompartmental methods using Phoenix® WinNonlin software program (version 8.0, Pharsight Corporation).

In rats and monkeys, cassette dosing of test compounds are conducted to obtain preliminary PK parameters.

In vivo pharmacokinetic experiments with male beagle dogs may be performed under the conditions described above.

Example L: Time Dependent Inhibition (TDI) of CYP Protocol

This assay is designed to characterize an increase in CYP inhibition as a test compounds is metabolized over time. Potential mechanisms for this include the formation of a tight-binding, quasi-irreversible inhibitory metabolite complex or the inactivation of P450 enzymes by covalent adduct formation of metabolites. While this experiment employs a 10-fold dilution to diminish metabolite concentrations and therefore effects of reversible inhibition, it is possible (but not common) that a metabolite that is an extremely potent CYP inhibitor could result in a positive result.

The results are from a cocktail of CYP specific probe substrates at 4 times their Km concentrations for CYP2C9, 2C19, 2D6 and 3A4 (midazolam) using human liver microsomes (HLM). The HLMs can be pre-incubated with test compounds at a concentration 10 µM for 30 min in the presence (+N) or absence (−N) of a NADPH regenerating system, diluted 10-fold, and incubated for 8 min in the presence of the substrate cocktail with the addition of a fresh aliquot of NADPH regenerating system. A calibration curve of metabolite standards can be used to quantitatively measure the enzyme activity using LC-MS/MS. In addition, incubations with known time dependent inhibitors, tienilic aicd (CYP2C9), ticlopidine (CYP2C19), paroxetine (CYP2D6), and troleandomycin (CYP3A4), used as positive controls are pre-incubated 30 min with or without a NADPH regenerating system.

The analytical system consists of a Shimadzu LC-30AD binary pump system and SIL-30AC autosampler (Shimadzu Scientific Instruments, Columbia, MD) coupled with a Sciex Triple Quad 6500+ mass spectrometer from Applied Biosystems (Foster City, CA). Chromatographic separation of test compounds and internal standard can be achieved using an ACQUITY UPLC BEH 130A, 2.1×50 mm, 1.7 µm HPLC column (Waters Corp, Milford, MA). Mobile phase A consists of 0.1% formic acid in water, and mobile phase B consists of 0.1% formic acid in acetonitrile. The total LC-MS/MS runtime will be 2.50 minutes with a flow rate of 0.9 mL/min. Peak area integrations and peak area ratio calculations are performed using Analyst software (version 1.6.3) from Applied Biosystems.

The percentage of control CYP2C9, CYP2C19, CYP2D6, and CYP3A4 activity remaining following preincubation of the compounds with NADPH is corrected for the corresponding control vehicle activity and then calculated based on 0 minutes as 100%. A linear regression plot of the natural log of % activity remaining versus time for each isozyme is used to calculate the slope. The −slope is equal to the rate of enzyme loss, or the $K_{obs}$.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A method of inhibiting KRAS activity, said method comprising contacting a compound selected from
    3-(1-((1R,4R,5S)-2-azabicyclo[2.1.1]hexan-5-yl)-2-((1R,3R,5S)-2-(cyclopropanecarbonyl)-2-azabicyclo[3.1.0]hexan-3-yl)-7-(2,3-dichlorophenyl)-6-fluoro-4-methyl-1H-pyrrolo[3,2-c]quinolin-8-yl)propanenitrile;
    methyl (1S,3R,5S)-3-(1-((1R,4R,5S)-2-azabicyclo[2.1.1]hexan-5-yl)-8-(2-cyanoethyl)-7-(2,3-dichlorophenyl)-4-(6-(dimethylcarbamoyl)pyridin-3-yl)-6-fluoro-1H-pyrrolo[3,2-c]quinolin-2-yl)-2-azabicyclo[3.1.0]hexane-2-carboxylate;
    methyl (1R,3R,5R)-3-(1-((1R,4R,5S)-2-azabicyclo[2.1.1]hexan-5-yl)-8-(2-cyanoethyl)-7-(2,3-dichlorophenyl)-4-(6-(dimethylcarbamoyl)pyridin-3-yl)-6-fluoro-1H-pyrrolo[3,2-c]quinolin-2-yl)-2-azabicyclo[3.1.0]hexane-2-carboxylate;
    3-(1-((1R,4R,5S)-2-azabicyclo[2.1.1]hexan-5-yl)-7-(2,3-dichlorophenyl)-6-fluoro-4-(1-hydroxyethyl)-2-((1R,3R,5R)-2-(1-methylcyclopropane-1-carbonyl)-2-azabicyclo[3.1.0]hexan-3-yl)-1H-pyrrolo[3,2-c]quinolin-8-yl)propanenitrile;
    3-(1-((1R,4R,5S)-2-azabicyclo[2.1.1]hexan-5-yl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-(1-hydroxyethyl)-1H-pyrrolo[3,2-c]quinolin-8-yl)propanenitrile;
    3-(1-((1R,4R,5S)-2-azabicyclo[2.1.1]hexan-5-yl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-methyl-1H-pyrrolo[3,2-c]quinolin-8-yl)propanenitrile;
    or a pharmaceutically acceptable salt thereof;
    with KRAS.

2. The method of claim 1, wherein the contacting comprises administering the compound to a patient.

3. A method of treating a disease or disorder associated with activity of a KRAS protein harboring a G12D mutation, said method comprising administering to a patient in need thereof a therapeutically effective amount of a compound selected from:
    3-(1-((1R,4R,5S)-2-azabicyclo[2.1.1]hexan-5-yl)-2-((1R,3R,5S)-2-(cyclopropanecarbonyl)-2-azabicyclo[3.1.0]hexan-3-yl)-7-(2,3-dichlorophenyl)-6-fluoro-4-methyl-1H-pyrrolo[3,2-c]quinolin-8-yl)propanenitrile;
    methyl (1S,3R,5S)-3-(1-((1R,4R,5S)-2-azabicyclo[2.1.1]hexan-5-yl)-8-(2-cyanoethyl)-7-(2,3-dichlorophenyl)-4-(6-(dimethylcarbamoyl)pyridin-3-yl)-6-fluoro-1H-pyrrolo[3,2-c]quinolin-2-yl)-2-azabicyclo[3.1.0]hexane-2-carboxylate;
    methyl (1R,3R,5R)-3-(1-((1R,4R,5S)-2-azabicyclo[2.1.1]hexan-5-yl)-8-(2-cyanoethyl)-7-(2,3-dichlorophenyl)-4-(6-(dimethylcarbamoyl)pyridin-3-yl)-6-fluoro-1H-pyrrolo[3,2-c]quinolin-2-yl)-2-azabicyclo[3.1.0]hexane-2-carboxylate;
    3-(1-((1R,4R,5S)-2-azabicyclo[2.1.1]hexan-5-yl)-7-(2,3-dichlorophenyl)-6-fluoro-4-(1-hydroxyethyl)-2-((1R,3R,5R)-2-(1-methylcyclopropane-1-carbonyl)-2-azabicyclo[3.1.0]hexan-3-yl)-1H-pyrrolo[3,2-c]quinolin-8-yl)propanenitrile;
    3-(1-((1R,4R,5S)-2-azabicyclo[2.1.1]hexan-5-yl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-(1-hydroxyethyl)-1H-pyrrolo[3,2-c]quinolin-8-yl)propanenitrile; and
    3-(1-((1R,4R,5S)-2-azabicyclo[2.1.1]hexan-5-yl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-methyl-1H-pyrrolo[3,2-c]quinolin-8-yl)propanenitrile;
    or a pharmaceutically acceptable salt thereof.

4. The method of claim 3, wherein the disease or disorder is a cancer, Alzheimer's disease, HIV, or tuberculosis.

5. The method of claim 4, wherein the disease or disorder is a cancer selected from a carcinoma, a hematological cancer, a sarcoma, and glioblastoma.

6. The method of claim 5, wherein the cancer is a hematological cancer selected from a myeloproliferative neoplasm, a myelodysplastic syndrome, chronic and juvenile myelomonocytic leukemia, acute myeloid leukemia, acute lymphocytic leukemia, and multiple myeloma.

7. The method of claim 5, wherein the cancer is a carcinoma selected from pancreatic, colorectal, lung, bladder, gastric, esophageal, breast, head and neck, cervical, skin, and thyroid.

8. The method of claim 3, wherein the disease or disorder is an immunological or inflammatory disorder.

9. The method of claim 8, wherein the immunological or inflammatory disorder is Ras-associated lymphoproliferative disorder or juvenile myelomonocytic leukemia caused by somatic mutations of KRAS.

10. The method of claim 1, wherein the compound is 3-(1-((1R,4R,5S)-2-azabicyclo[2.1.1]hexan-5-yl)-2-((1R,3R,5S)-2-(cyclopropanecarbonyl)-2-azabicyclo[3.1.0]hexan-3-yl)-7-(2,3-dichlorophenyl)-6-fluoro-4-methyl-1H-pyrrolo[3,2-c]quinolin-8-yl)propanenitrile, or a pharmaceutically acceptable salt thereof.

11. The method of claim 1, wherein the compound is 3-(1-((1R,4R,5S)-2-azabicyclo[2.1.1]hexan-5-yl)-2-((1R,3R,5S)-2-(cyclopropanecarbonyl)-2-azabicyclo[3.1.0]hexan-3-yl)-7-(2,3-dichlorophenyl)-6-fluoro-4-methyl-1H-pyrrolo[3,2-c]quinolin-8-yl)propanenitrile.

12. The method of claim 1, wherein the compound is a pharmaceutically acceptable salt of 3-(1-((1R,4R,5S)-2-azabicyclo[2.1.1]hexan-5-yl)-2-((1R,3R,5S)-2-(cyclopropanecarbonyl)-2-azabicyclo[3.1.0]hexan-3-yl)-7-(2,3-dichlorophenyl)-6-fluoro-4-methyl-1H-pyrrolo[3,2-c]quinolin-8-yl)propanenitrile.

13. The method of claim 3, wherein the compound is 3-(1-((1R,4R,5S)-2-azabicyclo[2.1.1]hexan-5-yl)-2-((1R,3R,5S)-2-(cyclopropanecarbonyl)-2-azabicyclo[3.1.0]hexan-3-yl)-7-(2,3-dichlorophenyl)-6-fluoro-4-methyl-1H-pyrrolo[3,2-c]quinolin-8-yl)propanenitrile, or a pharmaceutically acceptable salt thereof.

14. The method of claim 3, wherein the compound is 3-(1-((1R,4R,5S)-2-azabicyclo[2.1.1]hexan-5-yl)-2-((1R,3R,5S)-2-(cyclopropanecarbonyl)-2-azabicyclo[3.1.0]hexan-3-yl)-7-(2,3-dichlorophenyl)-6-fluoro-4-methyl-1H-pyrrolo[3,2-c]quinolin-8-yl)propanenitrile.

15. The method of claim 3, wherein the compound is a pharmaceutically acceptable salt of 3-(1-((1R,4R,5S)-2-azabicyclo[2.1.1]hexan-5-yl)-2-((1R,3R,5S)-2-(cyclopropanecarbonyl)-2-azabicyclo[3.1.0]hexan-3-yl)-7-(2,3-dichlorophenyl)-6-fluoro-4-methyl-1H-pyrrolo[3,2-c]quinolin-8-yl)propanenitrile.

16. The method of claim 1, wherein the compound is 3-(1-((1R,4R,5S)-2-azabicyclo[2.1.1]hexan-5-yl)-7-(2,3-dichlorophenyl)-6-fluoro-4-(1-hydroxyethyl)-2-((1R,3R,5R)-2-(1-methylcyclopropane-1-carbonyl)-2-azabicyclo[3.1.0]hexan-3-yl)-1H-pyrrolo[3,2-c]quinolin-8-yl)propanenitrile, or a pharmaceutically acceptable salt thereof.

17. The method of claim 1, wherein the compound is 3-(1-((1R,4R,5S)-2-azabicyclo[2.1.1]hexan-5-yl)-7-(2,3-dichlorophenyl)-6-fluoro-4-(1-hydroxyethyl)-2-((1R,3R,5R)-2-(1-methylcyclopropane-1-carbonyl)-2-azabicyclo[3.1.0]hexan-3-yl)-1H-pyrrolo[3,2-c]quinolin-8-yl)propanenitrile.

18. The method of claim 1, wherein the compound is a pharmaceutically acceptable salt of 3-(1-((1R,4R,5S)-2-azabicyclo[2.1.1]hexan-5-yl)-7-(2,3-dichlorophenyl)-6-fluoro-4-(1-hydroxyethyl)-2-((1R,3R,5R)-2-(1-methylcyclopropane-1-carbonyl)-2-azabicyclo[3.1.0]hexan-3-yl)-1H-pyrrolo[3,2-c]quinolin-8-yl)propanenitrile.

19. The method of claim 3, wherein the compound is 3-(1-((1R,4R,5S)-2-azabicyclo[2.1.1]hexan-5-yl)-7-(2,3-dichlorophenyl)-6-fluoro-4-(1-hydroxyethyl)-2-((1R,3R,5R)-2-(1-methylcyclopropane-1-carbonyl)-2-azabicyclo[3.1.0]hexan-3-yl)-1H-pyrrolo[3,2-c]quinolin-8-yl)propanenitrile, or a pharmaceutically acceptable salt thereof.

20. The method of claim 3, wherein the compound is 3-(1-((1R,4R,5S)-2-azabicyclo[2.1.1]hexan-5-yl)-7-(2,3-dichlorophenyl)-6-fluoro-4-(1-hydroxyethyl)-2-((1R,3R,5R)-2-(1-methylcyclopropane-1-carbonyl)-2-azabicyclo[3.1.0]hexan-3-yl)-1H-pyrrolo[3,2-c]quinolin-8-yl)propanenitrile.

21. The method of claim 3, wherein the compound is a pharmaceutically acceptable salt of 3-(1-((1R,4R,5S)-2-azabicyclo[2.1.1]hexan-5-yl)-7-(2,3-dichlorophenyl)-6-fluoro-4-(1-hydroxyethyl)-2-((1R,3R,5R)-2-(1-methylcyclopropane-1-carbonyl)-2-azabicyclo[3.1.0]hexan-3-yl)-1H-pyrrolo[3,2-c]quinolin-8-yl)propanenitrile.

22. The method of claim 1, wherein the compound is 3-(1-((1R,4R,5S)-2-azabicyclo[2.1.1]hexan-5-yl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-(1-hydroxyethyl)-1H-pyrrolo[3,2-c]quinolin-8-yl)propanenitrile, or a pharmaceutically acceptable salt thereof.

23. The method of claim 1, wherein the compound is 3-(1-((1R,4R,5S)-2-azabicyclo[2.1.1]hexan-5-yl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-(1-hydroxyethyl)-1H-pyrrolo[3,2-c]quinolin-8-yl)propanenitrile.

24. The method of claim 1, wherein the compound is a pharmaceutically acceptable salt of 3-(1-((1R,4R,5S)-2-azabicyclo[2.1.1]hexan-5-yl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-(1-hydroxyethyl)-1H-pyrrolo[3,2-c]quinolin-8-yl)propanenitrile.

25. The method of claim 3, wherein the compound is 3-(1-((1R,4R,5S)-2-azabicyclo[2.1.1]hexan-5-yl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-(1-hydroxyethyl)-1H-pyrrolo[3,2-c]quinolin-8-yl)propanenitrile, or a pharmaceutically acceptable salt thereof.

26. The method of claim 3, wherein the compound is 3-(1-((1R,4R,5S)-2-azabicyclo[2.1.1]hexan-5-yl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-(1-hydroxyethyl)-1H-pyrrolo[3,2-c]quinolin-8-yl)propanenitrile.

27. The method of claim 3, wherein the compound is a pharmaceutically acceptable salt of 3-(1-((1R,4R,5S)-2-azabicyclo[2.1.1]hexan-5-yl)-7-(2,3-dichlorophenyl)-6-fluoro-2-((1R,3R,5R)-2-(1-fluorocyclopropane-1-carbonyl)-2-azabicyclo[3.1.0]hexan-3-yl)-4-(1-hydroxyethyl)-1H-pyrrolo[3,2-c]quinolin-8-yl)propanenitrile.

28. The method of claim 3, wherein the disease or disorder is a cancer characterized by a KRAS protein harboring a G12D mutation.

29. The method of claim 28, wherein the cancer is pancreatic cancer.

30. The method of claim 29, wherein the pancreatic cancer is pancreatic ductal adenocarcinoma.

31. The method of claim 28, wherein the cancer is colorectal cancer.

32. The method of claim 31, wherein the colorectal cancer is colorectal carcinoma.

33. The method of claim 28, wherein the cancer is lung cancer.

34. The method of claim 33, wherein the lung cancer is non-small cell lung cancer.

* * * * *